US007572795B2

(12) United States Patent
Liu et al.

(10) Patent No.: US 7,572,795 B2
(45) Date of Patent: Aug. 11, 2009

(54) PYRROLOTRIAZINE ANILINE PRODRUG COMPOUNDS USEFUL AS KINASE INHIBITORS

(75) Inventors: Chunjian Liu, Pennington, NJ (US); Katerina Leftheris, Skillman, NJ (US); Vivekananda M. Vrudhula, Killingworth, CT (US); James Lin, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/682,331

(22) Filed: Mar. 6, 2007

(65) Prior Publication Data

US 2007/0213300 A1 Sep. 13, 2007

Related U.S. Application Data

(60) Provisional application No. 60/779,851, filed on Mar. 7, 2006.

(51) Int. Cl.
C07D 487/04 (2006.01)
A61K 31/53 (2006.01)
A61P 19/02 (2006.01)
A61P 17/06 (2006.01)
A61P 9/10 (2006.01)

(52) U.S. Cl. .................................... 514/243; 544/183
(58) Field of Classification Search .............. 544/183; 514/243
See application file for complete search history.

(56) References Cited

U.S. PATENT DOCUMENTS

| 5,658,903 | A | 8/1997 | Adams et al. |
|---|---|---|---|
| 5,932,576 | A | 8/1999 | Anantanarayan et al. |
| 5,945,418 | A | 8/1999 | Bemis et al. |
| 5,977,103 | A | 11/1999 | Adams et al. |
| 6,087,496 | A | 7/2000 | Anantanarayan et al. |
| 6,130,235 | A | 10/2000 | Mavunkel et al. |
| 6,147,080 | A | 11/2000 | Bemis et al. |
| 6,251,914 | B1 | 6/2001 | Adams et al. |
| 6,277,989 | B1 | 8/2001 | Chakravarty et al. |
| 6,670,357 | B2 | 12/2003 | Leftheris et al. |
| 6,982,265 | B1 | 1/2006 | Hunt et al. |
| 2005/0043306 | A1 | 2/2005 | Leftheris et al. |

FOREIGN PATENT DOCUMENTS

| WO | WO 00/12074 | 3/2000 |
|---|---|---|
| WO | WO 00/12497 | 3/2000 |
| WO | WO 00/56738 | 9/2000 |
| WO | WO 01/14378 | 3/2001 |
| WO | WO 01/27089 | 4/2001 |
| WO | WO 01/34605 | 5/2001 |
| WO | WO 01/36420 | 5/2001 |
| WO | WO 01/56358 | 8/2001 |
| WO | WO 03/090912 | 11/2003 |
| WO | WO 03/091229 | 11/2003 |
| WO | WO 2004/009784 | 1/2004 |
| WO | WO 2004/013145 | 2/2004 |
| WO | WO 2004/054514 | 7/2004 |
| WO | WO2004/072030 | 8/2004 |
| WO | WO 2005/028473 | 3/2005 |
| WO | WO 2007/138381 | 12/2007 |

OTHER PUBLICATIONS

Kaminska B., Biochimica et Biophysica Acta 1754, 253-262, 2005.*
Bundgaard, "Means to Enhance Penetration", Advanced Drug Delivery Reviews, 1992, 8, 1-38.
Bundgaard, Design of Prodrugs, 1985, Elsevier Science Publishers B.V. (Biomedical Division), Amsterdam, New York, Oxford.
Henry et al., "p38 Mitogen-Activated Protein Kinase as a Target for Drug Discovery", Drugs of the Future, 1999, 24 (12) 1345-1354.
Krogsgaard-Larsen et al., A Textbook of Drug Design and Development, 1991, Harwood Academic Publishers GmBH, Poststrasse 22,7000 Chur, Switzerland.
Moreland et al, "Etanercept Therapy in Rheumatoid Arthritis", Ann. Intern. Med., 1999, 130, 478-486.
Raingeaud et al., "MKK3- and MKK6-Regulated Gene Expression is Mediated by the p38 Mitogen-Activated Protein Kinase Signal Transduction Pathway", Molecular and Cellular Biology, 1996, 1247-1255.
Rankin et al., "The Therapeutic Effects of an Engineered Human Anti-Tumor Necrosis Factor Alpha Antibody (CDP571) in Rheumatoid Arthritis", British Journal of Rheumatology, 1995, 34, 334-342.
Salituro et al., "Inhibitors of p38 MAP Kinase: Therapeutic Intervention in Cytokine-Mediated Diseases", Current Medicinal Chemistry, 1999, 6, 807-823.
Takahama, U. et al., *FEBS Letters*, vol. 518, pp. 116-118 (2002).
C. Pargellis et al, *Current Opinion in Investigational Drugs*, vol. 4, No. 5, pp. 566-671, 2003.
Alexander, J. et al., Journal of Medicinal Chemistry, American Chemical Soc., vol. 31, No. 2, (1988) pp. 318-322.

* cited by examiner

*Primary Examiner*—Venkataraman Balasubramanian
(74) *Attorney, Agent, or Firm*—Laurelee A. Duncan

(57) ABSTRACT

Compounds having the Formula (I), including pharmaceutically acceptable salts thereof,

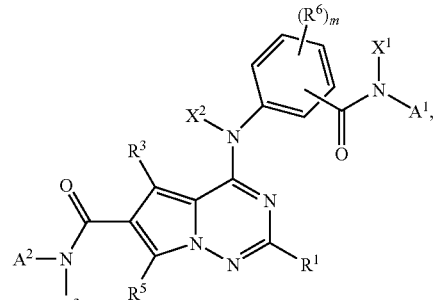

wherein at least one of $X^1$, $X^2$ or $X^3$ is

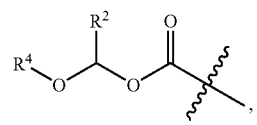

and any remaining $X^1$, $X^2$ or $X^3$ is hydrogen, which are useful as kinase inhibitors, wherein $R^1$, $R^2$, $R^3$, $R^4$, $R^5$, $R^6$, $A^1$, $A^2$ and m are as described herein.

34 Claims, No Drawings

PYRROLOTRIAZINE ANILINE PRODRUG COMPOUNDS USEFUL AS KINASE INHIBITORS

CROSS-REFERENCE TO RELATED APPLICATION

This application claims the benefit of U.S. Provisional Application No. 60/779,851, filed on Mar. 7, 2006, which is herein incorporated by reference in its entirety.

FIELD OF THE INVENTION

This invention relates to pyrrolotriazine compounds, more particularly, to prodrugs of pyrrolotriazine aniline compounds useful for treating p38 kinase-associated conditions. The invention further pertains to pharmaceutical compositions containing at least one compound according to the invention useful for treating p38 kinase-associated conditions and methods of inhibiting the activity of p38 kinase in a mammal.

BACKGROUND OF THE INVENTION

A large number of cytokines participate in the inflammatory response, including IL-1, IL-6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others [Henry et al., Drugs Fut., 24:1345-1354 (1999); Salituro et al., Curr. Med. Chem., 6:807-823 (1999)]. Evidence in human patients indicates that protein antagonists of cytokines are effective in treating chronic inflammatory diseases, such as, for example, monoclonal antibody to TNF-α (Enbrel) [Rankin et al., Br. J. Rheumatol., 34:334-342 (1995)], and soluble TNF-α receptor-Fc fusion protein (Etanercept) [Moreland et al., Ann. Intern. Med., 130:478-486 (1999)].

The biosynthesis of TNF-α occurs in many cell types in response to an external stimulus, such as, for example, a mitogen, an infectious organism, or trauma. Important mediators of TNF-α production are the mitogen-activated protein (MAP) kinases, and in particular, p38 kinase. These kinases are activated in response to various stress stimuli, including but not limited to proinflammatory cytokines, endotoxin, ultraviolet light, and osmotic shock. Activation of p38 requires dual phosphorylation by upstream MAP kinase kinases (MKK3 and MKK6) on threonine and tyrosine within a Thr-Gly-Tyr motif characteristic of p38 isozymes.

There are four known isoforms of p38, i.e., p38-α, p38β, p38γ, and p38δ. The α and β isoforms are expressed in inflammatory cells and are key mediators of TNF-α production. Inhibiting the p38α and β enzymes in cells results in reduced levels of TNF-α expression. Also, administering p38α and β inhibitors in animal models of inflammatory disease has proven that such inhibitors are effective in treating those diseases. Accordingly, the p38 enzymes serve an important role in inflammatory processes mediated by IL-1 and TNF-α. Compounds that reportedly inhibit p38 kinase and cytokines such as IL-1 and TNF-α for use in treating inflammatory diseases are disclosed in U.S. Pat. Nos. 6,277,989 and 6,130,235 to Scios, Inc; U.S. Pat. Nos. 6,147,080 and 5,945,418 to Vertex Pharmaceuticals Inc; U.S. Pat. Nos. 6,251,914, 5,977,103 and 5,658,903 to Smith-Kline Beecham Corp.; U.S. Pat. Nos. 5,932,576 and 6,087,496 to G. D. Searle & Co.; WO 00/56738 and WO 01/27089 to Astra Zeneca; WO 01/34605 to Johnson & Johnson; WO 00/12497 (quinazoline derivatives as p38 kinase inhibitors); WO 00/56738 (pyridine and pyrimidine derivatives for the same purpose); WO 00/12497 (discusses the relationship between p38 kinase inhibitors); and WO 00/12074 (piperazine and piperidine compounds useful as p38 inhibitors).

The present invention provides certain prodrugs of pyrrolotriazine compounds, particularly, pyrrolotriazine aniline compounds useful as kinase inhibitors, particularly kinases p38α and β. Pyrrolotriazine compounds useful as tyrosine kinase inhibitors are disclosed in U.S. patent application Ser. No. 09/573,829, filed May 18, 2000, assigned to the present assignee. Methods of treating p38 kinase-associated conditions as well as pyrrolotriazine compounds useful for that purpose are described in U.S. patent application Ser. No. 10/036,293, assigned to the present assignee and having common inventors herewith, which claims the benefit of U.S. Provisional Application No. 60/249,877, filed Nov. 17, 2000, and U.S. Provisional Application No. 60/310,561, filed Aug. 7, 2001. Pyrrolotriazine compounds substituted with an acidic group reportedly having sPLA$_2$-inhibitory activity are disclosed in WO 01/14378 A1 to Shionogi & Co., Ltd, published Mar. 1, 2001 in Japanese. Each of the patent applications, patents, and publications referred to herein is incorporated herein by reference.

Prodrug strategies or methodologies can be used to markedly enhance properties of a drug or to overcome an inherent deficiency in the pharmaceutical or pharmacokinetic properties of a drug. Prodrugs are new chemical entities which, upon administration to the patient, regenerates the parent molecule within the body. A myriad of prodrug strategies exist which provide choices in modulating the conditions for regeneration of the parent drug, the physical, pharmaceutic, or pharmacokinetic properties of the prodrug, and the functionality to which the prodrug modifications may be attached. However, none of the existing technologies teaches or suggests the specific prodrugs of the present disclosure. The identification of prodrugs with desired properties is often difficult and non straightforward.

SUMMARY OF THE INVENTION

In one embodiment, the instant invention pertains to compounds of Formula I:

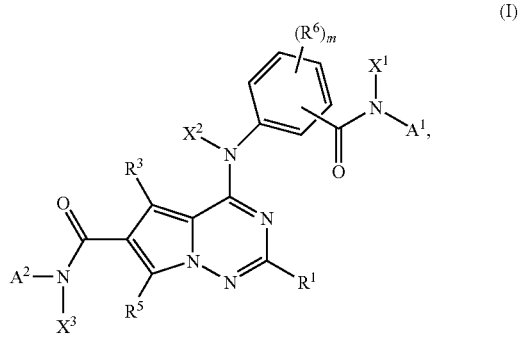

(I)

including pharmaceutically acceptable salts thereof, wherein at least one of $X^1$, $X^2$ or $X^3$ is

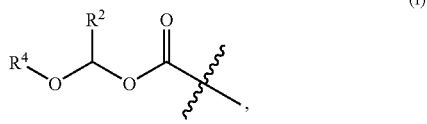

(i)

and any remaining $X^1$, $X^2$ or $X^3$ is hydrogen;

$A^1$ and $A^2$ are each independently selected from optionally-substituted alkyl, optionally-substituted cycloalkyl, optionally-substituted aryl, optionally-substituted aralkyl, optionally-substituted heterocyclo and optionally-substituted heteroaryl;

$R^1$, $R^3$ and $R^5$ are each independently selected from hydrogen, optionally-substituted alkyl, —$OR^{14}$, —C(=O)$NR^{14}R^{14a}$, —$NR^{14}R^{14a}$, —$SO_2NR^{14}R^{14a}$, —$NR^{14}SO_2NR^{14a}R^{14b}$, —$NR^{14a}SO_2R^{14}$, —$NR^{14}C(=O)R^{14a}$, —$NR^{14}CO_2R^{14a}$, —$NR^{14}C(=O)NR^{14a}R^{14b}$, halogen, cyano, optionally-substituted cycloalkyl, optionally-substituted aryl, optionally-substituted heterocyclo and optionally-substituted heteroaryl;

$R^2$ is independently selected from hydrogen and optionally-substituted alkyl;

$R^4$ is independently selected from:

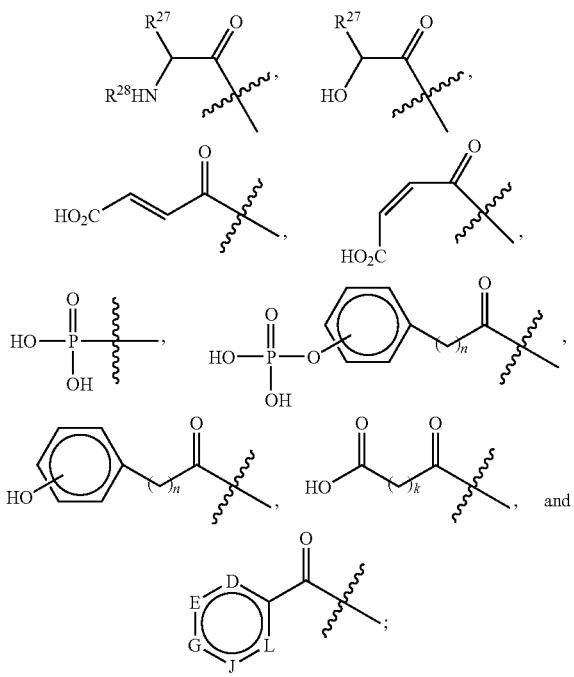

$R^6$ is attached to any available carbon atom of the phenyl ring and at each occurrence is independently selected from optionally-substituted alkyl, halogen, trifluoromethoxy, trifluoromethyl, hydroxy, alkoxy, alkanoyl, alkanoyloxy, thiol, alkylthio, ureido, nitro, cyano, carboxy, carboxyalkyl, carbamyl, alkoxycarbonyl, alkylthiono, arylthiono, arylsulfonylamine, alkylsulfonylamine, sulfonic acid, alkysulfonyl, sulfonamido, phenyl, benzyl, aryloxy and benzyloxy, wherein each $R^6$ group in turn may be further substituted by one to two $R^{18}$;

$R^{14}$, $R^{14a}$ and $R^{14b}$ are independently selected from hydrogen, optionally-substituted alkyl, optionally-substituted aryl, optionally-substituted cycloalkyl, optionally-substituted heterocyclo, and optionally-substituted heteroaryl, except when $R^{14}$ is joined to a sulfonyl group, as in —S(=O)$R^{14}$, —$SO_2R^{14}$, and —$NR^{14a}SO_2R^{14}$, then $R^{14}$ is not hydrogen;

$R^{18}$ is independently selected from $C_{1-6}$alkyl, $C_{2-6}$alkenyl, halogen, haloalkyl, haloalkoxy, cyano, nitro, amino, $C_{1-4}$alkylamino, amino$C_{1-4}$alkyl, hydroxy, hydroxy$C_{1-4}$alkyl, alkoxy, $C_{1-4}$alkylthio, aryl, heterocyclo, (aryl)alkyl, aryloxy, and (aryl)alkoxy;

$R^{27}$ and $R^{28}$ are independently selected from hydrogen, optionally-substituted alkyl, optionally-substituted cycloalkyl, optionally-substituted aryl, optionally-substituted aralkyl, optionally-substituted heterocyclo and optionally-substituted heteroaryl;

one of D, E, G, J or L is =N— and each remaining D, E, G, J or L is =C—;

m is 0, 1, 2 or 3;

n is 0 or 1; and k is 0, 1 or 2.

The invention further pertains to pharmaceutical compositions containing compounds of Formula I, and to methods of treating conditions associated with the activity of p38 kinase (α and β), comprising administering to a mammal a pharmaceutically effective amount of a compound of Formula I, including pharmaceutically acceptable salts thereof, and one or more pharmaceutically acceptable carriers, excipients or diluents.

In yet another embodiment, the present case is for a method of treating an inflammatory disorder comprising administering to a patient in need of such treatment a pharmaceutical composition as specified herein.

In still another embodiment, the instant invention is directed to the use of a carbamate substituted pyrrolotriazine compound of Formula I as a prodrug for releasing a parent drug containing the substituted pyrrolotriazine compound after removal of the carbamate moiety in animals or humans.

In another embodiment, the instant invention is for a compound having the Formula II:

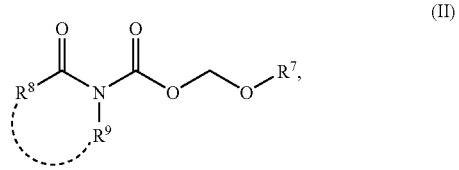

(II)

or pharmaceutically acceptable salts thereof, wherein
$R^7$ is independently selected from:

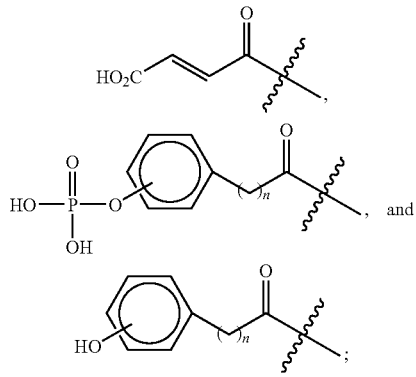

$R^8$ and $R^9$ are independently selected from optionally-substituted alkyl, optionally-substituted cycloalkyl, optionally-substituted aryl, optionally-substituted aralkyl, optionally-substituted heterocyclo and optionally-substituted heteroaryl, or $R^8$ and $R^9$ can be taken together to be optionally substituted lactam; and n is 0 or 1.

DESCRIPTION OF THE INVENTION

This disclosure relates to a prodrug approach which enhances the maximum exposure and/or the ability to increase exposure multiples (i.e., multiples of drug exposure greater than $EC_{50}$ or $EC_{90}$) upon dose escalation of efficacious members of a previously disclosed class of p38 kinase inhibitors. The improvements offered by the prodrug are beneficial, for they allow drug levels in the body to be increased, which provides greater efficacy.

Since the compounds of the present invention may possess asymmetric centers and, therefore, occur as mixtures of diastereomers and enantiomers, the present invention includes the individual diastereoisomeric and enantiomeric forms of the compounds of Formula I, Formula II and Formula III, in addition to the mixtures thereof.

In one embodiment, this invention relates to a carbamate prodrug of a pyrrolotriazine compound. The carbamate moiety increases the utility of the parent compounds by increasing the absorption of the compounds in the body.

In another embodiment, this disclosure describes prodrugs of amides which are effective at improving the oral utility of the parent molecules in the body.

An embodiment of the present invention is for compounds, and salts thereof, selected from the group consisting of:

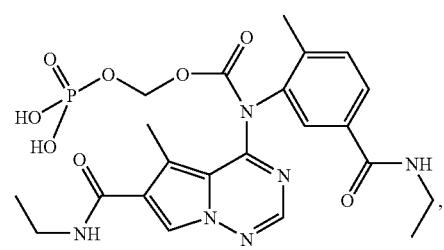

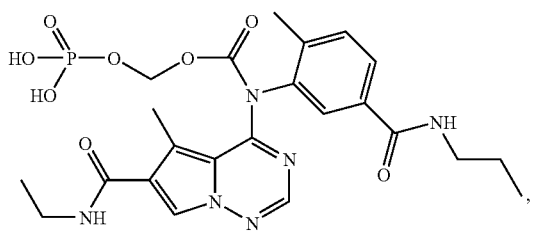

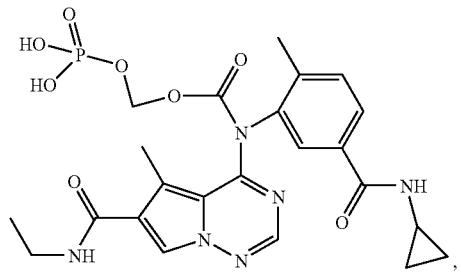

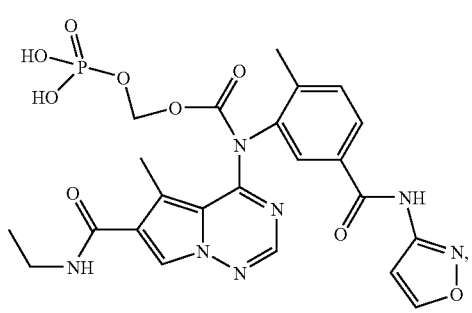

-continued

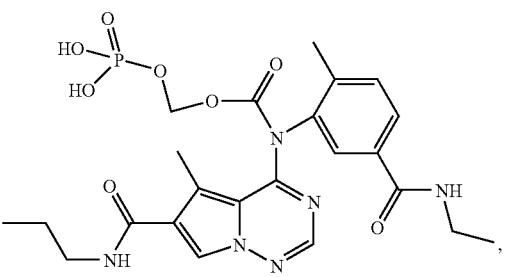

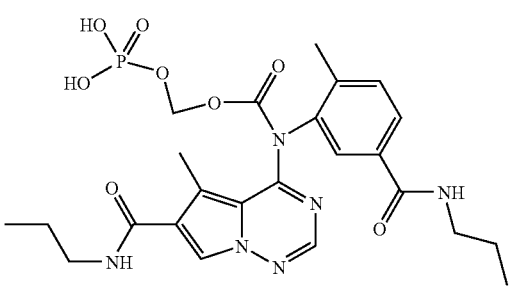

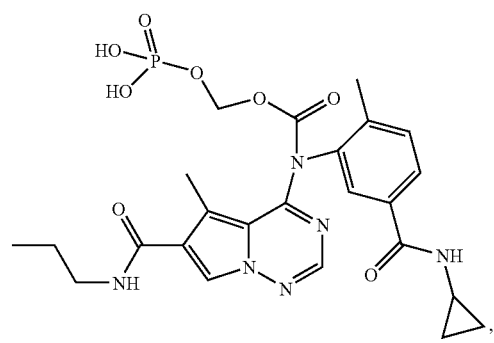

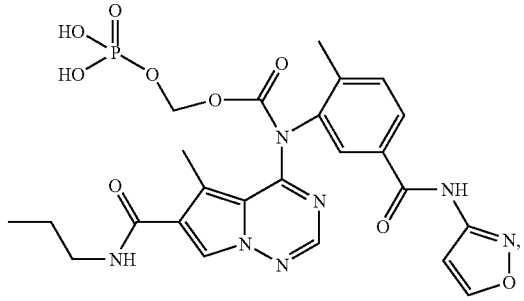

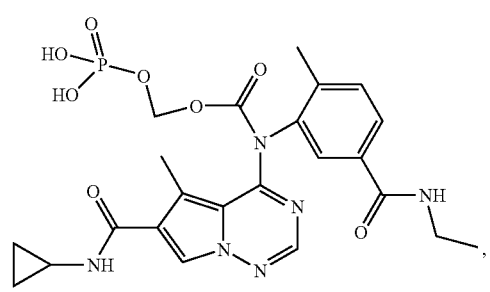

-continued
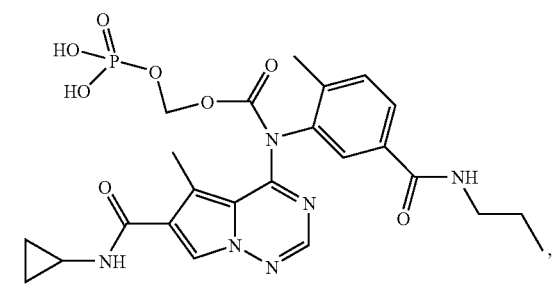
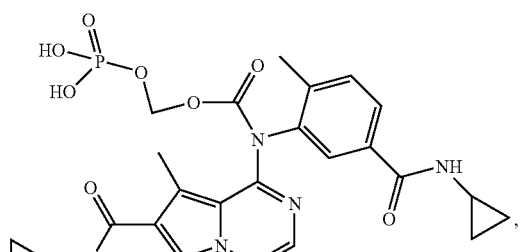
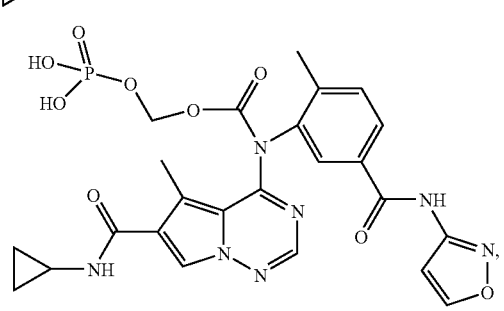
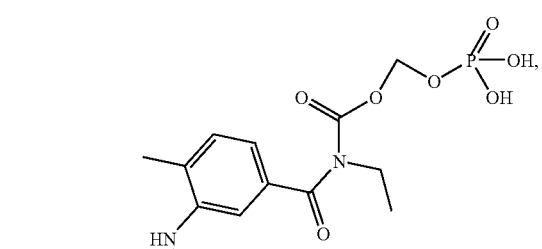
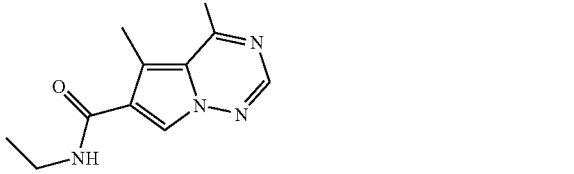
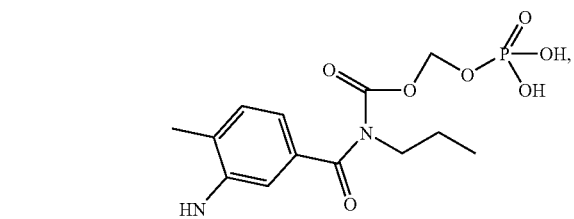
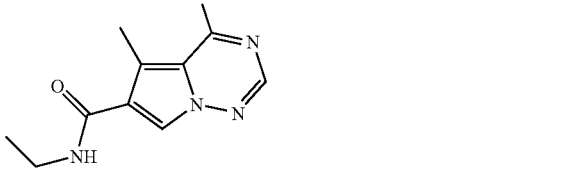
-continued
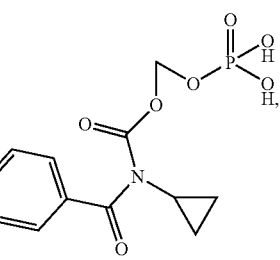
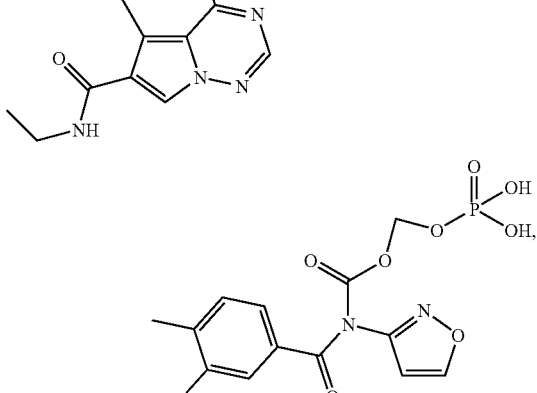
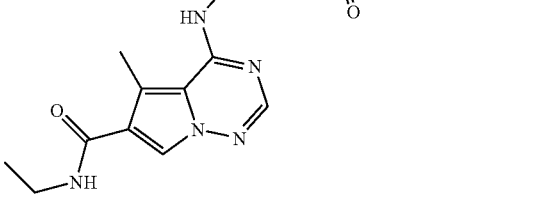
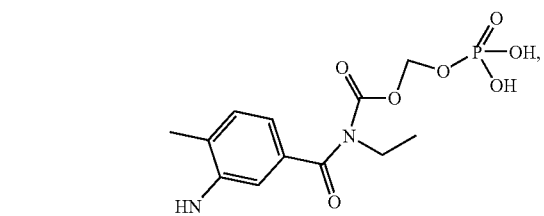
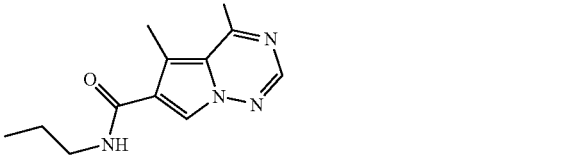
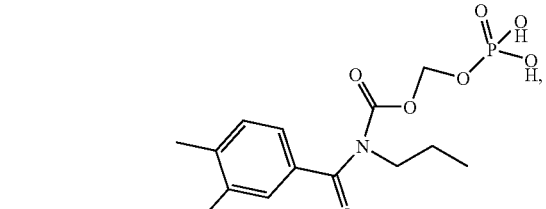
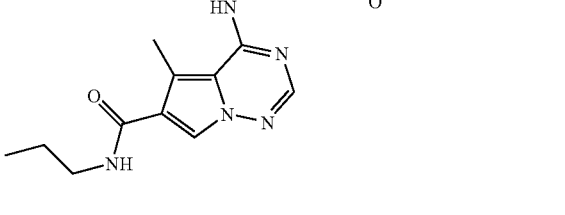

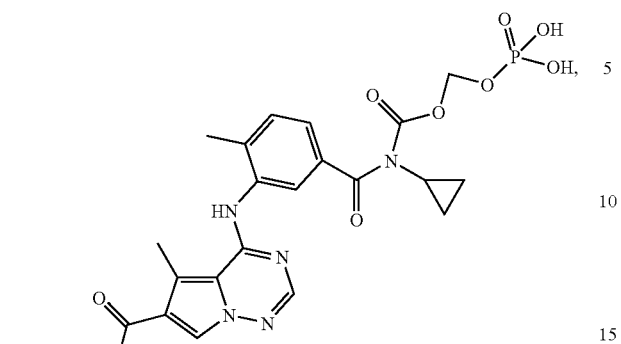
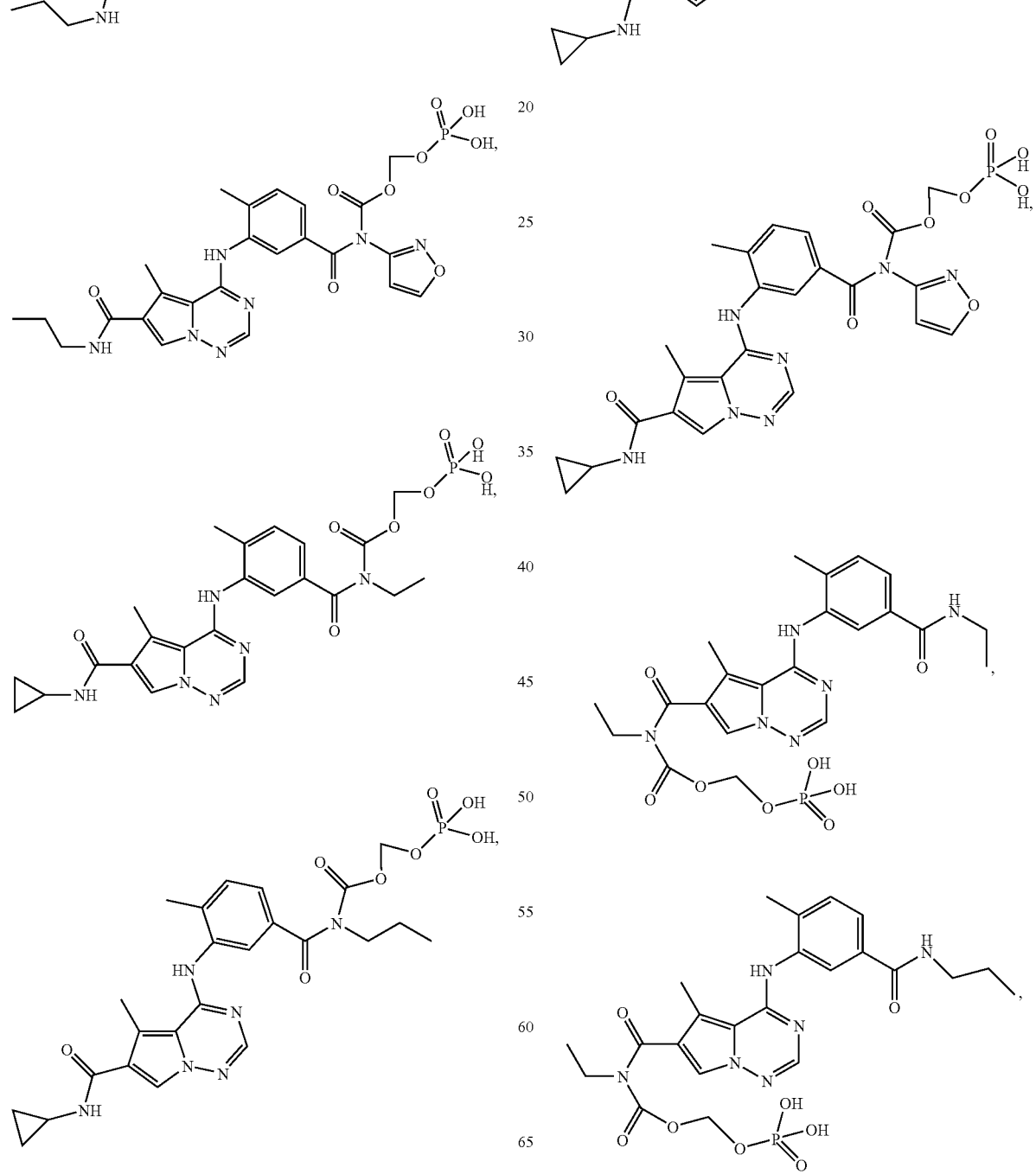

-continued
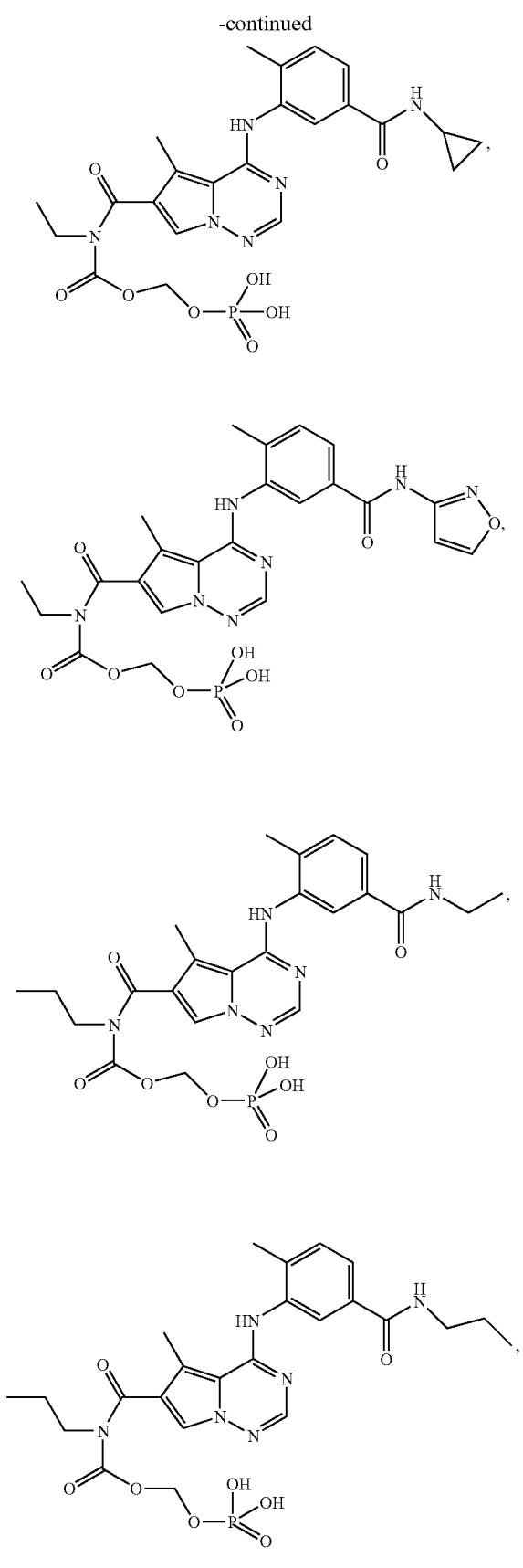
-continued
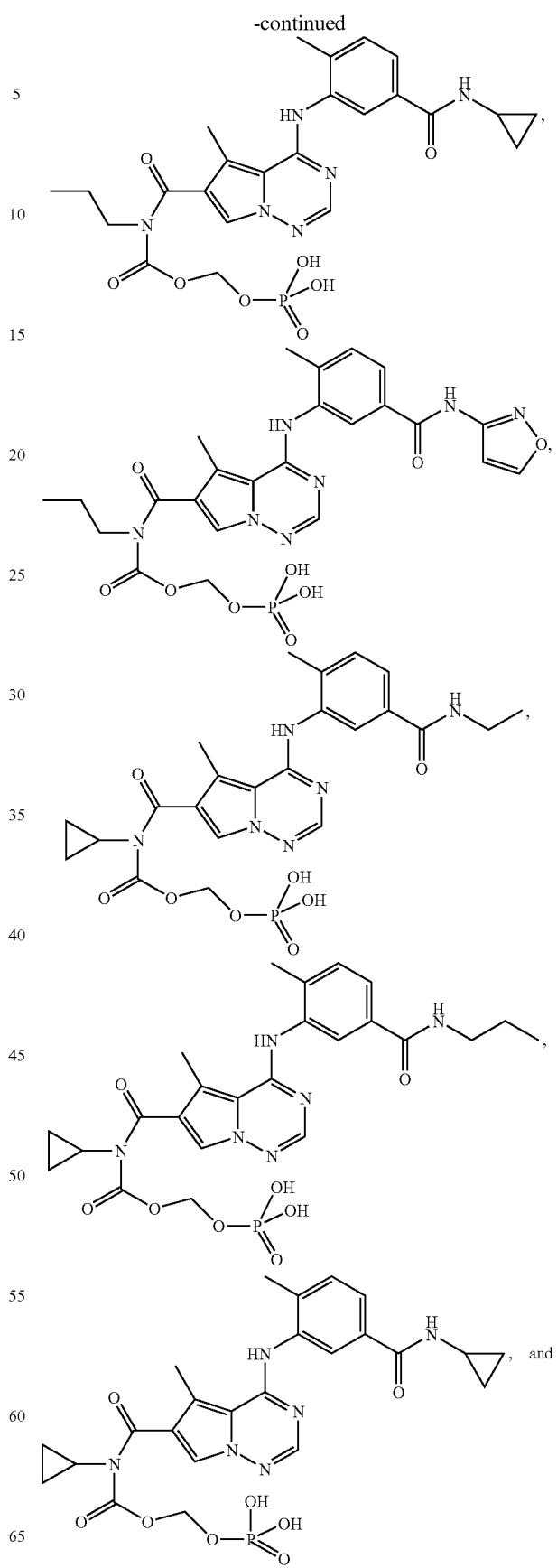

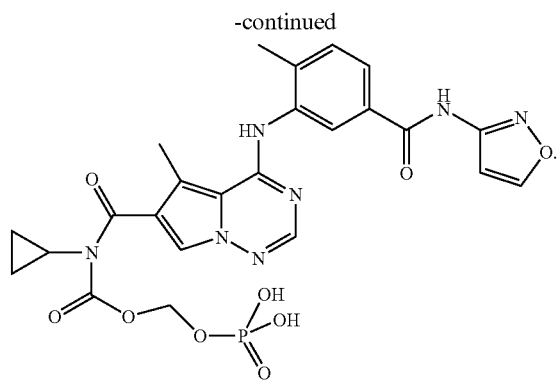
An embodiment of the present invention is for compounds, and salts thereof, selected from the group consisting of:
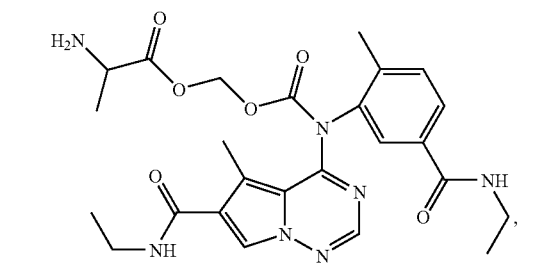
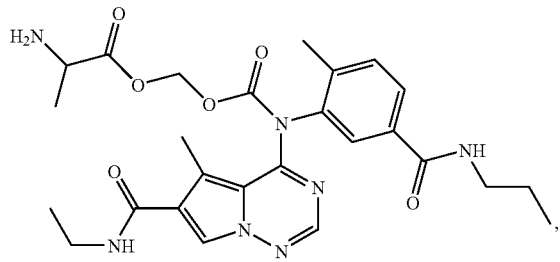
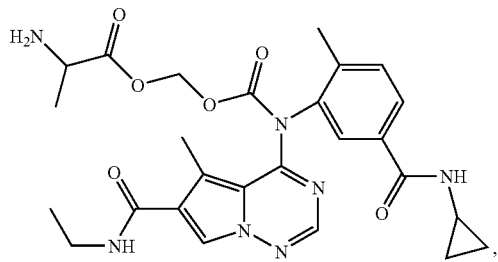
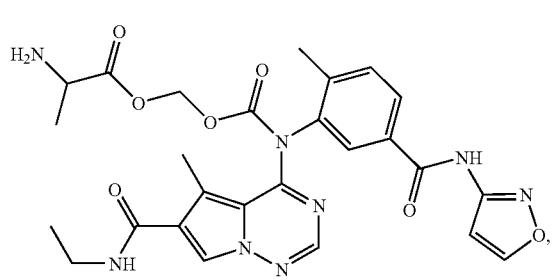
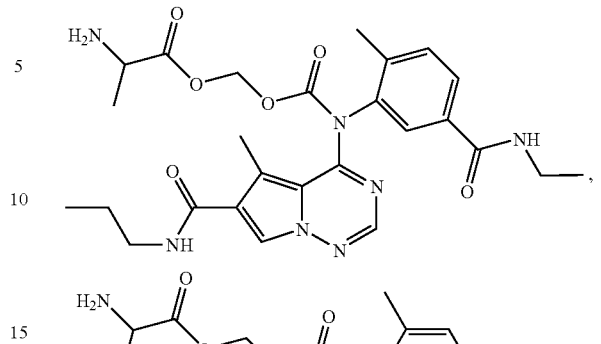
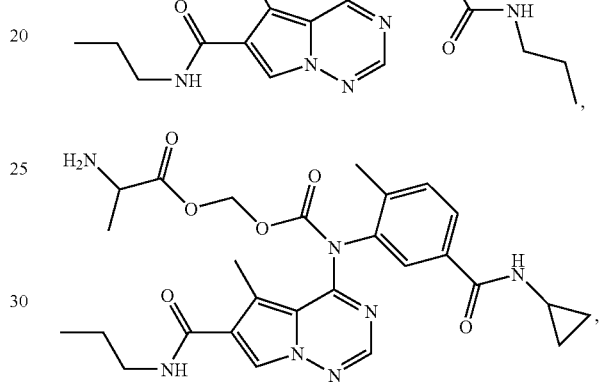
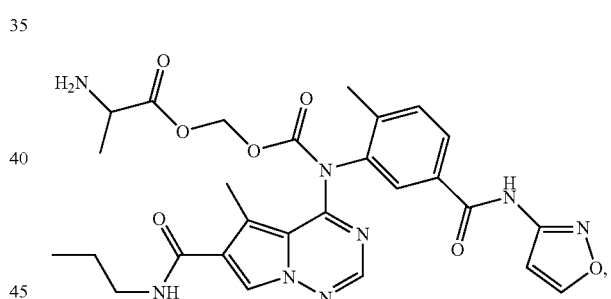
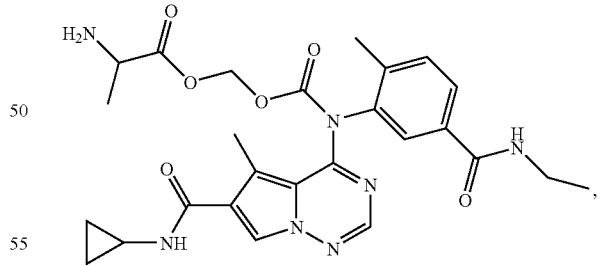
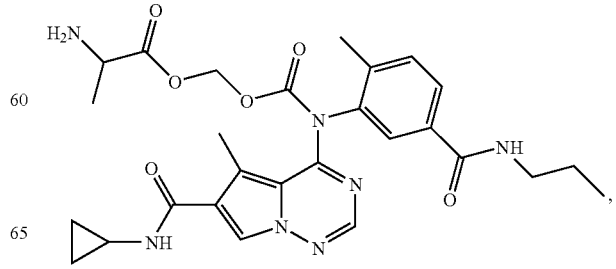

-continued
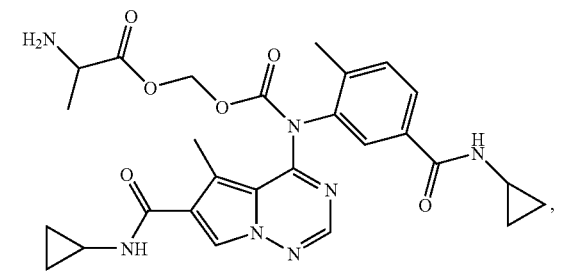
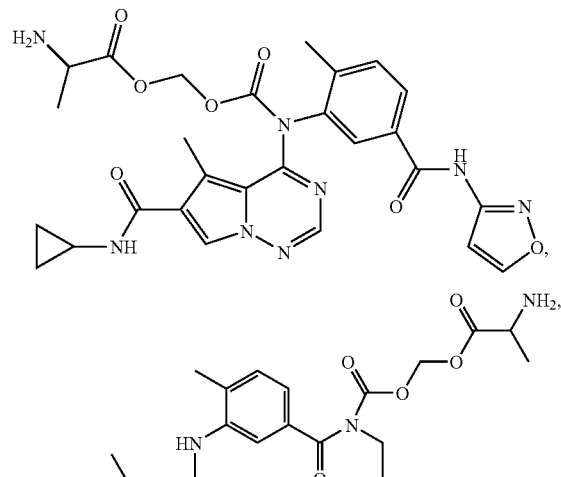
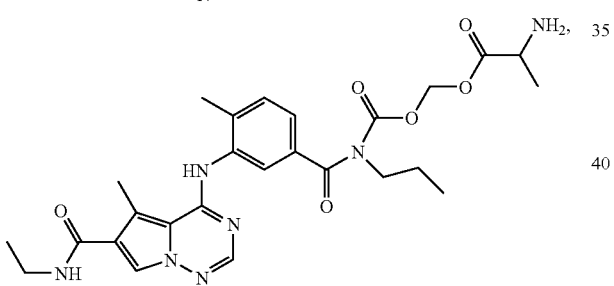
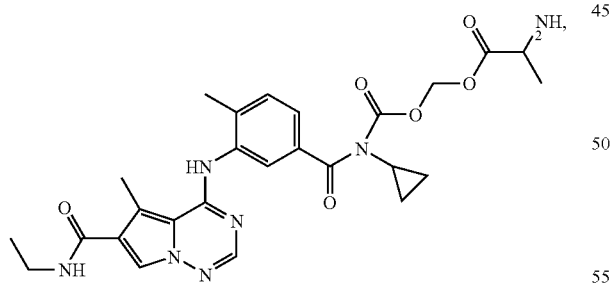
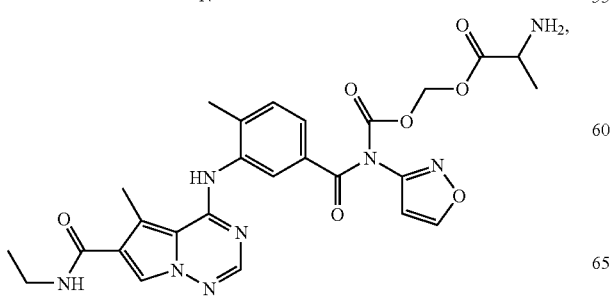
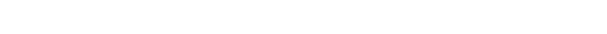
-continued
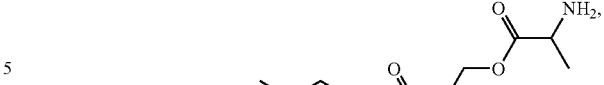
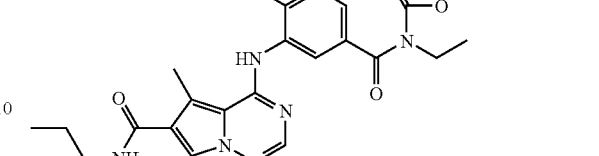
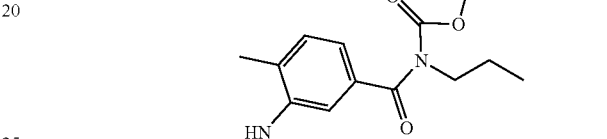
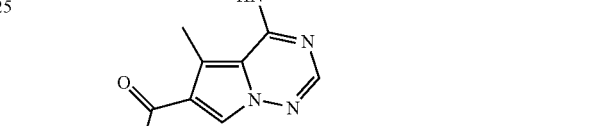
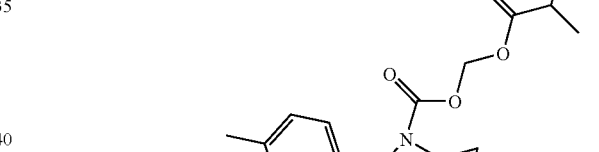
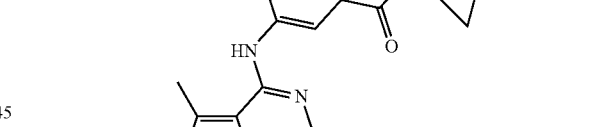
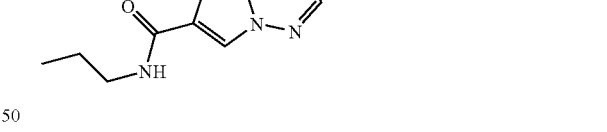
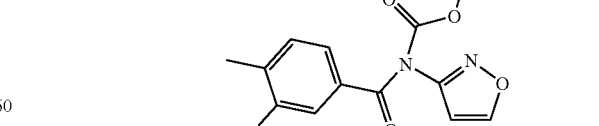
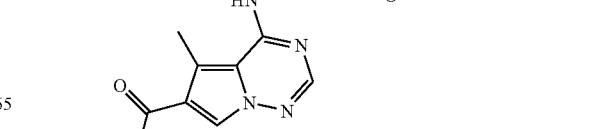

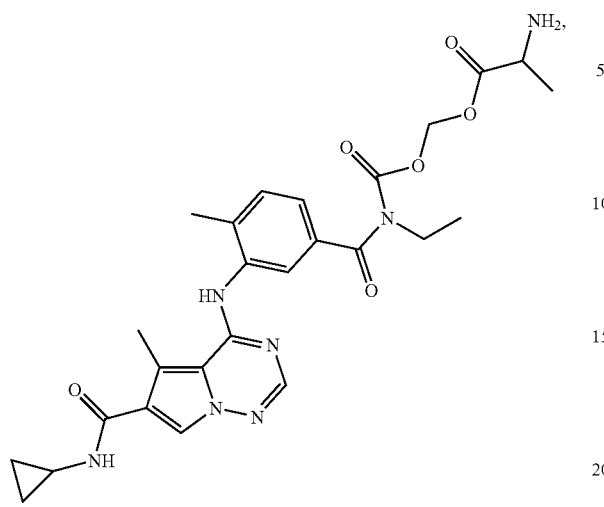
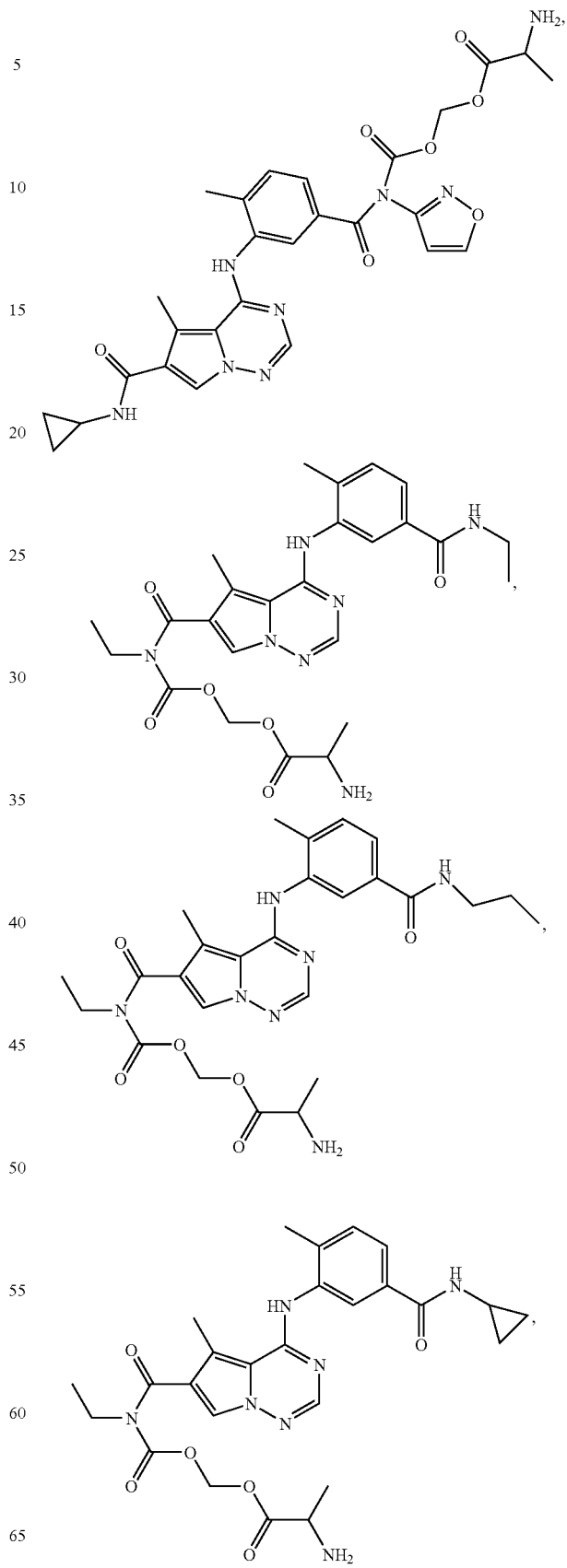

-continued
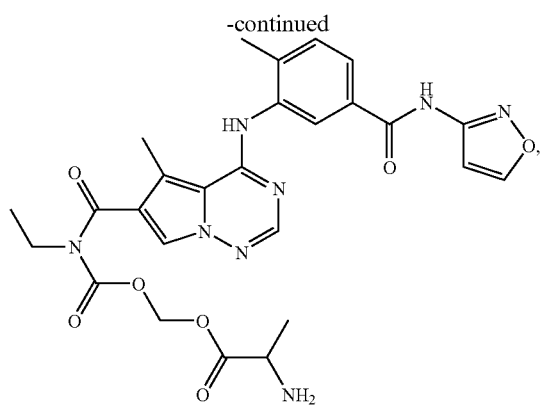
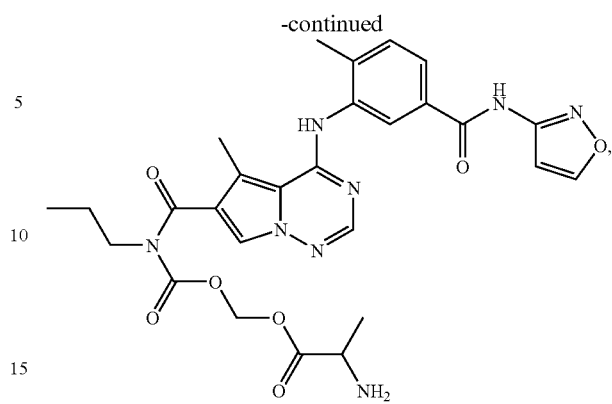
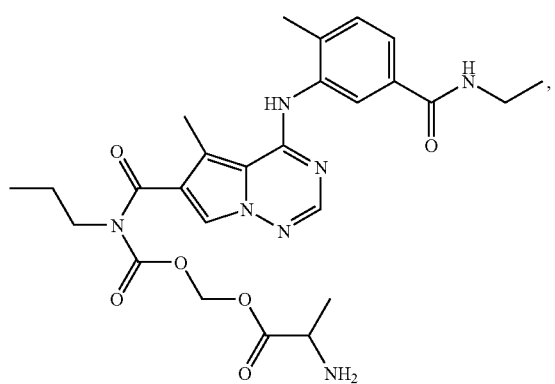
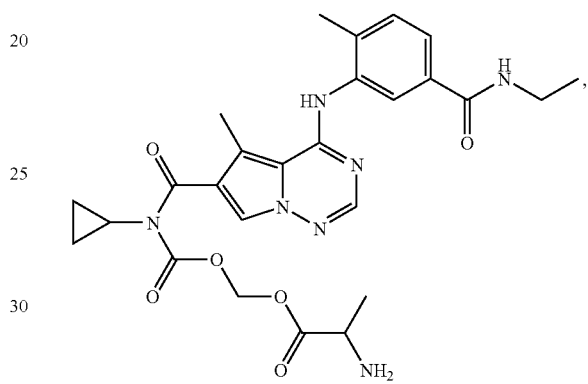
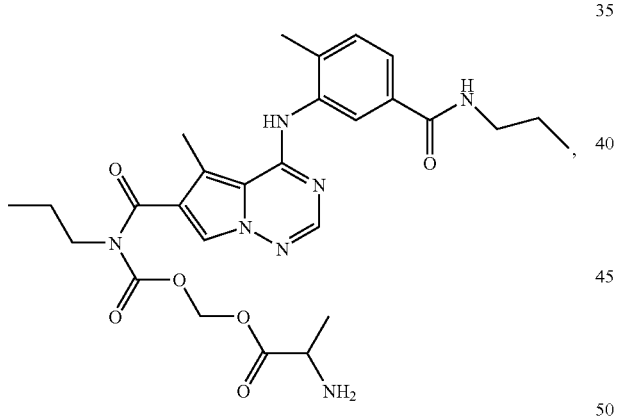
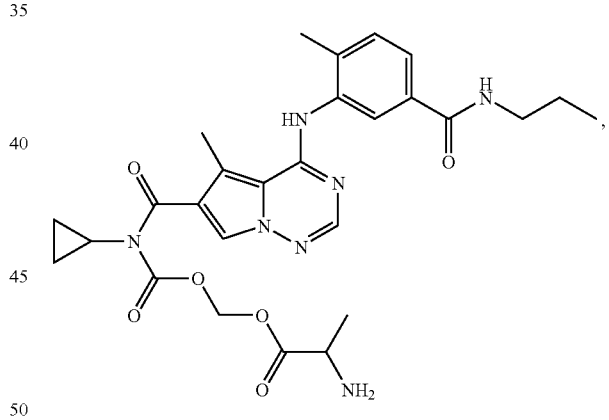
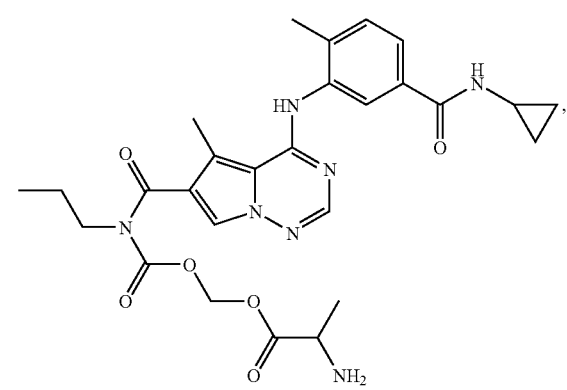
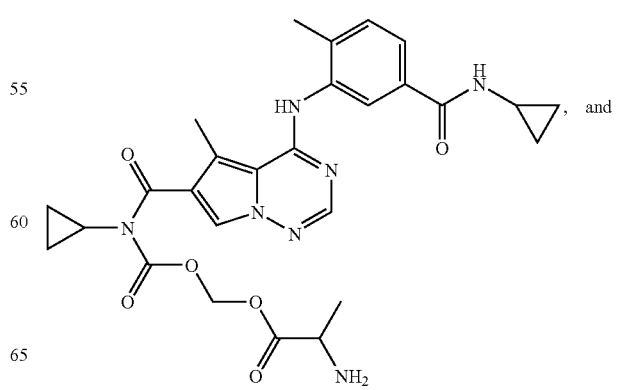, and

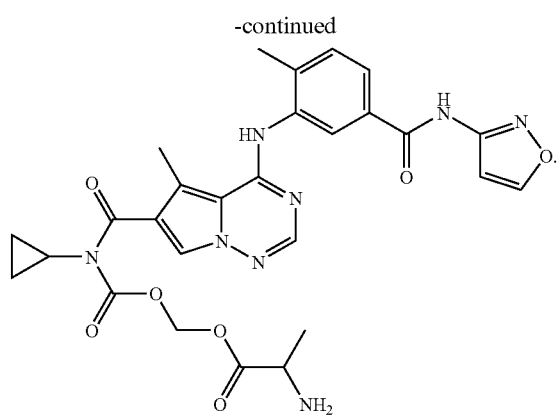
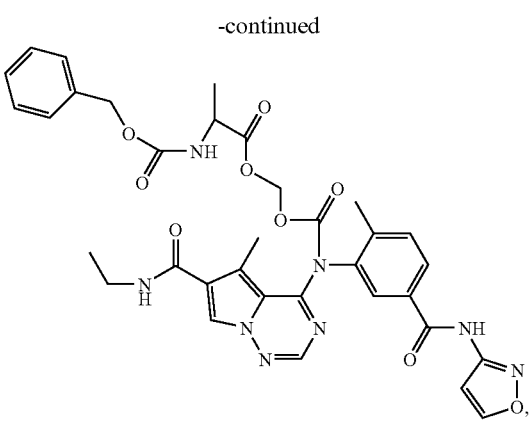
An embodiment of the present invention is for compounds, and salts thereof, selected from the group consisting of:
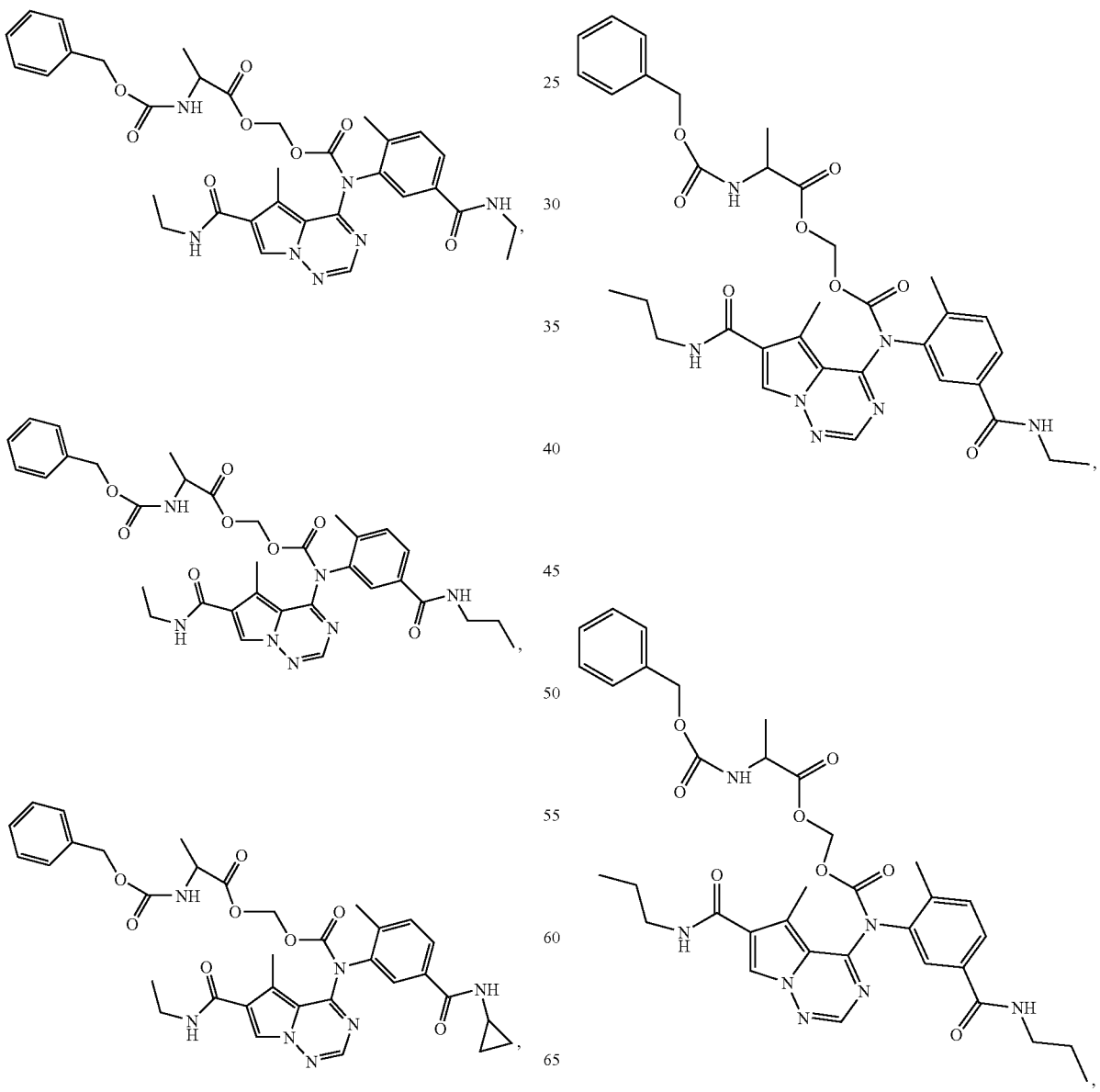

23
-continued
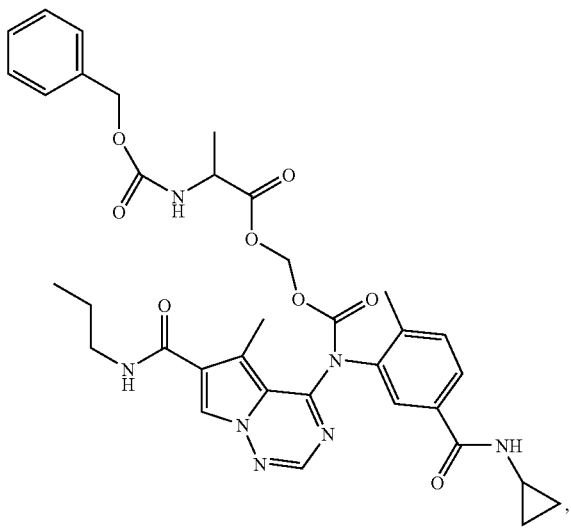
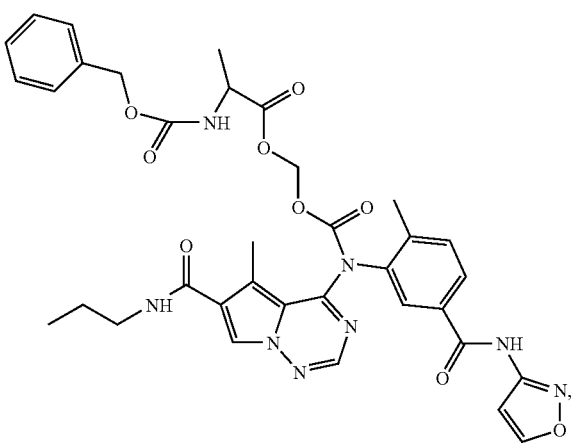
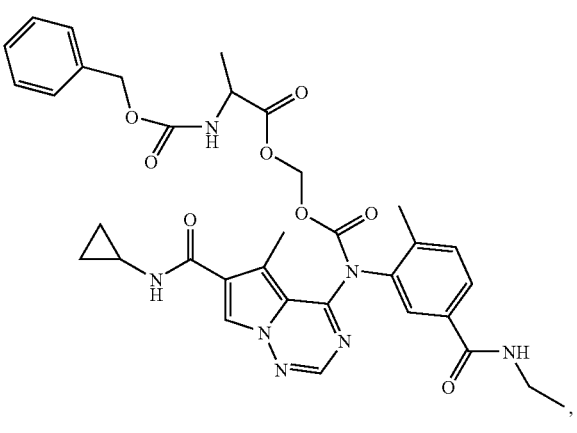
24
-continued
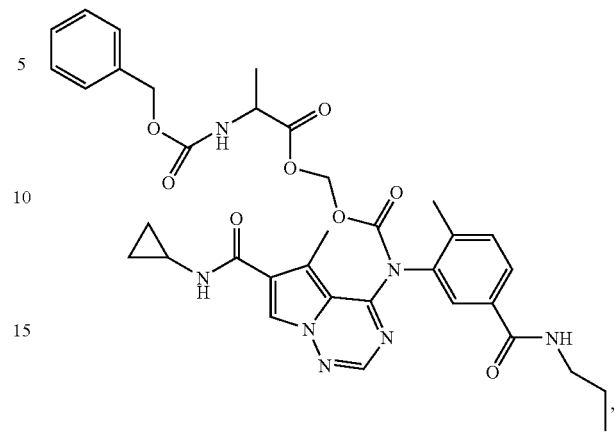
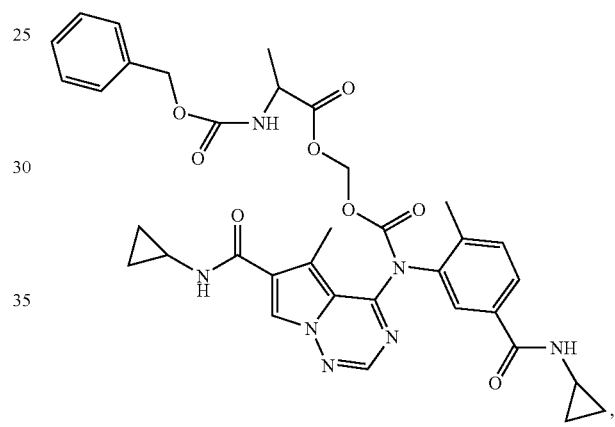
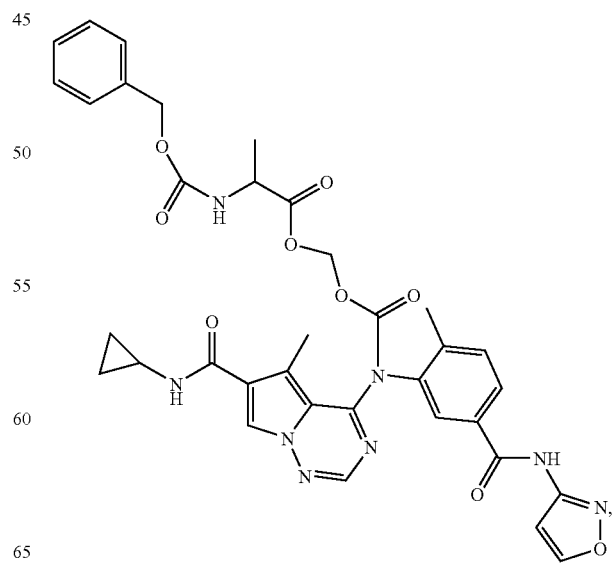

25
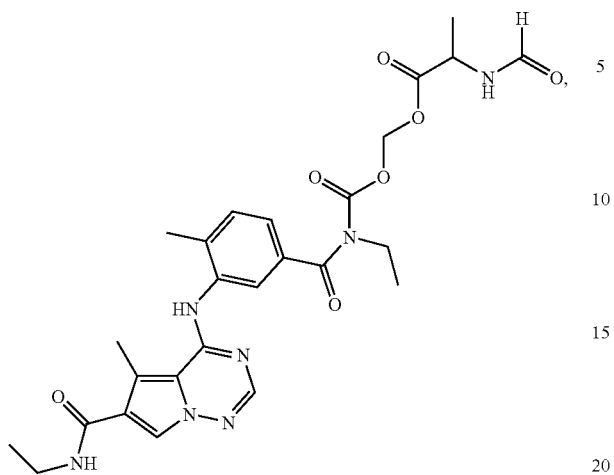
26
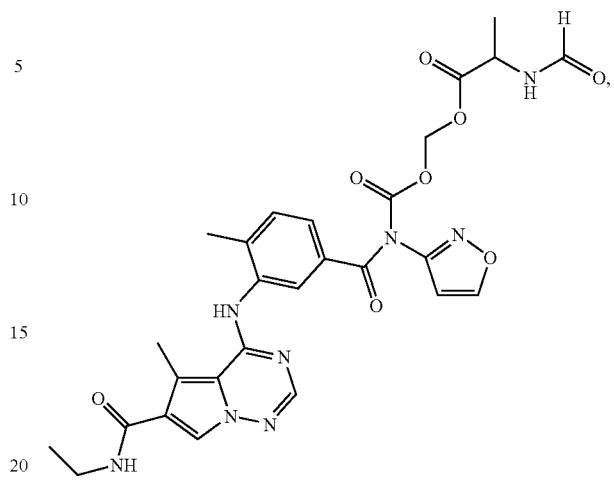
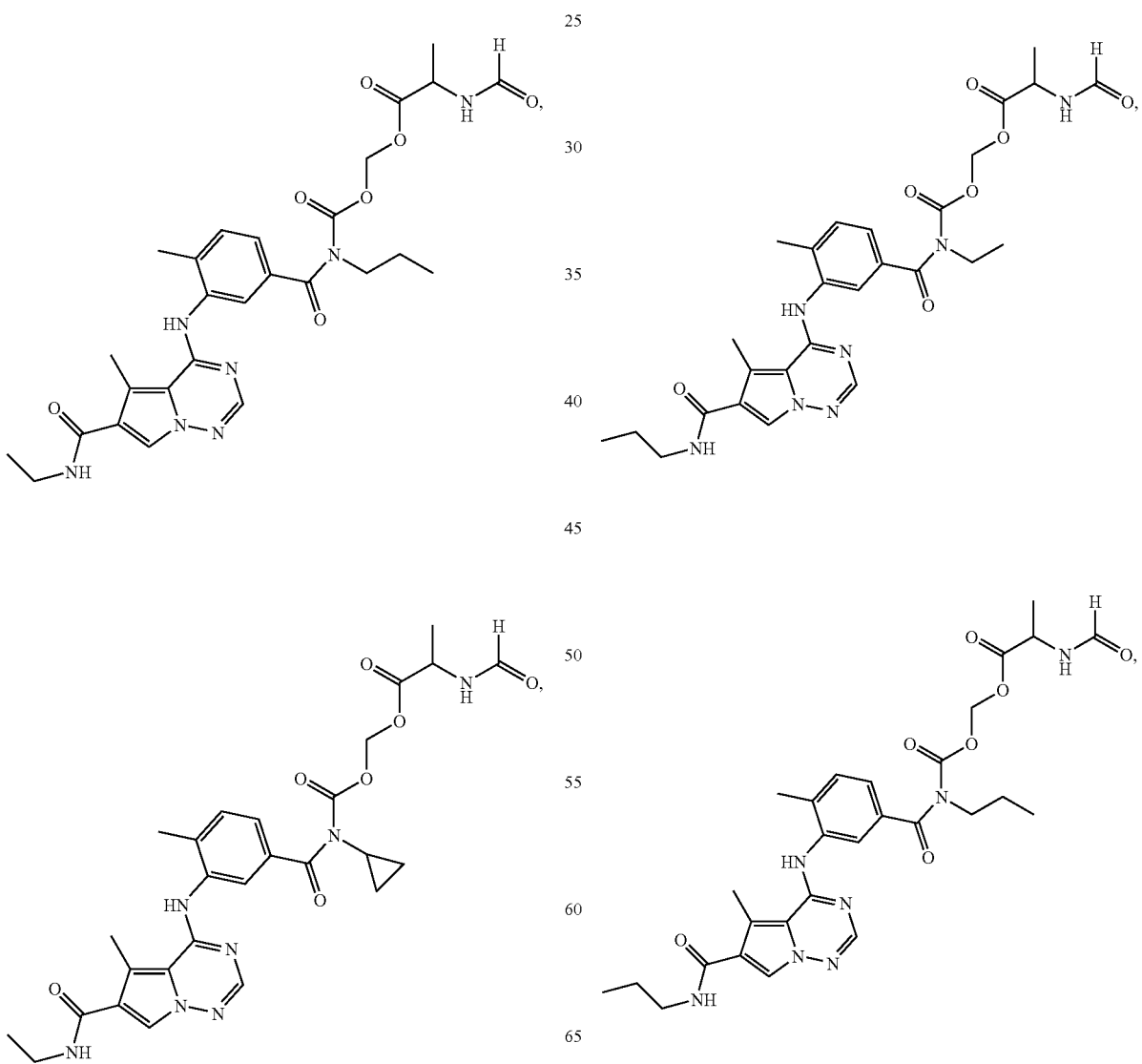

-continued
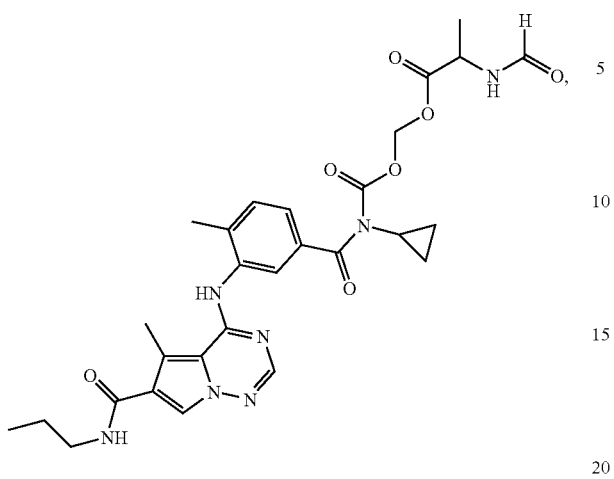
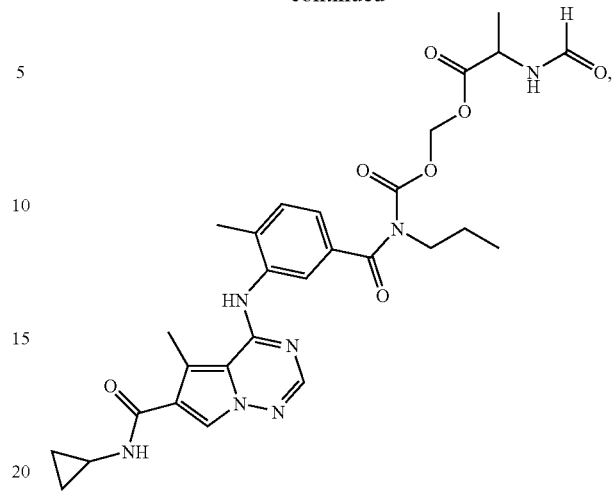
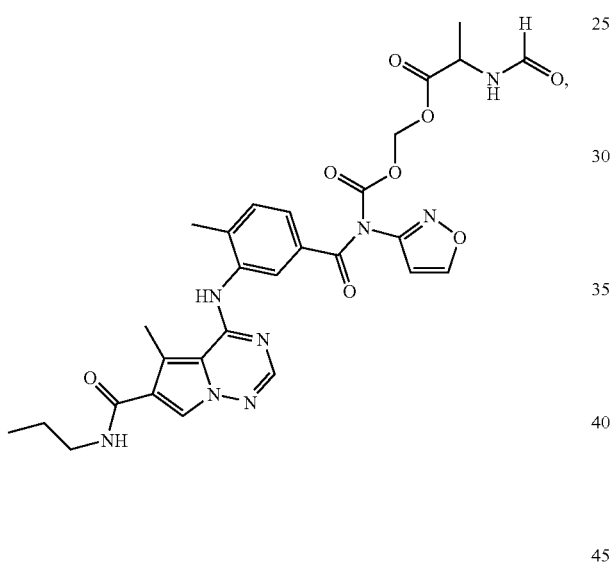
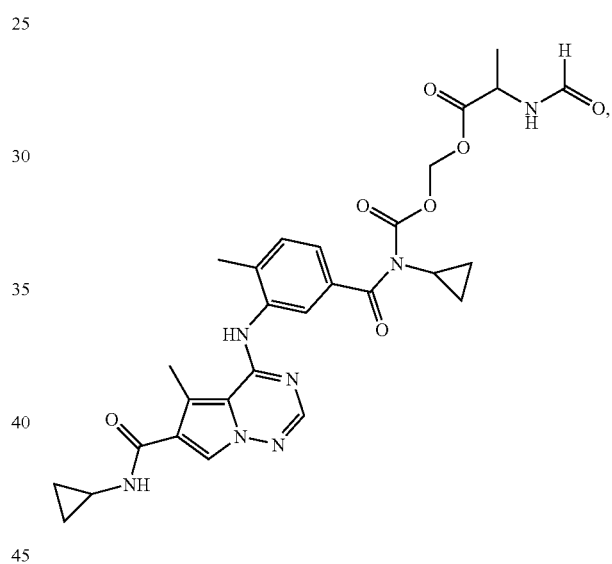
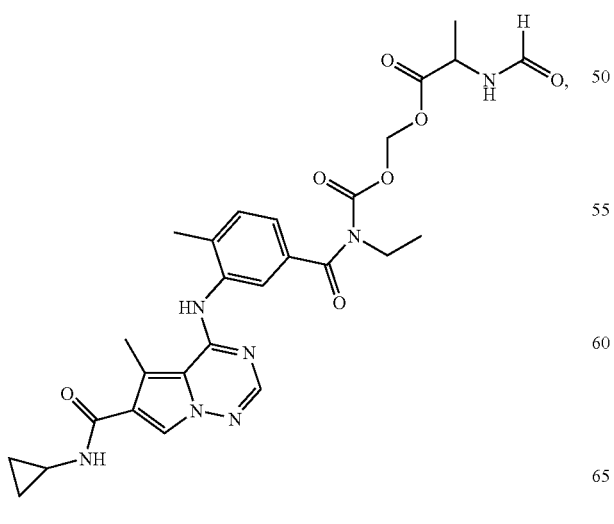
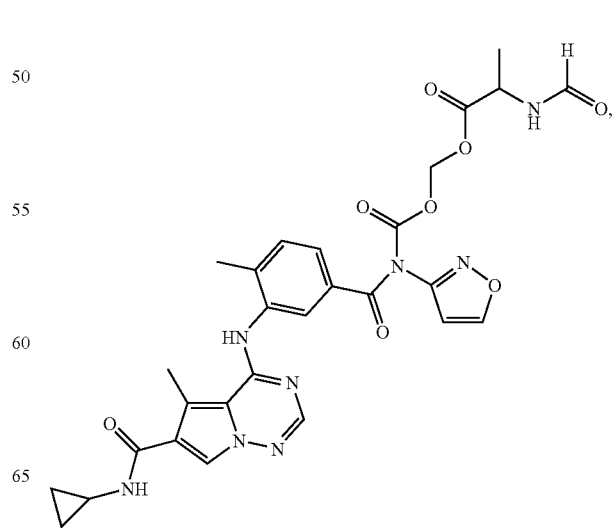

-continued
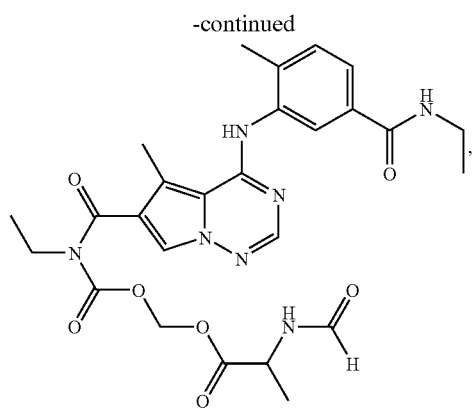
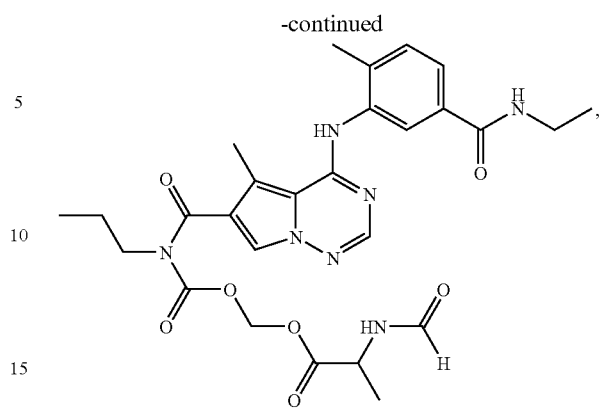
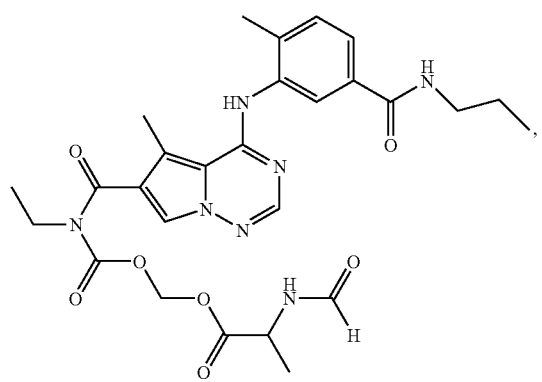
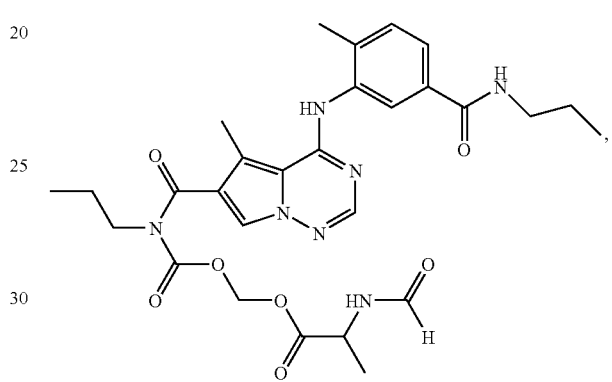
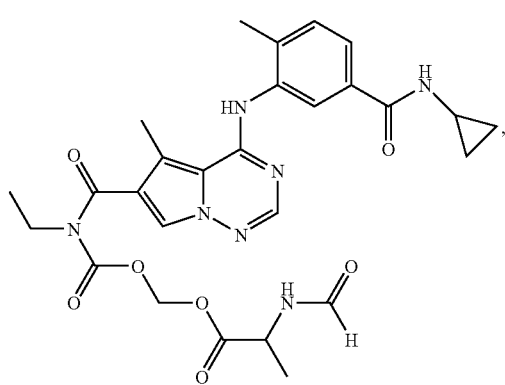
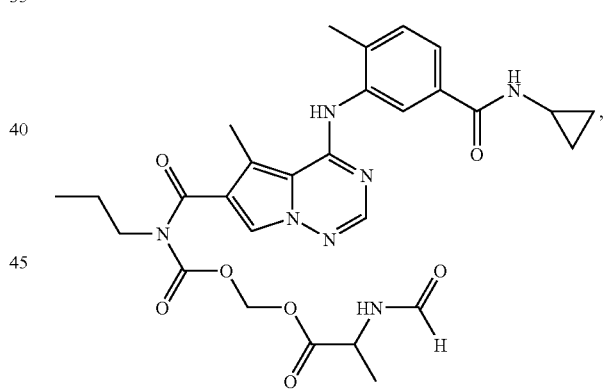
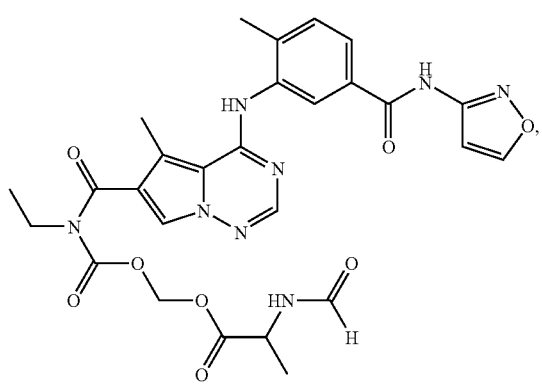
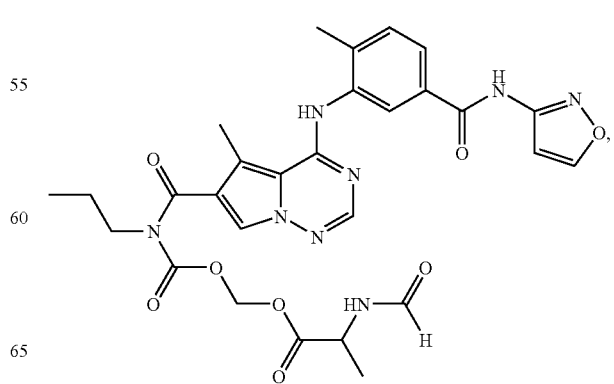

-continued
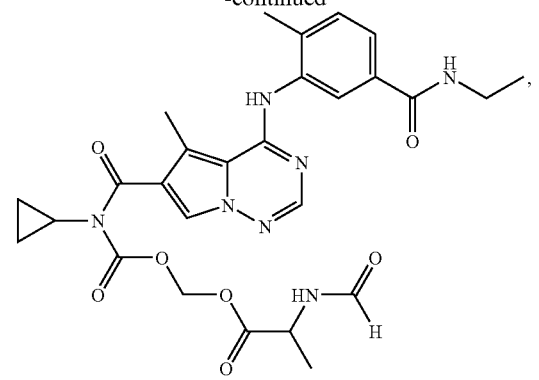
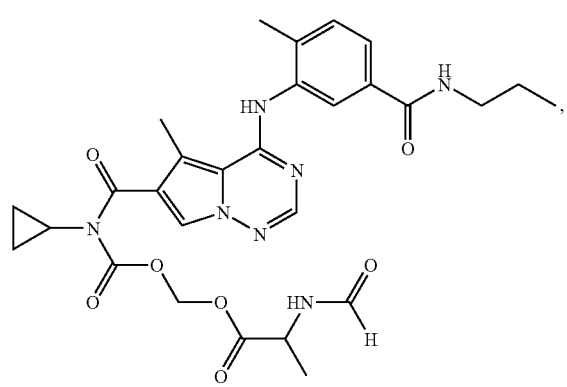
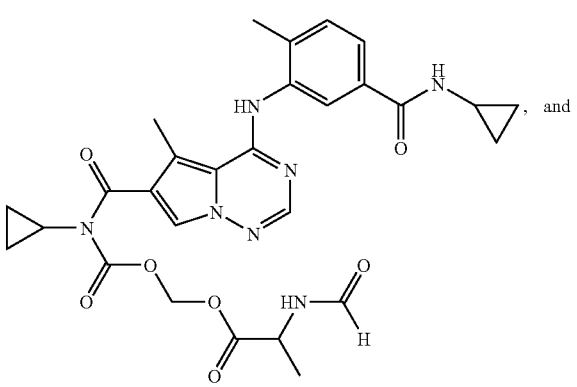
, and
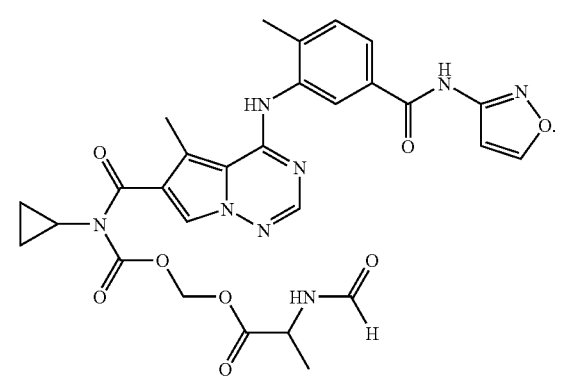
An embodiment of the present invention is for compounds, and salts thereof, selected from the group consisting of:
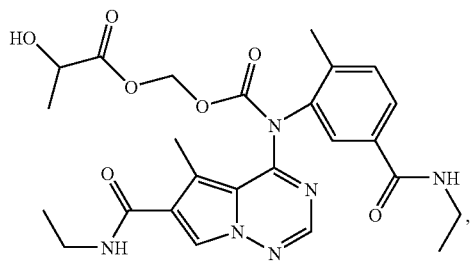
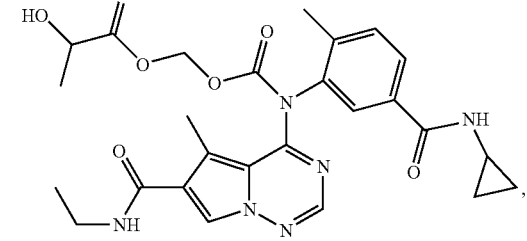
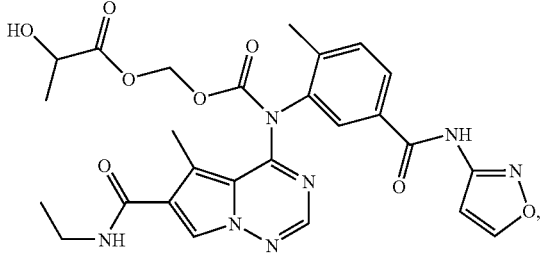
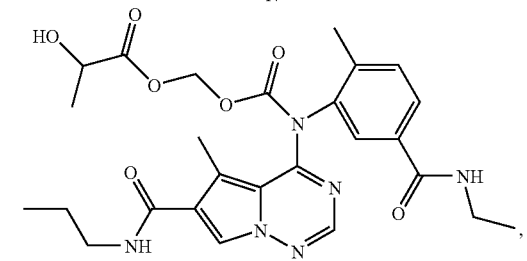
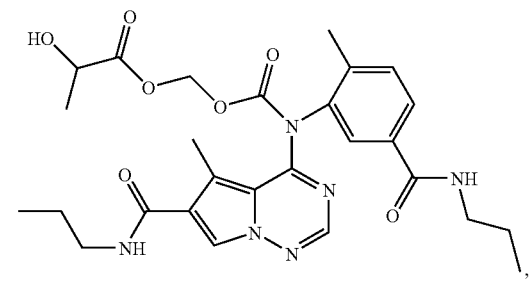

33
-continued
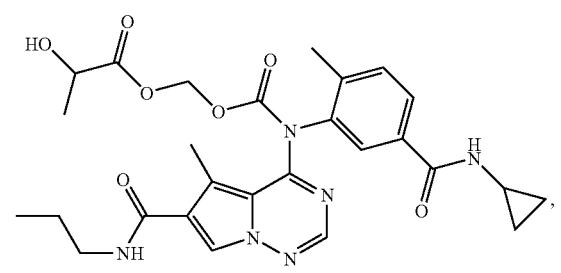
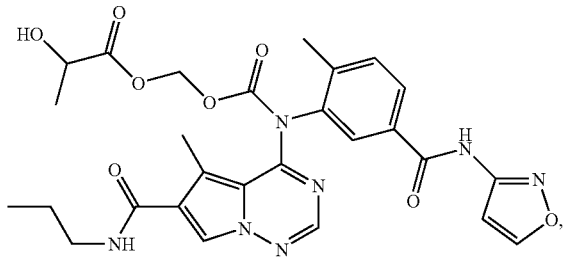
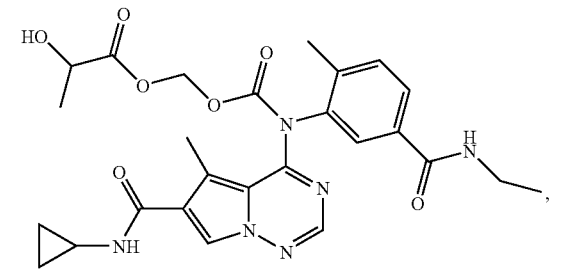
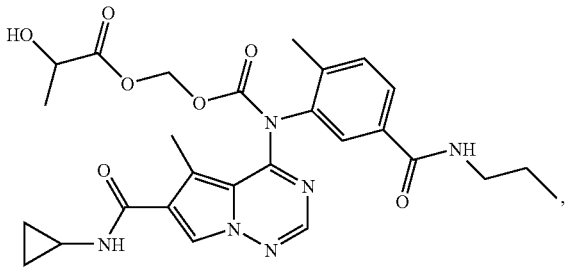
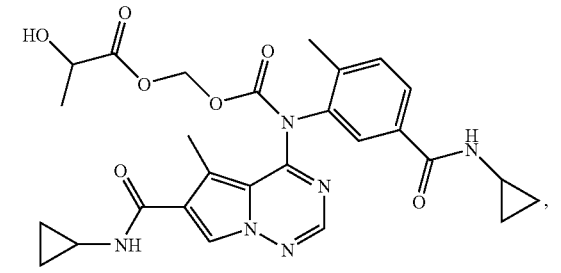
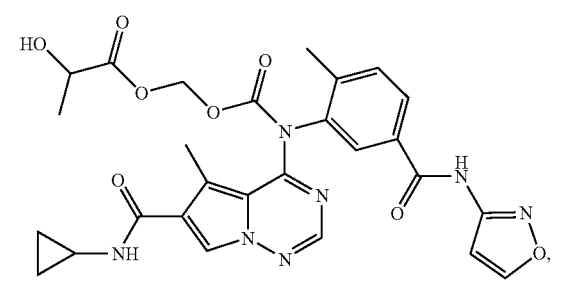
34
-continued
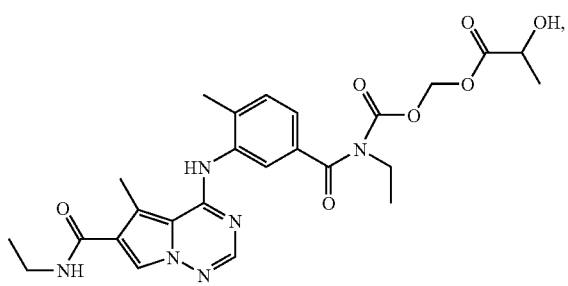
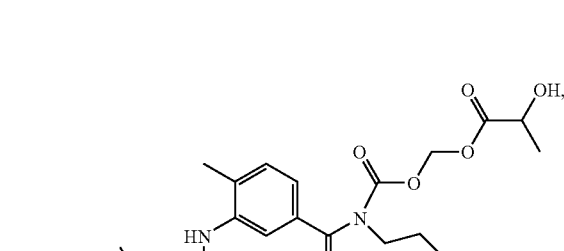
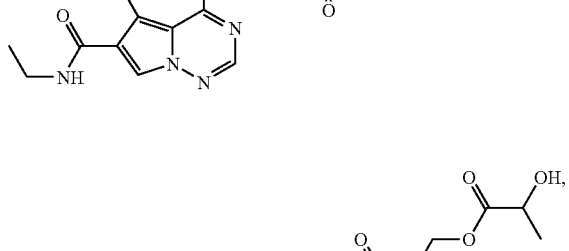
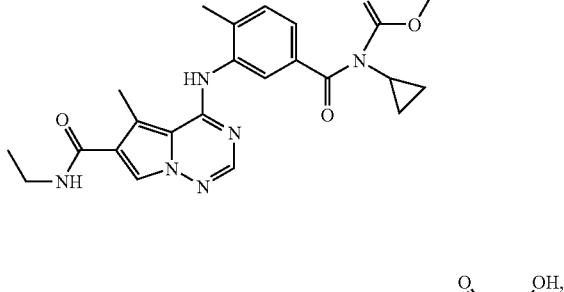
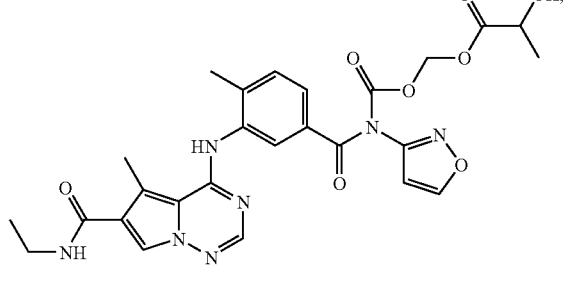
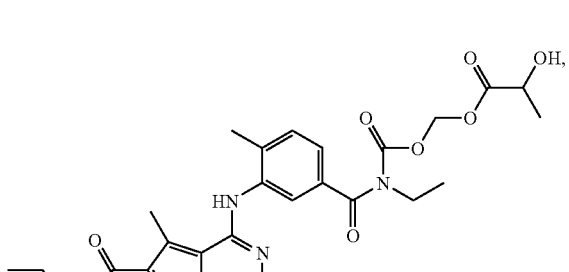

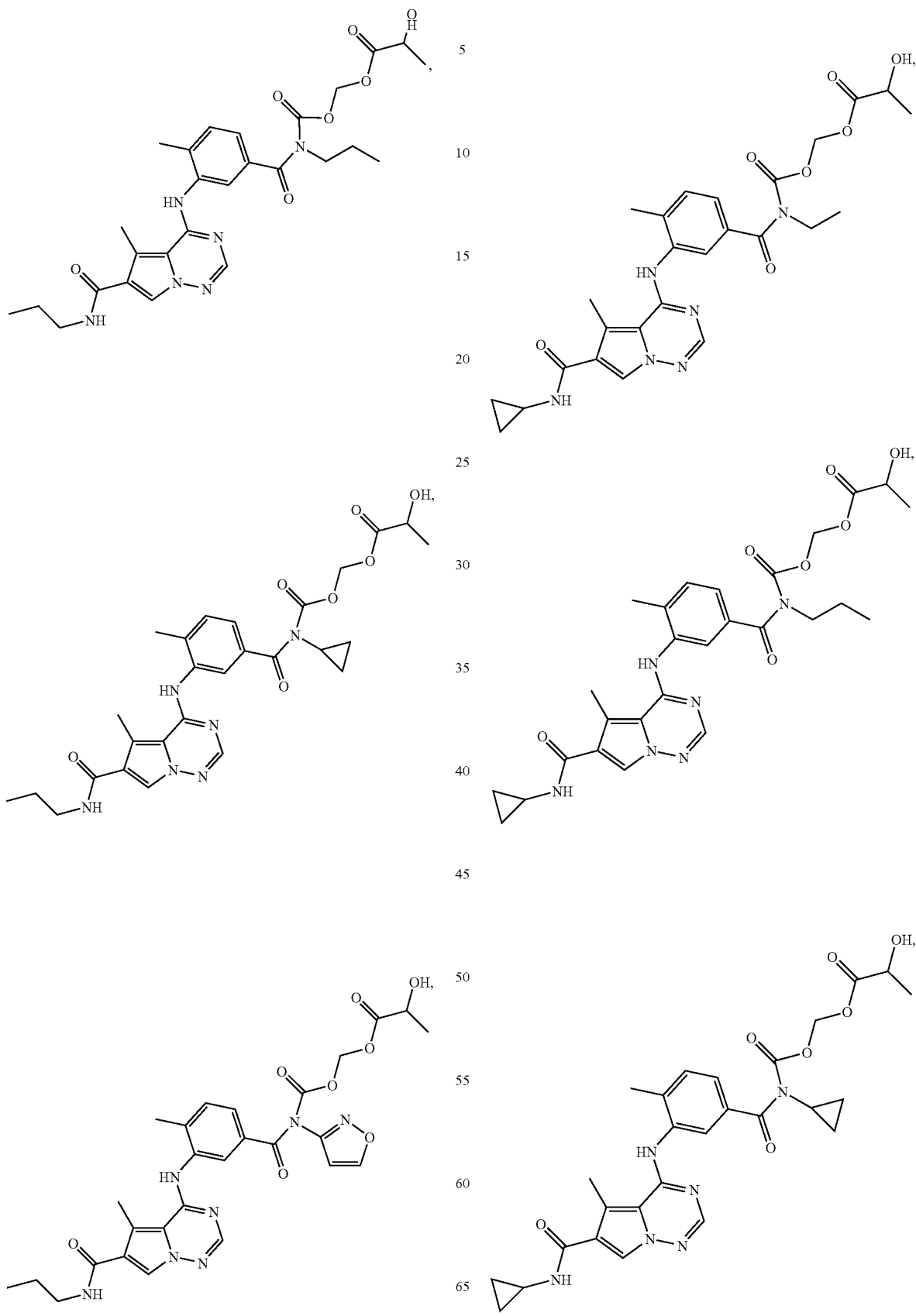

-continued
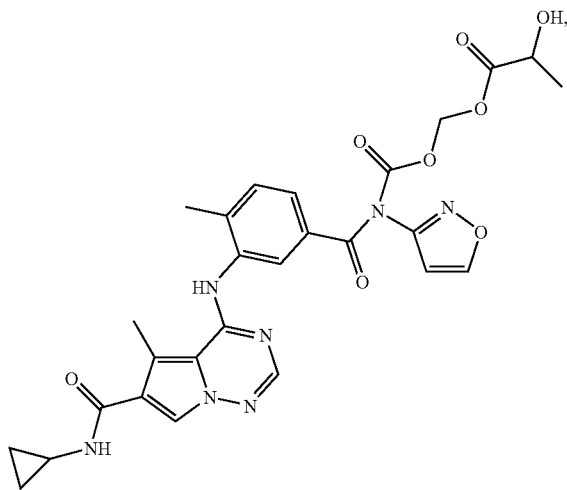
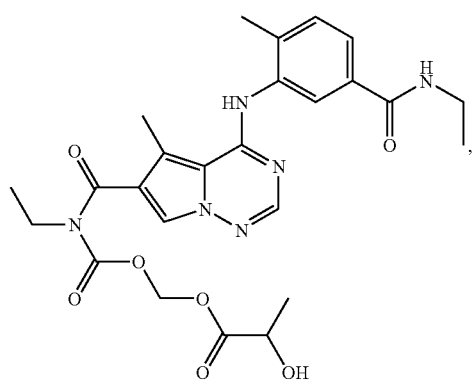
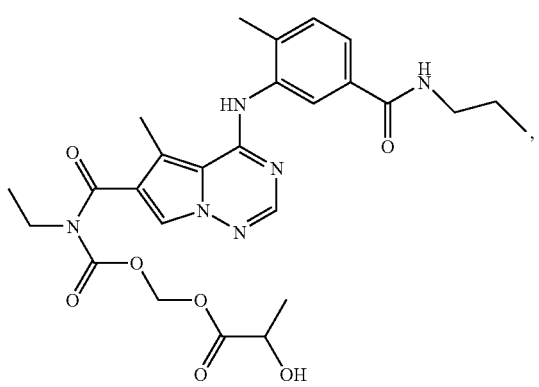
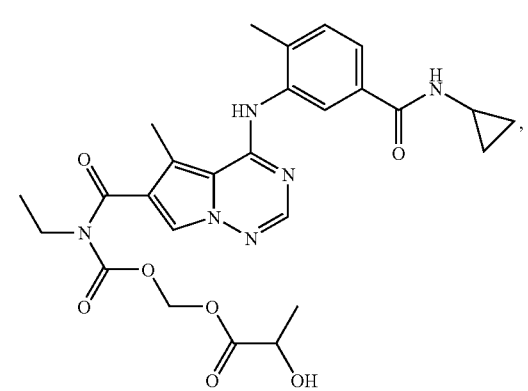
-continued
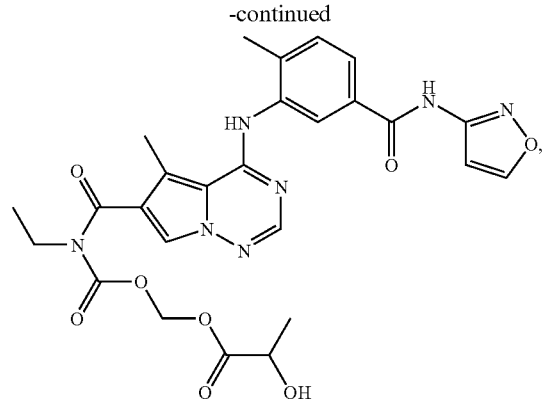
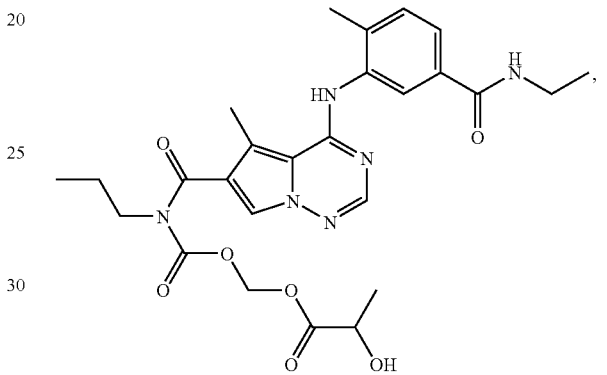
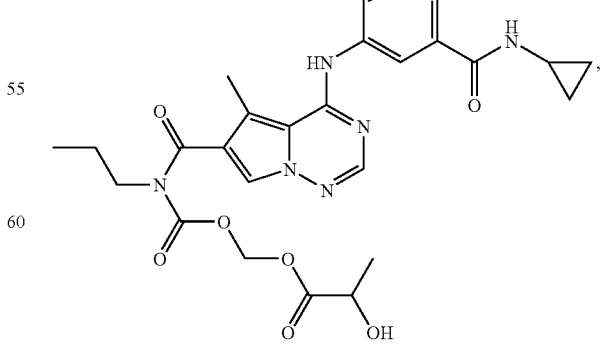

-continued
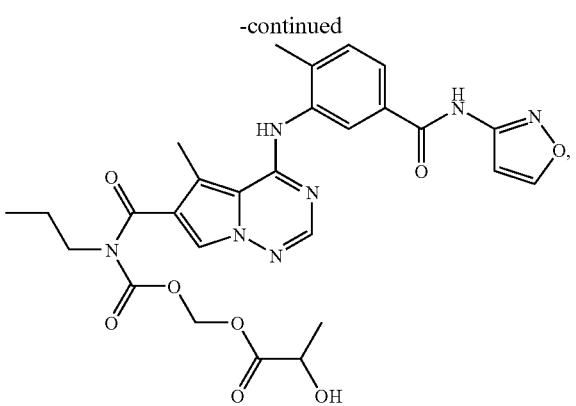
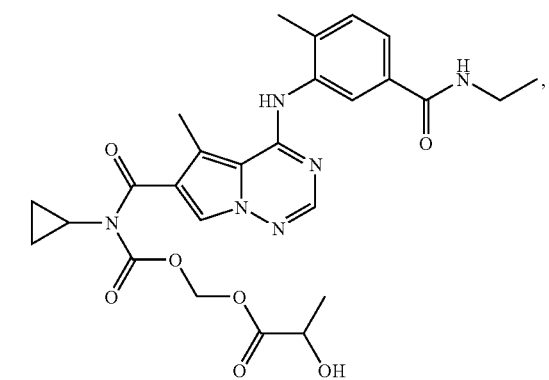
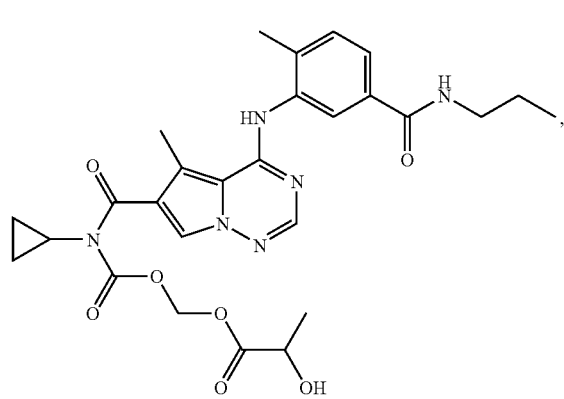
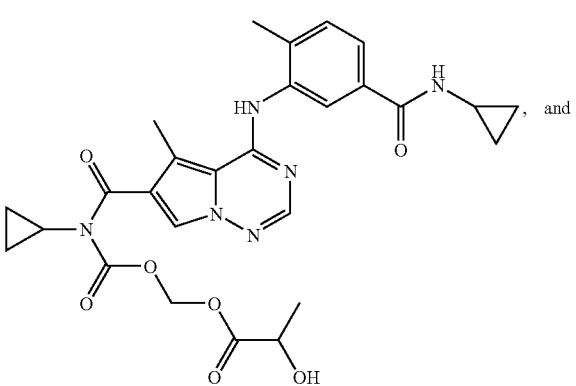
-continued
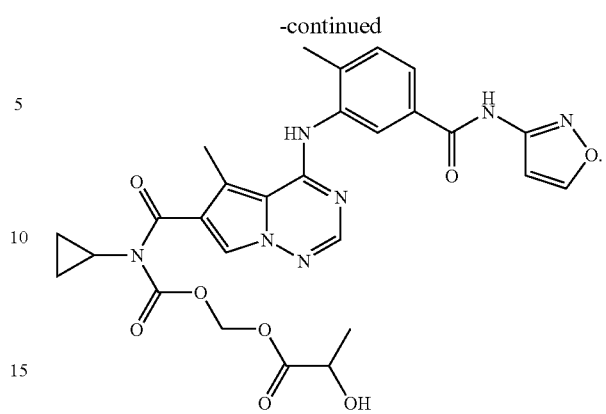
An embodiment of the present invention is for compounds, and salts thereof, selected from the group consisting of:
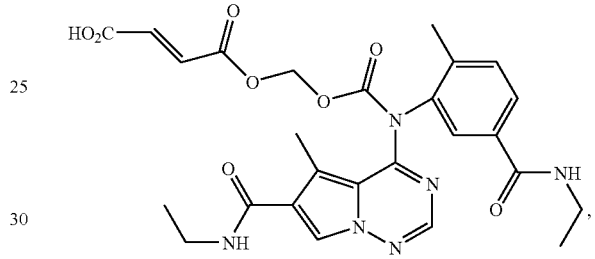
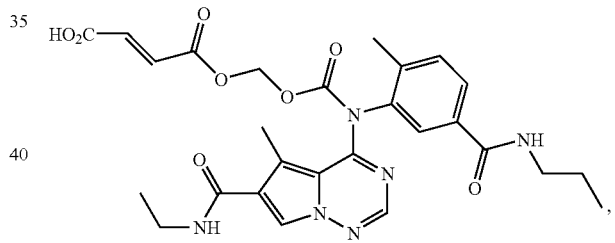
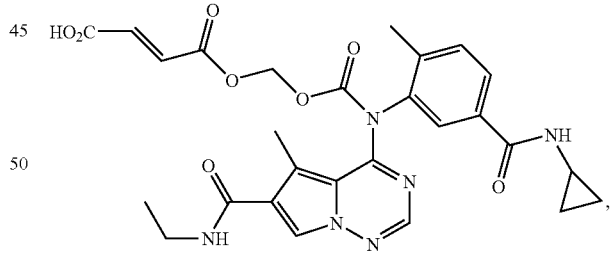
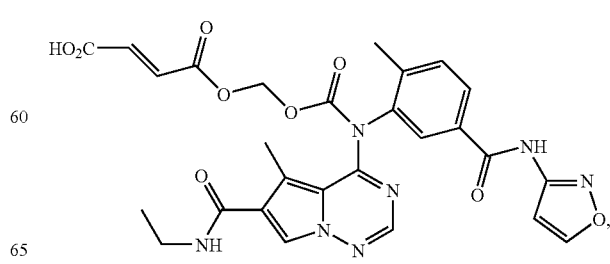

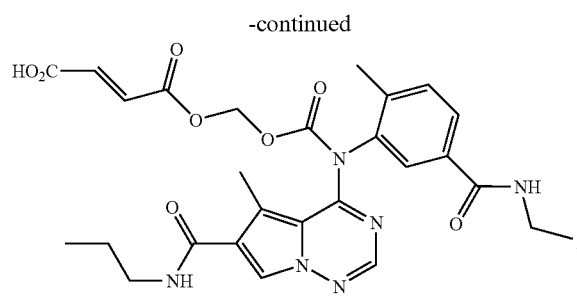
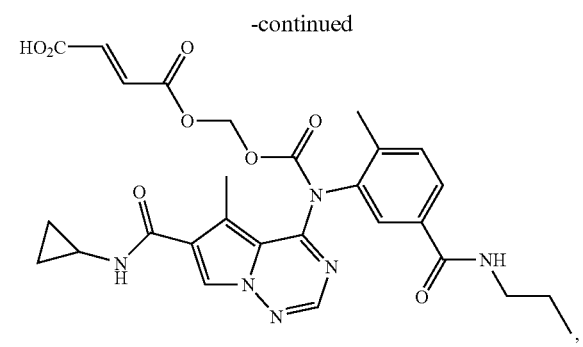
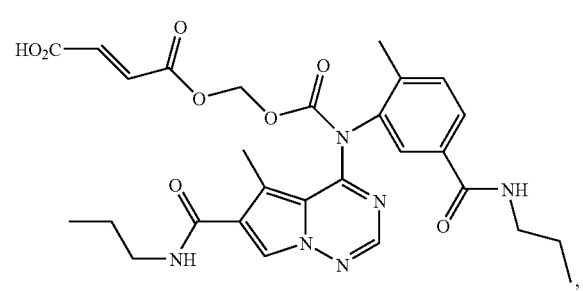
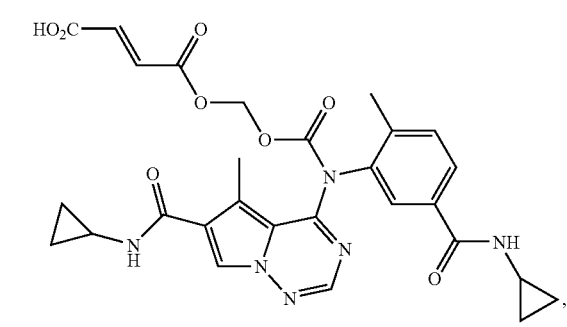
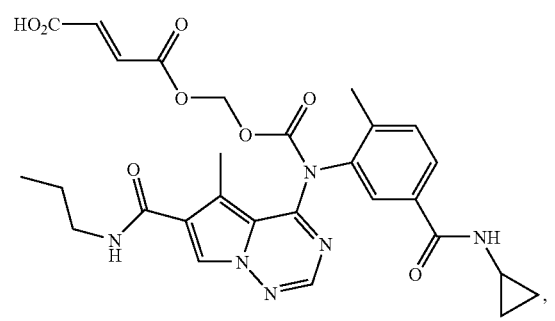
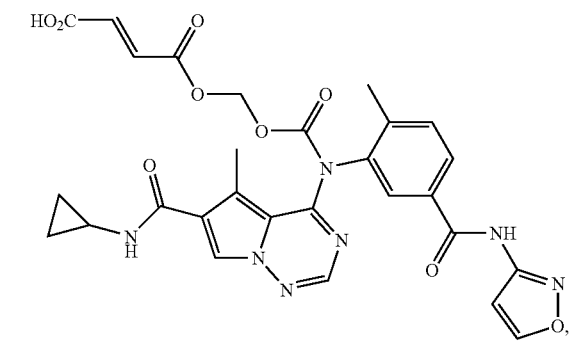
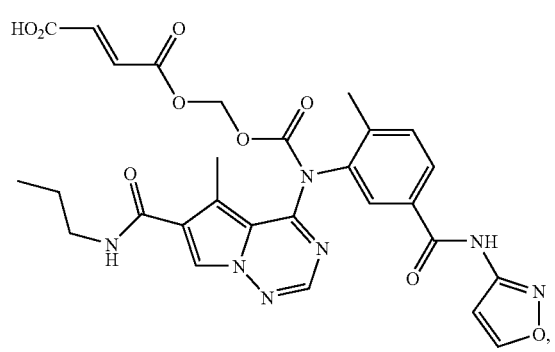
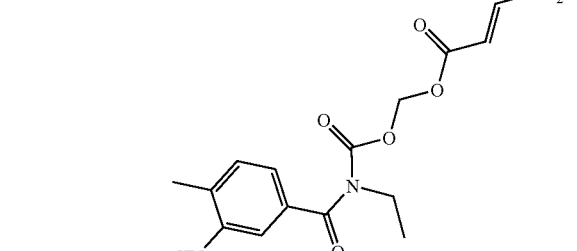
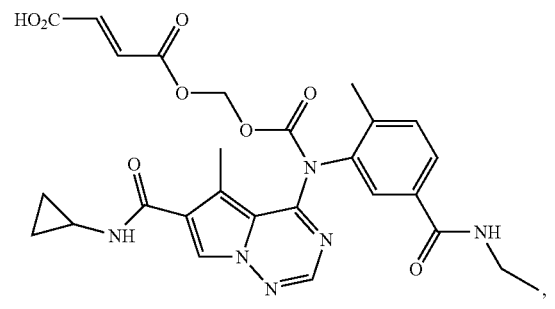
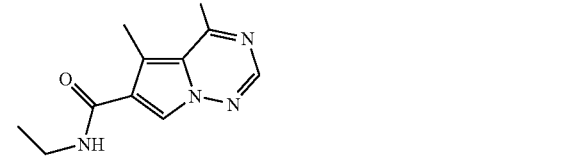

-continued
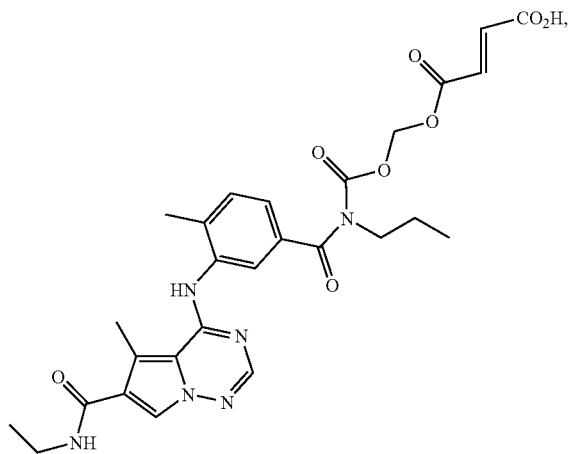
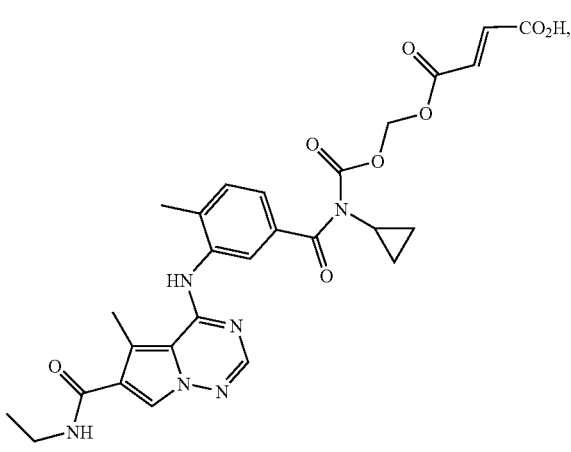
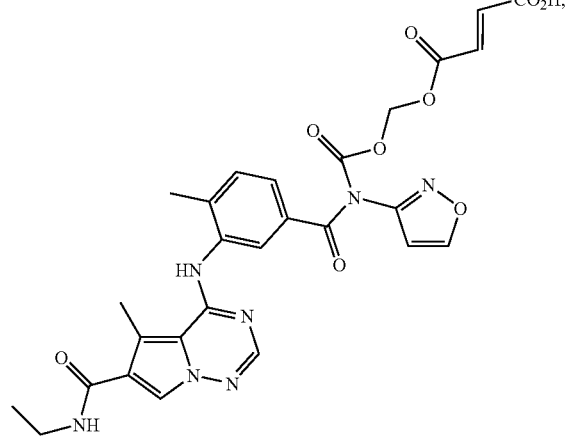
-continued
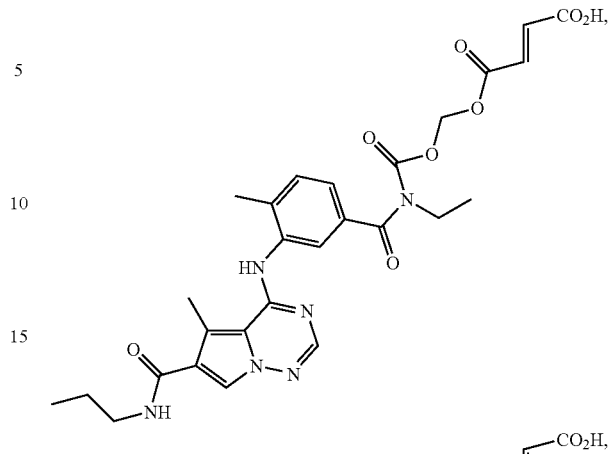
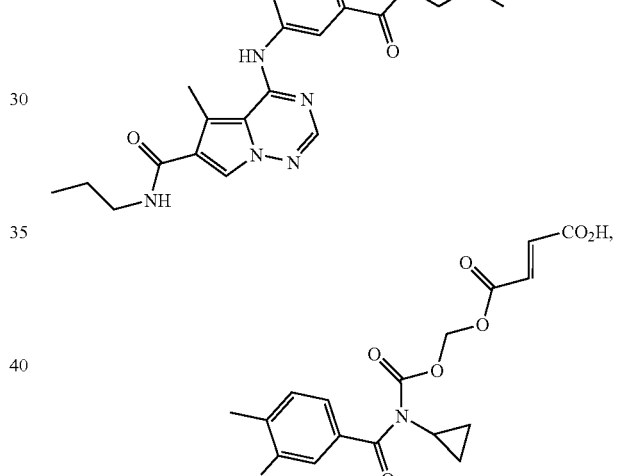
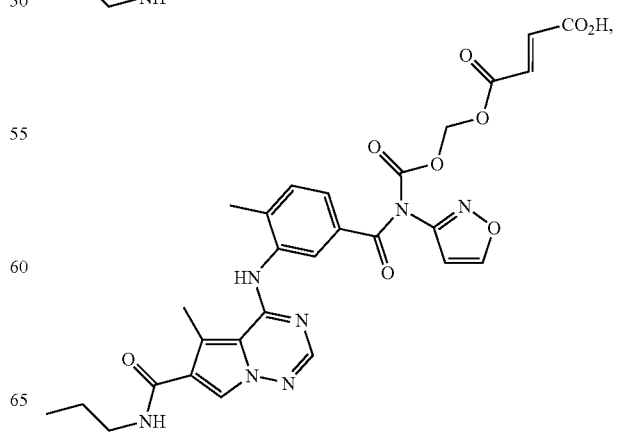

-continued
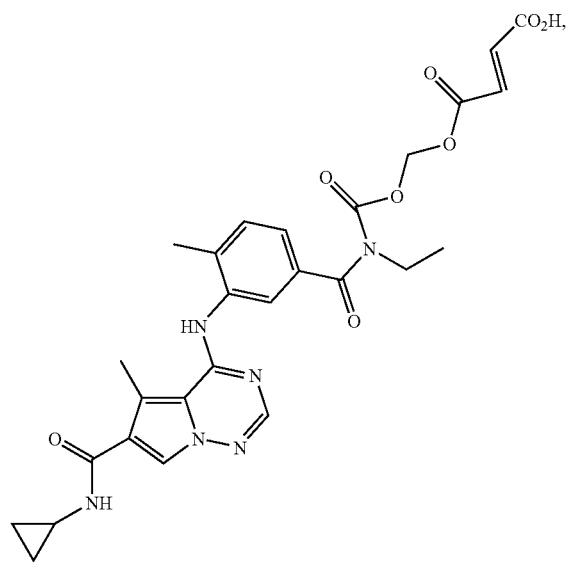
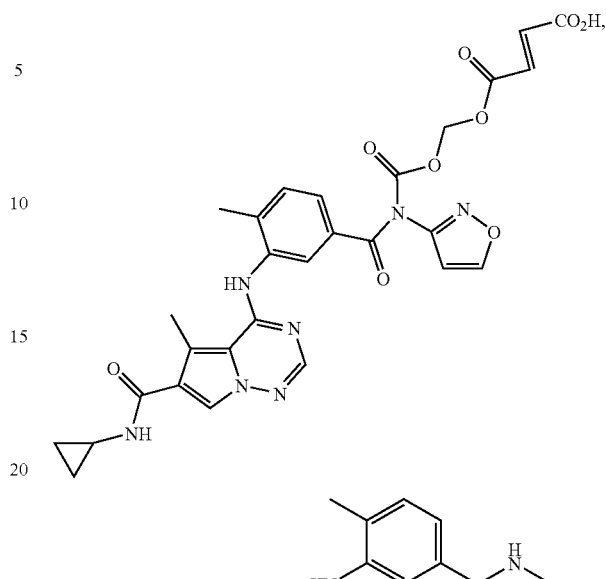

47
-continued
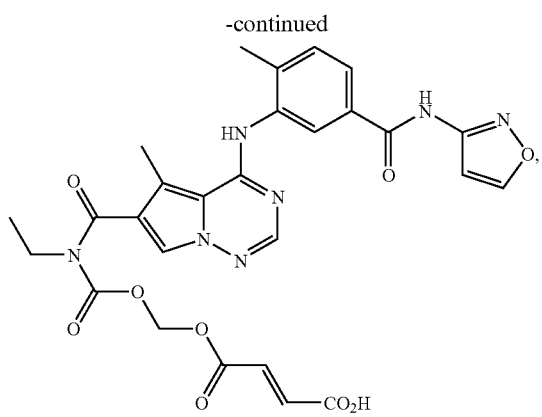
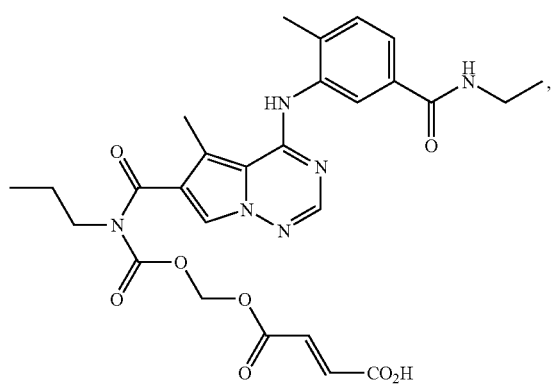
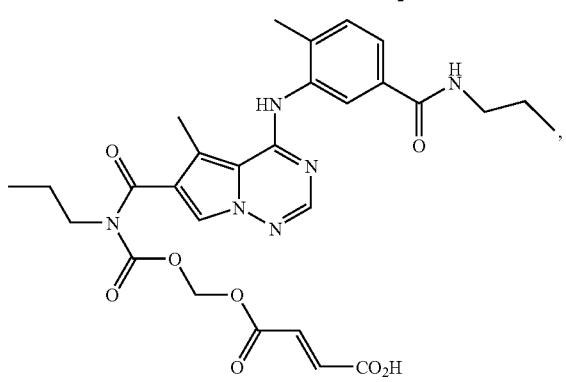
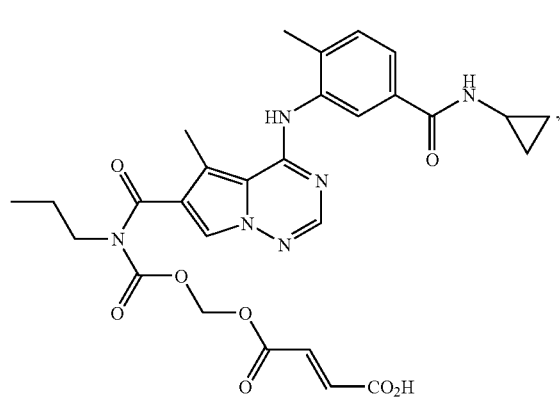
48
-continued
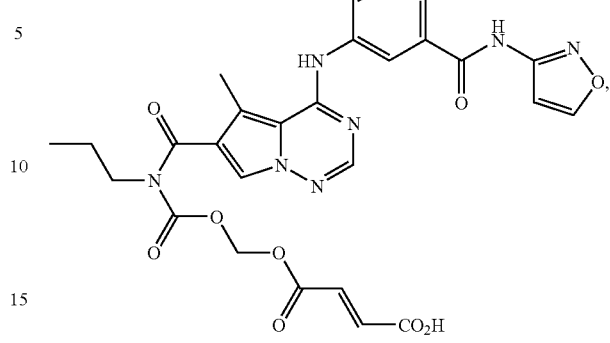
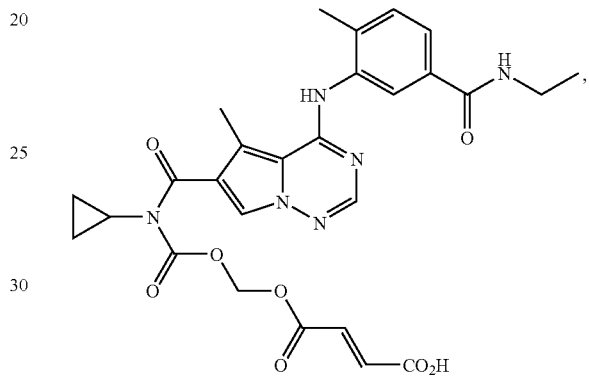
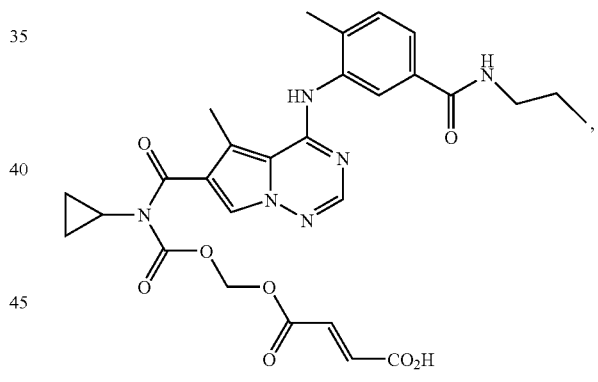
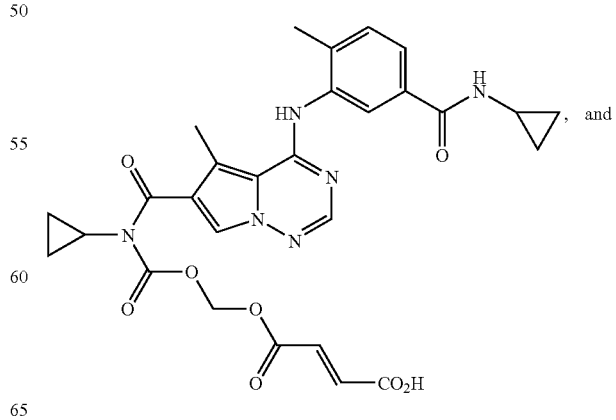
and -continued
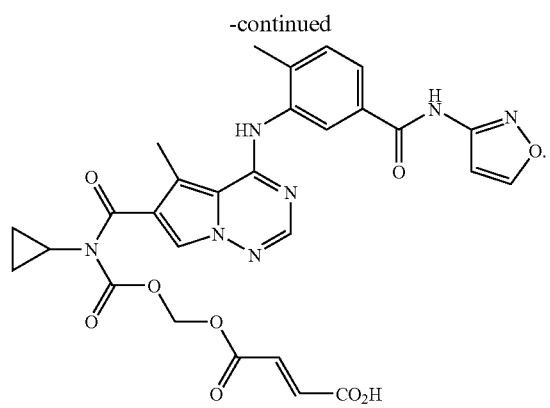
An embodiment of the present invention is for compounds, and salts thereof, selected from the group consisting of:
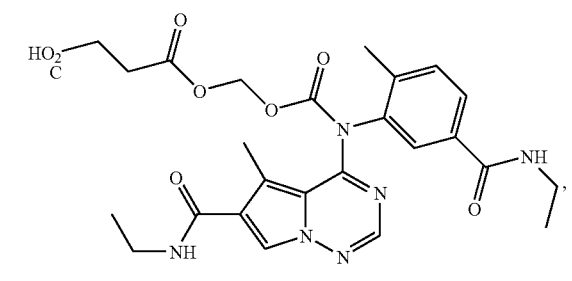
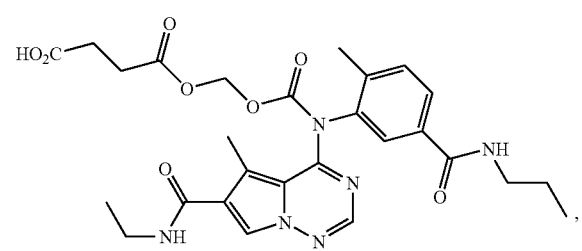
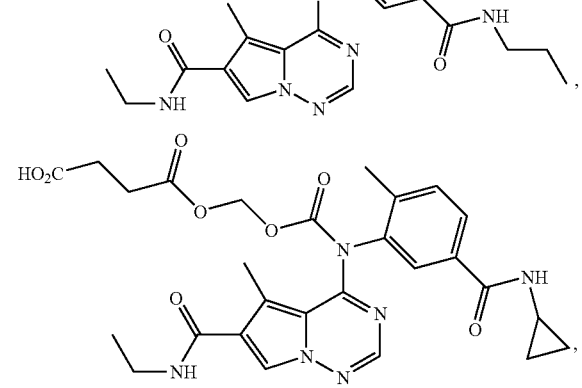
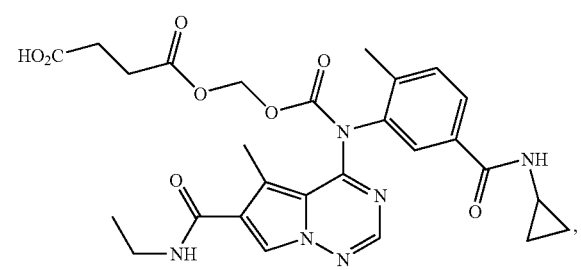
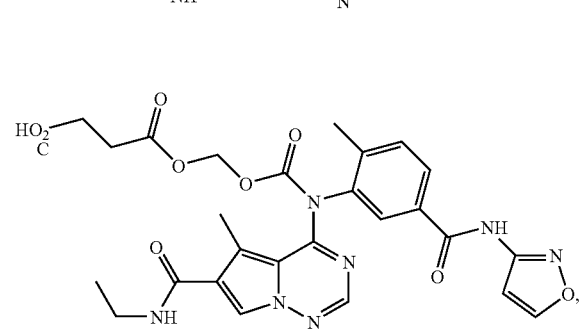
-continued
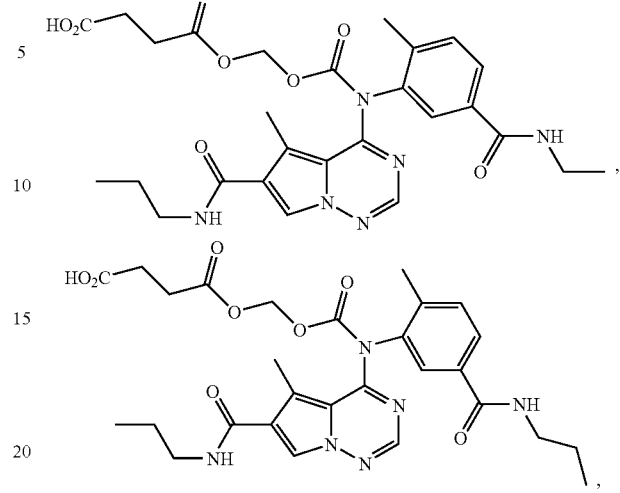
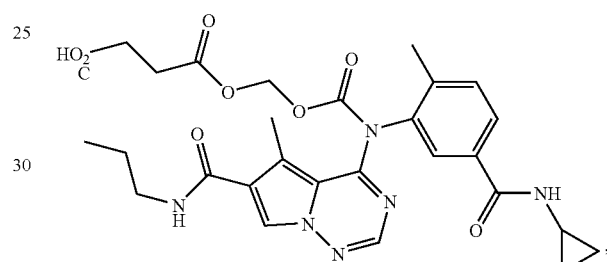
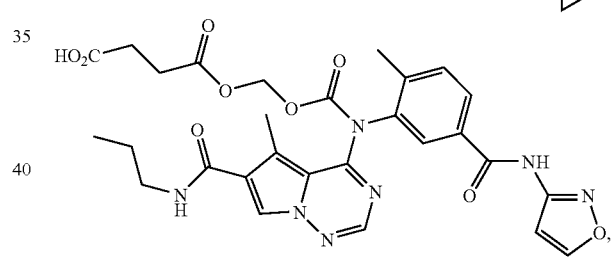
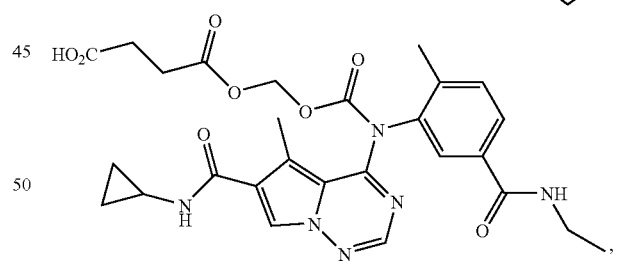
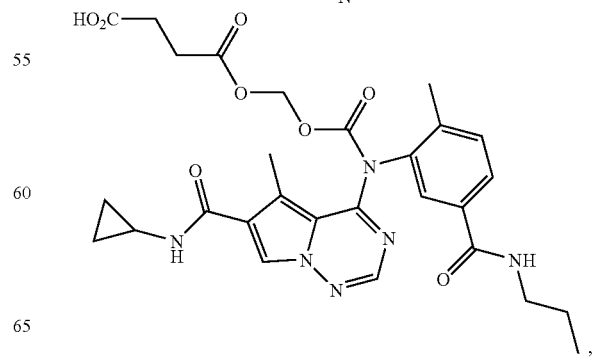

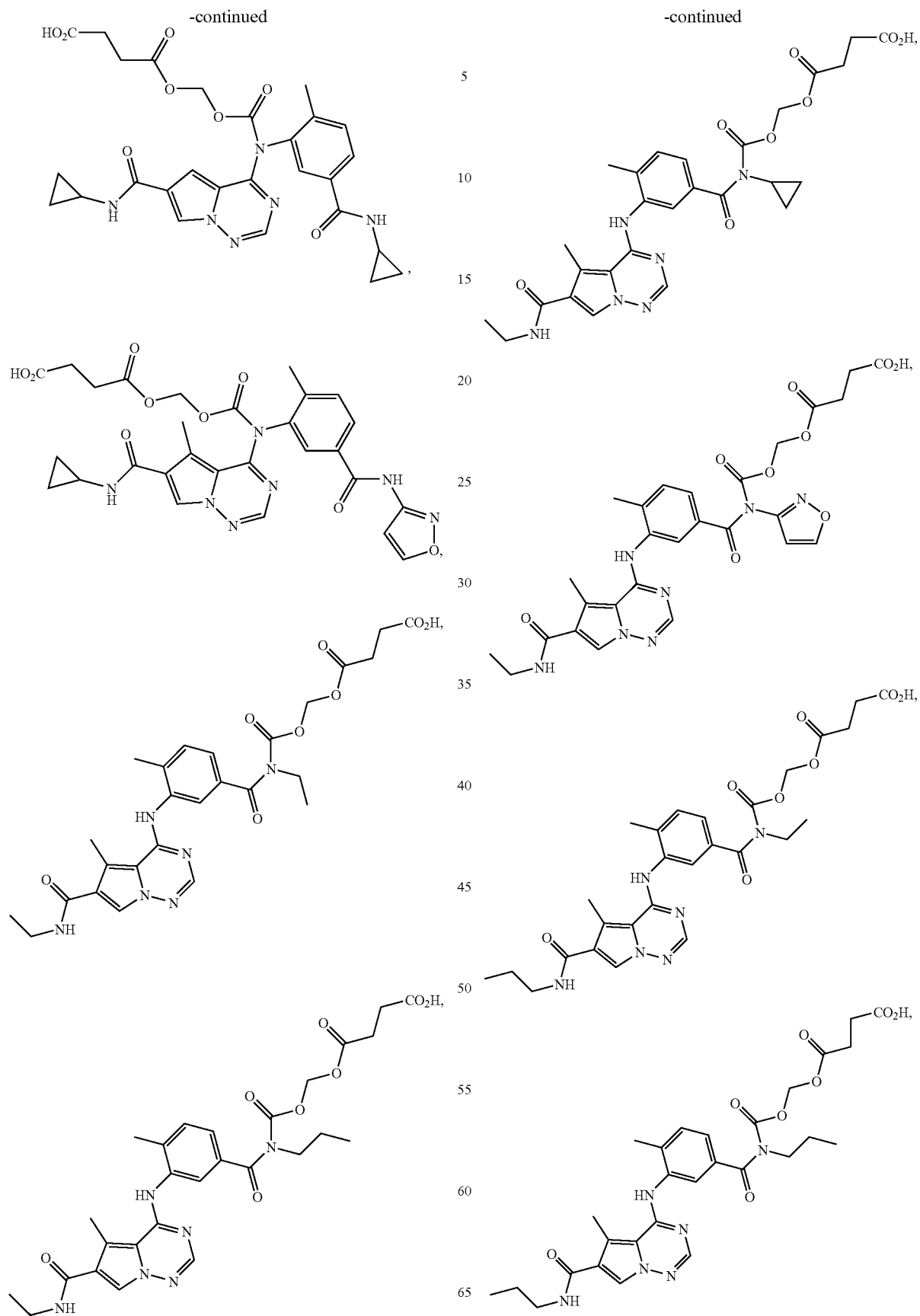

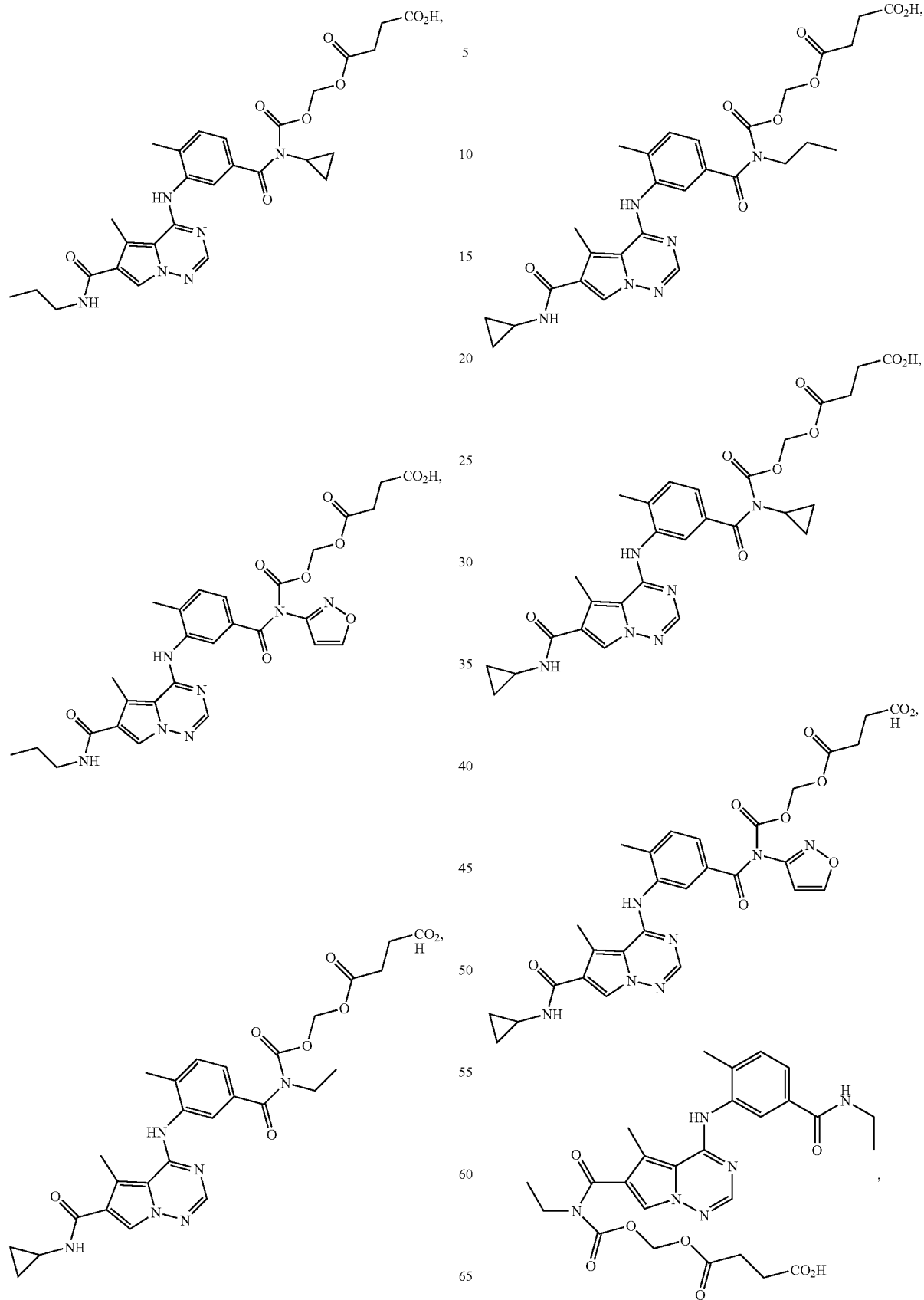

55
-continued
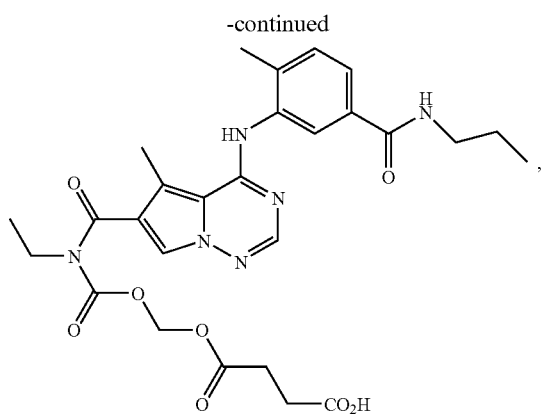
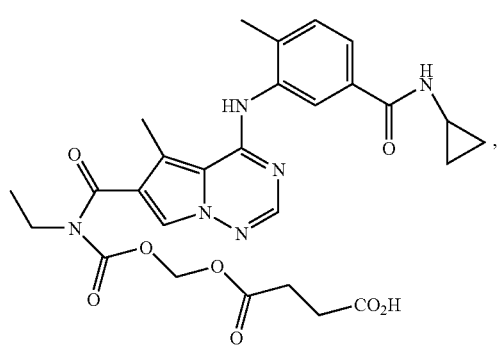
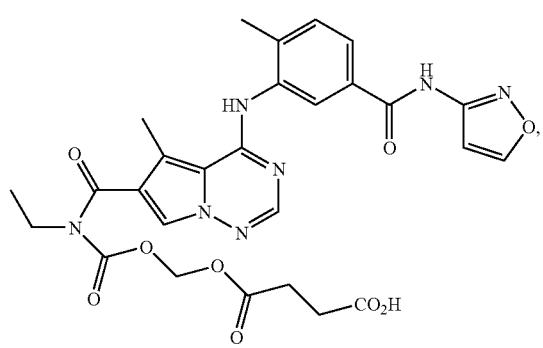
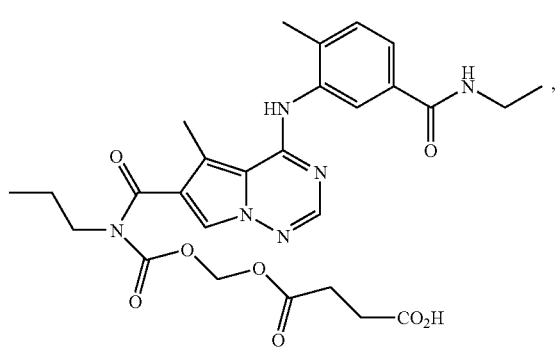
56
-continued
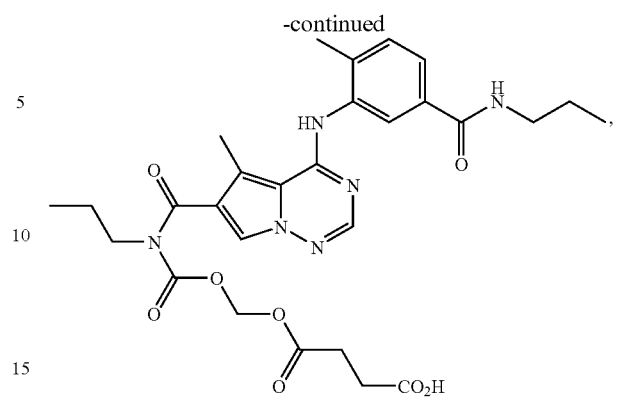
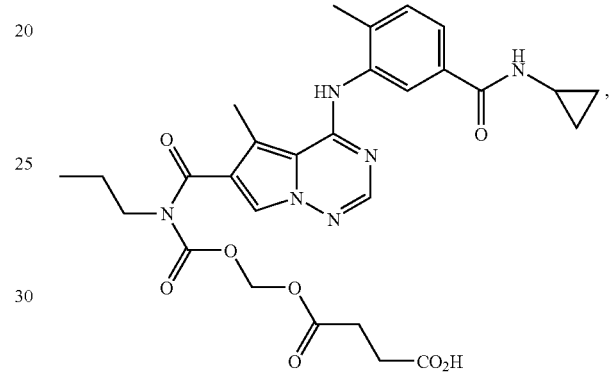
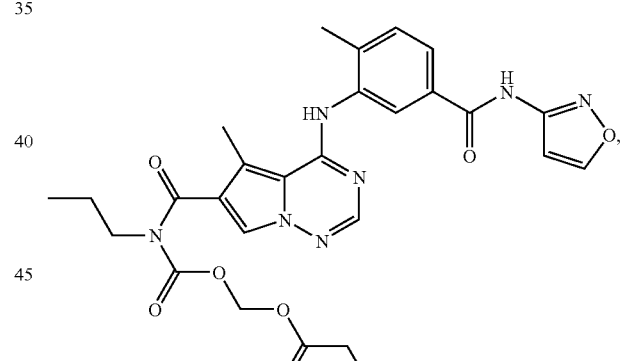
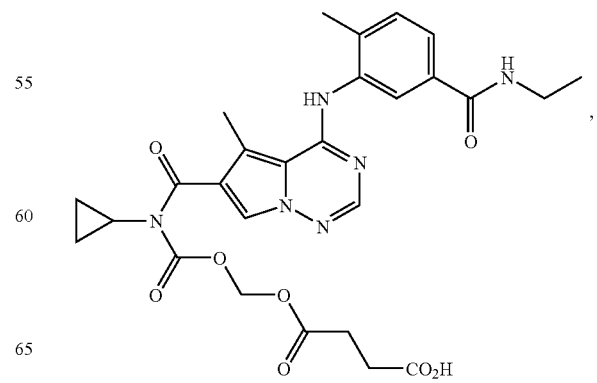

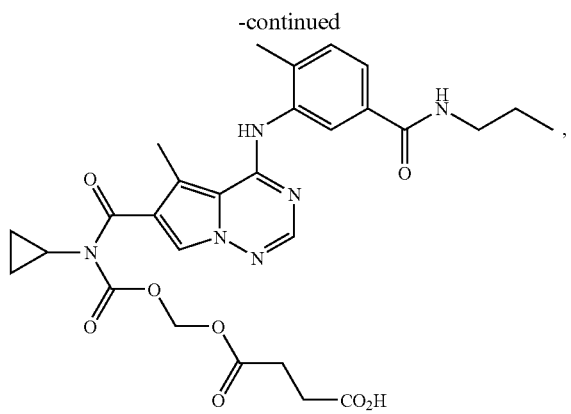
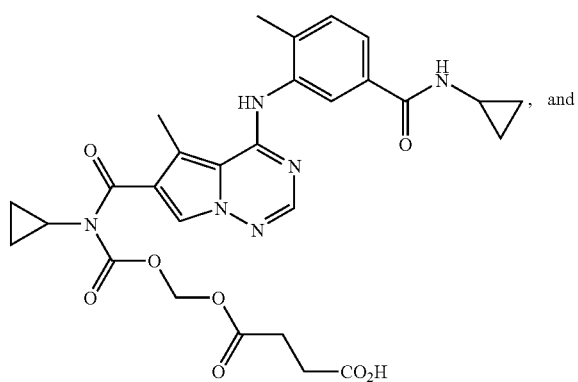, and
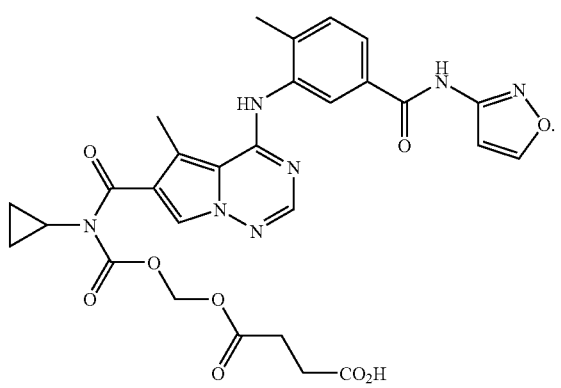
An embodiment of the present invention is for compounds, and salts thereof, selected from the group consisting of:
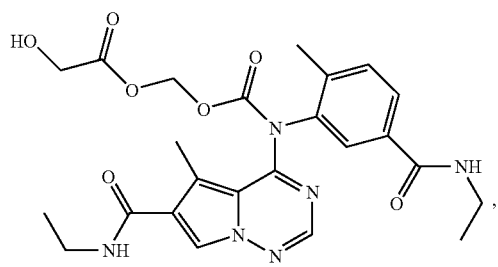
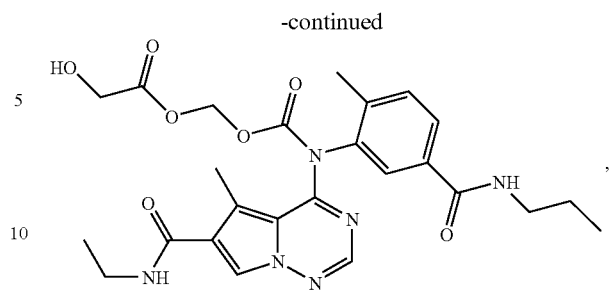
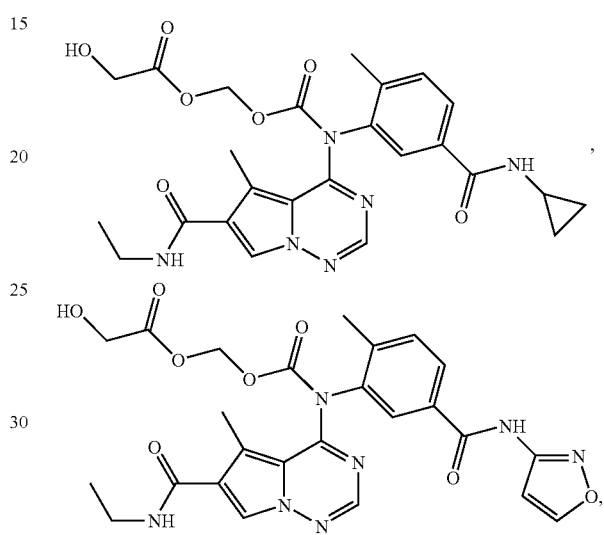
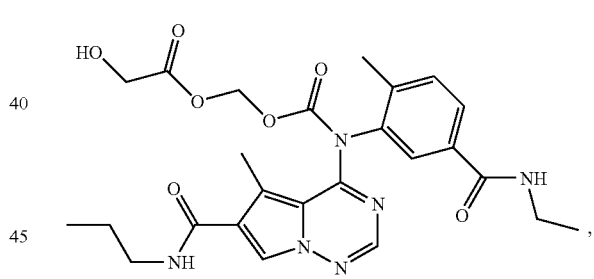
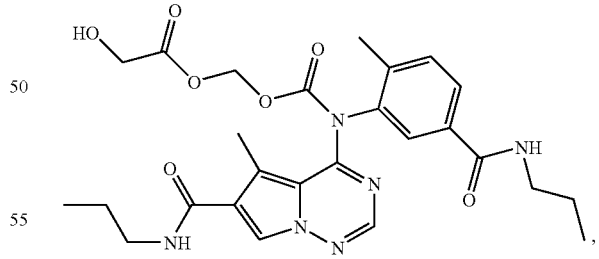
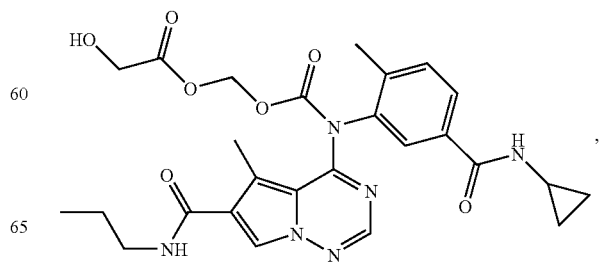

59
-continued
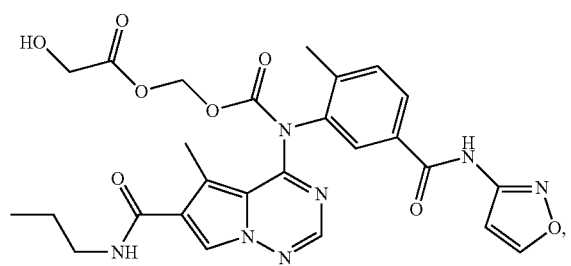
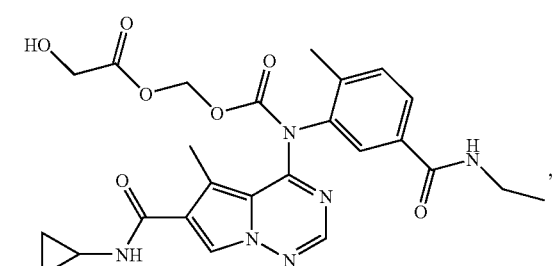
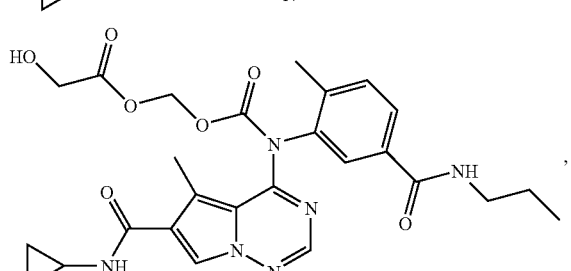
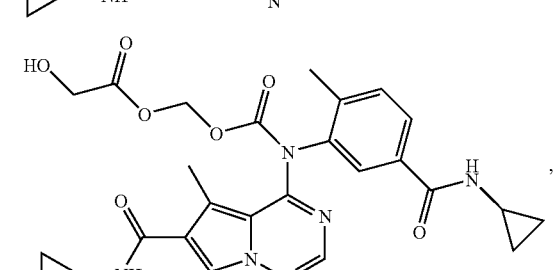
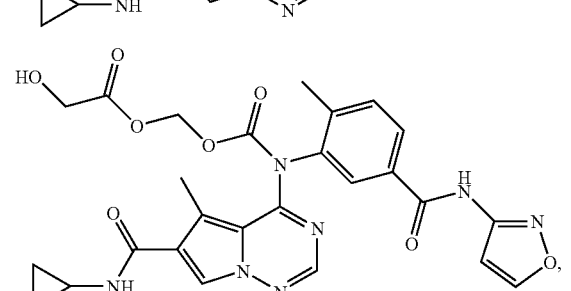
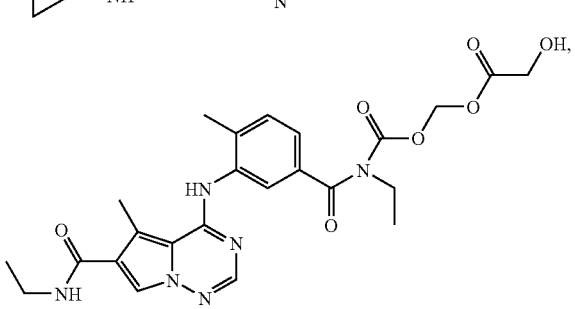
60
-continued
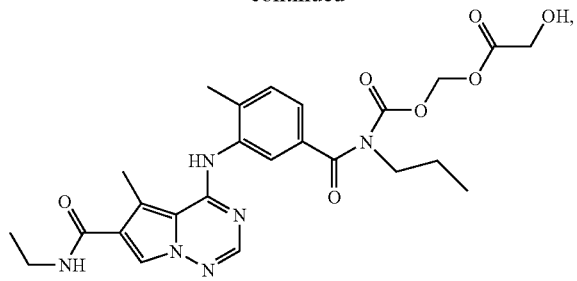
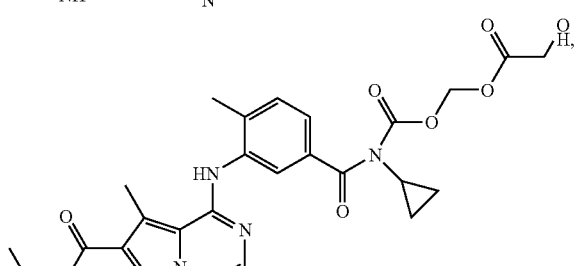
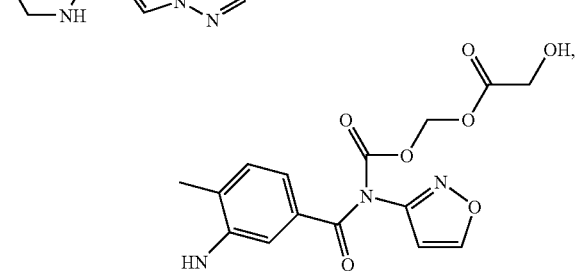
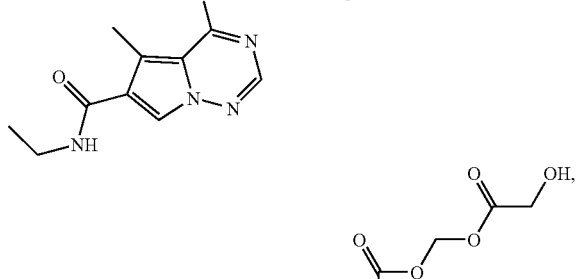
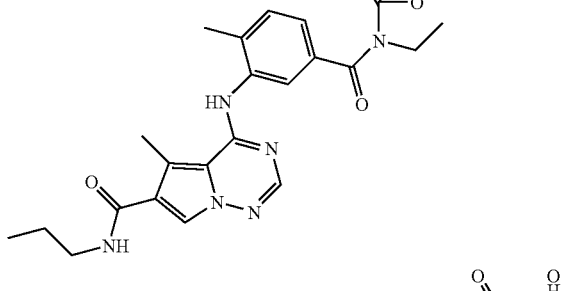
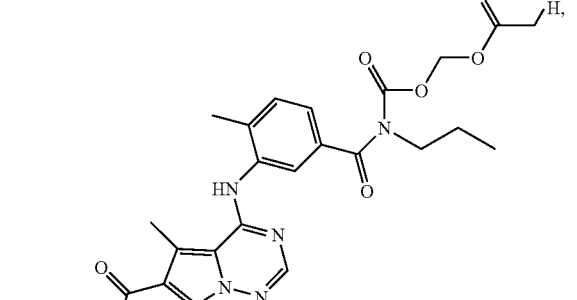

-continued
61
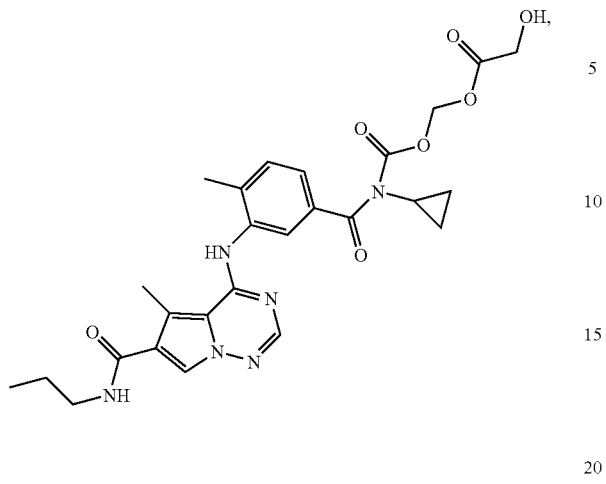
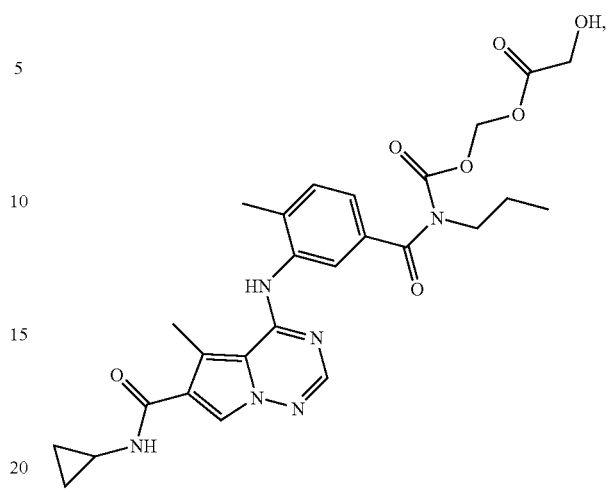
62
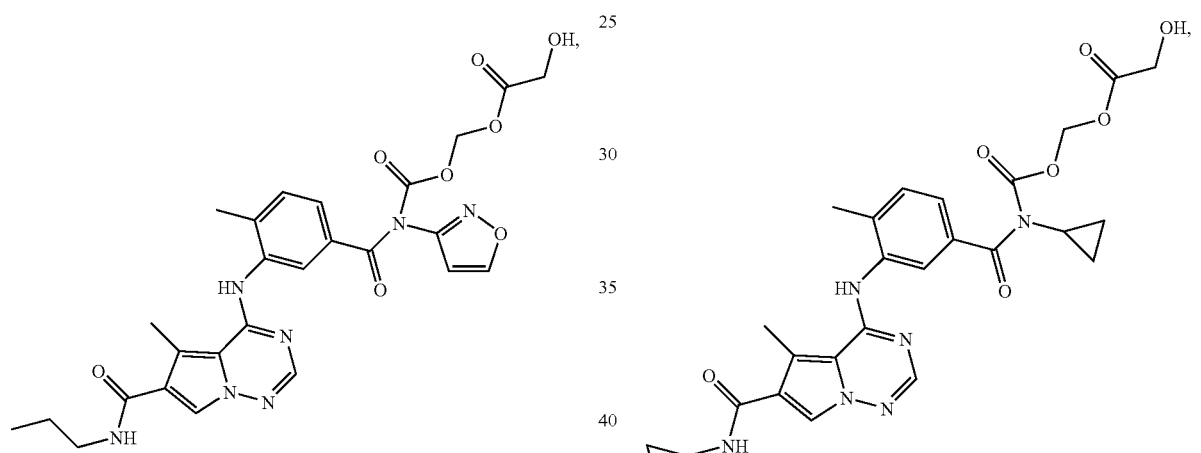
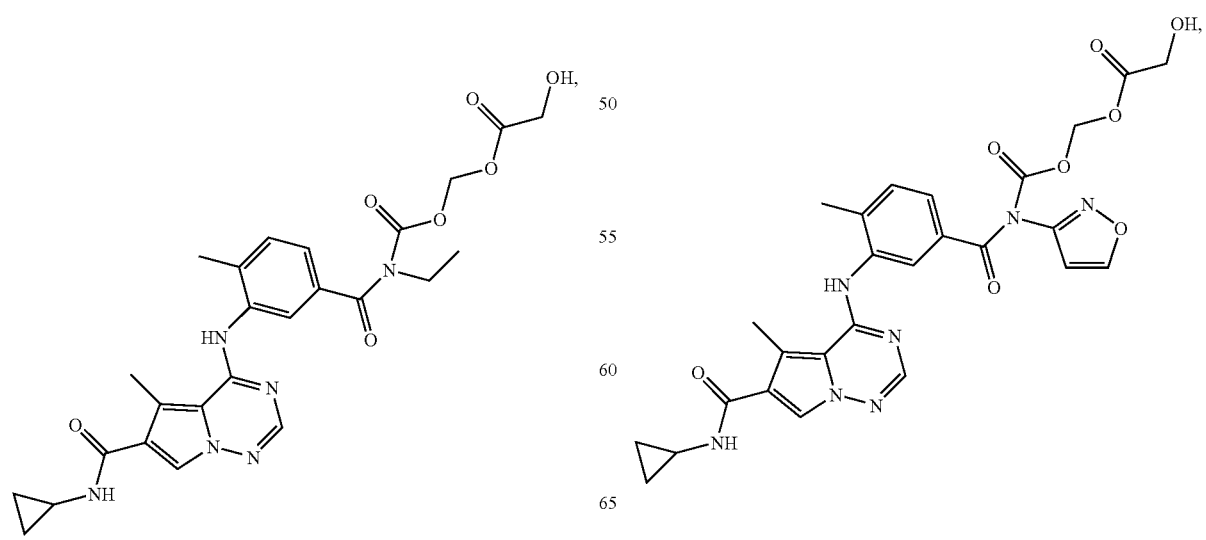

63
-continued
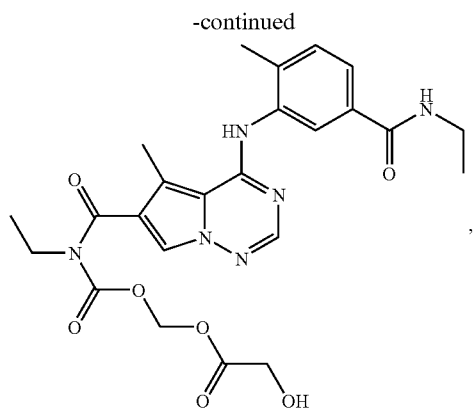
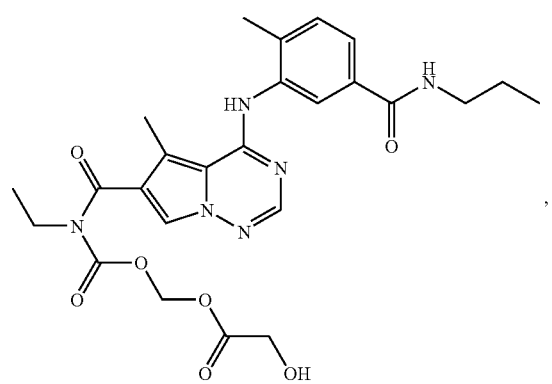
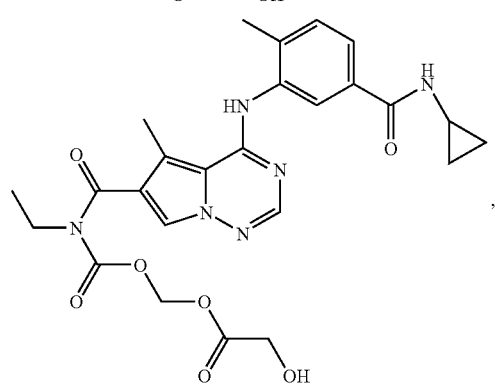
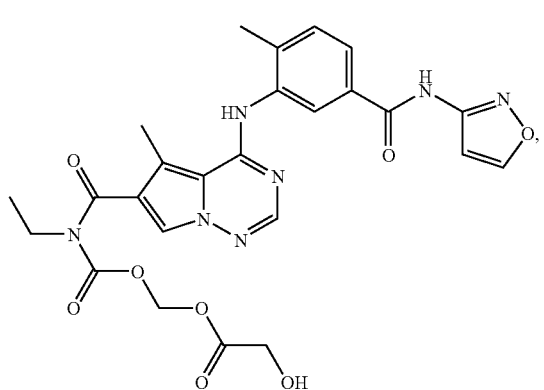
64
-continued
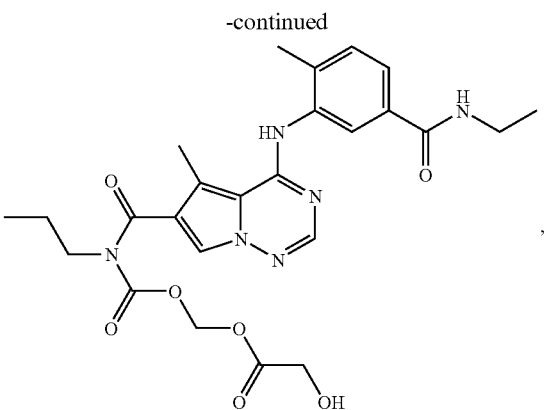
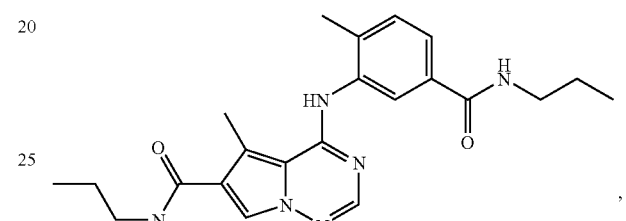
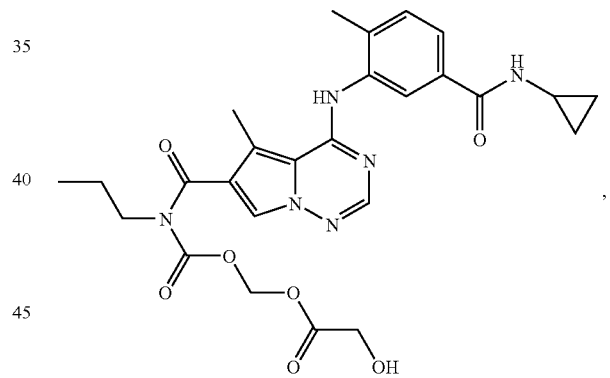
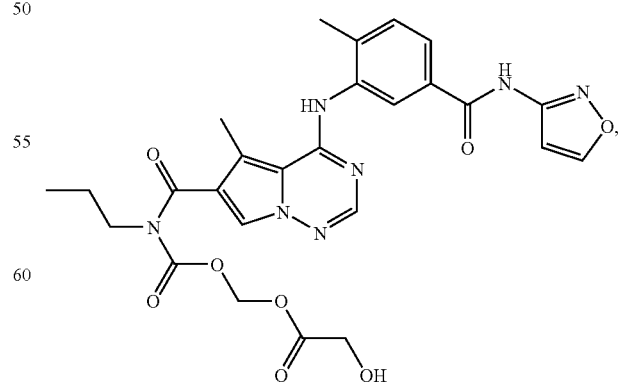

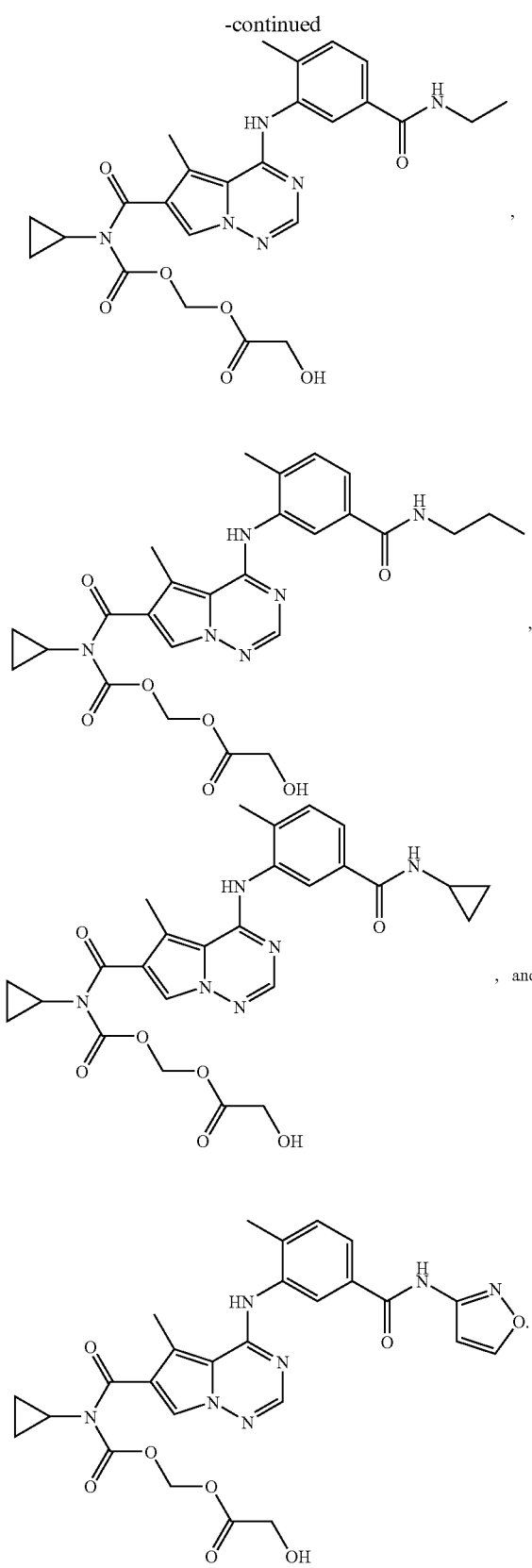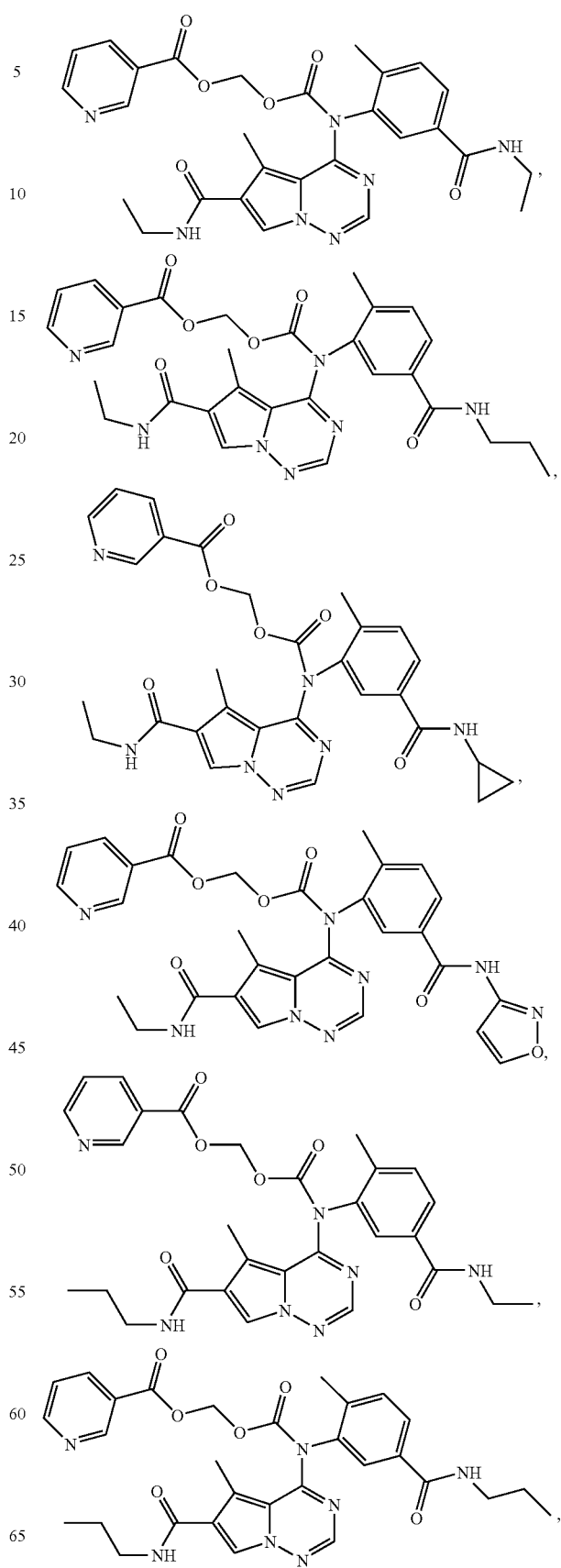
An embodiment of the present invention is for compounds, and salts thereof, selected from the group consisting of:

67                                                            68
-continued                                                    -continued
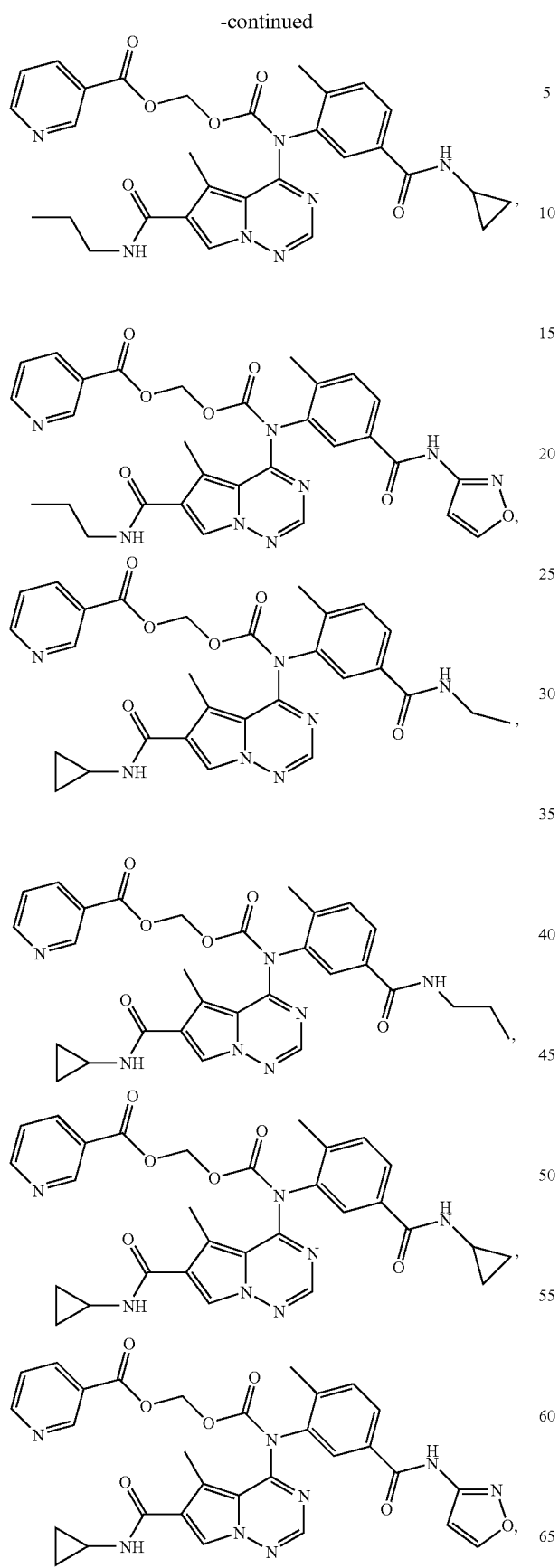
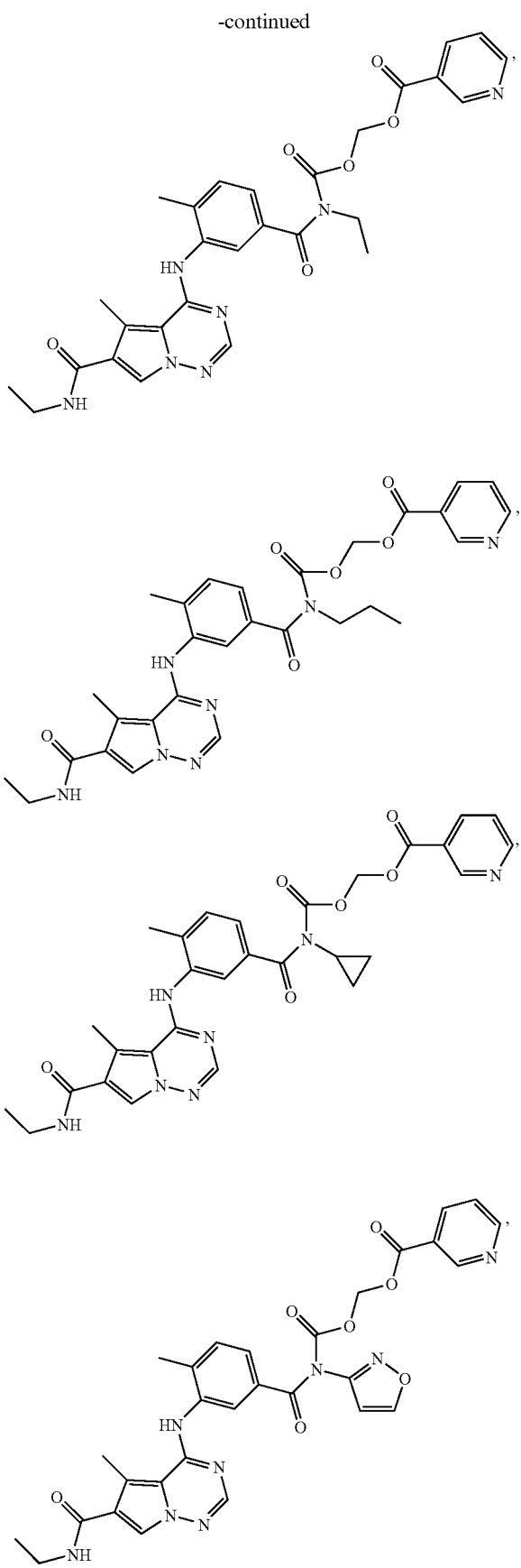

69
-continued
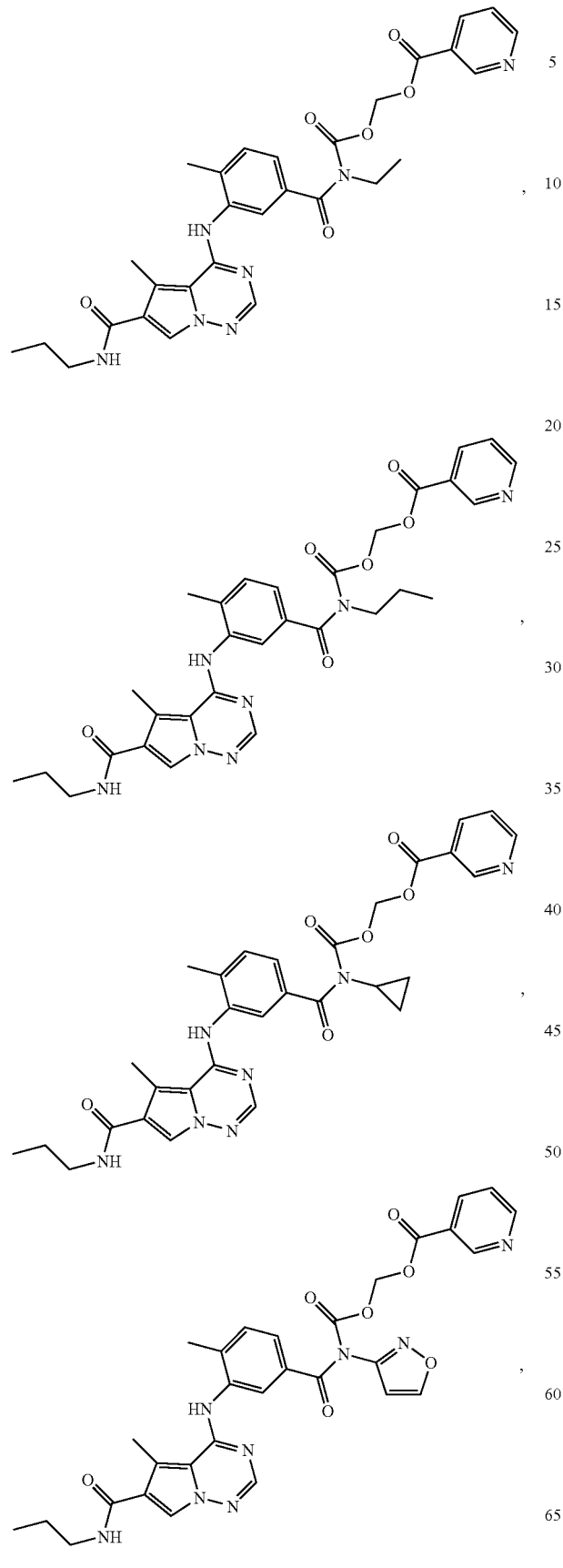
70
-continued
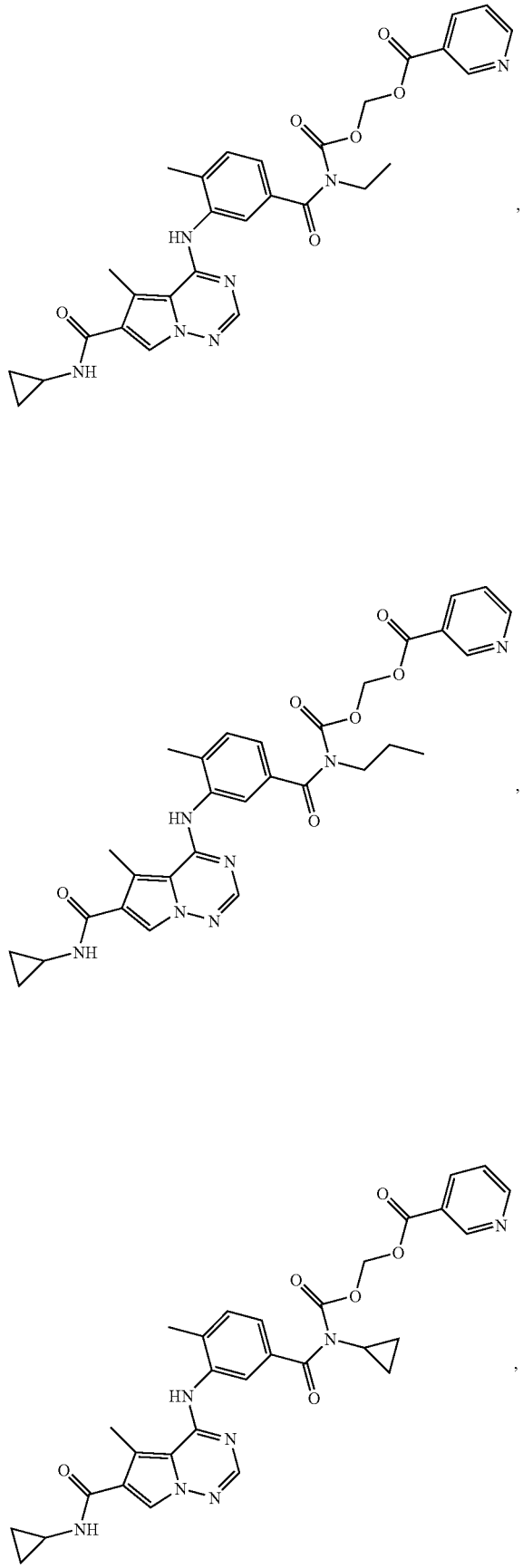

71
-continued
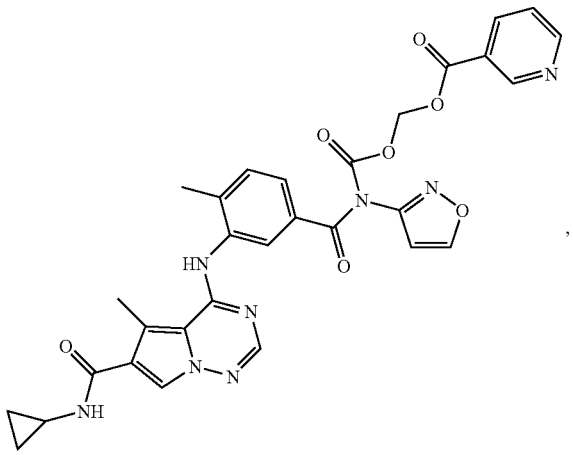
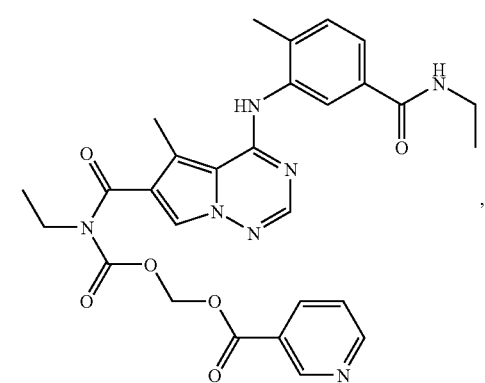
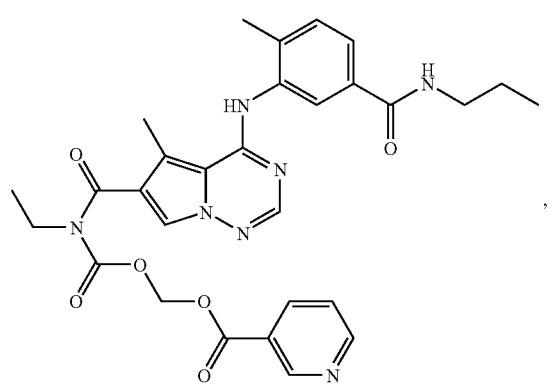
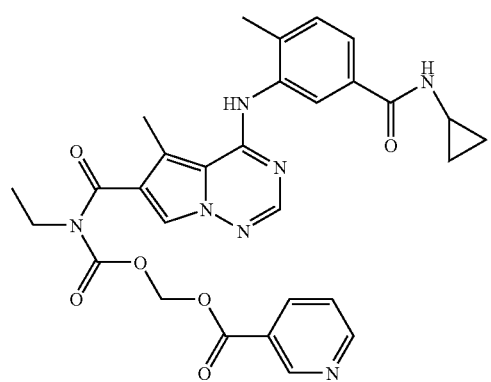
72
-continued
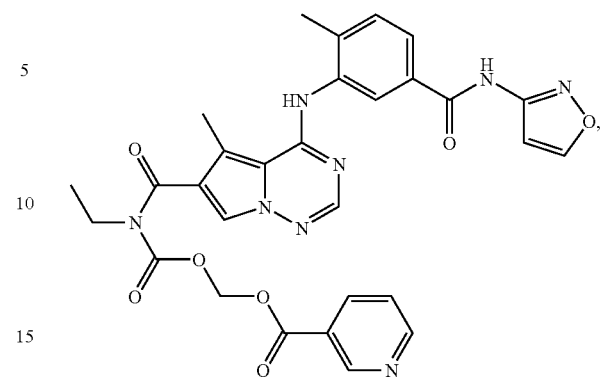
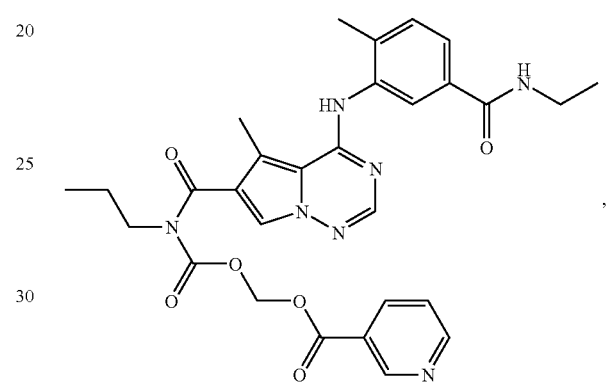
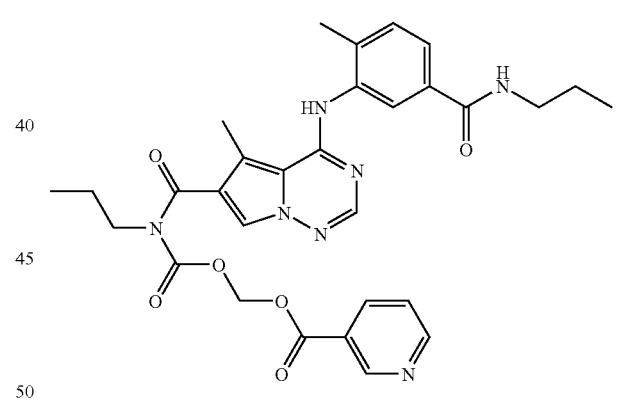
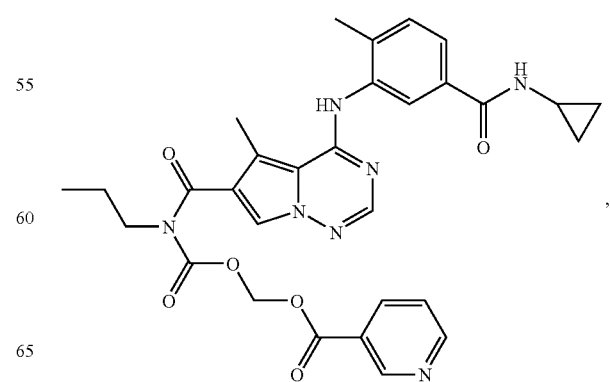

-continued
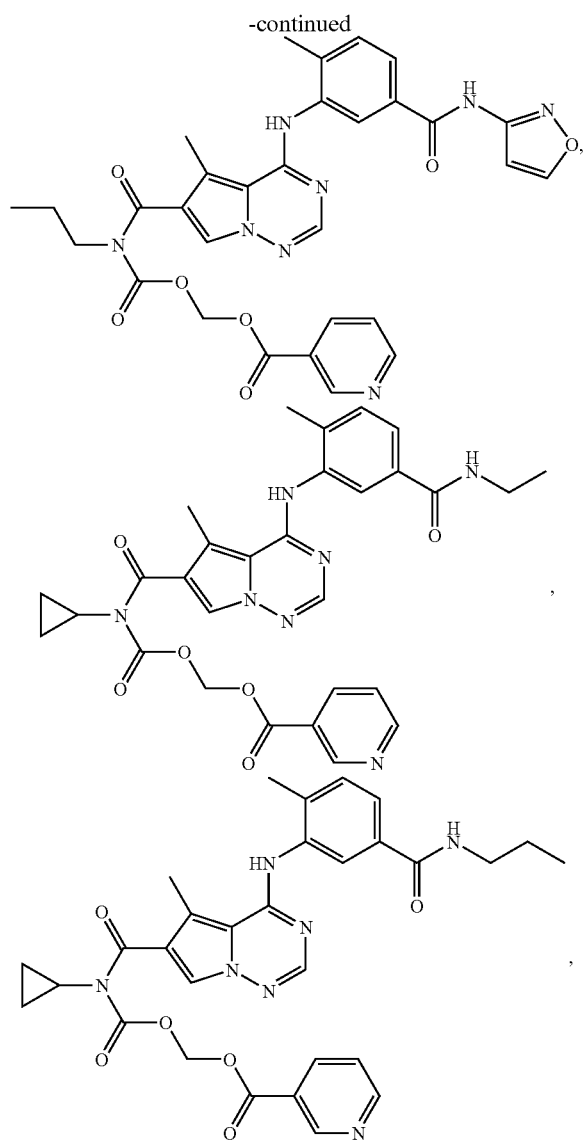
-continued
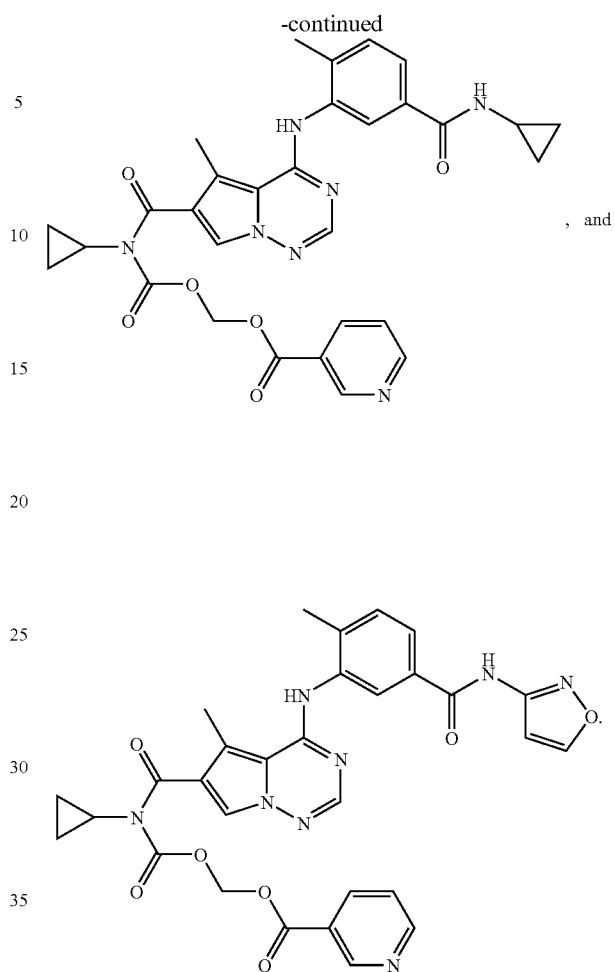
, and
An embodiment of the present invention is for compounds, and salts thereof, selected from the group consisting of:
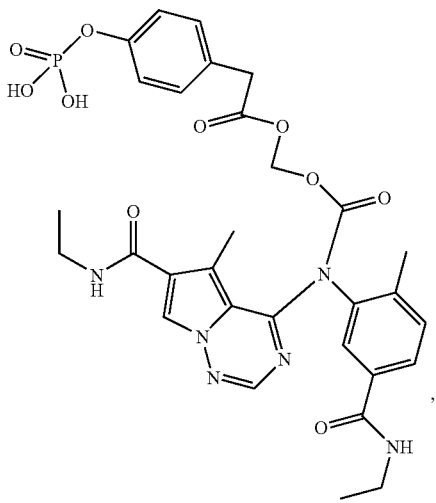
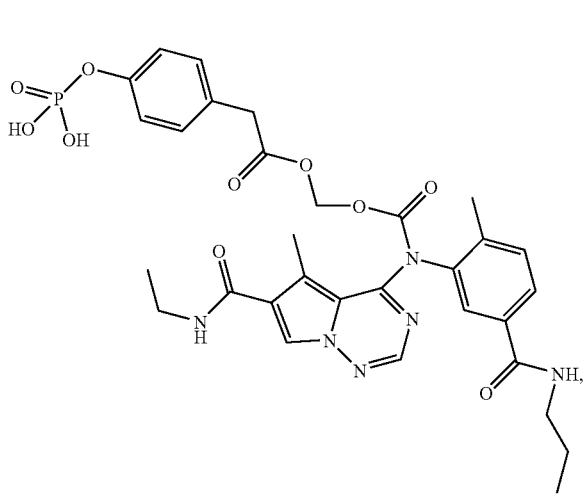

75
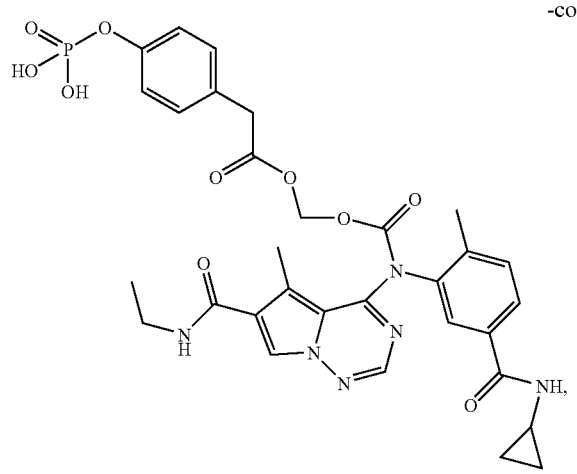
76
-continued
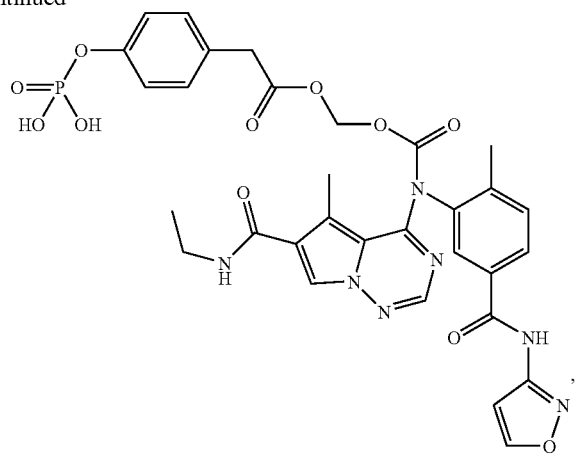
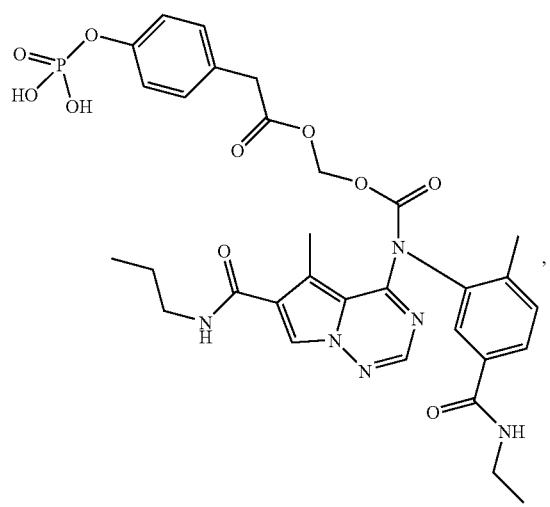
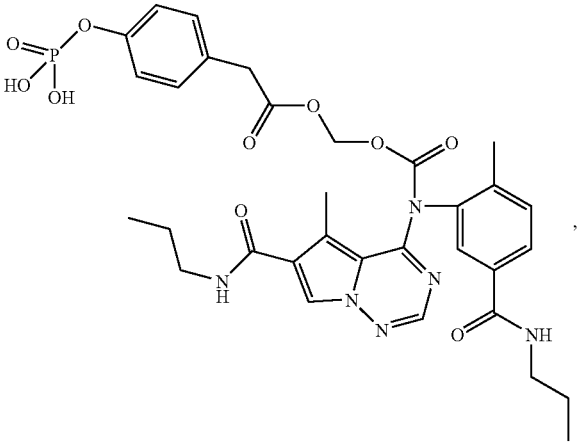
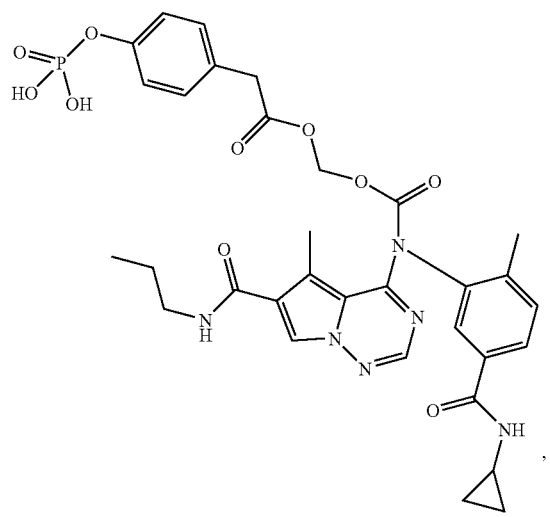
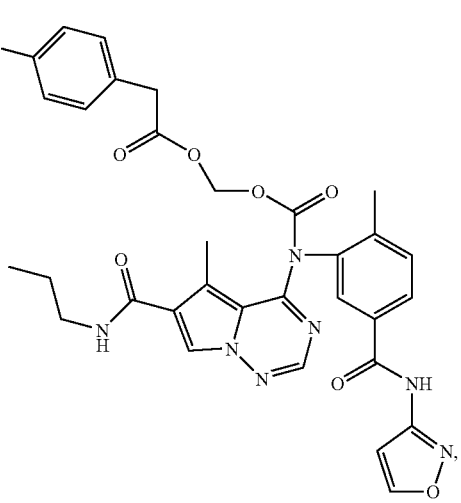

77
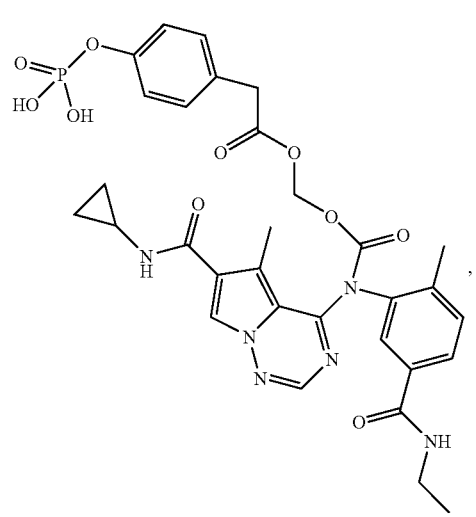
78
-continued
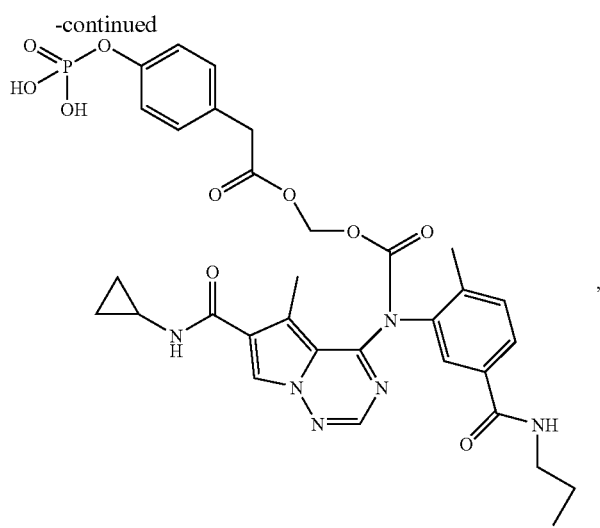
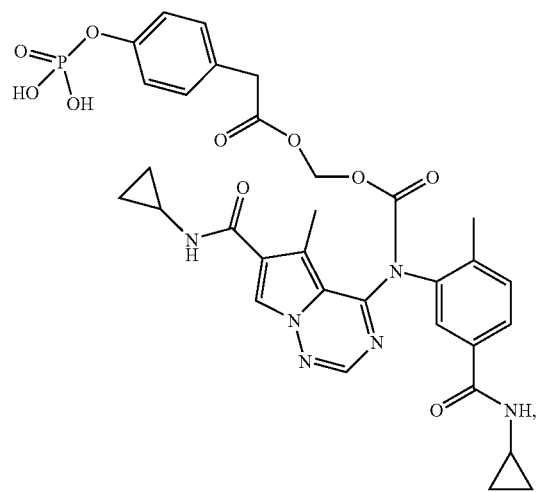
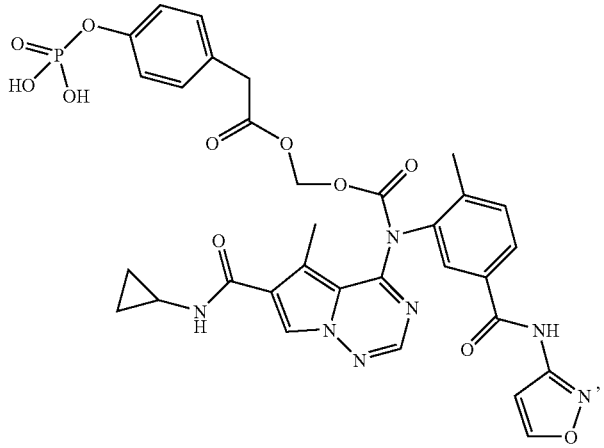
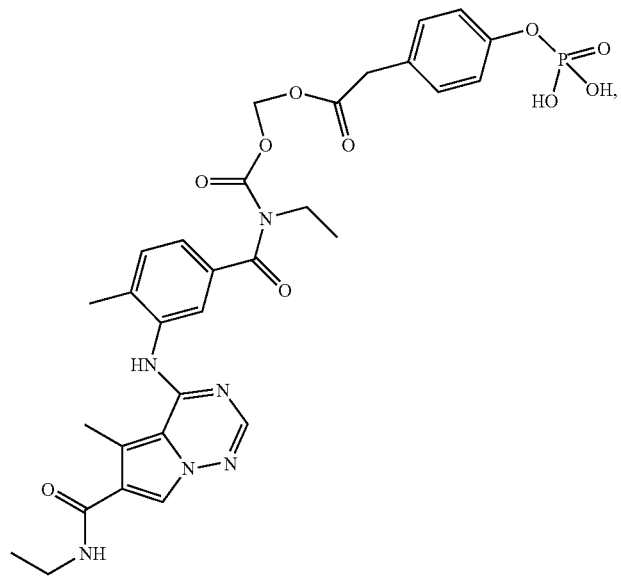

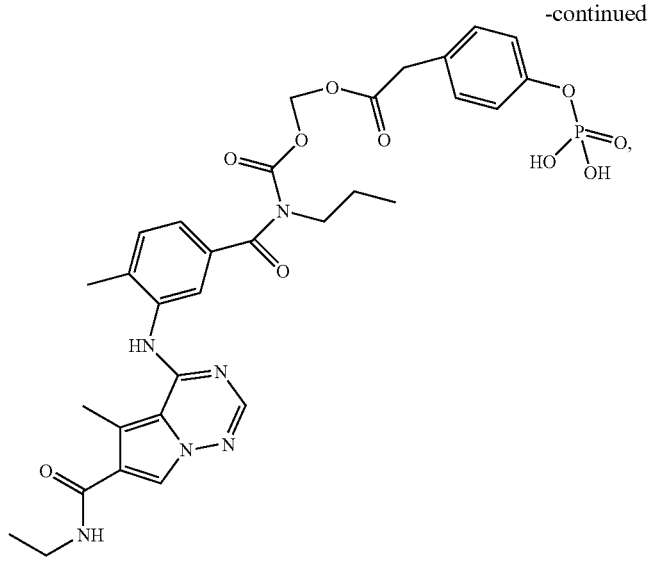
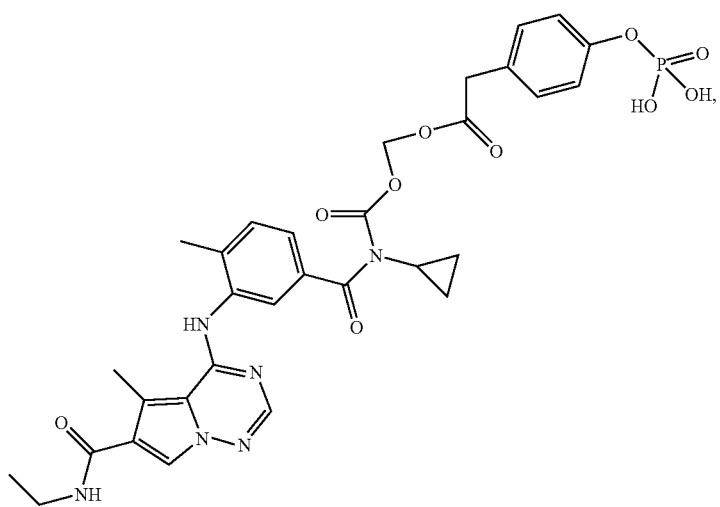
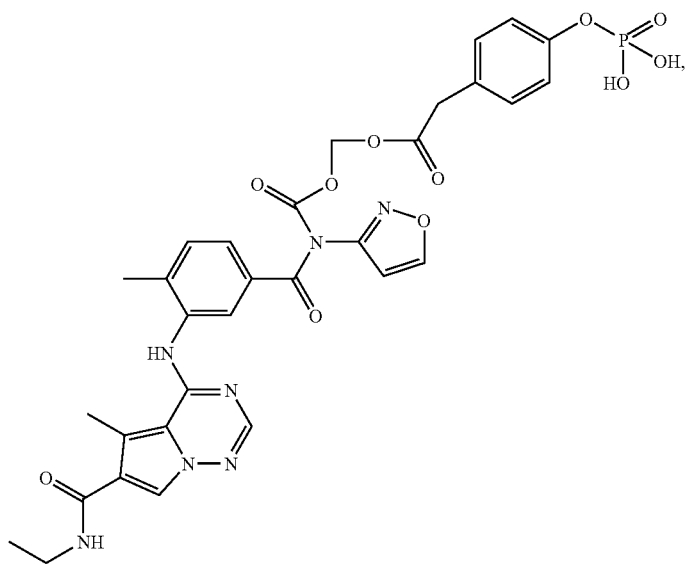

-continued
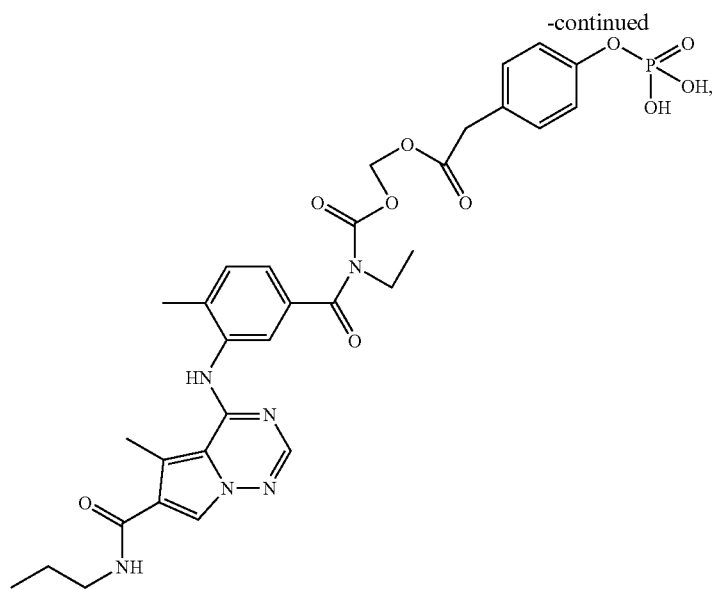
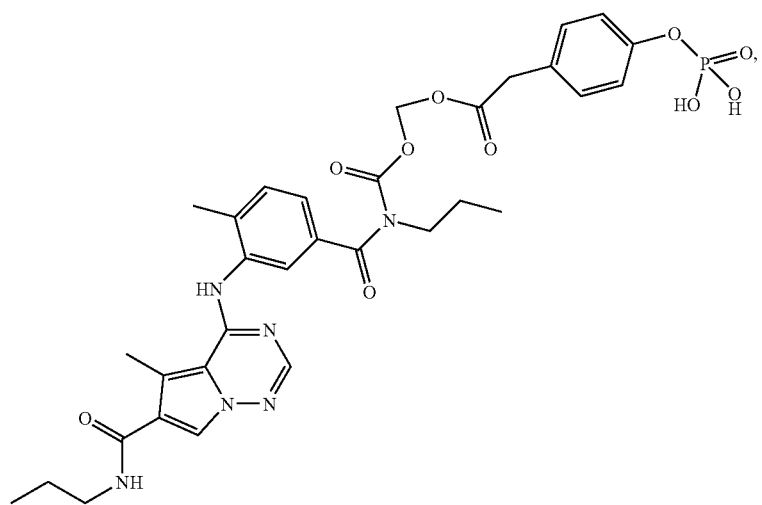
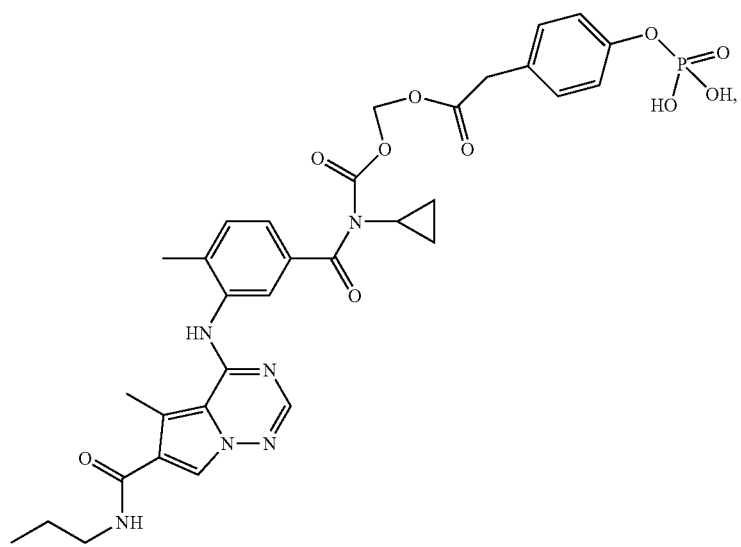

-continued
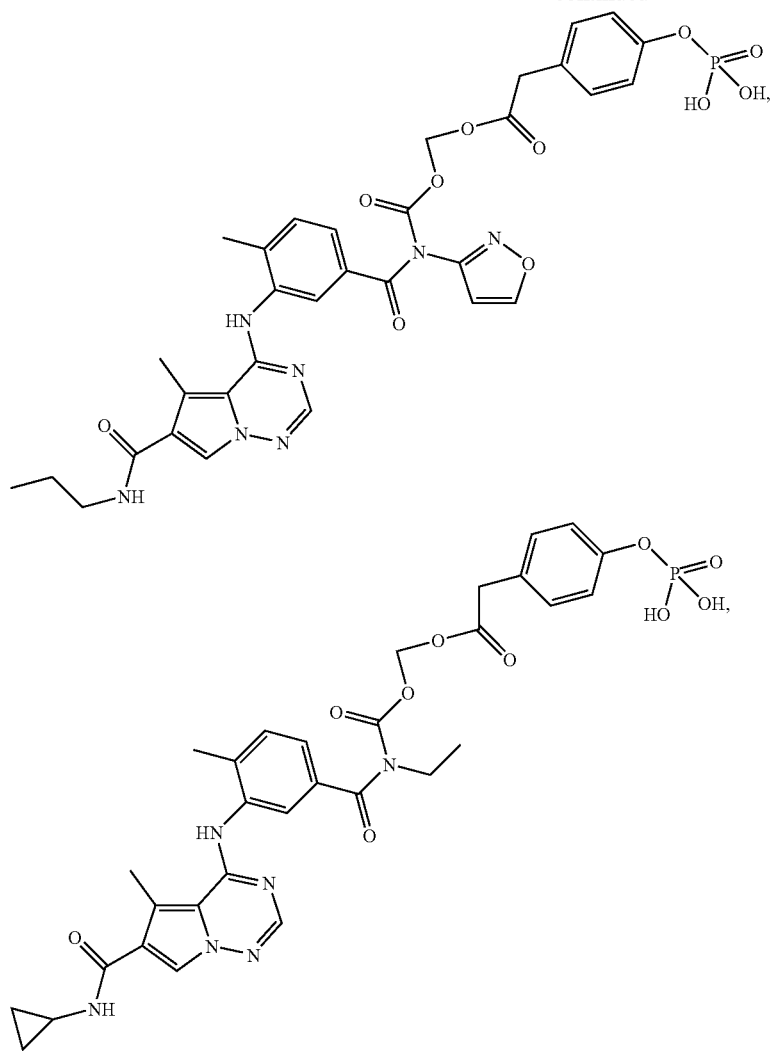
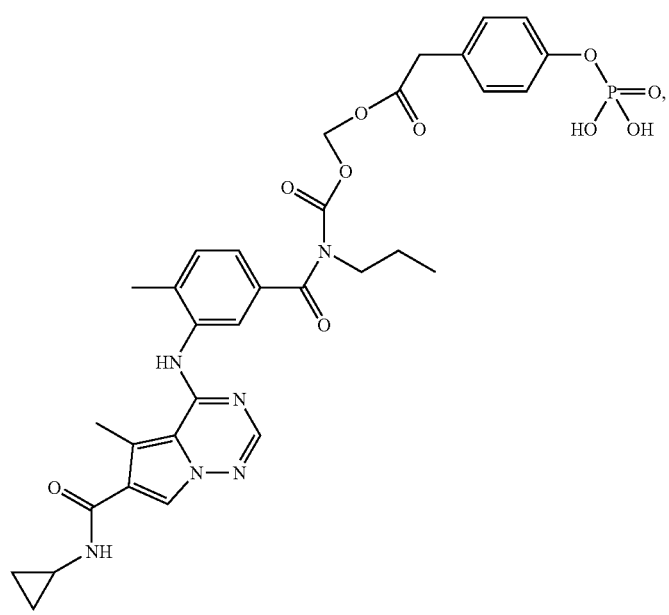

-continued
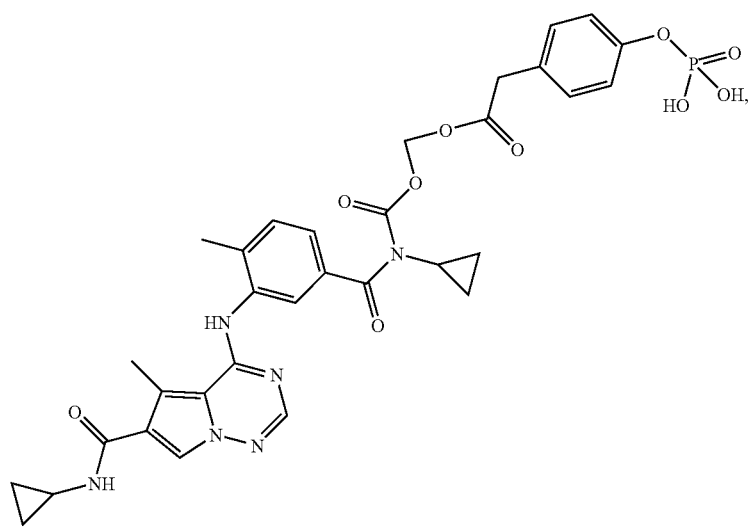
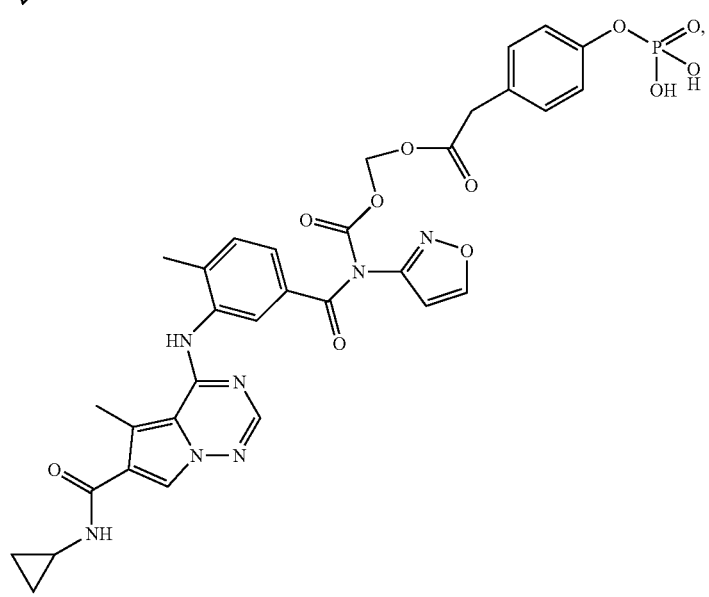
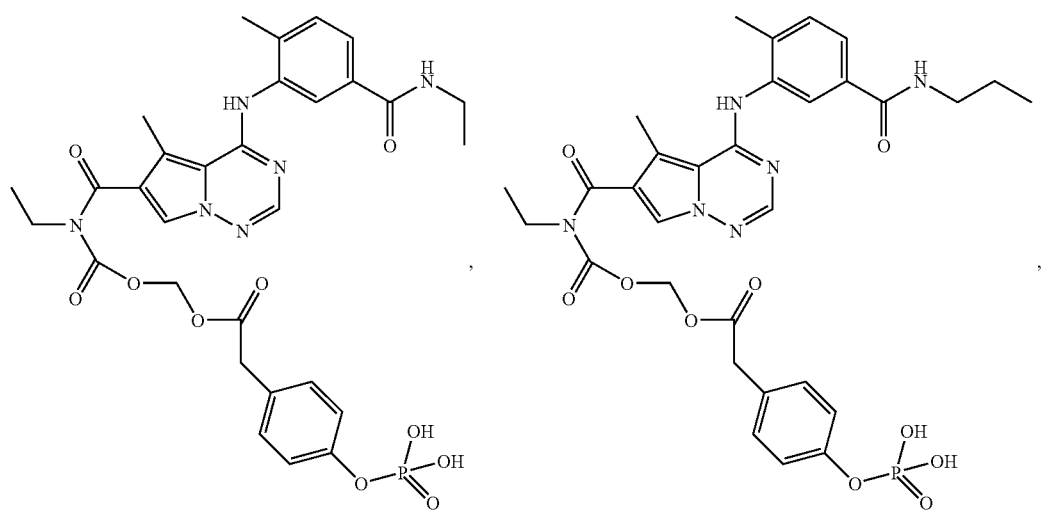

87
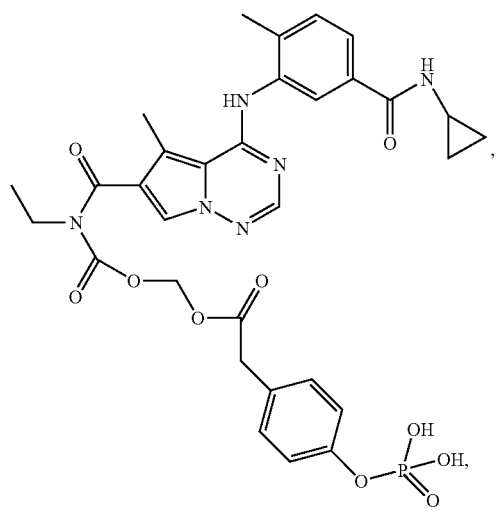
88
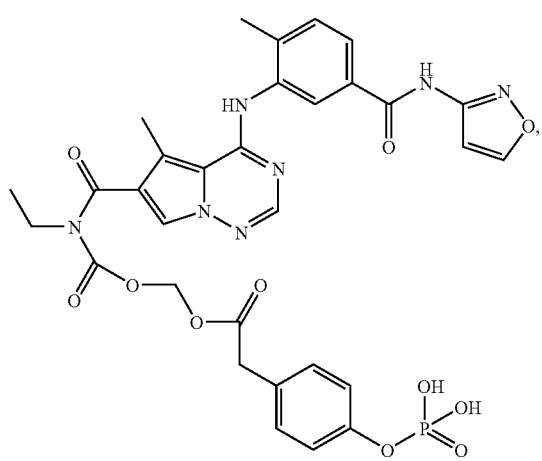
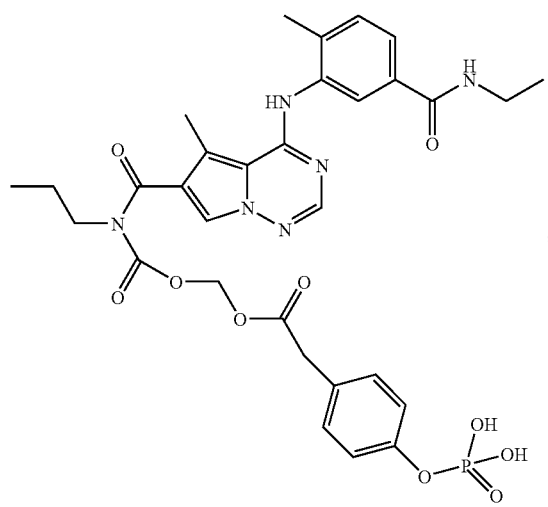
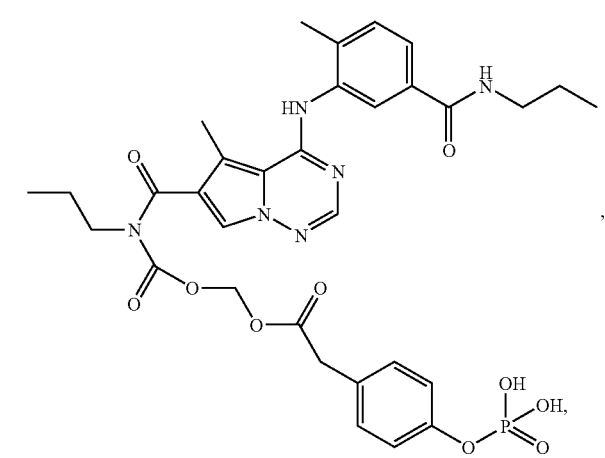
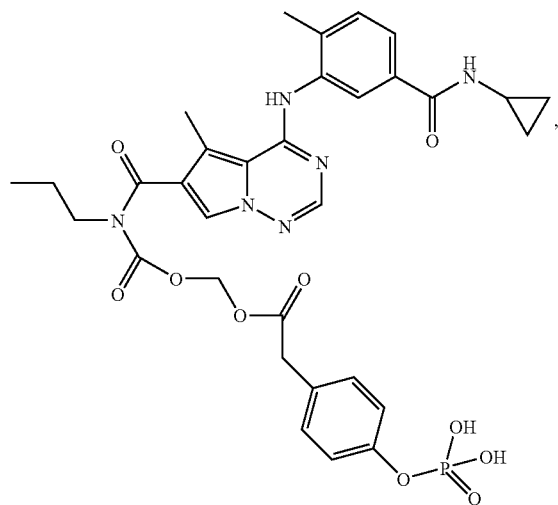
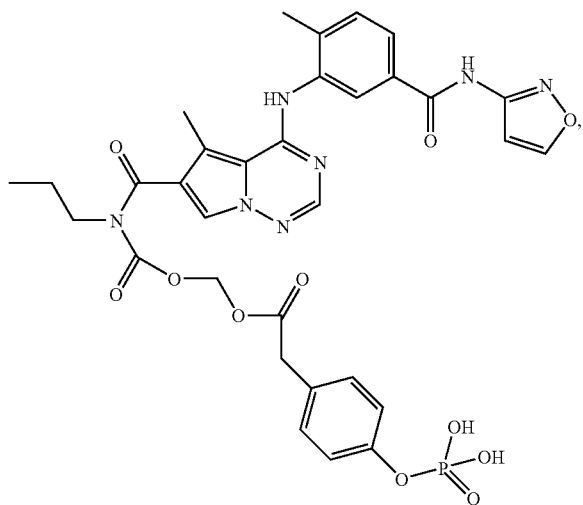

89 90
-continued
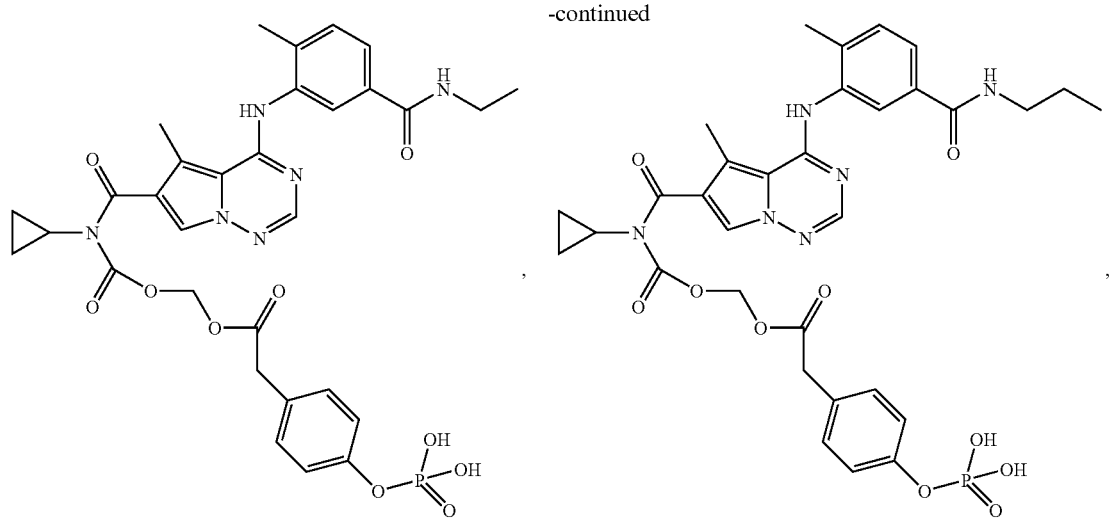
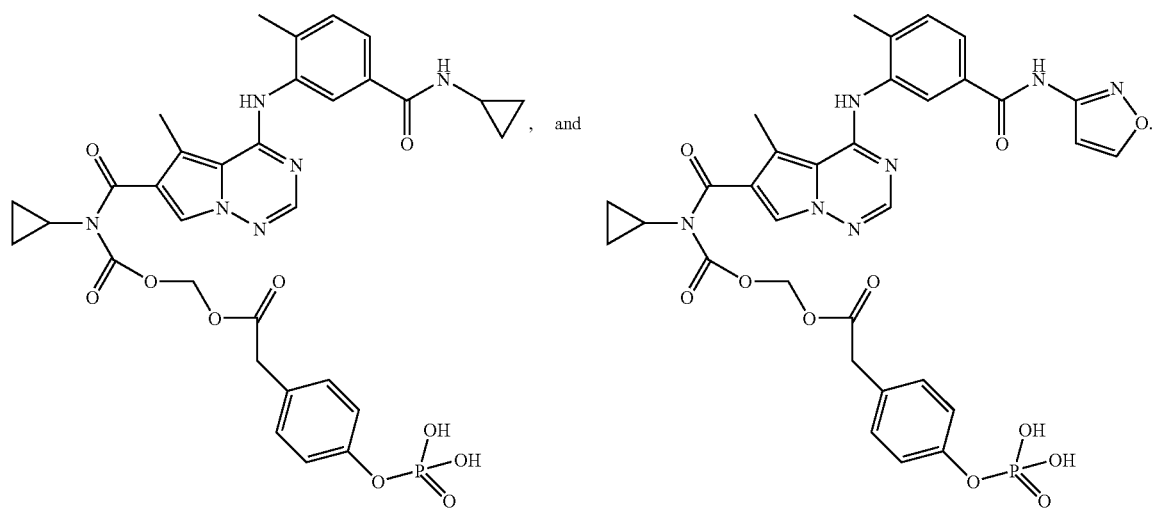
An embodiment of the present invention is for compounds, and salts thereof, selected from the group consisting of:
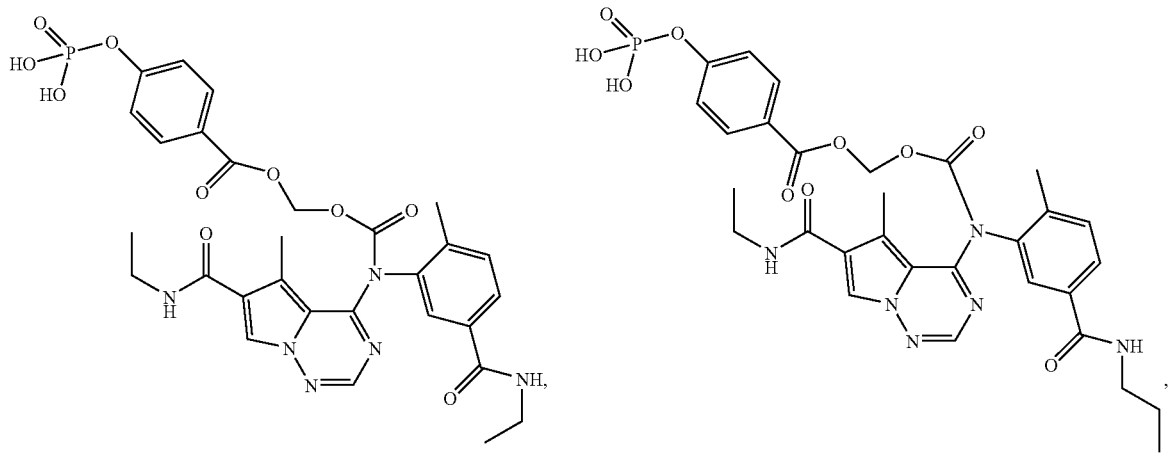

91
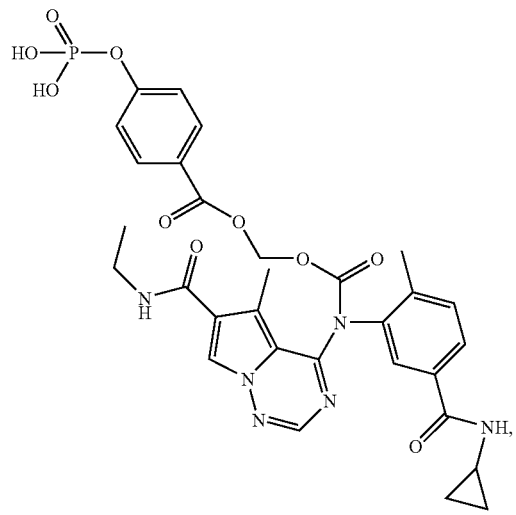
92
-continued
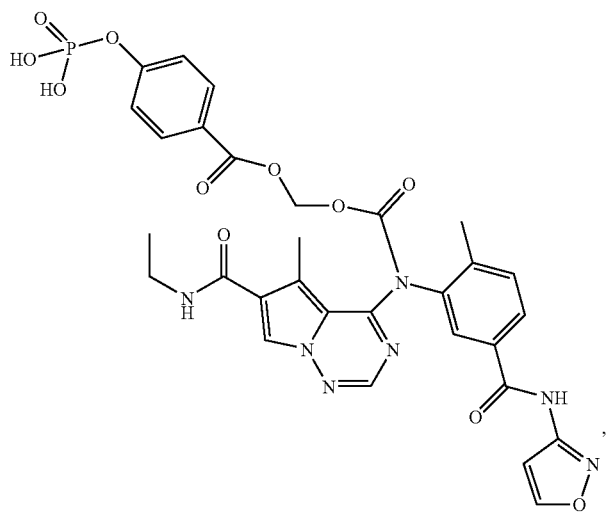
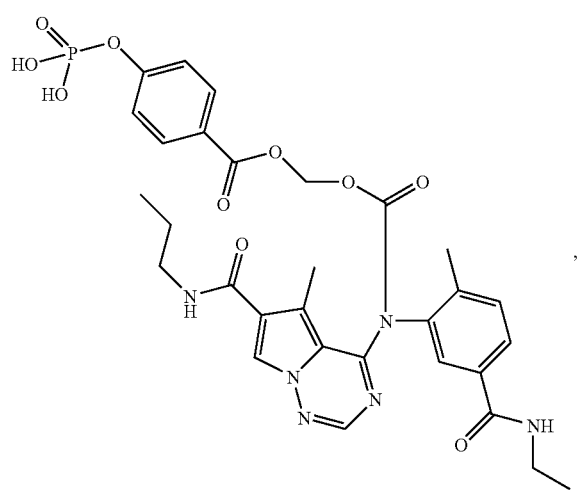
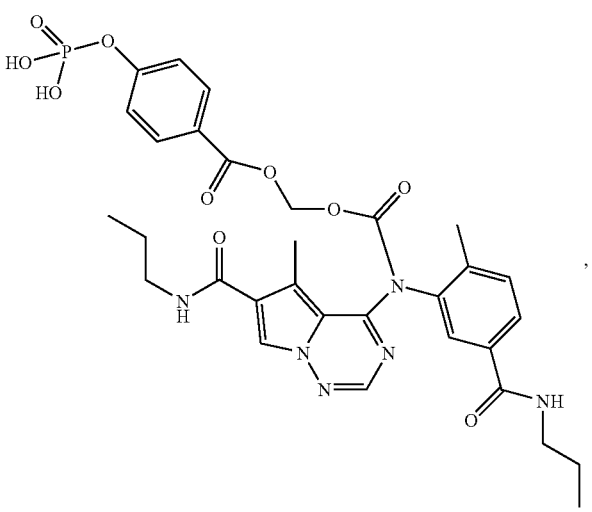
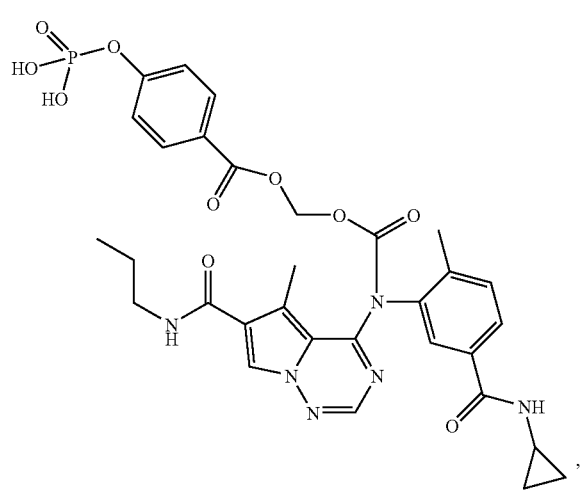
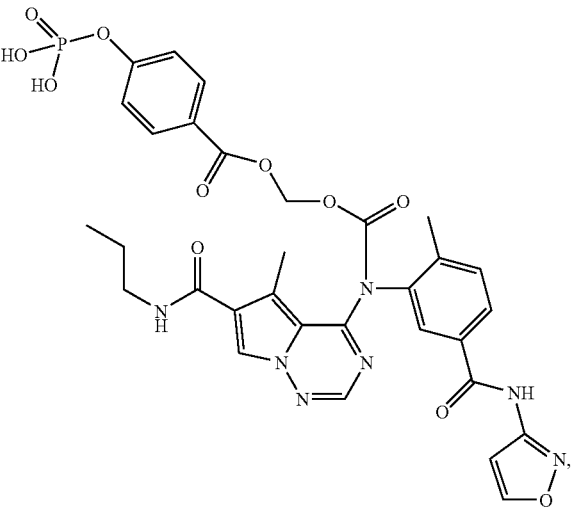

93
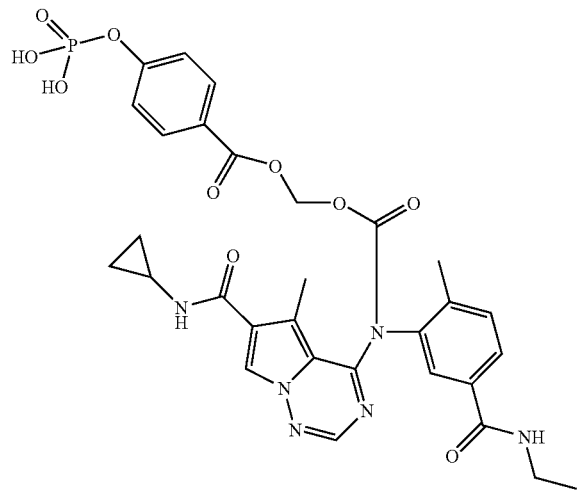
94
-continued
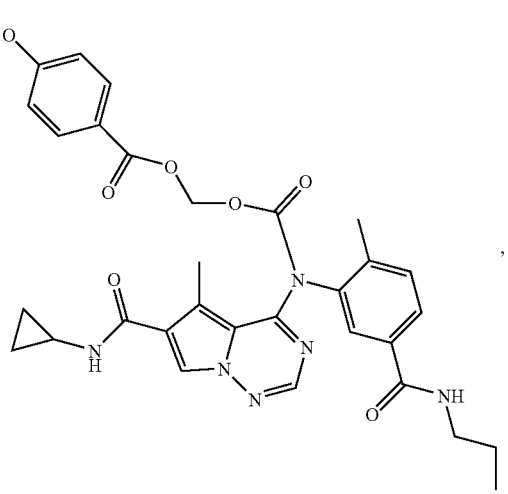
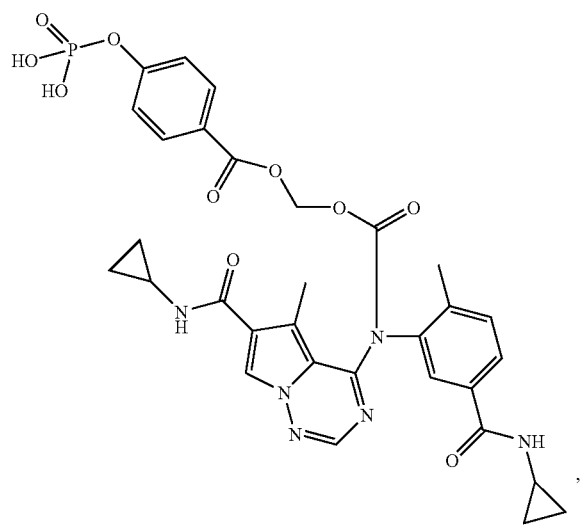
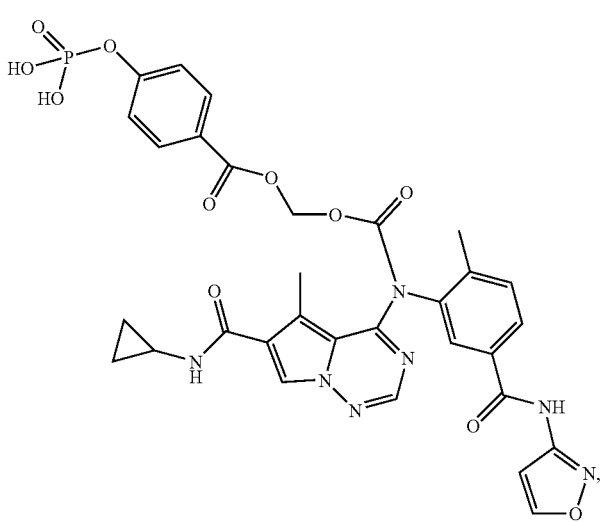
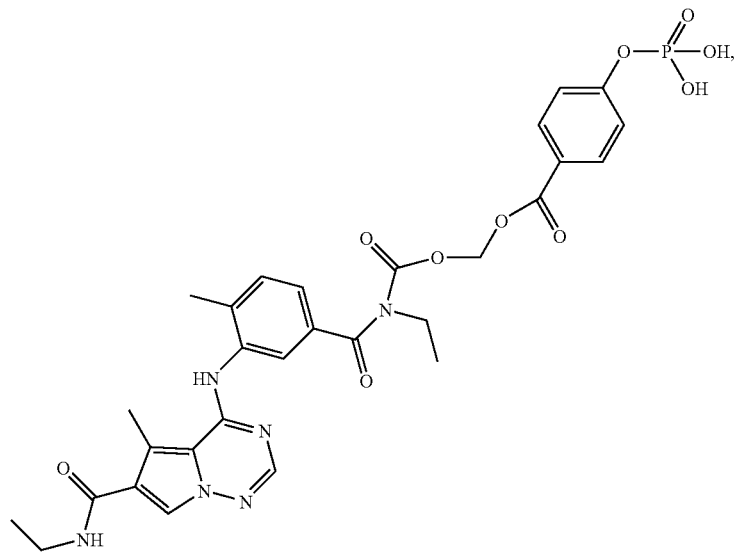

-continued
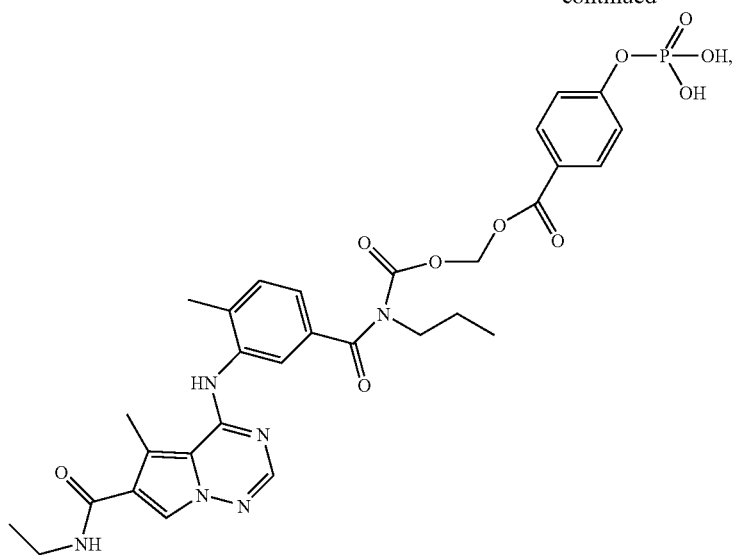
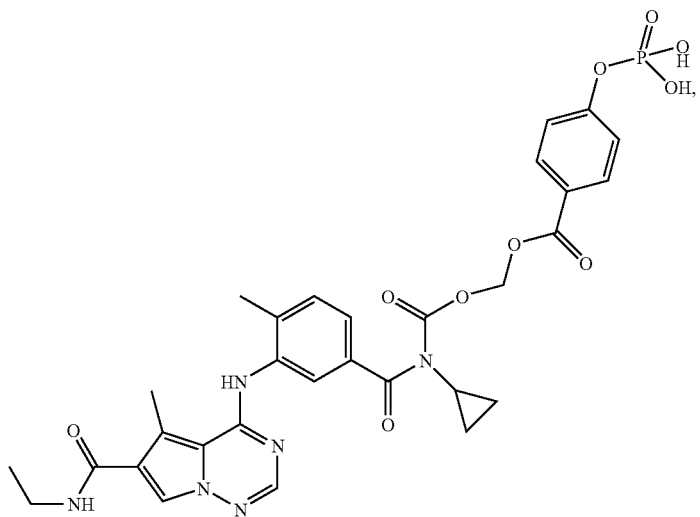
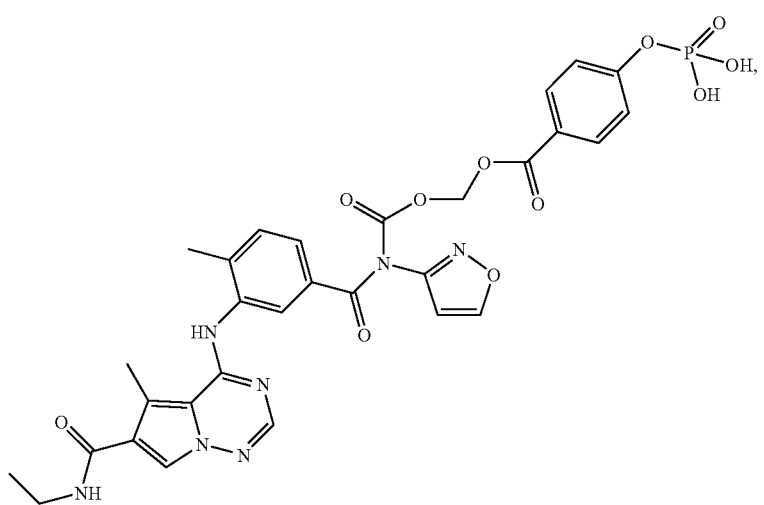

-continued
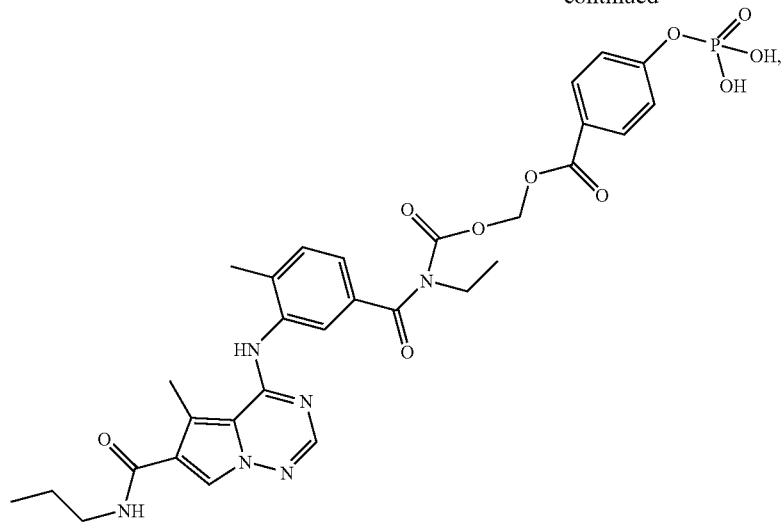
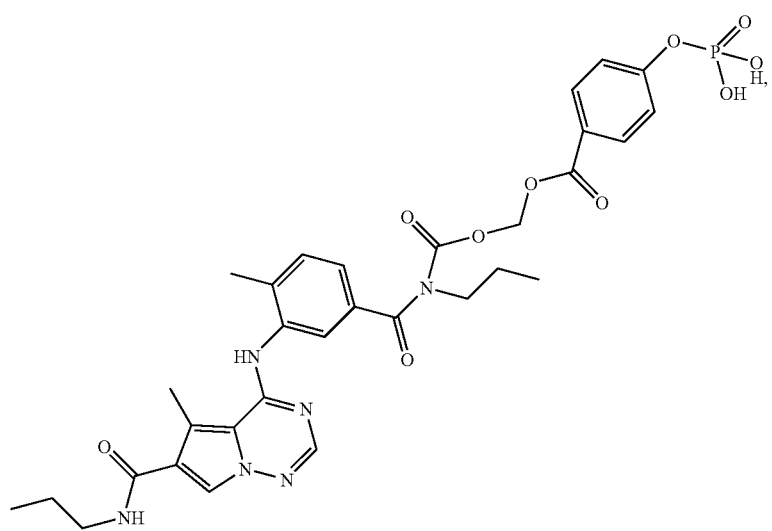
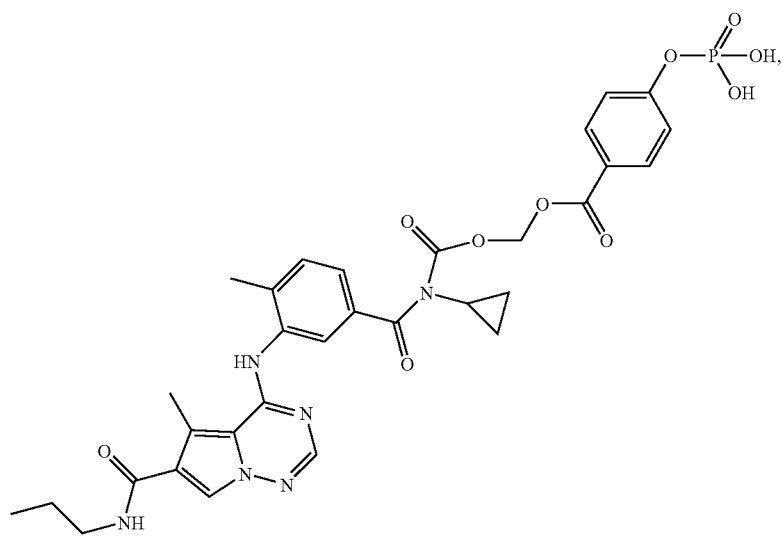

-continued
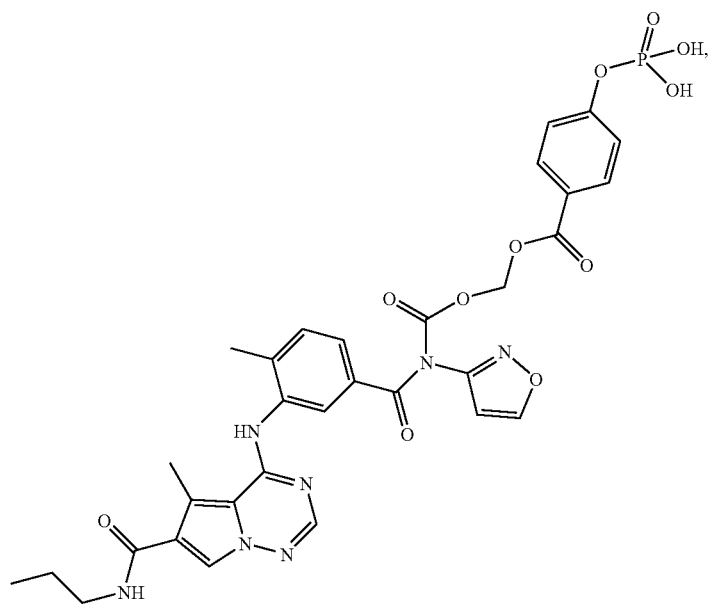
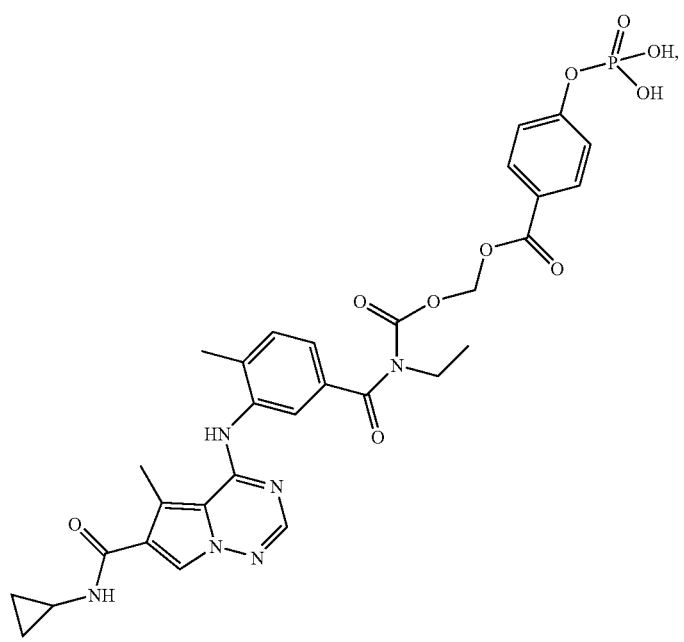

-continued
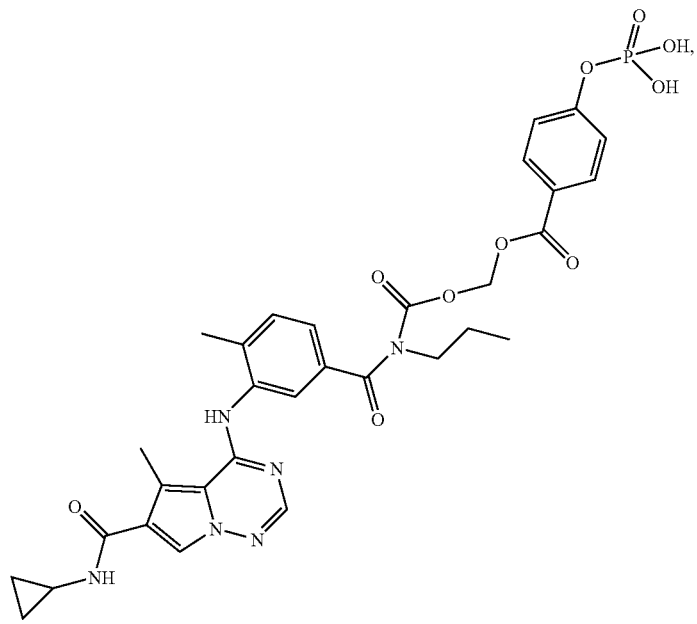
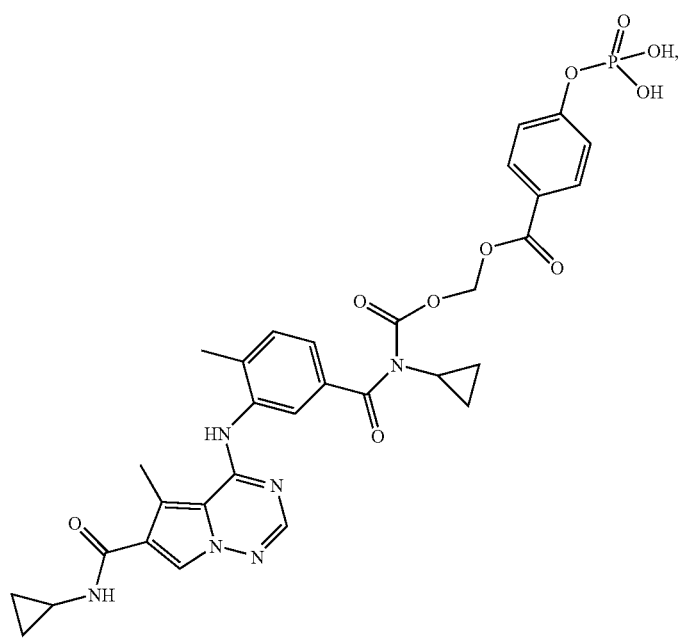

-continued
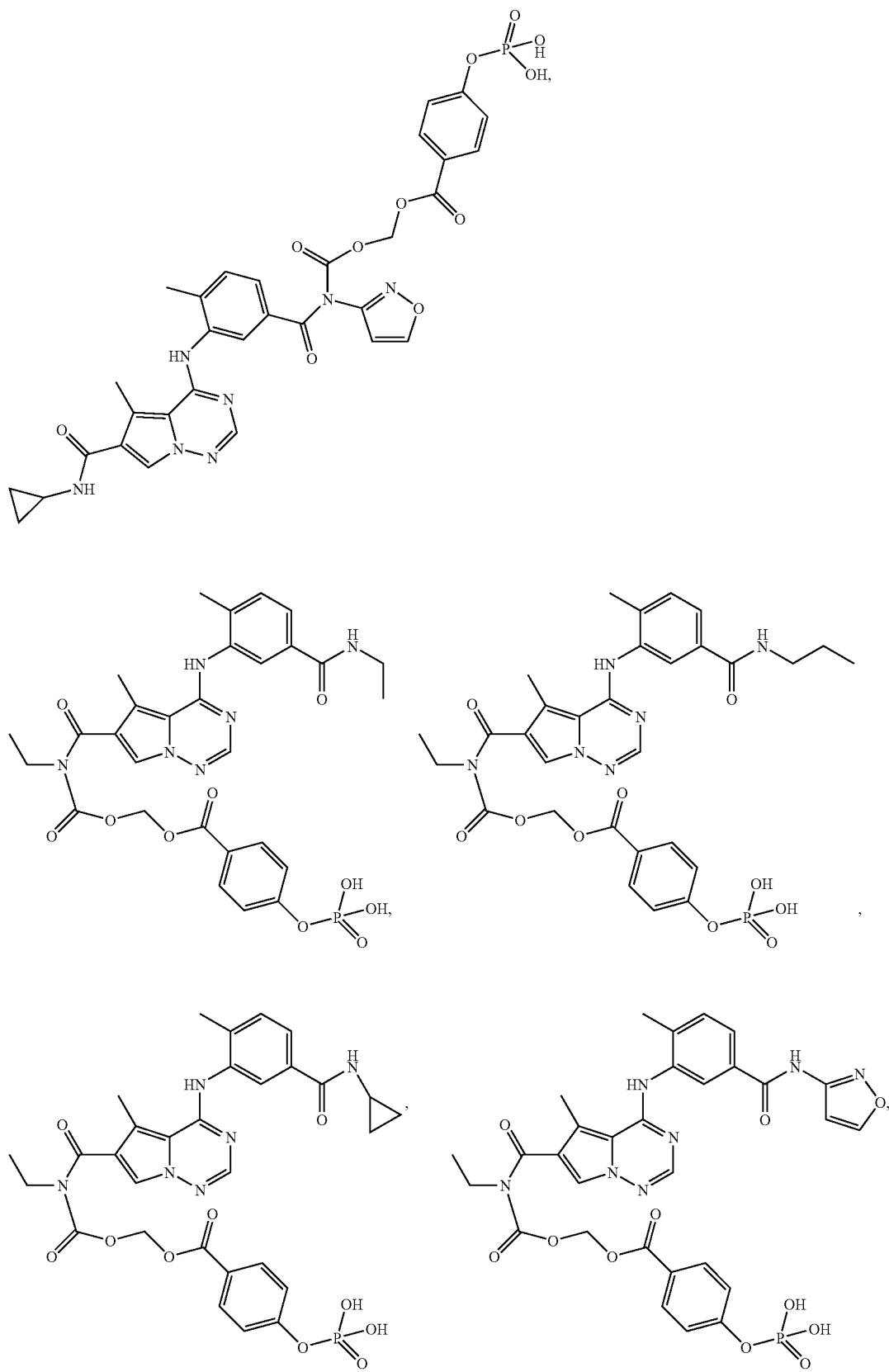

-continued
105
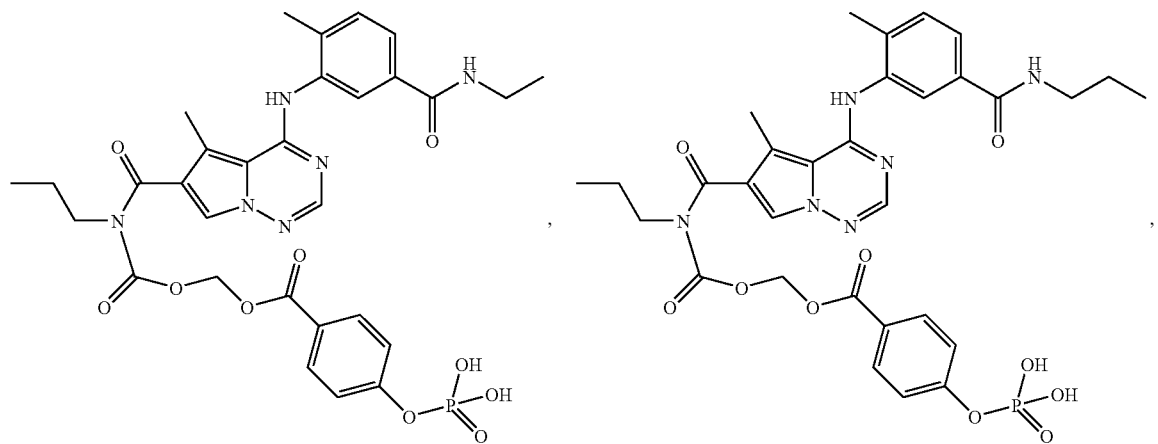
106
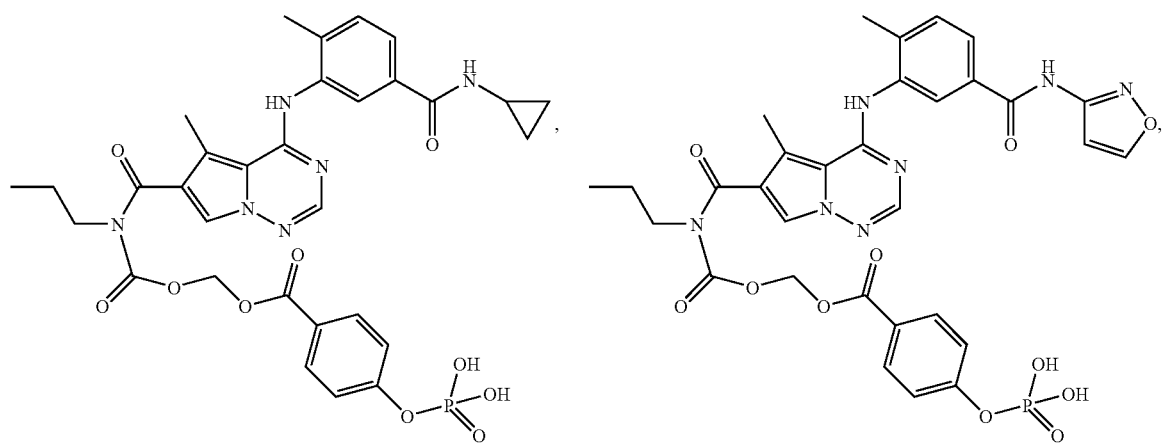
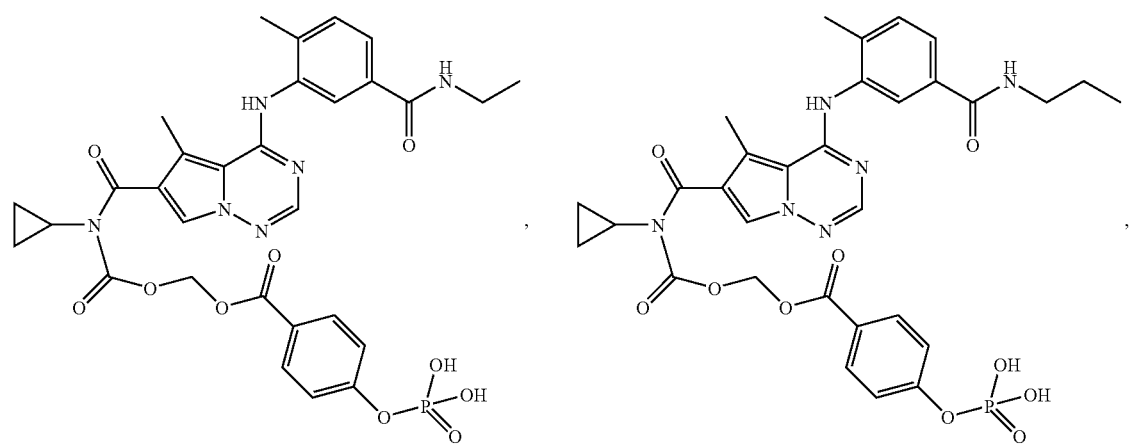

-continued
107 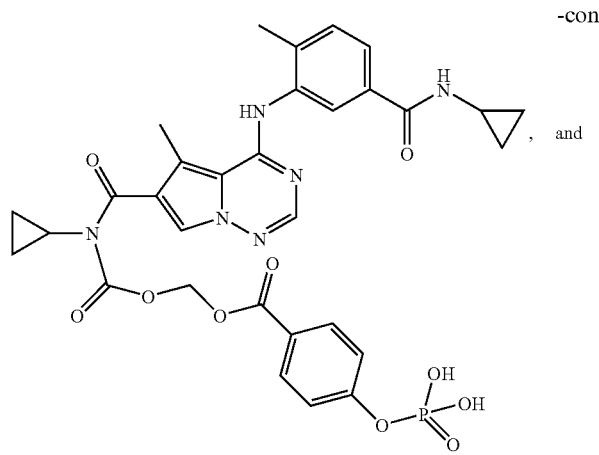, and
108 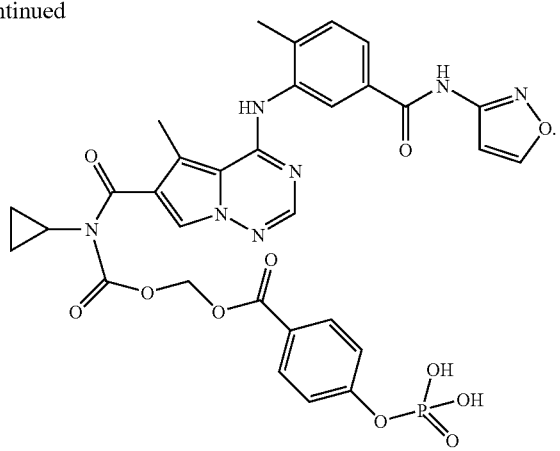.
An embodiment of the present invention is for compounds, and salts thereof, selected from the group consisting of:
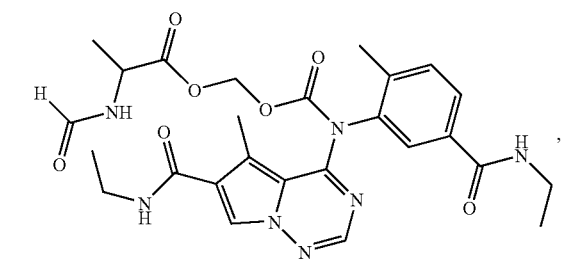,
-continued
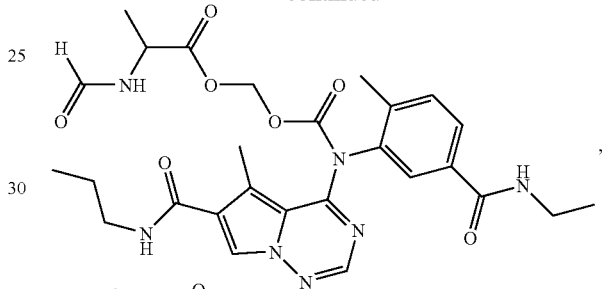,
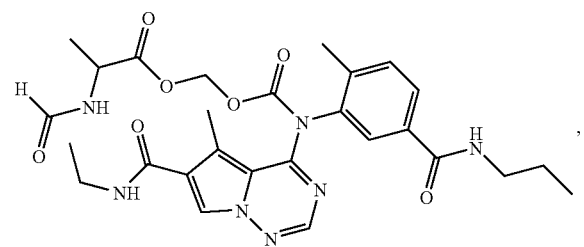,
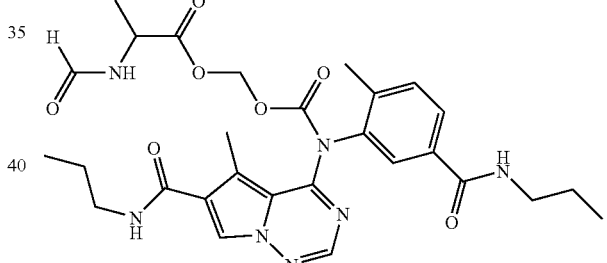,
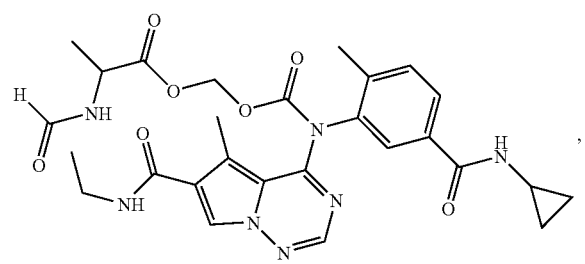,
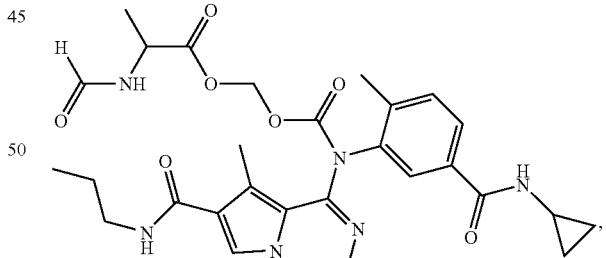,
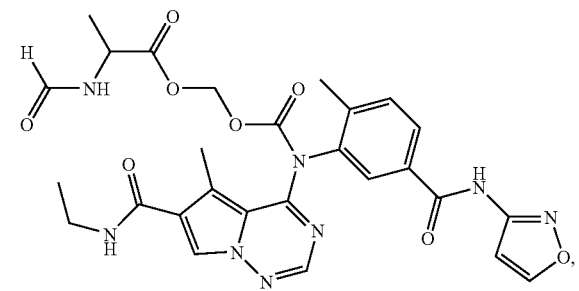,
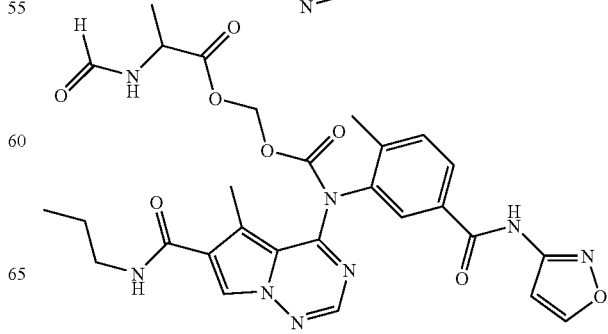, -continued
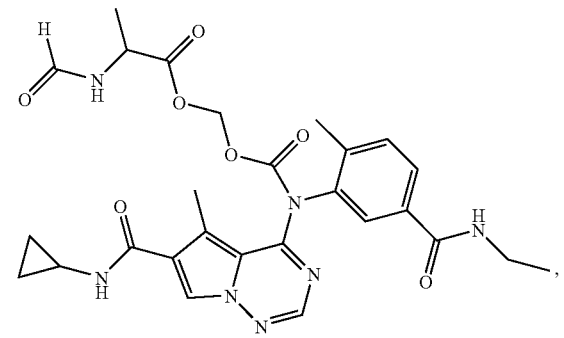
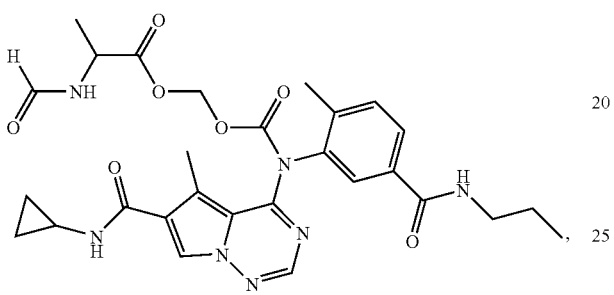
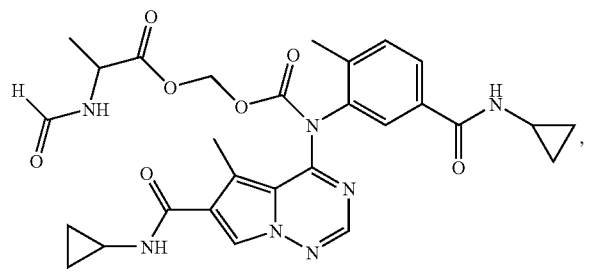
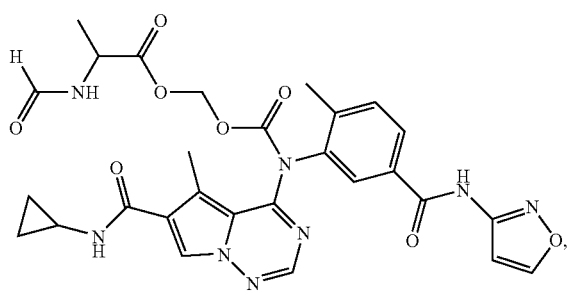
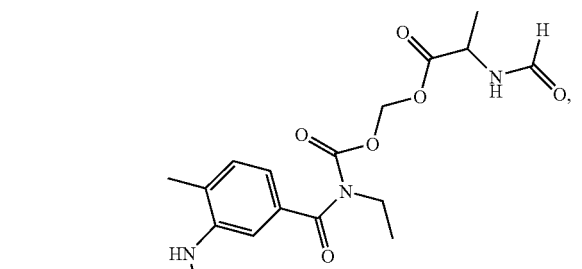
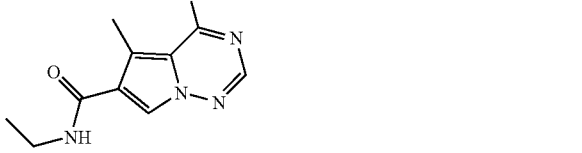
-continued
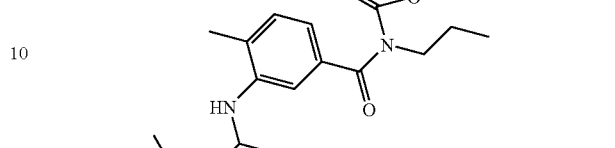
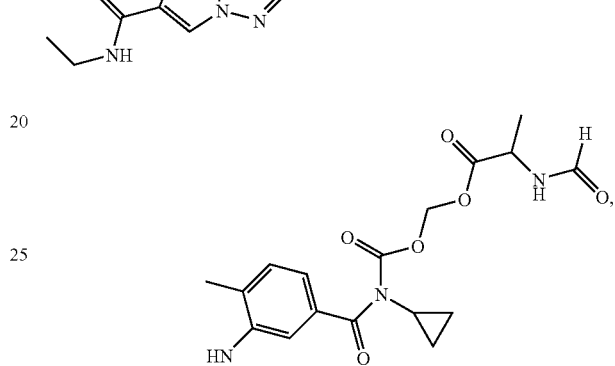
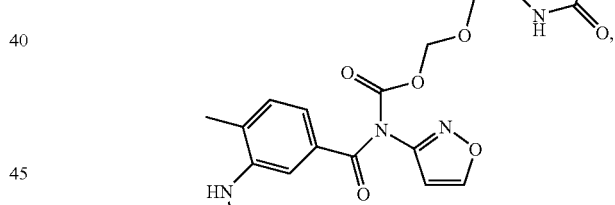
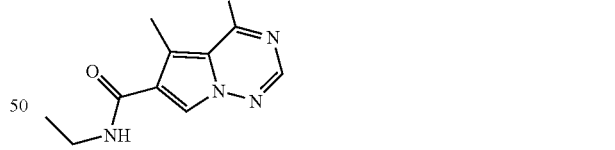
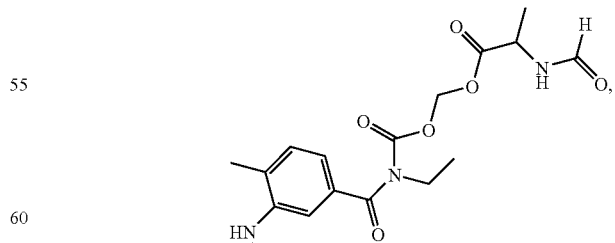

111 112
-continued
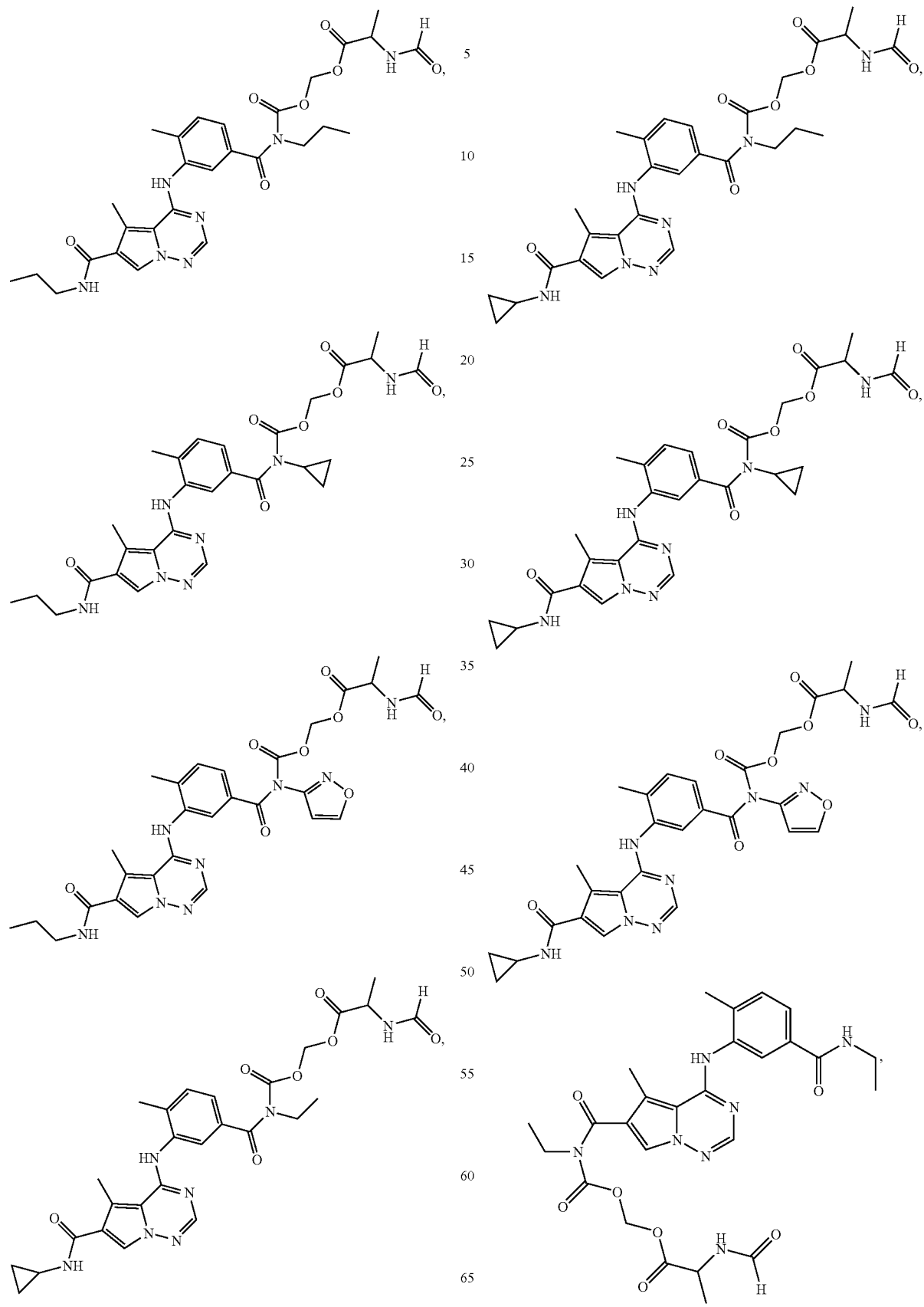

113
-continued
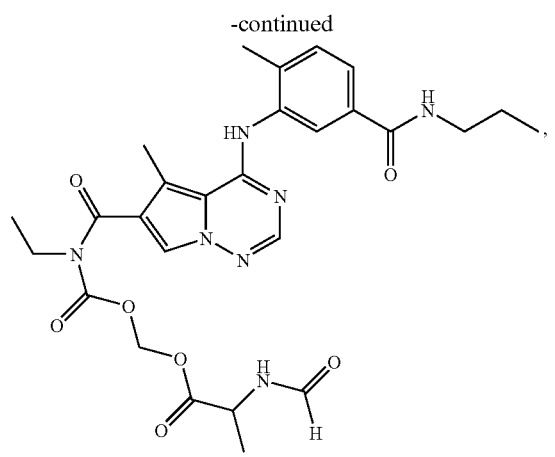
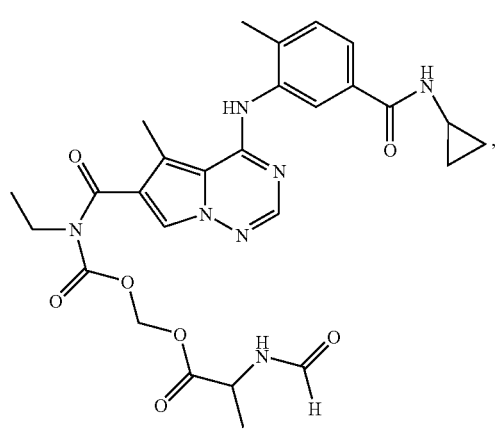
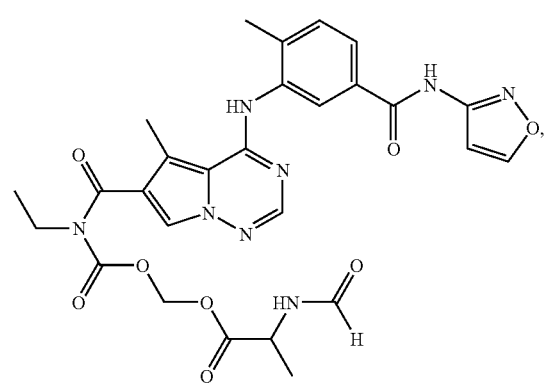
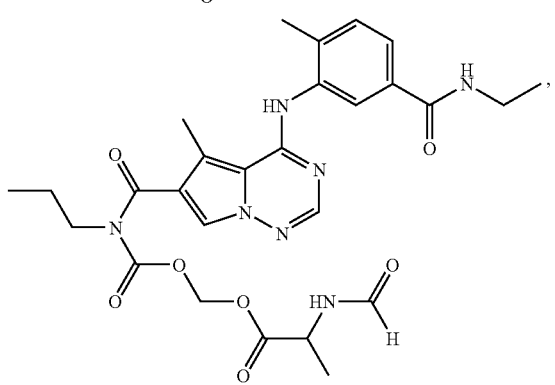
114
-continued
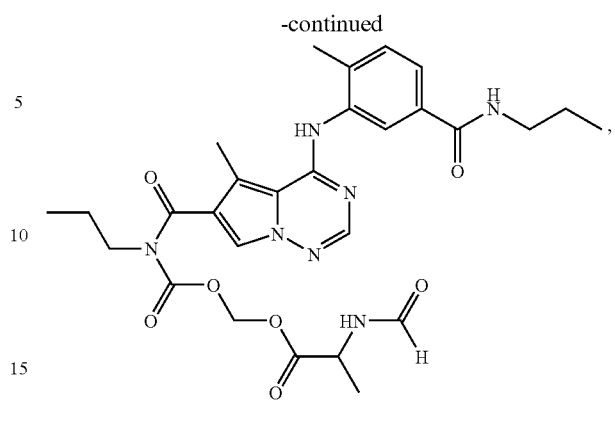
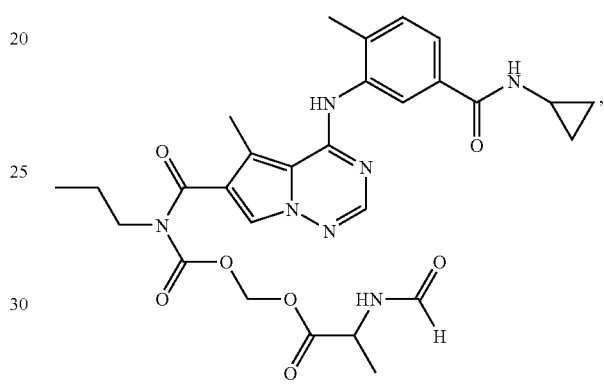
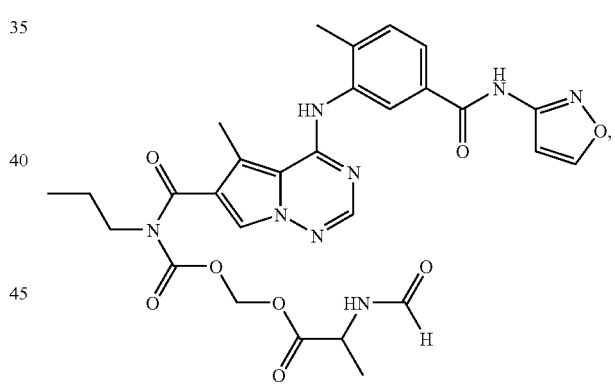
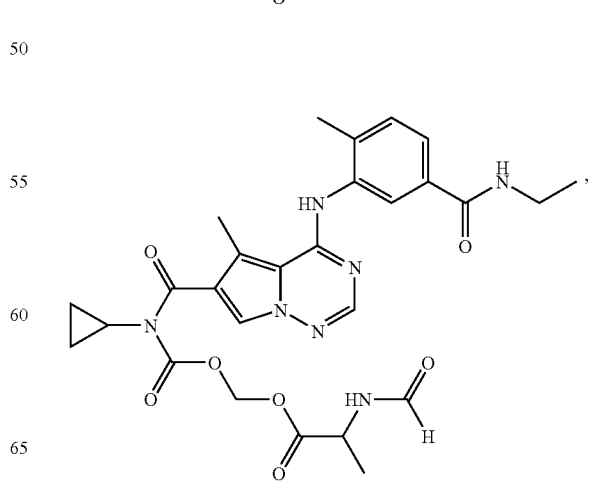

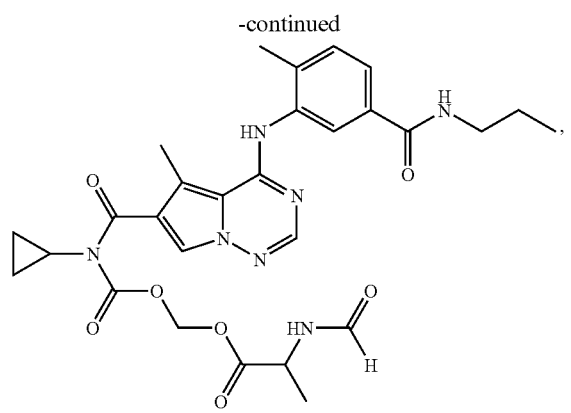
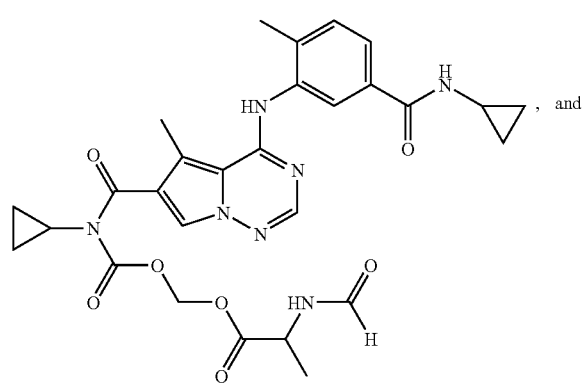, and
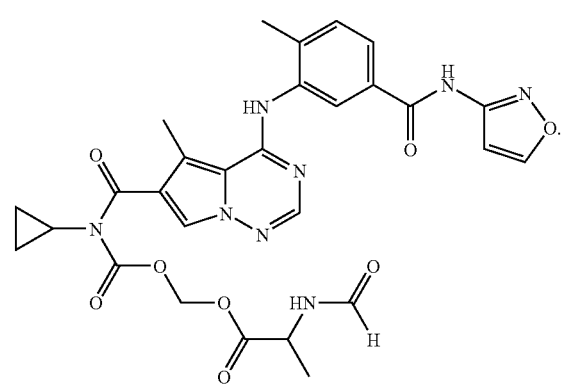
An embodiment of the present invention is for compounds, and salts thereof, selected from the group consisting of:
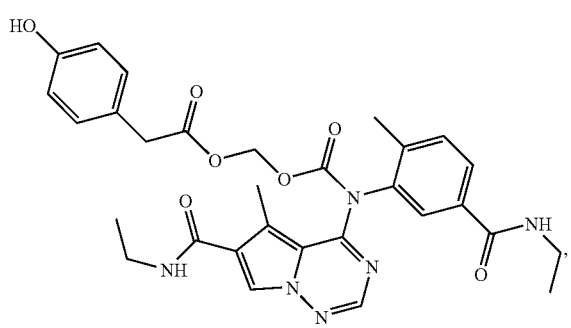
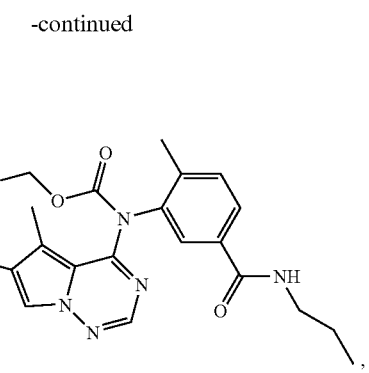
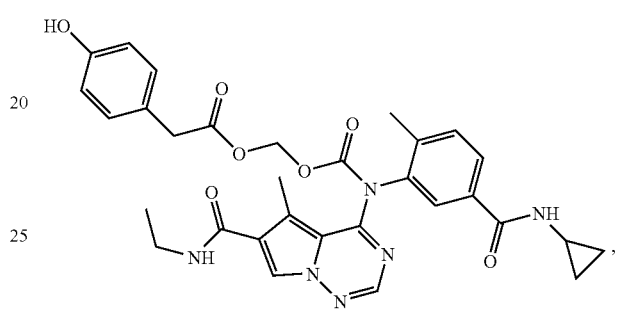
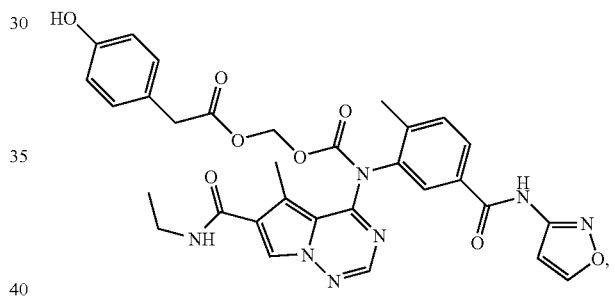
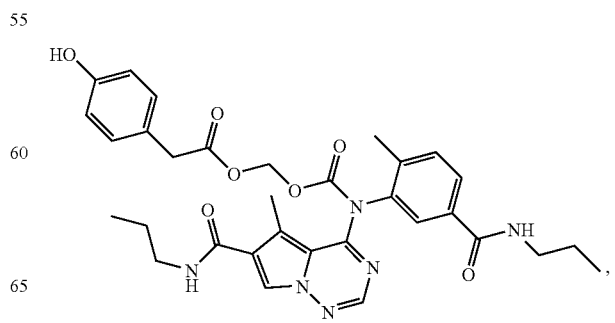

117
-continued
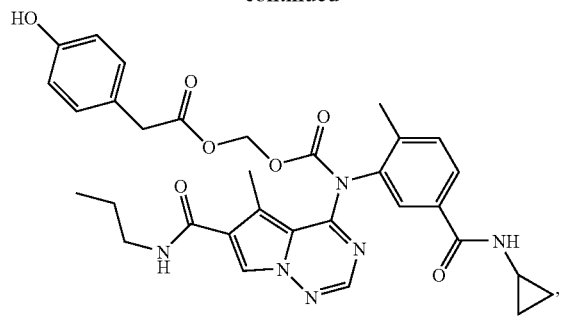
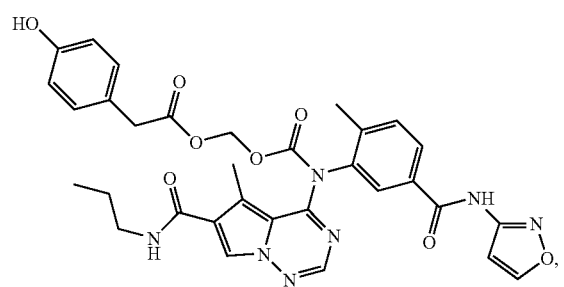
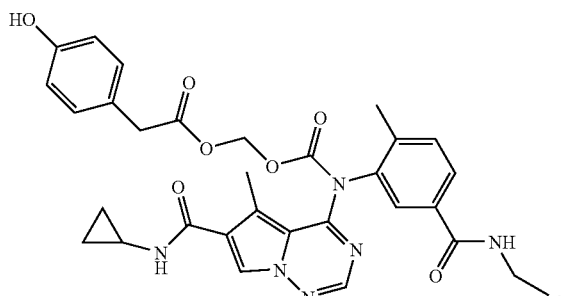
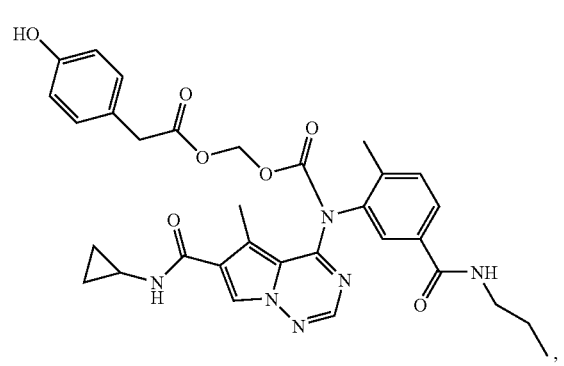
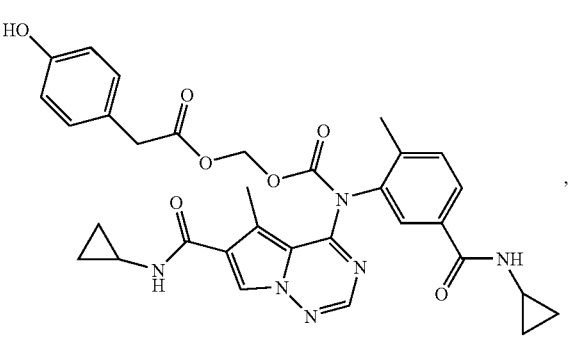
118
-continued
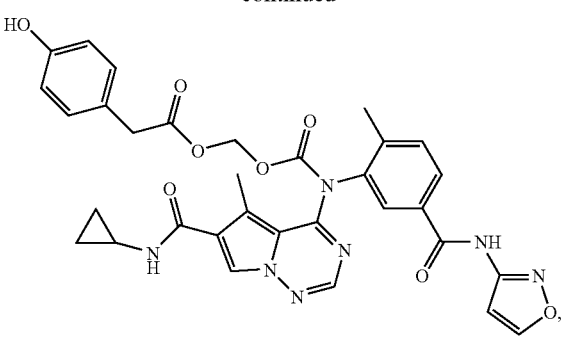
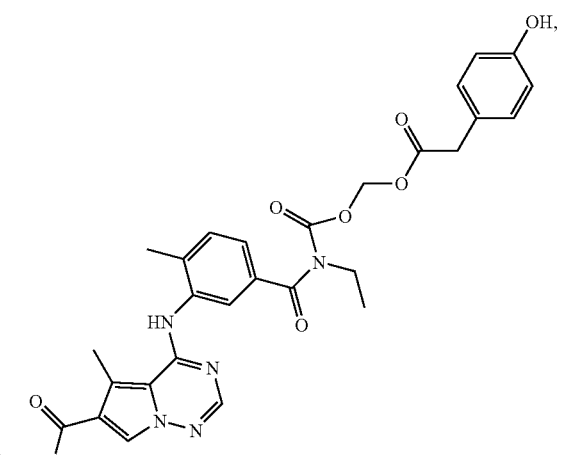
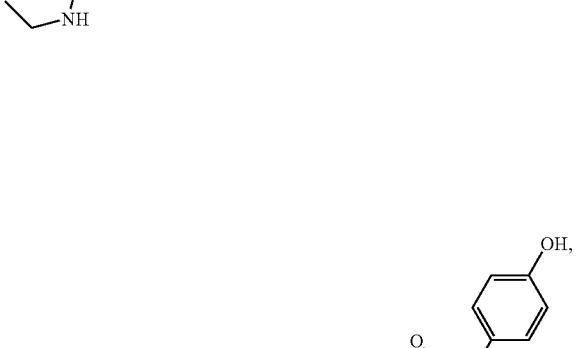
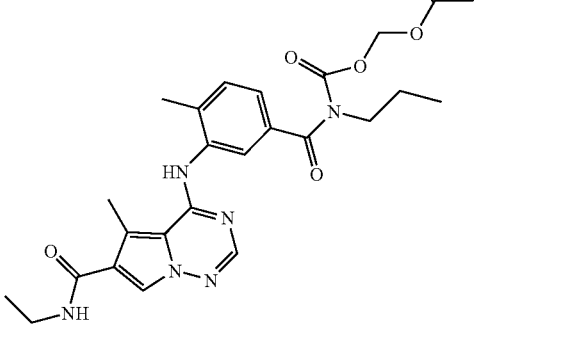

119
-continued
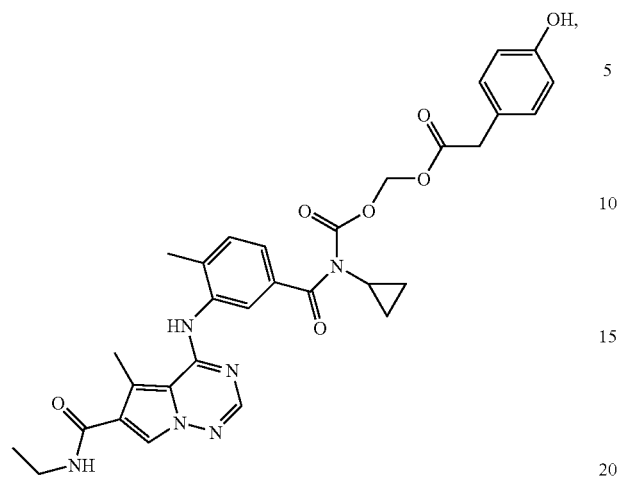
120
-continued
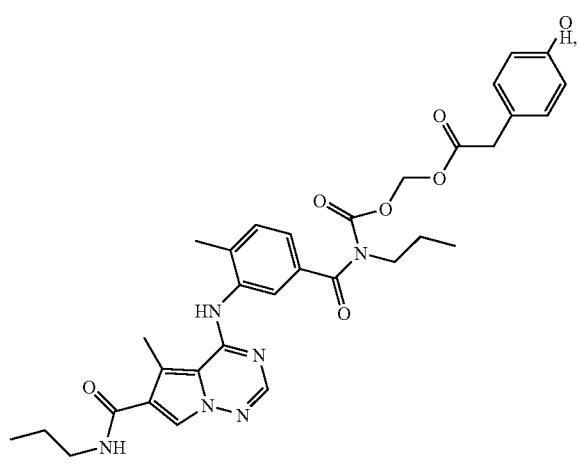
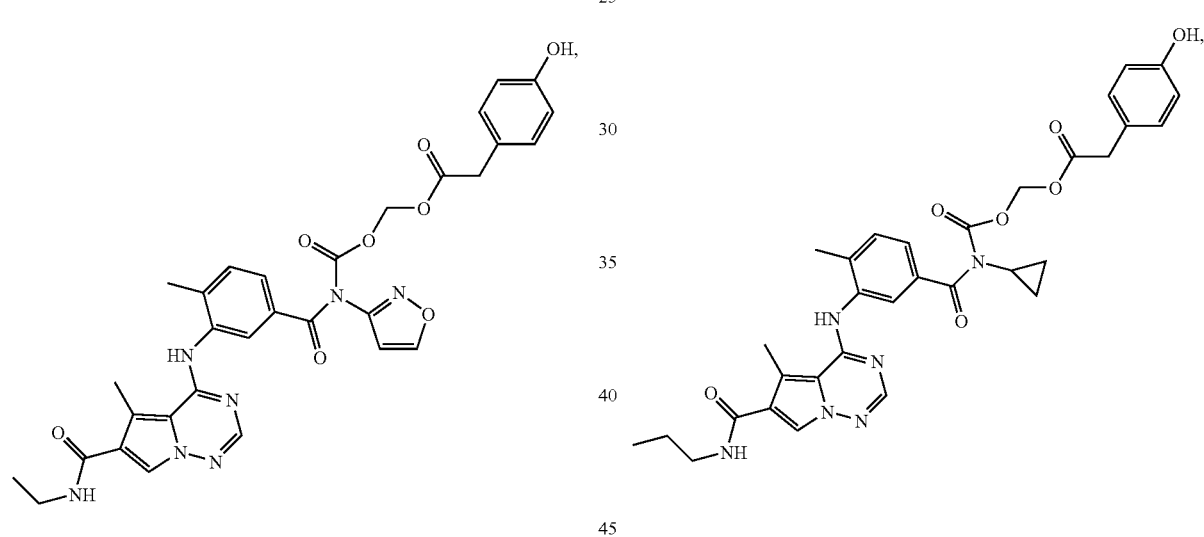
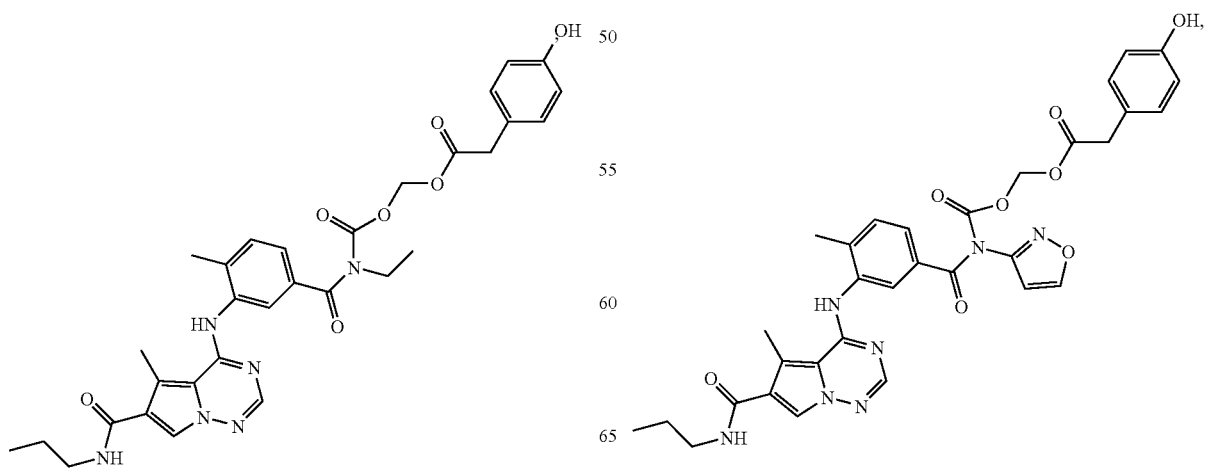

121
-continued
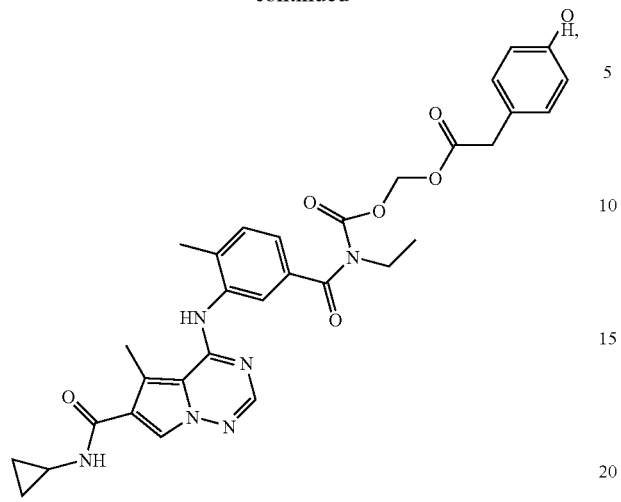
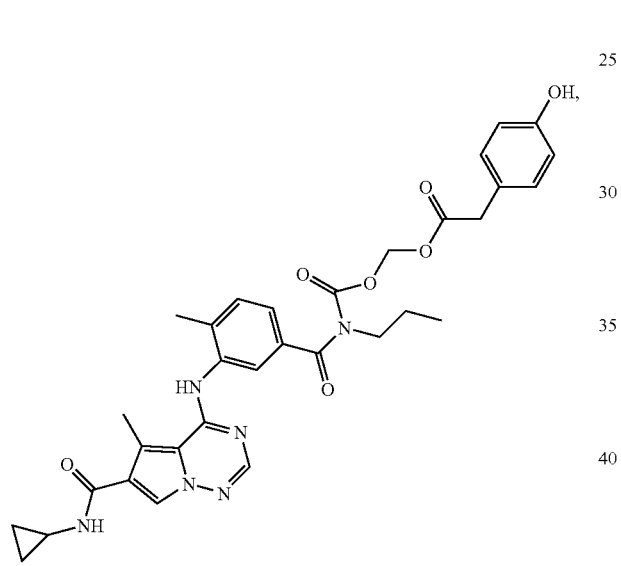
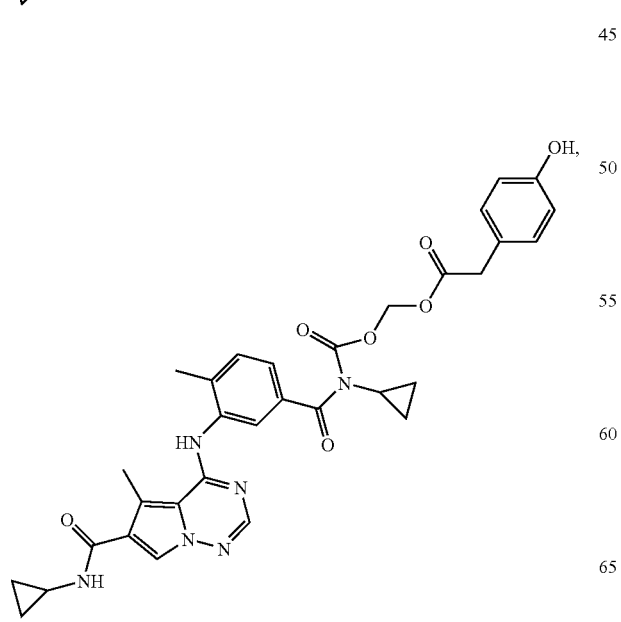
122
-continued
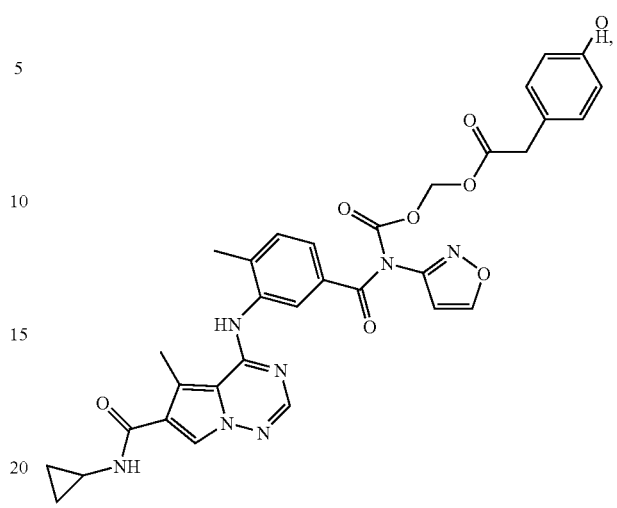
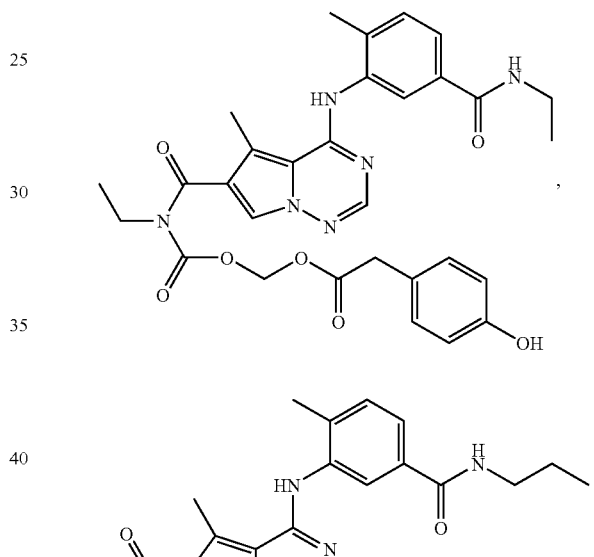
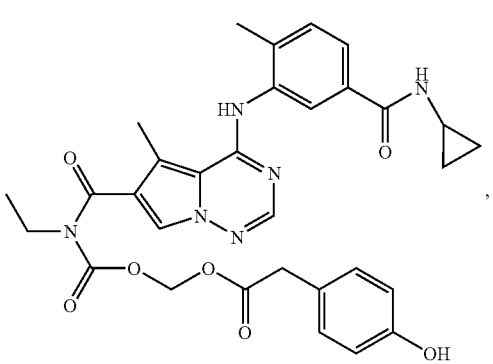

123
-continued
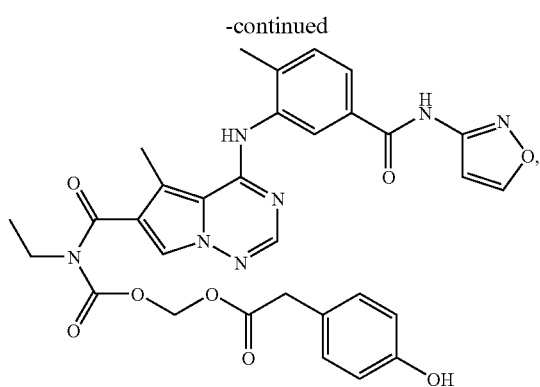
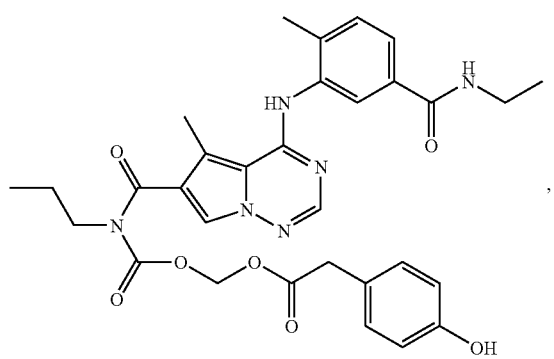
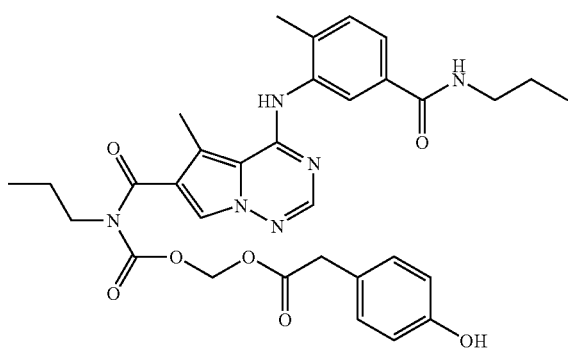
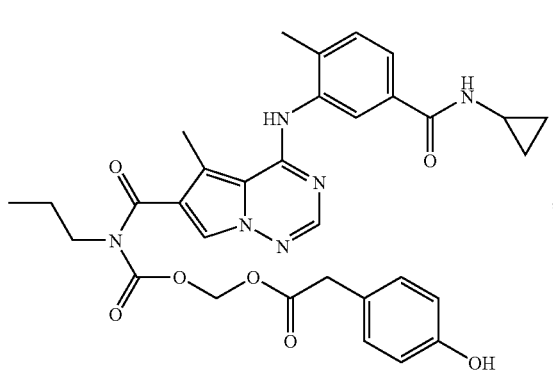
124
-continued
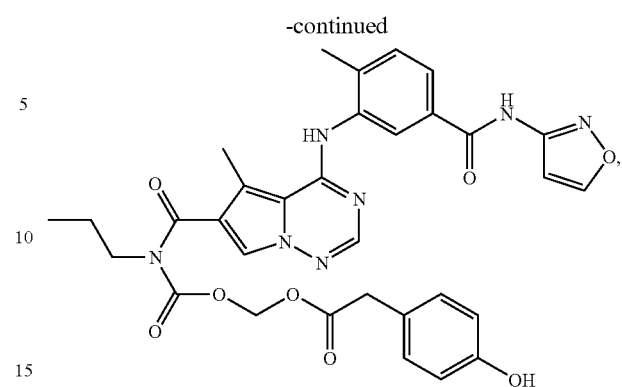
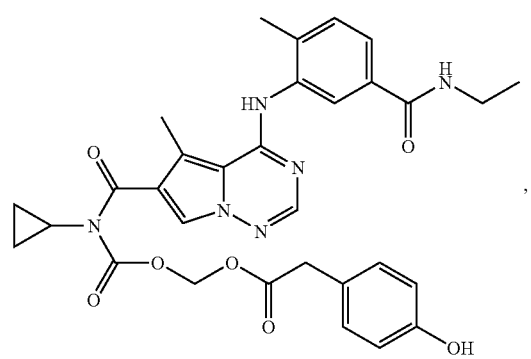
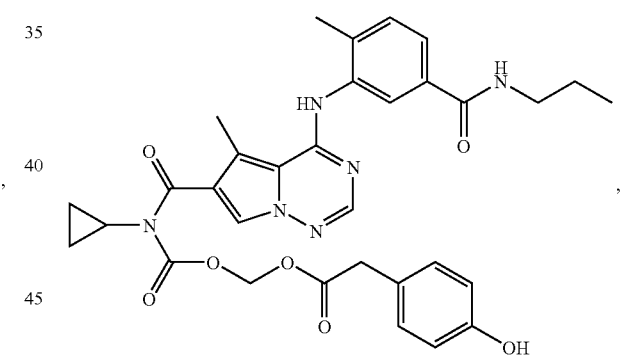
, and
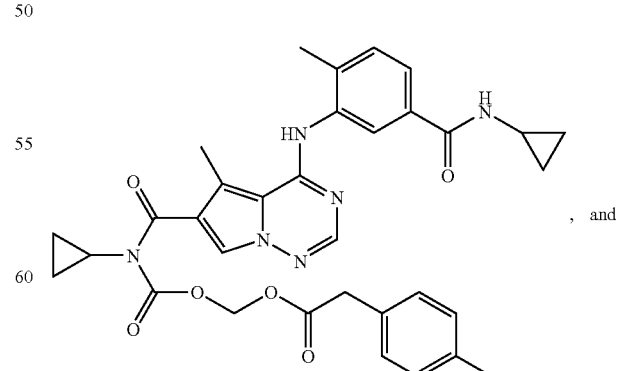

-continued
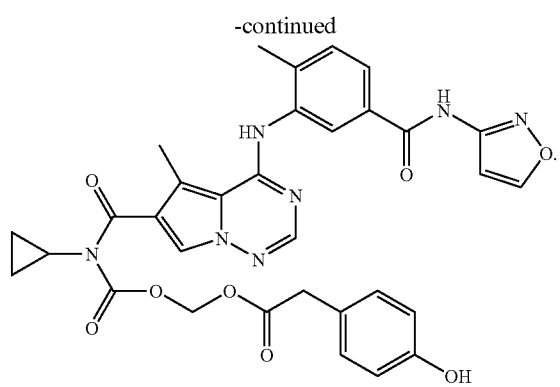
An embodiment of the present invention is for compounds, and salts thereof, selected from the group consisting of:
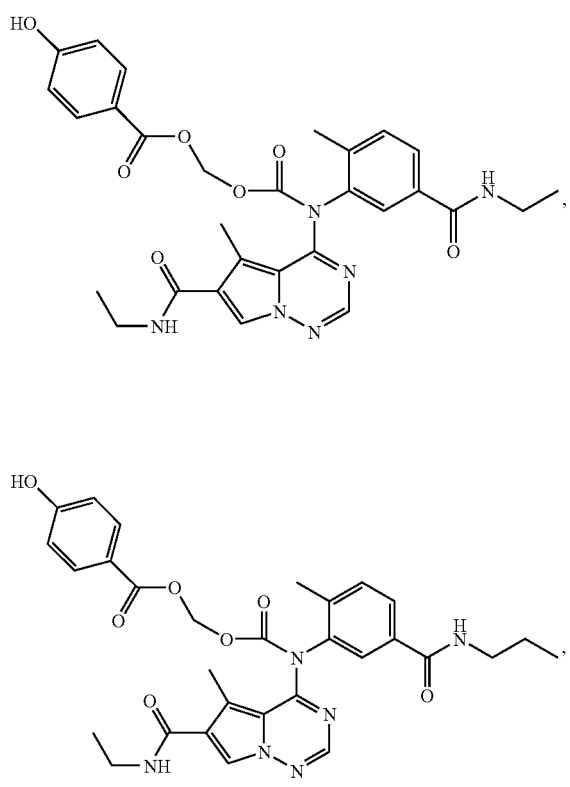
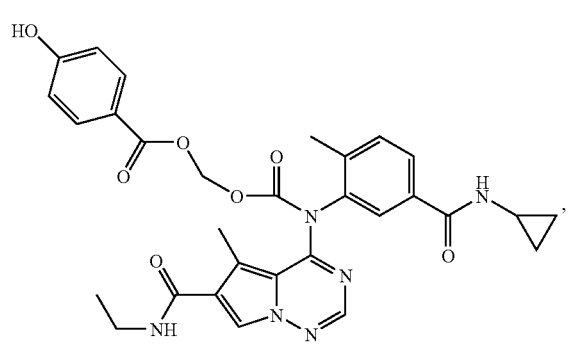
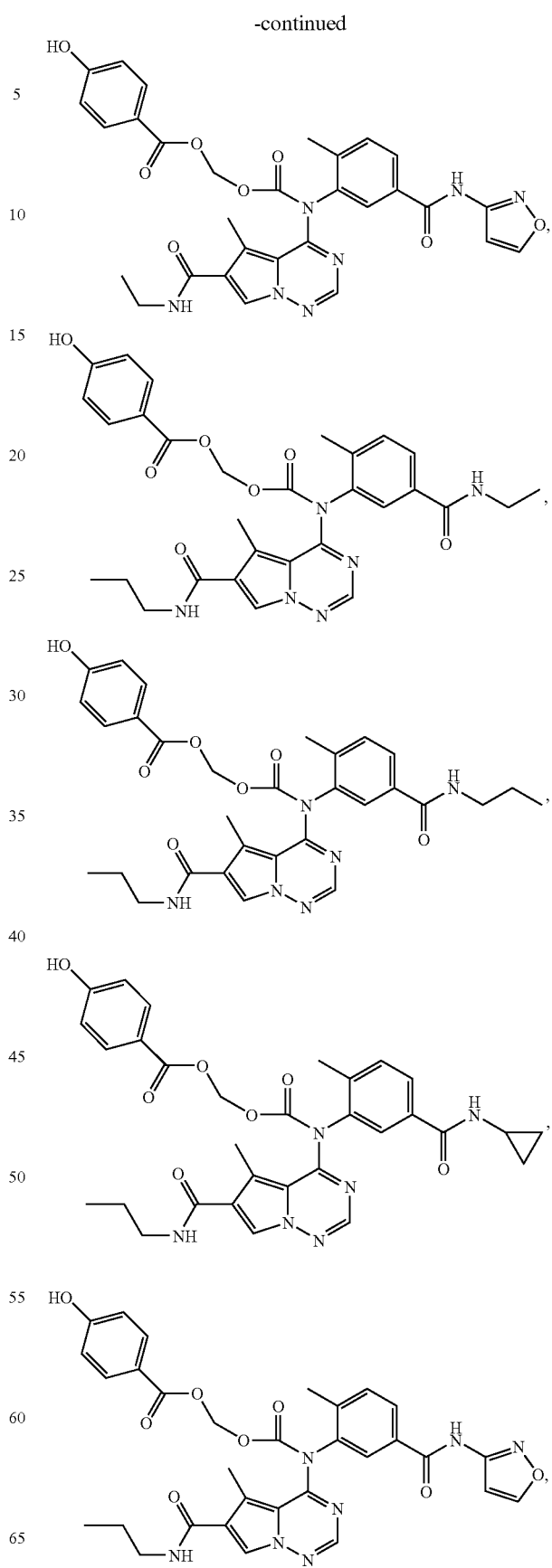
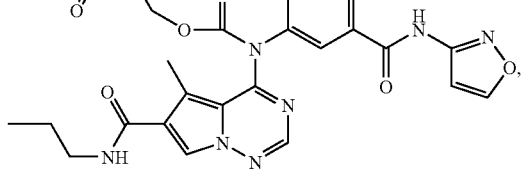

127
-continued
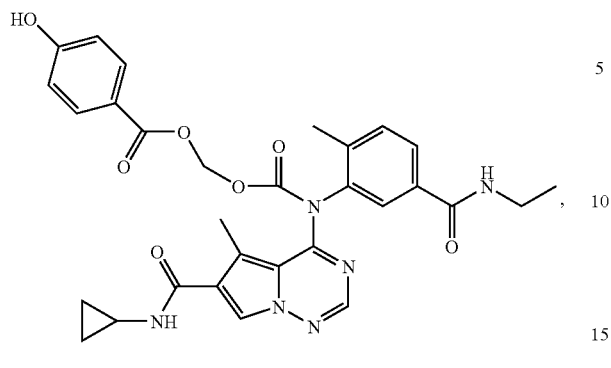
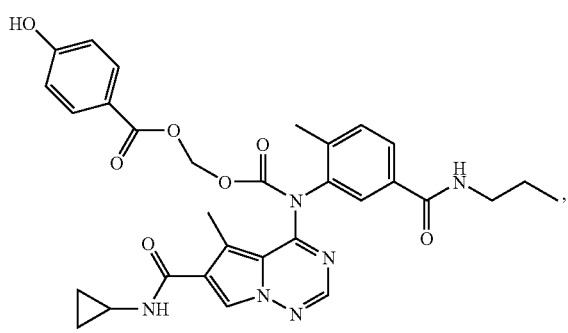
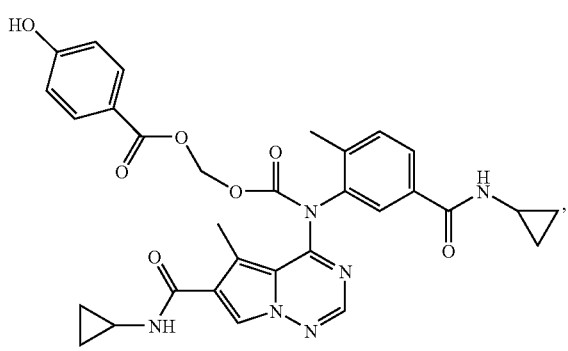
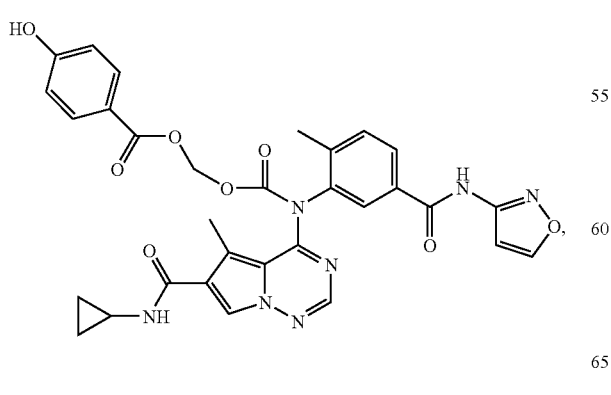
128
-continued
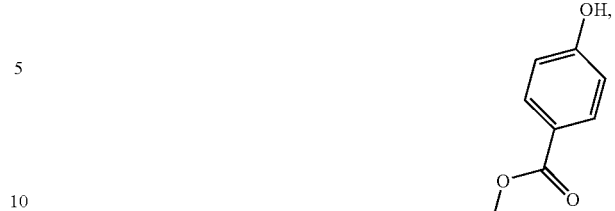
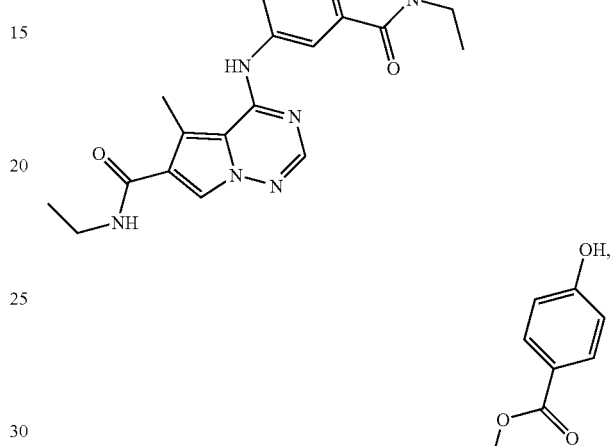
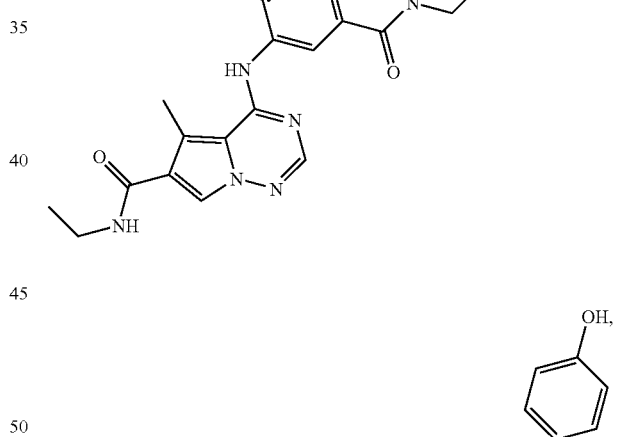
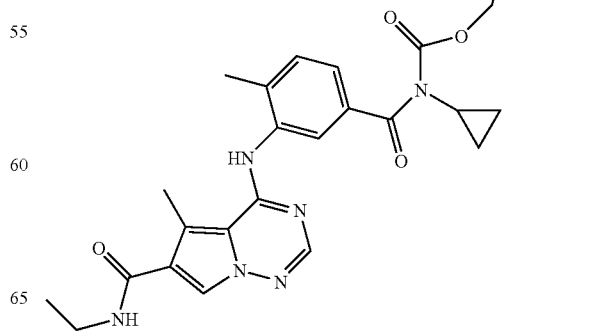

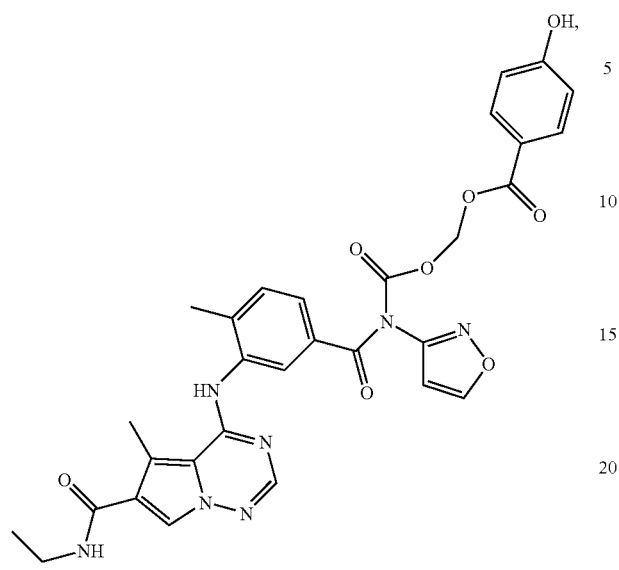
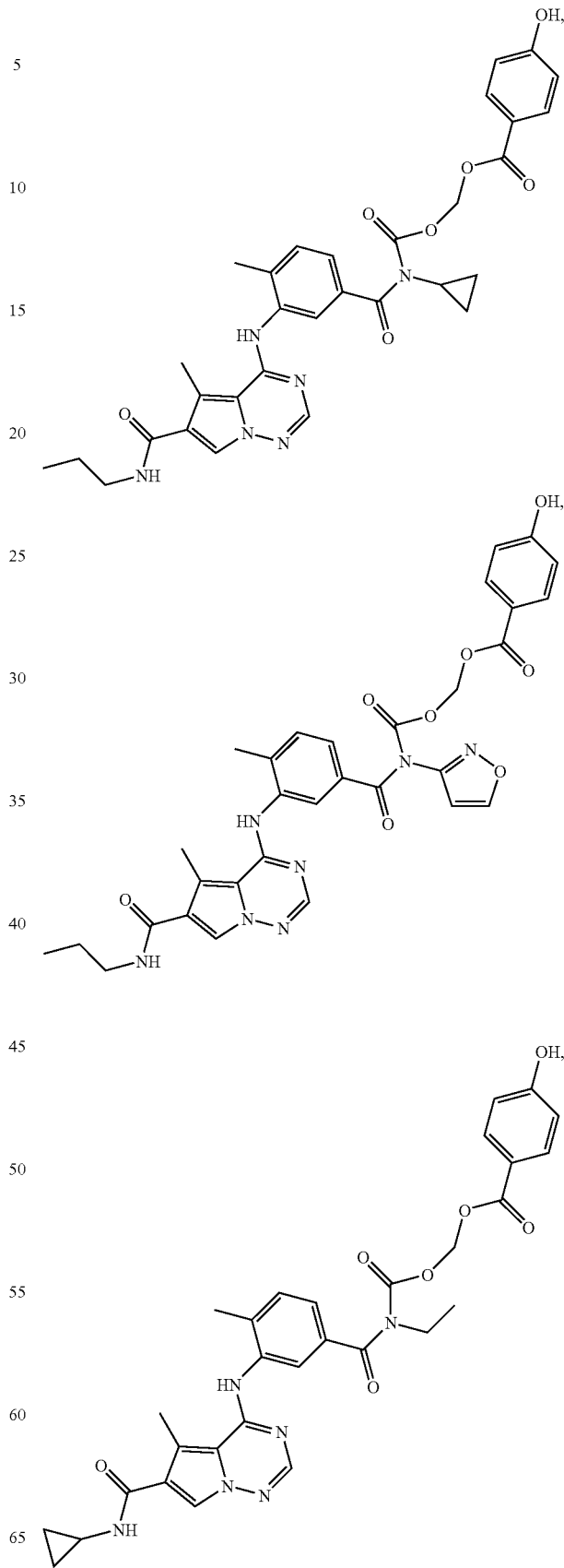

131
-continued
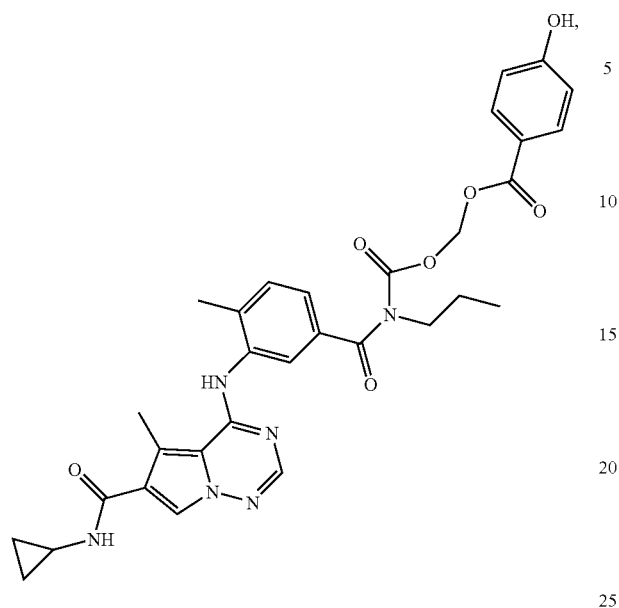
132
-continued
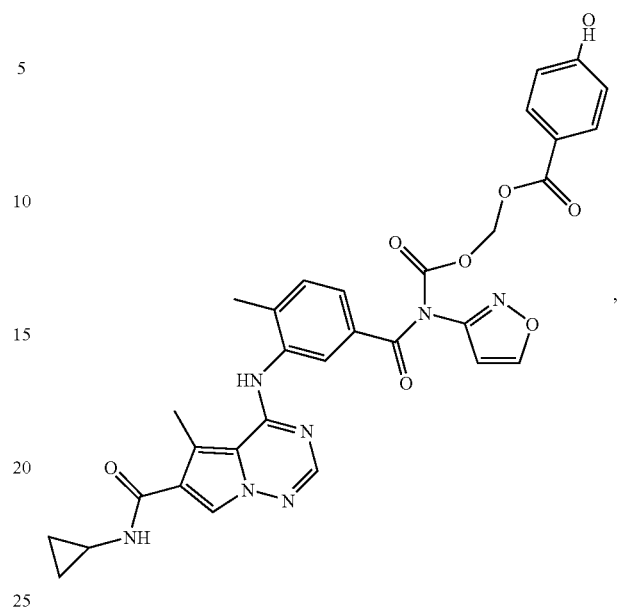
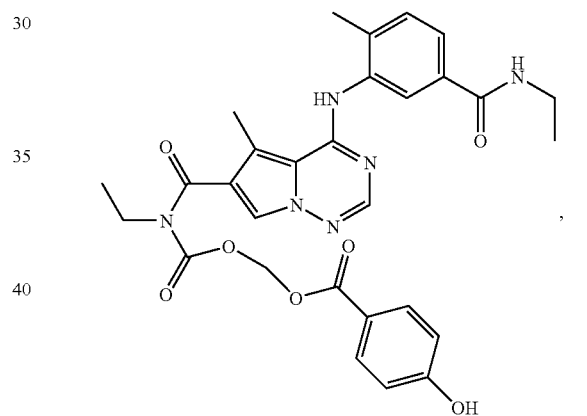
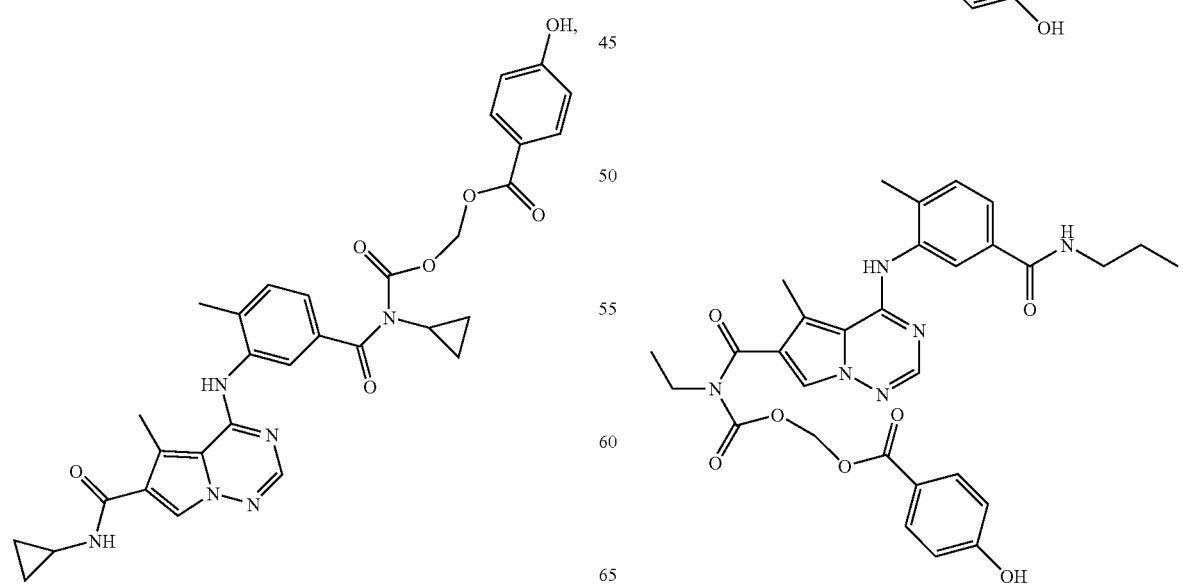

133
-continued
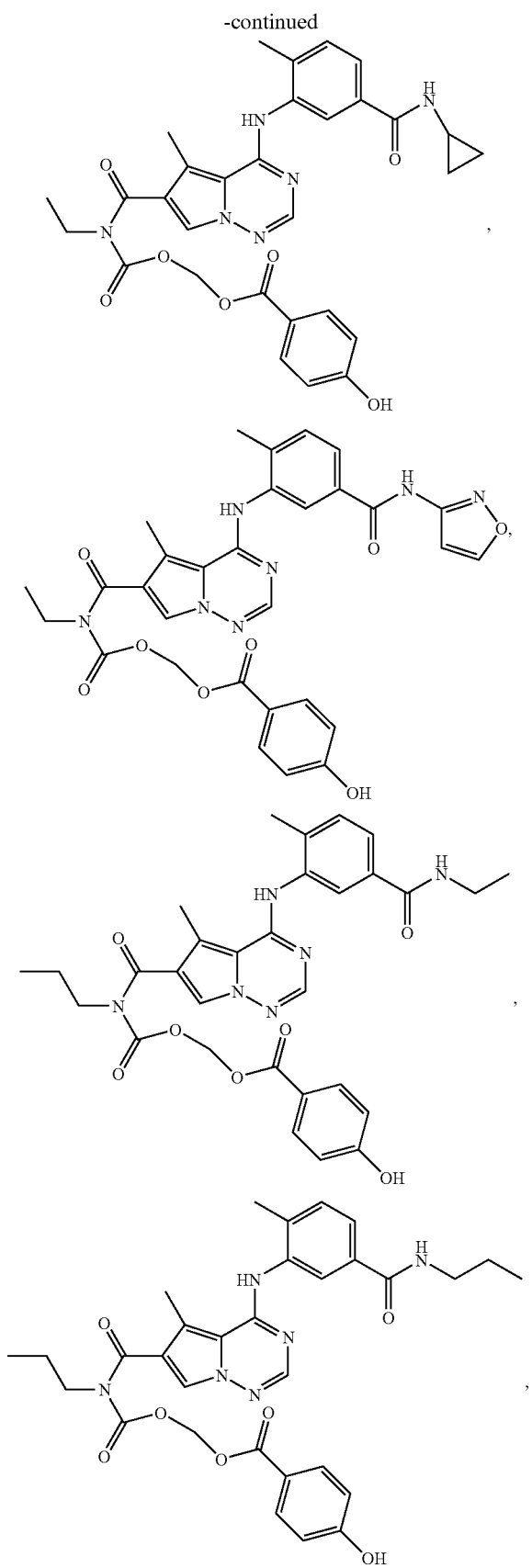
134
-continued
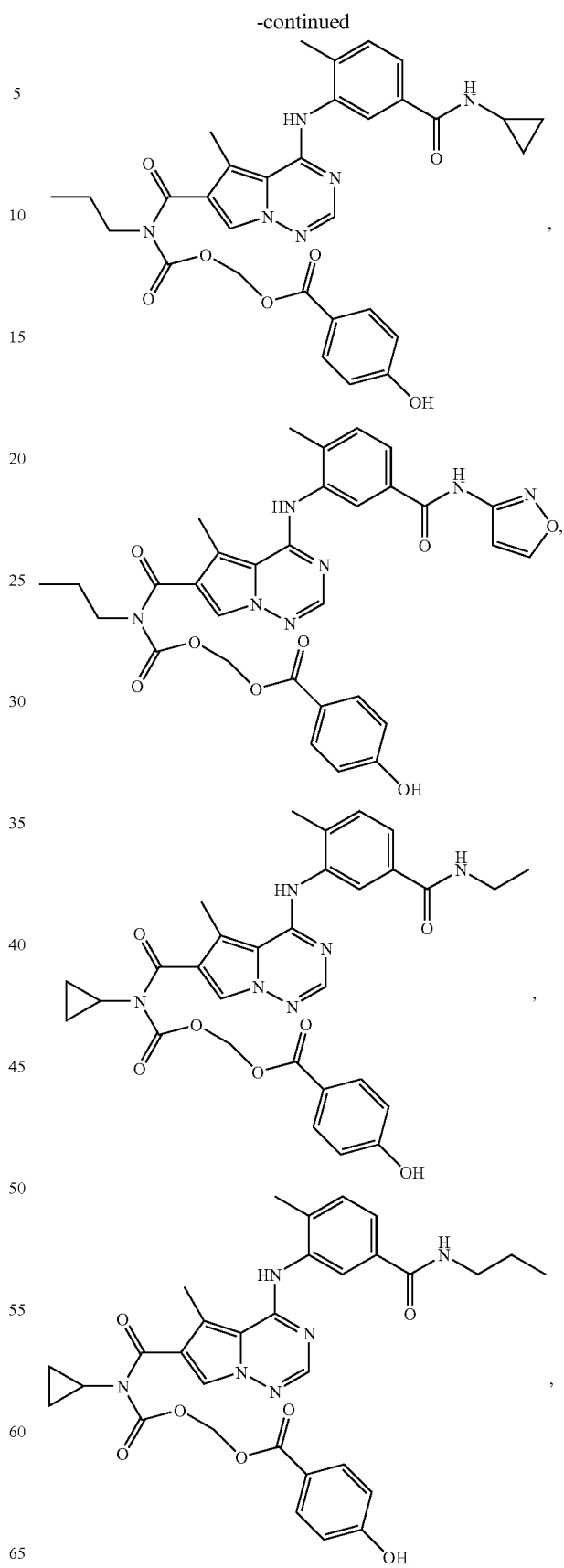

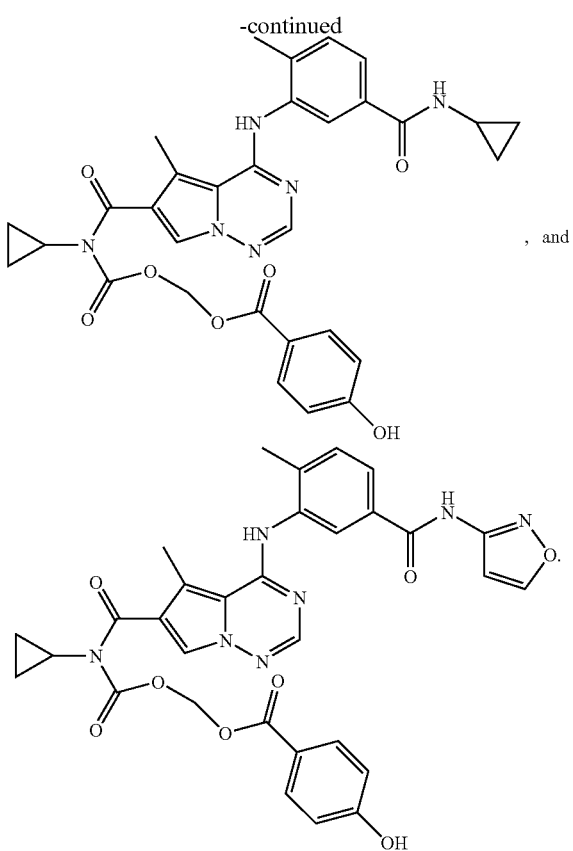, and

With the prodrug of the present disclosure, more of the drug will be absorbed and reach the target, and pill burden, cost to the patient and dosing intervals could be reduced. The following discussion will show that the prodrugs described in this invention work surprisingly well. They release parent drug quickly and efficiently and enhance the exposure to levels which are higher than reported for many prodrugs.

A successful prodrug strategy requires that a chemically reactive site in a molecule be modified via addition of the prodrug moiety and that later, under the desired conditions in the patients, the prodrug moiety will unmask and release parent drug. The prodrug molecule must have suitable stability in an acceptable dosage form prior to dosing. In addition, the release mechanism must allow the prodrug to regenerate parent drug efficiently and with kinetics that provide therapeutic levels of parent drug at the disease target.

Definitions

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms. When a subscript is used with reference to an alkyl or other group, the subscript refers to the number of carbon atoms that the group may contain. For example, the term "$C_{0-4}$alkyl" includes a bond and alkyl groups of 1 to 4 carbon atoms.

The term "substituted alkyl" refers to an alkyl group substituted by one to four substituents selected from halogen, hydroxy, alkoxy, keto (C=O), alkanoyl, aryloxy, alkanoyloxy, $NR_aR_b$, alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, —$SO_2NR_aR_b$, nitro, cyano, —$CO_2H$, —$CONR_aR_b$, alkoxycarbonyl, aryl, guanidino and heteroaryls or heterocyclos (such as indolyl, imidazolyl, furyl, thienyl, thiazolyl, pyrrolidyl, pyridyl, pyrimidyl and the like), wherein $R_a$ and $R_b$ are selected from hydrogen, alkyl, aryl, aralkyl, cycloalkyl, cycloalkylalkyl, heteroaryl, heteroarylalkyl, heterocycle, and heterocyclealkyl. The substituent on the alkyl optionally in turn may be further substituted, in which case it will be with substituted one or more of $C_{1-4}$alkyl, $C_{2-4}$alkenyl, halogen, haloalkyl, haloalkoxy, cyano, nitro, amino, $C_{1-4}$alkylamino, amino$C_{1-4}$alkyl, hydroxy, hydroxy$C_{1-4}$alkyl, alkoxy, alkylthio, phenyl, benzyl, phenyloxy, and/or benzyloxy.

The term "alkenyl" refers to straight or branched chain hydrocarbon groups of 2 to 20 carbon atoms, preferably 2 to 15 carbon atoms, and most preferably 2 to 8 carbon atoms, having at least one double bond, and depending on the number of carbon atoms, up to four double bonds.

The term "substituted alkenyl" refers to an alkenyl group substituted by one to two substituents selected from those recited above for substituted alkyl groups.

The term "alkynyl" refers to straight or branched chain hydrocarbon groups of 2 to 20 carbon atoms, preferably 2 to 15 carbon atoms, and most preferably 2 to 8 carbon atoms, having at least one triple bond, and depending on the number of carbon atoms, up to four triple bonds.

The term "substituted alkynyl" refers to an alkynyl group substituted by one to two substituents selected from those recited above for alkyl groups.

When the term alkyl is used in connection with another group, as in heterocycloalkyl or cycloalkylalkyl, this means the identified (first named) group is bonded directly through an alkyl group which may be branched or straight chain (e.g., cyclopropyl$C_{1-4}$alkyl means a cyclopropyl group bonded through a straight or branched chain alkyl group having one to four carbon atoms.). In the case of substituents, as in "substituted cycloalkylalkyl," the alkyl portion of the group, besides being branched or straight chain, may be substituted as recited above for substituted alkyl groups and/or the first named group (e.g., cycloalkyl) may be substituted as recited herein for that group.

The term "halogen" refers to fluorine, chlorine, bromine and iodine, and the term "halo" refers to fluoro, choro, bromo and iodo.

The term "aryl" refers to monocyclic or bicyclic aromatic substituted or unsubstituted hydrocarbon groups having 6 to 12 carbon atoms in the ring portion, such as phenyl, naphthyl, and biphenyl groups. Aryl groups may optionally include one to three additional rings (either cycloalkyl, heterocyclo or heteroaryl) fused thereto.

Examples include:

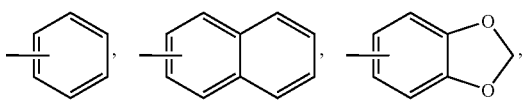

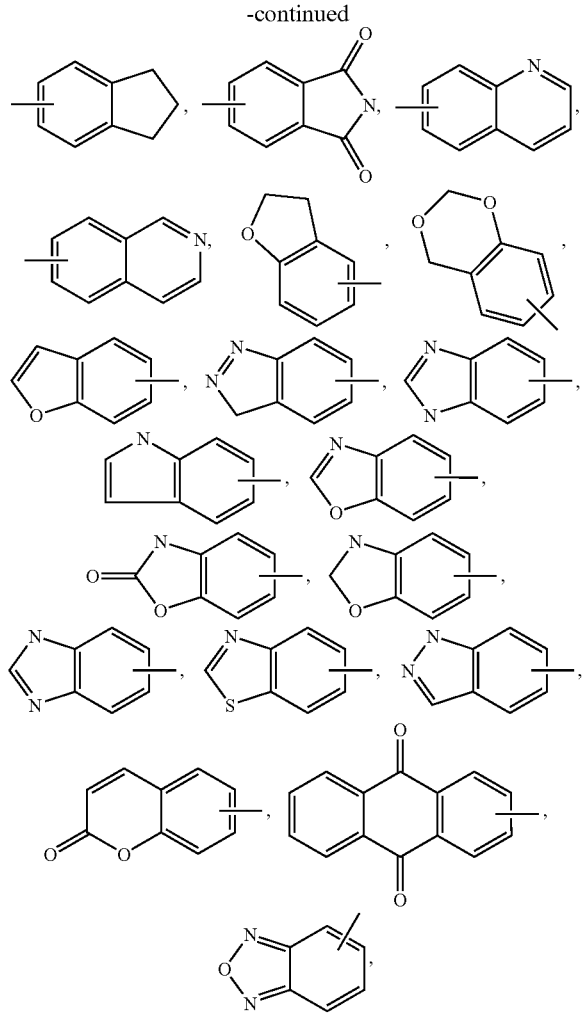

and the like. Each ring of the aryl may be optionally substituted with one to three $R_c$ groups, wherein $R_c$ at each occurrence is selected from alkyl, substituted alkyl, halogen, trifluoromethoxy, trifluoromethyl, —SR, —OR, —NRR', —NRSO$_2$R', —SO$_2$R, —SO$_2$NRR', —CO$_2$R', —C(=O)R', —C(=O)NRR', —OC(=O)R', —OC(=O)NRR', —NRC(=O)R', —NRCO$_2$R', phenyl, $C_{3-7}$ cycloalkyl, and five-to-six membered heterocyclo or heteroaryl, wherein each R and R' is selected from hydrogen, alkyl, substituted alkyl, alkenyl, substituted alkenyl, phenyl, $C_{3-7}$cycloalkyl, and five-to-six membered heterocyclo or heteroaryl, except in the case of a sulfonyl group, then R is not going to be hydrogen. Each substituent $R_c$ optionally in turn may be further substituted by one or more (preferably β to 2) $R_d$ groups, wherein $R_d$ is selected from $C_{1-6}$alkyl, $C_{2-6}$alkenyl, halogen, haloalkyl, haloalkoxy, cyano, nitro, amino, $C_{1-4}$alkylamino, amino$C_{1-4}$alkyl, hydroxy, hydroxy$C_{1-4}$alkyl, alkoxy, alkylthio, phenyl, benzyl, phenylethyl, phenyloxy, and benzyloxy.

The term "aralkyl" refers to an aryl group bonded directly through an alkyl group, such as benzyl, wherein the alkyl group may be branched or straight chain. In the case of a "substituted aralkyl," the alkyl portion of the group besides being branched or straight chain, may be substituted as recited above for substituted alkyl groups and/or the aryl portion may be substituted as recited herein for aryl. Thus, the term "optionally substituted benzyl" refers to the group

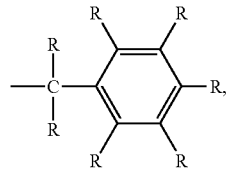

wherein each R group may be hydrogen or may also be selected from $R_c$ as defined above, in turn optionally substituted with one or more $R_d$. At least two of these "R" groups should be hydrogen and preferably at least five of the "R" groups is hydrogen. A preferred benzyl group involves the alkyl-portion being branched to define

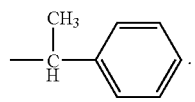

The term "heteroaryl" refers to a substituted or unsubstituted aromatic group for example, which is a 4 to 7 membered monocyclic, 7 to 11 membered bicyclic, or 10 to 15 membered tricyclic ring system, which has at least one heteroatom and at least one carbon atom-containing ring. Each ring of the heteroaryl group containing a heteroatom can contain one or two oxygen or sulfur atoms and/or from one to four nitrogen atoms, provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. It may optionally be substituted with one to three (preferably 0 to 2) $R_c$ groups, as defined above for aryl, which in turn may be substituted with one or more (preferably 0 to 2) $R_d$ groups, also as recited above.

Exemplary monocyclic heteroaryl groups include pyrrolyl, pyrazolyl, pyrazolinyl, imidazolyl, oxazolyl, isoxazolyl, thiazolyl (i.e., 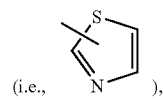 ), thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "cycloalkyl" refers to a saturated or partially unsaturated non-aromatic cyclic hydrocarbon ring system, preferably containing 1 to 3 rings and 3 to 7 carbon atoms per ring, which may be substituted or unsubstituted and/or which may be fused with a $C_3$-$C_7$ carbocylic ring, a heterocyclic ring, or which may have a bridge of 3 to 4 carbon atoms. The cycloalkyl groups including any available carbon or nitrogen atoms on any fused or bridged rings optionally may have 0 to 3 (preferably 0-2) substituents selected from $R_c$ groups, as recited above, and/or from keto (where appropriate) which in turn may be substituted with one to three $R_d$ groups, also as recited above. Thus, when it is stated that a carbon-carbon bridge may be optionally substituted, it is meant that the carbon atoms in the bridged ring optionally may be substituted with an $R_c$ group, which preferably is seleted from $C_{1-4}$alkyl, $C_{2-4}$alkenyl, halogen, haloalkyl, haloalkoxy, cyano, amino, $C_{1-4}$alkylamino, amino$C_{1-4}$alkyl, hydroxy, hydroxy$C_{1-4}$alkyl, and $C_{1-4}$alkoxy. Exemplary cycloalkyl groups include cyclopropyl, cyclobutyl, cyclopentyl, cyclohexyl, cycloheptyl, bicycloheptane, cycloctyl, cyclodecyl, cyclododecyl, and adamantyl.

The terms "heterocycle", "heterocyclic" and "heterocyclo" each refer to a fully saturated or partially unsaturated nonaromatic cyclic group, which may be substituted or unsubstituted, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen, oxygen, and sulfur atoms, where the nitrogen and sulfur heteroatoms also optionally may be oxidized and the nitrogen heteroatoms also optionally may be quatemized. Preferably two adjacent heteroatoms are not simultaneously selected from oxygen and nitrogen. The heterocyclic group may be attached at any nitrogen or carbon atom. The heterocyclo groups optionally may have 0 to 3 (preferably 0-2) substituents selected from keto (C=O), and/ or one or more $R_c$ groups, as recited above, which in turn may be substituted with one to three $R_d$ groups, also as recited above.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic hetrocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Also included are smaller heterocyclos, such as epoxides and aziridines.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., indolyl), the reference is intended to include rings having 0 to 3, preferably 0-2, substituents selected from those recited above for the the aryl, cycloalkyl, heterocyclo and/or heteroaryl groups, as appropriate. Additionally, when reference is made to a specific heteroaryl or heterocyclo group, the reference is intended to include those systems having the maximum number of non-cumulative double bonds or less than the maximum number of double bonds. Thus, for example, the term "isoquinoline" refers to isoquinoline and tetrahydroisoquinoline.

Additionally, it should be understood that one skilled in the field may make appropriate selections for the substituents for the aryl, cycloalkyl, heterocyclo, and heteroaryl groups to provide stable compounds and compounds useful as pharmaceutically-acceptable compounds and/or intermediate compounds useful in making pharmaceutically-acceptable compounds. Thus, for example, in compounds of formula (I), when B is a cyclopropyl ring, preferably the ring has no more than two substituents, and preferably said substituents do not comprise nitro ($NO_2$), more than one cyano group, or three halogen groups. Similarly, when m is 3, preferably $R^6$, the substituents on the phenyl ring A, are not all nitro, and so forth.

The term "heteroatoms" shall include oxygen, sulfur and nitrogen.

The term "haloalkyl" means an alkyl having one or more halo substituents.

The term "perfluoromethyl" means a methyl group substituted by one, two, or three fluoro atoms, i.e., $CH_2F$, $CHF_2$ and $CF_3$. The term "perfluoroalkyl" means an alkyl group having from one to five fluoro atoms, such as pentafluoroethyl.

The term "haloalkoxy" means an alkoxy group having one or more halo substituents. For example, "haloalkoxy" includes —$OCF_3$.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Definitions for the various other groups that are recited above in connection with substituted alkyl, substituted alkenyl, aryl, cycloalkyl, and so forth, are as follows: alkoxy is —$OR^e$, alkanoyl is —$C(=O)R^e$, aryloxy is —OAr, alkanoyloxy is —$OC(=O)R^e$, amino is —$NH_2$, alkylamino is —$NHR^e$ or —$N(R^e)_2$, arylamino is —NHAr or —$NR^eAr$, aralkylamino is —NH—$R^f$—Ar, alkanoylamino is —NH—$C(=O)R^e$, aroylamino is —NH—C(=O)Ar, aralkanoylamino is —NH—$C(=O)R^f$—Ar, thiol is —SH, alkylthio is —$SR^e$, arylthio is —SAr, aralkylthio is —S—$R^f$—Ar, alkylthiono is —$S(=O)R^e$, arylthiono is —S(=O)Ar, aralkylthiono is —$S(=O)R^f$—Ar, alkylsulfonyl is —$SO_{(q)}R^e$, arylsulfonyl is —$SO_{(q)}Ar$, arylsulfonylamine is —$NHSO_{(q)}Ar$, alkylsulfonylamine is —$NHSO_2R^e$, aralkylsulfonyl is —$SO_{(q)}$ $R^fAr$, sulfonamido is —$SO_2NH_2$, substituted sulfonamide is —$SO_2NHR^e$ or —$SO_2N(R^e)_2$, nitro is —$NO_2$, carboxy is —CO$_2$H, carbamyl is —CONH$_2$, substituted carbamyl is —C(=O)NHR$^g$ or —C(=O)NR$^g$R$^h$, alkoxycarbonyl is —C(=O)OR$^e$, carboxyalkyl is —R$^f$—CO$_2$H, sulfonic acid is —SO$_3$H, arylsulfonylamine is —NHSO$_{(q)}$Ar, guanidino is

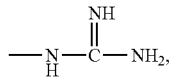

and ureido is

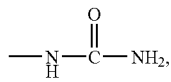

wherein R$^e$ is alkyl or substituted alkyl as defined above, R$^f$ is alkylene or substituted alkylene as defined above, R$^g$ and R$^h$ are selected from alkyl, substituted alkyl, aryl, aralkyl, cycloalkyl, heterocyclo, and heteraryl; Ar is an aryl as defined above, and q is 2 or 3.

Throughout the specification, groups and substituents thereof may be chosen by one skilled in the field to provide stable moieties and compounds.

The compounds of the present invention may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of the present invention may form salts with alkali metal hydroxides such as sodium hydroxide, potassium hydroxide and lithium hydroxide; with alkaline earth metal hydroxides such as calcium hydroxide and magnesium hydroxide; with organic bases such as triethanolamine, tributylamine and pyridine triethanolamine; and with amino acids such as arginine, lysine and the like. Such salts can be formed as known to those skilled in the art.

The compounds of the present invention may form salts with a variety of organic and inorganic acids and bases. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art. Salt forms of the compounds may be advantageous for improving the compound dissolution rate and oral bioavailability.

In addition, zwitterions ("inner salts") may be formed.

All stereoisomers of the compounds of the instant invention are contemplated, either in a mixture or in pure or substantially pure form. The definition of compounds according to the invention embraces all the possible stereoisomers and their mixtures. It embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

It is generally known in the art that any compound that will be converted in vivo to provide the bioactive agent or parent (i.e., the compound for formula I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, 8, pp. 1-38 (1992), each of which is incorporated herein by reference.

It should further be understood that solvates (e.g., hydrates) of the compounds of Formula I are also with the scope of the present invention. Methods of solvation are generally known in the art.

Utility

The compounds of the invention are prodrugs that release selective inhibitors of p38 kinase activity, and in particular, isoforms p38α and p38β. Accordingly, compounds of formula (I) have utility in treating conditions associated with p38 kinase activity. Such conditions include diseases in which cytokine levels are modulated as a consequence of intracellular signaling via p38, and in particular, diseases that are associated with an overproduction of cytokines IL-1, IL-4, IL-8, and TNF-α. As used herein, the terms "treating" or "treatment" encompass either or both responsive and prophylaxis measures, e.g. measures designed to inhibit or delay the onset of the disease or disorder, achieve a full or partial reduction of the symptoms or disease state, and/or to alleviate, ameliorate, lessen, or cure the disease or disorder and/or its symptoms. When reference is made herein to inhibition of "p-38α/β kinase," this means that either p38α and/or p38β kinase are inhibited. Thus, reference to an IC$_{50}$ value for inhibiting p-38α/β kinase means that the compound has such effectiveness for inhibiting at least one of, or both of, p38α and p38β kinases.

In view of their utility as prodrugs that release inhibitors of p-38α/β kinase activity, the compounds of Formula (I) are useful in treating p-38 associated conditions including, but not limited to, inflammatory diseases, autoimmune diseases, destructive bone disorders, proliferative disorders, angiogenic disorders, infectious diseases, neurodegenerative diseases, and viral diseases.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, ankylosing spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, myeloid formation, scar tissue formation, ulcerative colitis, pyresis, influenza, osteoporosis, osteoarthritis and multiple myeloma-related bone disorder, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, and conditions associated with prostaglandin endoperoxidase syndase-2.

In addition, p38 inhibitors of this invention inhibit the expression of inducible pro-inflammatory proteins such as prostaglandin endoperoxide synthase-2 (PGHS-2), also referred to as cyclooxygenase-2 (COX-2). Accordingly, additional p38-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "p38 associated condition" or "p38 associated disease or disorder" are used herein, each is intended to encompass all of the conditions identified above as if repeated at length, as well as any other condition that is affected by p38 kinase activity.

The present invention thus provides methods for treating such conditions, comprising administering to a subject in need thereof an effective amount of at least one compound of Formula (I) or a salt thereof. The methods of treating p38 kinase-associated conditions may comprise administering compounds of Formula (I) alone or in combination with each other and/or other suitable therapeutic agents useful in treating such conditions. Exemplary of such other therapeutic agents include corticosteroids, rolipram, calphostin, CSAIDs, 4-substituted imidazo [1,2-A]quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The present invention also provides pharmaceutical compositions capable of treating p38-kinase associated conditions, including TNF-α, IL-1, and/or IL-8 mediated conditions, as described above. The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrastemal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of p38 enzyme levels.

Compounds of formula (I), including the compounds described in the examples hereof, have been tested in one or more of the assays described below and have shown activity as inhibitors of p38α/β enzymes and TNF-α.

Biological Assays

Generation of p38 Kinases cDNAs of human p38α, β and γ isozymes were cloned by PCR. These cDNAs were subcloned in the pGEX expression vector (Pharmacia). GST-p38 fusion protein was expressed in *E. Coli* and purified from bacterial pellets by affinity chromatography using glutathione agarose. p38 fusion protein was activated by incubating with constitutively active MKK6. Active p38 was separated from MKK6 by affinity chromatography. Constitutively active MKK6 was generated according to Raingeaud et al. [*Mol. Cell. Biol.*, 1247-1255 (1996)].

TNF-α Production by LPS-Stimulated PBMCs

Heparinized human whole blood was obtained from healthy volunteers. Peripheral blood mononuclear cells (PBMCs) were purified from human whole blood by Ficoll-Hypaque density gradient centrifugation and resuspended at a concentration of $5 \times 10^6$/ml in assay medium (RPMI medium containing 10% fetal bovine serum). 50 ul of cell suspension was incubated with 50 ul of test compound (4× concentration in assay medium containing 0.2% DMSO) in 96-well tissue culture plates for 5 minutes at RT. 100 ul of LPS (200 ng/ml stock) was then added to the cell suspension and the plate was incubated for 6 hours at 37° C. Following incubation, the culture medium was collected and stored at −20° C. TNF-α concentration in the medium was quantified using a standard ELISA kit (Pharmingen-San Diego, Calif.). Concentrations of TNF-α and $IC_{50}$ values for test compounds (concentration of compound that inhibited LPS-stimulated TNF-α production by 50%) were calculated by linear regression analysis.

p38 Assay

The assays were performed in V-bottomed 96-well plates. The final assay volume was 60 µl prepared from three 20 µl additions of enzyme, substrates (MBP and ATP) and test compounds in assay buffer (50 mM Tris pH 7.5, 10 mM $MgCl_2$, 50 mM NaCl and 1 mM DTT). Bacterially expressed, activated p38 was pre-incubated with test compounds for 10 min. prior to initiation of reaction with substrates. The reaction was incubated at 25° C. for 45 min. and terminated by adding 5 µl of 0.5 M EDTA to each sample. The reaction mixture was aspirated onto a pre-wet filtermat using a Skatron Micro96 Cell Harvester (Skatron, Inc.), then washed with PBS. The filtermat was then dried in a microwave oven for 1 min., treated with MeltilLex A scintillation wax (Wallac), and counted on a Microbeta scintillation counter Model 1450 (Wallac). Inhibition data were analyzed by nonlinear least-squares regression using Prizm (GraphPadSoftware). The final concentration of reagents in the assays are ATP, 1 µM; [γ-$^{33}$P]ATP, 3 nM; MBP (Sigma, #M1891), 2 µg/well; p38, 10 nM; and DMSO, 0.3%.

TNF-α Production by LPS-Stimulated Mice

Mice (Balb/c female, 6-8 weeks of age, Harlan Labs; n=8/treatment group) were injected intraperitoneally with 50 ug/kg lipopolysaccharide (LPS; *E coli* strain 0111:B4, Sigma) suspended in sterile saline. Ninety minutes later, mice were sedated by $CO_2:O_2$ inhalation and a blood sample was obtained. Serum was separated and analyzed for TNF-alpha concentrations by commercial ELISA assay per the manufacturer's instructions (R&D Systems, Minneapolis, Minn.).

Test compounds were administered orally at various times before LPS injection. The compounds were dosed either as suspensions or as solutions in various vehicles or solubilizing agents.

Abbreviations

For ease of reference, the following abbreviations are employed herein, including the methods of preparation and Examples that follow:

µL=microliter
aq.=aqueous
Boc=tert-butyloxycarbonyl
Bz=benzyl
DCE=1,2-dichloroethane
DCM=dichloromethane
DIPEA=diisopropylethylamine
DMF=dimethyl formamide
DMSO=dimethyl sulfoxide
EDC or EDCI=1-(3-Dimethylaminopropyl)-3-ethylcarbodiimide hydrochloride
Et=ethyl
EtOAc=ethyl acetate
EtOH=ethanol
g=gram(s)
HATU=O-(7-Azabenzotriazol-1-yl-N,N,N',N'-tetramethyluronim hexafluorophosphate
HOBt=1-hydroxybenzotriazole hydrate
HPLC=high performance liquid chromatography
Iso-P=isopropyl
$K_2CO_3$=potassium carbonate
KOH=potassium hydroxide
L=liter
LC/MS=high performance liquid chromatography/mass spectrometry
m-CPBA=m-chloroperbenzoic acid
Me=methyl
MeOH=methanol
Meq=milliequivalent
Mg=milligram(s)
Min=minute(s)
mL=milliliter
mmol=millimole(s)
mol=moles
mp=melting point
MS=mass spectrometry
NaH=sodium hydride
NaOH=sodium hydroxide NMR=nuclear magnetic resonance
Pd=palladium
Pd/C=palladium on carbon
Ph=phenyl
POCl$_3$=phosphorous oxychloride
Pr=propyl
ret. t.=HPLC retention time (minutes)
RP HPLC=reverse phase HPLC
RT or rt=room temperature
sat or sat'd=saturated
t-Bu=tertiary butyl
TFA=trifluoroacetic acid
THF=tetrahydrofuran
TLC=thin layer chromatography In the Examples, designations associated with HPLC data reflect the following conditions:

a. Column: YMC ODSA S-5 5u C18 4.6×50 mm; Solvent: solvent A=10% MeOH/90% water/0.1% THF, and solvent B=90% MeOH/10%water/0.1% THF; Method: 4 min gradient;

b. Column: YMC s5 ODS 4.6×50 mm; Solvent: solvent A=10% MeOH/90% water/0.2% H$_3$PO$_4$, and solvent B=90% MeOH/10% water/0.2% H$_3$PO$_4$; Method: 4 min gradient.

Methods of Preparation

Compounds of Formula I may generally be prepared according to the following schemes and the knowledge of one skilled in the art, and/or the methods described in U.S. patent applications Ser. Nos. 10/036,293 and/or 09/573,829, incorporated herein by reference. In the schemes, the groups A$^1$ and A$^2$ are as described herein for compounds of Formula (I), and said groups are also further exemplified in the Examples described hereinbelow.

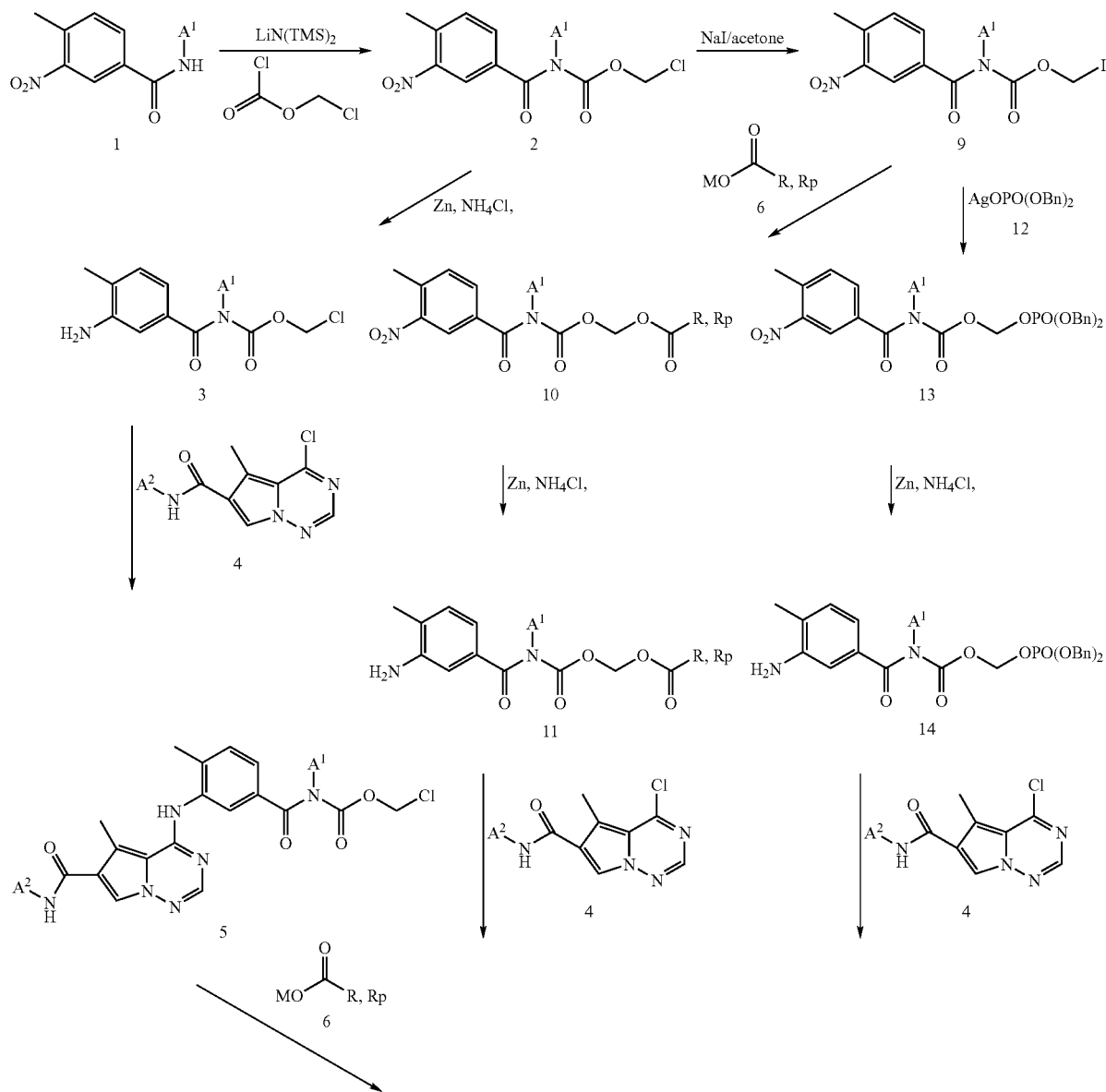

SCHEME 1

149 150

-continued

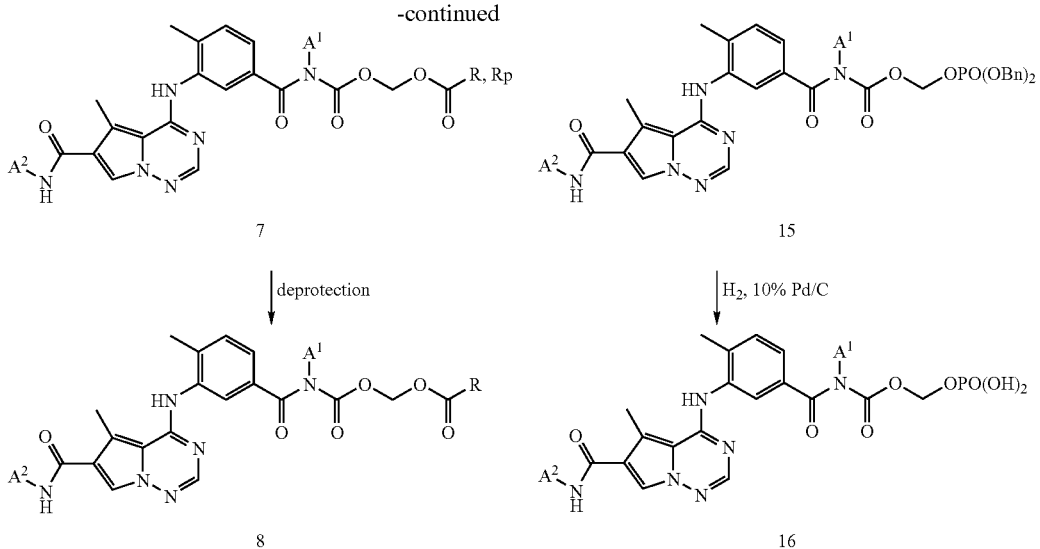

There are three nitrogen atoms in the parent drug molecule that can be used for the construction of prodrugs. Scheme 1 outlines the synthesis of the carbamoyl prodrugs where the carbamoyl is built on the benzamido nitrogen. Treatment of 4-methyl-3-nitrobenzamide 1 with strong base such as LiN(TMS)$_2$, followed by chloroformic acid chloromethyl ester provides carbamate 2. Nitro reduction affords aniline 3, which reacts with 4-chloro-5-methylpyrrolo[1,2-f][1,2,4]triazine-6-carboxamide 4 to give rise to compound 5. Reaction of 5 with carboxylate 6 furnishes prodrug 7 or 8 after deprotection. Prodrug 7 and 8 can also be prepared via an alternative route where O-chloromethyl carbamate 2 is converted into O-iodomethyl carbamate 9, followed by treatment with carboxylate 6, nitro reduction, and reaction with 4. On the other hand, treatment of 9 with the silver salt of dibenzyl hydrogen phosphate 12 supplies phosphate 13. Reduction of the nitro into amino (14) and subsequent reaction with 4 gives compound 15, which is hydrogenated to prodrug 16.

SCHEME 2

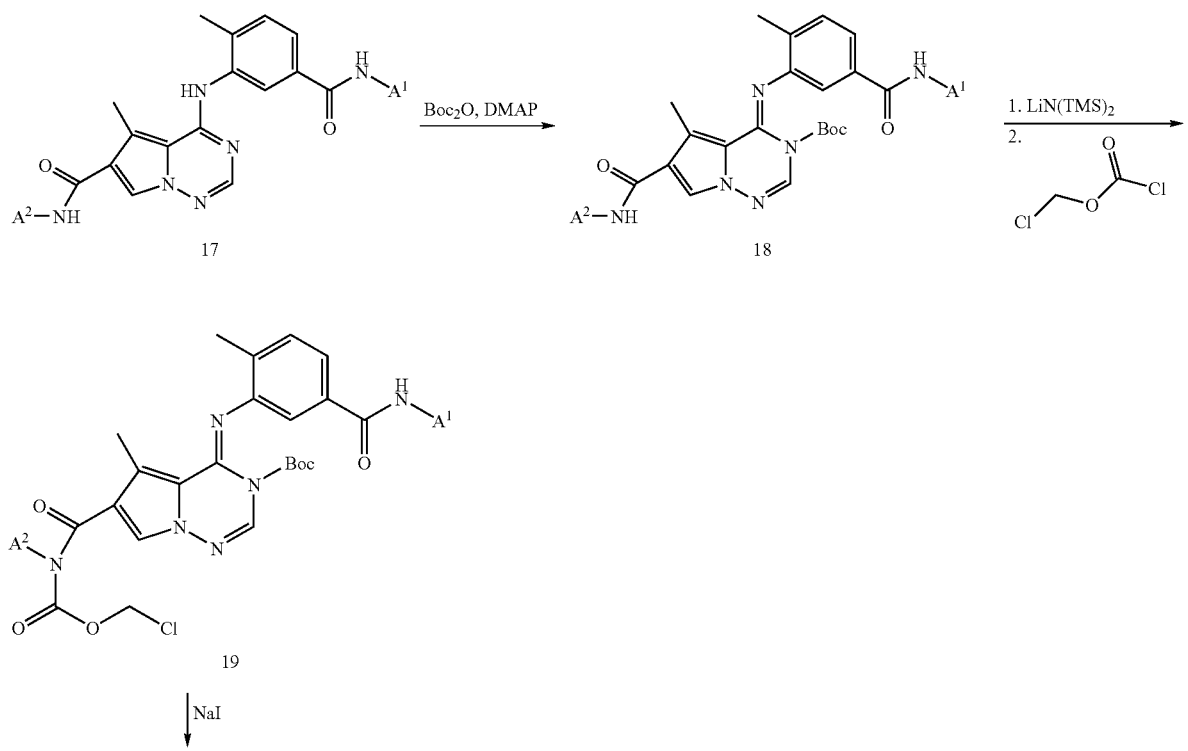

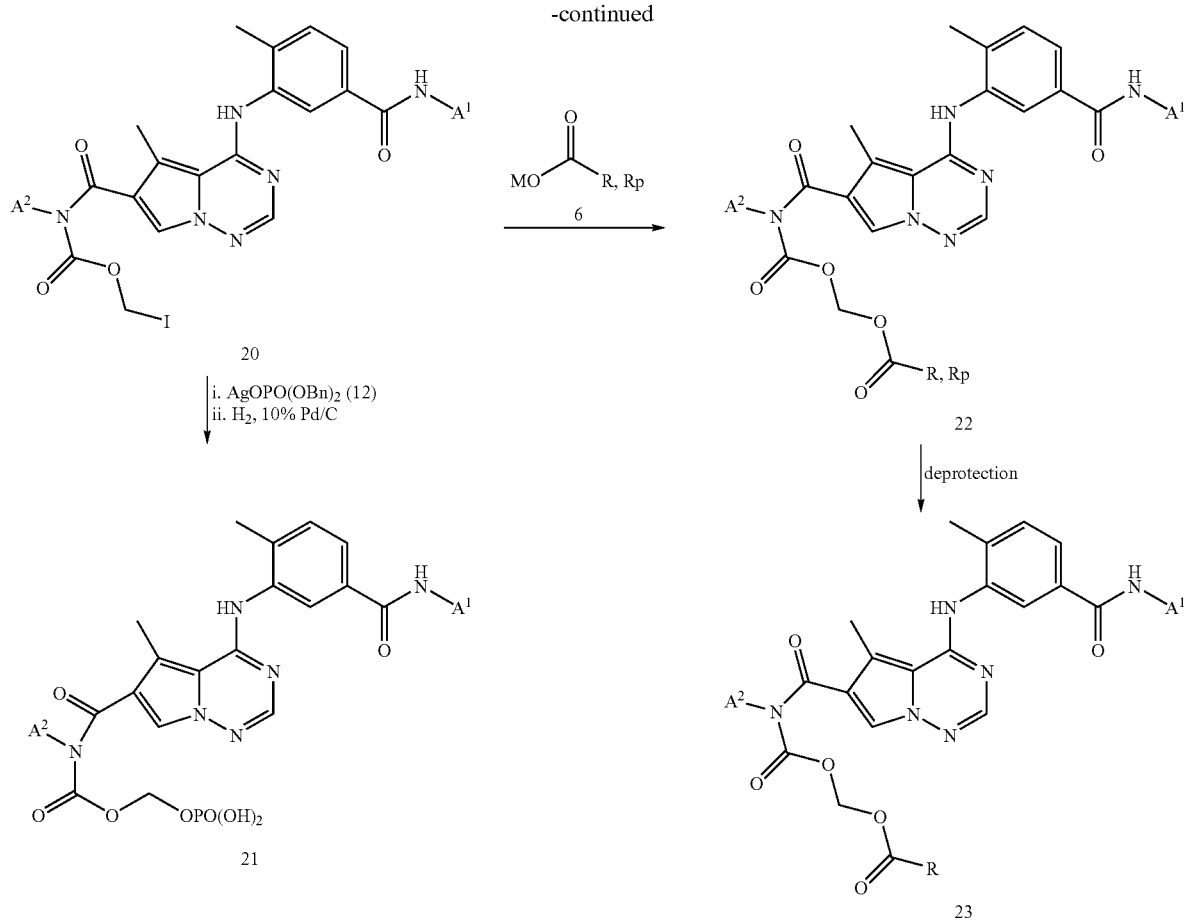

Scheme 2 illustrates the preparation of the carbamoyl prodrugs where the carbamoyl is built on the pyrrolo[1,2-f][1,2,4]triazine-6-carboxamido nitrogen. Treatment of parent drug 17 with Boc anhydride in the presence of DMAP affords Boc protected compound 18. The structure of 18 has been confirmed by x-ray crystallography. Regioselective carbamoylation of 18 can be realized by deprotonation with two equivalent of strong base such as LiN(TMS)$_2$, followed by treatment with one equivalent of chloroformic acid chloromethyl ester at low temperature. The rest of the transformations are similar to those in Scheme 1.

SCHEME 3

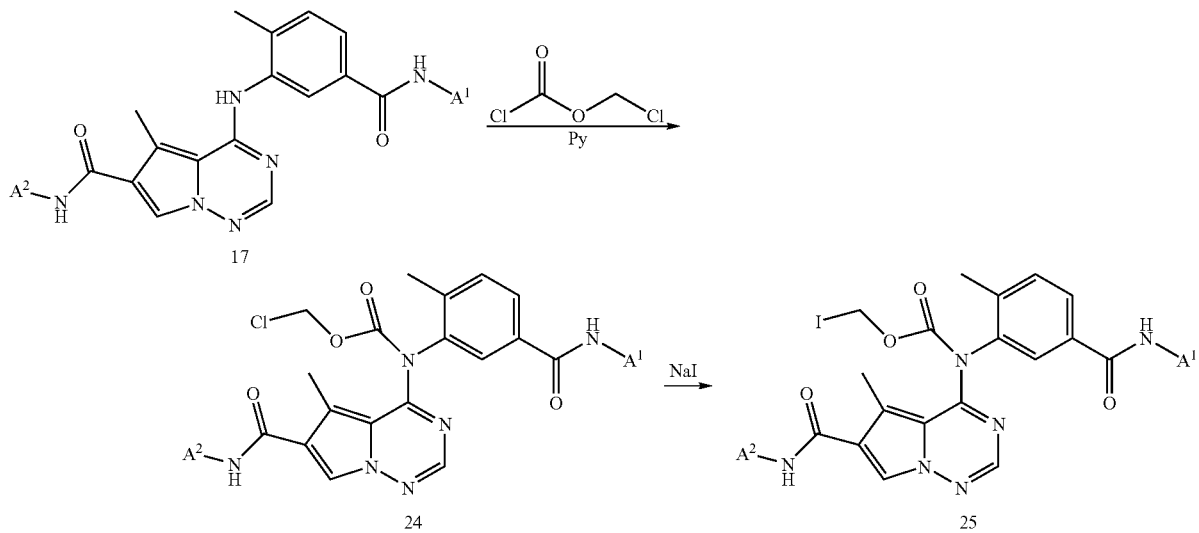

-continued

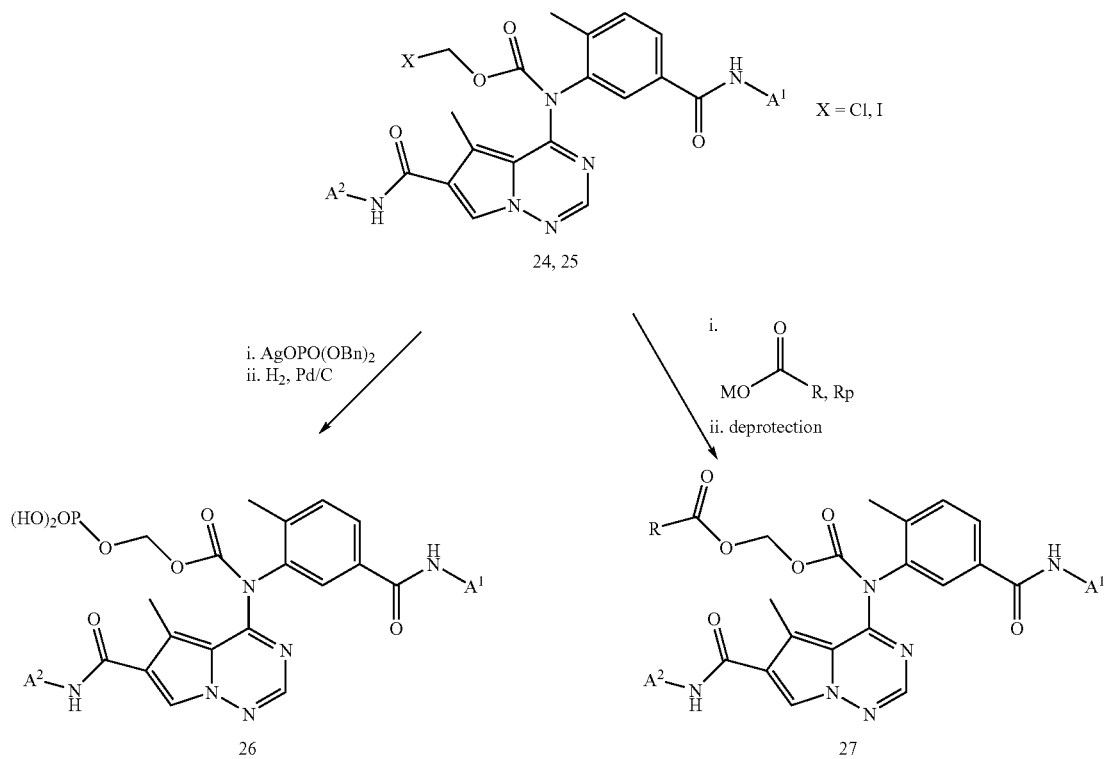

Scheme 3 shows the preparation of the carbamoyl prodrugs where the carbamoyl is built on the anilino nitrogen. Reaction of the parent drug 17 with chloroformic acid chloromethyl ester gives carbamate 24. The rest of the transformations are similar to those in Scheme 1 and 2.

EXAMPLE 1

Phosphonooxymethylcyclopropyl(4-methyl-3-(5-methyl-6-(propylcarbamoylpyrrolo-[1,2-f][1,2,4]triazin-4-ylamino)benzoyl)carbamate

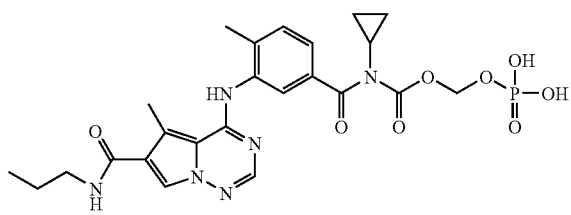

1. Chloromethyl cyclopropyl(4-methyl-3-nitrobenzoyl)carbamate

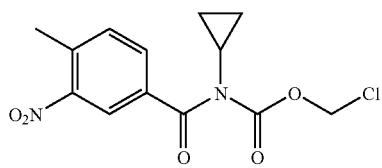

To a solution of N-cyclopropyl-4-methyl-3-nitrobenzamide (2.10 g, 9.5 mmol) in THF (48 mL) under nitrogen at −78° C. was added lithium bis(trimethylsilyl)amide (1M, THF, 11.4 mL) over 10 min. After 0.5 h, chloromethyl carbonochloridate (1.1 mL, 12.4 mmol) was added. After 10 min., the cold bath was removed, and the reaction was stirred to room temperature for 1.5 h, quenched with water and concentrated in vacuo. It was then diluted with EtOAc and water. After the layers were separated, the organic layer was dried over $Na_2SO_4$, filtered, and concentrated in vacuo. Silica gel chromatography using hexanes:EtOAc (5:1) as eluent afforded the title compound as a colorless oil (2.14 g, 72% yield).

2. Iodomethyl cyclopropyl(4-methyl-3-nitrobenzoyl)carbamate

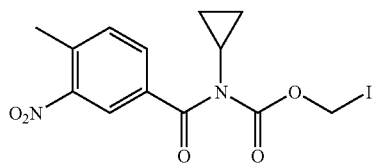

A solution of chloromethyl cyclopropyl(4-methyl-3-nitrobenzoyl)carbamate (2.14 g, 6.8 mmol), NaI (4.14 g, 27.6 mmol) and acetone (50 mL) was refluxed for 1.25 h. After cooling to room temperature, the solution was diluted with EtOAc and washed with water, saturated aqueous sodium thiosulfate, and brine successively, dried over $Na_2SO_4$, filtered, and concentrated in vacuo to give the title compound as a light yellow oil (2.47 g, 90%).

3. (Bis(benzyloxy)phosphoryloxy)methylcyclopropyl(4-methyl-3-nitrobenzoyl)carbamate

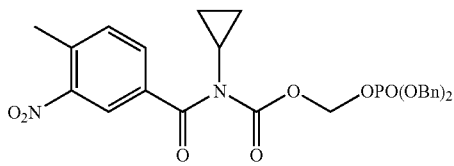

A solution of iodomethyl cyclopropyl(4-methyl-3-nitrobenzoyl)carbamate (1.00 g, 2.5 mmol) and dibenzyl hydrogen phosphate silver salt (3.83 g, 9.9 mmol) in toluene (85 mL) was refluxed for 1.25 h. After cooling to room temperature, the reaction mixture was filtered through a wad of Celite, rinsed with toluene, and the filtrate was concentrated in vacuo. Silica gel chromatography using hexanes:EtOAc (5:3) as eluent afforded the title compound as a colorless oil (1.14 g, 83% yield). $(M+H)^+=555.21$.

4. (Bis(benzyloxy)phosphoryloxy)methyl-3-amino-4-methylbenzoyl(cyclopropyl)-carbamate

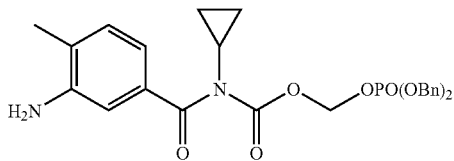

To a solution of (bis(benzyloxy)phosphoryloxy)methyl-cyclopropyl(4-methyl-3-nitrobenzoyl)carbamate (0.53 g, 1.0 mmol) in MeOH/THF (1:1, 50 mL) under nitrogen were added ammonium chloride (0.79 g, 14.8 mmol) and zinc (0.75 g, 11.5 mmol). After 3 h, the precipitate was filtered, and the filtrate was concentrated in vacuo, diluted with EtOAc and washed with water (2×), brine successively, dried over $Na_2SO_4$, filtered, and concentrated in vacuo to give the title compound as a colorless oil (0.51 g, 100% yield). $(M+H)^+= 525.19$.

5. (Bis(benzyloxy)phosphoryloxy)methylcyclopropyl(4-methyl-3-(5-methyl-6-(propylcarbamoyl)pyrrolo[1,2-f][1,2,4]triazin-4-ylamino)benzoyl)carbamate

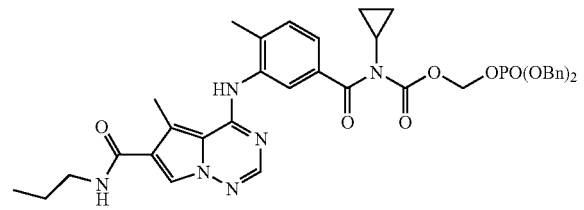

A solution of (bis(benzyloxy)phosphoryloxy)methyl-3-amino-4-methylbenzoyl-(cyclopropyl)carbamate (0.258 g, 0.50 mmol) and 4-chloro-5-methyl-N-propylpyrrolo[1,2-f][1,2,4]triazine-6-carboxamide (0.128 g, 0.50 mmol) in DMF (1.2 mL) was stirred overnight under nitrogen. The solution was diluted with EtOAc and washed with water. After separation of the layers, the aqueous layer was extracted with EtOAc. The organic layers were combined, dried over $Na_2SO_4$, filtered, and concentrated in vacuo. Silica gel chromatography using hexanes:EtOAc (5:7, then 5:10) as eluent afforded the title compound as a white solid (0.157 g, 43% yield). $(M+H)^+=741.41$.

6. Phosphonooxymethylcyclopropyl(4-methyl-3-(5-methyl-6-(propylcarbamoyl)-pyrrolo-[1,2-f][1,2,4]triazin-4-ylamino)benzoyl)carbamate A solution of (bis(benzyloxy)phosphoryloxy)methylcyclopropyl(4-methyl-3-(5-methyl-6-(propylcarbamoyl)pyrrolo[1,2-f][1,2,4]triazin-4-ylamino)benzoyl)carbamate (0.240 g, 0.32 mmol) and Pd/C (10%, 0.070 g) in THF/MeOH (1:1, 10 mL) was stirred overnight under hydrogen. After flushing with nitrogen, the solution was passed through a wad of Celite, rinsed with MeOH/THF (1:1), and the filtrate was concentrated in vacuo. Trituration with EtOAc afforded the title compound as an off-white solid (0.108 g, 60% yield). $(M+H)^+=561.28$.

EXAMPLES 2 to 12

The compounds shown below in Table 1 can be prepared in a similar manner as described in Example 1.

TABLE 1

| Example | A¹ | A² |
|---------|----|----|
| 2 | isobutyl | isopropyl |
| 3 | n-butyl | isopropyl |
| 4 | cyclopropylmethyl | isopropyl |
| 5 | isoxazol-3-ylmethyl | isopropyl |
| 6 | neopentyl | sec-butyl |
| 7 | n-butyl | sec-butyl |

TABLE 1-continued

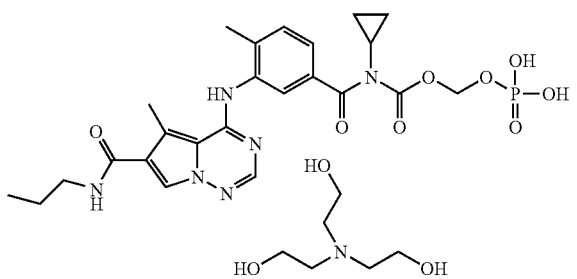

| Example | A¹ | A² |
|---|---|---|
| 8 | isoxazolyl | pentyl |
| 9 | isobutyl | cyclopropylmethyl |
| 10 | n-butyl | cyclopropylmethyl |
| 11 | cyclopropylmethyl | cyclopropylmethyl |
| 12 | isoxazolyl | cyclopropylmethyl |

EXAMPLE 13

Triethylaminoethanol salt of phosphonooxymethyl-cyclopropyl(4-methyl-3-(5-methyl-6-(propylcarbamoyl)-pyrrolo[1,2-f][1,2,4]triazin-4-ylamino)benzoyl)-carbamate

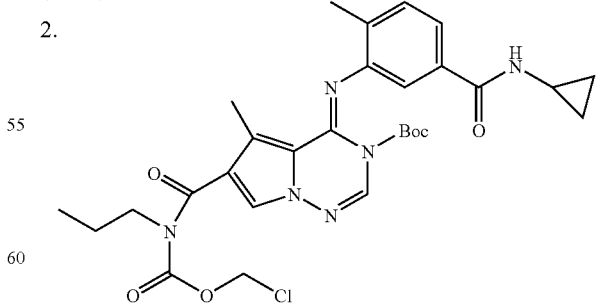

To a solution of phosphonooxymethylcyclopropyl(4-methyl-3-(5-methyl-6-(propylcarbamoyl)-pyrrolo[1,2-f][1,2,4]triazin-4-ylamino)benzoyl)carbamate (0.0211 g, 0.038 mmol) in EtOAc (1.0 mL) was added a solution of triethylaminoethanol (0.0056 g, 0.038 mmol) in EtOAc (1.0 mL). After stirring for 0.5 h, the reaction solution was concentrated in vacuo to give the title compound as a white solid (0.0247 g, 92% yield). (M+H)⁺=561.30.

EXAMPLE 14

Phosphonooxymethyl-4-(5-(cyclopropylcarbamoyl)-2-methylphenylamino)-5-methylpyrrolo[1,2-f][1,2,4]triazine-6-carbonyl(propyl)carbamate

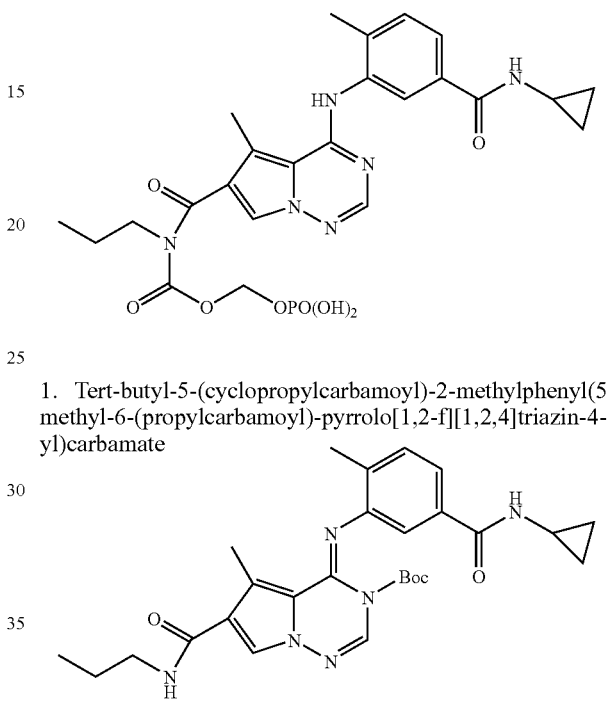

1. Tert-butyl-5-(cyclopropylcarbamoyl)-2-methylphenyl(5-methyl-6-(propylcarbamoyl)-pyrrolo[1,2-f][1,2,4]triazin-4-yl)carbamate To a solution of 4-(5-(cyclopropylcarbamoyl)-2-methylphenylamino)-5-methyl-N-propylpyrrolo[1,2-f][1,2,4]triazine-6-carboxamide (4.06 g, 10.0 mmol) in DMF (34 mL) at 0° C. under nitrogen were added Boc anhydride (4.37 g, 20.0 mmol) and N,N-dimethylpyridin-4-amine (0.26 g, 2.1 mmol). After 5 min., the cold bath was removed, and the reaction was stirred to room temperature for 10 min. and then heated at 60° C. After 1.25 h, the reaction was cooled to room temperature and added slowly to water (300 mL). The precipitate was filtered, triturated with hexanes, and dried to give the title compound as a light yellow solid (3.52 g, 70% yield). (M+H)⁺=507.19.

2.

To a solution of tert-butyl-5-(cyclopropylcarbamoyl)-2-methylphenyl(5-methyl-6-(propylcarbamoyl)-pyrrolo[1,2-f][1,2,4]triazin-4-yl)carbamate (10.00 g, 19.7 mmol) in THF (200 mL) under nitrogen at −78° C. was added lithium bis (trimethylsilyl)amide (1M, THF, (40.0 mL, 40.0 mmol)) over 30 min. The cold bath was removed, and the reaction mixture was allowed to worm to −45° C. and stirred at the temperature for 30 min. The mixture was then cooled to −78° C. again before chloromethyl carbonochloridate (2.0 mL, 22.5 mmol) in THF (4.4 mL) was added. After 1 h, the reaction was diluted with EtOAc and water. The cold bath was removed, and the reaction was stirred to room temperature. After the layers were separated, the organic layer was washed with brine, dried over $Na_2SO_4$, filtered, and concentrated in vacuo. Silica gel chromatography using ISCO afforded the title compound as a yellow foam (9.00 g, 76% yield). $(M+H)^+=599.39$.

3. Iodomethyl 4-(5-(cyclopropylcarbamoyl)-2-methylphenylamino)-5-methylpyrrolo[1,2-f][1,2,4]triazine-6-carbonyl(propyl)carbamate

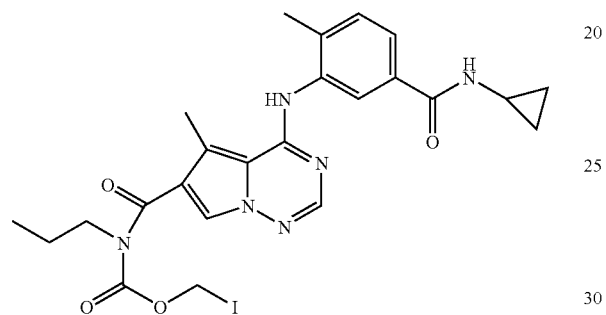

Following the procedure for step 2 in Ex. 1, the title compound was obtained. $(M+H)^+=591.01$.

4. (Bis(benzyloxy)phosphoryloxy)methyl 4-(5-(cyclopropylcarbamoyl)-2-methylphenylamino)-5-methylpyrrolo[1,2-f][1,2,4]triazine-6-carbonyl(propyl)carbamate

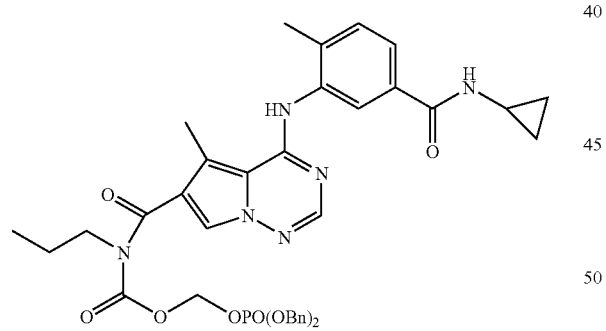

Following the procedure for step 3 in Ex. 1, the title compound was obtained. $(M+H)^+=741.22$.

5. Phosphonooxymethyl-4-(5-(cyclopropylcarbamoyl)-2-methylphenylamino)-5-methylpyrrolo[1,2-f][1,2,4]triazine-6-carbonyl(propyl)carbamate Following the procedure for step 6 in Ex. 1, the title compound was obtained. $(M+H)^+=561.11$.

EXAMPLES 15 to 25

The compounds shown below in Table 2 can be prepared in a similar manner as described in Example 14.

TABLE 2

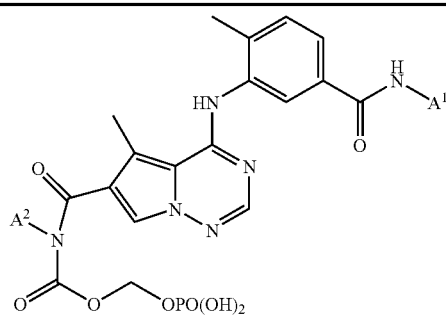

| Example | A¹ | A² |
|---------|----|----|
| 15 |  |  |
| 16 | | |
| 17 | | |
| 18 | | |
| 19 | | |
| 20 | | |
| 21 | | |
| 22 | | |

TABLE 2-continued

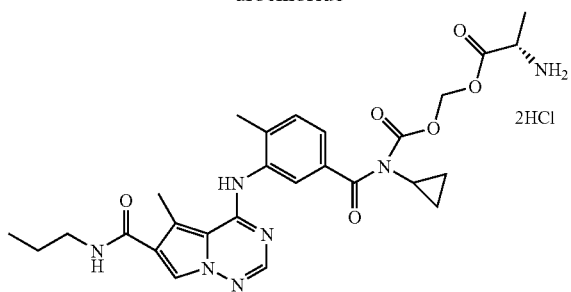

| Example | A¹ | A² |
|---|---|---|
| 23 | (butyl) | (1-cyclopropylethyl) |
| 24 | (cyclopropylmethyl) | (1-cyclopropylethyl) |
| 25 | (isoxazol-3-ylmethyl) | (1-cyclopropylethyl) |

EXAMPLE 26

(S)-(cyclopropyl(4-methyl-3-(5-methyl-6-(propylcarbamoyl)pyrrolo[1,2-f][1,2,4]-triazin-4-ylamino)benzoyl)carbamoyloxy)methyl-2-aminopropanoate dihydrochloride

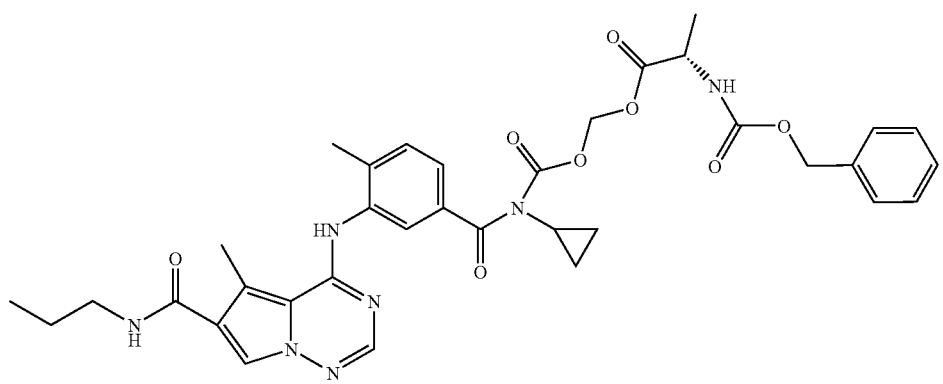

1. (S)-(cyclopropyl(4-methyl-3-nitrobenzoyl)carbamoyloxy)methyl 2-(benzyloxycarbonyl)propanoate

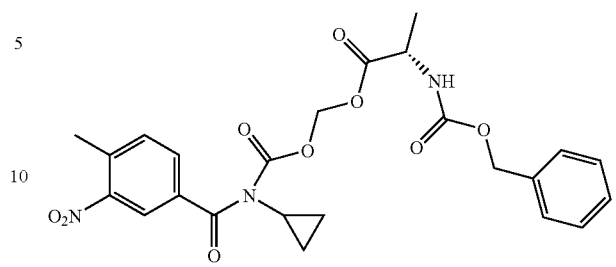

A solution of iodomethyl cyclopropyl(4-methyl-3-nitrobenzoyl)carbamate (0.49 g, 1.2 mmol) and (S)-2-(benzyloxycarbonyl)propanoic acid silver salt (1.22 g, 3.7 mmol) in toluene (40 mL) was heated at 75° C. under nitrogen for 0.5 h, cooled to room temperature, filtered through a wad of Celite, and rinsed with toluene. The filtrate was concentrated in vacuo. Silica gel chromatography using hexanes:EtOAc (1:1) as eluent afforded the title compound as a colorless oil (0.40 g, 66%). (M+H)⁺=500.13.

2. (S)-((3-amino-4-methylbenzoyl)(cyclopropyl)carbamoyloxy)methyl 2-(benzyloxycarbonyl)propanoate

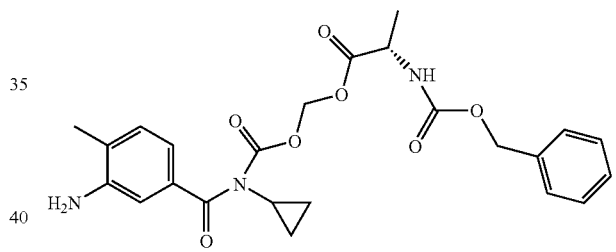

Following the procedure for step 4 of Ex. 1, the title compound was obtained as a yellow solid. (M+H)⁺=470.27.

3. (S)-(cyclopropyl(4-methyl-3-(5-methyl-6-(propylcarbamoyl)pyrrolo[1,2-f][1,2,4]-triazin-4-ylamino)benzoyl)carbamoyloxy)methyl 2-(benzyloxycarbonyl)propanoate Following the procedure for step 5 of Ex. 1, the title compound was obtained as a yellow solid. (M+H)⁺=686.20.

4. (S)-(cyclopropyl(4-methyl-3-(5-methyl-6-(propylcarbamoyl)pyrrolo[1,2-f][1,2,4]triazin-4-ylamino)benzoyl)carbamoyloxy)methyl 2-aminopropanoate dihydrochloride A solution of (S)-(cyclopropyl(4-methyl-3-(5-methyl-6-(propylcarbamoyl)pyrrolo[1,2-f][1,2,4]triazin-4-ylamino)benzoyl)-carbamoyloxy) methyl 2-(benzyloxycarbonyl)-propanoate (0.0396 g, 0.058 mmol), HCl (1N, dioxane, 0.17 mL, 0.17 mmol) and Pd/C (10%, 0.0125 g) in MeOH (2.0 mL) was stirred for 8 min. under hydrogen. After flushing with nitrogen, the solution was passed through a wad of Celite, rinsed with MeOH, and the filtrate was concentrated in vacuo. Trituration with Et₂O afforded the title compound as a light yellow solid (0.0240 g, 67% yield). (M+H)⁺=552.11.

EXAMPLES 27 to 37

The compounds shown below in Table 3 can be prepared in a similar manner as described in Example 26.

EXAMPLE 38

(S)-((4-(5-(cyclopropylcarbamoyl)-2-methylphenylamino)-5-methylpyrrolo[1,2-f][1,2,4]-triazine-6-carbonyl)(propyl)carbamoyloxy)methyl 2-aminopropanoate dihydrochloride

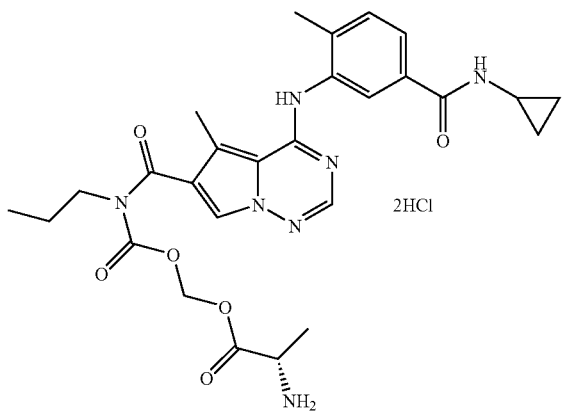

1. (S)-((4-(5-(cyclopropylcarbamoyl)-2-methylphenylamino)-5-methylpyrrolo[1,2-f][1,2,4]triazine-6-carbonyl)(propyl)carbamoyloxy)methyl 2-(benzyloxycarbonyl)propanoate

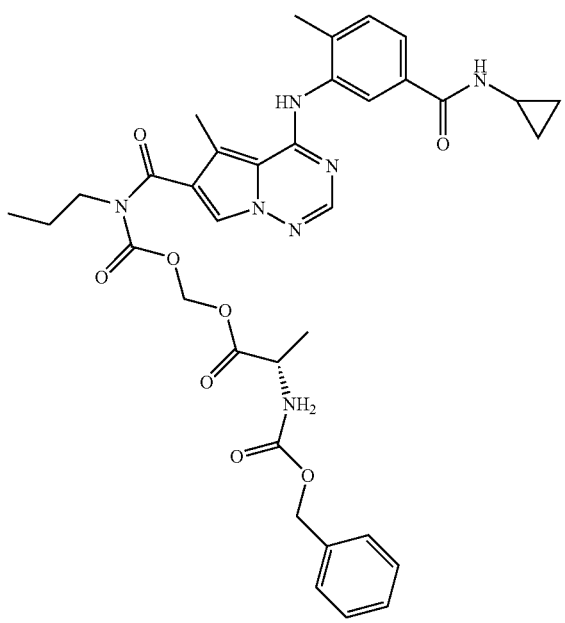

Following the procedure for step 1 of Ex. 26, the title compound was obtained as an off-white solid. (M+H)$^+$= 686.19.

2. (S)-((4-(5-(cyclopropylcarbamoyl)-2-methylphenylamino)-5-methylpyrrolo[1,2-f]-[1,2,4]triazine-6-carbonyl)(propyl)carbamoyloxy)methyl 2-aminopropanoate dihydrochloride Following the procedure for step 4 of Ex. 26, the title compound was obtained as a white solid. (M+H)$^+$=552.15.

EXAMPLES 39 to 49

The compounds shown below in Table 4 can be prepared in a similar manner as described in Example 38.

TABLE 4

| Example | A$^1$ | A$^2$ |
|---|---|---|
| 39 | tert-butyl | isopropyl |
| 40 | n-butyl | isopropyl |
| 41 | cyclopropyl | isopropyl |
| 42 | isoxazol-3-yl | isopropyl |
| 43 | tert-butyl | n-butyl |
| 44 | n-butyl | n-butyl |

TABLE 4-continued

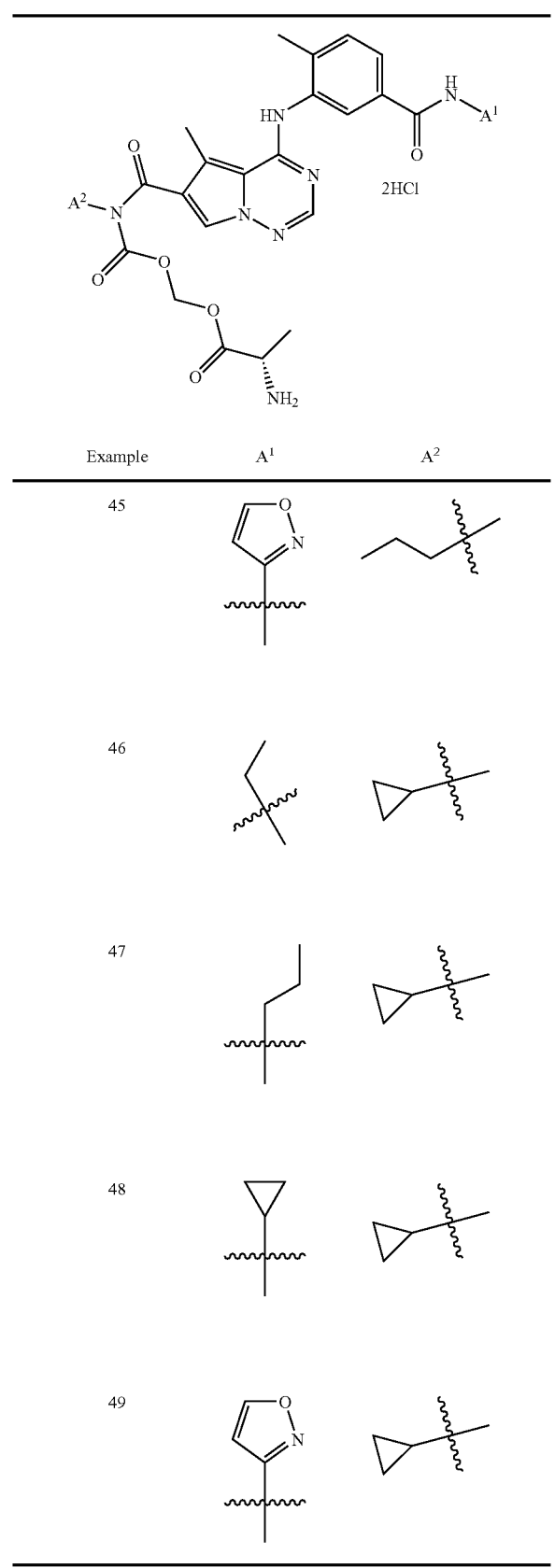

| Example | A[1] | A[2] |
|---|---|---|
| 45 | isoxazol-3-yl (attached via C3) | pentan-3-yl |
| 46 | tert-butyl-CH | cyclopropyl-CH |
| 47 | n-butyl-CH | cyclopropyl-CH |
| 48 | cyclopropyl-CH | cyclopropyl-CH |
| 49 | isoxazol-3-yl | cyclopropyl-CH |

EXAMPLE 50

Phosphonooxymethyl 5-(cyclopropylcarbamoyl)-2-methylphenyl(5-methyl-6-(propylcarbamoyl)pyrrolo[1,2-f][1,2,4]triazin-4-yl)carbamate

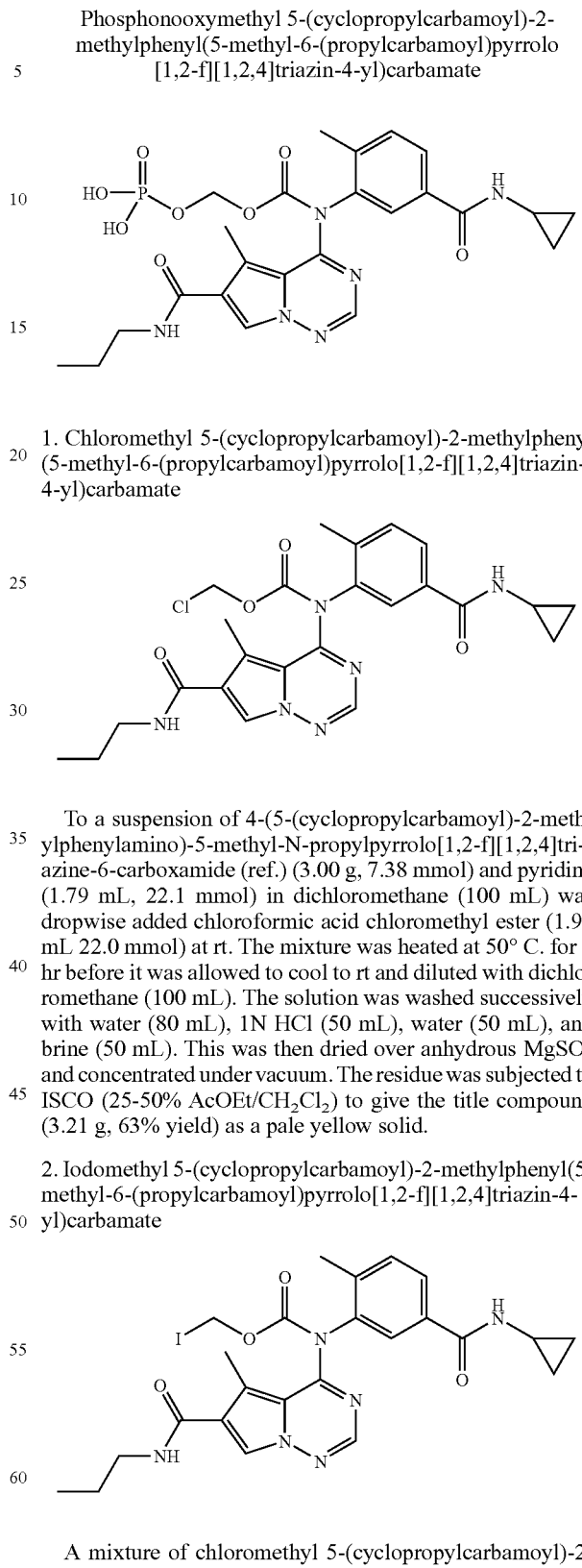

1. Chloromethyl 5-(cyclopropylcarbamoyl)-2-methylphenyl (5-methyl-6-(propylcarbamoyl)pyrrolo[1,2-f][1,2,4]triazin-4-yl)carbamate To a suspension of 4-(5-(cyclopropylcarbamoyl)-2-methylphenylamino)-5-methyl-N-propylpyrrolo[1,2-f][1,2,4]triazine-6-carboxamide (ref.) (3.00 g, 7.38 mmol) and pyridine (1.79 mL, 22.1 mmol) in dichloromethane (100 mL) was dropwise added chloroformic acid chloromethyl ester (1.96 mL 22.0 mmol) at rt. The mixture was heated at 50° C. for 5 hr before it was allowed to cool to rt and diluted with dichloromethane (100 mL). The solution was washed successively with water (80 mL), 1N HCl (50 mL), water (50 mL), and brine (50 mL). This was then dried over anhydrous $MgSO_4$ and concentrated under vacuum. The residue was subjected to ISCO (25-50% AcOEt/$CH_2Cl_2$) to give the title compound (3.21 g, 63% yield) as a pale yellow solid.

2. Iodomethyl 5-(cyclopropylcarbamoyl)-2-methylphenyl(5-methyl-6-(propylcarbamoyl)pyrrolo[1,2-f][1,2,4]triazin-4-yl)carbamate A mixture of chloromethyl 5-(cyclopropylcarbamoyl)-2-methylphenyl(5-methyl-6-(propylcarbamoyl)pyrrolo[1,2-f][1,2,4]triazin-4-yl)carbamate (0.940 g, 1.88 mmol) and sodium iodide (1.27 g, 8.47 mmol) in acetone (60 mL) was heated at reflux for 2.5 hr. It was diluted with AcOEt (150 mL), washed successively with water, saturated $Na_2S_2O_3$ solution, and brine. The solution was dried over anhydrous $MgSO_4$. Evaporation of solvent under vacuum gave the title compound (0.750 g) as a pale yellow solid. This product was used in the next step without further purification.

3. (Bis(benzyloxy)phosphoryloxy)methyl 5-(cyclopropylcarbamoyl)-2-methylphenyl(5-methyl-6-(propylcarbamoyl)pyrrolo[1,2-f][1,2,4]triazin-4-yl)carbamate

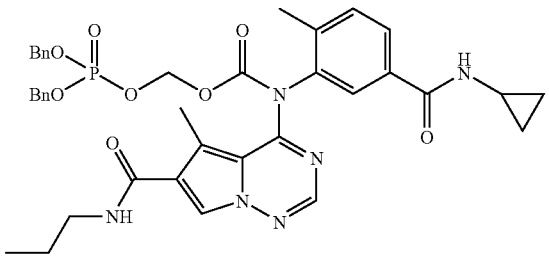

A mixture of iodomethyl 5-(cyclopropylcarbamoyl)-2-methylphenyl(5-methyl-6-(propylcarbamoyl)pyrrolo[1,2-f][1,2,4]triazin-4-yl)carbamate (0.750 g, step 2) and dibenzyl phosphate silver salt (1.22 g, 3.17 mmol) in toluene (75 mL) was heated at reflux for 1.5 hr. The solid phase was removed by suction filtration through Celite® 545, and the filtrate was concentrated under vacuum. The residue was subjected to chromatography (silical gel, 80% AcOEt/hexane) to provide the title compound (0.711 g, 51% yield over two steps) as a pale yellow solid.

4. Phosphonooxymethyl 5-(cyclopropylcarbamoyl)-2-methylphenyl(5-methyl-6-(propylcarbamoyl)pyrrolo[1,2-f][1,2,4]triazin-4-yl)carbamate A mixture of (bis(benzyloxy)phosphoryloxy)methyl 5-(cyclopropylcarbamoyl)-2-methylphenyl(5-methyl-6-(propylcarbamoyl)pyrrolo[1,2-f][1,2,4]triazin-4-yl)carbamate (0.720 g, 0.972 mmol) and 10% Pd/C (0.223 g) in THF (15 mL) and MeOH (20 mL) was stirred at rt under $H_2$, provided with a $H_2$ balloon, for 2 hr. The solid phase was removed by suction filtration through Celite® 545. The filtrate was concentrated to dryness under vacuum to give the title compound (0.545 g, 100% yield) as a yellow solid. 94% pure by HPLC; $(M+H)^+$=561.23.

EXAMPLES 51 to 61

The compounds shown below in Table 5 can be prepared in a similar manner as described in Example 50.

TABLE 5-continued

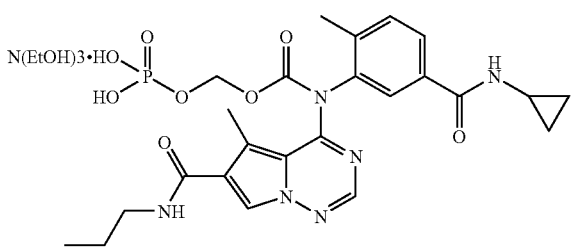

| Example | A[1] | A[2] |
|---|---|---|
| 60 | (cyclopropyl, wavy bond) | (cyclopropylmethyl, wavy bond) |
| 61 | (isoxazol-3-yl, wavy bond) | (cyclopropylmethyl, wavy bond) |

EXAMPLE 62

Phosphonooxymethyl 5-(cyclopropylcarbamoyl)-2-methylphenyl(5-methyl-6-(propylcarbamoyl)pyrrolo[1,2-f][1,2,4]triazin-4-yl)carbamate triethanolamine salt

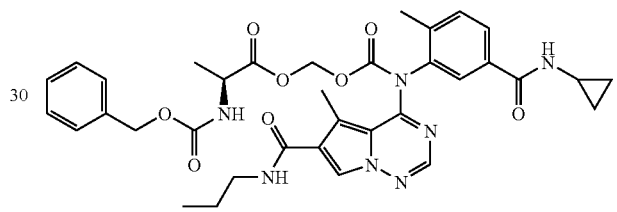

To a suspension of posphonooxymethyl 5-(cyclopropylcarbamoyl)-2-methylphenyl(5-methyl-6-(propylcarbamoyl) pyrrolo[1,2-f][1,2,4]triazin-4-yl)carbamate (26.9 mg, 0.0480 mmol) in AcOEt (8 mL) and THF (2 mL) was added a solution of triethanolamine (7.16 mg, 0.0480 mmol) in AcOEt (0.5 mL). The mixture was stirred at rt for 15 min and then concentrated to dryness under vacuum to provide the title compound a pale yellow sold. 96.4% pure by HPLC; $(M+H)^+=$ 561.29.

EXAMPLE 63

(S)-((5-(cyclopropylcarbamoyl)-2-methylphenyl)(5-methyl-6-(propylcarbamoyl)pyrrolo[1,2-f][1,2,4]triazin-4-yl)carbamoyloxy)methyl 2-aminopropanoate hydrogen chloride

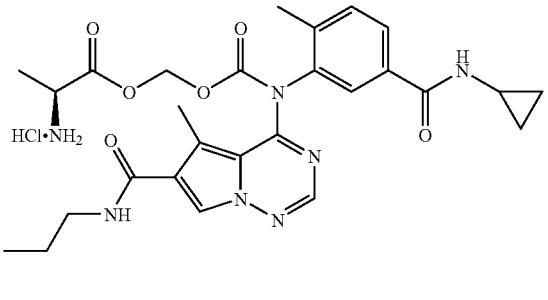

1. (S)-((5-(cyclopropylcarbamoyl)-2-methylphenyl)(5-methyl-6-(propylcarbamoyl)pyrrolo[1,2-f][1,2,4]triazin-4-yl) carbamoyloxy)methyl 2-(benzyloxycarbonyl)propanoate A mixture of chloromethyl 5-(cyclopropylcarbamoyl)-2-methylphenyl(5-methyl-6-(propylcarbamoyl)pyrrolo[1,2-f][1,2,4]triazin-4-yl)carbamate (0.400 g, 0.802 mmol) and (S)-2-(benzyloxycarbonyl)propanoic acid silver salt (0.792 g, 2.40 mmol) in toluene (35 mL) was heated at reflux for 9 hr. The solid phase was removed by suction filtration through Celite® 545. The filtrate was concentrated and the residue was subjected to ISCO (silica gel, 15-60% AcOEt/CH$_2$Cl$_2$) to provide the title compound (0.217 g, 39% yield) as a pale yellow solid.

2. (S)-((5-(cyclopropylcarbamoyl)-2-methylphenyl)(5-methyl-6-(propylcarbamoyl)pyrrolo[1,2-f][1,2,4]triazin-4-yl) carbamoyloxy)methyl 2-aminopropanoate hydrogen chloride A solution of (S)-((5-(cyclopropylcarbamoyl)-2-methylphenyl)(5-methyl-6-(propylcarbamoyl)pyrrolo[1,2-f][1,2,4]triazin-4-yl)carbamoyloxy)methyl 2-(benzyloxycarbonyl) propanoate (44 mg, 0.064 mmol) in MeOH (4 mL) was evacuated on a vacuum line and refilled with H$_2$, provided with a H$_2$ balloon. To this solution was added 1N HCl in dioxane (0.19 mL, 0.19 mmol), followed by 10% Pd/C (13 mg). The mixture was stirred under H$_2$ for 8 min. The solid phase was removed by suction filtration through Celite® 545. The filtrate was concentrated to dryness under vacuum to give the title compound (030 mg, 80% yield) as a yellow solid. 96% pure by HPLC; $(M+H)^+=552.21$.

EXAMPLES 64 to 74

The compounds shown below in Table 6 can be prepared in a similar manner as described in Example 63.

TABLE 6

| Example | A¹ | A² |
|---------|-----|-----|
| 64 | | |
| 65 | | |
| 66 | | |
| 67 | | |
| 68 | | |
| 69 | | |
| 70 | | |
| 71 | | |
| 72 | | |
| 73 | | |
| 74 | | |

EXAMPLE 75

(S)-((5-(cyclopropylcarbamoyl)-2-methylphenyl)(5-methyl-6-(propylcarbamoyl)pyrrolo[1,2-f][1,2,4]triazin-4-yl)carbamoyloxy)methyl 2-hydroxypropanoate

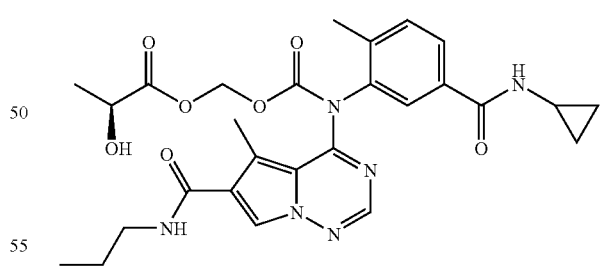

A mixture of chloromethyl 5-(cyclopropylcarbamoyl)-2-methylphenyl(5-methyl-6-(propylcarbamoyl)pyrrolo[1,2-f][1,2,4]triazin-4-yl)carbamate (100 mg, 0.200 mmol) and L-(+)-lactic acid silver salt (90%, 131 mg, 0.600 mmol) in toluene (8 mL) was heated at reflux for 2 hr. Additional L-(+)-lactic acid silver salt (90%, 80 mg, 0.366 mmol) was added and the mixture was refluxed for another 3 hr. The solid phase was removed by suction filtration through Celite® 545. The filtrate was concentrated and the residue was subjected to ISCO (silica gel, 30-80% AcOEt/CH$_2$Cl$_2$) to provide the title compound (26 mg, 24% yield) as a yellow solid. 93% pure by HPLC; (M+H)$^+$=553.20.

EXAMPLE 76

(E)-4-(((5-(cyclopropylcarbamoyl)-2-methylphenyl) (5-methyl-6-(propylcarbamoyl)-pyrrolo[1,2-f][1,2,4] triazin-4-yl)carbamoyloxy)methoxy)-4-oxobut-2-enoic acid trifluoroacetic acid

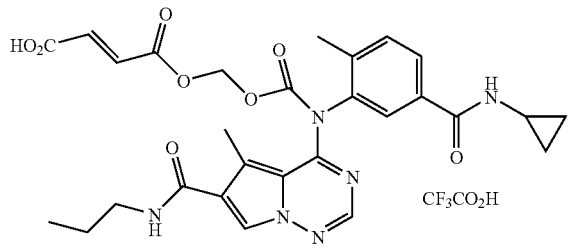

A solution of chloromethyl 5-(cyclopropylcarbamoyl)-2-methylphenyl(5-methyl-6-(propylcarbamoyl)pyrrolo[1,2-f][1,2,4]triazin-4-yl)carbamate (0.211 g, 0.42 mmol) and fumaric acid monosodium salt (0.178 g, 1.3 mmol) in DMF (4.0 mL) was heated at 115° C. for 5.5 h and cooled to room temperature. The precipitate was filtered, and the filtrate was diluted with EtOAc and washed with water, brine and 10% aqueous LiCl, successively, dried over Na$_2$SO$_4$, filtered, and concentrated in vacuo. After autoprep, the appropriate fractions were collected, concentrated in vacuo not to dryness and lyophilized to give the title compound as a yellow solid (0.0603 g, 21% yield). (M+H)$^+$=579.25$^+$.

EXAMPLES 77 to 87

The compounds shown below in Table 7 can be prepared in a similar manner as described in Example 76.

TABLE 7

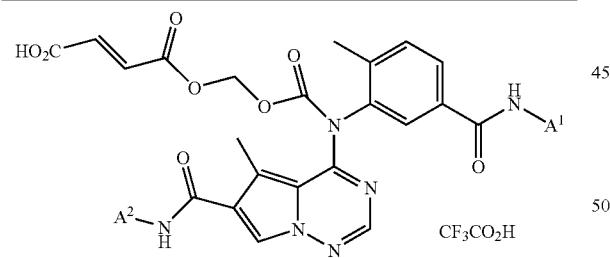

TABLE 7-continued

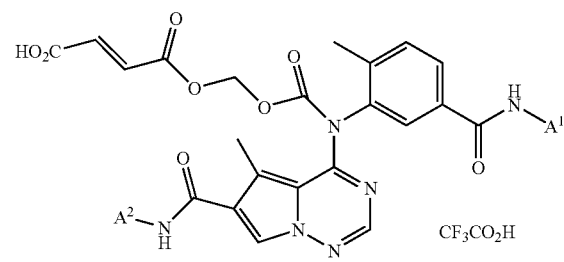

| Example | A¹ | A² |
|---|---|---|
| 87 | (isoxazol-3-yl) | (cyclopropyl) |

EXAMPLE 88

4-(((5-(cyclopropylcarbamoyl)-2-methylphenyl)(5-methyl-6-(propylcarbamoyl)-pyrrolo[1,2-f][1,2,4]triazin-4-yl)carbamoyloxy)methoxy)-4-oxobutanoic acid trifluoroacetic acid

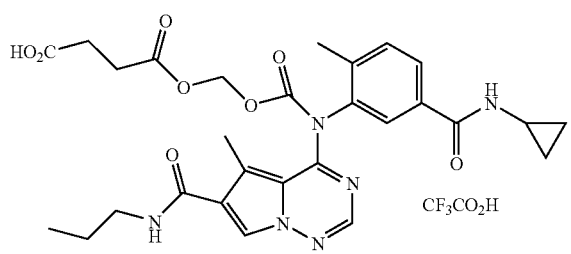

A solution of (E)-4-(((5-(cyclopropylcarbamoyl)-2-methylphenyl)(5-methyl-6-(propylcarbamoyl)pyrrolo[1,2-f][1,2,4]triazin-4-yl)carbamoyloxy)methoxy)-4-oxobut-2-enoic acid trifluoroacetic acid (0.0178 g, 0.026 mmol) and Pd/C (10%, 0.0056 g) in MeOH (1.0 mL) was stirred under hydrogen for 1 h and flushed with nitrogen. The solution was filtered through a wad of Celite, rinsed with MeOH, and the filtrate was concentrated in vacuo to give the title compound as a yellow solid (0.0142 g, 79%). (M+H)⁺=581.27.

EXAMPLES 89 to 99

The compounds shown below in Table 8 can be prepared in a similar manner as described in Example 88.

TABLE 8

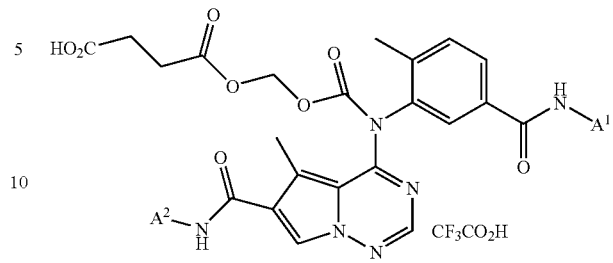

| Example | A¹ | A² |
|---|---|---|
| 89 | (isopropyl) | (ethyl) |
| 90 | (n-propyl) | (ethyl) |
| 91 | (cyclopropyl) | (ethyl) |
| 92 | (isoxazol-3-yl) | (ethyl) |
| 93 | (isopropyl) | (n-propyl) |
| 94 | (n-propyl) | (n-propyl) |
| 95 | (isoxazol-3-yl) | (n-propyl) |
| 96 | (isopropyl) | (cyclopropyl) |

TABLE 8-continued

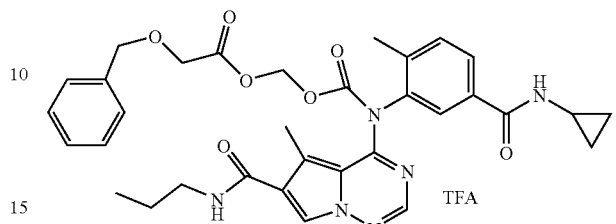

| Example | A[1] | A[2] |
|---|---|---|
| 97 | propyl chain | cyclopropyl |
| 98 | cyclopropyl-methylene chain | cyclopropyl |
| 99 | isoxazolyl-methylene chain | cyclopropyl |

EXAMPLE 100

((5-(cyclopropylcarbamoyl)-2-methylphenyl)(5-methyl-6-(propylcarbamoyl)-pyrrolo[1,2-f][1,2,4]triazin-4-yl)carbamoyloxy)methyl-2-hydroxyacetate trifluoroacetic acid

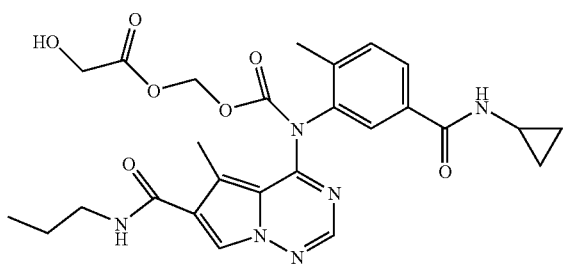

1. 2-(benzyloxy)acetic acid silver salt

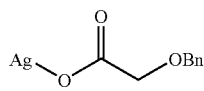

To a solution of 2-(benzyloxy)acetic acid (3.58 g, 21.5 mmol) in water (108 mL) at 0° C. was added aqueous NaOH (1.000N, 21.5 mmol). The cold bath was removed, and the reaction was stirred to room temperature for 0.25 h. After the reaction vessel was wrapped in aluminum foil, a solution of silver nitrate (4.07 g, 24.0 mmol) in water (40 mL) was added over 10 min. After 1 h, the precipitate was filtered, washed and dried over $P_2O_5$ in a dessicator to give the title compound as an off-white solid (4.90 g, 84% yield).

2. ((5-(cyclopropylcarbamoyl)-2-methylphenyl)(5-methyl-6-(propylcarbamoyl)pyrrolo-[1,2-f][1,2,4]triazin-4-yl)carbamoyloxy)methyl 2-(benzyloxy)acetate trifluoroacetic acid

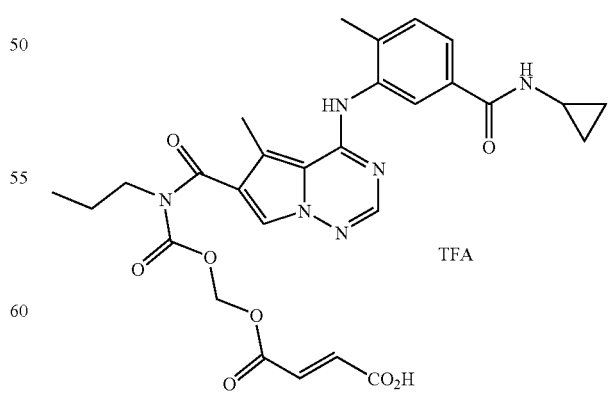

A solution of chloromethyl 5-(cyclopropylcarbamoyl)-2-methylphenyl(5-methyl-6-(propylcarbamoyl)pyrrolo[1,2-f][1,2,4]triazin-4-yl)carbamate (0.0890 g, 0.18 mmol) and 2-(benzyloxy)acetic acid silver salt (0.1483 g, 0.54 mmol) in toluene (9.0 mL) was refluxed overnight, cooled to room temperature, filtered through a wad of Celite, rinsed with EtOAc. The filtrate was concentrated in vacuo. After autoprep, the appropriate fractions were collected, concentrated in vacuo not to dryness and lyophilized to give the title compound as a light yellow solid (0.0484 g, 37% yield). $(M+H)^+ = 629.37$.

3. ((5-(cyclopropylcarbamoyl)-2-methylphenyl)(5-methyl-6-(propylcarbamoyl)-pyrrolo-[1,2-f][1,2,4]triazin-4-yl)carbamoyloxy)methyl-2-hydroxyacetate trifluoroacetic acid A solution of ((5-(cyclopropylcarbamoyl)-2-methylphenyl)(5-methyl-6-(propylcarbamoyl)pyrrolo-[1,2-f][1,2,4]triazin-4-yl)carbamoyloxy)methyl 2-(benzyloxy)acetate trifluoroacetic acid (0.0232 g, 0.031 mmol) and Pd/C (10%, 0.0084 g) in MeOH (1.0 mL) was stirred under hydrogen overnight and flushed with nitrogen. The solution was filtered through a wad of Celite, rinsed with MeOH, and the filtrate was concentrated in vacuo to give the title compound as a yellow solid (0.0050 g, 25%). After autoprep, the appropriate fractions were collected, concentrated in vacuo not to dryness and lyophilized to give the title compound as a yellow solid (0.0603 g, 21% yield). $(M+H)^+ = 539.30$.

EXAMPLE 101

(E)-4-(((4-(5-(cyclopropylcarbamoyl)-2-methylphenylamino)-5-methylpyrrolo[1,2-f][1,2,4]triazine-6-carbonyl)(propyl)carbamoyloxy)methoxy)-4-oxobut-2-enoic acid trifluoroacetic acid Following the procedure for step 2 of Ex. 100 and using fumaric acid monosilver salt (prepared similarly as step 1 of Ex. 100), the title compound was obtained as an off-white solid. $(M+H)^+ = 579.31$.

EXAMPLES 102 to 112
The compounds shown below in Table 9 can be prepared in a similar manner as described in Example 101.
TABLE 9
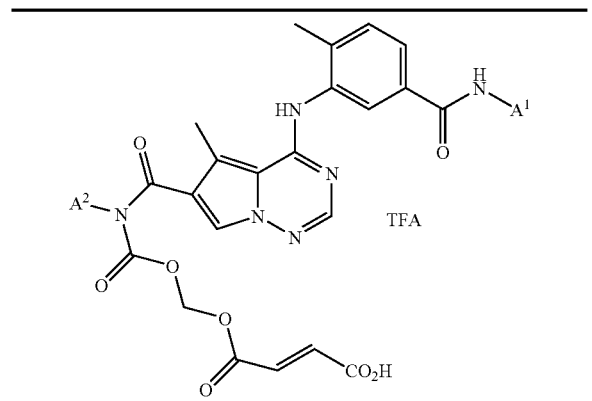
TABLE 9-continued
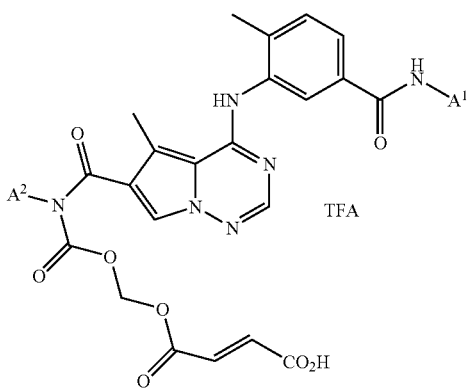

EXAMPLE 113

((4-(5-(cyclopropylcarbamoyl)-2-methylphenylamino)-5-methylpyrrolo[1,2-f][1,2,4]-triazine-6-carbonyl)(propyl)carbamoyloxy)methyl nicotinate trifluoroacetic acid

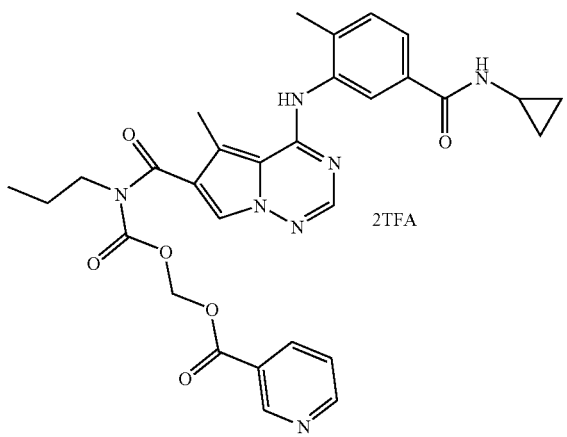

1. Chloromethyl 3-amino-4-methylbenzoyl(cyclopropyl)carbamate

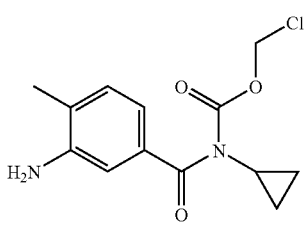

Following the procedure for step 4 of Ex. 1, the title compound was obtained as a yellow solid. (M+H)$^+$=283.22$^+$.

2. Chloromethyl cyclopropyl(4-methyl-3-(5-methyl-6-(propylcarbamoyl)pyrrolo[1,2-f][1,2,4]triazin-4-ylamino)benzoyl)carbamate

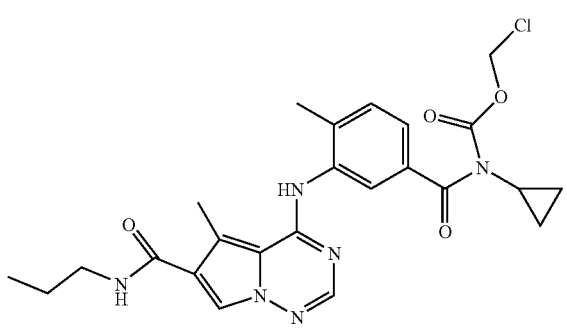

Following the procedure for step 2 of Ex. 100 and using nicotinic acid silver salt (prepared similarly as step 1 of Ex. 100), the title compound was obtained as an white solid. (M+H)$^+$=586.27.

EXAMPLE 114

(E)-4-((cyclopropyl(4-methyl-3-(5-methyl-6-(propylcarbamoyl)pyrrolo[1,2-f][1,2,4]-triazin-4-ylamino)benzoyl)carbamoyloxy)methoxy)-4-oxobut-2-enoic acid trifluoroacetic acid

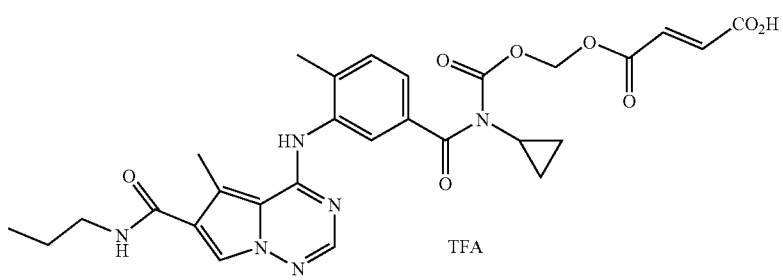

Following the procedure for step 5 of Ex. 1, the title compound was obtained as a yellow solid. (M+H)$^+$=499.30.

3. (E)-4-((cyclopropyl(4-methyl-3-(5-methyl-6-(propylcarbamoyl)pyrrolo[1,2-f][1,2,4]-triazin-4-ylamino)benzoyl)carbamoyloxy)methoxy)-4-oxobut-2-enoic acid trifluoroacetic acid Following the procedure for Ex. 76, the title compound was obtained as a white solid. (M+H)$^+$=579.33.

EXAMPLES 115 to 125

The compounds shown below in Table 10 can be prepared in a similar manner as described in Example 114.

TABLE 10
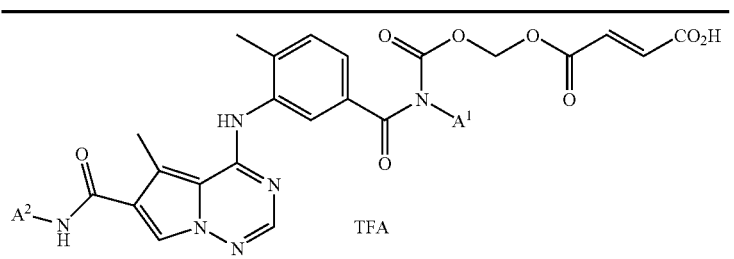
| Example | A¹ | A² |
|---|---|---|
| 115 | | |
| 116 | | |
| 117 | | |
| 118 | | |
| 119 | | |
| 120 | | |
| 121 | | |
| 122 | | |

TABLE 10-continued

| Example | A¹ | A² |
|---|---|---|
| 123 | propyl | cyclopropyl |
| 124 | cyclopropyl | cyclopropyl |
| 125 | isoxazol-3-yl | cyclopropyl |

EXAMPLE 126

((4-(5-(cyclopropylcarbamoyl)-2-methylphenylamino)-5-methylpyrrolo[1,2-f][1,2,4]triazine-6-carbonyl)(propyl)carbamoyloxy)methyl 4-(phosphonooxy)benzoate

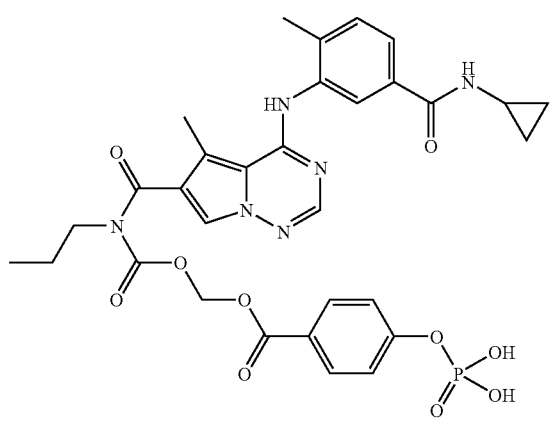

1. Dibenzyl 4-formylphenyl phosphate

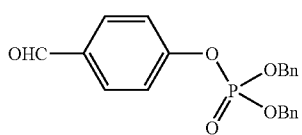

To a solution of 4-hydroxybenzaldehyde (1.10 g, 9.00 mmol) in THF (40 mL) was added t-BuOK (1.0 M in THF, 9.6 mL, 9.6 mmol) at rt over 10 min. The resulting heterogeneous mixture was heated to 70° C., and a solution of tetrabenzyl pyrophosphate (5.05 g, 9.37 mmol) in THF 20 mL was added over 10 min. The mixture was continued to be heated at 70° C. for 1 hr. After it cooled to rt, the mixture was poured into a mixture of THF (100 mL) and hexane (200 mL). The insoluble material was removed by suction filtration through Celite® 545. The filtrate was concentrated and the residue was subjected to ISCO (silica gel, 30% AcOEt/hexane) to provide the title compound (3.29 g, 96% yield) as a colorless oil.

2. 4-(bis(benzyloxy)phosphoryloxy)benzoic acid

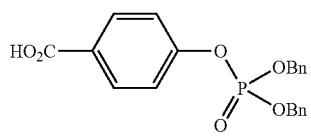

To a solution of dibenzyl 4-formylphenyl phosphate (1.00 g, 2.62 mmol) in acetone (50 mL) was added a solution of potassium permanganate (0.837 g, 5.30 mmol) in acetone (40 mL) and water (40 mL) at rt over 1.5 hr. To the resulting purple mixture was poured 10% $NaHSO_3$ in 1N HCl (100 mL) at rt. The purple solution became colorless and extracted with AcOEt (3×60 mL). The combined extract was washed with brine and dried anhydrous $MgSO_4$. The title compound (0.940 g, 90% yield) was isolated as a white solid by ISCO (5% MeOH/$CH_2Cl_2$).

3. 4-(bis(benzyloxy)phosphoryloxy)benzoic acid silver salt

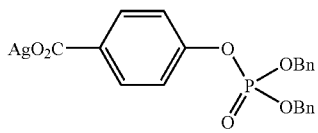

4-(bis(benzyloxy)phosphoryloxy)benzoic acid (0.940 g, 2.36 mmol) was dissolved in THF (1.5 mL) and then diluted with water (50 mL). To the resulting suspension was added 1.000 N NaOH solution (2.30 mL, 2.30 mmol) at 0° C. The mixture was stirred at 0° C. for 30 min before a solution of silver nitrate (0.421 g, 2.48 mmol) in water (4 mL) was added over 5 min. Precipitate formed during the addition. The heterogeneous mixture was stirred at rt for 45 min before AcOEt (30 mL) was poured. The whole was stirred at rt for 10 min. The title compound (1.05 g, 88% yield) was collected as a white solid by suction filtration and dried over Drierite® under vacuum.

4. ((4-(5-(cyclopropylcarbamoyl)-2-methylphenylamino)-5-methylpyrrolo[1,2-f][1,2,4]triazine-6-carbonyl)(propyl)carbamoyloxy)methyl 4-(bis(benzyloxy)phosphoryloxy)benzoate

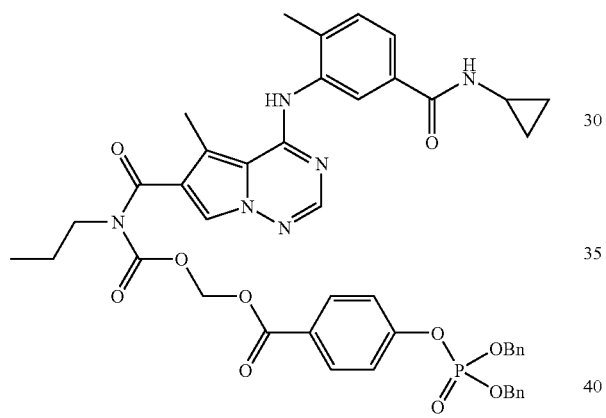

A mixture of iodomethyl 4-(5-(cyclopropylcarbamoyl)-2-methylphenylamino)-5-methylpyrrolo[1,2-f][1,2,4]triazine-6-carbonyl(propyl)carbamate (285 mg, 0.483 mmol) and 4-(bis(benzyloxy)phosphoryloxy)benzoic acid silver salt (490 mg, 0.966 mmol) in toluene (20 mL) was heated at 70° C. for 40 min. The solid phase was removed by suction filtration through Celite® 545. The filtrate was concentrated and the residue was subjected to ISCO (silica gel, 20-60% AcOEt/CH$_2$Cl$_2$) to provide the title compound (134 mg, 34% yield) as a white solid.

5. ((4-(5-(cyclopropylcarbamoyl)-2-methylphenylamino)-5-methylpyrrolo[1,2-f][1,2,4]triazine-6-carbonyl)(propyl)carbamoyloxy)methyl 4-(phosphonooxy)benzoate A mixture of ((4-(5-(cyclopropylcarbamoyl)-2-methylphenylamino)-5-methylpyrrolo[1,2-f][1,2,4]triazine-6-carbonyl)(propyl)carbamoyloxy)methyl 4-(bis(benzyloxy)phosphoryloxy)benzoate (134 mg, 0.156 mmol) and 10% Pd/C (40 mg) in MeOH (18 mL) was stirred at rt under H$_2$, provider with a H$_2$ balloon, for 40 min. The solid phase was removed by suction filtration through Celite® 545. The filtrate was concentrated and the residue was subjected to prep HPLC to provide the title compound TFA salt (20.0 mg, 16% yield) as a white powder. 98% pure by HPLC; (M+H)$^+$= 681.35.

EXAMPLES 127 to 137

The compounds shown below in Table 11 can be prepared in a similar manner as described in Example 126.

TABLE 11

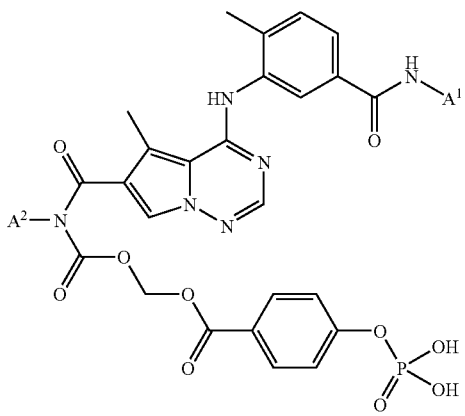

| Example | A$^1$ | A$^2$ |
|---|---|---|
| 127 | | |
| 128 | | |
| 129 | | |
| 130 | | |
| 131 | | |
| 132 | | |

TABLE 11-continued

| Example | A¹ | A² |
|---|---|---|
| 133 | isoxazol-3-yl | 2-methylbutyl |
| 134 | tert-butyl | cyclopropylmethyl |
| 135 | n-butyl(branched) | cyclopropylmethyl |
| 136 | cyclopropylmethyl | cyclopropylmethyl |
| 137 | isoxazol-3-yl | cyclopropylmethyl |

EXAMPLE 138

4-(((((5-(cyclopropylcarbamoyl)-2-methylphenyl)(5-methyl-6-(propylcarbamoyl)pyrrolo[1,2-f][1,2,4]triazin-4-yl)carbamoyloxy)methoxy)carbonyl)phenylphosphonic acid

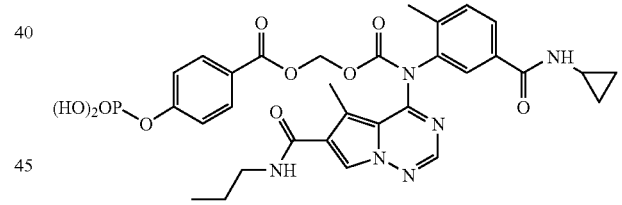

A mixture of chloromethyl 5-(cyclopropylcarbamoyl)-2-methylphenyl(5-methyl-6-(propylcarbamoyl)pyrrolo[1,2-f][1,2,4]triazin-4-yl)carbamate (44 mg, 0.089 mmol) and 4-((bis(benzyloxy))phosphoryl)benzoic acid silver salt (90 mg, 0.178 mmol) in toluene (5 mL) was heated at reflux for 15 hr. The mixture was cooled to rt, diluted with ethyl acetate (20 mL), sonicated, filtered and concentrated. The residue was subjected to prep HPLC to provide a yellow powder. The mixture of the yellow solid and 10% Pd/C (2 mg) in MeOH (5 mL) was stirred at rt under $H_2$, provided with a $H_2$ balloon, for 2 hr. The solid phase was filtered and rinsed with MeOH. The filtrate was concentrated to dryness under vacuum. The residue was subjected to prep HPLC to provide the title compound (7 mg, 11.8% yield two steps) as a yellow powder. 99.5% pure by HPLC; $(M+H)^+=681.3$.

EXAMPLES 139 to 149

The compounds shown below in Table 12 can be prepared in a similar manner as described in Example 138.

TABLE 12
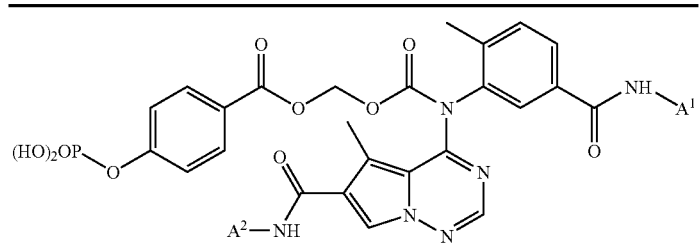
| Example | A¹ | A² |
|---|---|---|
| 139 | isobutyl | isopropyl |
| 140 | n-pentyl | isopropyl |
| 141 | cyclopropyl | isopropyl |
| 142 | isoxazol-3-yl | isopropyl |
| 143 | isobutyl | n-propyl |
| 144 | n-pentyl | n-propyl |
| 145 | isoxazol-3-yl | n-propyl |
| 146 | isobutyl | cyclopropyl |

TABLE 12-continued

| Example | A¹ | A² |
|---------|-----|-----|
| 147 | (butyl) | (cyclopropyl) |
| 148 | (cyclopropyl) | (cyclopropyl) |
| 149 | (isoxazol-3-yl) | (cyclopropyl) |

EXAMPLE 150

((5-(cyclopropylcarbamoyl)-2-methylphenyl)(5-methyl-6-(propylcarbamoyl)pyrrolo[1,2-f][1,2,4]triazin-4-yl)carbamoyloxy)methyl nicotinate

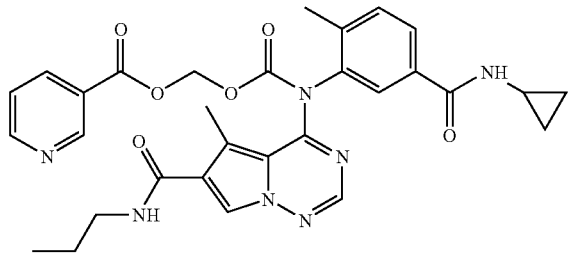

A mixture of chloromethyl 5-(cyclopropylcarbamoyl)-2-methylphenyl(5-methyl-6-(propylcarbamoyl)pyrrolo[1,2-f][1,2,4]triazin-4-yl)carbamate (100 mg, 0.17 mmol) and nicotinic acid silver salt (118 mg, 0.51 mmol) in toluene (5 mL) was heated at reflux for 15 hr. The mixture was cooled to rt, diluted with ethyl acetate (20 mL), sonicated, filtered and concentrated. The residue was subjected to prep HPLC to provide the title compound (56 mg, 56% yield) as a TFA salt. 99% pure by HPLC; (M+H)⁺=586.31.

EXAMPLES 151 to 161

The compounds shown below in Table 13 can be prepared in a similar manner as described in Example 150.

TABLE 13

| Example | A¹ | A² |
|---------|-----|-----|
| 151 | (ethyl) | (ethyl) |
| 152 | (butyl) | (ethyl) |
| 153 | (cyclopropyl) | (ethyl) |

TABLE 13-continued

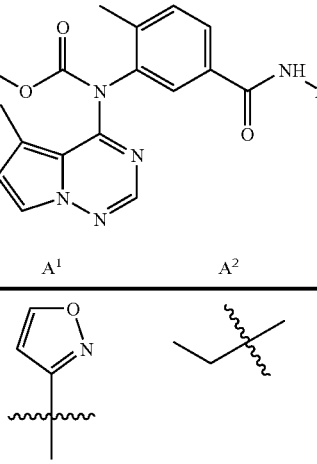

| Example | A¹ | A² |
|---|---|---|
| 154 |  | 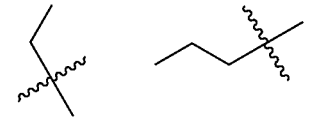 |
| 155 |  | 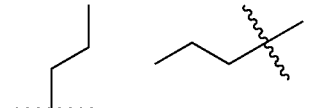 |
| 156 |  | 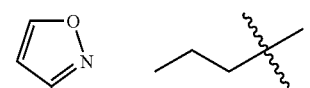 |
| 157 |  |  |
| 158 |  |  |
| 159 |  |  |
| 160 | 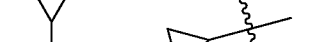 |  |
| 161 | 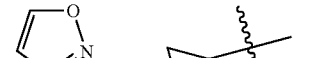 | 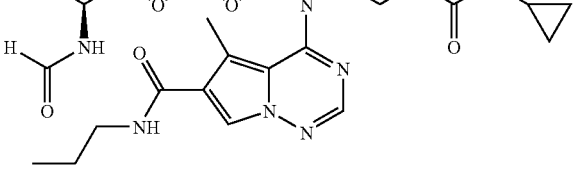 |

EXAMPLE 162

(S)-((5-(cyclopropylcarbamoyl)-2-methylphenyl)(5-methyl-6-(propylcarbamoyl)pyrrolo[1,2-f][1,2,4]triazin-4-yl)carbamoyloxy)methyl 2-formamidopropanoate

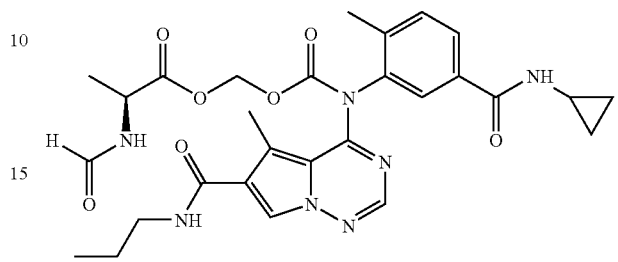

A mixture of chloromethyl 5-(cyclopropylcarbamoyl)-2-methylphenyl(5-methyl-6-(propylcarbamoyl)pyrrolo[1,2-f][1,2,4]triazin-4-yl)carbamate (50 mg, 0.12 mmol) and (S)-2-formamidopropanoic acid silver salt (81 mg, 0.36 mmol) in toluene (5 mL) was heated at reflux for 15 hr. The mixture was cooled to rt, diluted with ethyl acetate (20 mL), sonicated, filtered and concentrated. The residue was subjected to prep HPLC to provide the title compound (9.3 mg, 13.3% yield) as a yellow powder. 98% pure by HPLC; $(M+H)^+=580.41$.

EXAMPLES 163 to 173

The compounds shown below in Table 14 can be prepared in a similar manner as described in Example 162.

TABLE 14

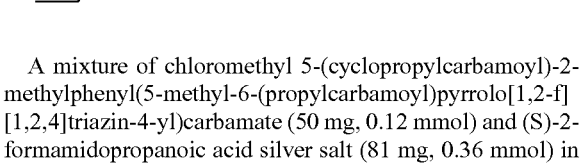

| Example | A¹ | A² |
|---|---|---|
| 163 | 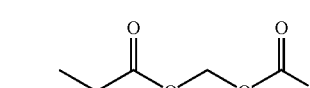 |  |
| 164 | 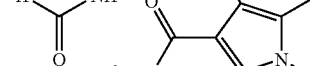 |  |
| 165 | 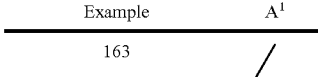 |  |

TABLE 14-continued

| Example | A¹ | A² |
|---------|----|----|
| 166 | isoxazol-3-yl | sec-butyl |
| 167 | isobutyl | n-propyl |
| 168 | n-butyl | sec-butyl |
| 169 | isoxazol-3-yl | n-propyl |
| 170 | isobutyl | cyclopropyl |
| 171 | n-propyl | cyclopropyl |
| 172 | cyclopropyl | cyclopropyl |
| 173 | isoxazol-3-yl | cyclopropyl |

EXAMPLE 174

((5-(cyclopropylcarbamoyl)-2-methylphenyl)(5-methyl-6-(propylcarbamoyl)pyrrolo[1,2-f][1,2,4]triazin-4-yl)carbamoyloxy)methyl 2(4(phosphonooxy)phenyl)acetate

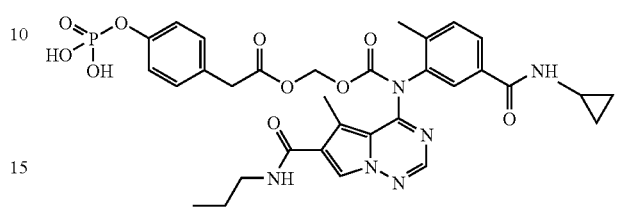

1. Methyl 2-(4-(bis(benzyloxy)phosphoryloxy)phenyl)acetate

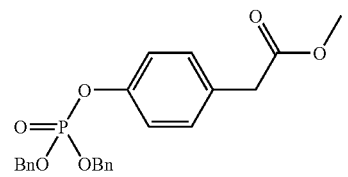

To a solution of methyl 2-(4-hydroxyphenyl)acetate (1.89 g, 11.4 mmol) in acetonitrile (90 mL) at −10° C. was added CCl₄ (5.5 mL, 57 mmol), DIPEA (4.16 mL, 23.9 mmol) and DMAP (139 mg, 1.14 mmol). After stirring for 10 mins, the mixture was added dibenzyl phosphite (3.7 mL, 16.5 mmol) slowly to keep the temperature below −10° C. The reaction was stirred at −10° C. for 1 h. The reaction was quenched with aqueous K₂HPO₄ (0.5 M) in acetonitrile (60 mL) and allowed to stirred at rt. The mixture was extracted by ethyl acetate (150 mL×3). The combined organic layers was washed with water and brine, dried over Na₂SO₄, filtered and concentrated under vacuum. The residue was subjected to ISCO (30-50% AcOEt/hexanes) to give the title compound (4.3 g, 88.5% yield) as a colorless oil.

2. 2-(4-(bis(benzyloxy)phosphoryloxy)phenyl)acetic acid

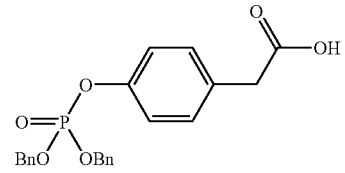

LiOH (1N, 9 mL, 5 mmol) was added into a mixture of methyl 2-(4-(bis(benzyloxy)phosphoryloxy)phenyl)acetate (1.53 g, 3.59 mmol) in THF (15 mL) and methanol (5 mL) at 0° C. The reaction was stirred at 0° C. for 3.5 h, than 0.5 h at rt. The reaction was monitored by LC-MS until the hydrolysis was completed. The mixture was cooled to 0° C. and acidified by 1N HCl to pH=2. The mixture was concentrated and extracted by ethyl acetate (50 mL×3). The extraction was dried over Na₂SO₄ and concentrated to dryness to give the acid (1.5 g, 67.6% yield) as a light yellow oil.

3. 2-(4-(bis(benzyloxy)phosphoryloxy)phenyl)acetic acid silver salt

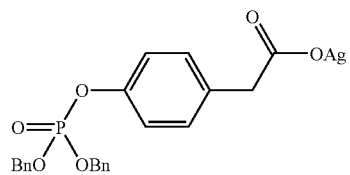

To a suspension of 2-(4-(bis(benzyloxy)phosphoryloxy)phenyl)acetic acid (1.5 g, 3.63 mmol) in water (50 mL) at 0° C. was added 1N NaOH slowly. The mixture was stirred at rt for 10 mins. Then AgNO3 (0.68 g, 4 mmol) was added. The reaction was stirred vigorously for 1 h in the dark. The title compound (1.5 g, 79.4% yield) was collected as a grey solid by suction filtration and dried over Drierite® under vacuum.

4. ((5-(cyclopropylcarbamoyl)-2-methylphenyl)(5-methyl-6-(propylcarbamoyl)pyrrolo[1,2-f][1,2,4]triazin-4-yl)carbamoyloxy)methyl 2-(4-(bis(benzyloxy)phosphoryloxy)phenyl)acetate

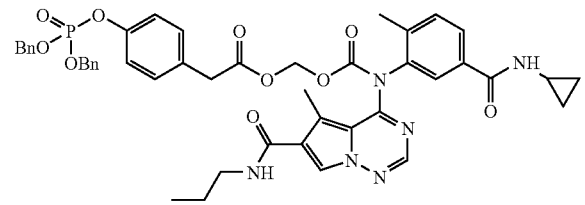

A mixture of chloromethyl 5-(cyclopropylcarbamoyl)-2-methylphenyl(5-methyl-6-(propylcarbamoyl)pyrrolo[1,2-f][1,2,4]triazin-4-yl)carbamate (70 mg, 0.14 mmol) and 2-(4-(bis(benzyloxy)phosphoryloxy)phenyl)acetic acid silver salt (182 mg, 0.351 mmol) in toluene (5 mL) was heated at reflux for 15 hr. The mixture was cooled to rt, diluted with ethyl acetate (20 mL), sonicated, filtered and concentrated. The residue was subjected to prep HPLC to provide the title compound (30 mg, 24% yield) as a yellow powder. 99% pure by HPLC; $(M+H)^+$=875.38.

5. ((5-(cyclopropylcarbamoyl)-2-methylphenyl)(5-methyl-6-(propylcarbamoyl)pyrrolo[1,2-f][1,2,4]triazin-4-yl)carbamoyloxy)methyl 2-(4-(phosphonooxy)phenyl)acetate A mixture of ((5-(cyclopropylcarbamoyl)-2-methylphenyl)(5-methyl-6-(propylcarbamoyl)pyrrolo[1,2-f][1,2,4]triazin-4-yl)carbamoyloxy)methyl 2-(4-(bis(benzyloxy)phosphoryloxy)phenyl)acetate (18 mg, 0.021 mmol) and 10% Pd/C (3 mg) in THF (2 mL) and MeOH (2 mL) was stirred at rt under $H_2$, provided with a $H_2$ balloon, for 2 hr. The solid phase was filtered and rinsed with MeOH. The filtrate was concentrated to dryness under vacuum. The residue was The residue was subjected to prep HPLC to provide the title compound (10 mg, 69.9% yield) as a yellow powder. 98% pure by HPLC; $(M+H)^+$=695.35.

EXAMPLES 175 to 185

The compounds shown below in Table 15 can be prepared in a similar manner as described in Example 174.

TABLE 15

| Example | A¹ | A² |
|---|---|---|
| 175 | | |
| 176 | | |
| 177 | | |

TABLE 15-continued
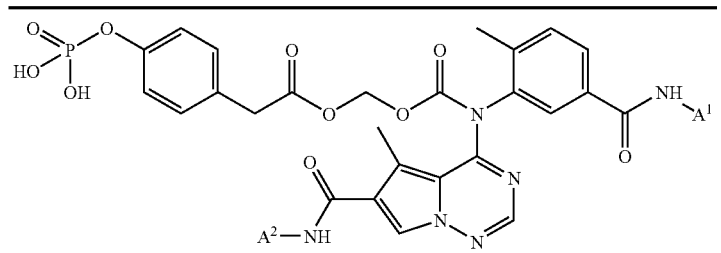
| Example | A¹ | A² |
|---|---|---|
| 178 | isoxazol-3-yl | sec-butyl |
| 179 | tert-butyl | n-butyl |
| 180 | n-butyl | n-butyl |
| 181 | isoxazol-3-yl | n-butyl |
| 182 | tert-butyl | cyclopropyl |
| 183 | n-butyl | cyclopropyl |
| 184 | cyclopropyl | cyclopropyl |
| 185 | isoxazol-3-yl | cyclopropyl |

EXAMPLE 186

((4-(5-(cyclopropylcarbamoyl)-2-methylphenylamino)-5-methylpyrrolo[1,2-f][1,2,4]triazine-6-carbonyl)(propyl)carbamoyloxy)methyl 2-(4-(phosphonooxy)phenyl)acetate

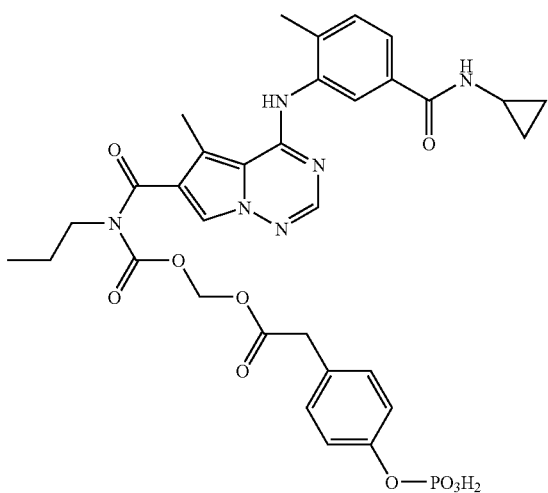

1. ((4-(5-(cyclopropylcarbamoyl)-2-methylphenylamino)-5-methylpyrrolo[1,2-f][1,2,4]triazine-6-carbonyl)(propyl)carbamoyloxy)methyl 2-(4-(bis(benzyloxy)phosphoryloxy)phenyl)acetate

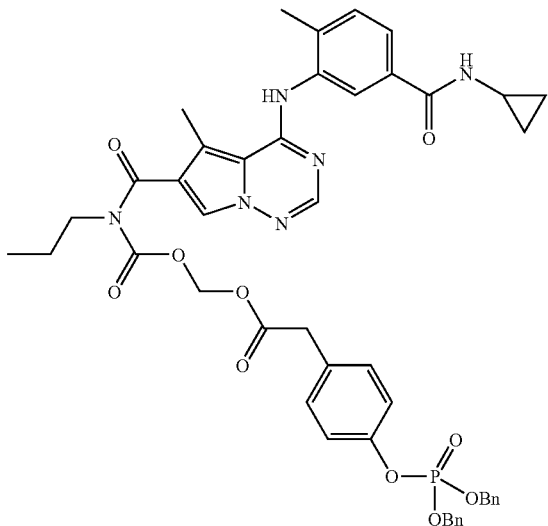

A mixture of iodomethyl 4-(5-(cyclopropylcarbamoyl)-2-methylphenylamino)-5-methylpyrrolo[1,2-f][1,2,4]triazine-6-carbonyl(propyl)carbamate (6.65g, 11.3 mmol) and 2-(4-(bis(benzyloxy)phosphoryloxy)phenyl)acetic acid silver salt (10.0 g, 19.2 mmol) in toluene (450 mL) was heated at 65° C. for 30 min. The solid phase was removed by suction filtration through Celite® 545. The filtrate was concentrated and the residue was subjected to ISCO (silica gel, 20-60% AcOEt/$CH_2Cl_2$) to provide the title compound (3.05 mg, 31%) as a pale solid. This product was 90% pure by HPLC, but it was used in the next step without further purification.

2. ((4-(5-(cyclopropylcarbamoyl)-2-methylphenylamino)-5-methylpyrrolo[1,2-f][1,2,4]triazine-6-carbonyl)(propyl)carbamoyloxy)methyl 2-(4-(phosphonooxy)phenyl)acetate A mixture of ((4-(5-(cyclopropylcarbamoyl)-2-methylphenylamino)-5-methylpyrrolo[1,2-f][1,2,4]triazine-6-carbonyl)(propyl)carbamoyloxy)methyl 2-(4-(bis(benzyloxy)phosphoryloxy)phenyl)acetate (2.50 g, 2.86 mmol) and 10% Pd/C (0.50 g) in MeOH (200 mL) and THF (50 mL) was stirred under $H_2$, provided with a $H_2$ balloon, for 40 min. The solid phase was removed by suction filtration through Celite® 545. The filtrate was concentrated under vacuum to dryness. To the residue was added 50 mL 5% MeOH/AcOEt, and the heterogeneous mixture was stirred at rt for 30 min. The title compound (1.79 g, 90% yield) was collected by suction filtration. 100 % pure by HPLC; $(M+H)^+=695.42^+$.

EXAMPLES 187 to 197

The compounds shown below in Table 16 can be prepared in a similar manner as described Example 186.

TABLE 16

| Example | A¹ | A² |
|---|---|---|
| 187 | ![] | ![] |
| 188 | ![] | ![] |
| 189 | ![] | ![] |

TABLE 16-continued

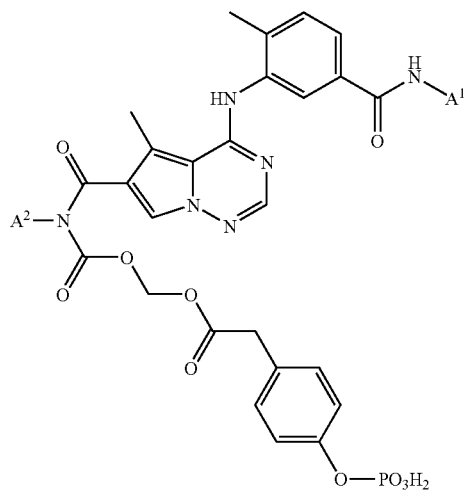

| Example | A¹ | A² |
|---|---|---|
| 190 | isoxazol-3-yl | sec-butyl |
| 191 | isobutyl | butyl |
| 192 | butyl | butyl |
| 193 | isoxazol-3-yl | butyl |
| 194 | isobutyl | cyclopropylmethyl |
| 195 | butyl | cyclopropylmethyl |

TABLE 16-continued

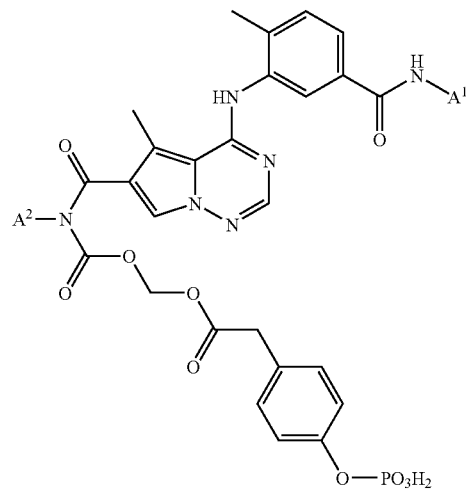

| Example | A¹ | A² |
|---|---|---|
| 196 | cyclopropyl | cyclopropylmethyl |
| 197 | isoxazol-3-yl | cyclopropylmethyl |

EXAMPLE 198

((4-(5-(cyclopropylcarbamoyl)-2-methylphenylamino)-5-methylpyrrolo[1,2-f][1,2,4]triazine-6-carbonyl)(propyl)carbamoyloxy)methyl 2-(4-(phosphonooxy)phenyl)acetate, sodium salt

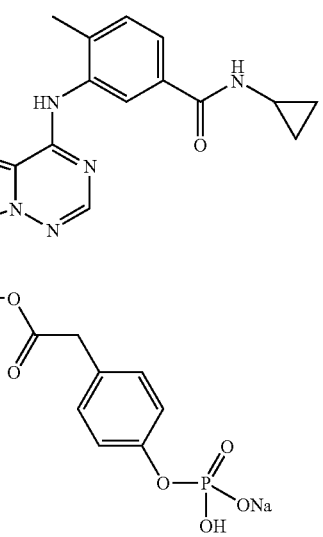

209

To a suspension of ((4-(5-(cyclopropylcarbamoyl)-2-methylphenylamino)-5-methylpyrrolo[1,2-f][1,2,4]triazine-6-carbonyl)(propyl)carbamoyloxy)methyl 2-(4-(phosphonooxy)phenyl)acetate (0.500 g, 0.720mmol) in water (650 mL) was added NaOH solution made from 0.74 mL 1.000 N NaOH solution and 8 mL water at 0° C. The resulting mixture was stirred at 0° C. for 30 min to become a light milky solution. This solution was then frozen at −78° C., and lyophilized to provide the title compound as a white amorphous powder. A crystalline form of the salt was obtained as follow. A portion of the amorphous sodium salt (164 mg) was dissolved in methanol (20 mL) at rt. A small amount of insoluble material was removed from the solution by filtration through a Nylon acrodisc. The clear filtrate was placed in a 100 mL beaker, and isopropyl alcohol (15 mL) was added. The resulting solution was placed in a cold room (5° C.) for the compound to crystallize. Twenty-four hours later, the white crystalline material (47 mg) was collected by suction filtration.

EXAMPLES 199 to 209

The compounds shown below in Table 17 can be prepared in a similar manner as described Example 198.

TABLE 17

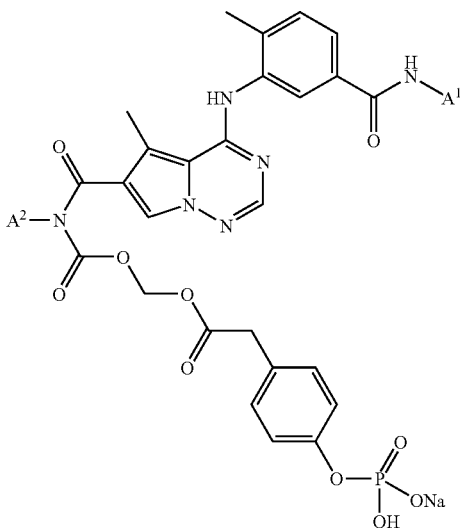

| Example | A¹ | A² |
|---------|----|----|
| 199 | | |
| 200 | | |
| 201 | | |
| 202 | | |
| 203 | | |
| 204 | | |
| 205 | | |
| 206 | | |
| 207 | | |

TABLE 17-continued

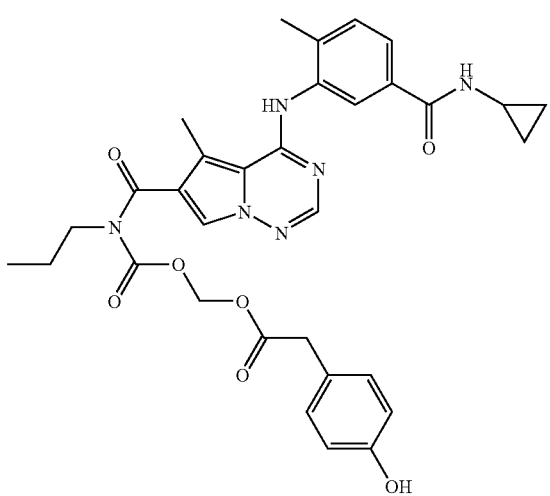

| Example | A¹ | A² |
|---|---|---|
| 208 | cyclopropyl (wavy bond) | cyclopropyl (wavy bond) |
| 209 | isoxazol-3-yl (wavy bond) | cyclopropyl (wavy bond) |

EXAMPLE 210

((4-(5-(cyclopropylcarbamoyl)-2-methylphenylamino)-5-methylpyrrolo[1,2-f][1,2,4]triazine-6-carbonyl)(propyl)carbamoyloxy)methyl 2-(4-hydroxyphenyl)acetate 1. ((4-(5-(cyclopropylcarbamoyl)-2-methylphenylamino)-5-methylpyrrolo[1,2-f][1,2,4]triazine-6-carbonyl)(propyl)carbamoyloxy)methyl 2-(4-(benzyloxy)phenyl)acetate

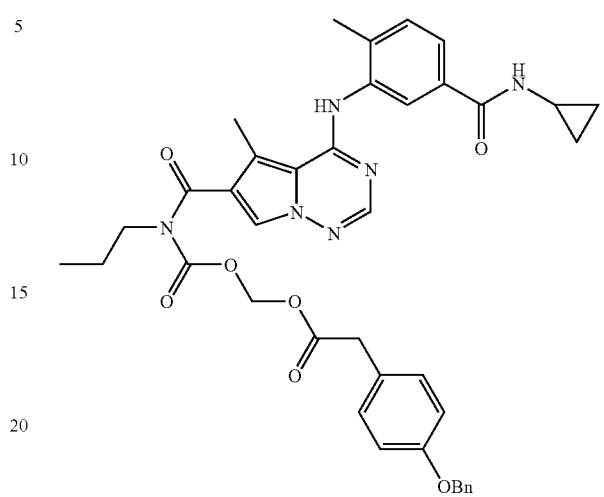

A mixture of step 2 in Ex. 14 (0.300 g, 0.501 mmol) and 2-(4-(benzyloxy)phenyl)acetic acid silver salt (0.350 g, 1.00 mmol) in toluene (25 mL) was heated at reflux for 16 hr. Additional 2-(4-(benzyloxy)phenyl)acetic acid silver salt (0.200 g, 0.573 mmol) was added, and the mixture was continued to be heated for additional 24 hr. The insoluble material was removed by suction filtration through Celite® 545. The filtrate was concentrated under vacuum to dryness. The residue was dissolved in $CH_2Cl_2$ (3 mL) and to this solution was added TFA (2.5 mL) at 0° C. The resulting solution was stirred at 0° C. for 1 hr, and then concentrated under vacuum. The residue was diluted with AcOEt, washed with saturated $NaHCO_3$ solution (twice) and brine, dried over anhydrous $MgSO_4$. The title compound (0.252 g) was isolated as a white solid by ISCO (12 g, silica gel, 40-70% AcOEt/hexane). This product was only 50% pure but used in the next step without further purification.

2. ((4-(5-(cyclopropylcarbamoyl)-2-methylphenylamino)-5-methylpyrrolo[1,2-f][1,2,4]triazine-6-carbonyl)(propyl)carbamoyloxy)methyl 2-(4-hydroxyphenyl)acetate A mixture of ((4-(5-(cyclopropylcarbamoyl)-2-methylphenylamino)-5-methylpyrrolo[1,2-f][1,2,4]triazine-6-carbonyl)(propyl)carbamoyloxy)methyl 2-(4-(benzyloxy)phenyl)acetate (0.252 g, 50% pure) and 10% Pd/C (75 mg) in THF (20 mL) and MeOH (15 mL) was stirred under $H_2$, provided with a $H_2$ balloon, for 3 hr. The solid phase was removed by suction filtration through Celite® 545, and the filtrate was concentrated under vacuum. The title compound (18 mg) as a white solid was isolated by prep. HPLC.

EXAMPLES 211 to 221

The compounds shown below in Table 18 can be prepared in a similar manner as described Example 210.

TABLE 18
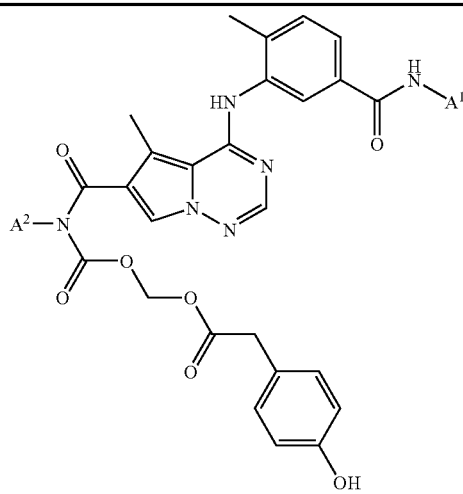
| Example | A¹ | A² |
|---|---|---|
| 211 | | |
| 212 | | |
| 213 | | |
| 214 | | |
| 215 | | |
| 216 | | |
| 217 | | |
TABLE 18-continued
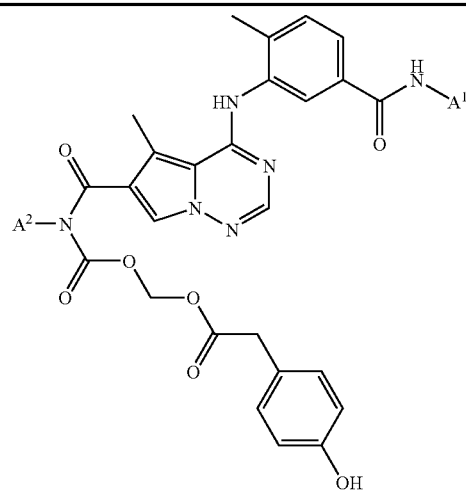
| Example | A¹ | A² |
|---|---|---|
| 218 | | |
| 219 | | |
| 220 | | |
| 221 | | |
We claim:
1. A compound of Formula I:
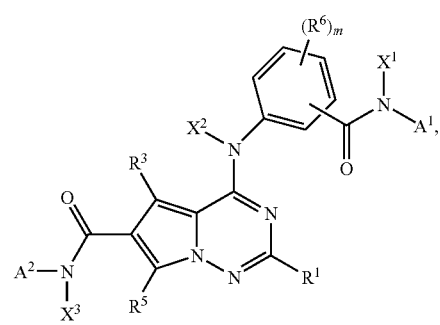
or a pharmaceutically acceptable salts thereof, wherein at least one of $X^1$, $X^2$ or $X^3$ is

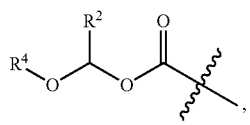
(i)

and any remaining $X^1$, $X^2$ or $X^3$ is hydrogen;

$A^1$ and $A^2$ are each independently selected from the group consisting of optionally-substituted alkyl, optionally-substituted cycloalkyl, optionally-substituted aryl, optionally-substituted aralkyl, optionally-substituted heterocyclo and optionally-substituted heteroaryl;

$R^1$, $R^3$ and $R^5$ are each independently selected from the group consisting of hydrogen, optionally-substituted alkyl, —$OR^{14}$, —$C(=O)NR^{14}R^{14a}$, —$NR^{14}R^{14a}$, —$SO_2NR^{14}R^{14a}$, —$NR^{14}SO_2NR^{14a}R^{14b}$, —$NR^{14a}SO_2R^{14}$, —$NR^{14}C(=O)R^{14a}$, —$NR^{14}CO_2R^{14a}$, —$NR^{14}C(=O)NR^{14a}R^{14b}$, halogen, cyano, optionally-substituted cycloalkyl, optionally-substituted aryl, optionally-substituted heterocyclo and optionally-substituted heteroaryl;

$R^2$ is independently selected from the group consisting of hydrogen and optionally-substituted alkyl;

$R^4$ is independently selected from the group consisting of:

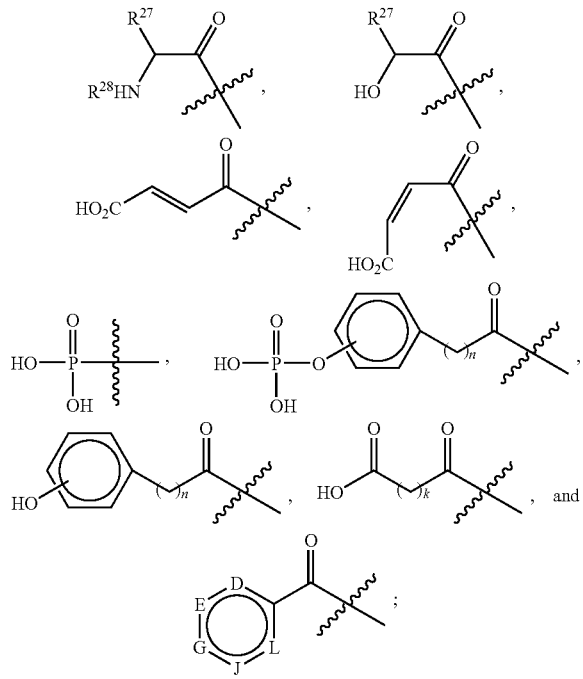

$R^6$ is attached to any available carbon atom of the phenyl ring and at each occurrence is independently selected from the group consisting of optionally-substituted alkyl, halogen, trifluoromethoxy, trifluoromethyl, hydroxy, alkoxy, alkanoyl, alkanoyloxy, thiol, alkylthio, ureido, nitro, cyano, carboxy, carboxyalkyl, alkoxycarbonyl, alkylthiono, arylthiono, arylsulfonylamine, alkylsulfonylamine, sulfonic acid, alkysulfonyl, sulfonamido, phenyl, benzyl, aryloxy and benzyloxy, wherein each $R^6$ group in turn may be further substituted by one to two $R^{18}$;

$R^{14}$, $R^{14a}$ and $R^{14b}$ are independently selected from the group consisting of hydrogen, optionally-substituted alkyl, optionally-substituted aryl, optionally-substituted cycloalkyl, optionally-substituted heterocyclo, and optionally-substituted heteroaryl, except when $R^{14}$ is joined to a sulfonyl group, as in —$S(=O)R^{14}$, —$SO_2R^{14}$, and —$NR^{14a}SO_2R^{14}$, then $R^{14}$ is not hydrogen;

$R^{18}$ is selected from the group consisting of $C_{1-6}$alkyl, $C_{2-6}$alkenyl, halogen, haloalkyl, haloalkoxy, cyano, nitro, amino, $C_{1-4}$alkylamino, amino$C_{1-4}$alkyl, hydroxy, hydroxy$C_{1-4}$alkyl, alkoxy, $C_{1-4}$alkylthio, aryl, heterocyclo, (aryl)alkyl, aryloxy, and (aryl)alkoxy;

$R^{27}$ and $R^{28}$ are independently selected from the group consisting of hydrogen, optionally-substituted alkyl, optionally-substituted cycloalkyl, optionally-substituted aryl, optionally-substituted aralkyl, optionally-substituted heterocyclo and optionally-substituted heteroaryl;

one of D, E, G, J or L is =N— and each remaining D, E, G, J or L is =C—;

m is 0, 1, 2 or 3;

n is 0 or 1; and k is 0, 1 or 2.

2. The compound of claim 1, wherein k is 1 or 2.

3. The compound of claim 1, wherein $A^1$ is selected from the group consisting of optionally-substituted $C_1$-$C_6$ alkyl, optionally-substituted $C_1$-$C_6$ cycloalkyl and optionally-substituted $C_1$-$C_6$ heteroaryl.

4. The compound of claim 1, wherein $A^1$ is ethyl.

5. The compound of claim 1, wherein $A^1$ is propyl.

6. The compound of claim 1, wherein $A^1$ is cyclopropyl.

7. The compound of claim 1, wherein $A^1$ is isoxazole.

8. The compound of claim 1, wherein $A^2$ is selected from the group consisting of optionally substituted $C_1$-$C_6$ alkyl and optionally-substituted $C_1$-$C_6$ cycloalkyl.

9. The compound of claim 1, wherein $A^2$ is ethyl.

10. The compound of claim 1, wherein $A^2$ is propyl.

11. The compound of claim 1, wherein $A^2$ is cyclopropyl.

12. The compound of claim 1, wherein $R^1$, $R^3$ and $R^5$ are each independently selected from the group consisting of hydrogen and optionally-substituted $C_1$-$C_4$ alkyl.

13. The compound of claim 1, wherein $R^1$ and $R^5$ are each hydrogen and $R^3$ is methyl.

14. The compound of claim 1, wherein $R_2$ is selected from the group consisting of hydrogen and $C_1$-$C_4$ alkyl.

15. A pharmaceutical composition, which comprises (a) a pharmaceutically effective amount of a compound of Formula I or a pharmaceutically acceptable salt thereof, as claimed in claim 1, and (b)one or more pharmaceutically acceptable carriers, excipients or diluents.

16. A method of treating an inflammatory disorder which is selected the group consisting of rheumatoid arthritis, psoriasis and atherosclerosis comprising administering to a patient in need of such treatment a pharmaceutical composition according to claim 15.

17. A compound having the formula selected from the group consisting of:
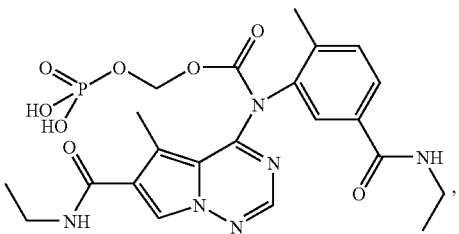
,
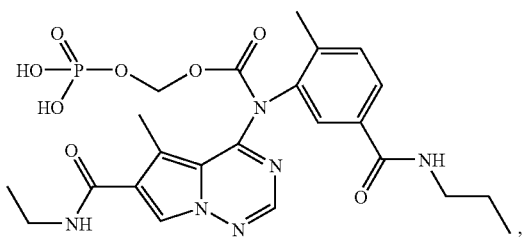
,
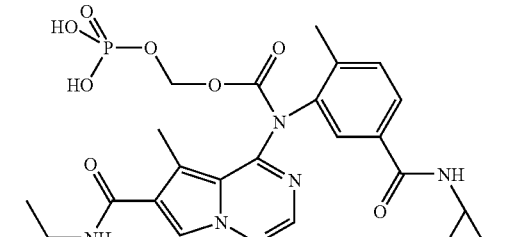
,
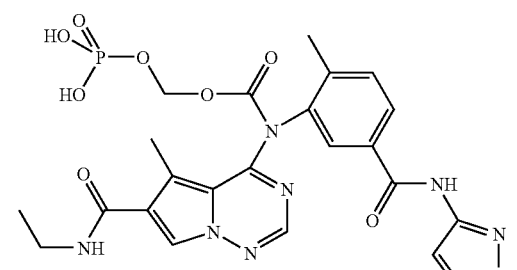
,
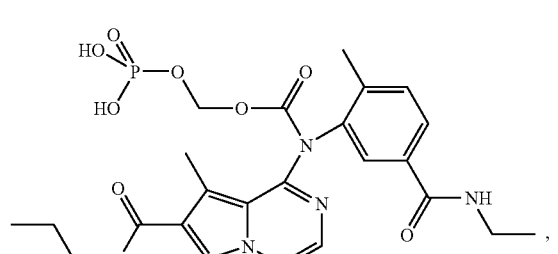
,
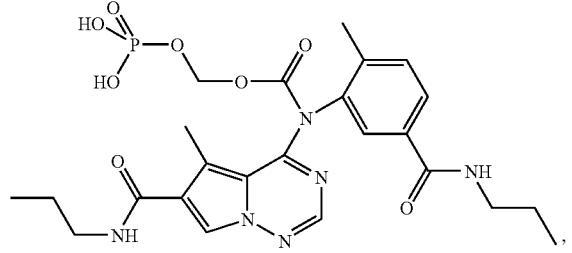
,
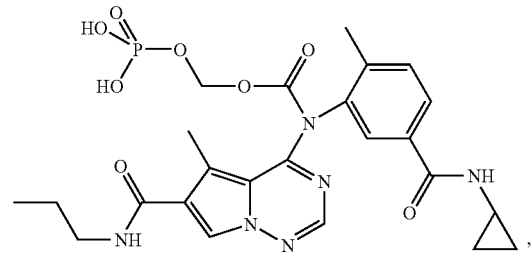
,
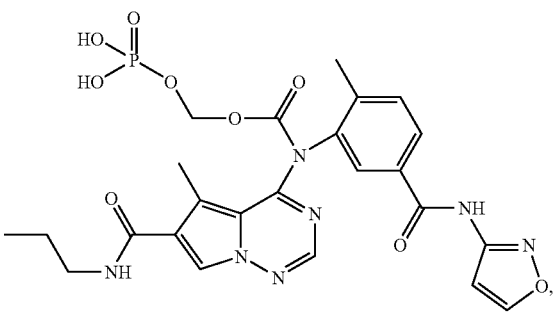
,
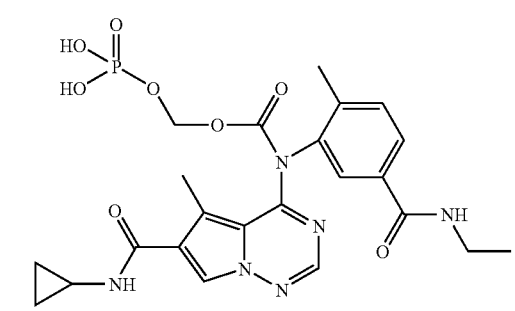
,
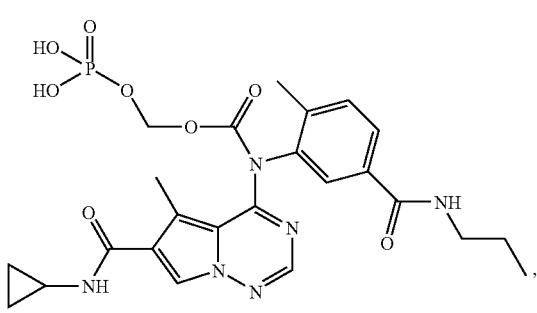
,
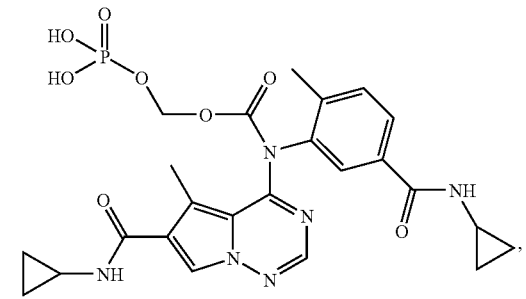
, -continued
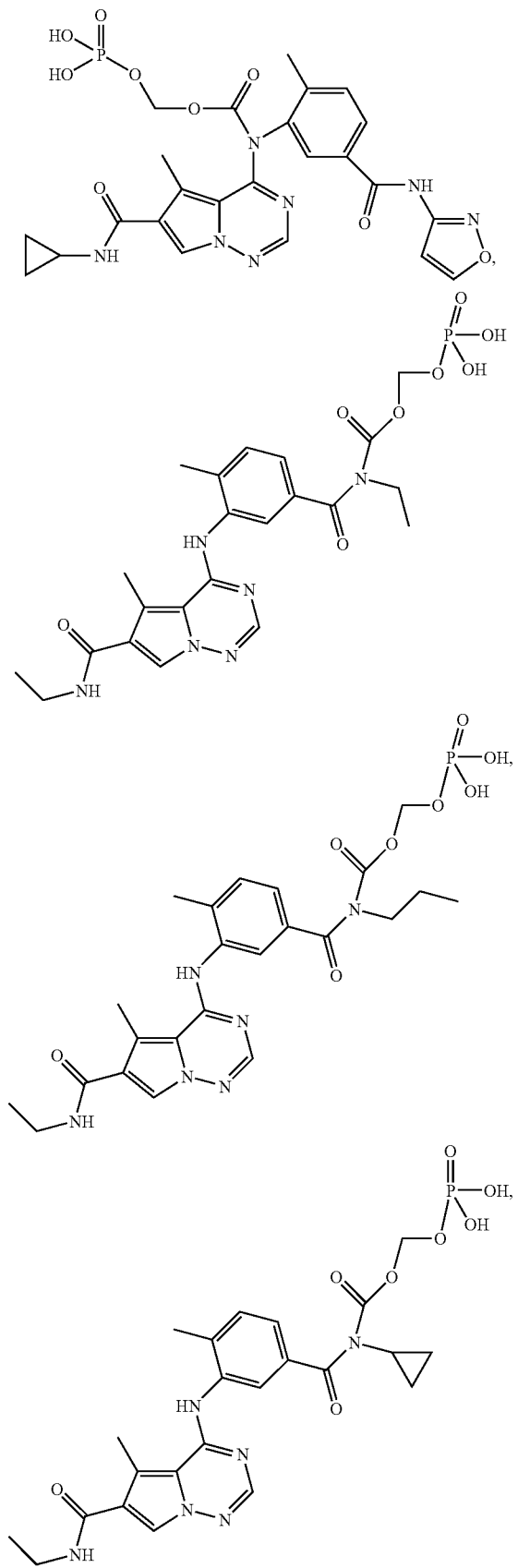
-continued
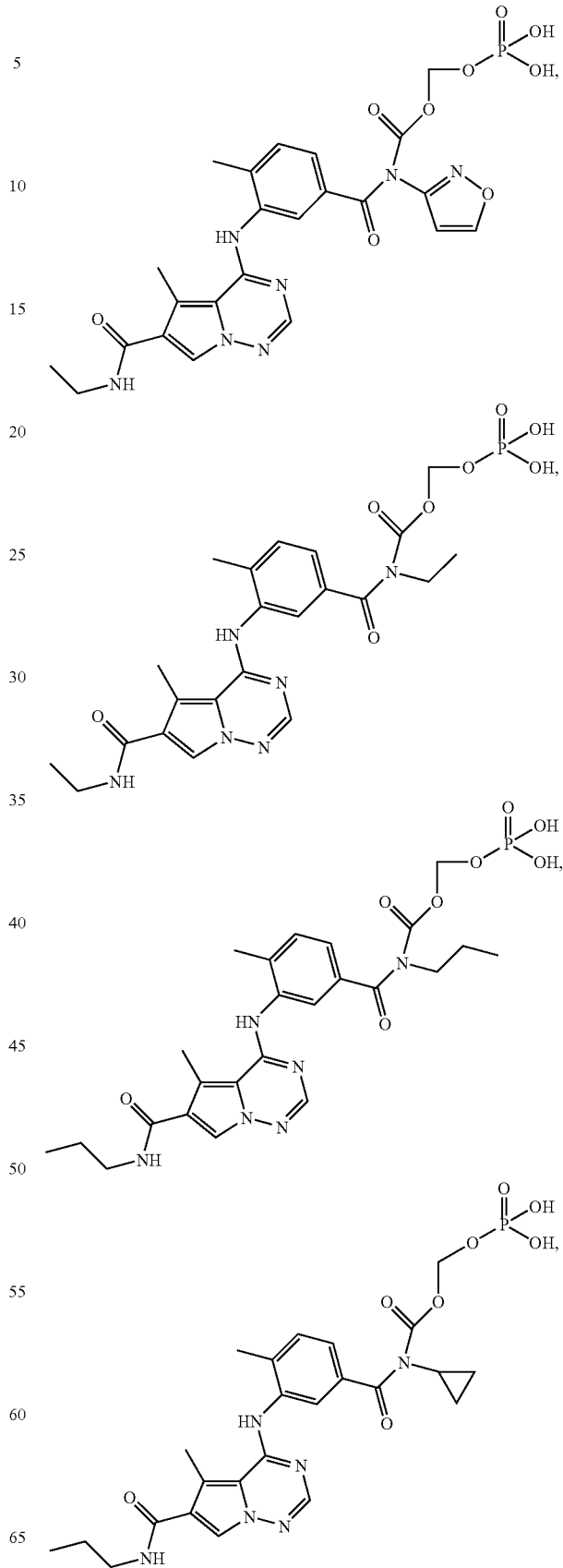

221
-continued
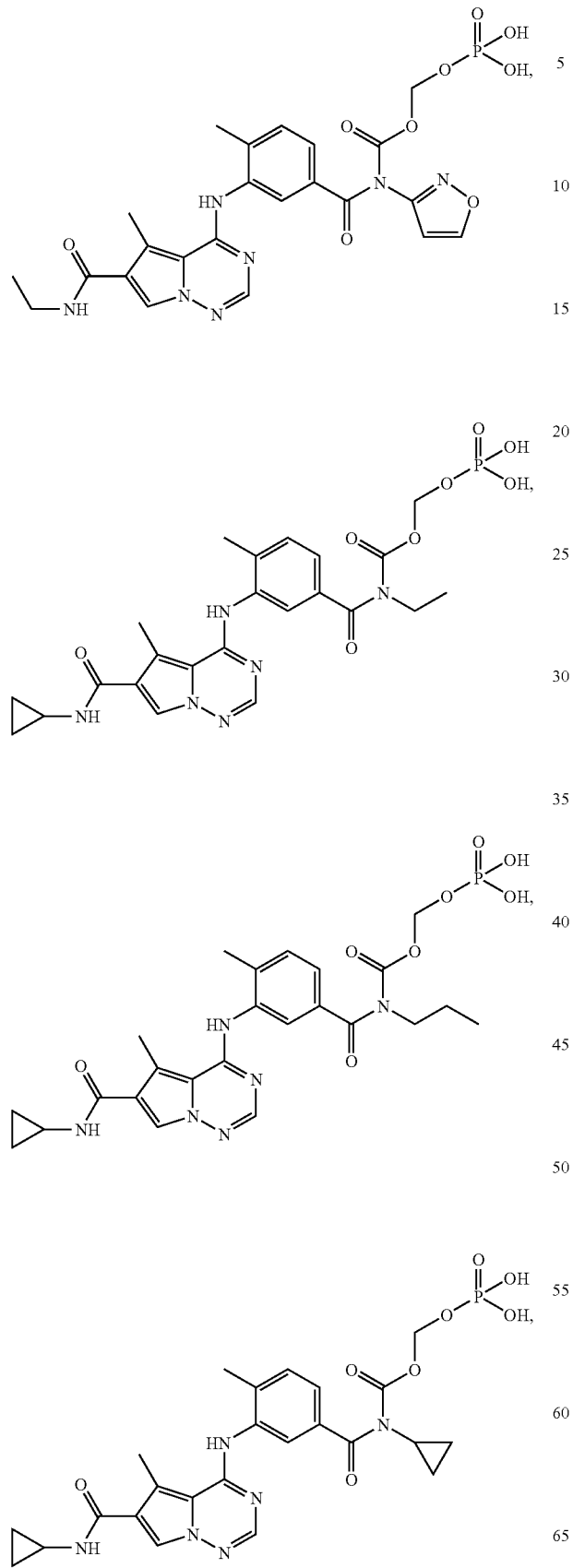
222
-continued
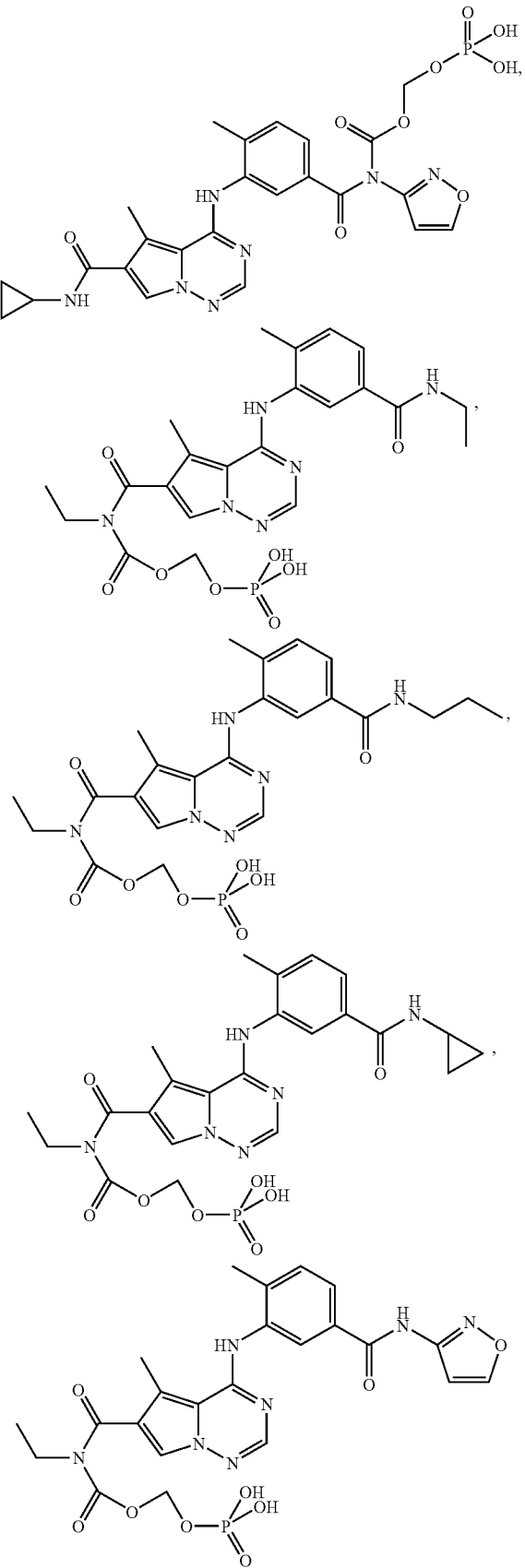

-continued
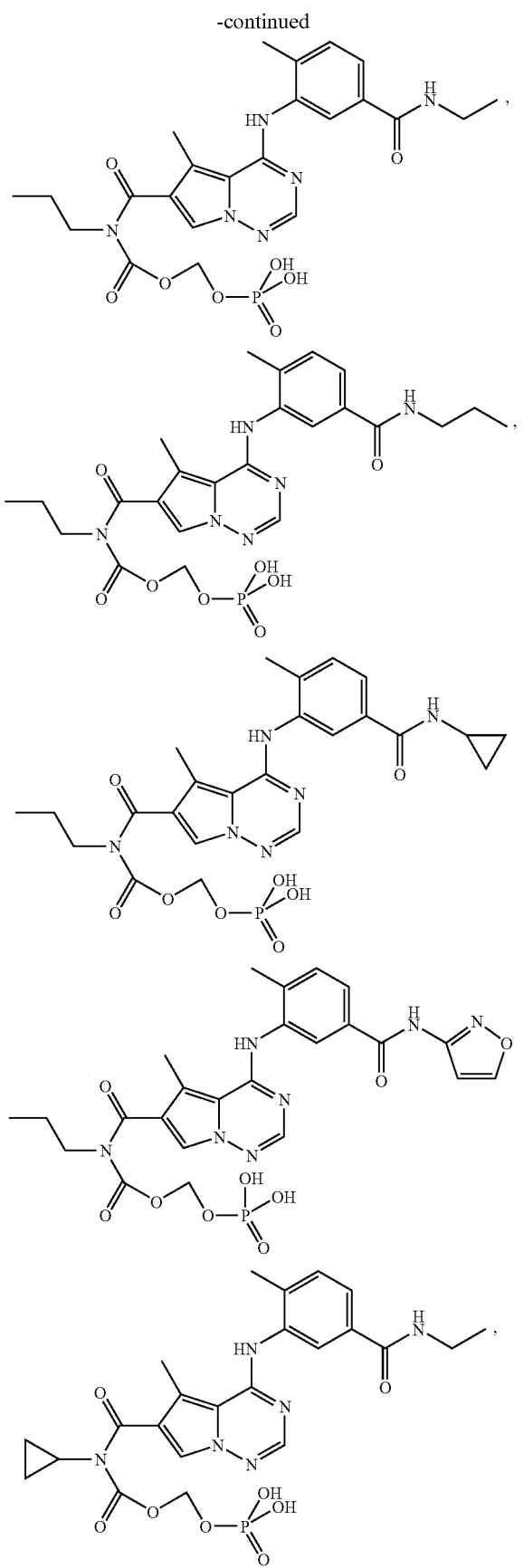
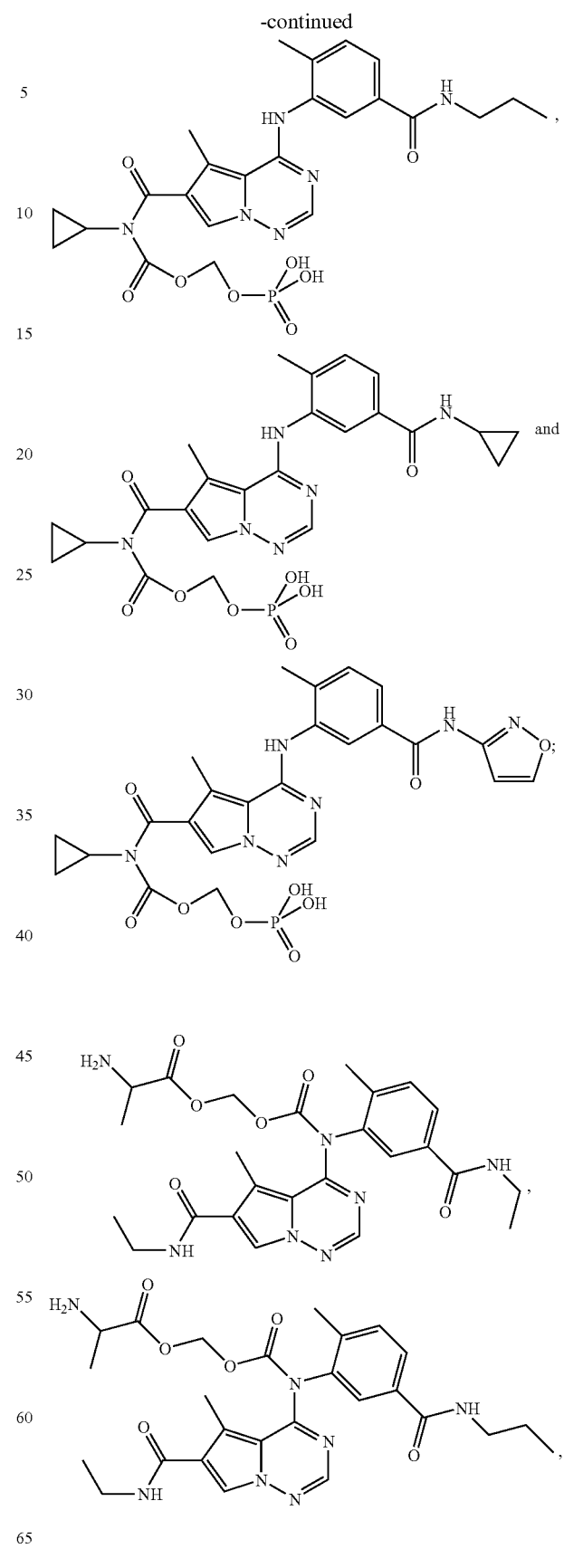

225
-continued
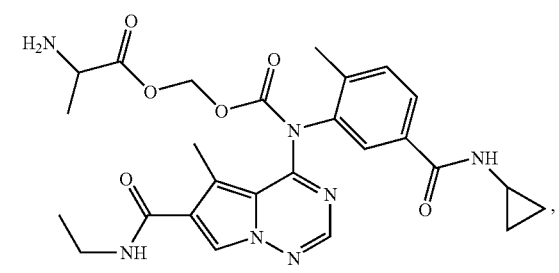
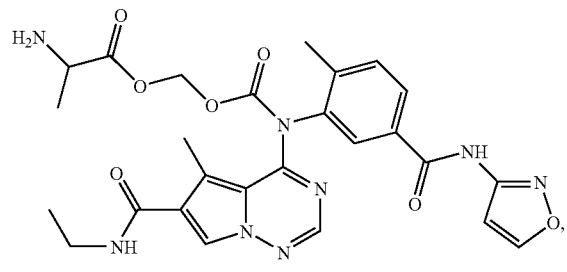
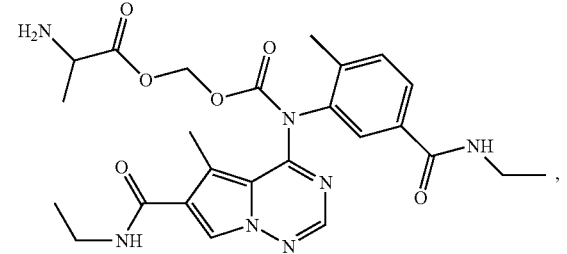
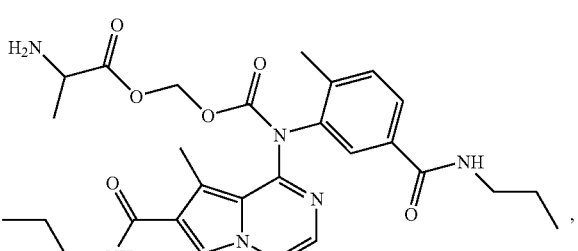
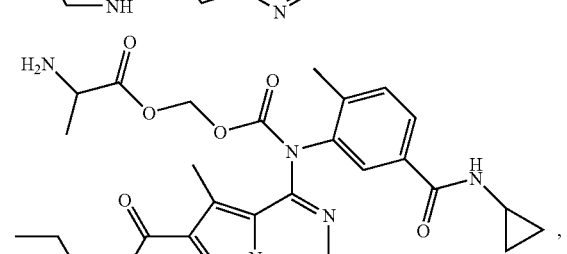
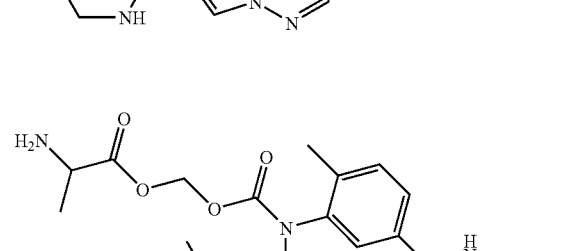
226
-continued
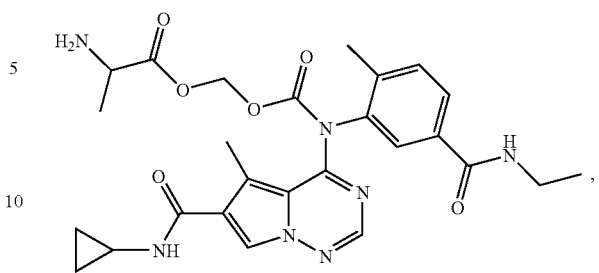
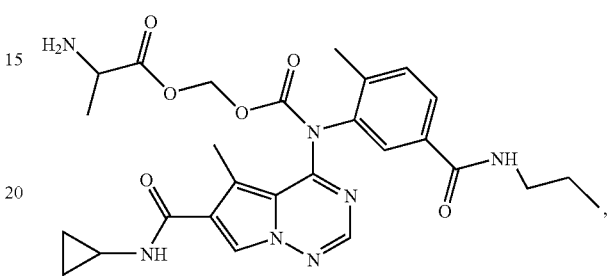
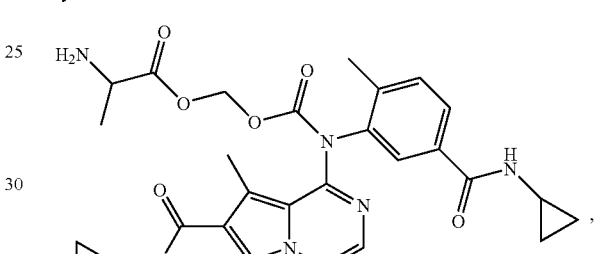
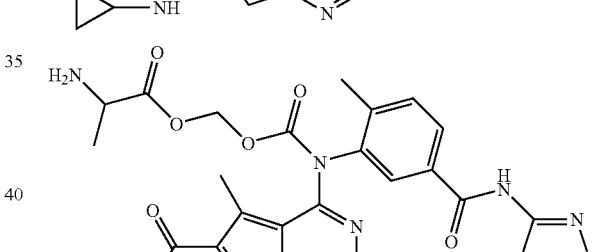
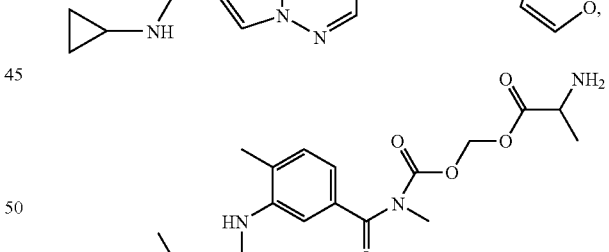
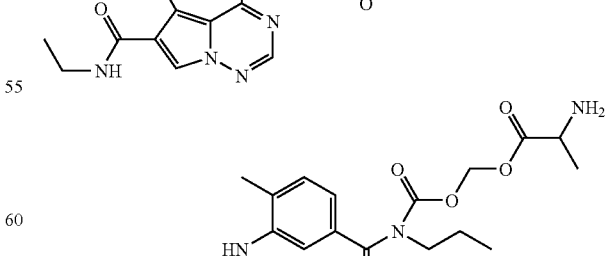

227
-continued
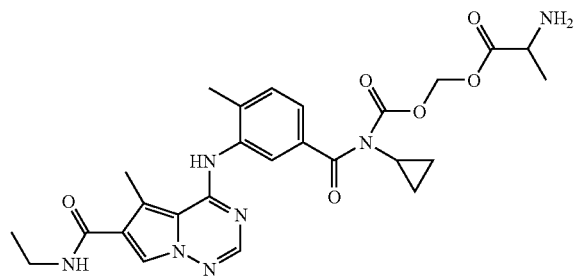
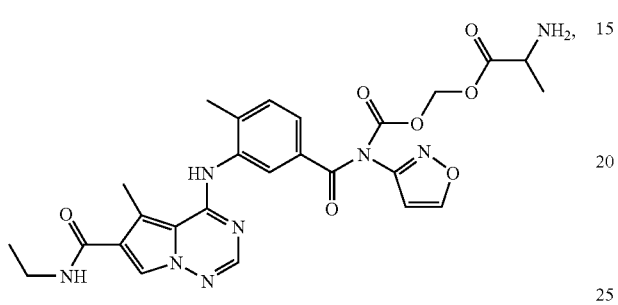
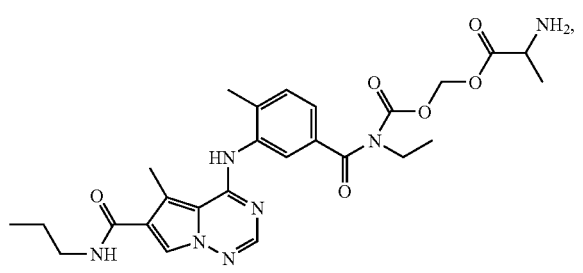
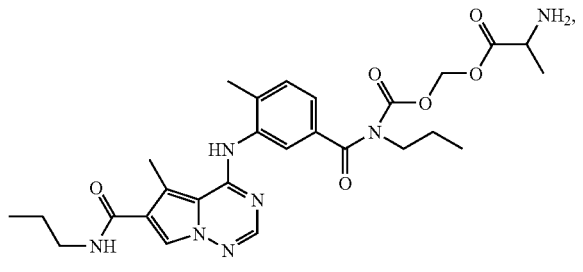
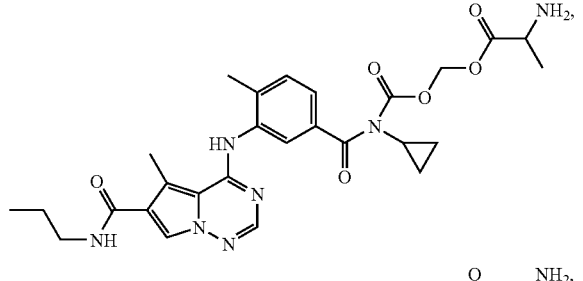
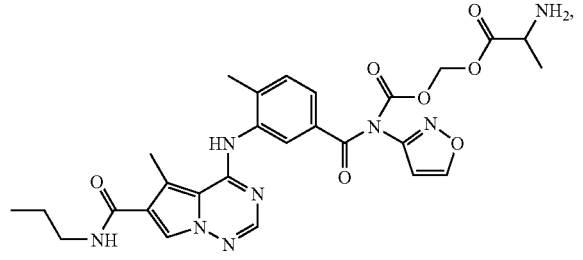
228
-continued
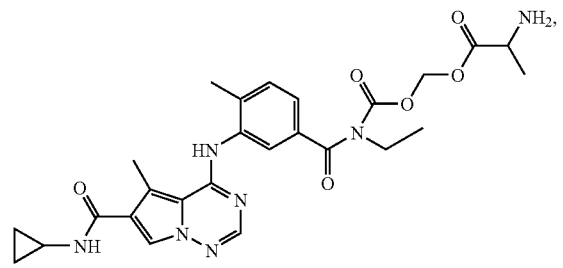
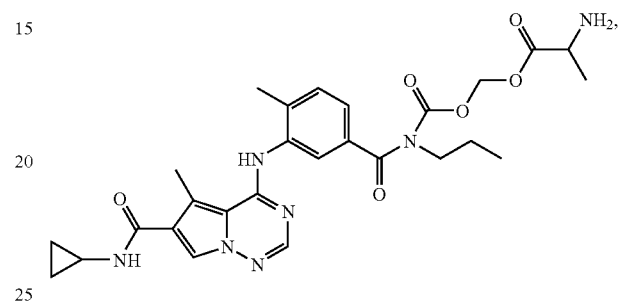
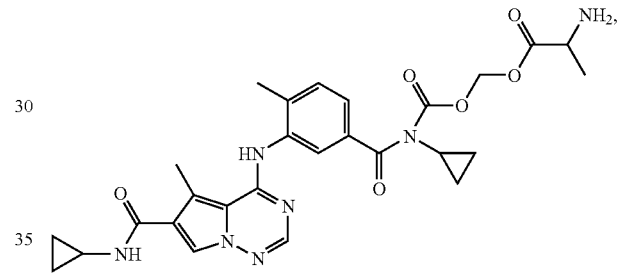
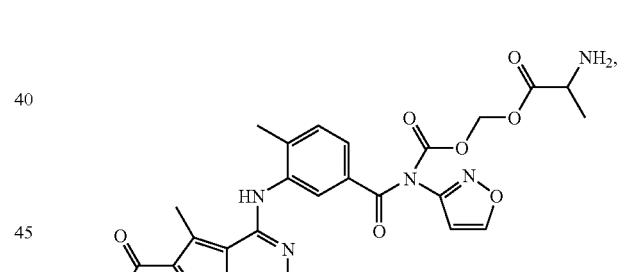
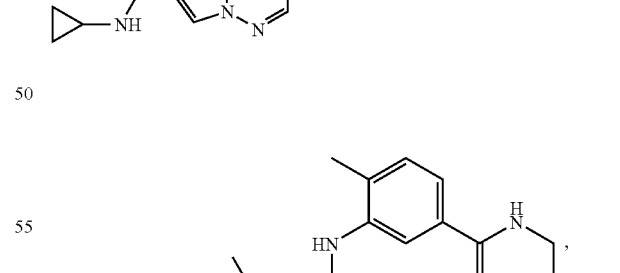
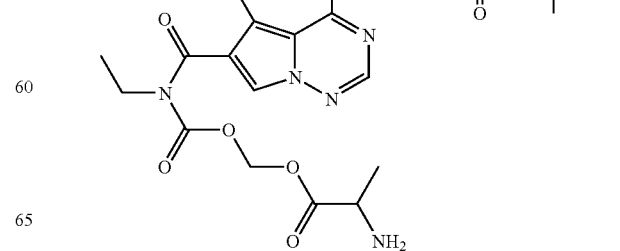

229
-continued
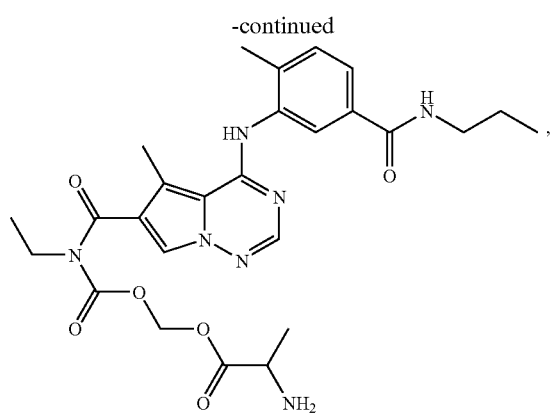
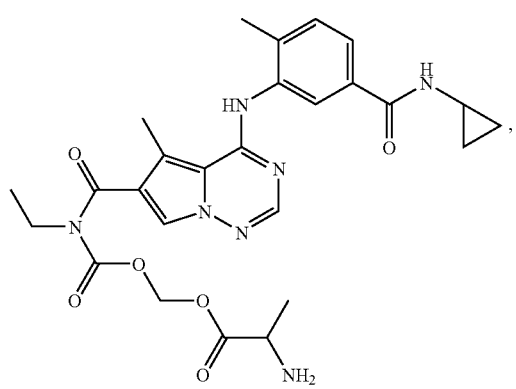
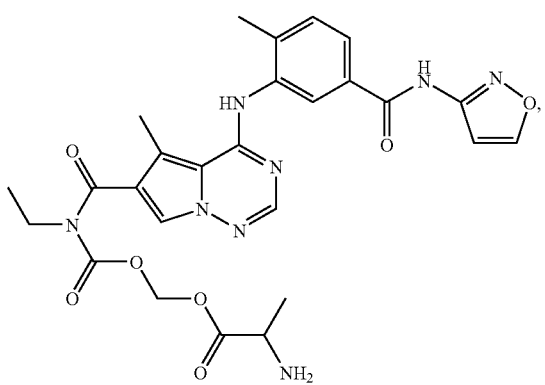
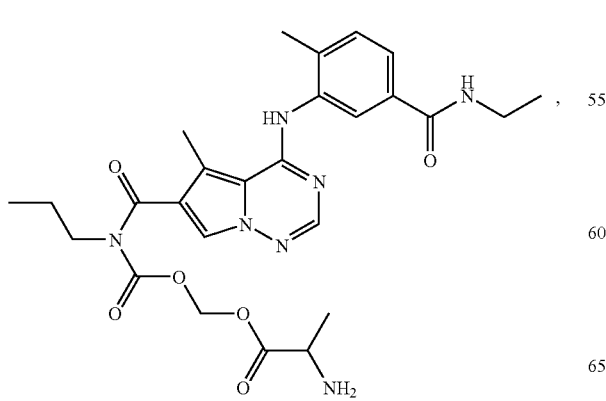
230
-continued
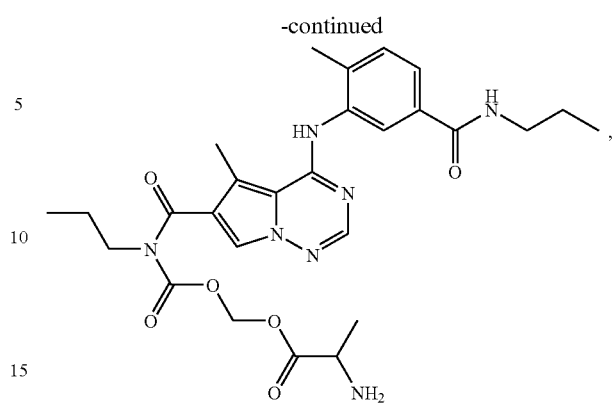
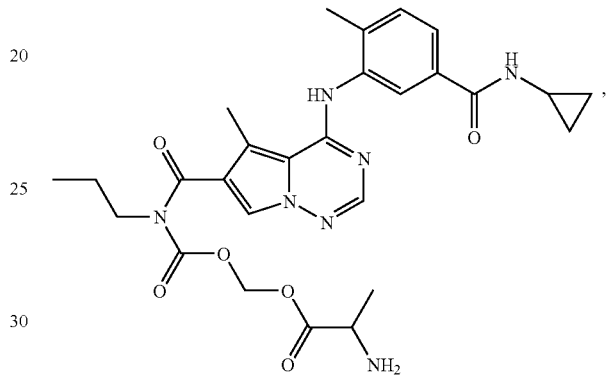
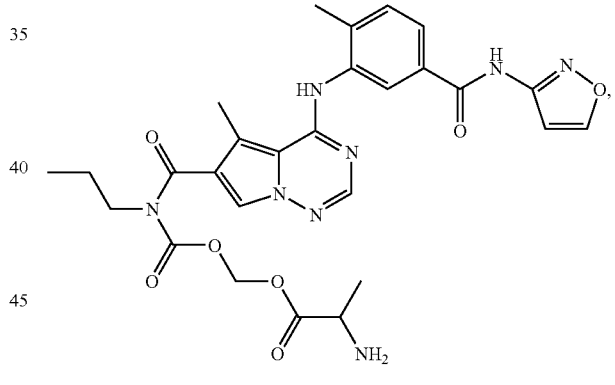
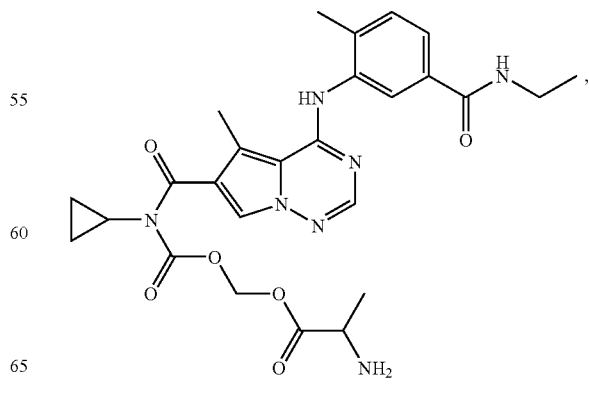

-continued
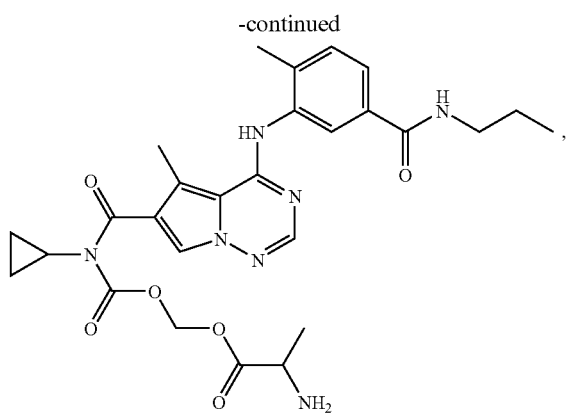
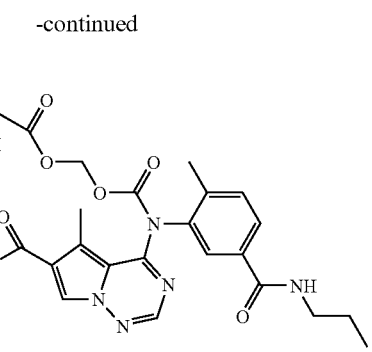
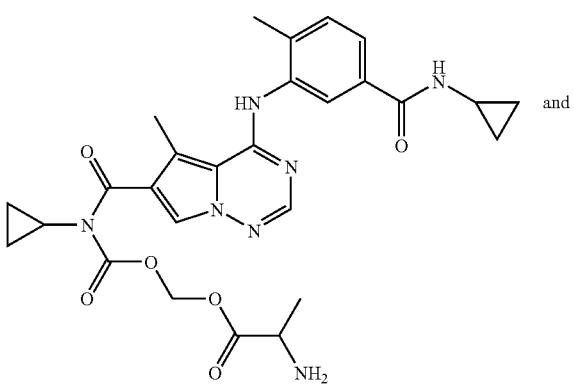
and
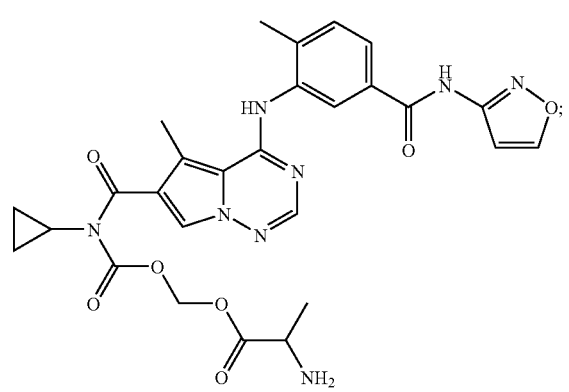
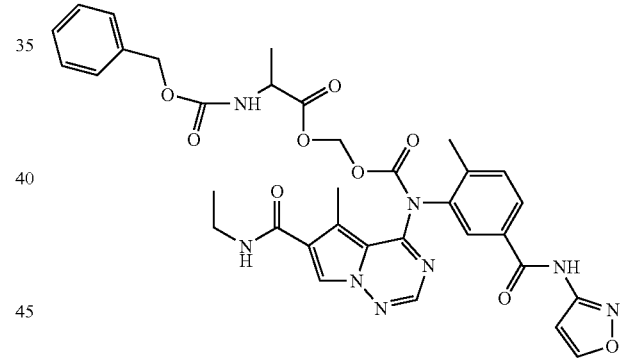
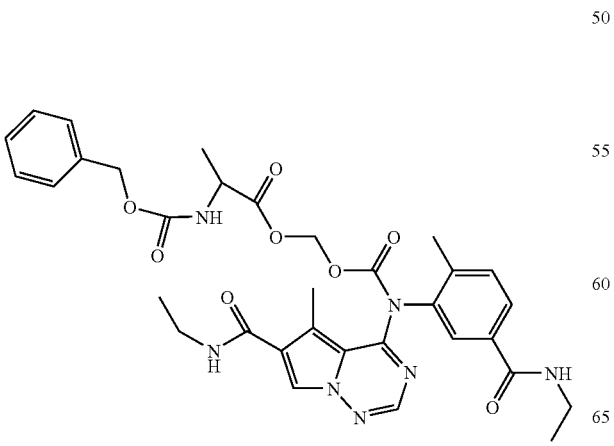
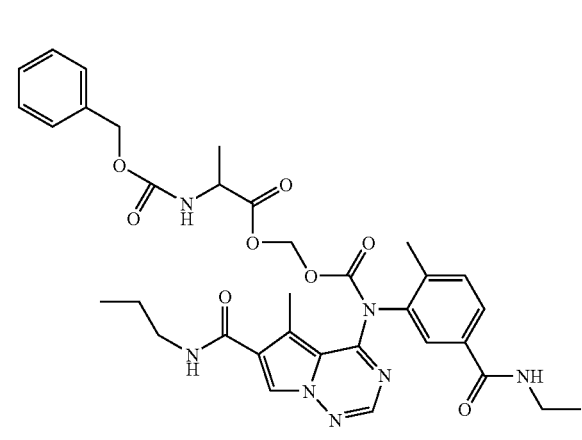

233
-continued
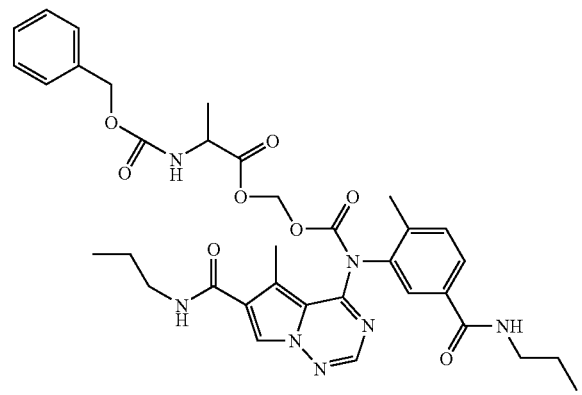
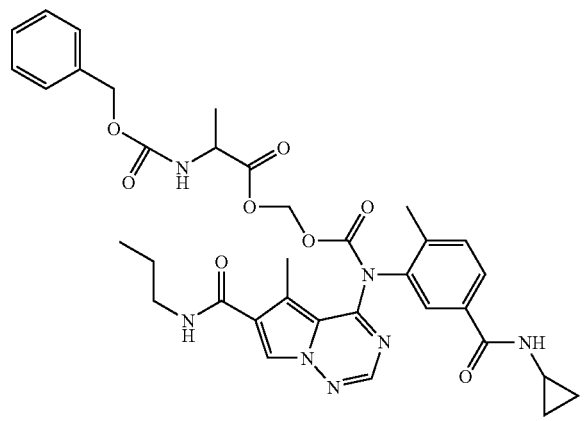
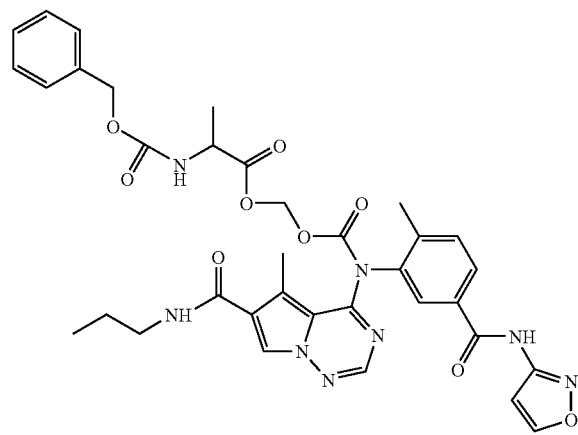
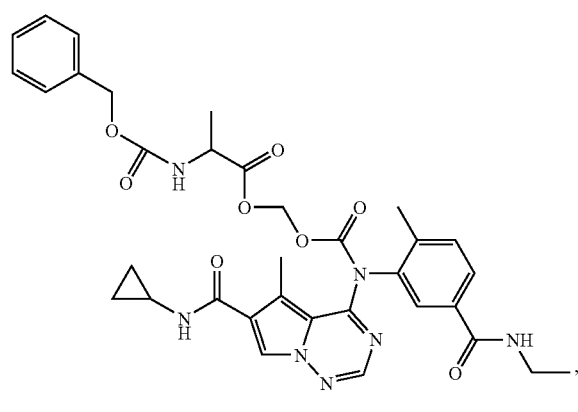
234
-continued
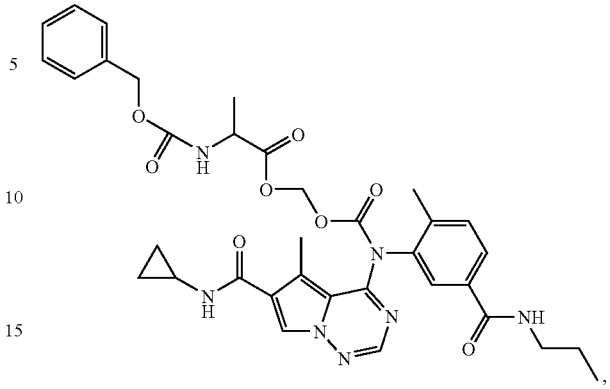
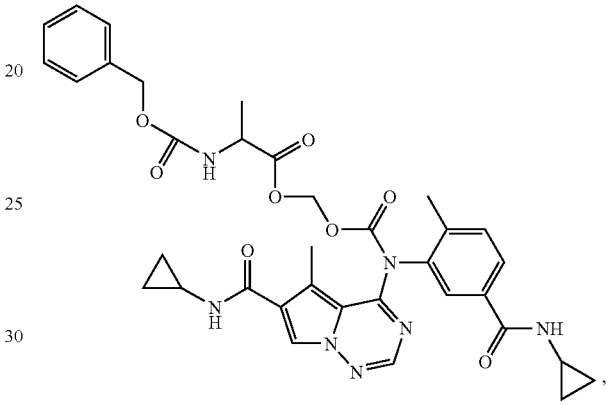
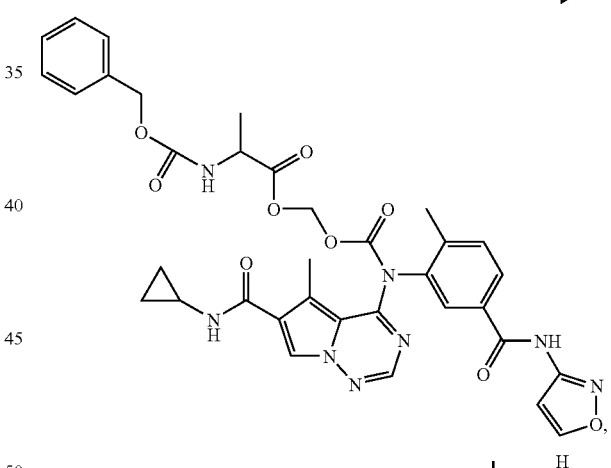
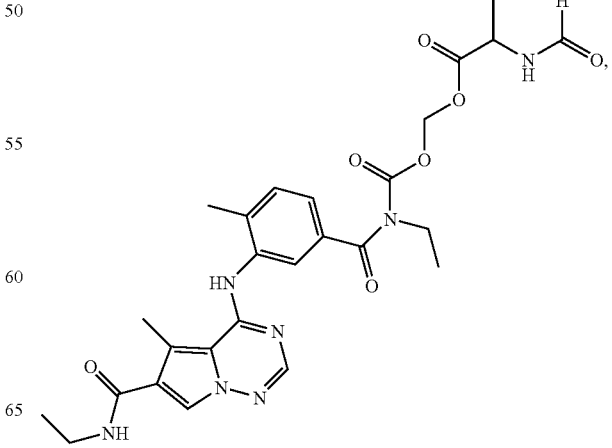

235
-continued
236
-continued
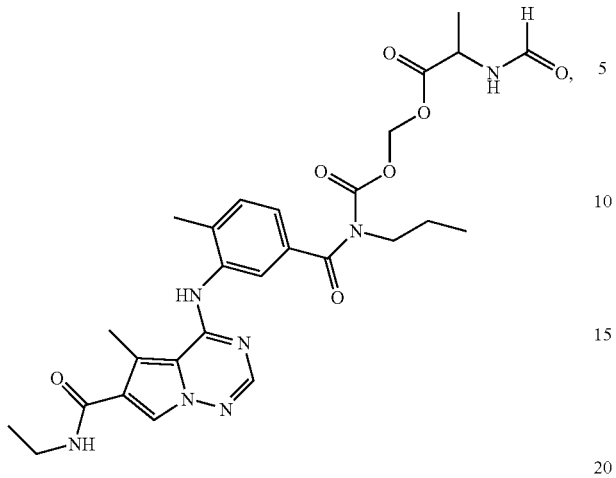
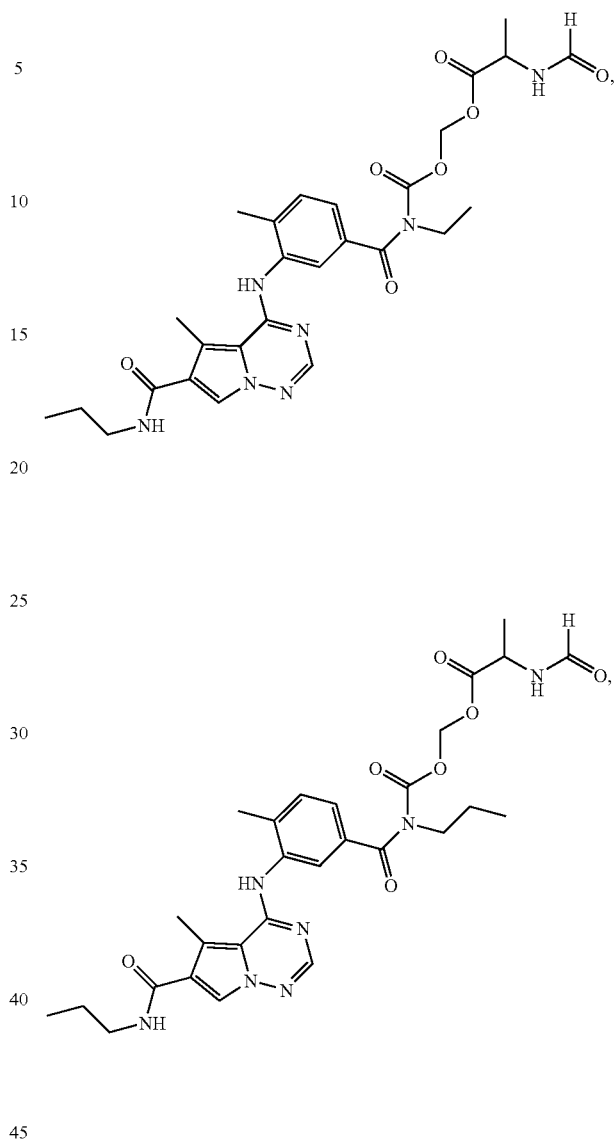
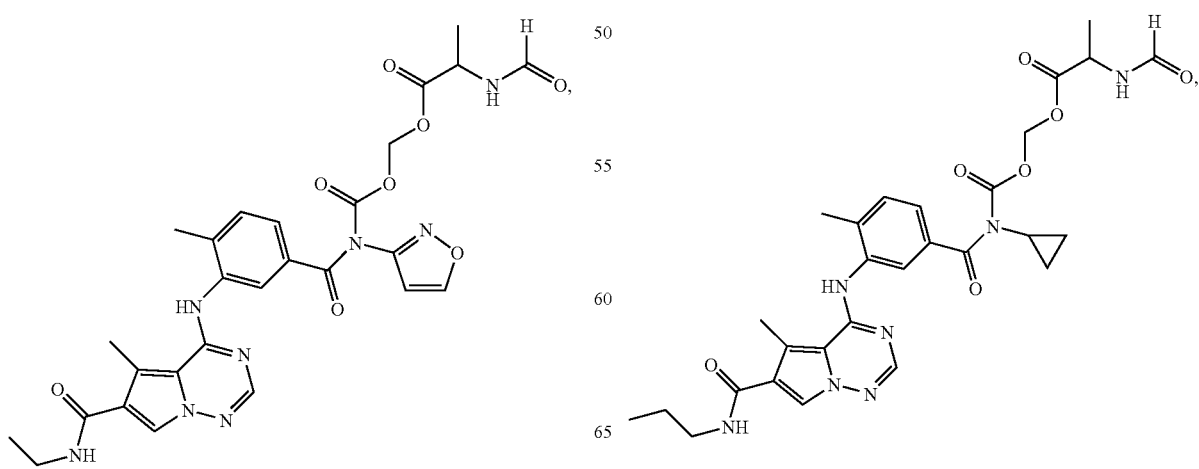

237
-continued
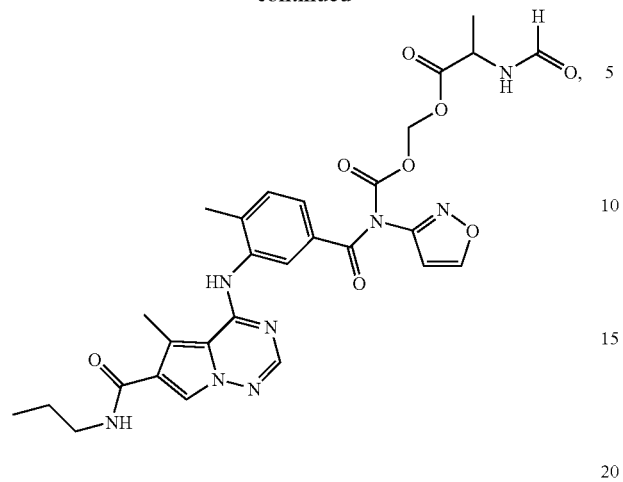
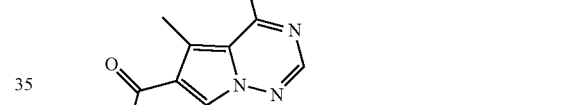
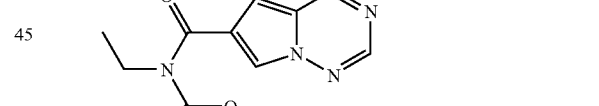
238
-continued
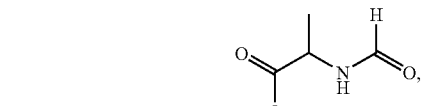
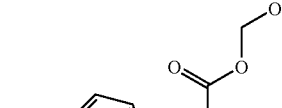
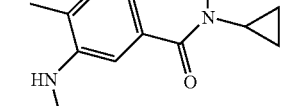
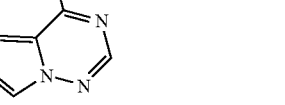
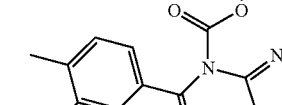
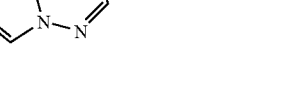
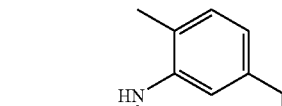
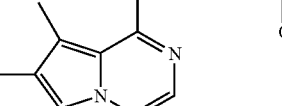
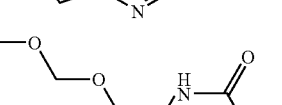
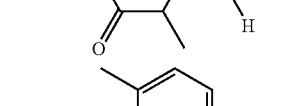

239
-continued
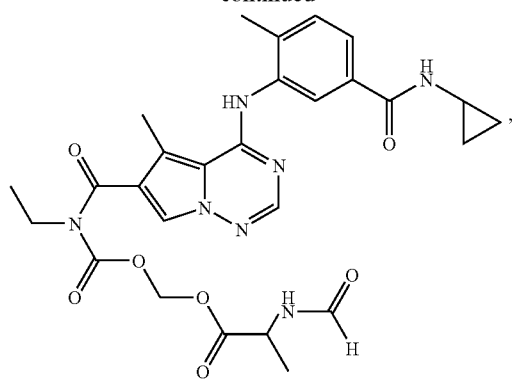
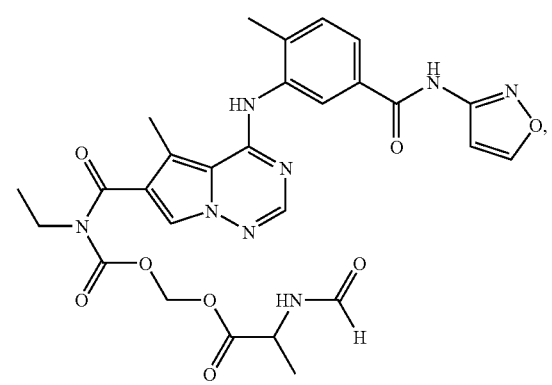
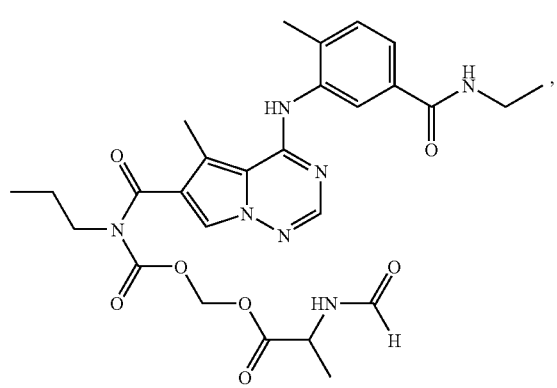
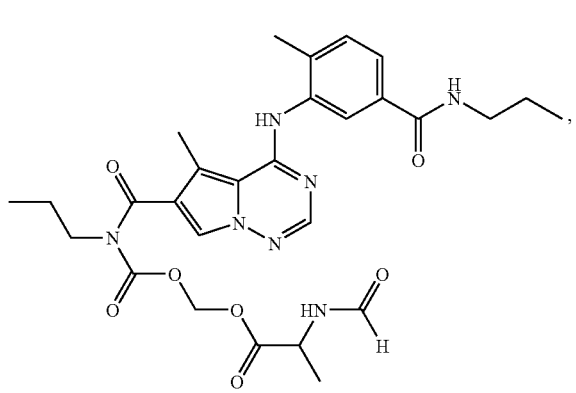
240
-continued
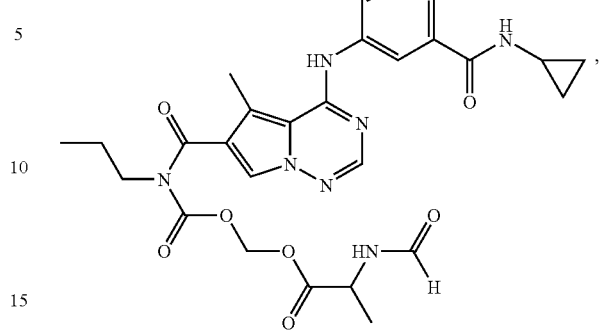
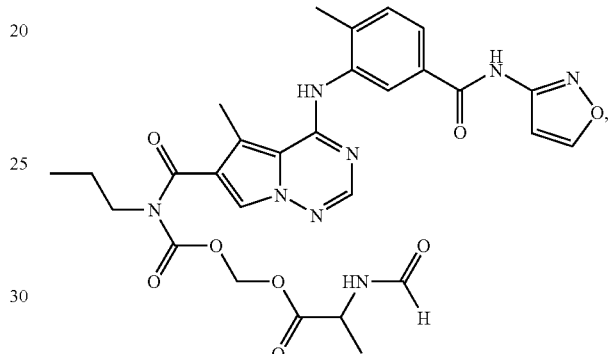
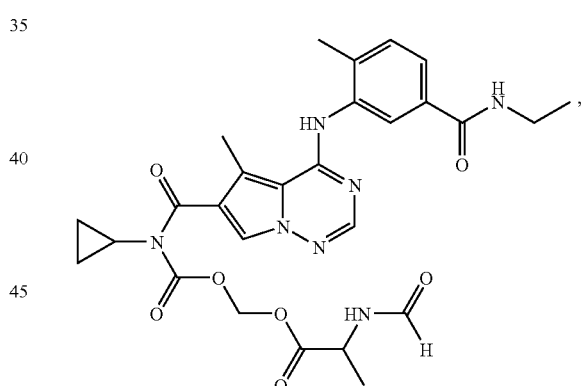
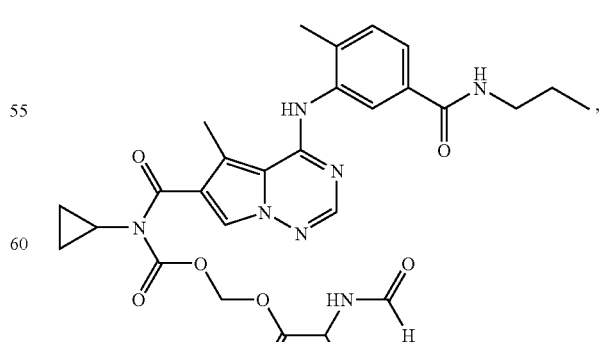

241
-continued
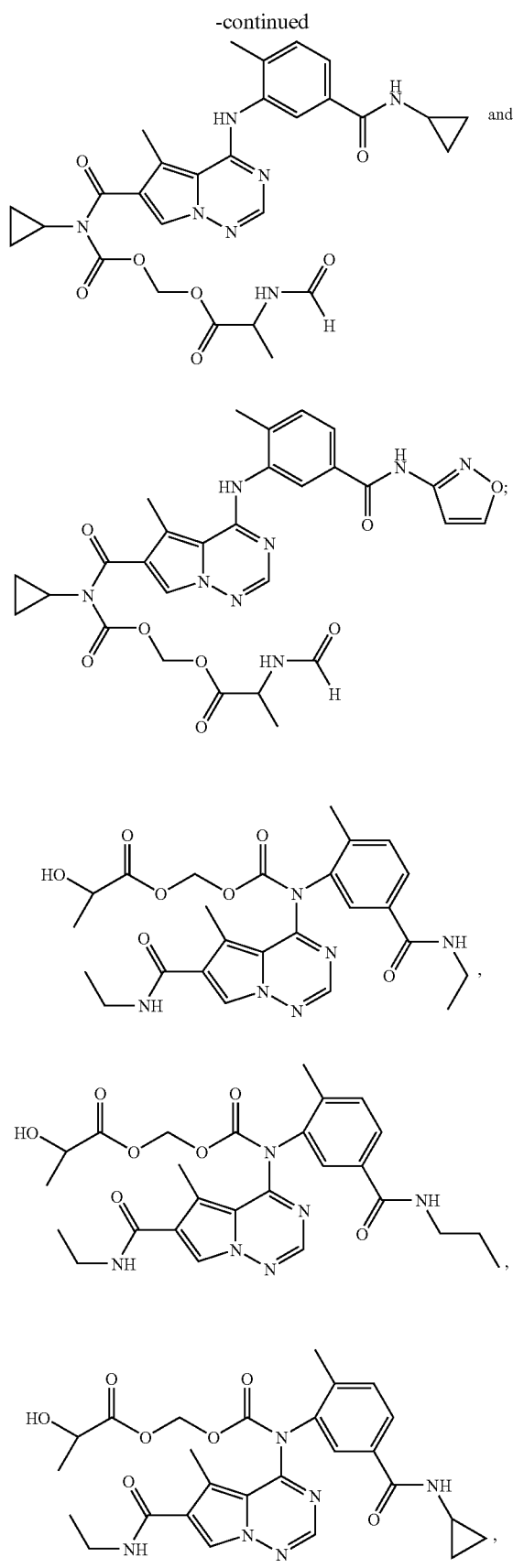
and
242
-continued
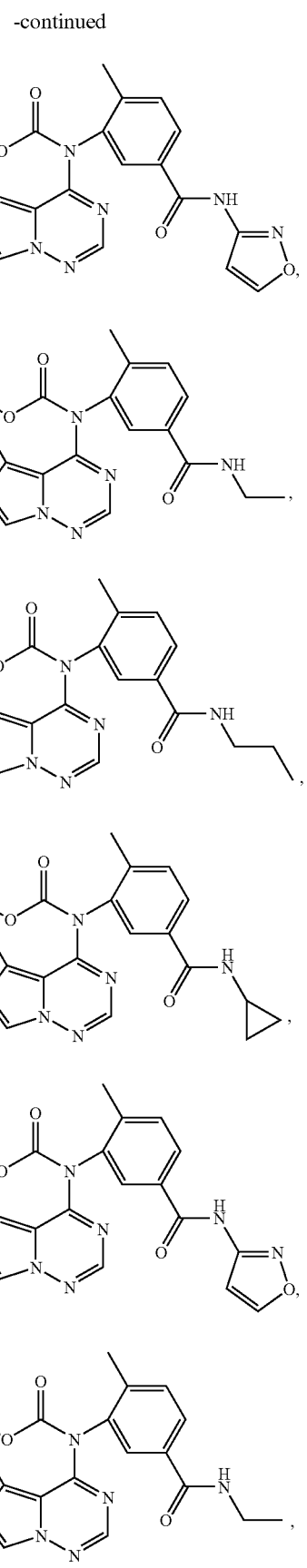

243
-continued
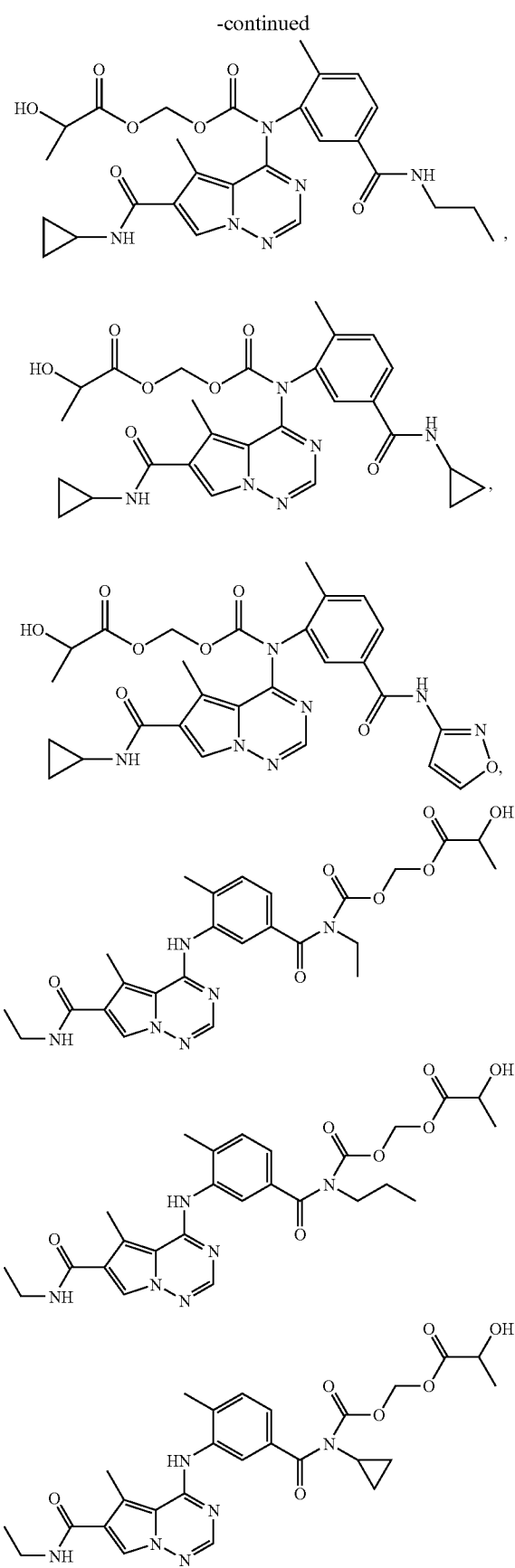
244
-continued
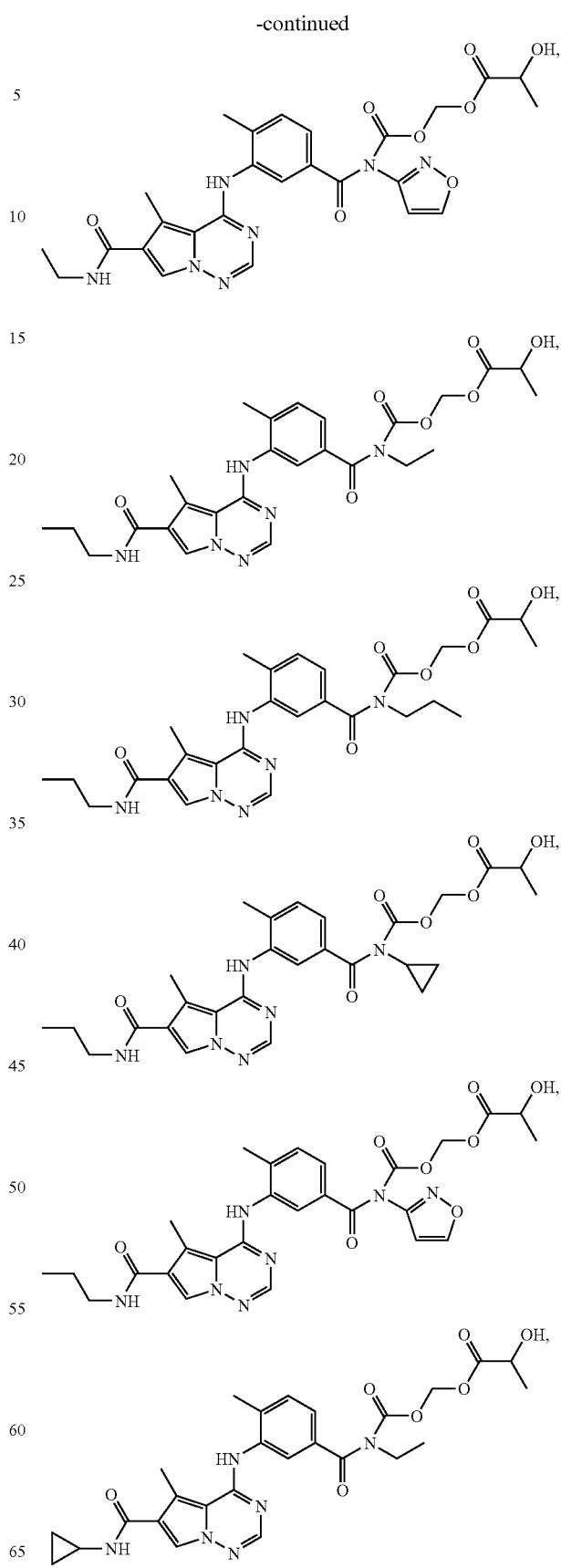

-continued
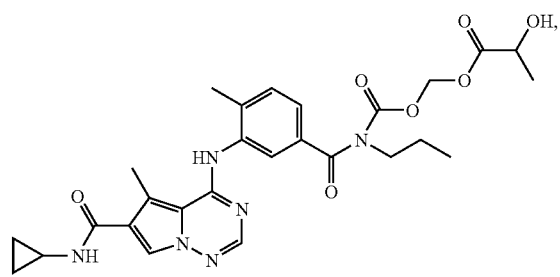
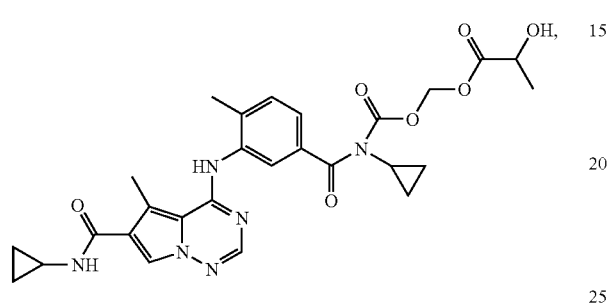
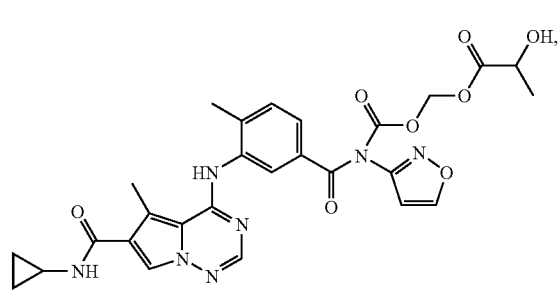
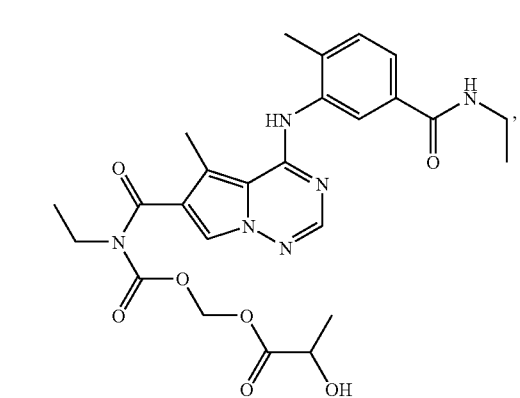
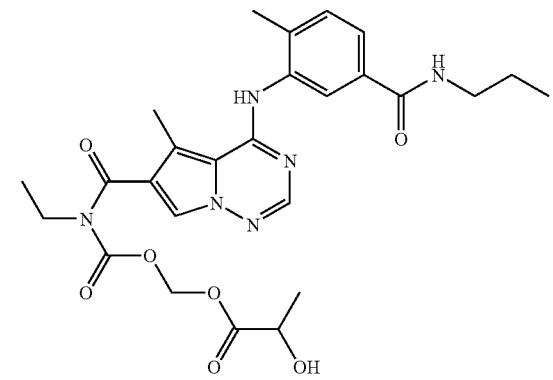
-continued
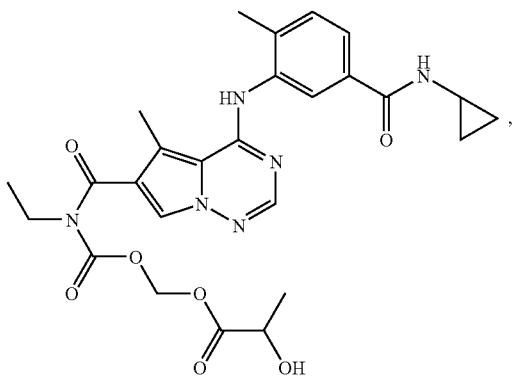
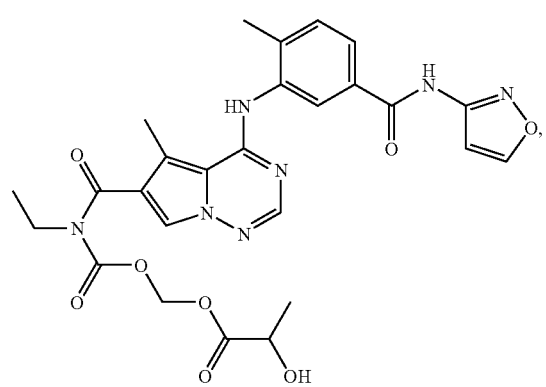
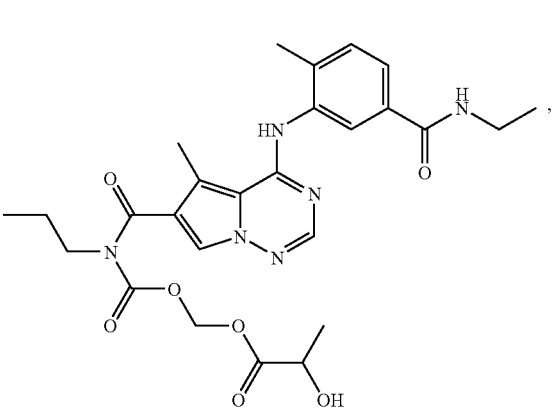
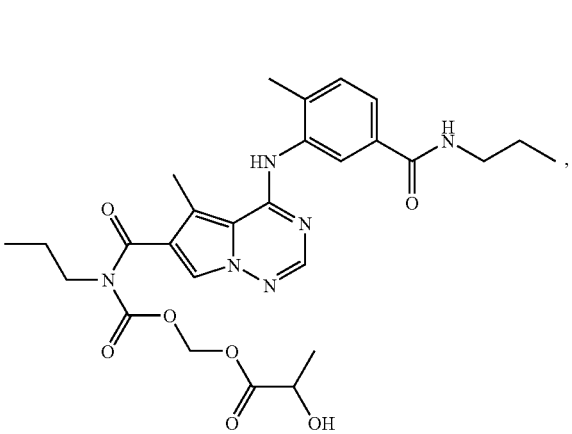

247
-continued
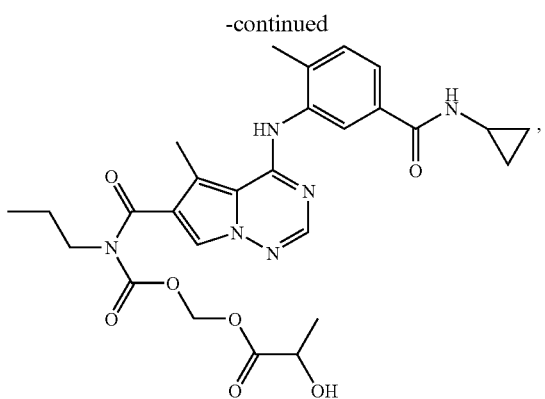
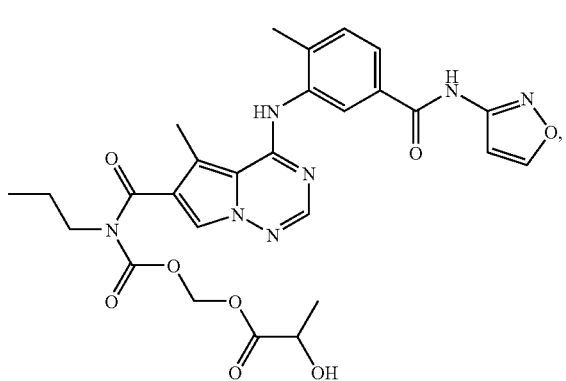
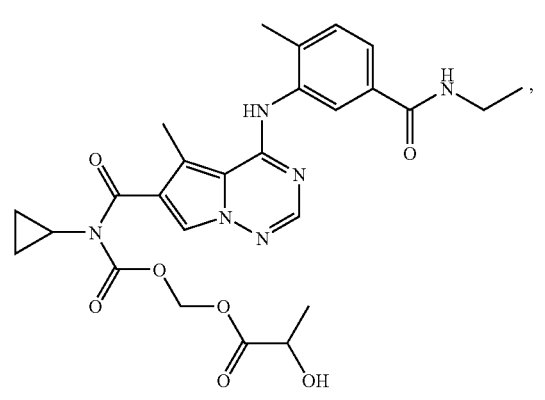
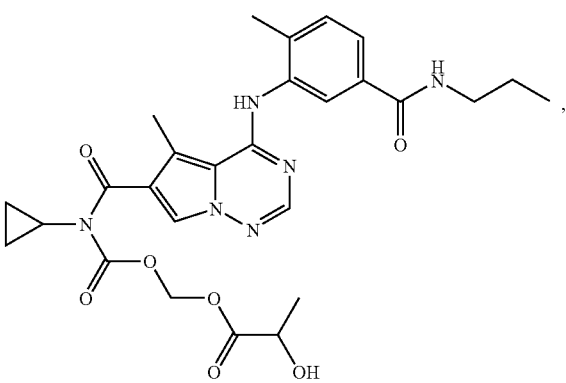
248
-continued
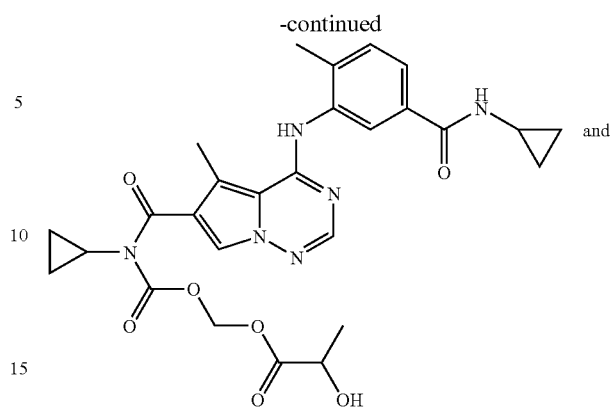 and
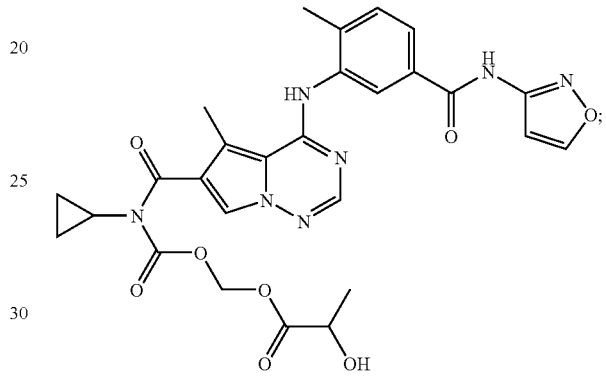
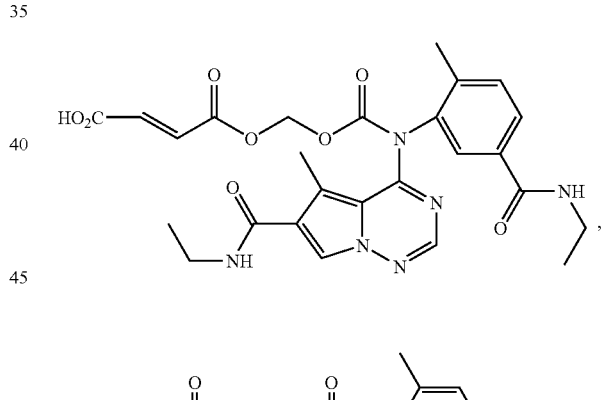
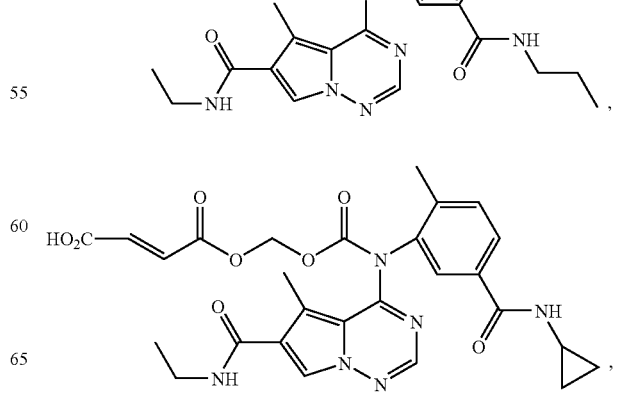

249
-continued
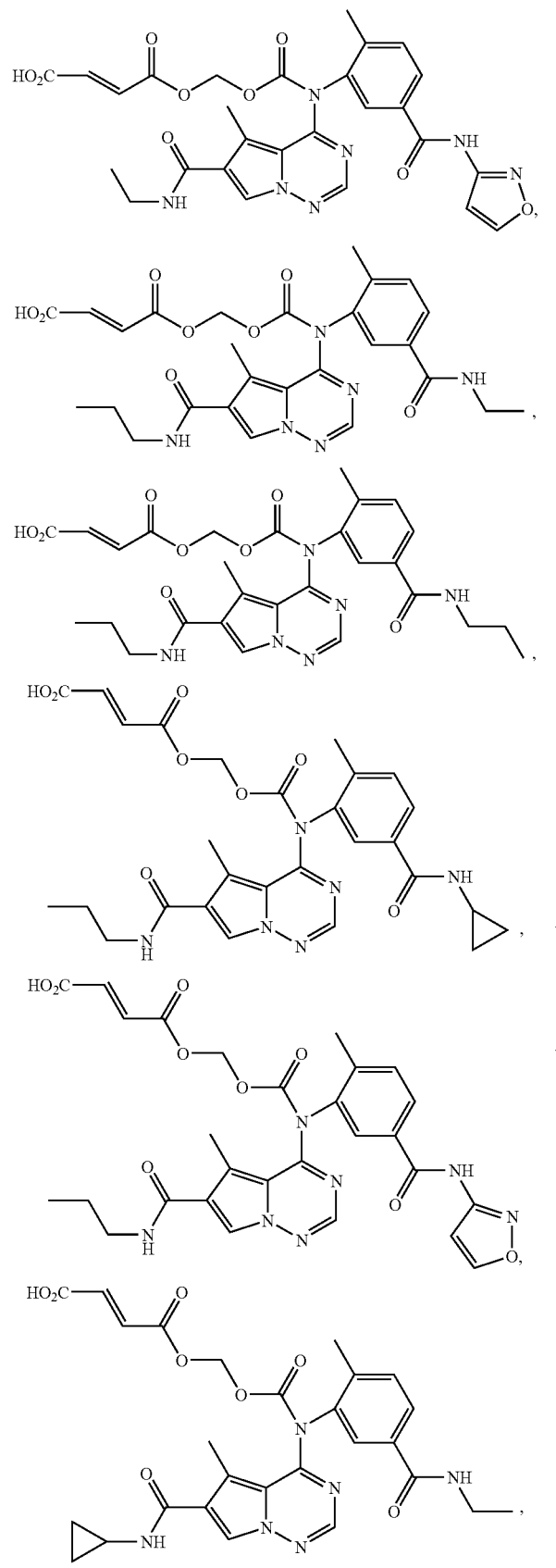
250
-continued
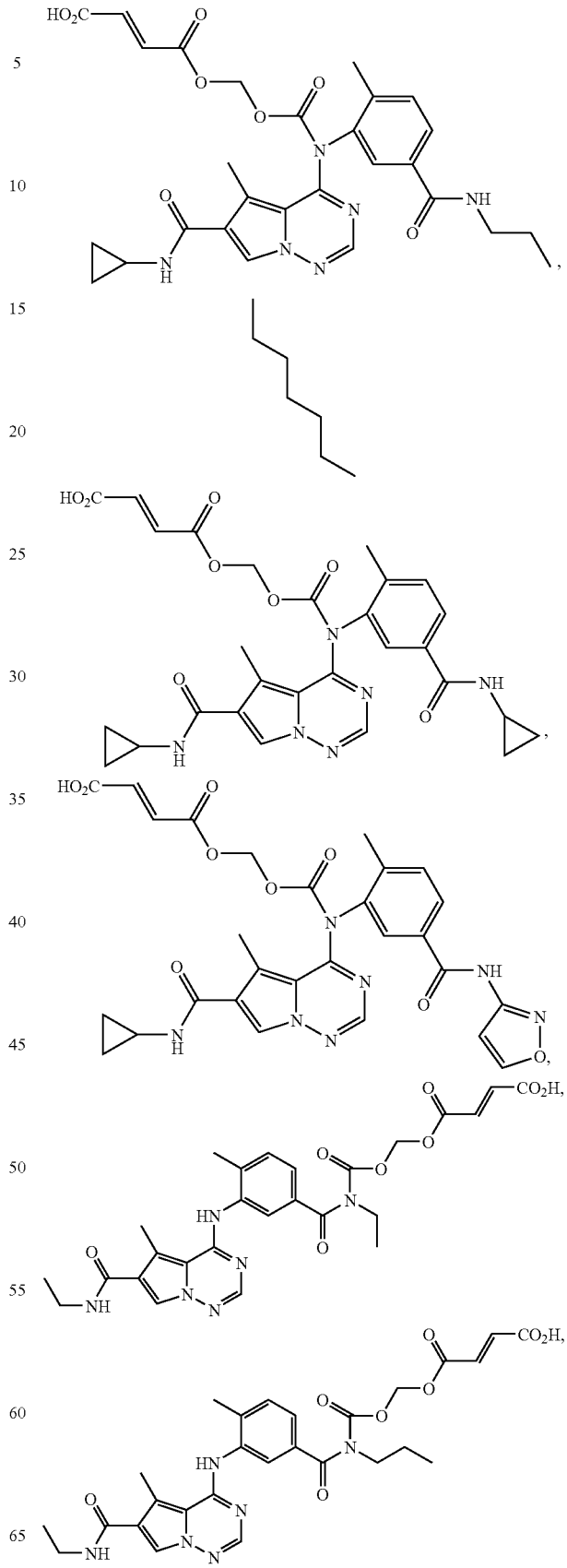

251
-continued
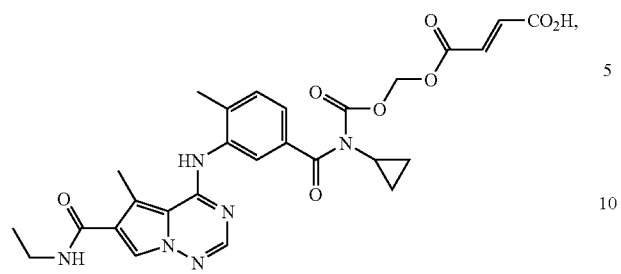
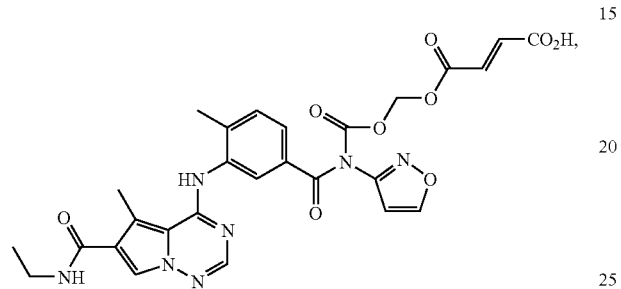
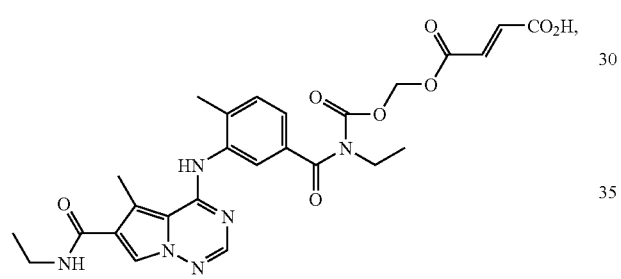
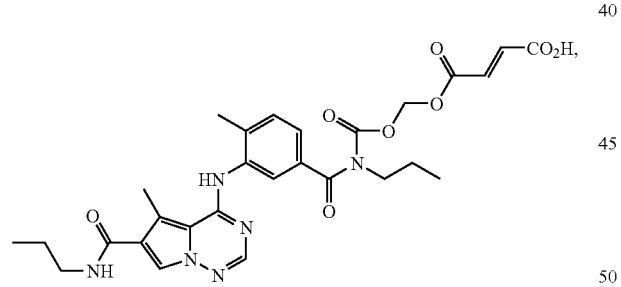
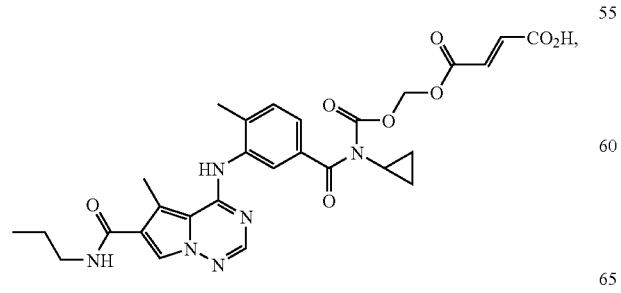
252
-continued
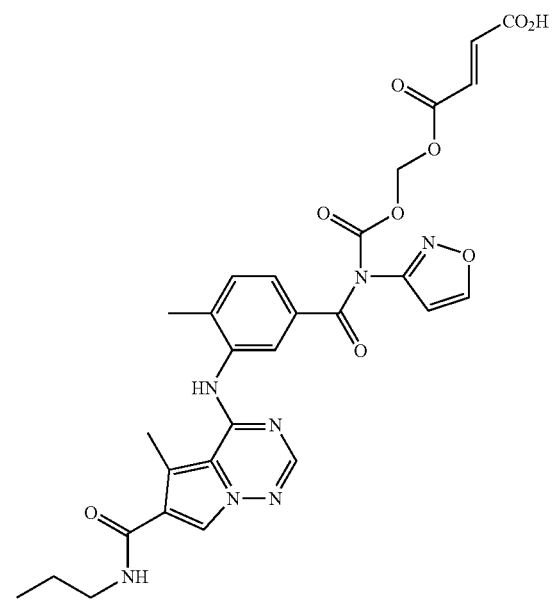
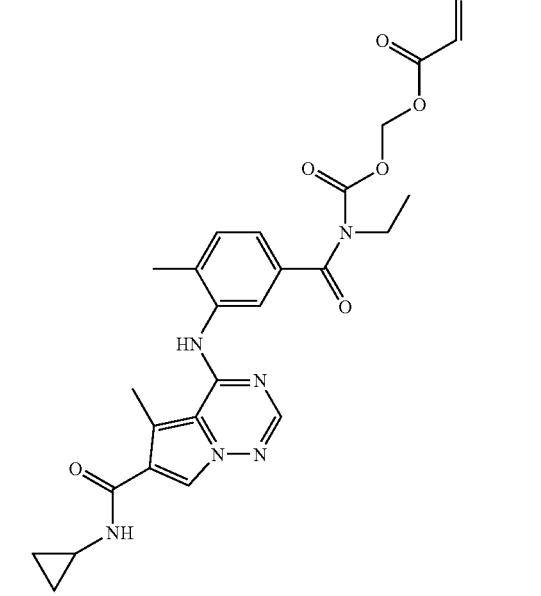

253
254
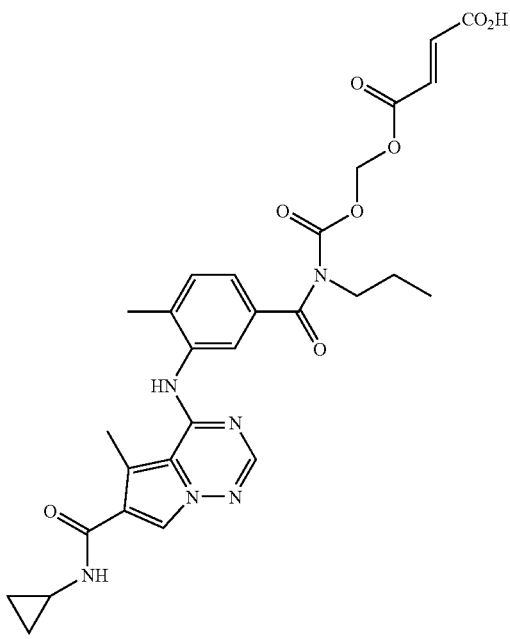
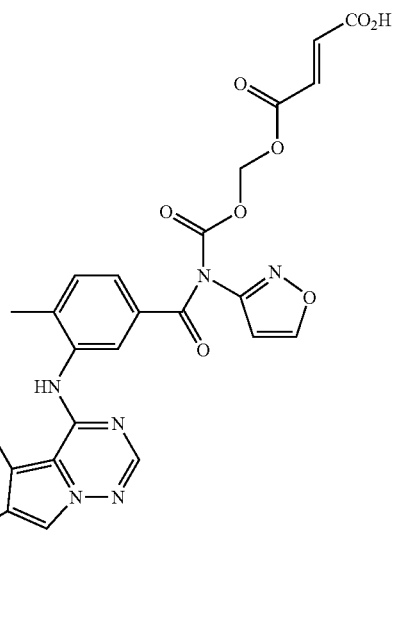
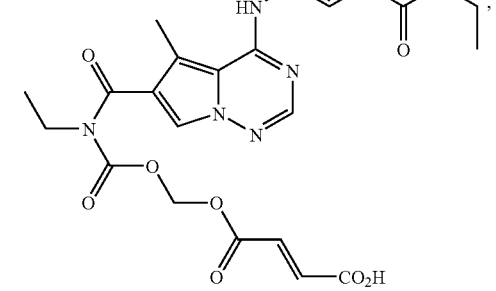
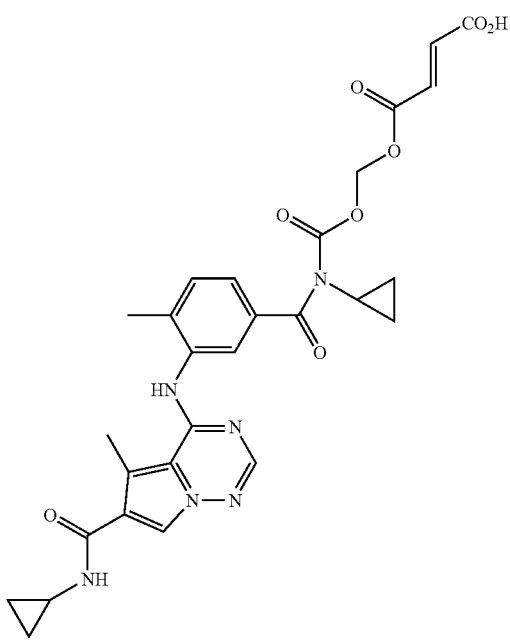
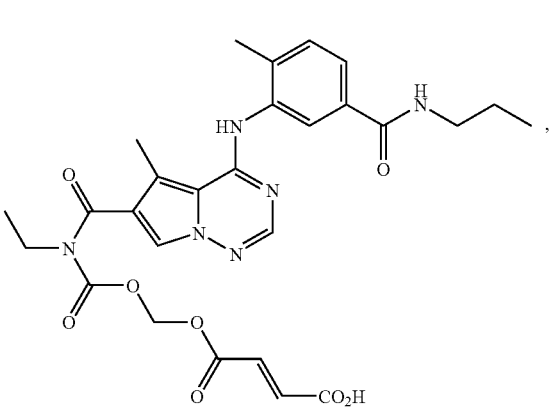

255
-continued
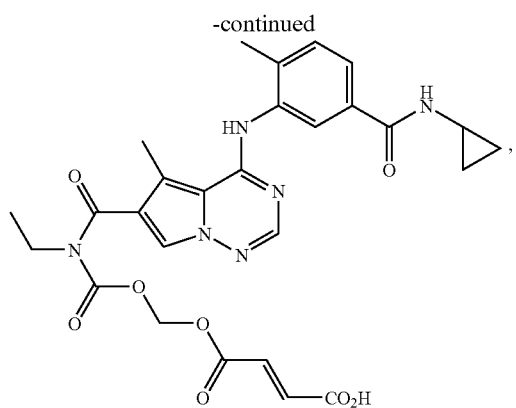
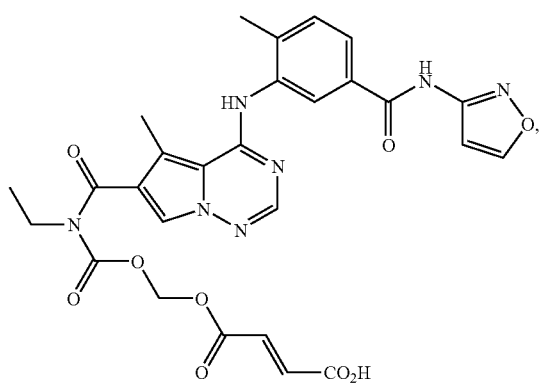
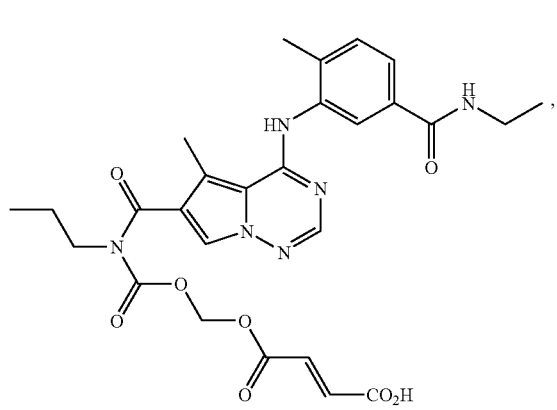
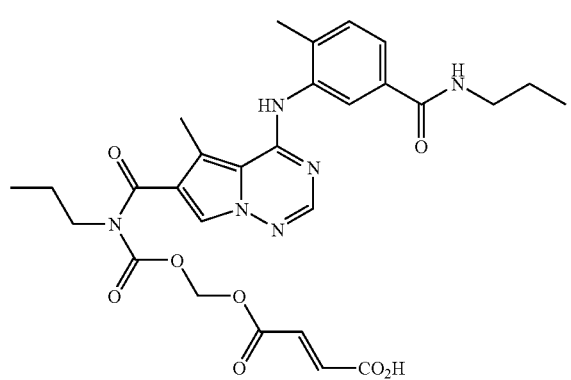
256
-continued
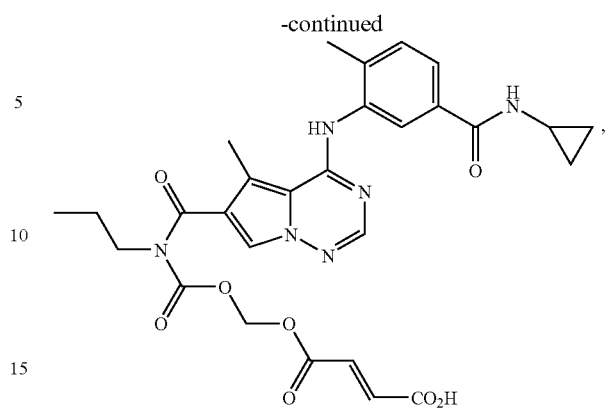
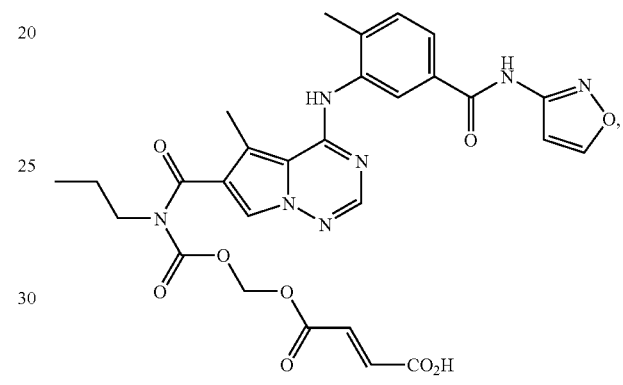
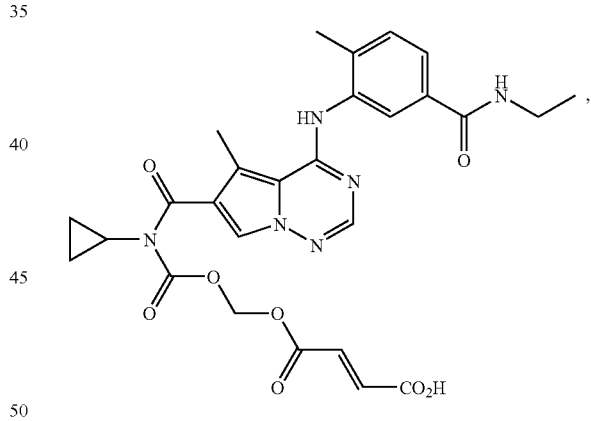
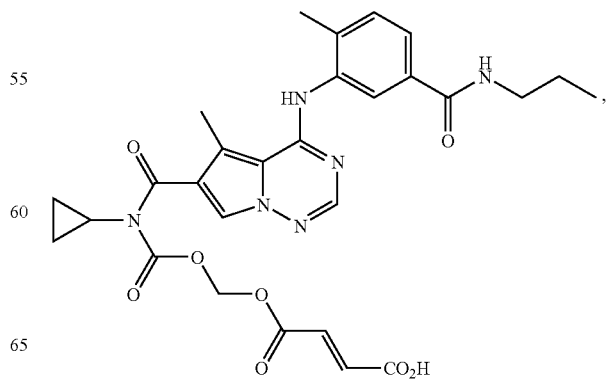

-continued
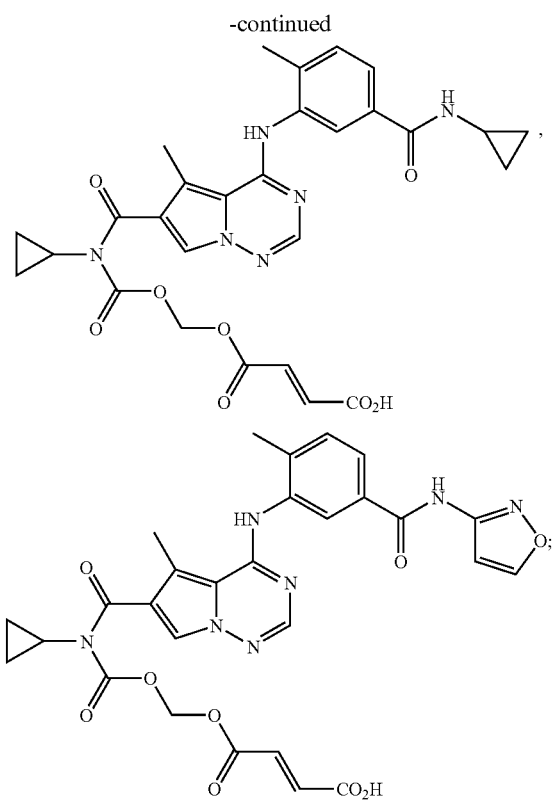
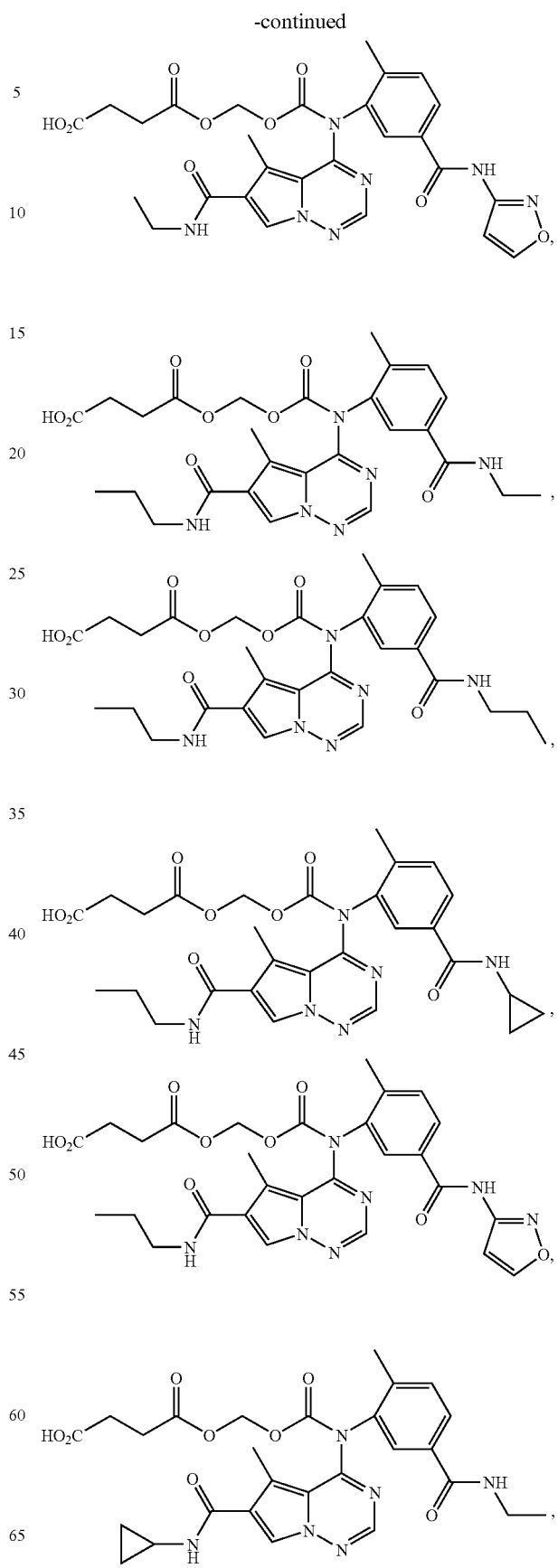

259
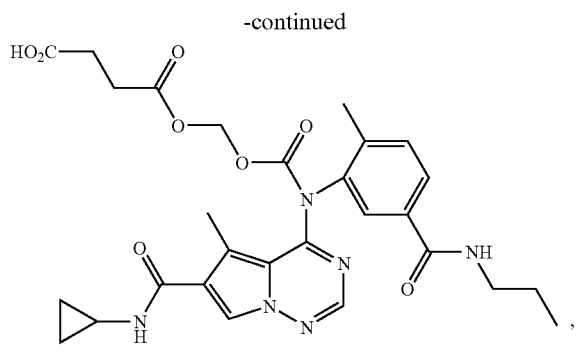
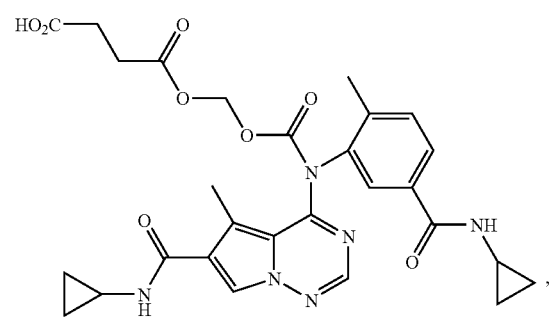
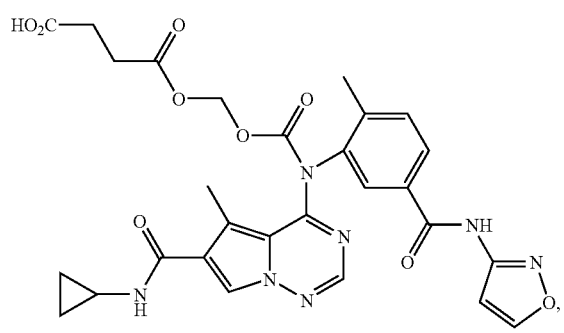
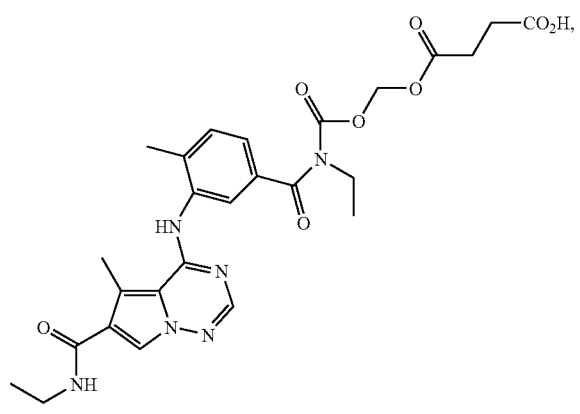
260
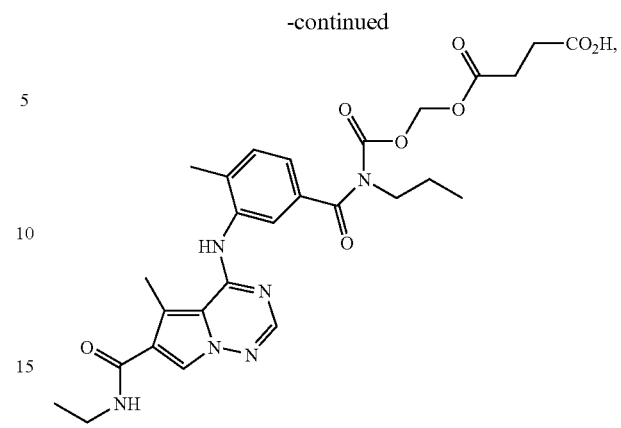
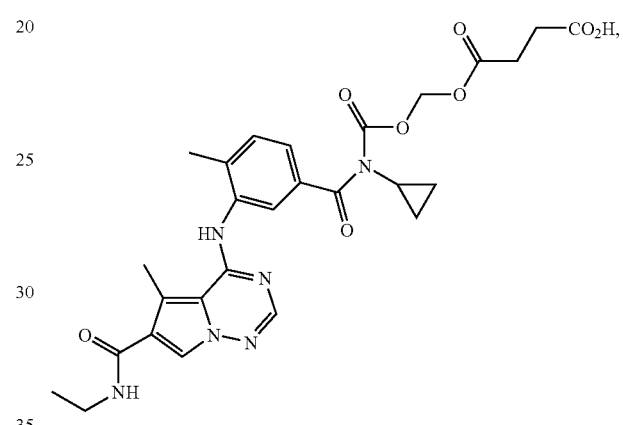
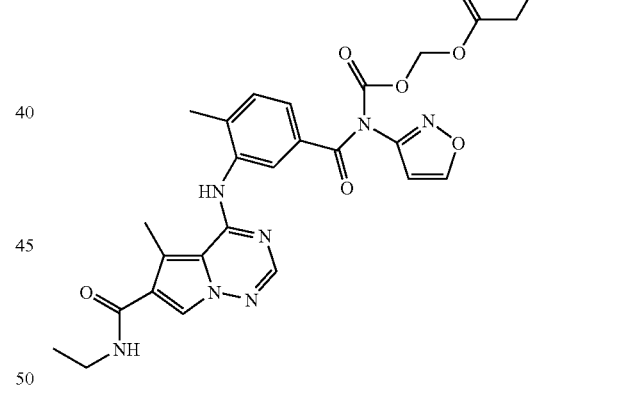
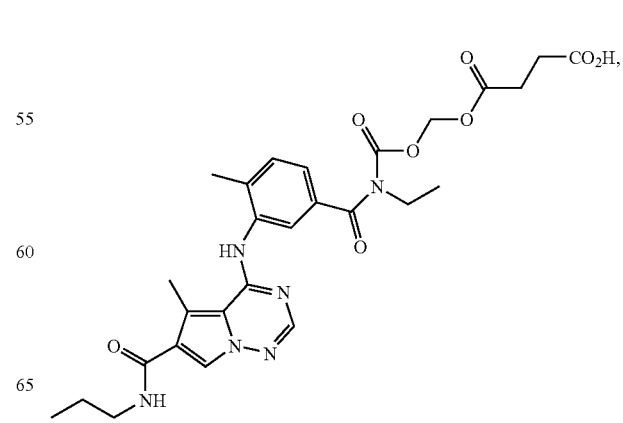

-continued
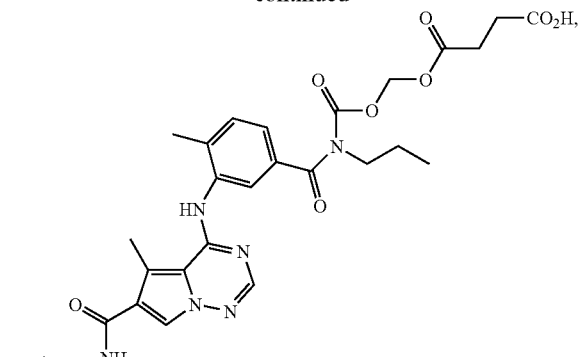
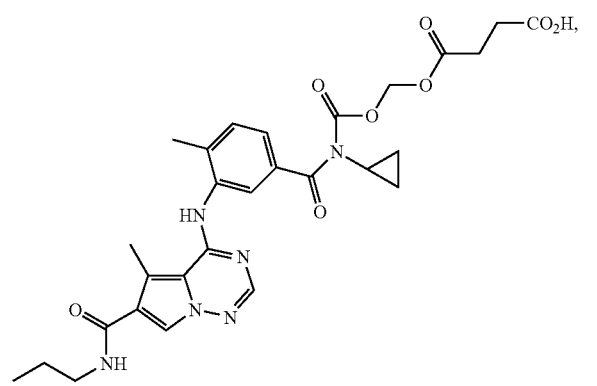
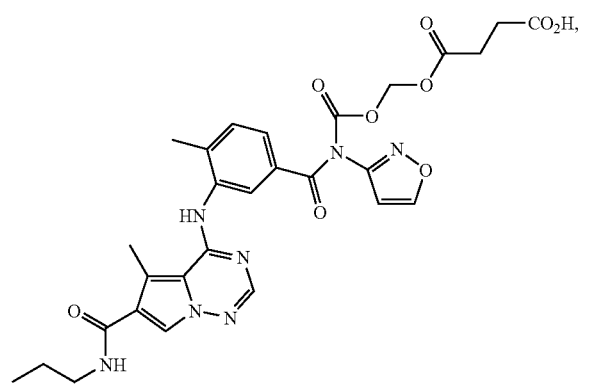
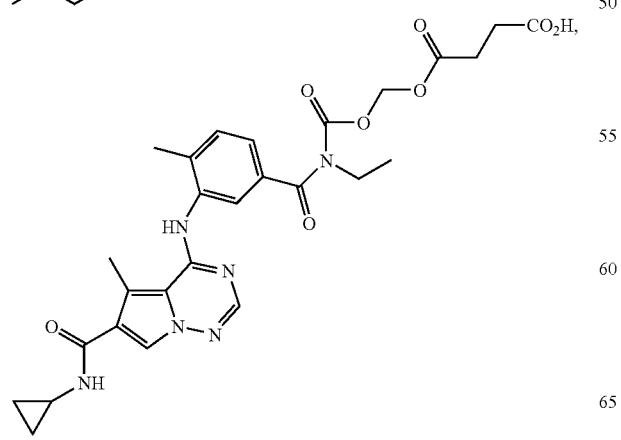
-continued
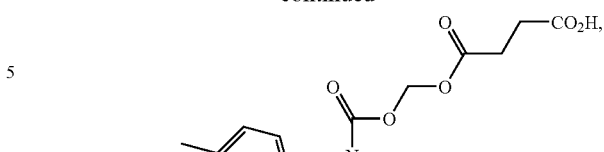
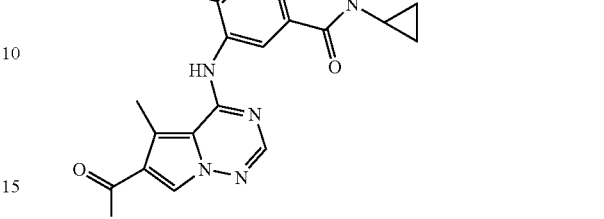
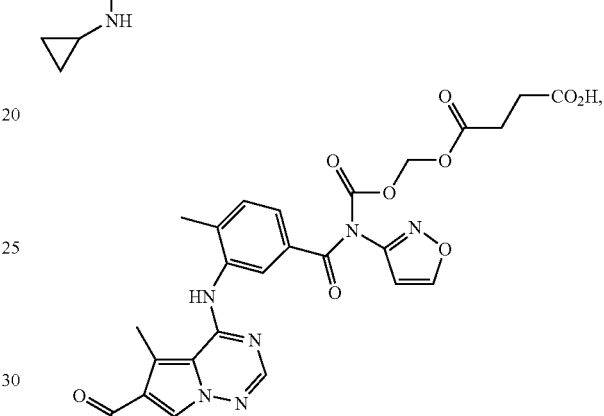
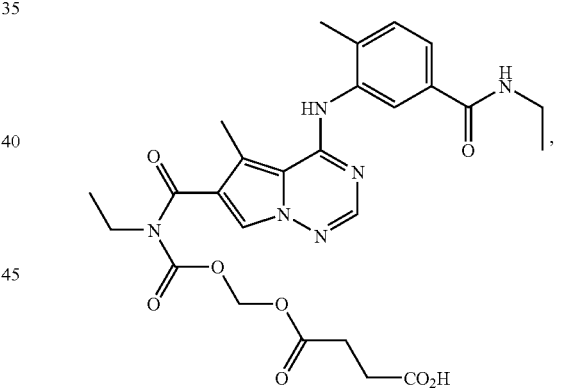
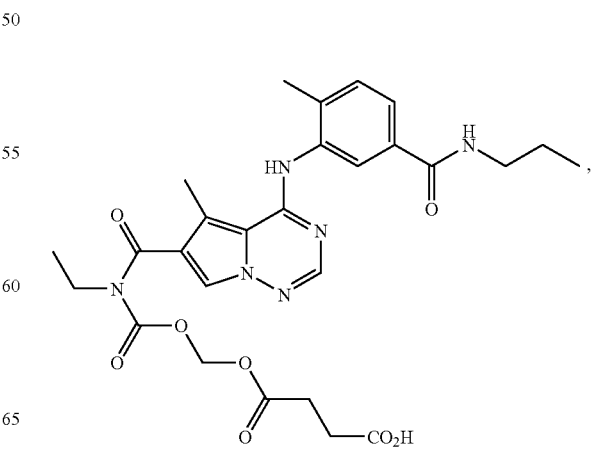

263
-continued
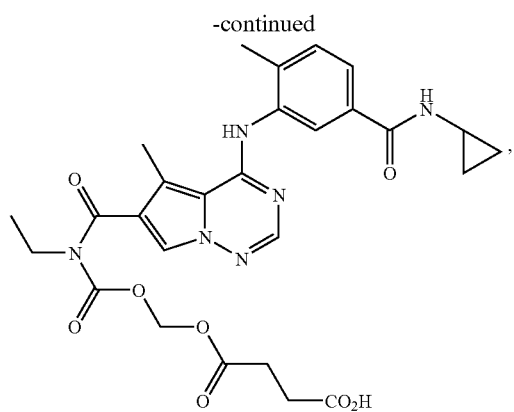
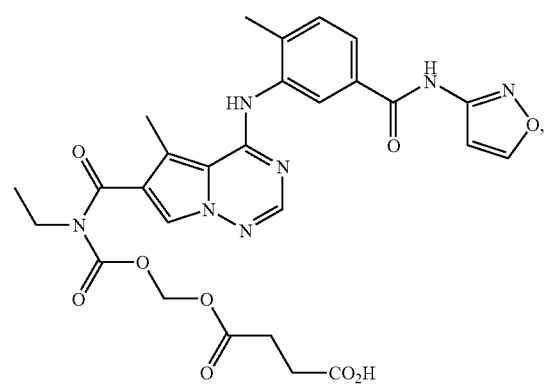
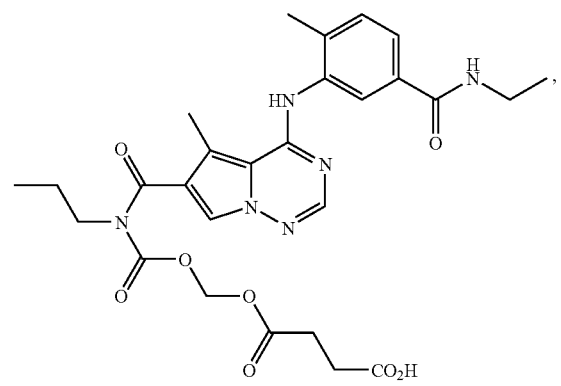
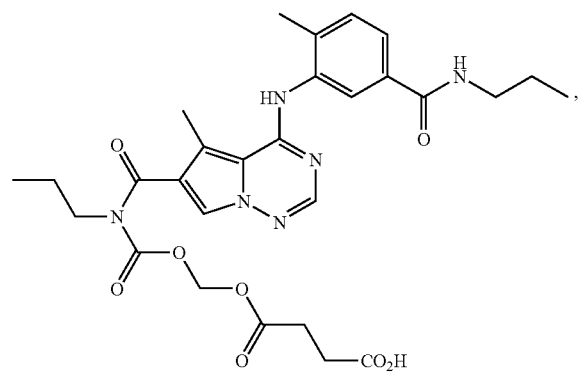
264
-continued
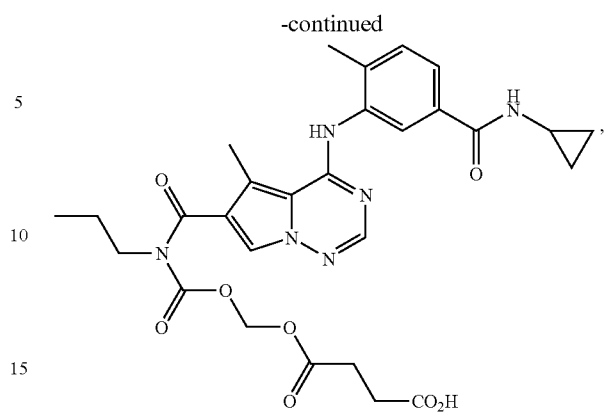
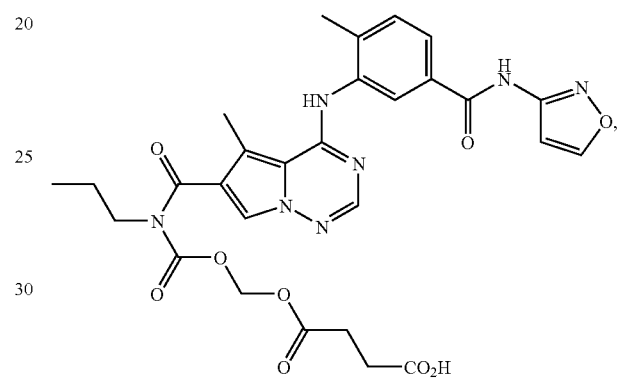
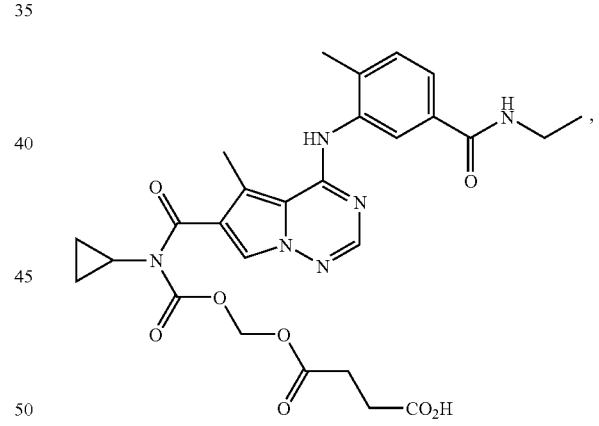
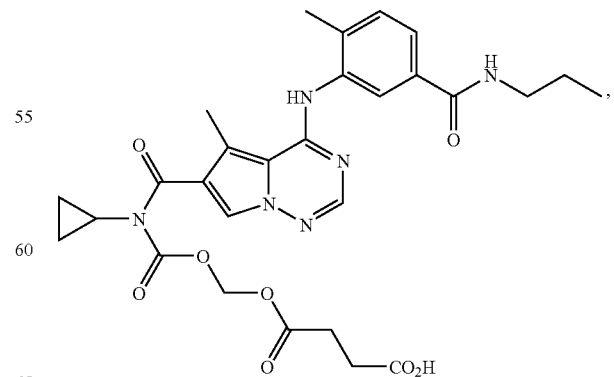

265
-continued
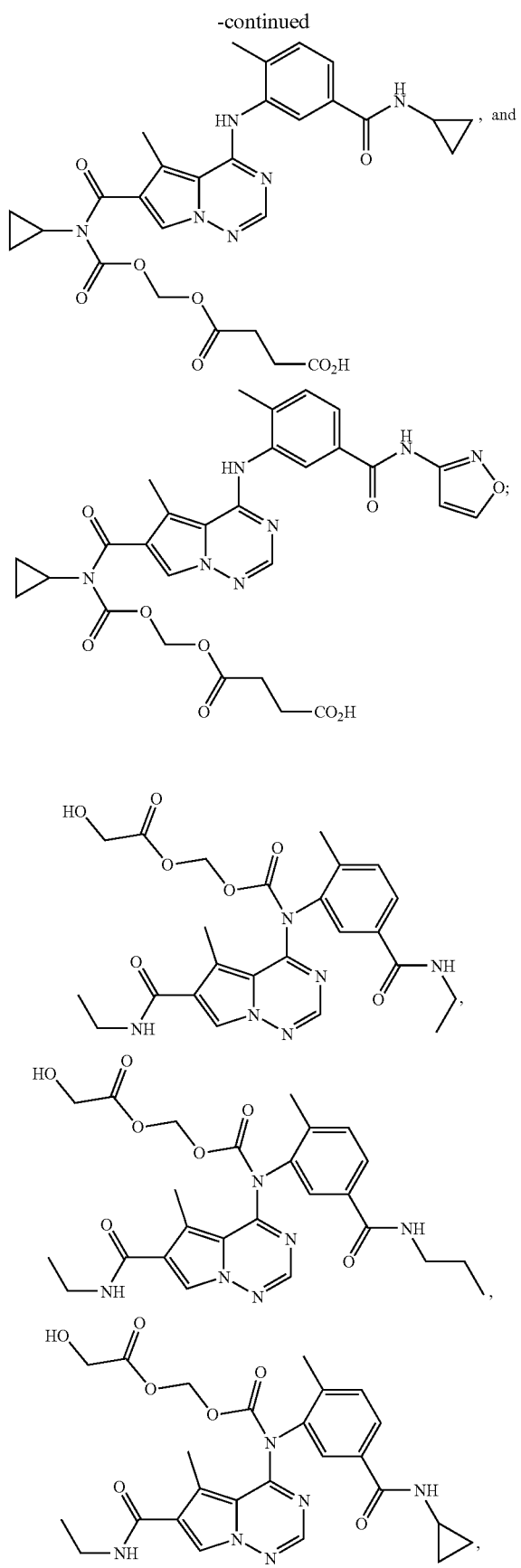
266
-continued
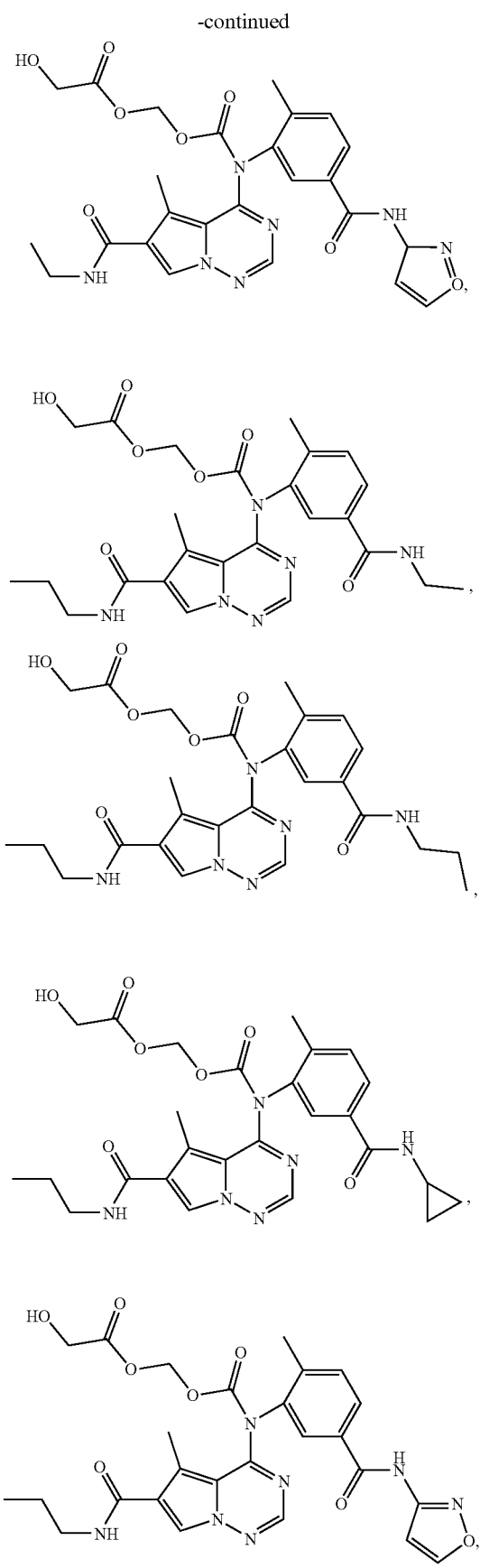

267
268
-continued
-continued
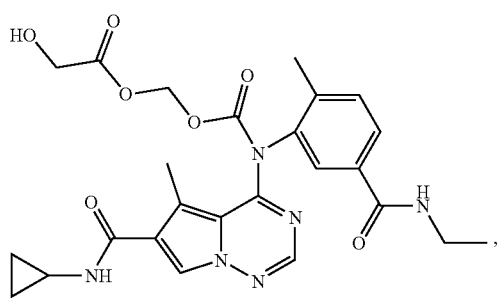
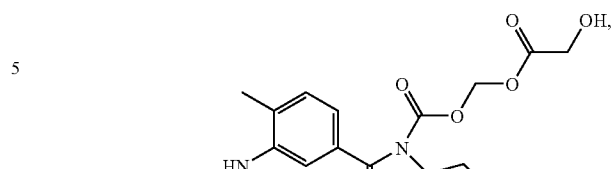
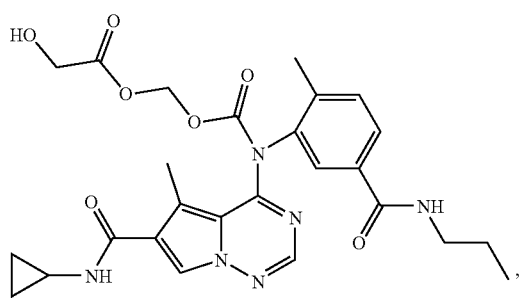
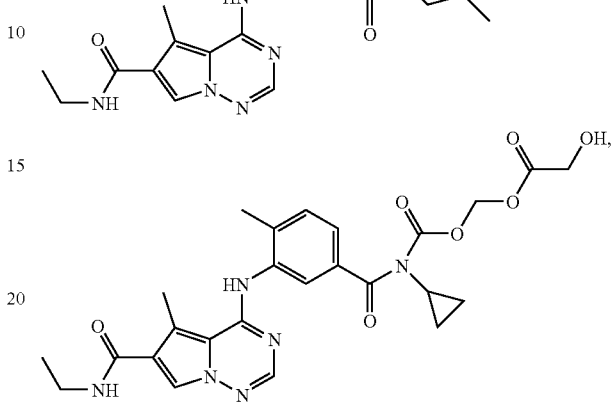
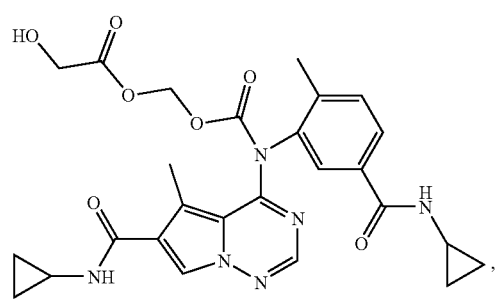
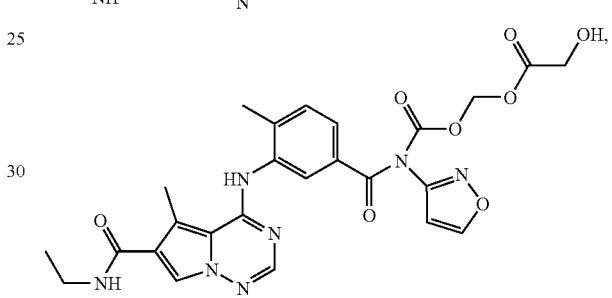
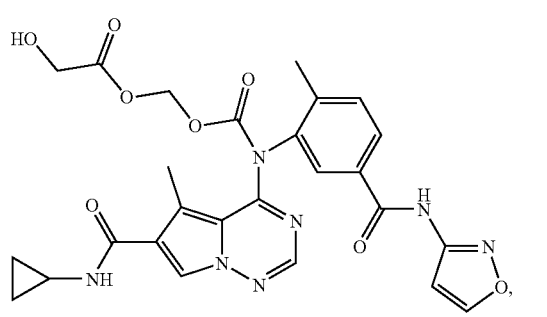
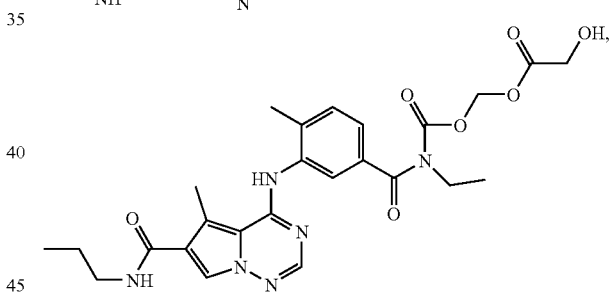
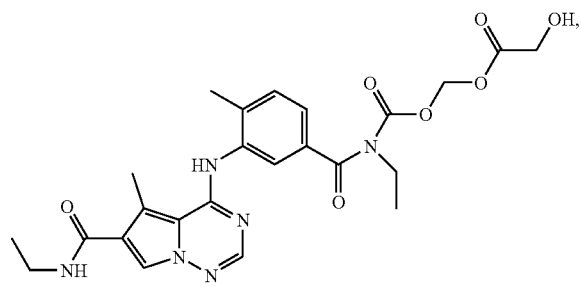
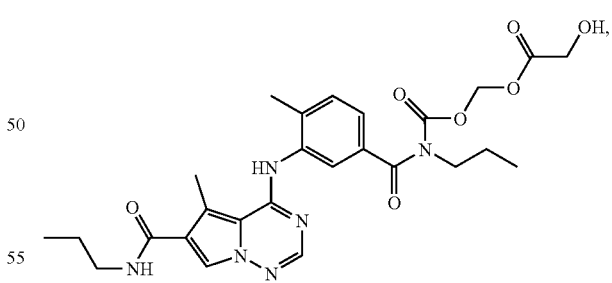
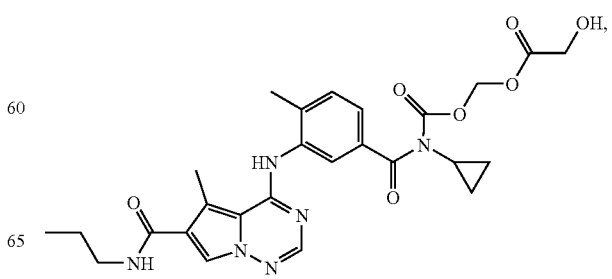

269
-continued
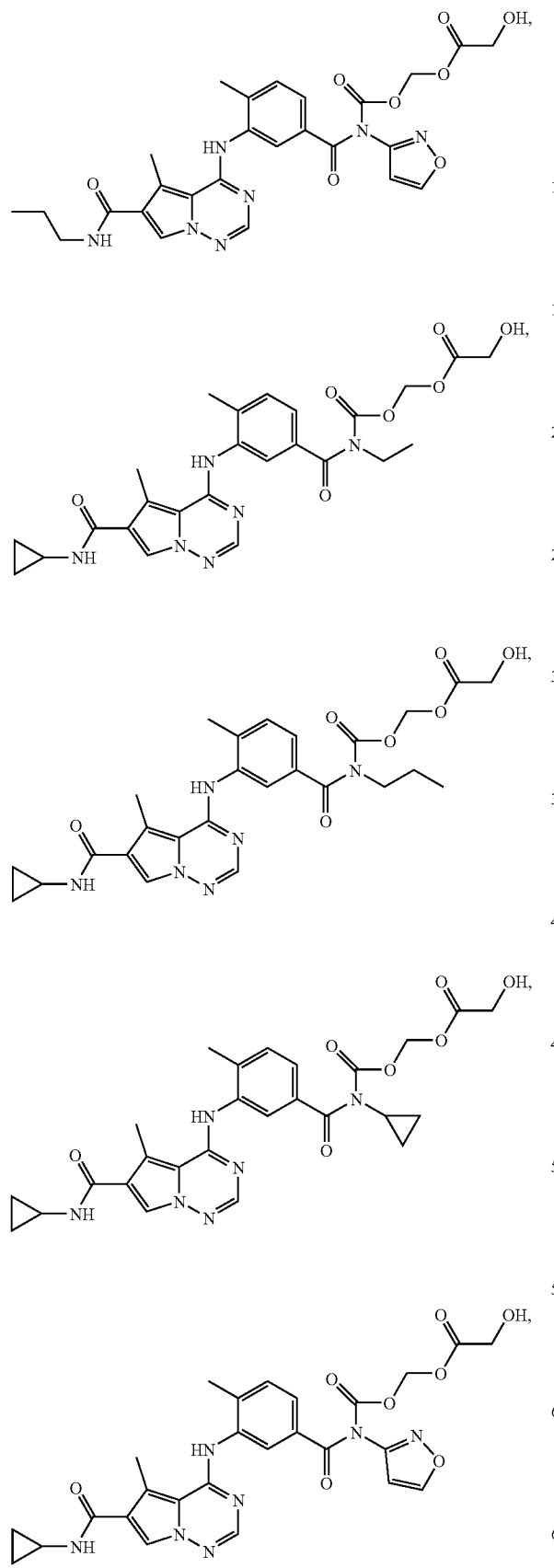
270
-continued
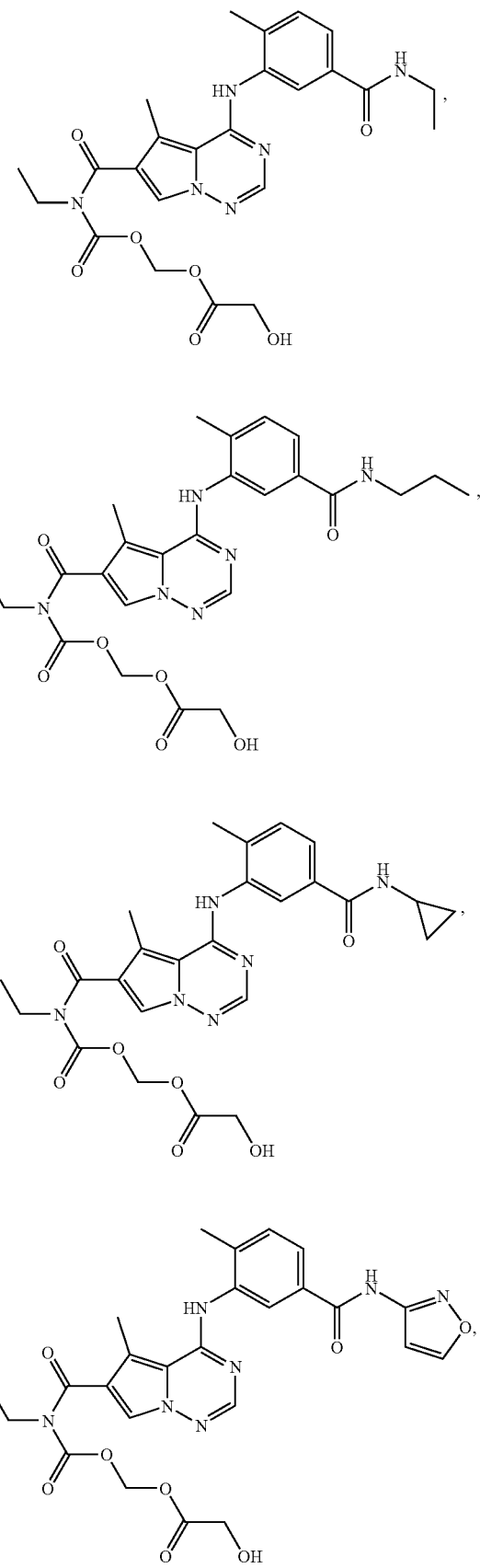

-continued
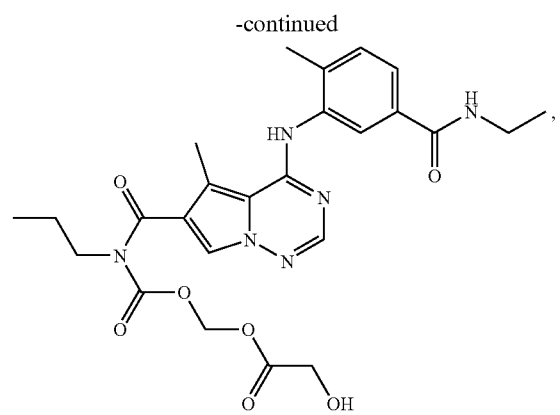
,
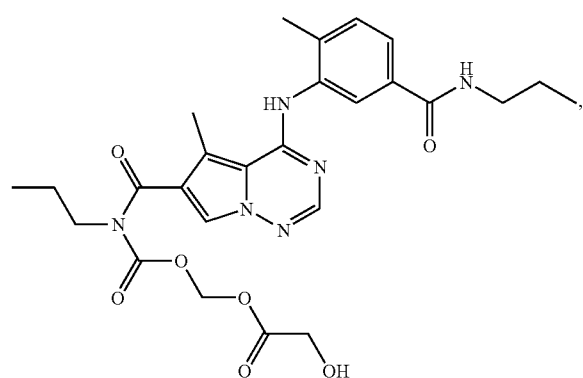
,
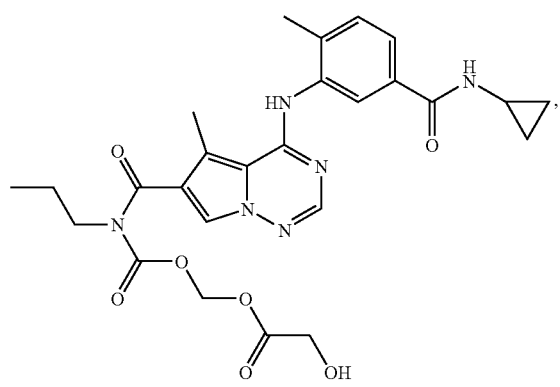
,
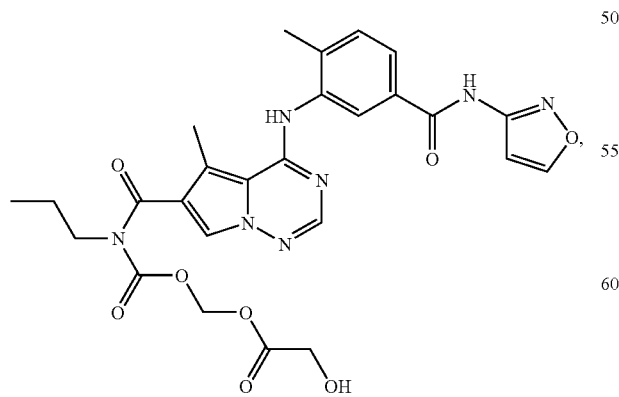
,
-continued
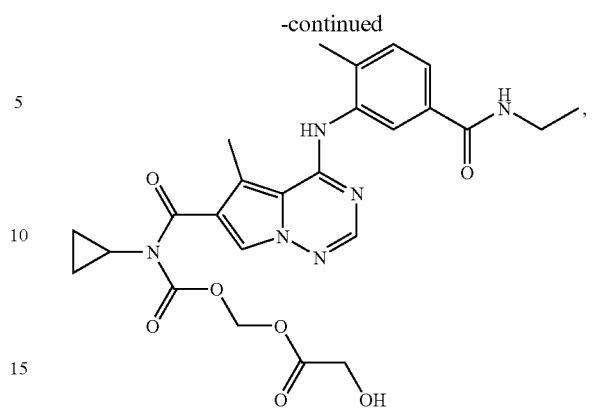
,
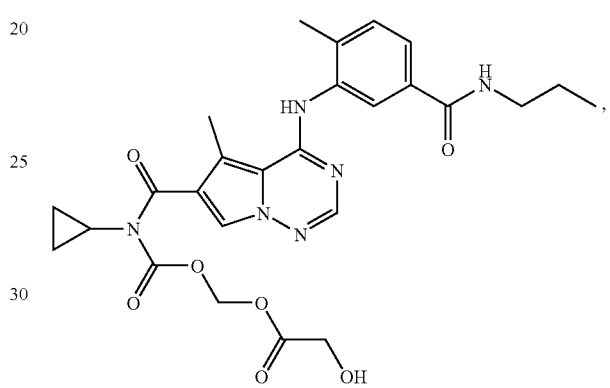
,
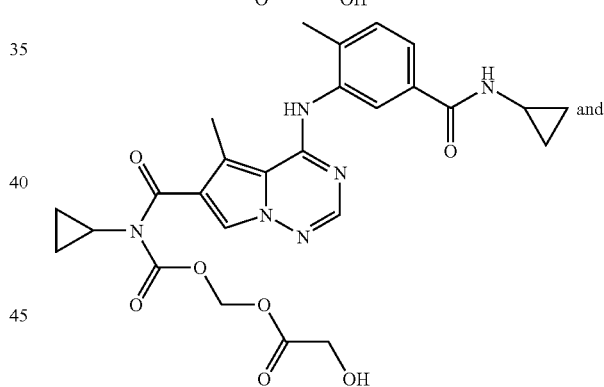 and
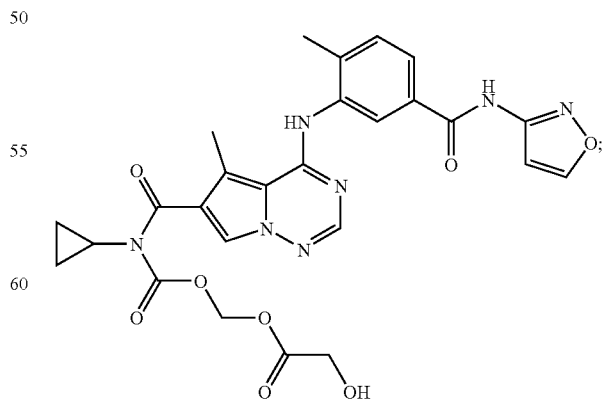;

273
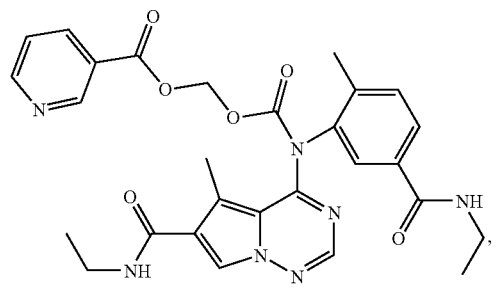
274
-continued
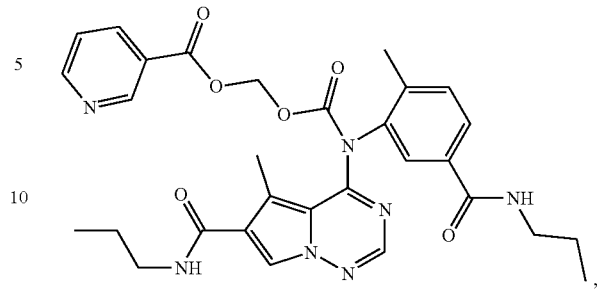
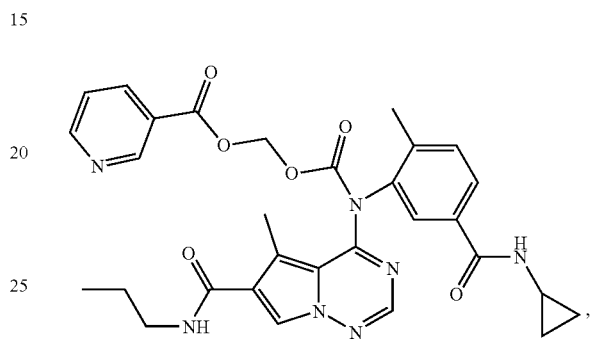
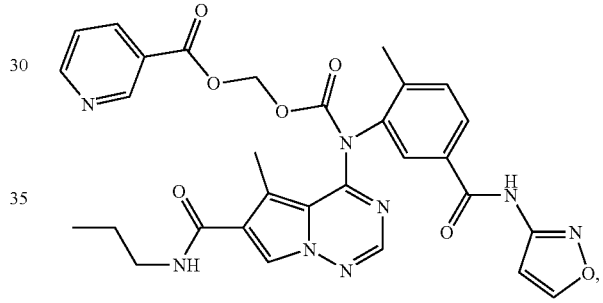
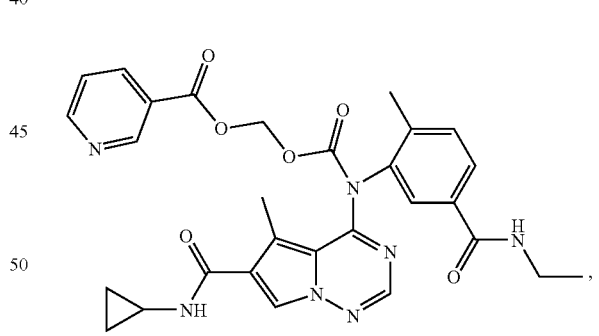
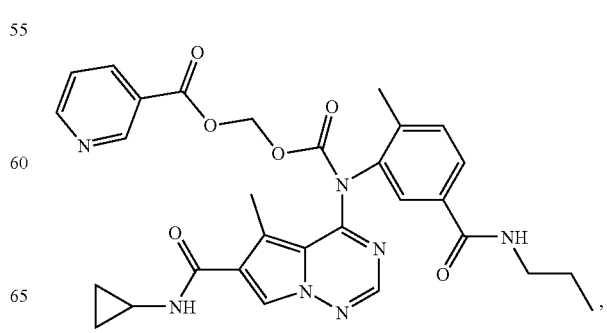

-continued
275
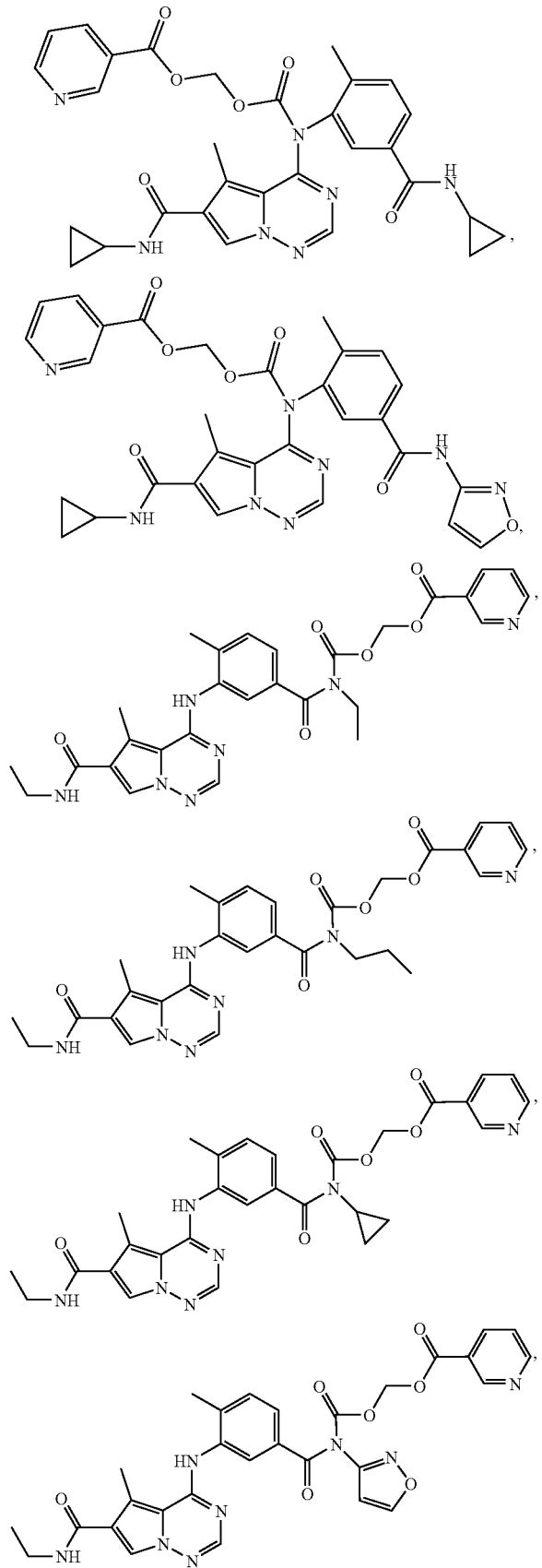
276
-continued
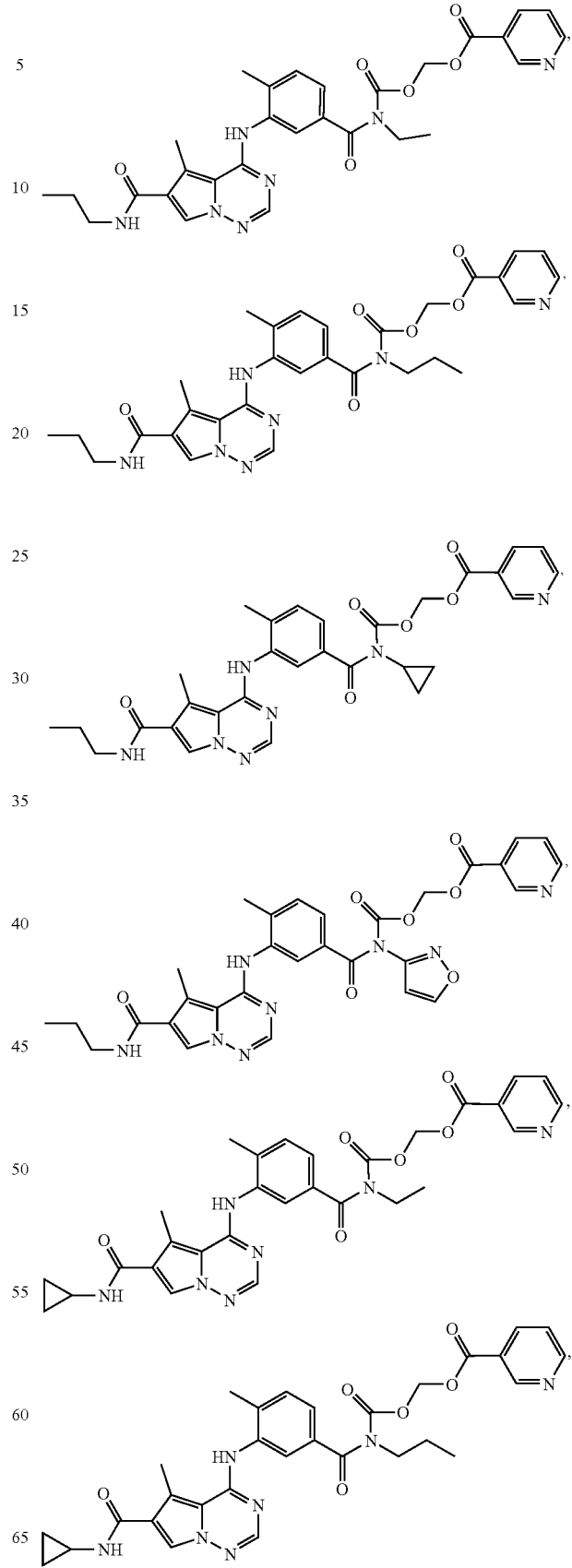

-continued
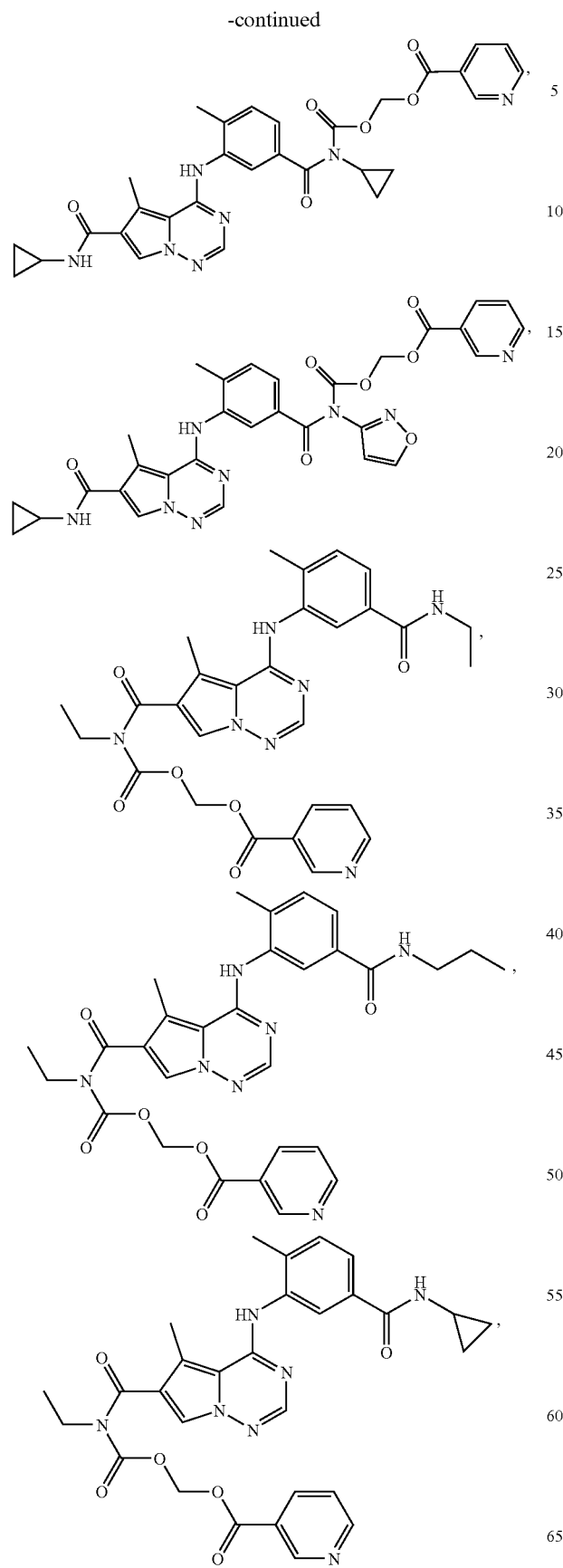
-continued
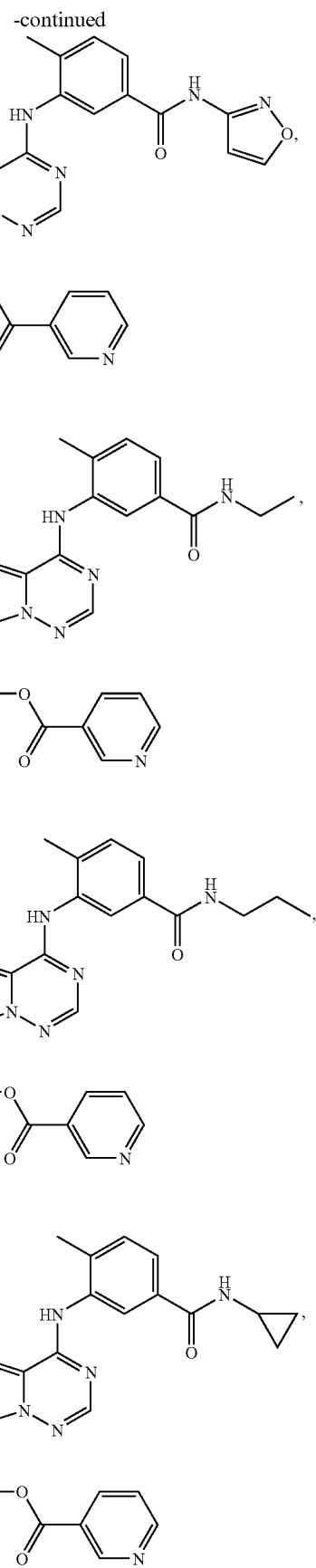

279
-continued
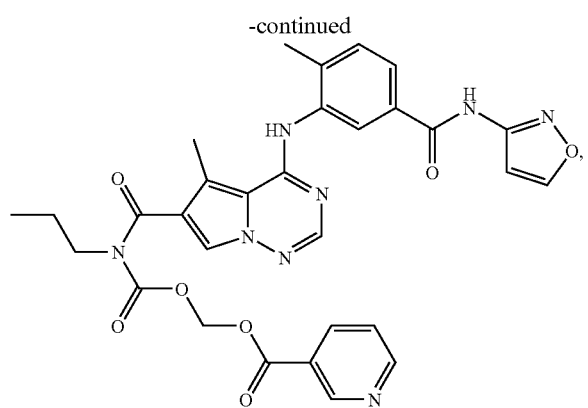
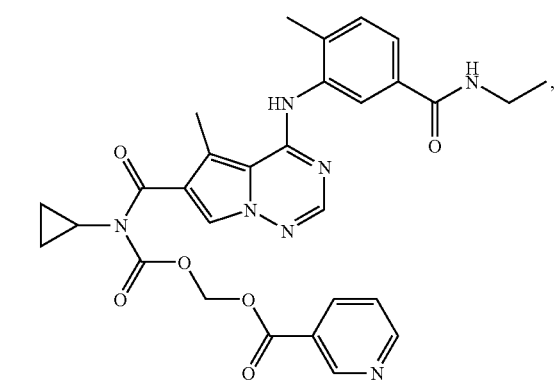
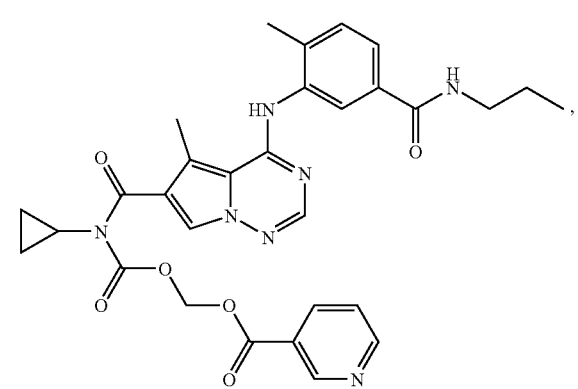
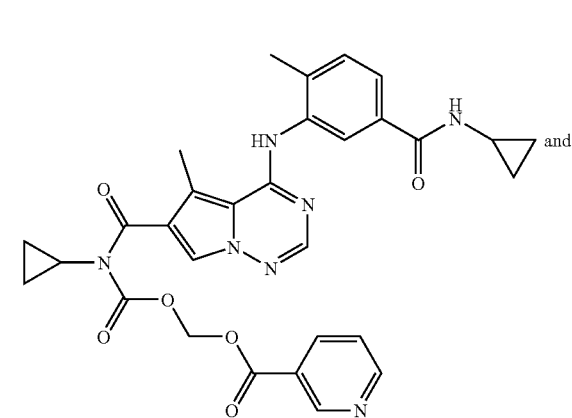
and
280
-continued
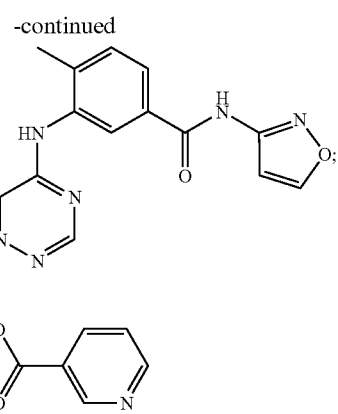
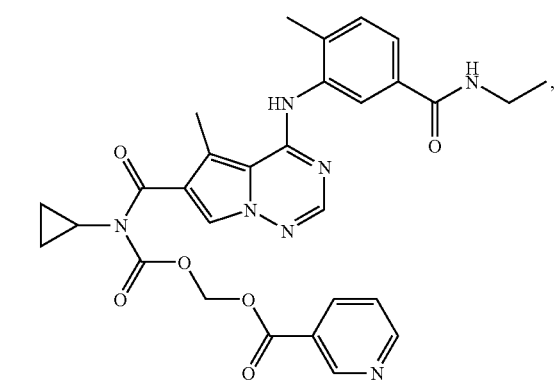
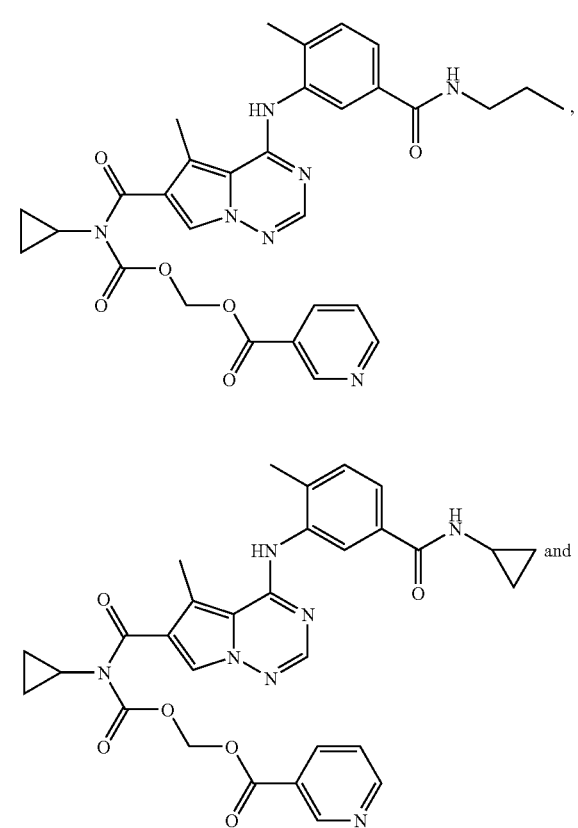

281
-continued
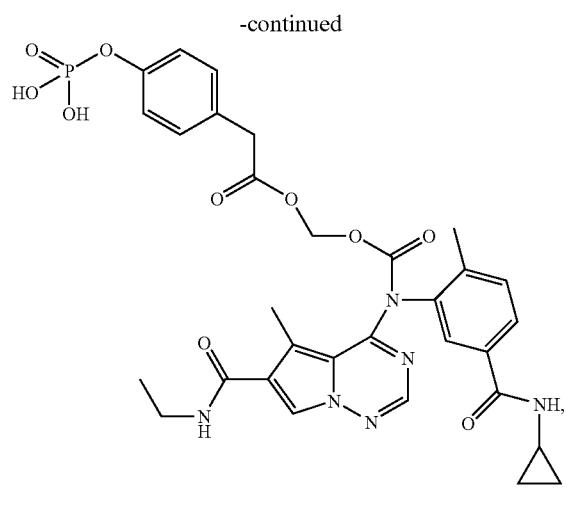
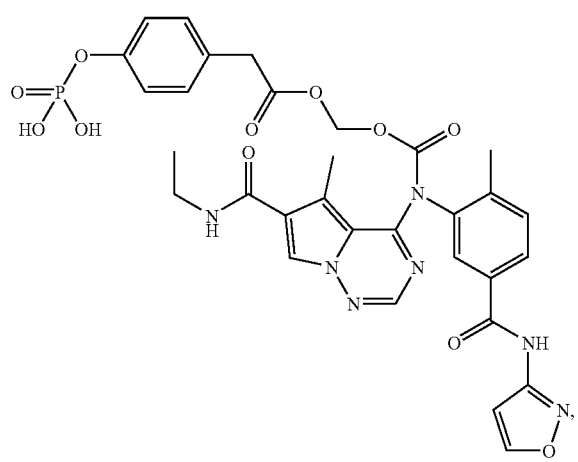
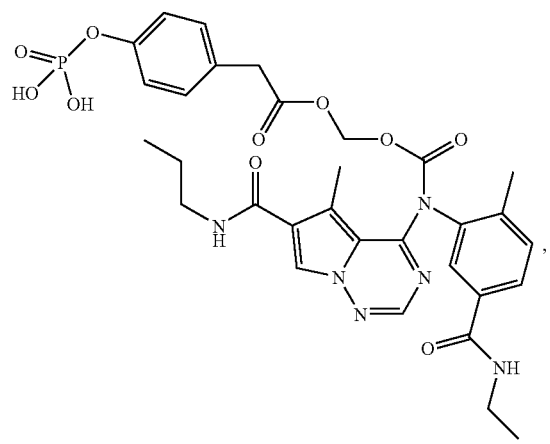
282
-continued
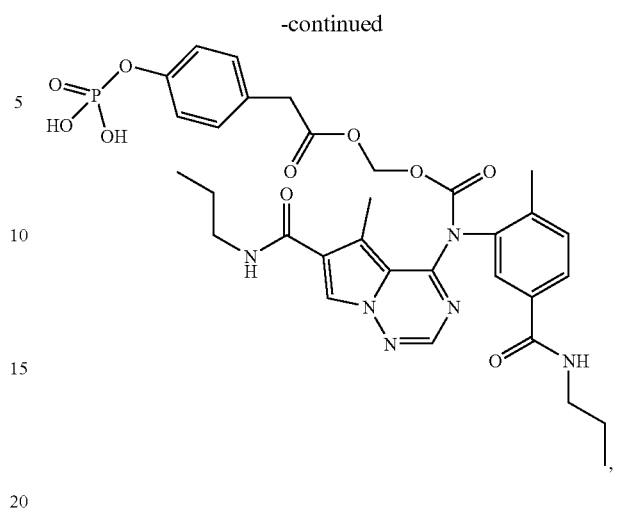
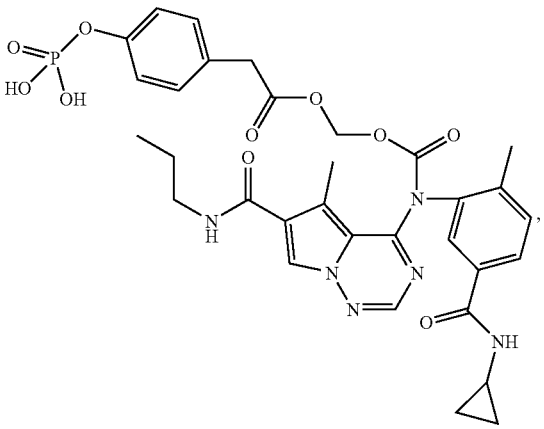
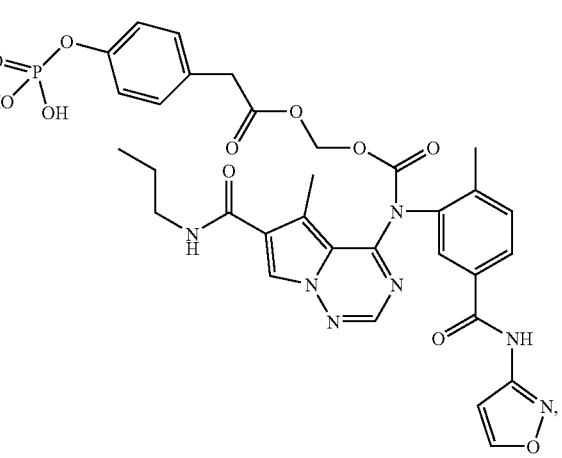

283
-continued
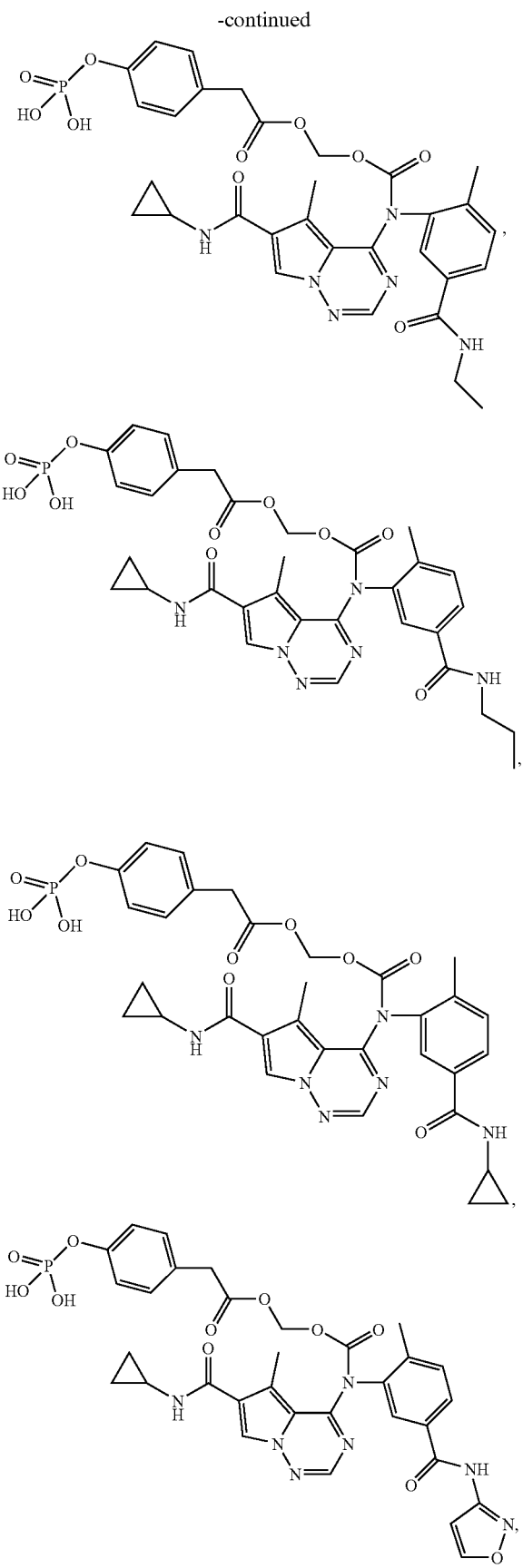
284
-continued
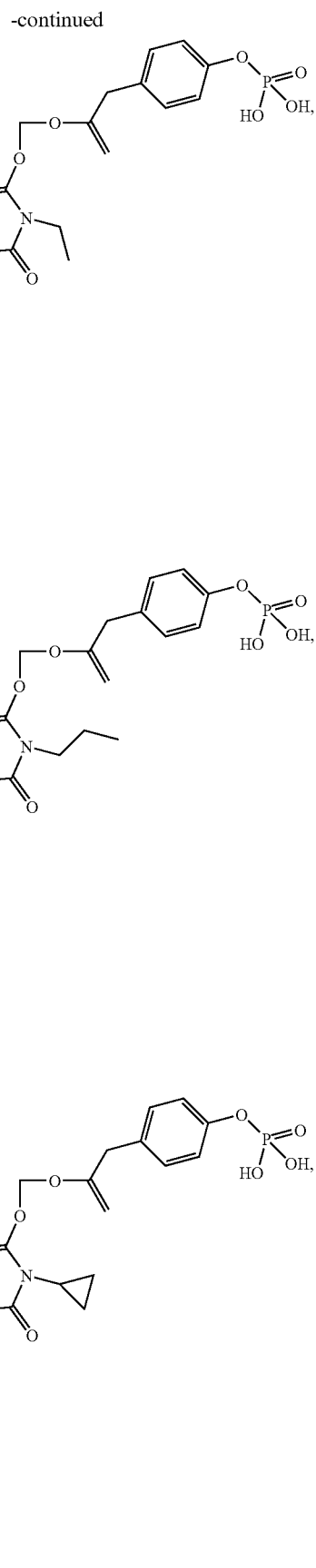

-continued
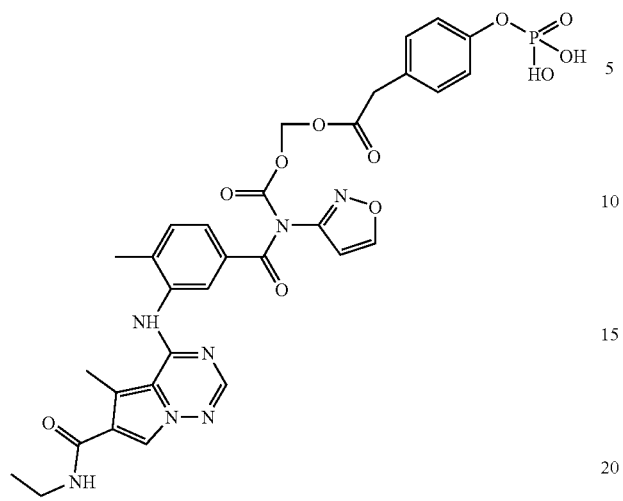
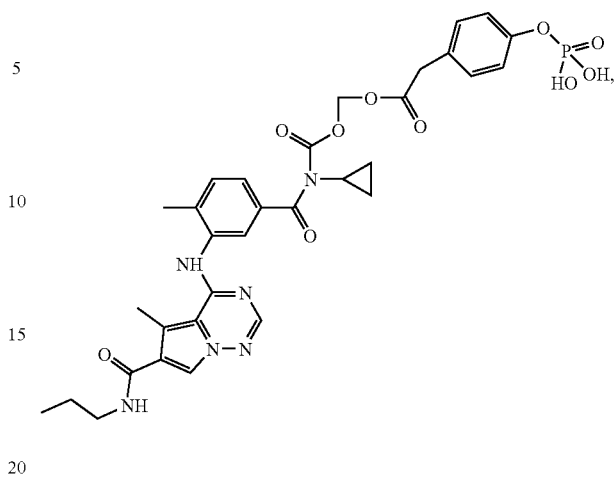
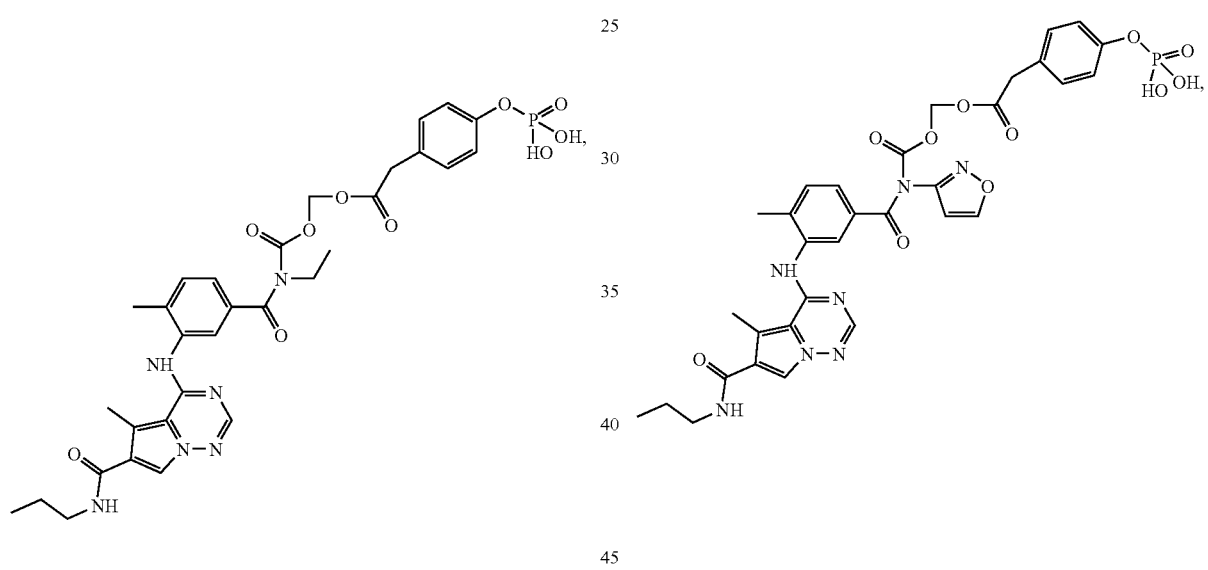
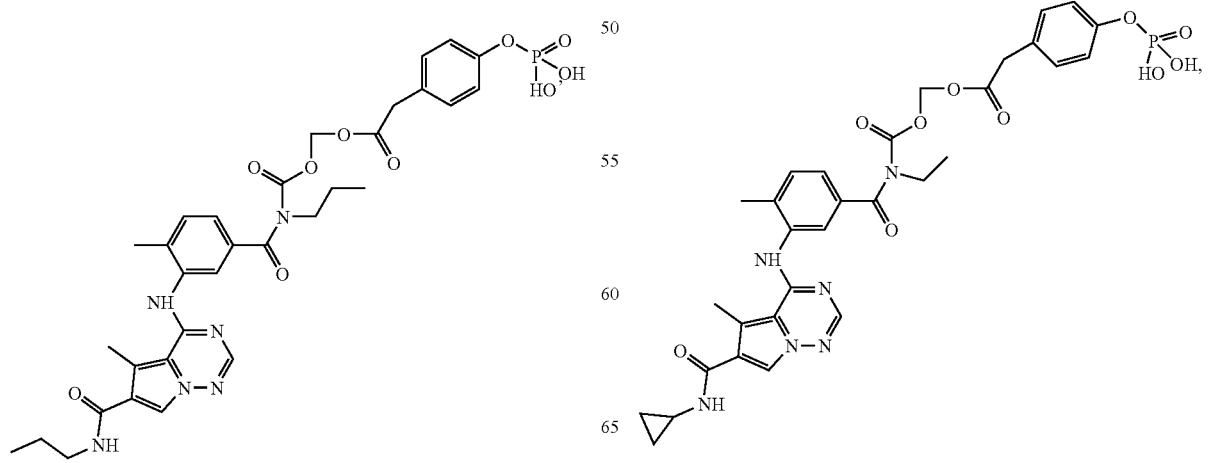

287
-continued
288
-continued
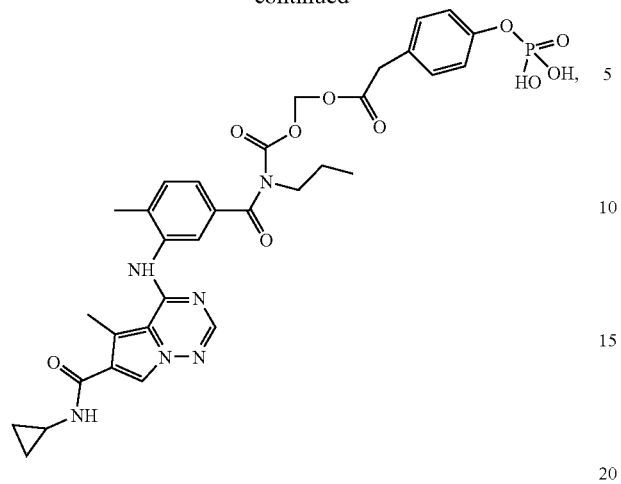
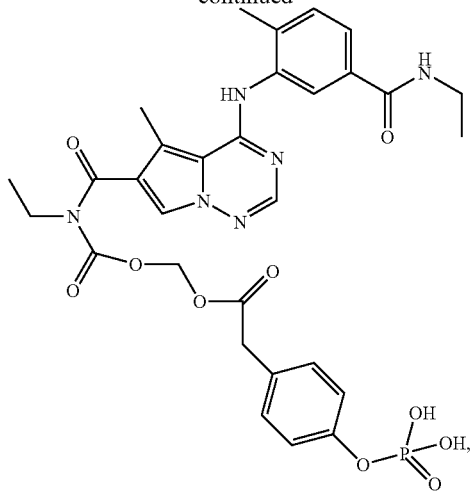
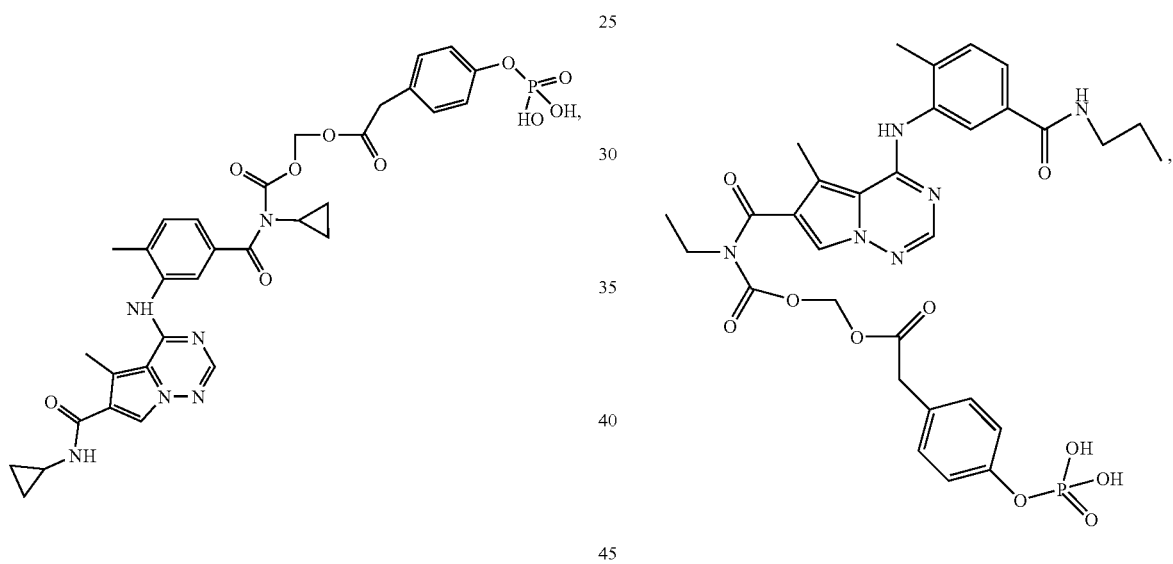
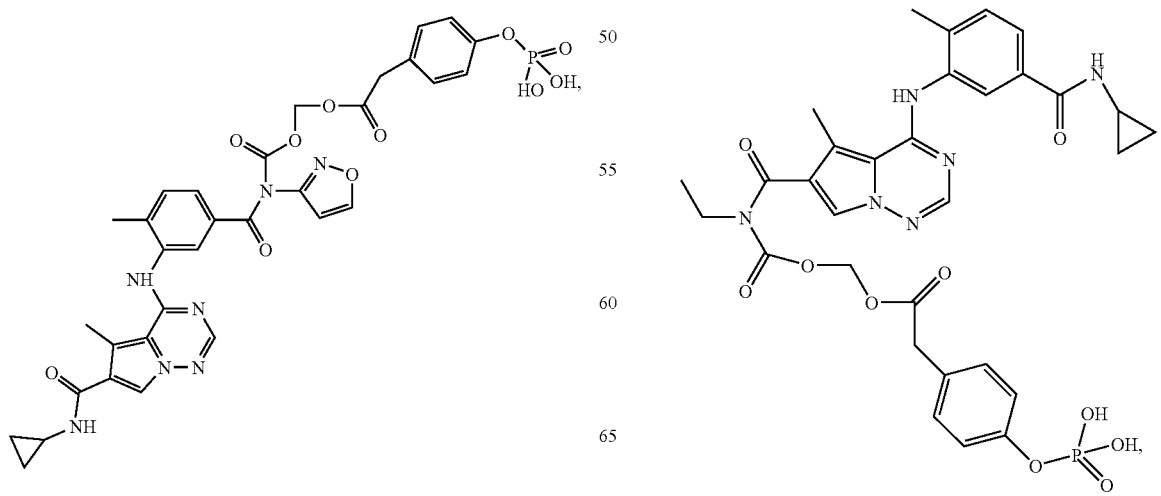

289
-continued
290
-continued
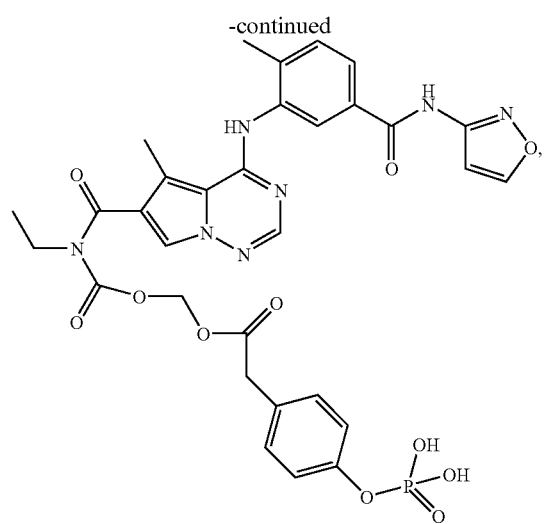
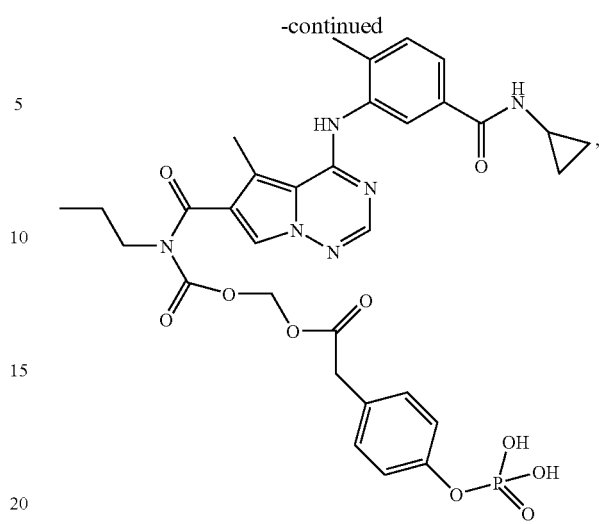
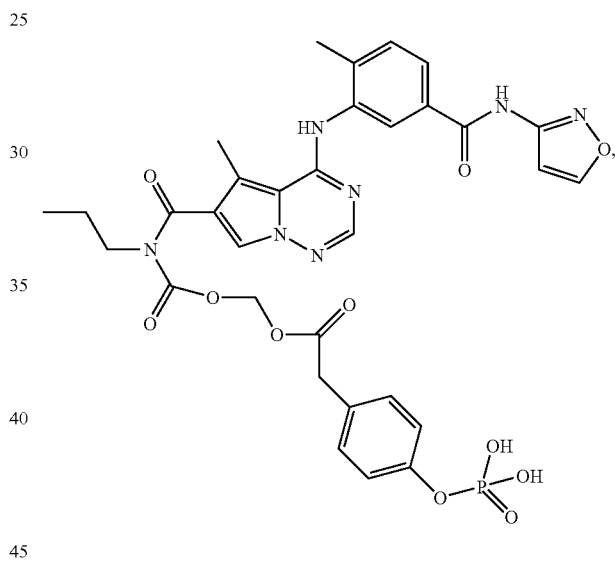
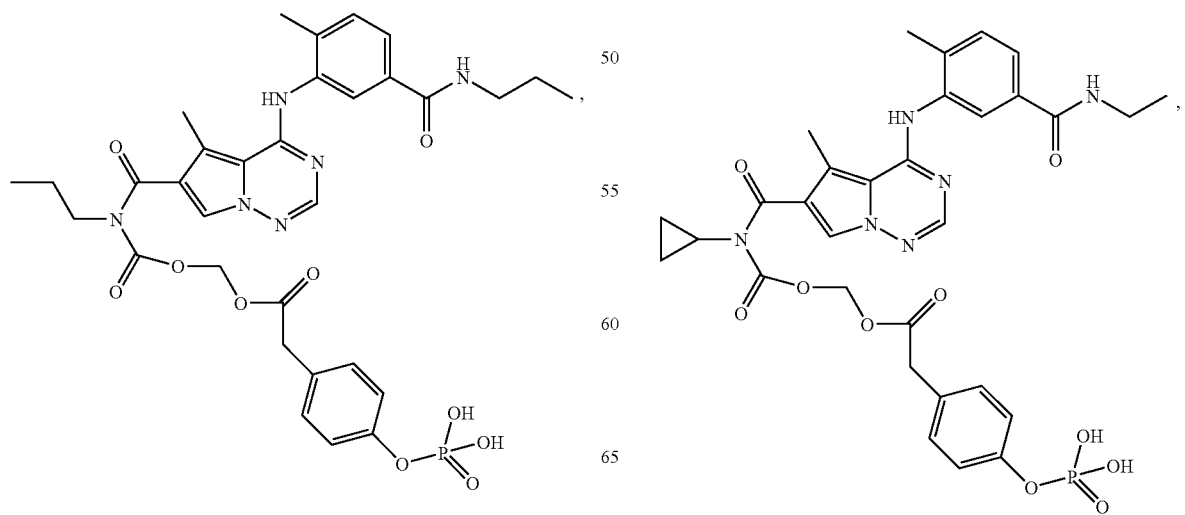

291
-continued
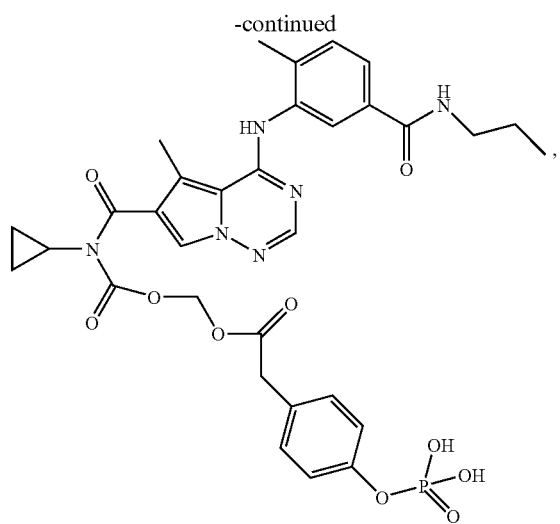
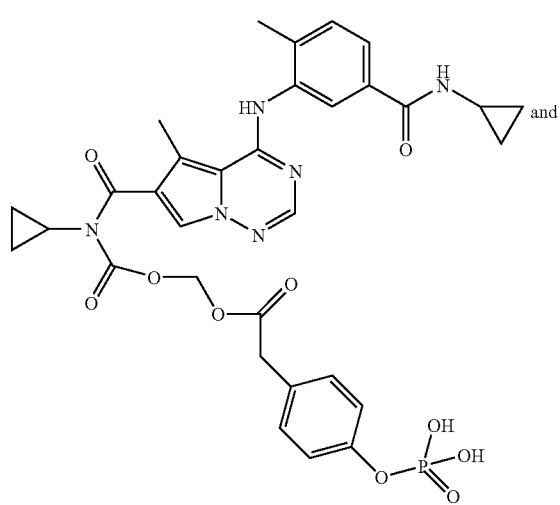
and
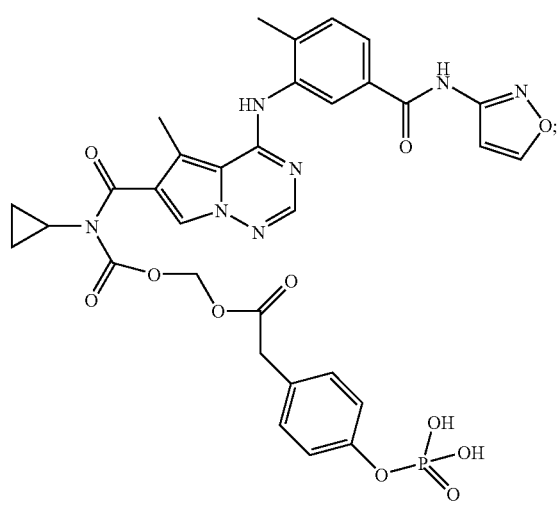
292
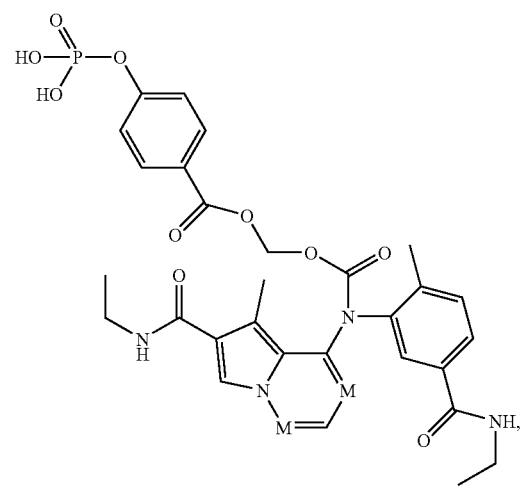
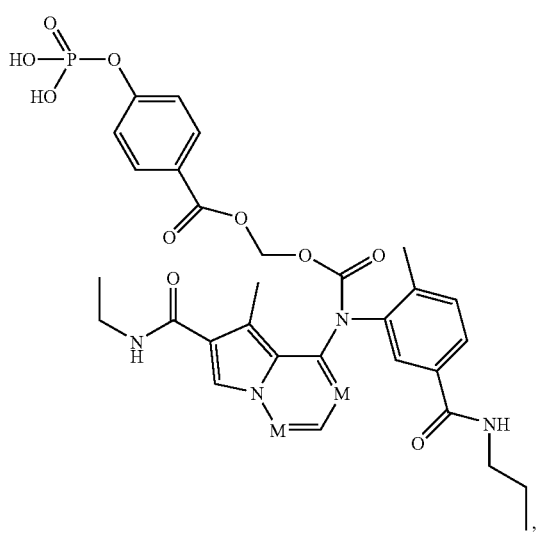
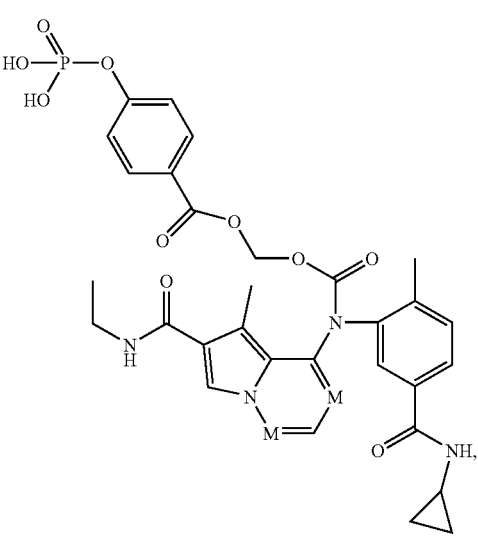

293
-continued
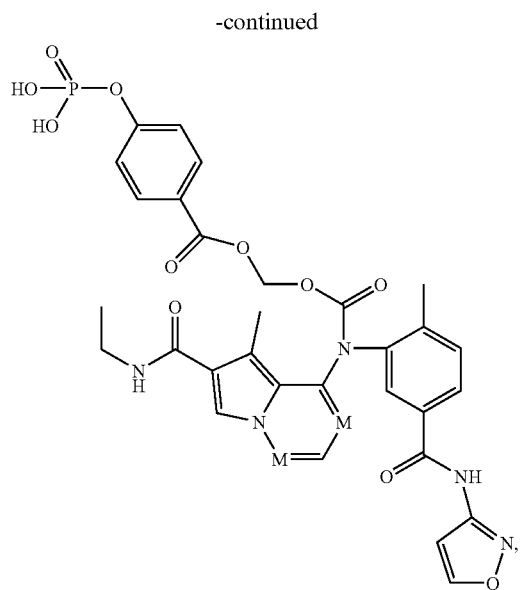
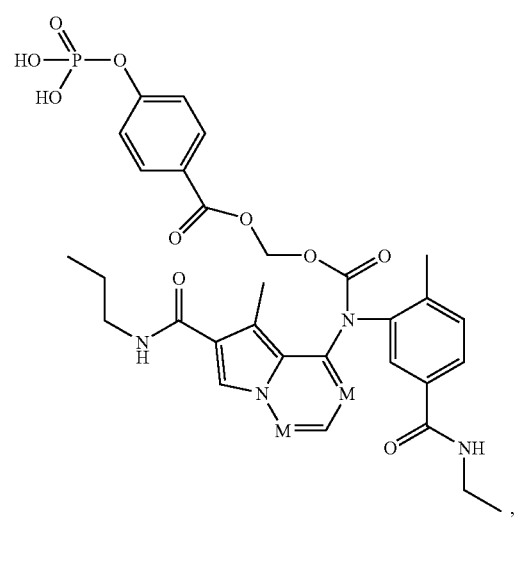
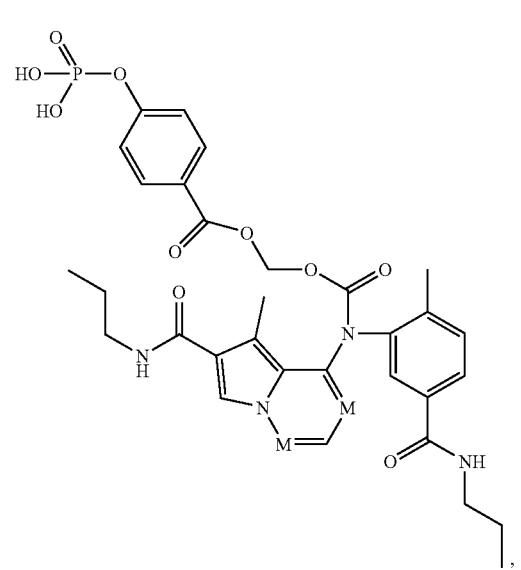
294
-continued
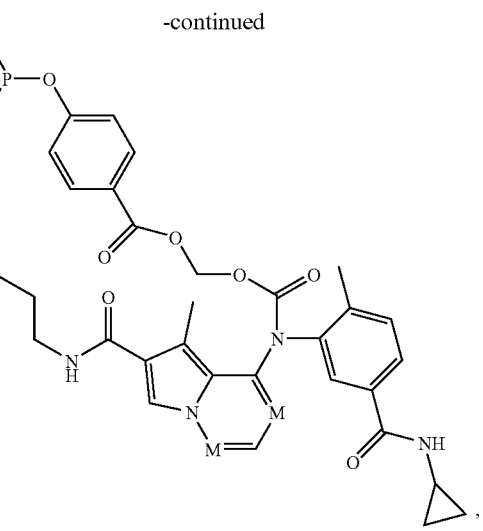
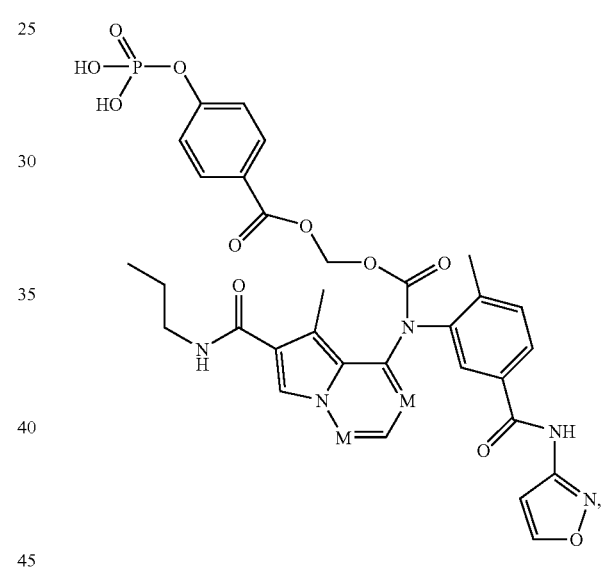
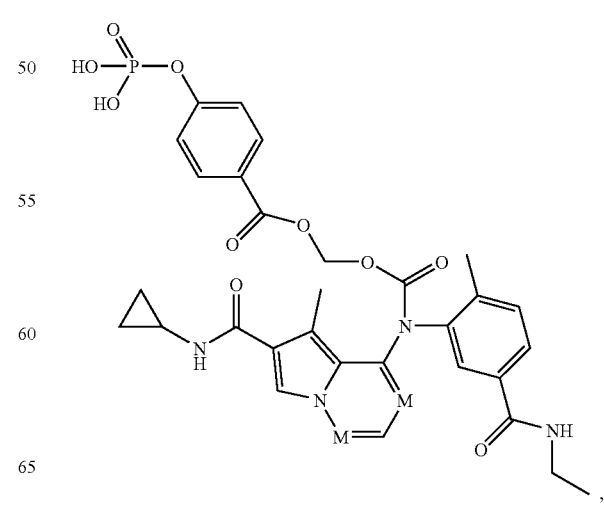

295
-continued
296
-continued
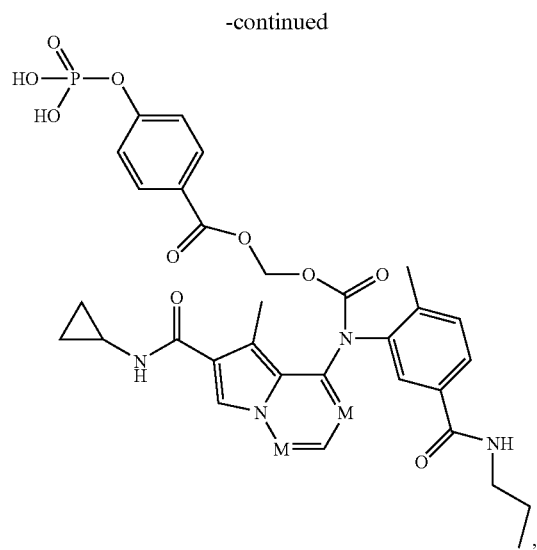
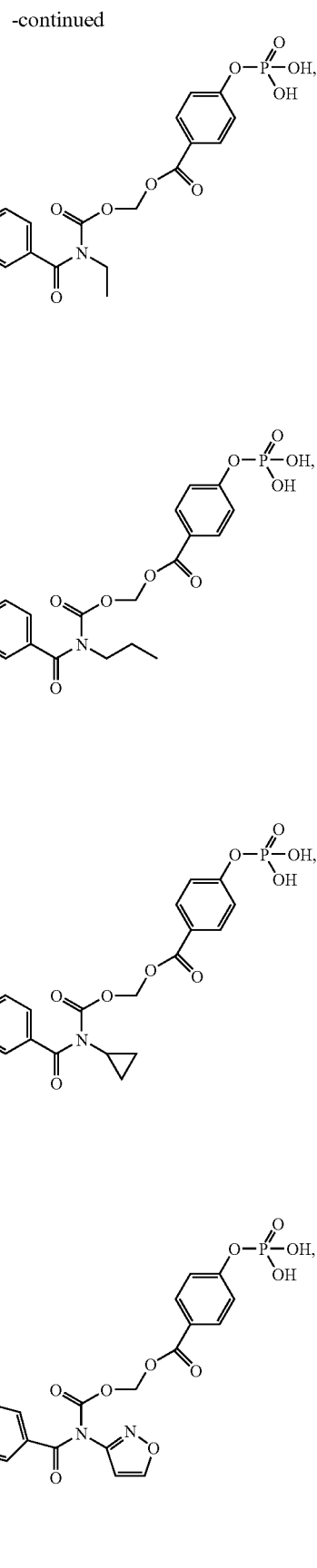

297 298
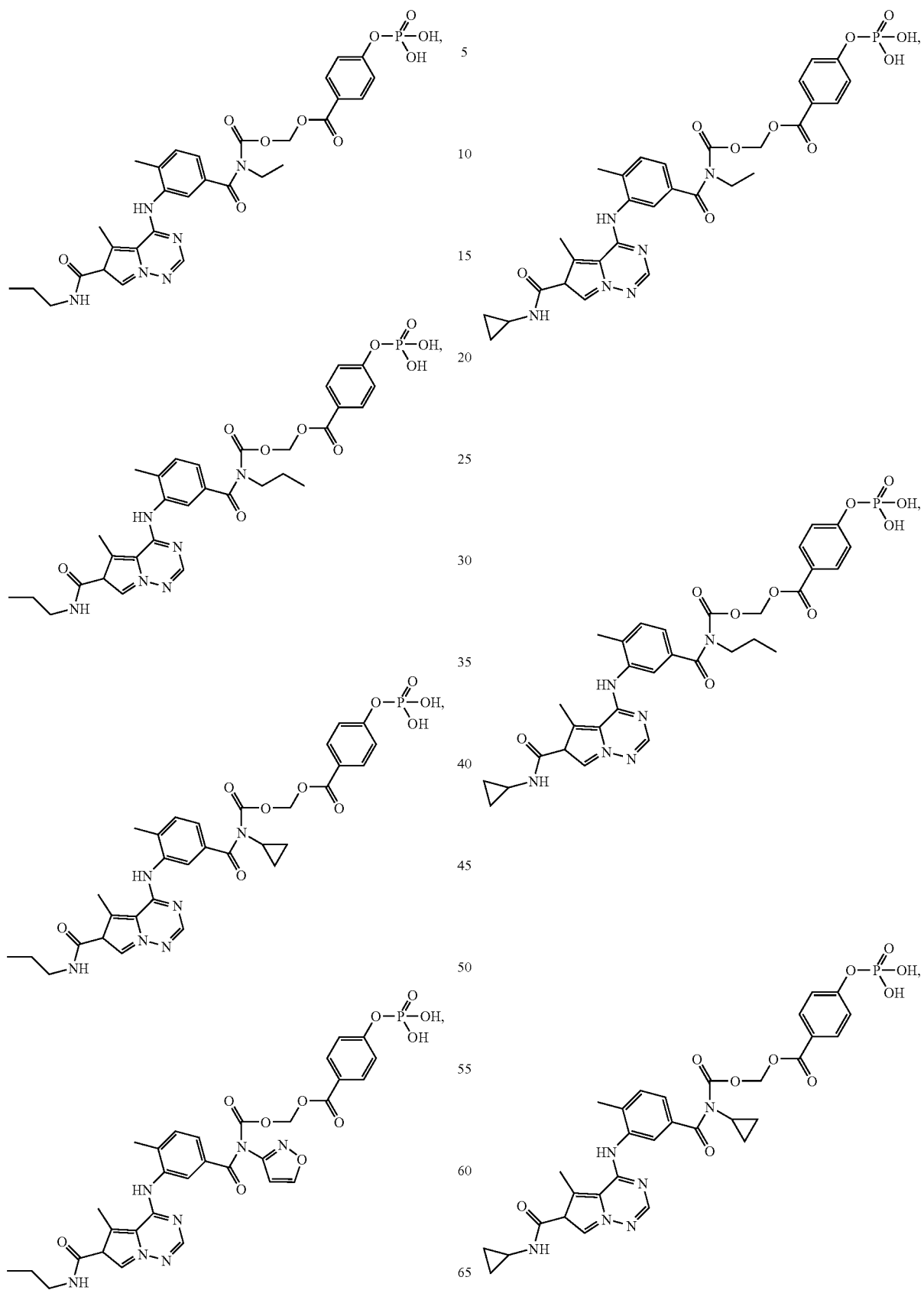

299
-continued
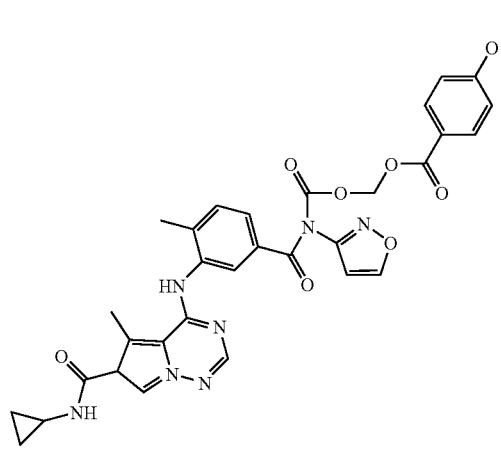
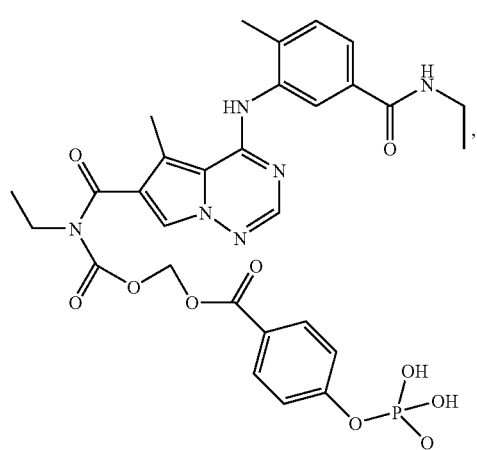
300
-continued
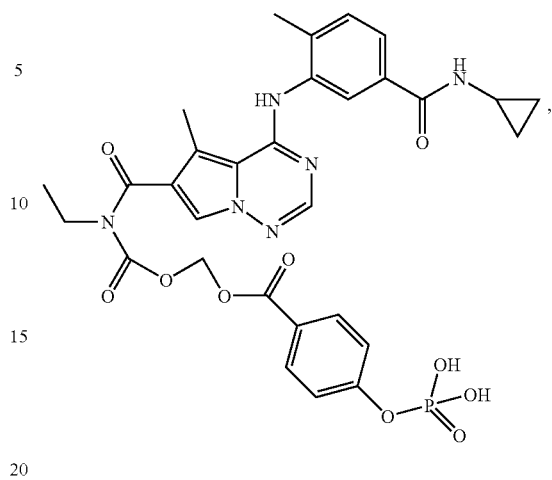
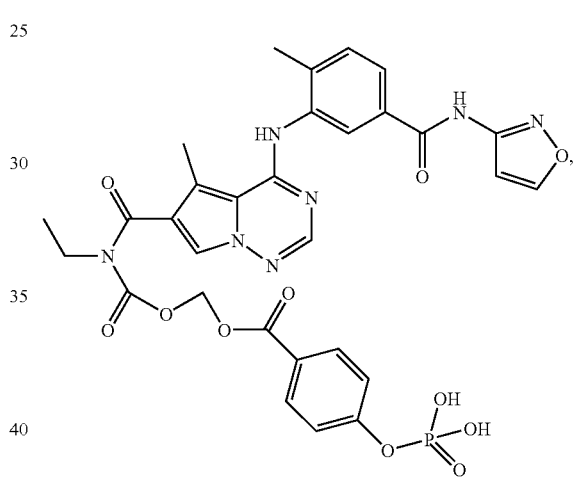
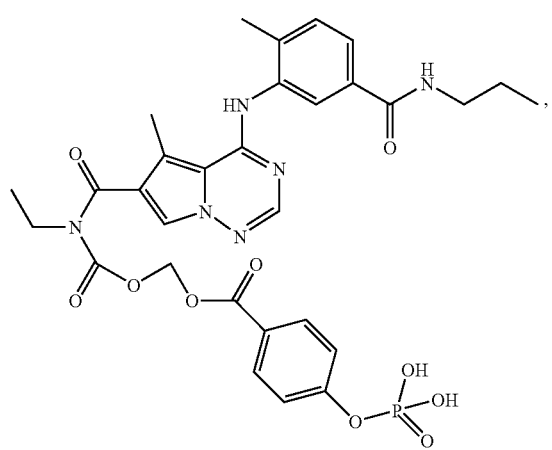
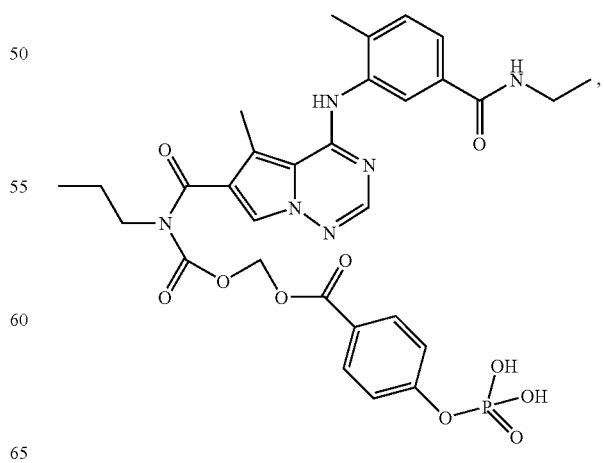

301
-continued
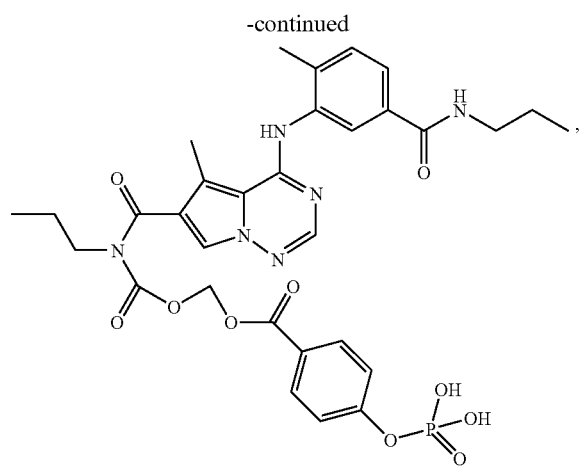
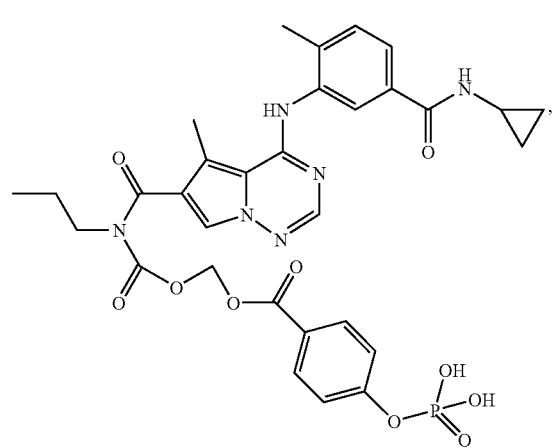
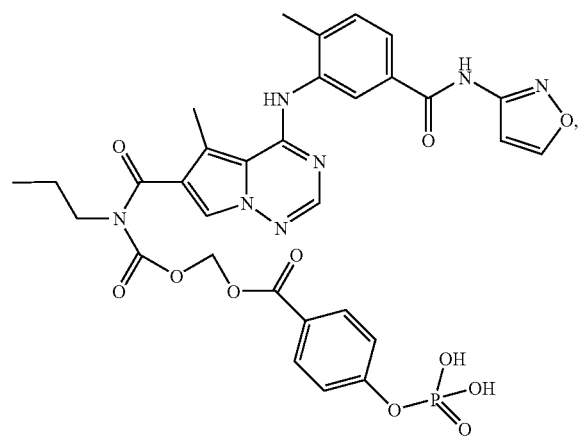
302
-continued
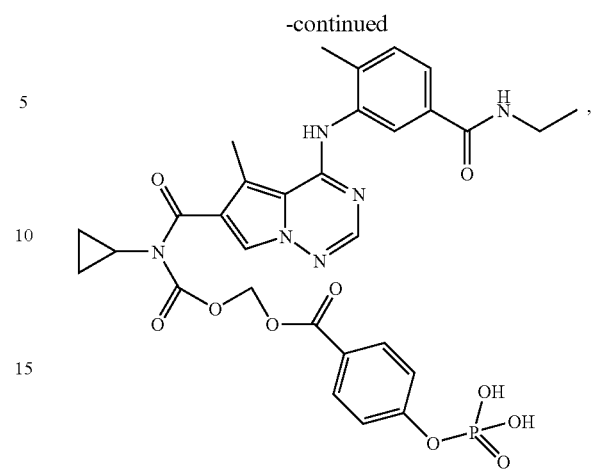
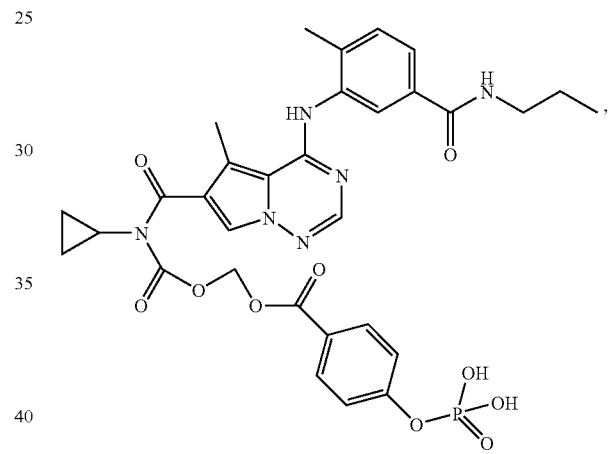
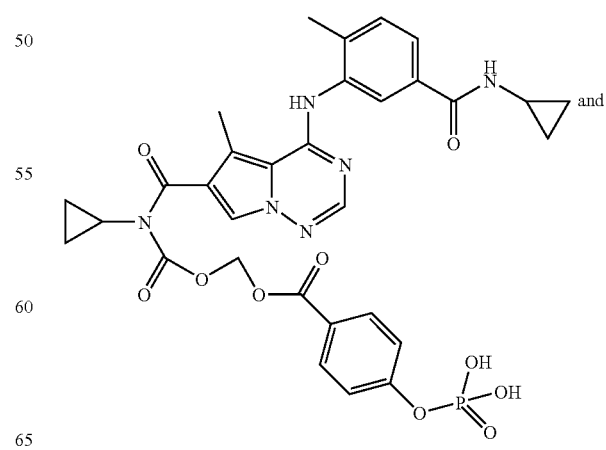
and

303
-continued
304
-continued
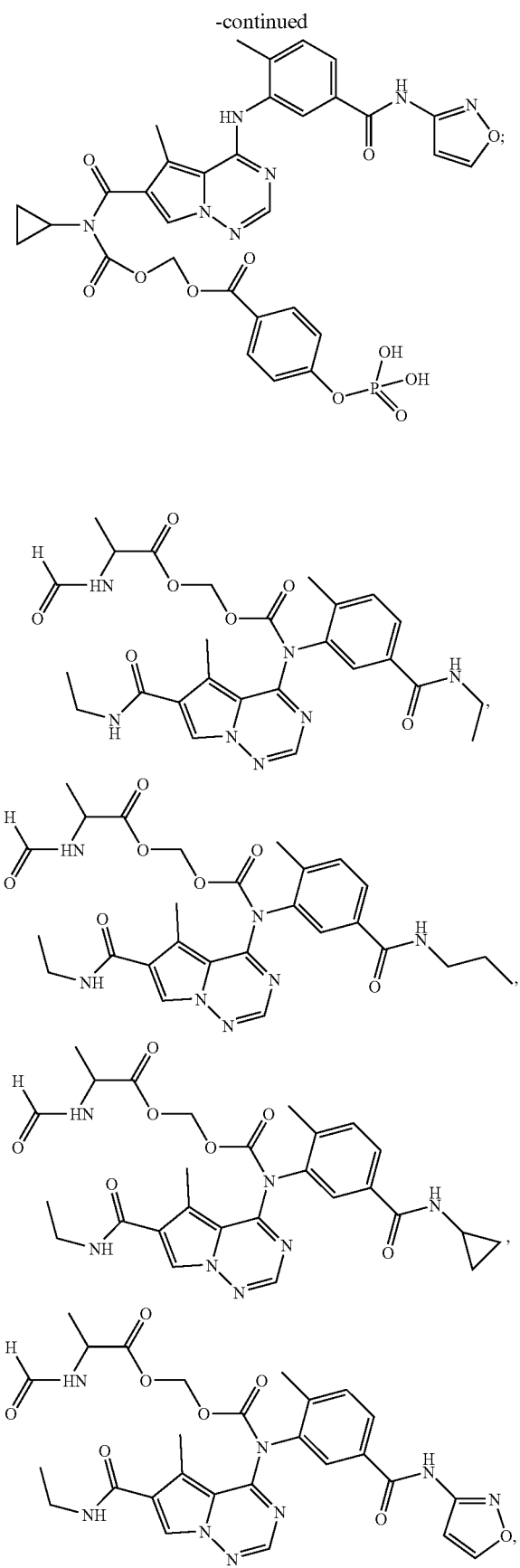
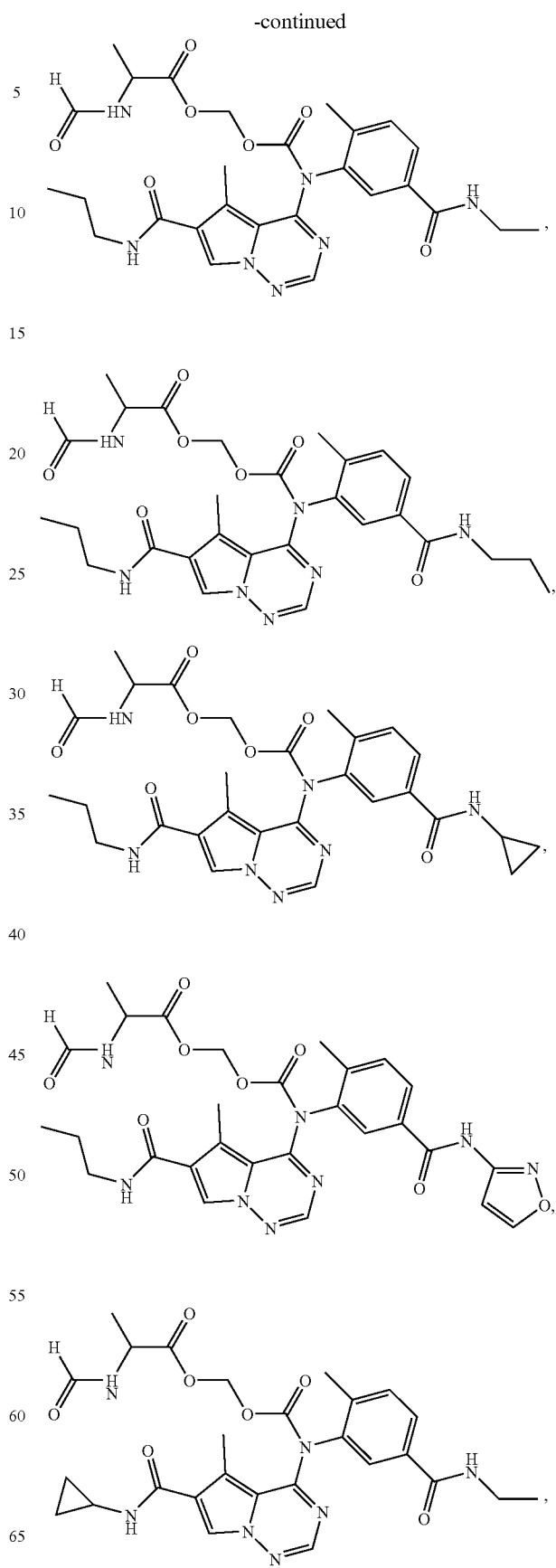

-continued
305
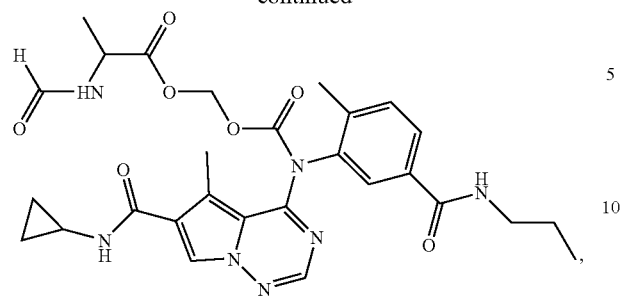
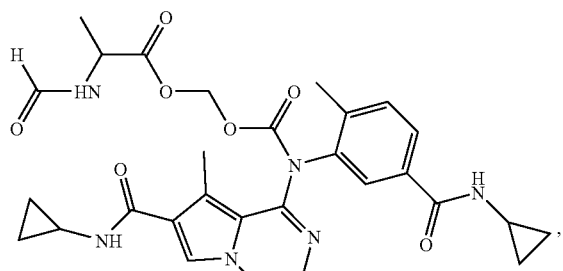
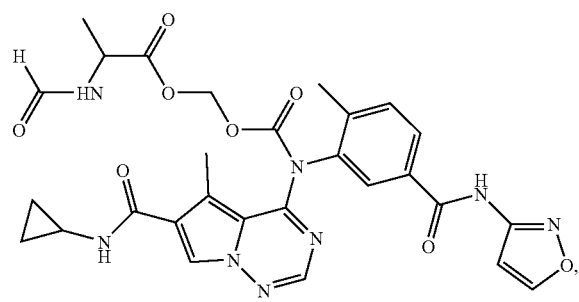
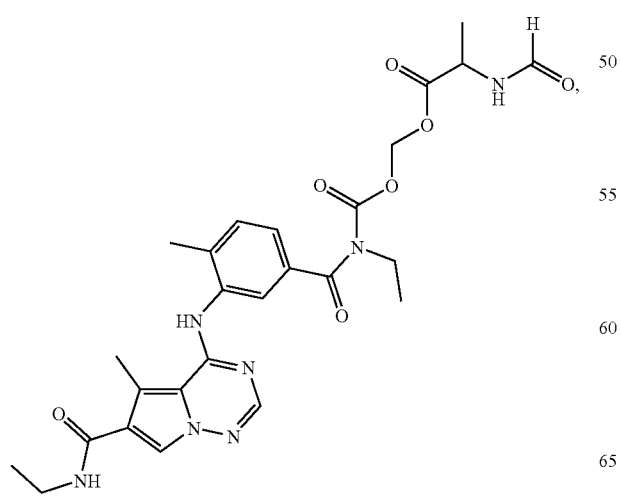
306
-continued
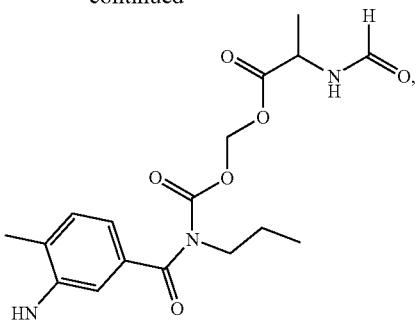
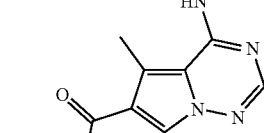
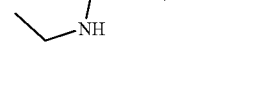
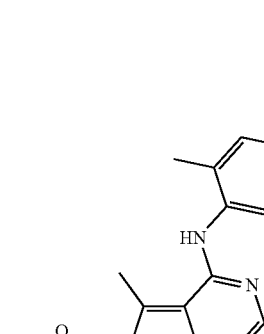
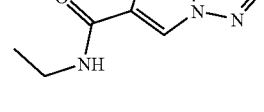

307
-continued
308
-continued
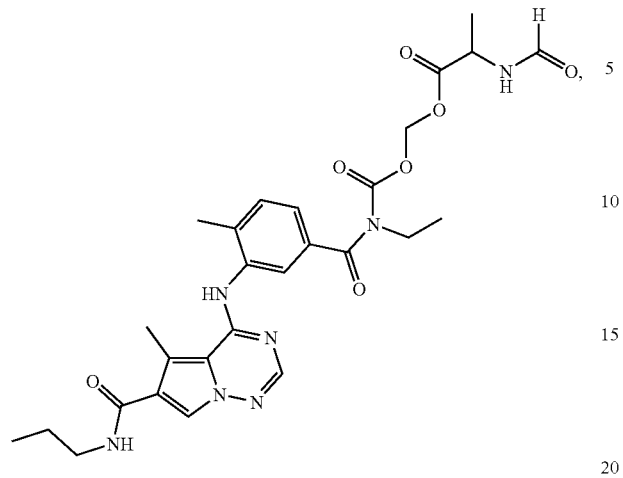
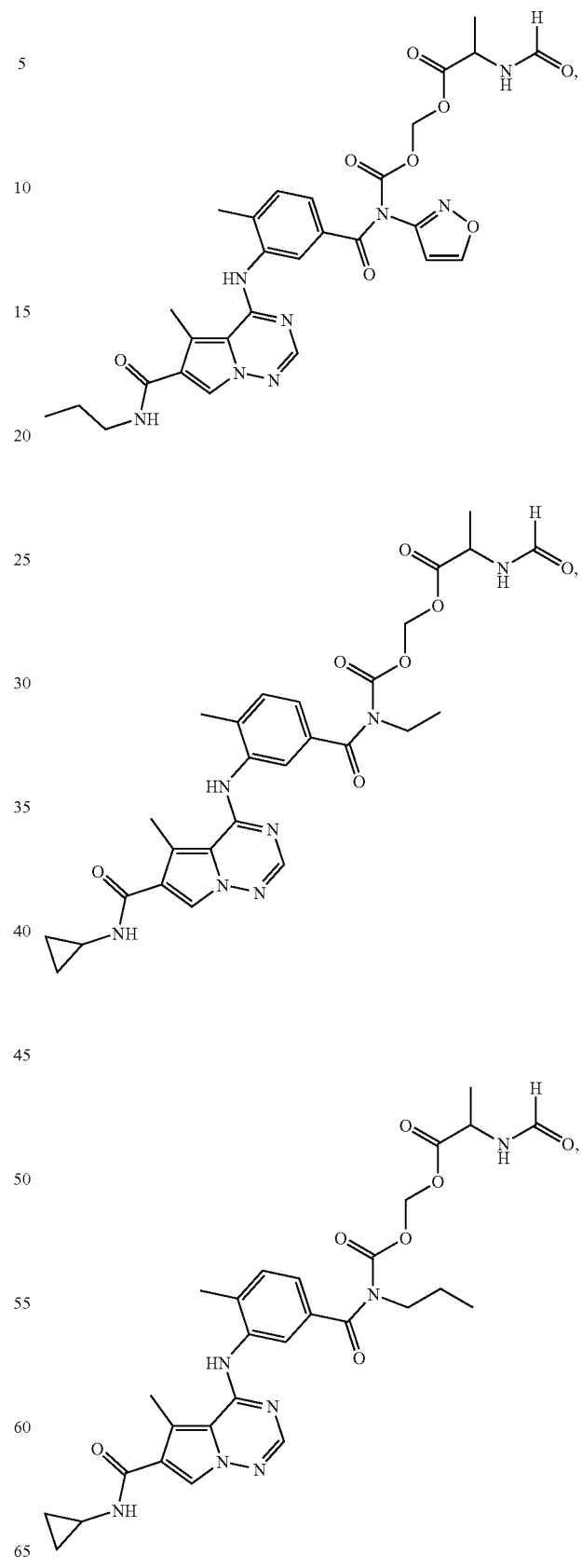

309
-continued
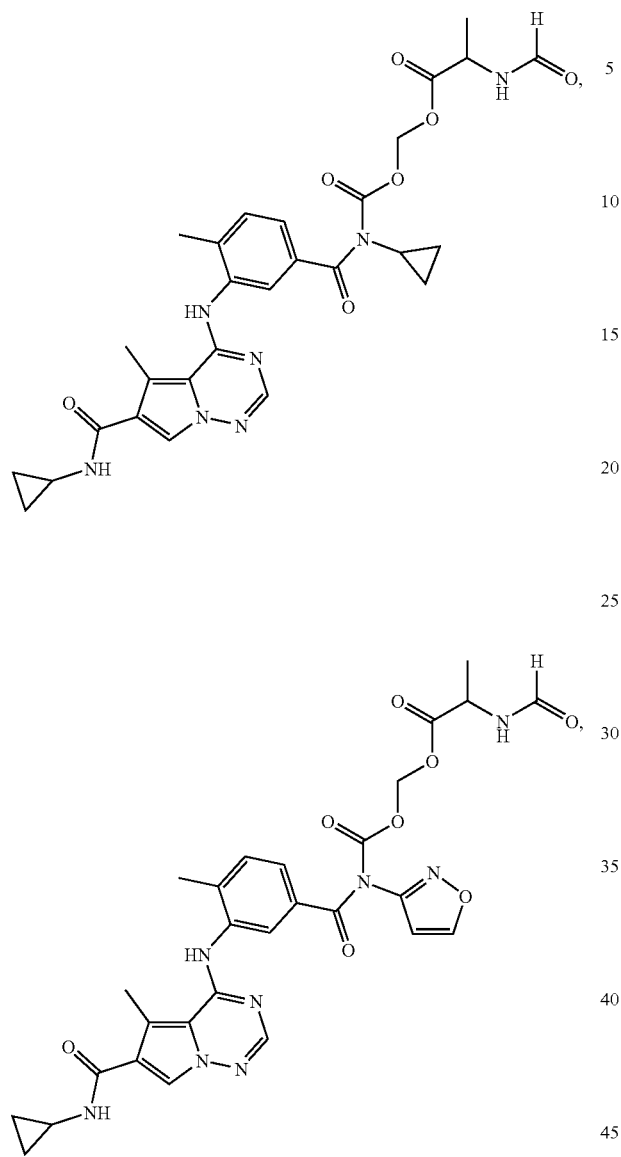
310
-continued
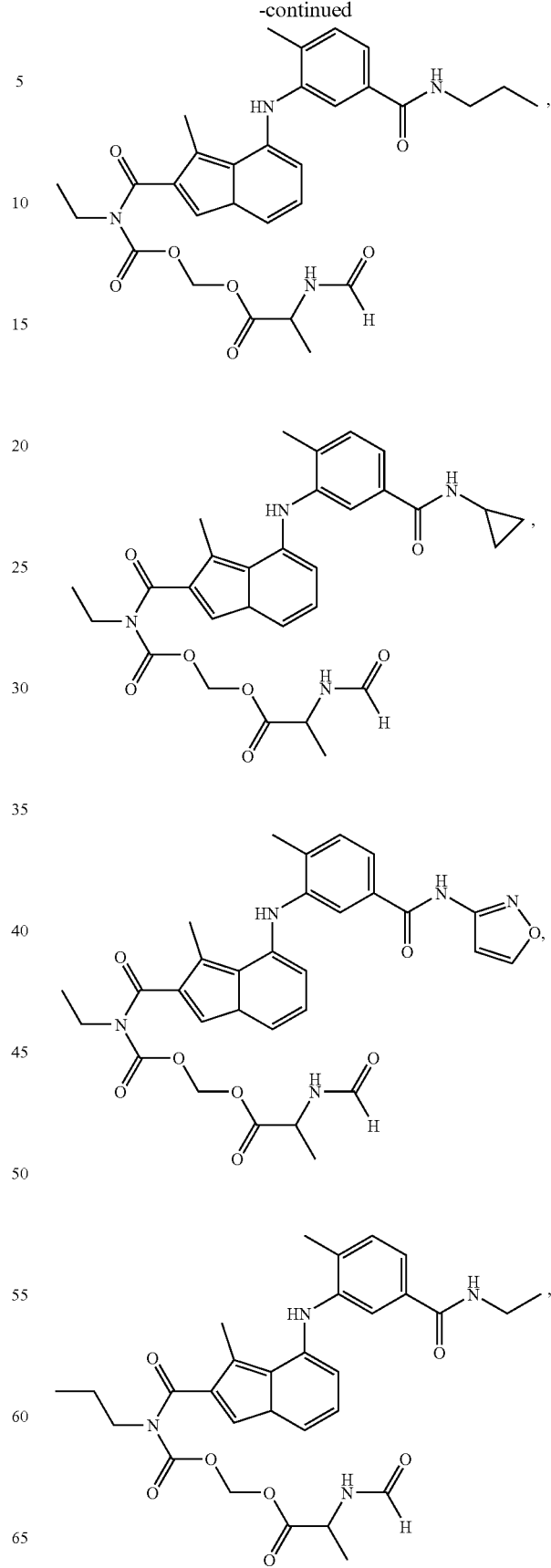

311
-continued
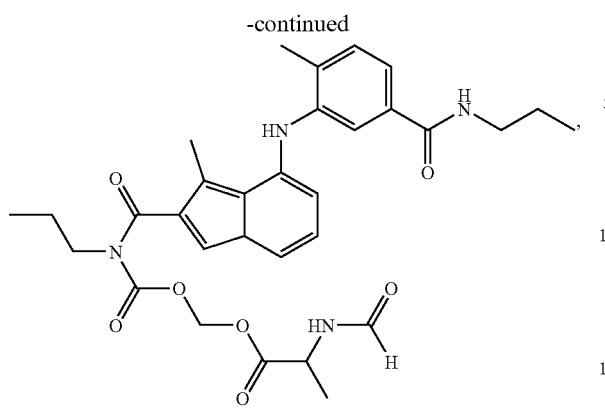
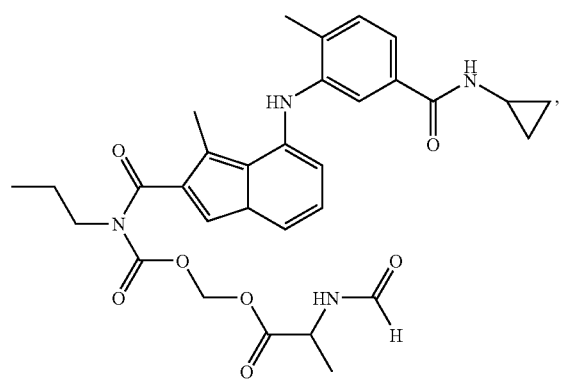
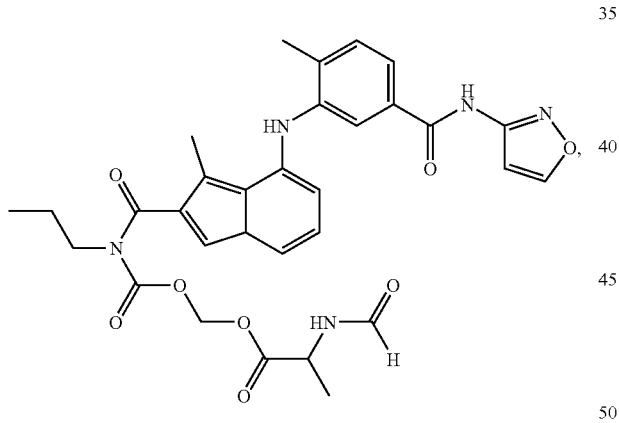
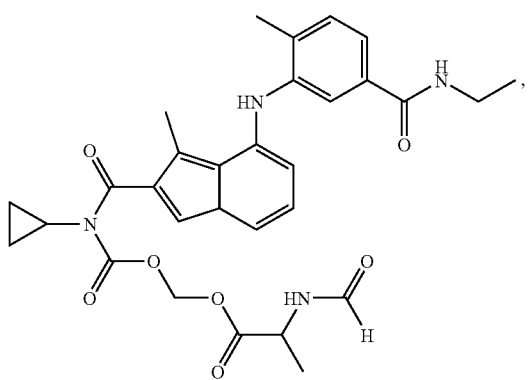
312
-continued
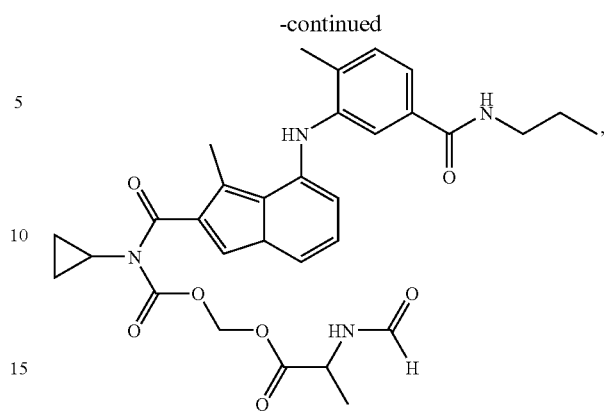
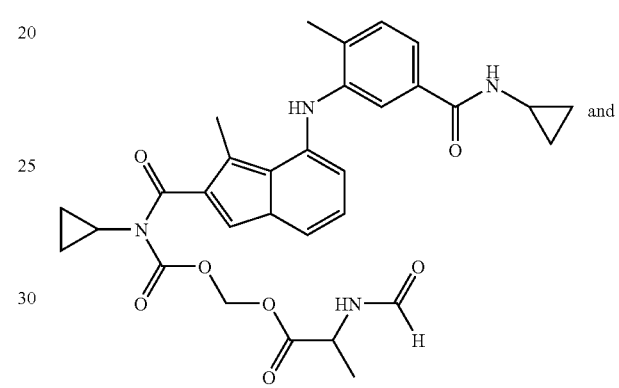
and
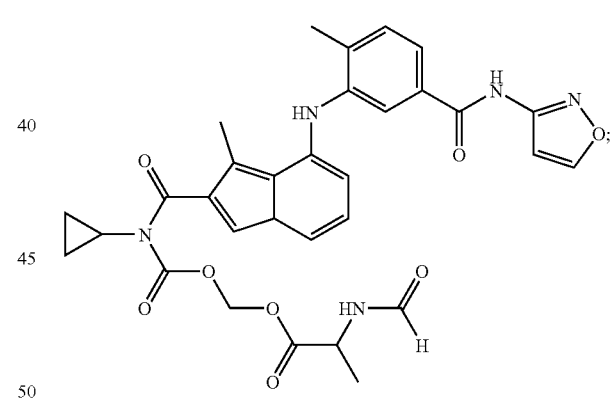
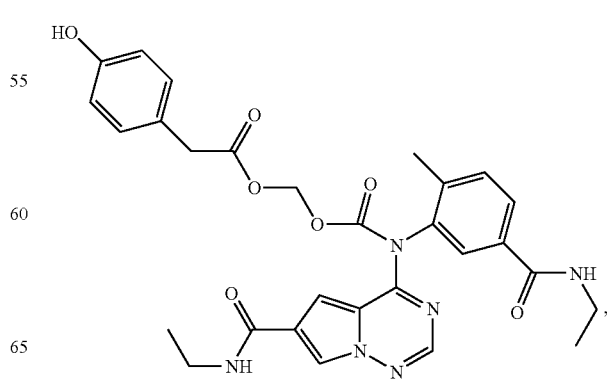

313
-continued
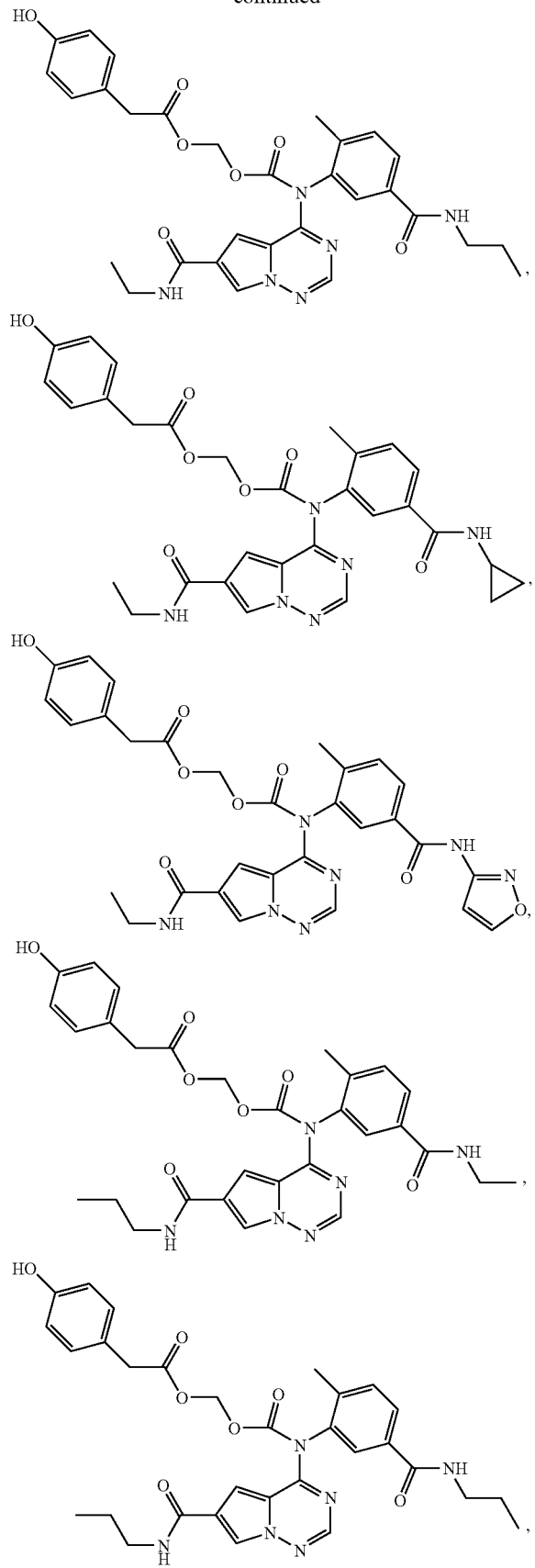
314
-continued
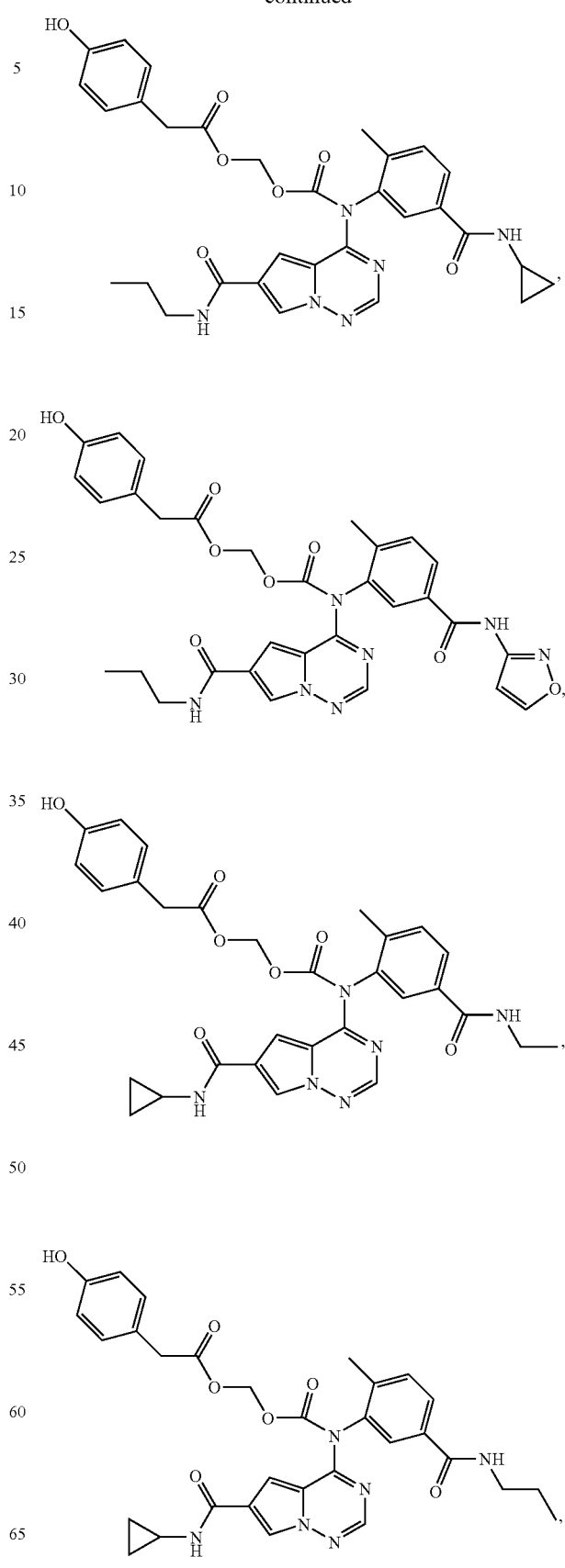

315
-continued
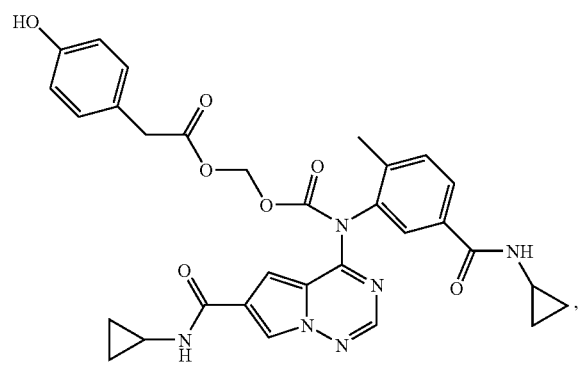
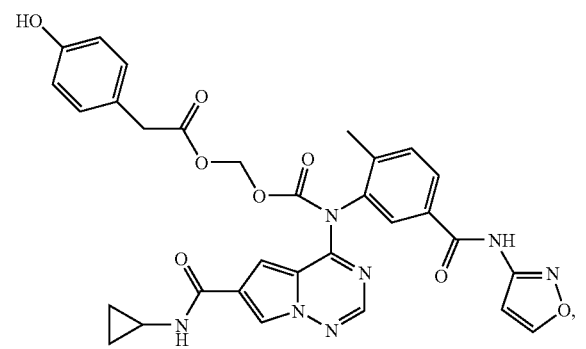
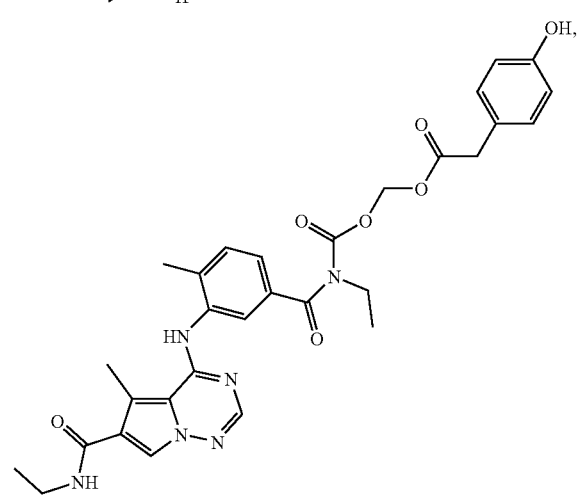
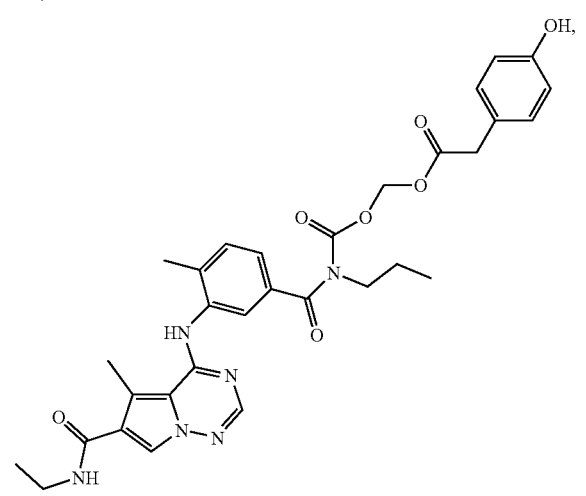
316
-continued
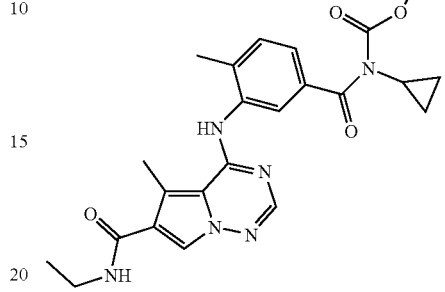
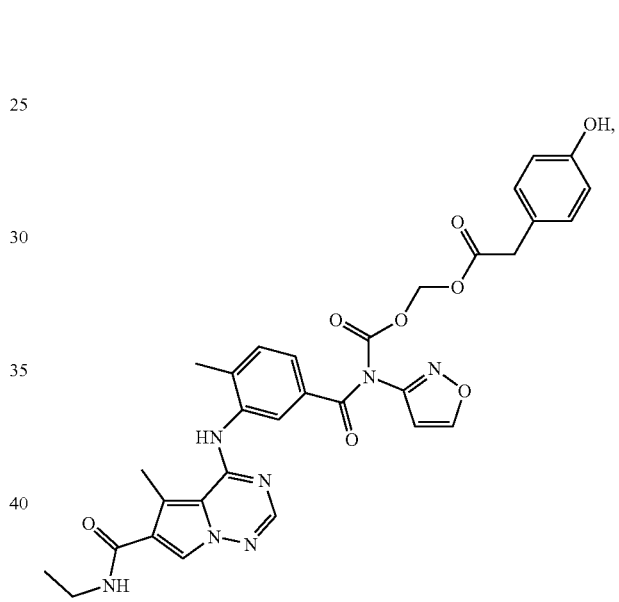
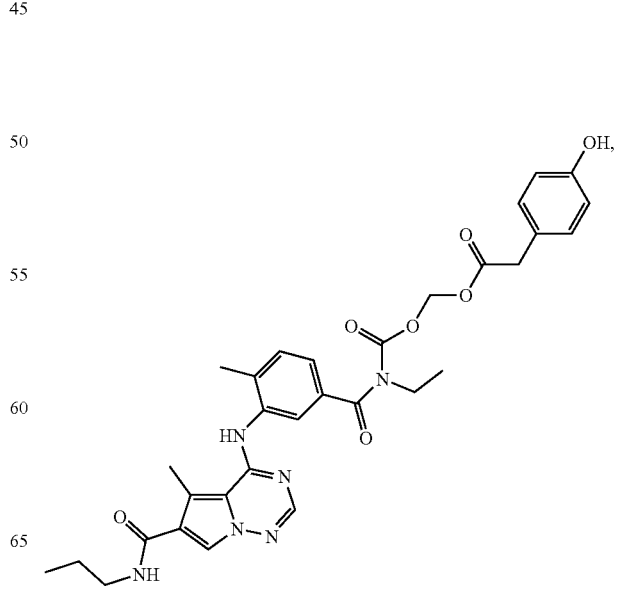

317 318
-continued -continued
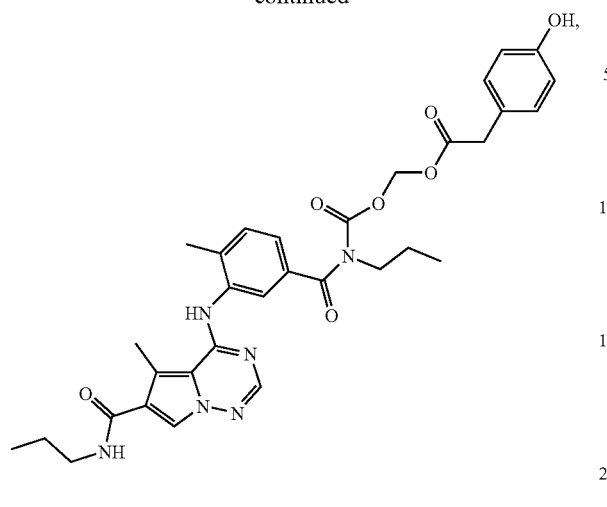
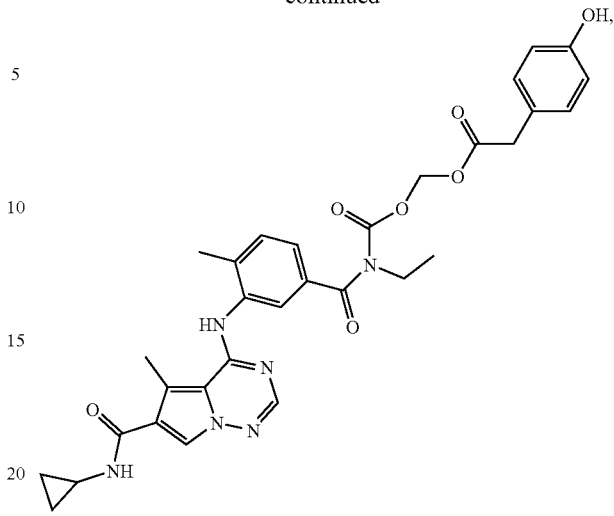
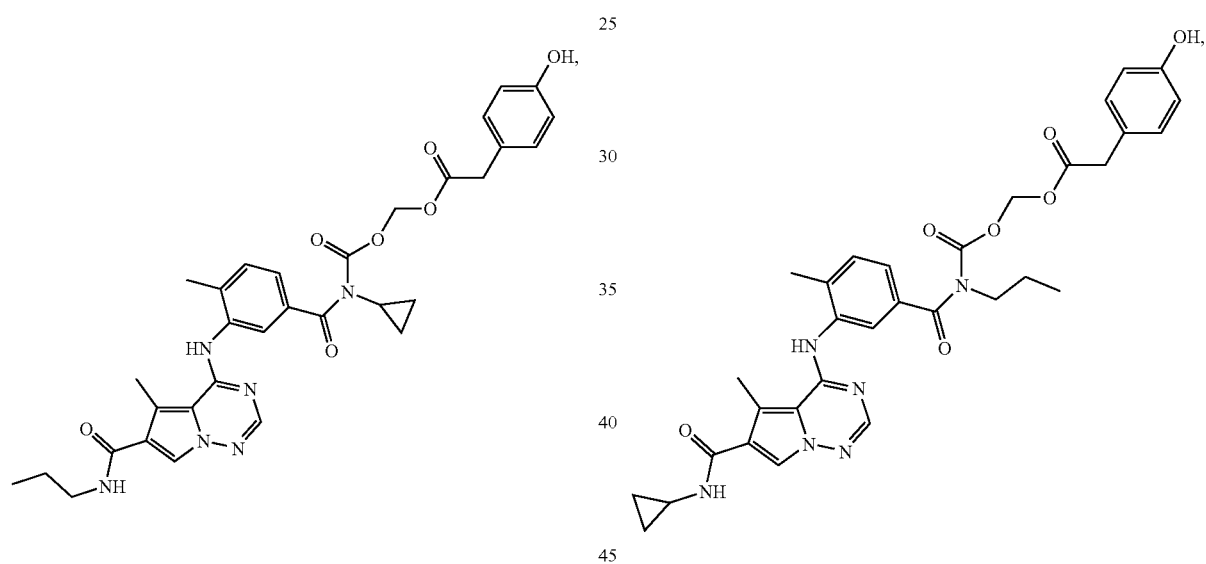
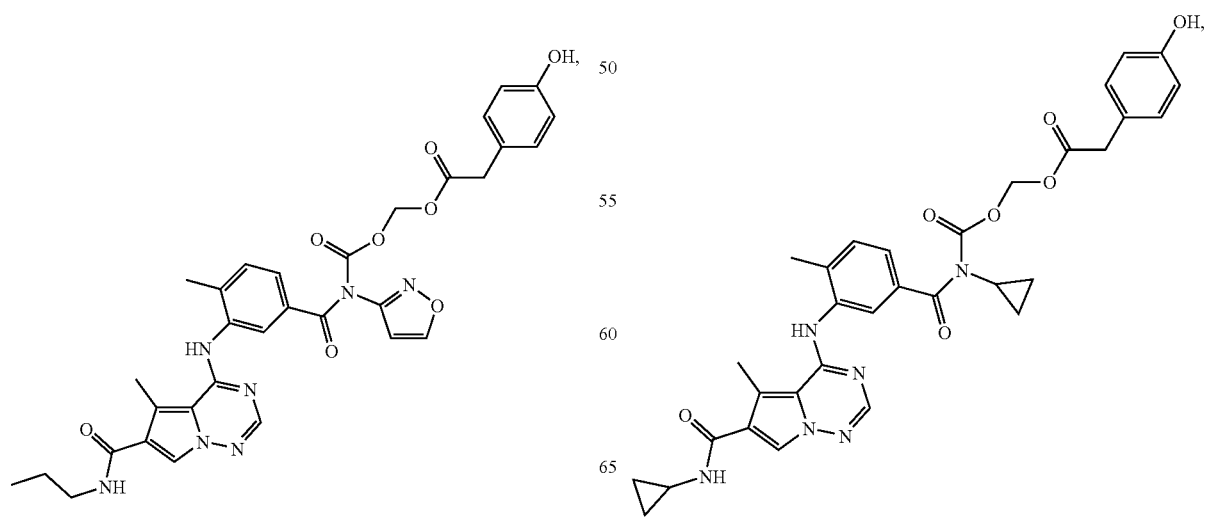

319
-continued
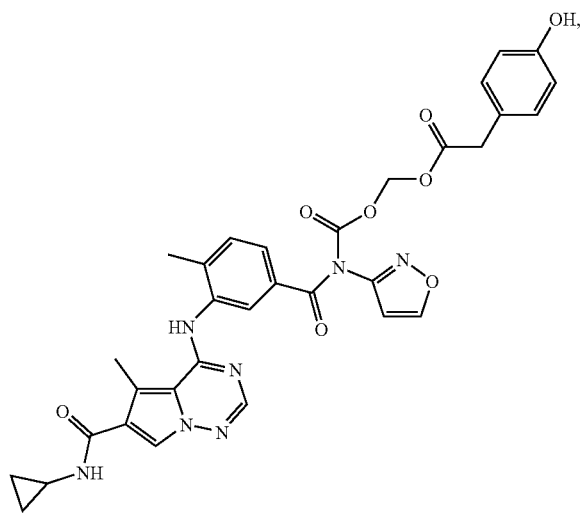
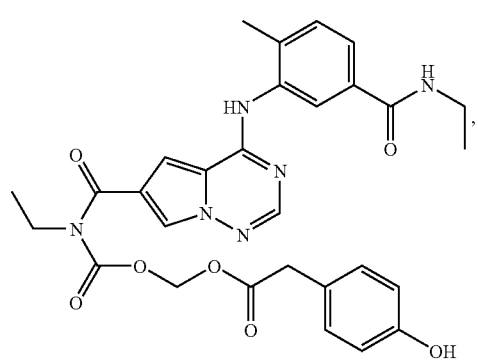
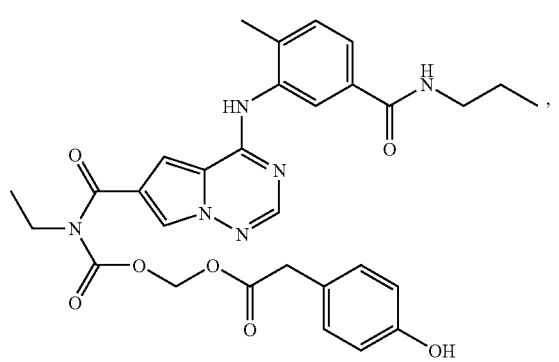
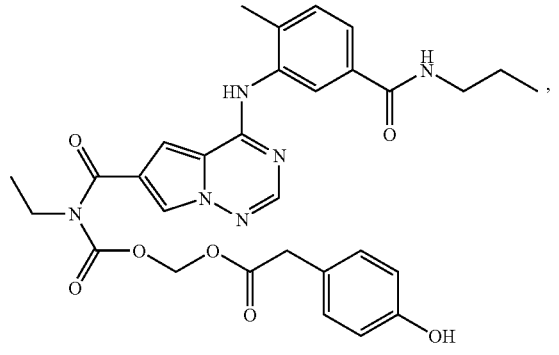
320
-continued
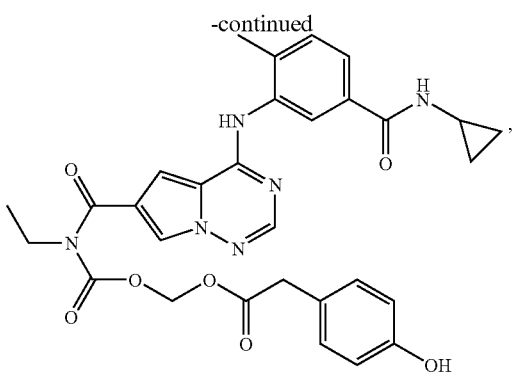
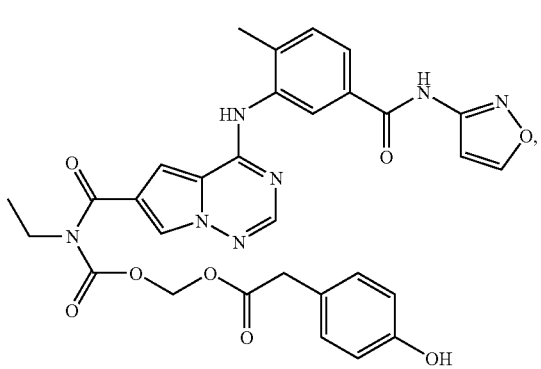
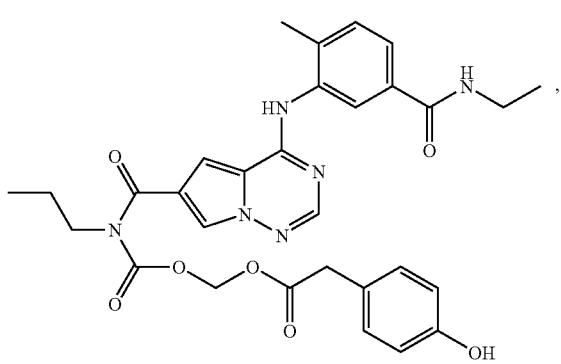
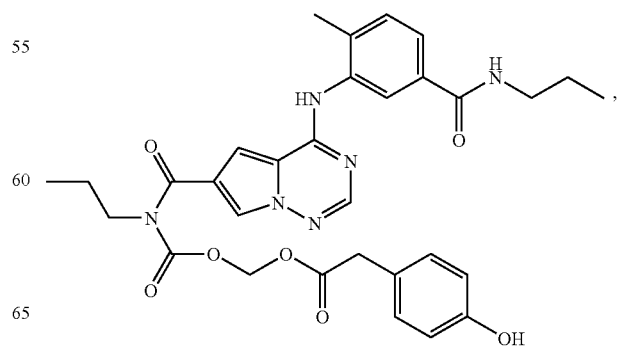

321
-continued
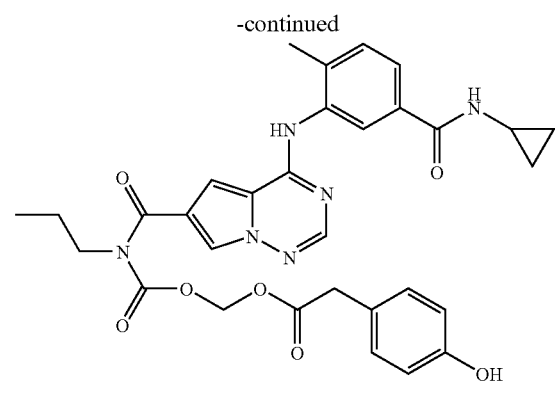
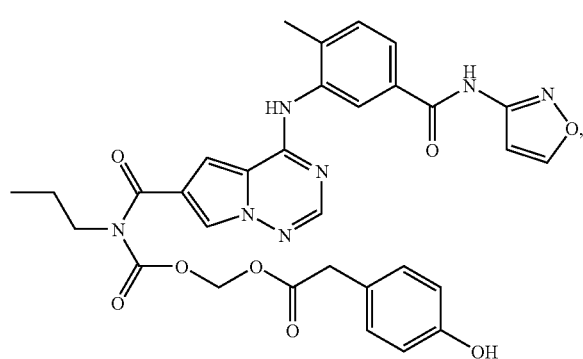
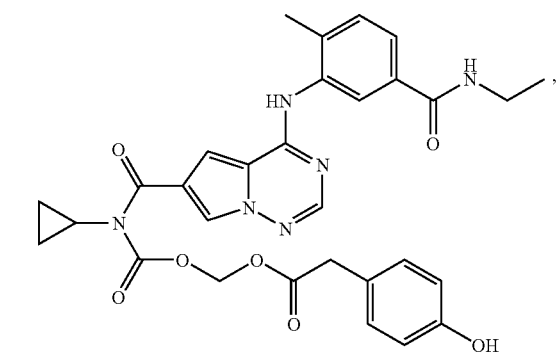
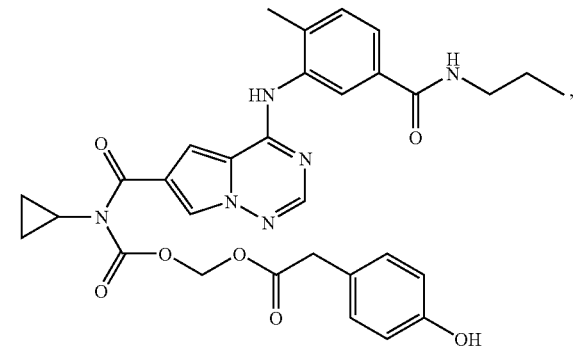
322
-continued
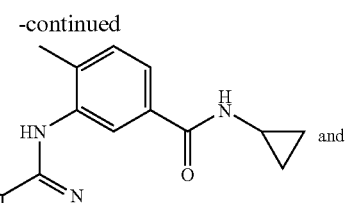
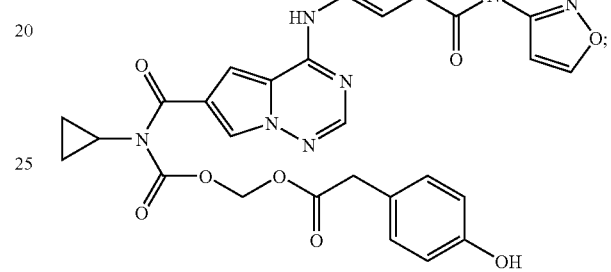
and
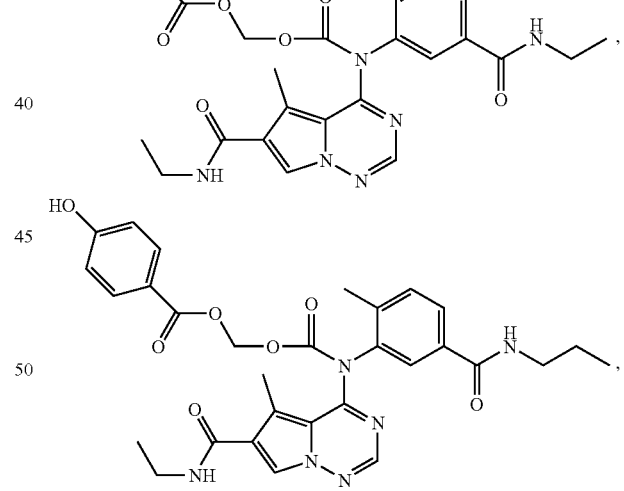

323
-continued
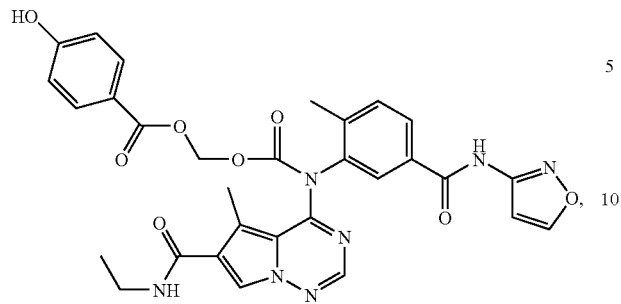
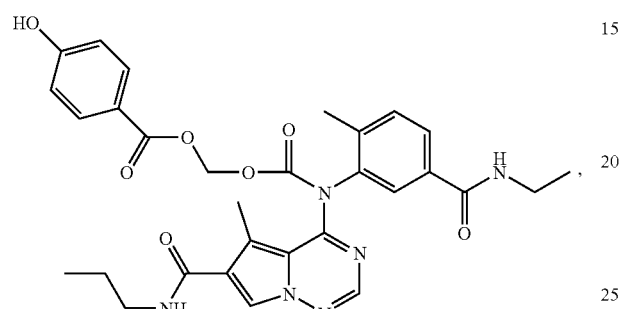
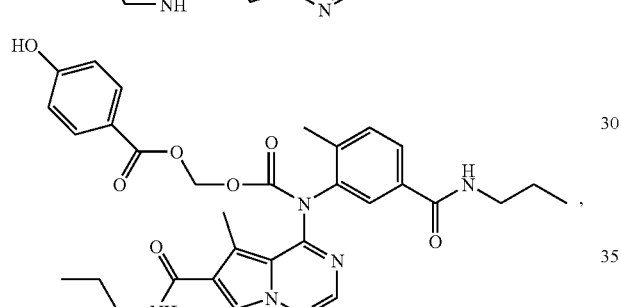
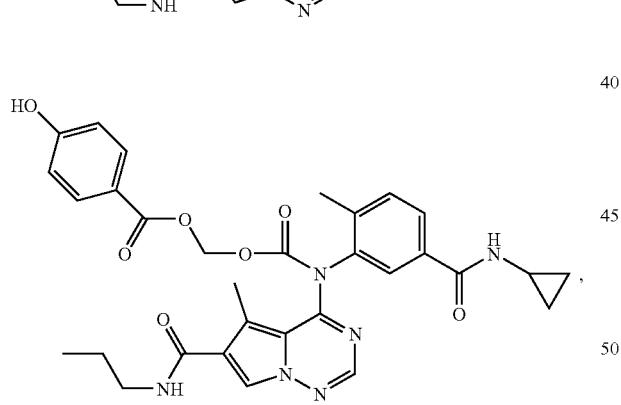
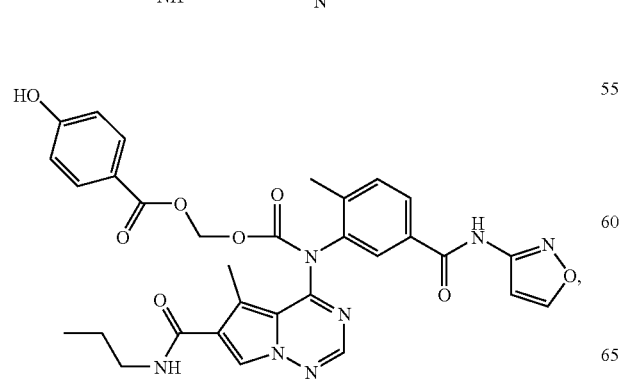
324
-continued
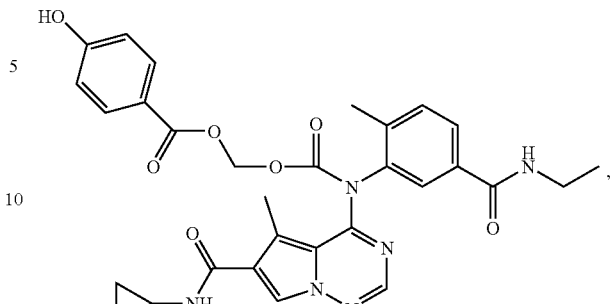
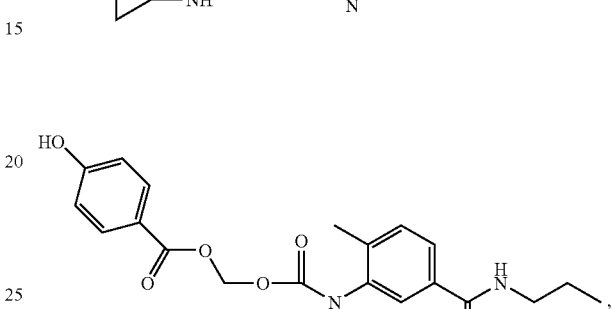
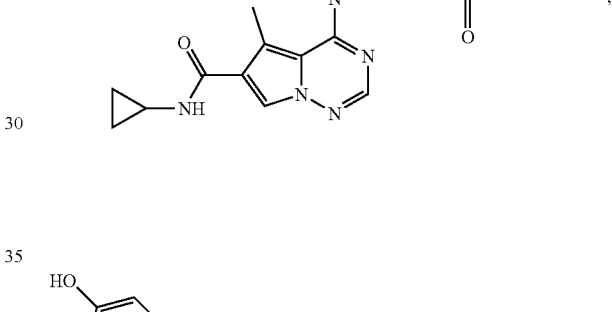
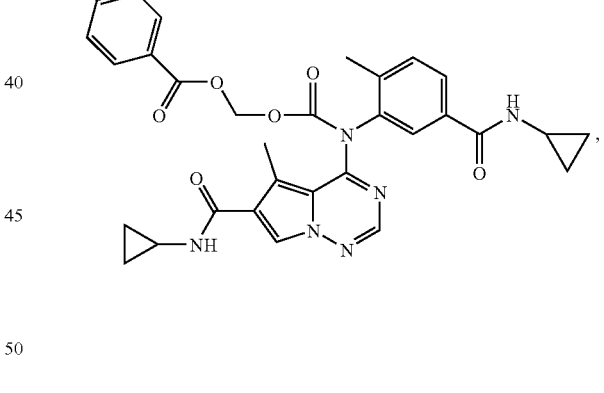
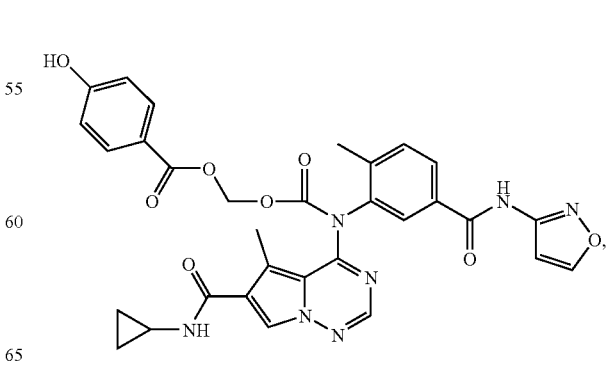

325
-continued
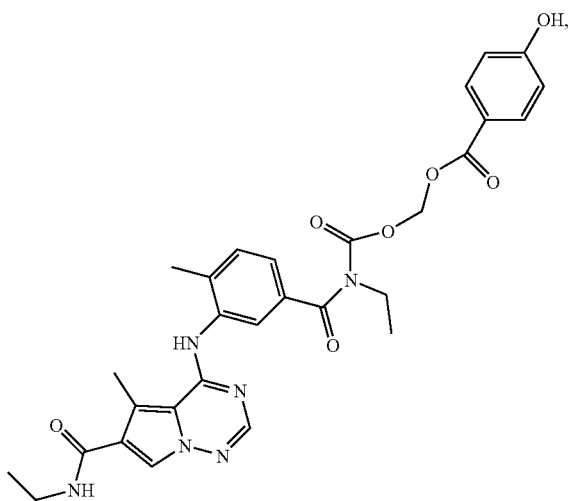
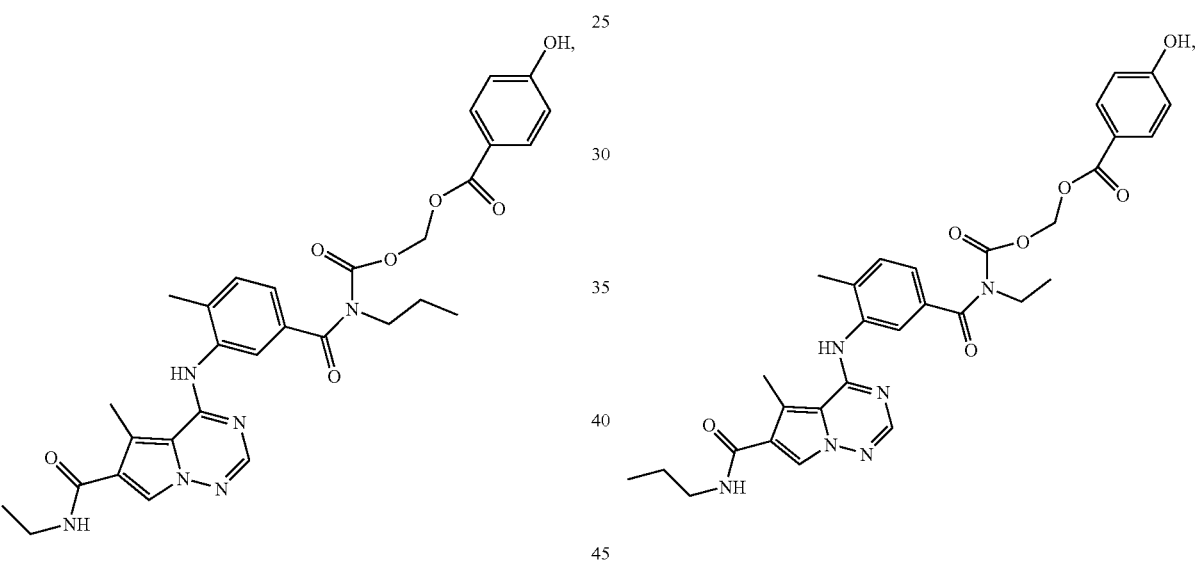
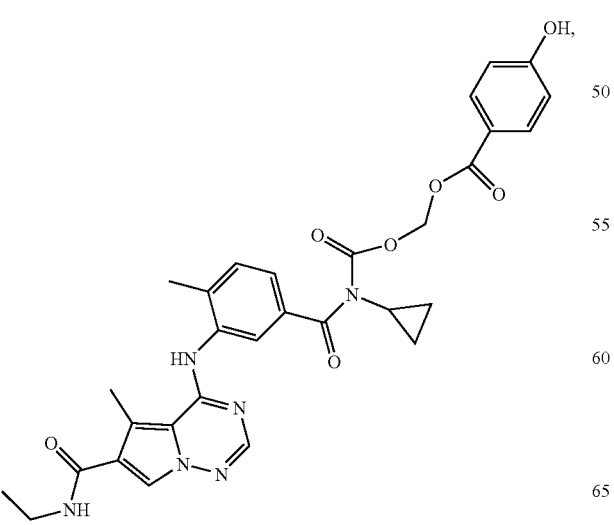
326
-continued
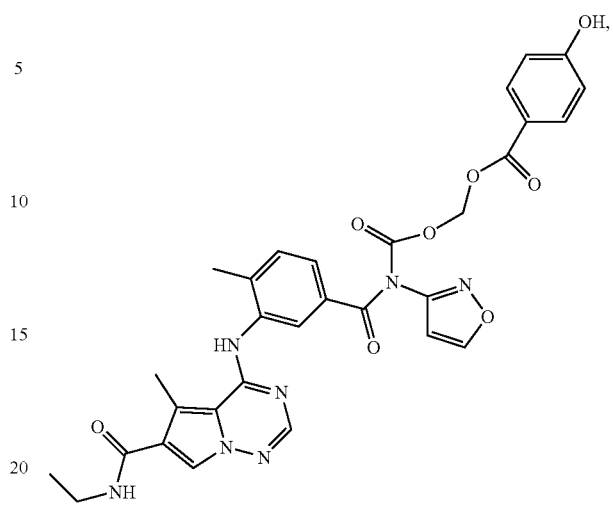
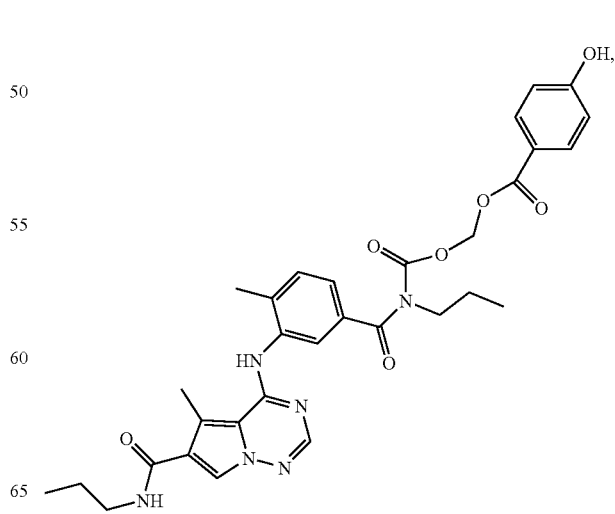

327
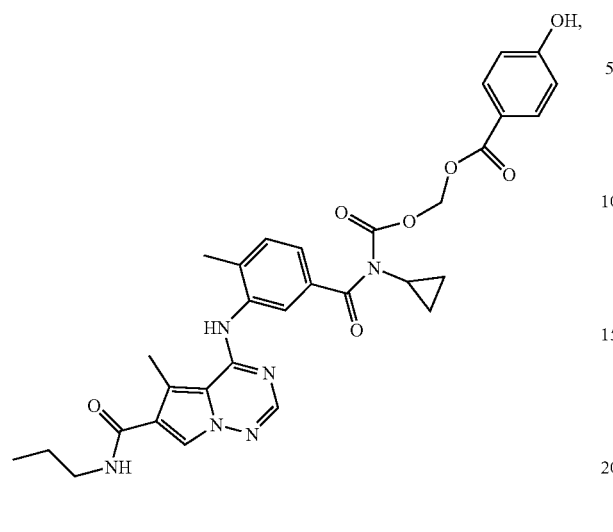
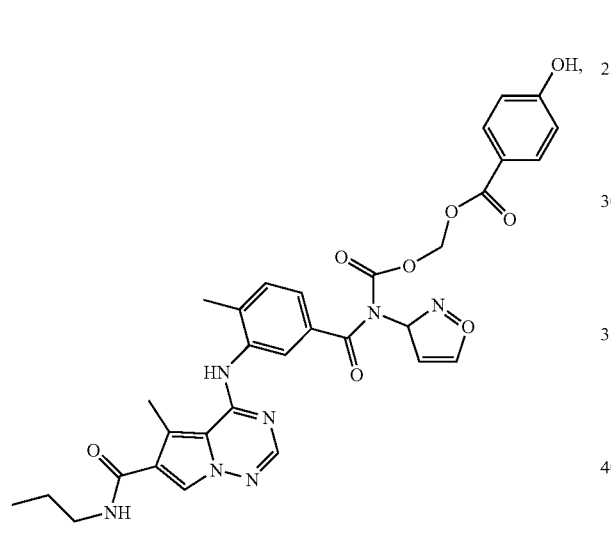
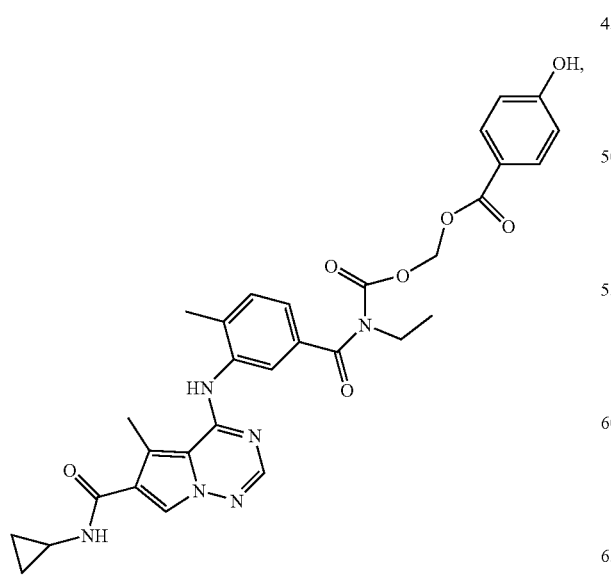
328
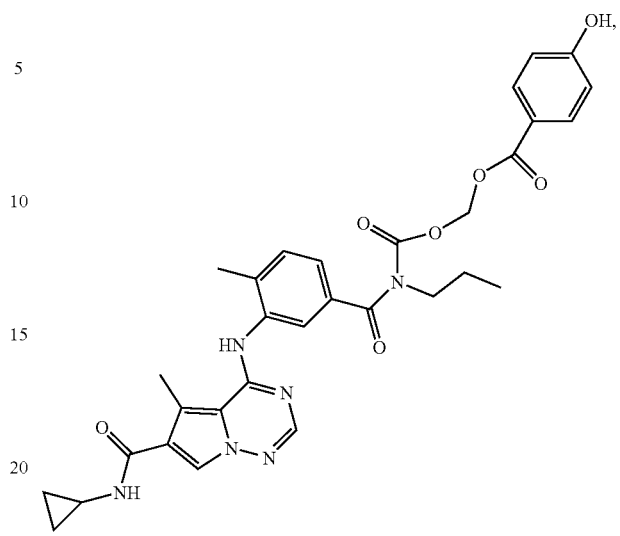
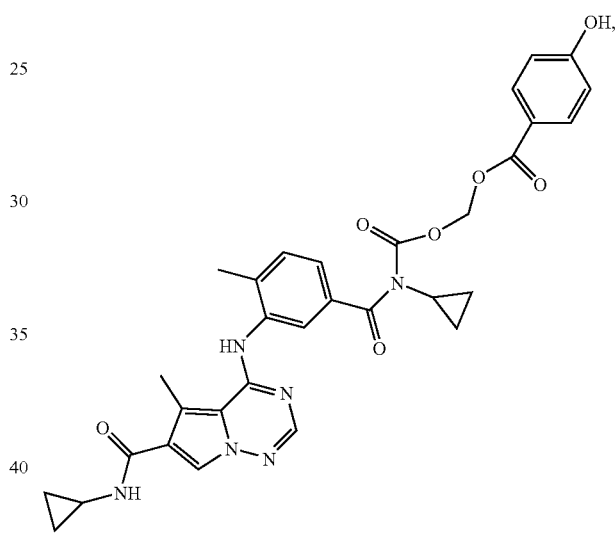
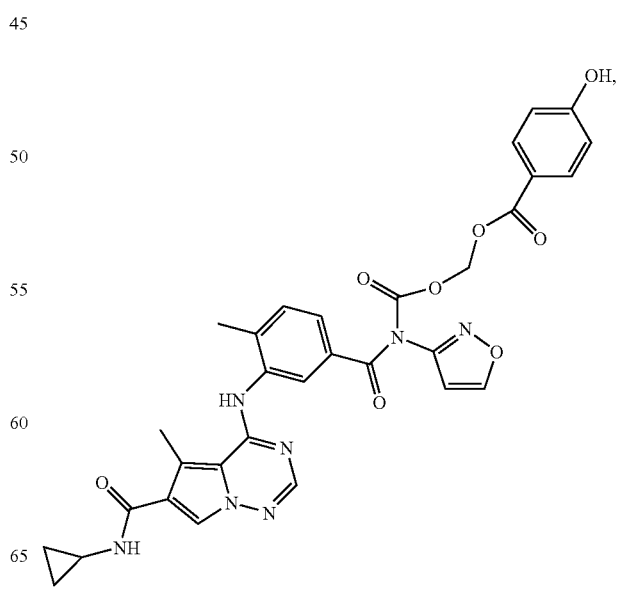

329
-continued
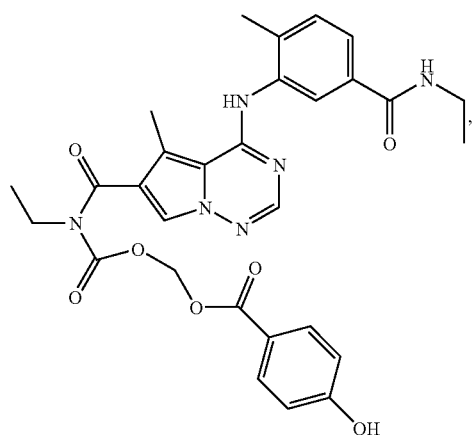
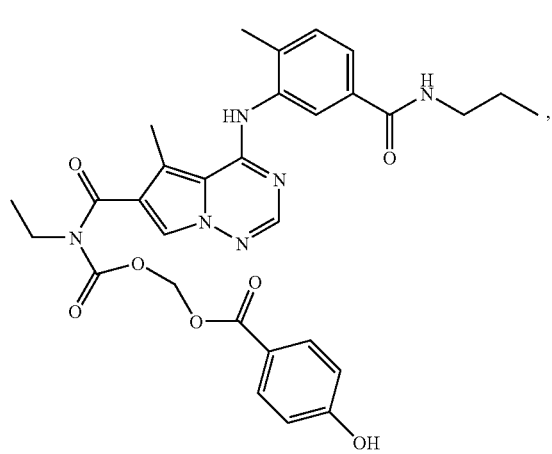
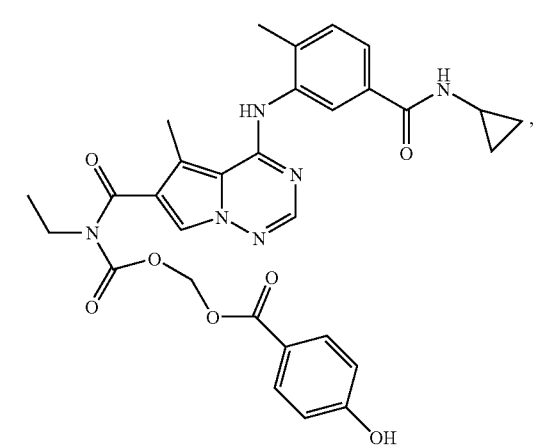
330
-continued
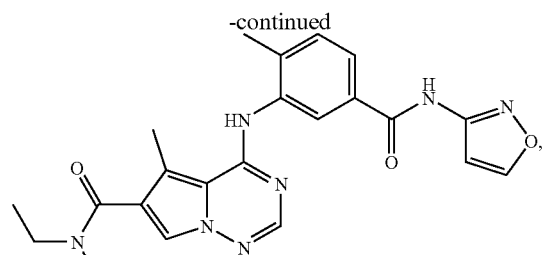
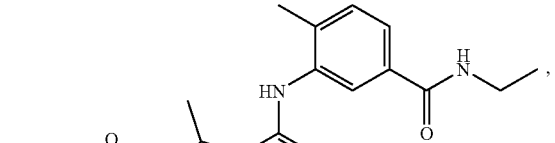
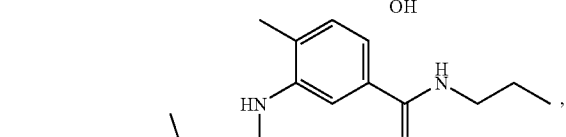
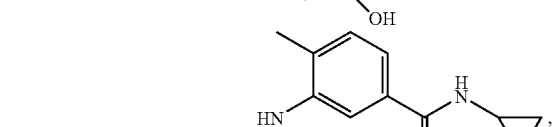
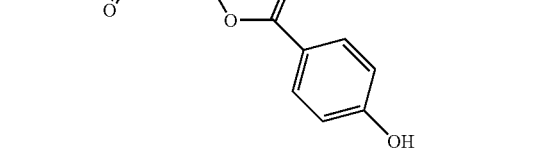

331
-continued
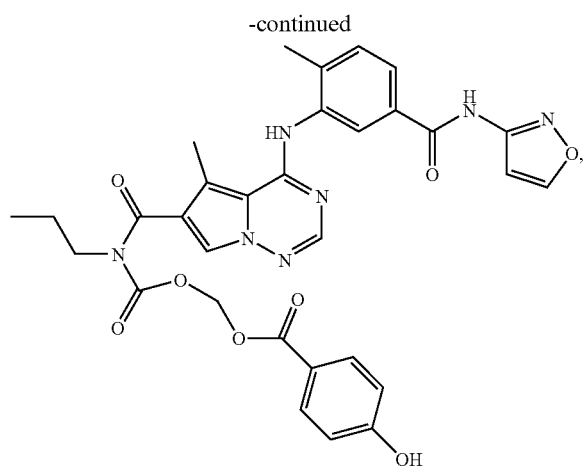
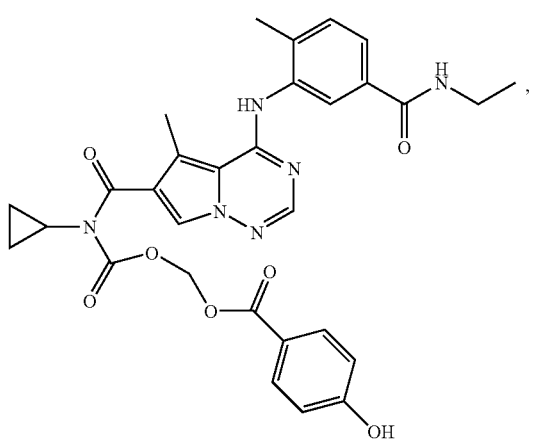
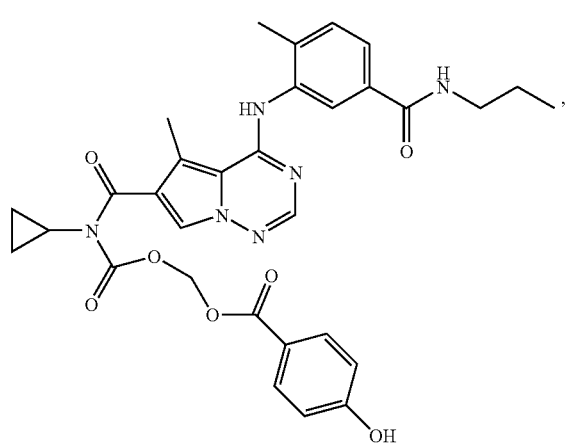
332
-continued
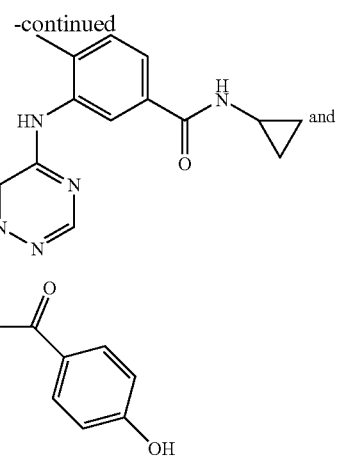
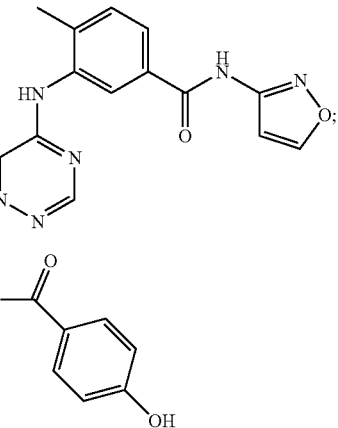
or a pharmaceutically-acceptable salt of any of the foregoing.
18. A compound according to claim 17 having the formula selected from the group consisting of:
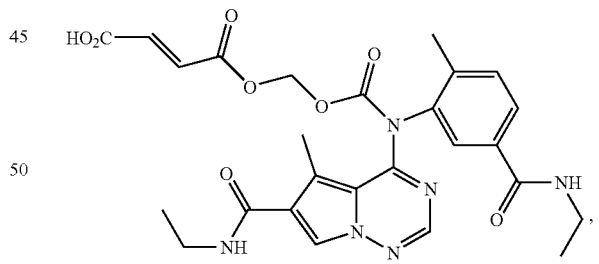
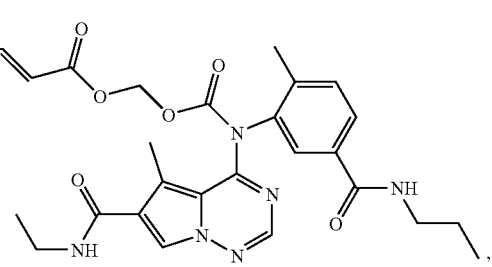

333
-continued
334
-continued
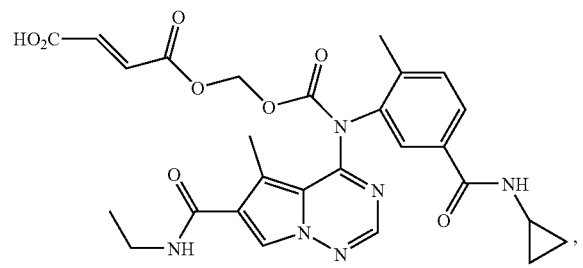
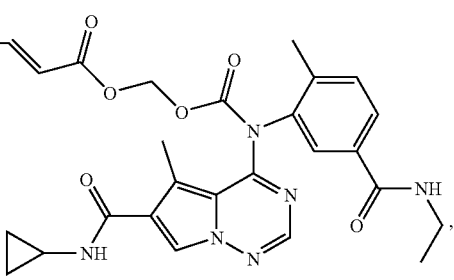

-continued
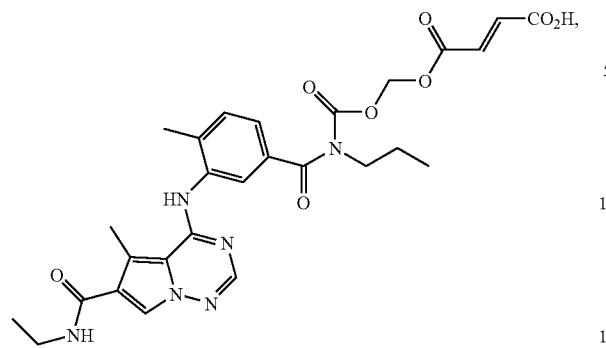
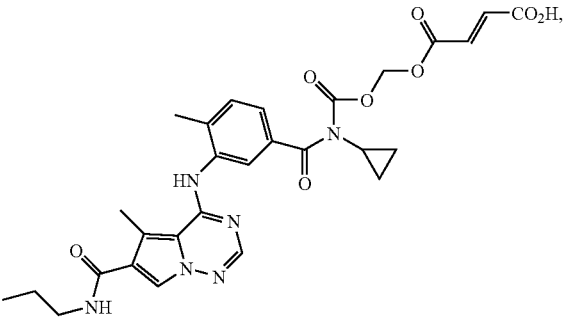

337
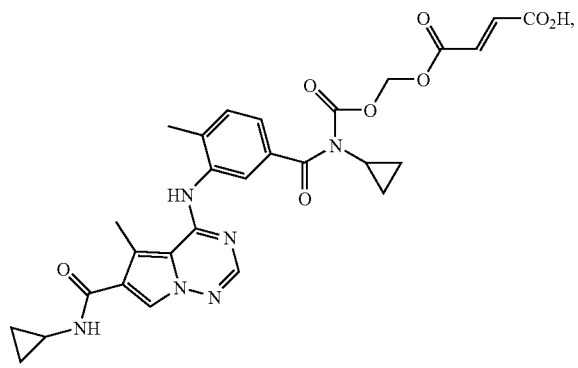
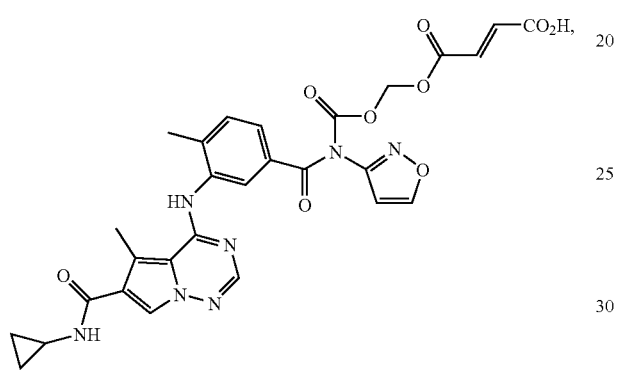
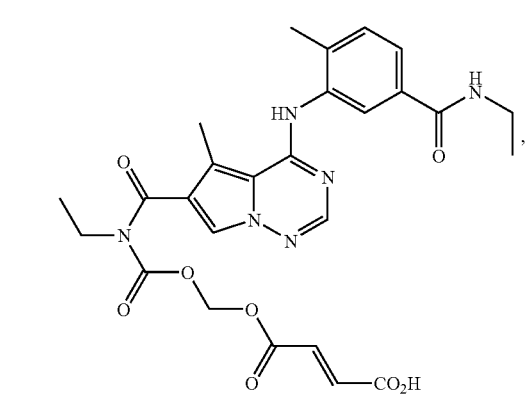
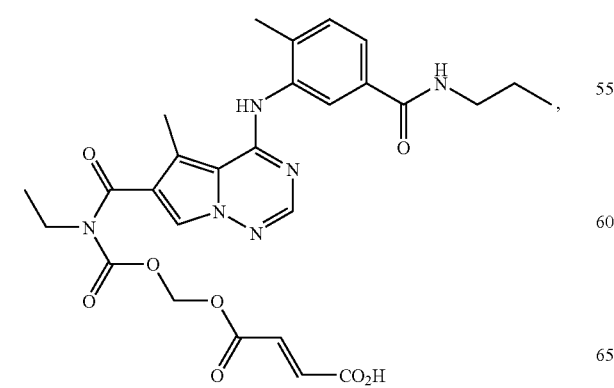
338
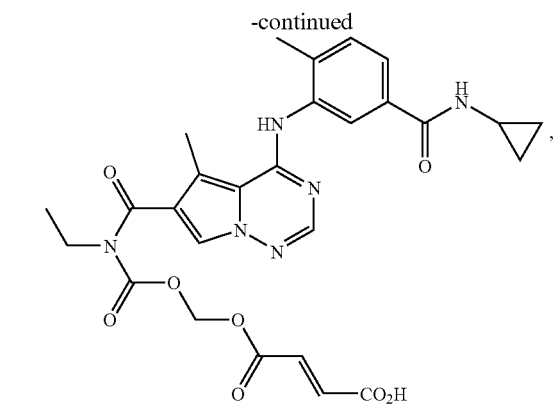
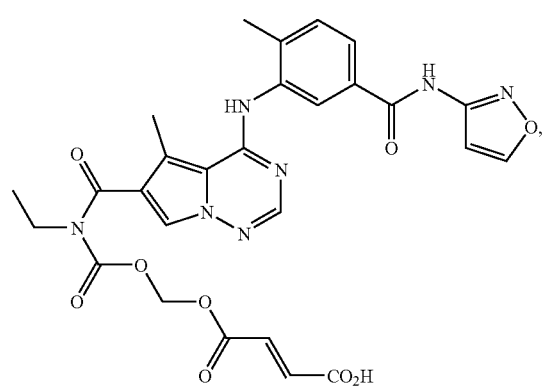
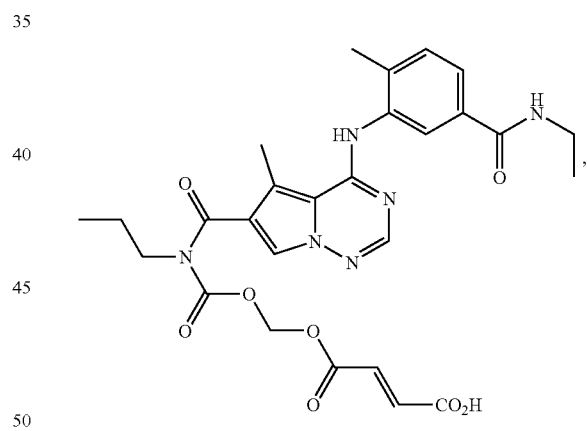
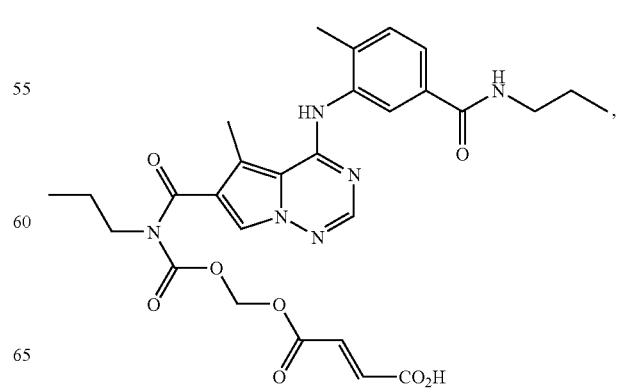

-continued
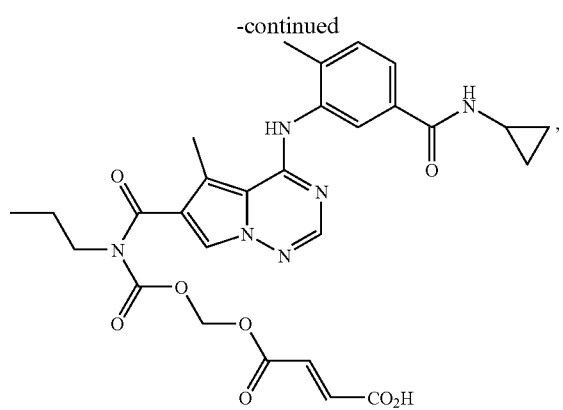
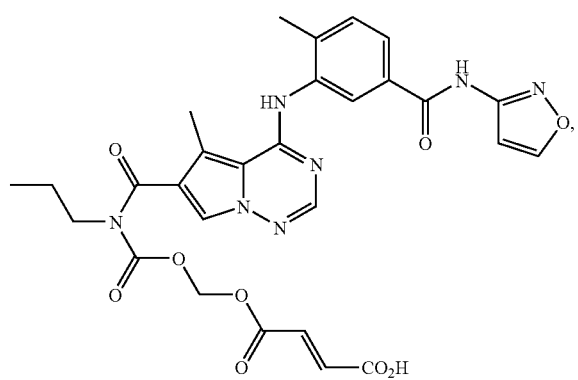
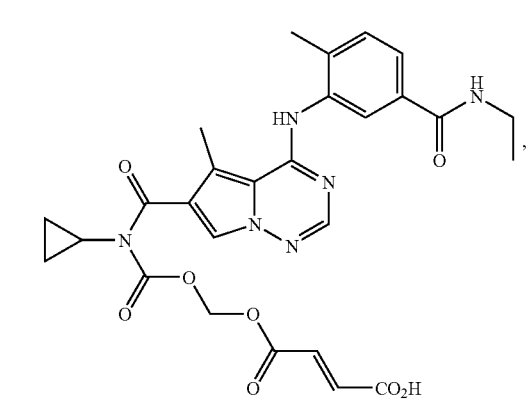
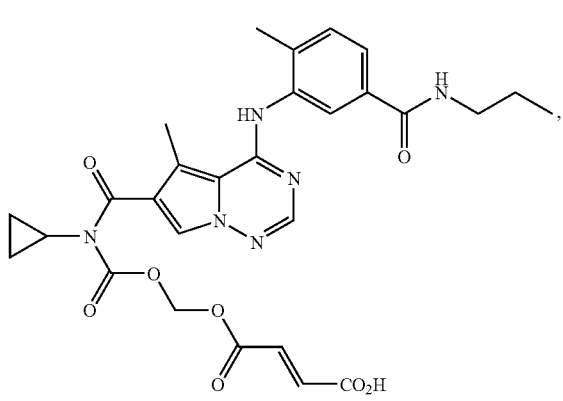
-continued
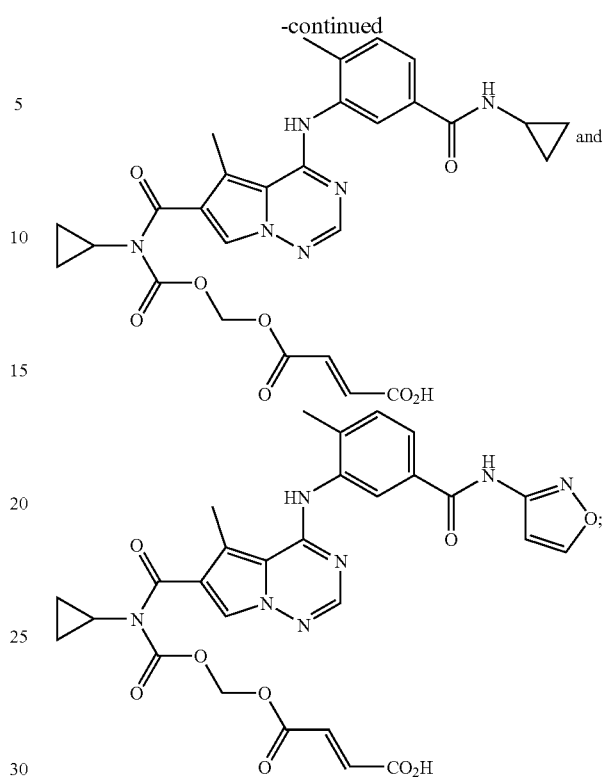
or a pharmaceutically-acceptable salt of any of the foregoing.
19. A compound according to claim 17 having the formula selected from the group consisting of:
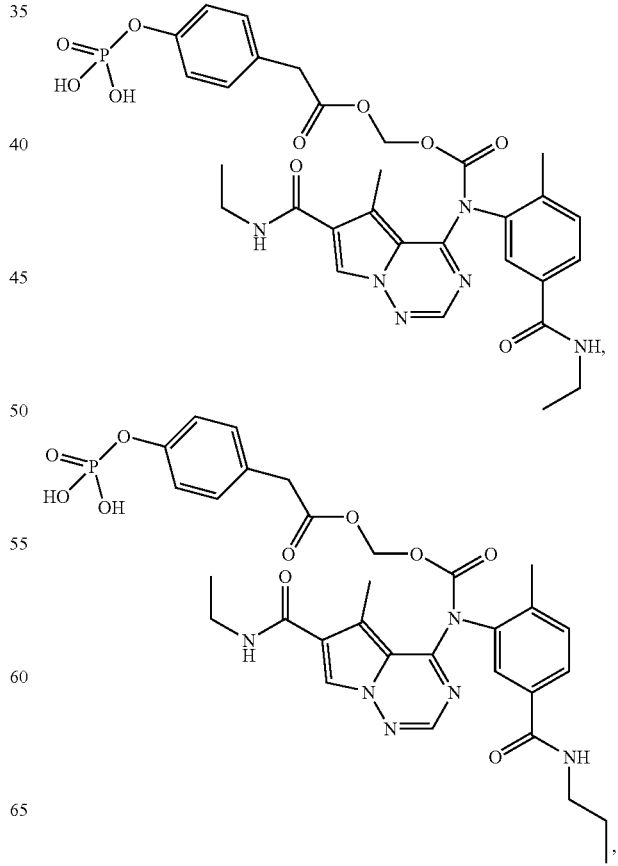

341
-continued
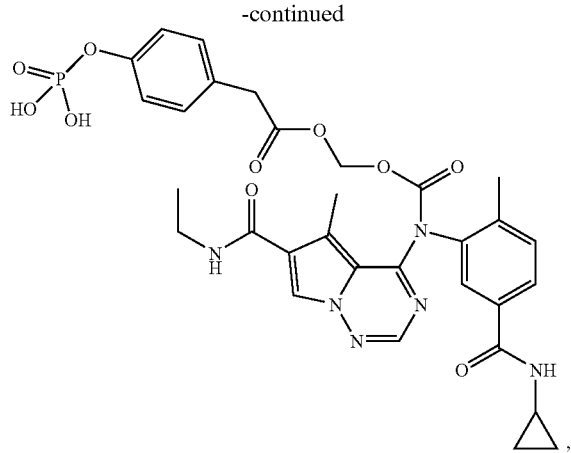
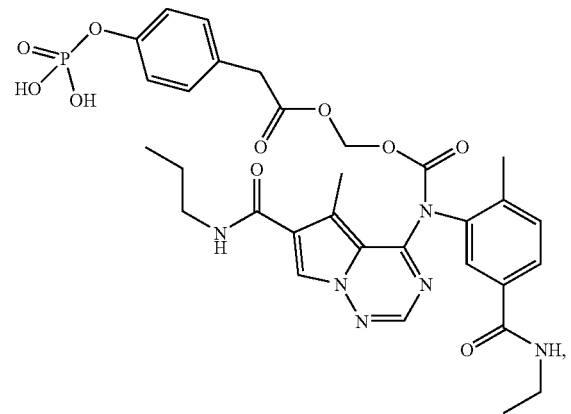
342
-continued
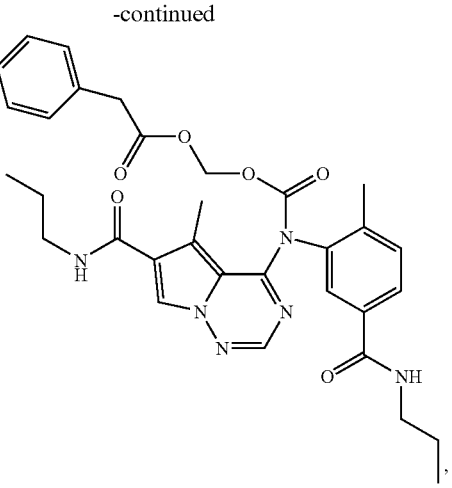
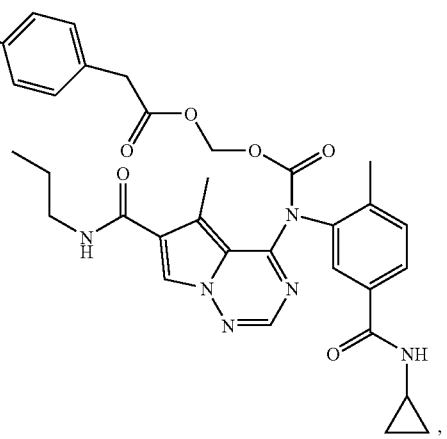
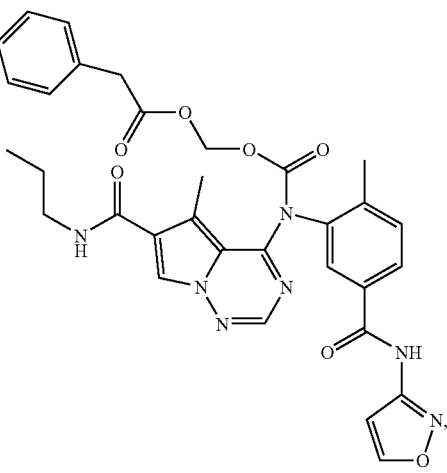

343
-continued
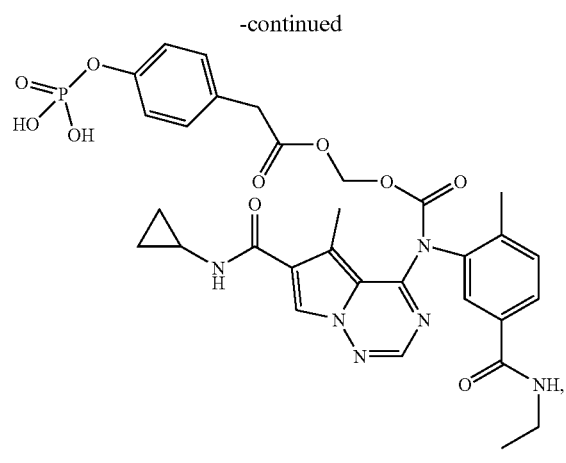
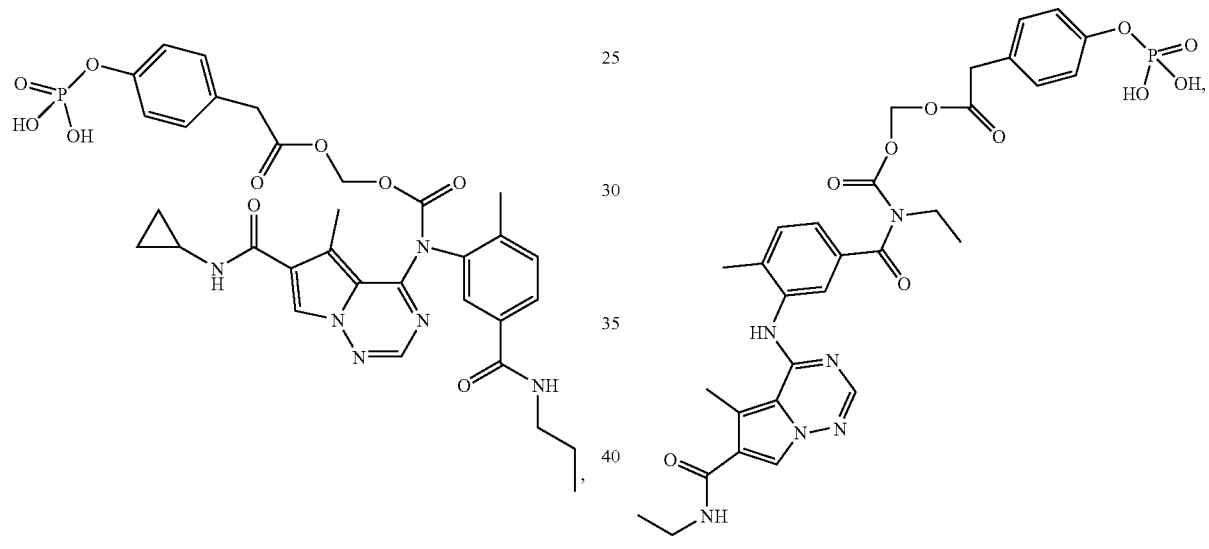
344
-continued
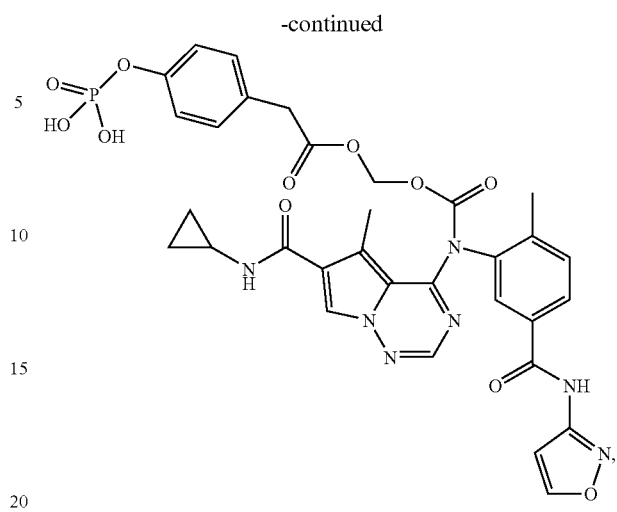
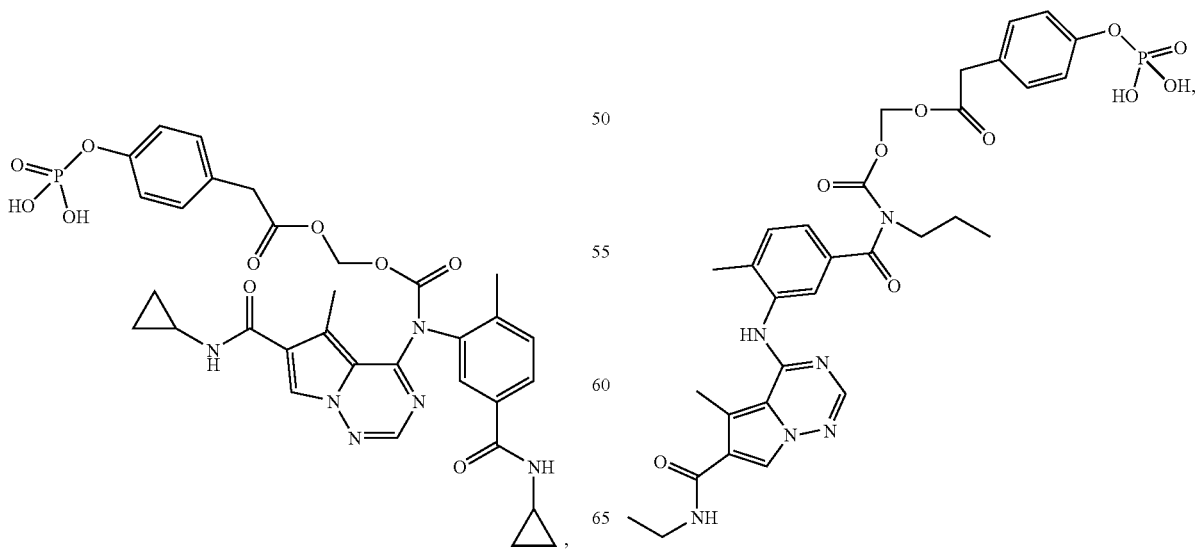

345
-continued
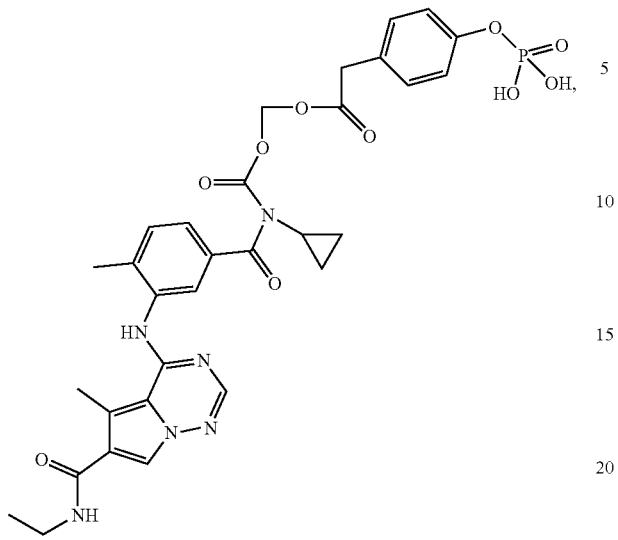
346
-continued
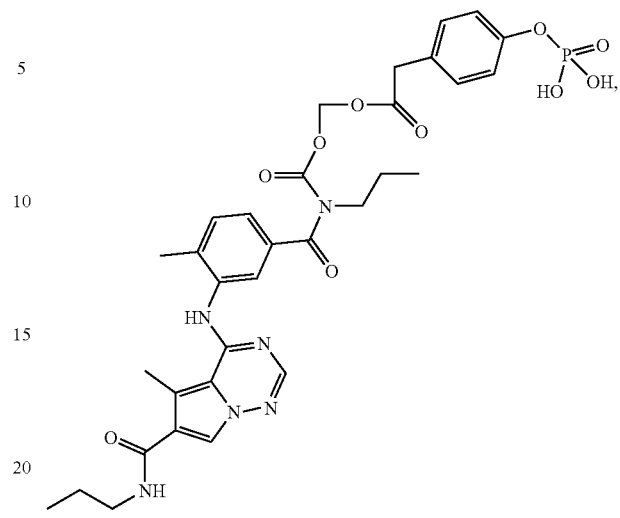
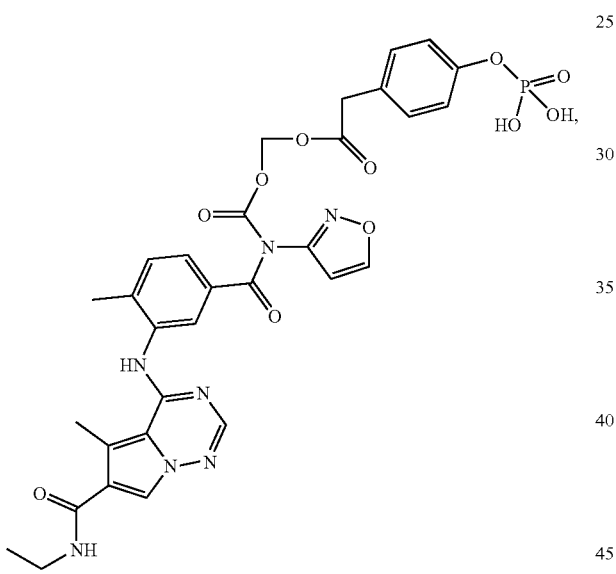
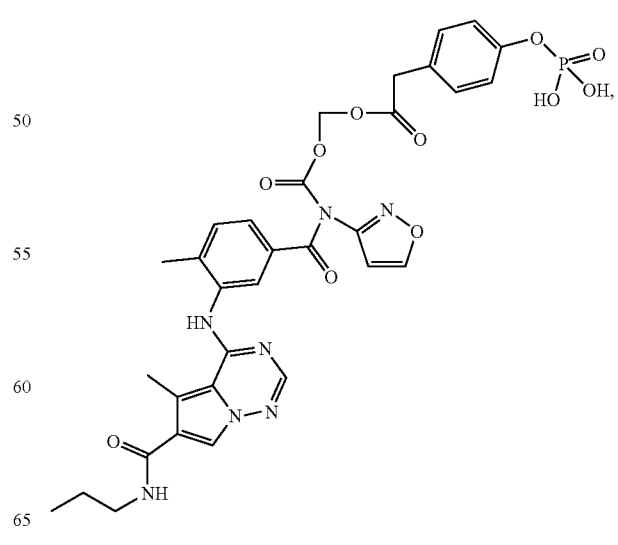

347
-continued
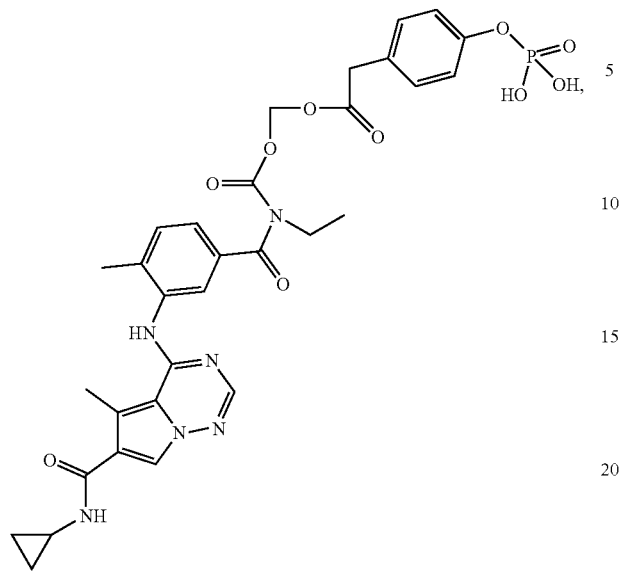
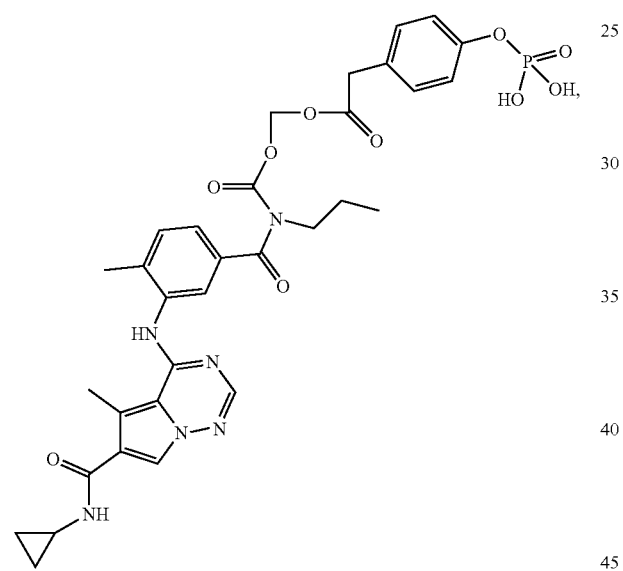
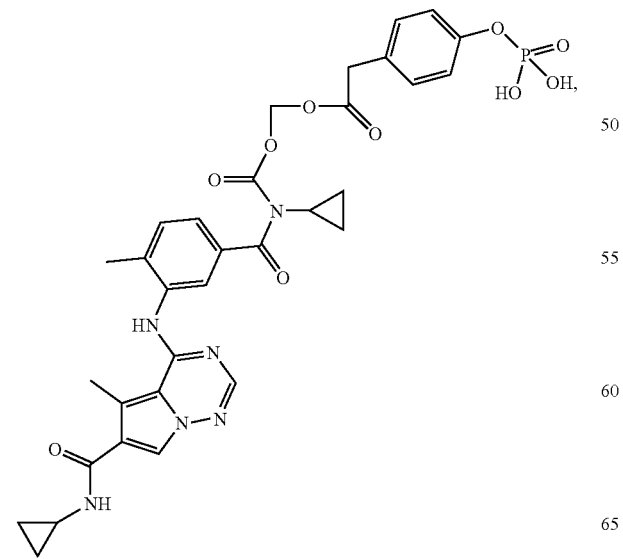
348
-continued
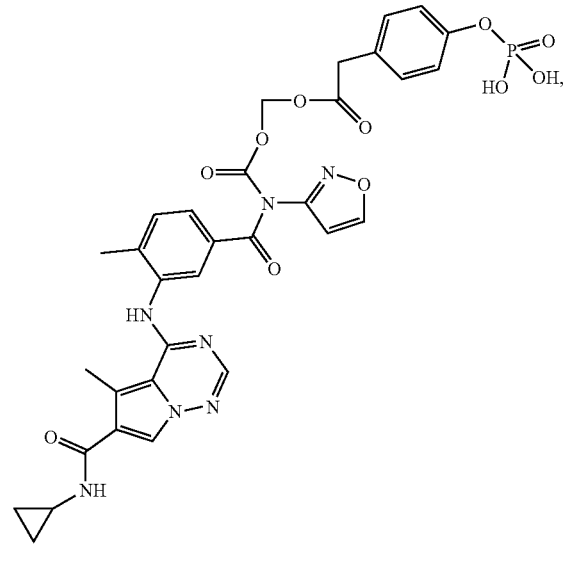
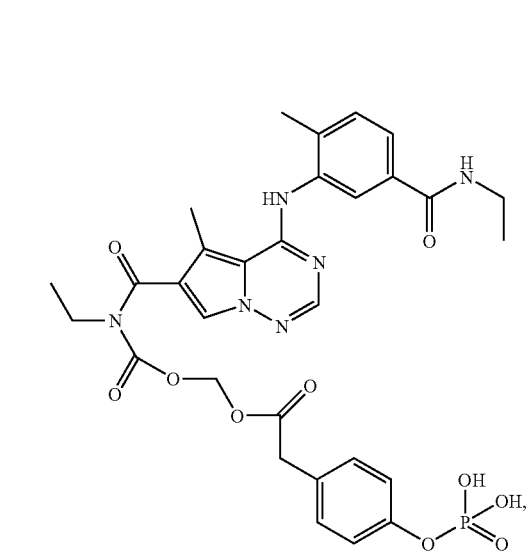
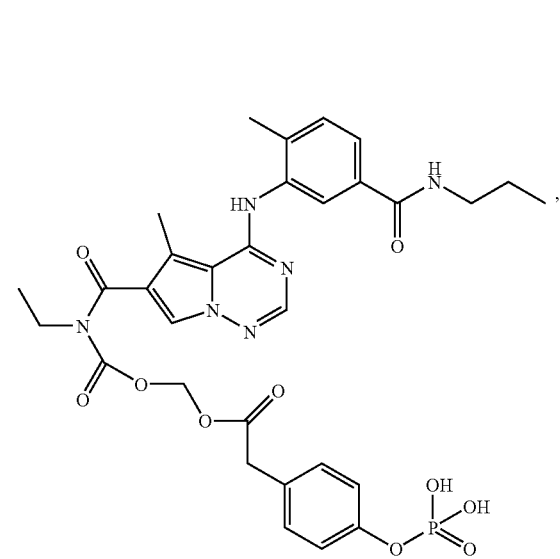

349
-continued
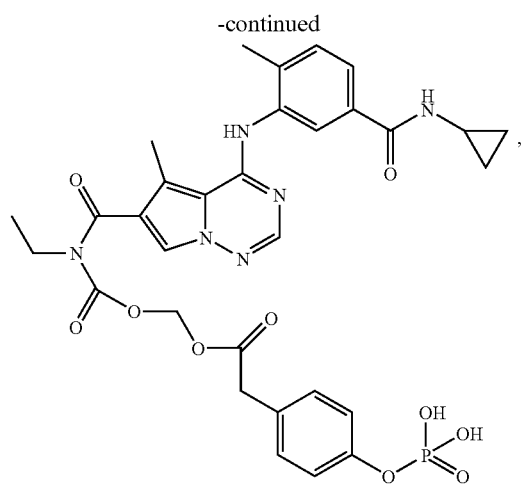
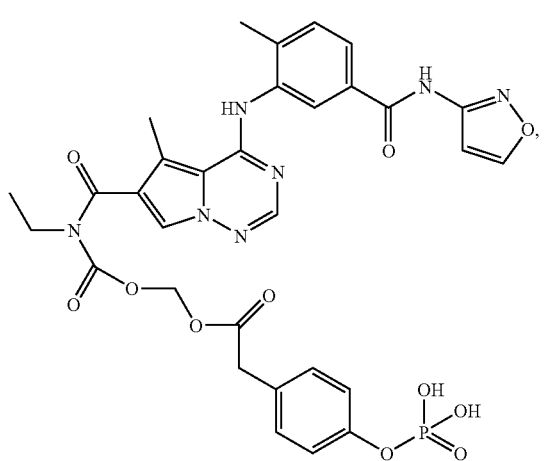
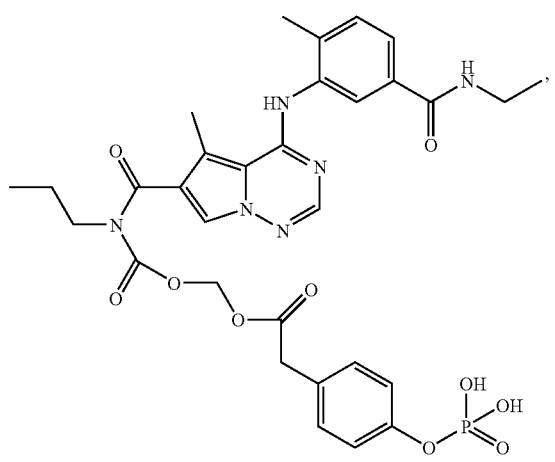
350
-continued
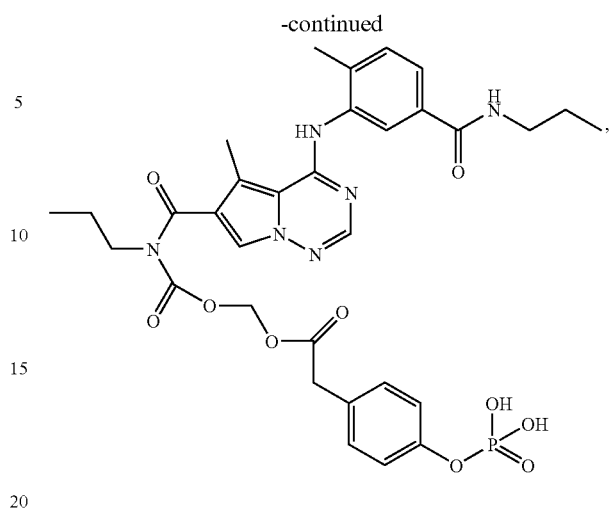
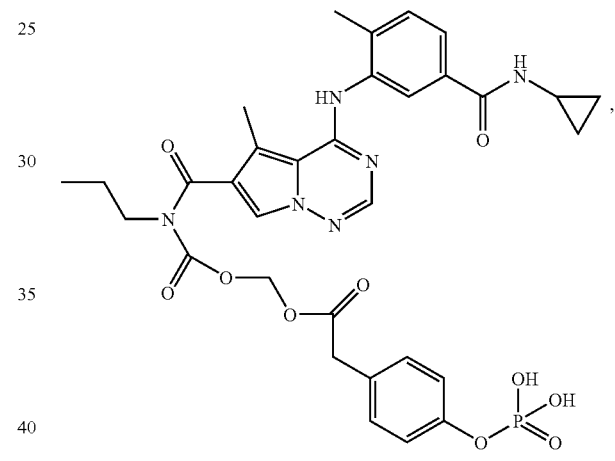
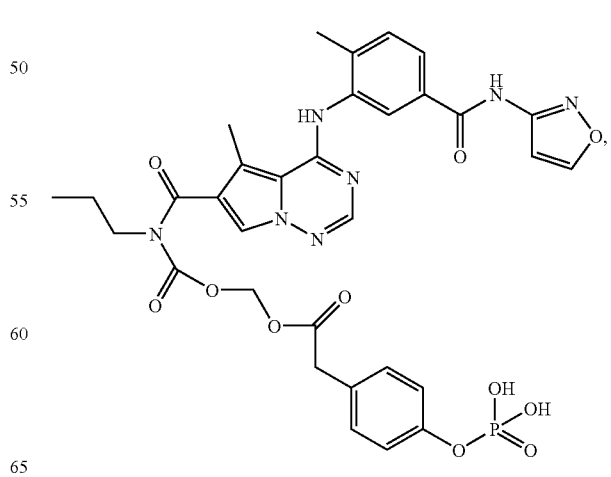

-continued
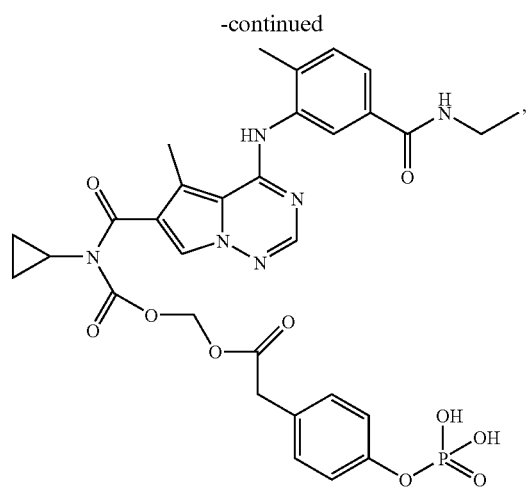
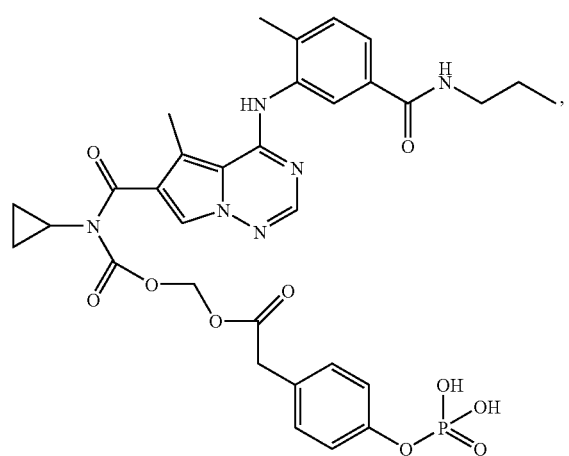
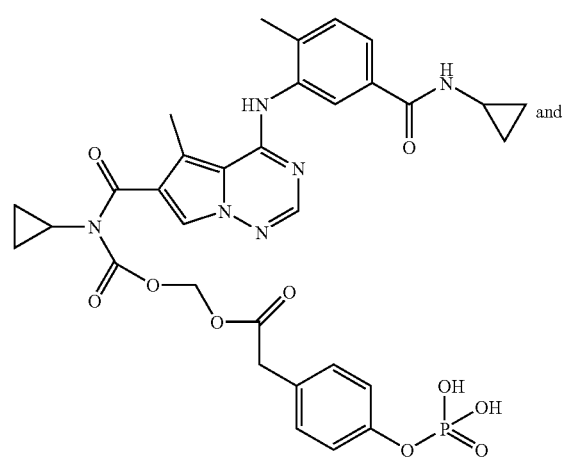
-continued
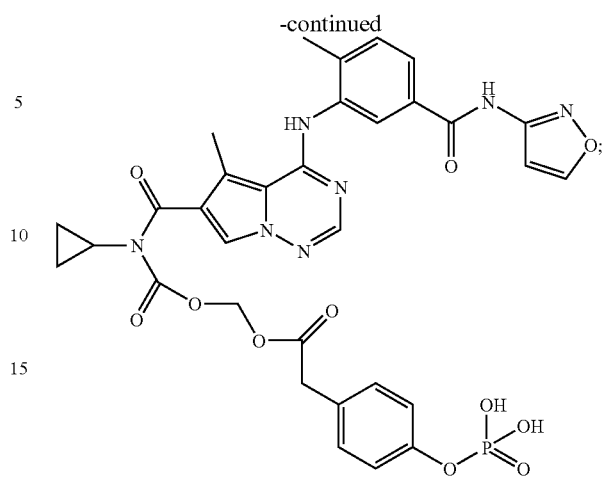
or a pharmaceutically-acceptable salt of any of the foregoing.
20. A compound according to claim 17 selected from the group consisting of:
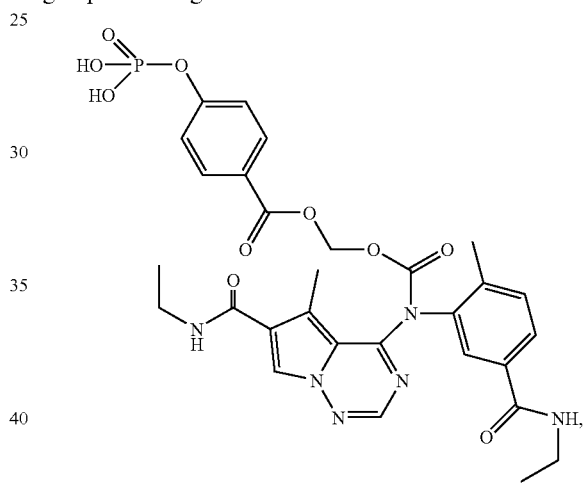
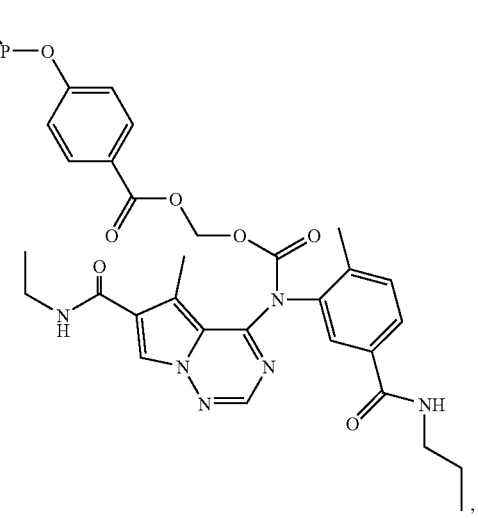

353
-continued
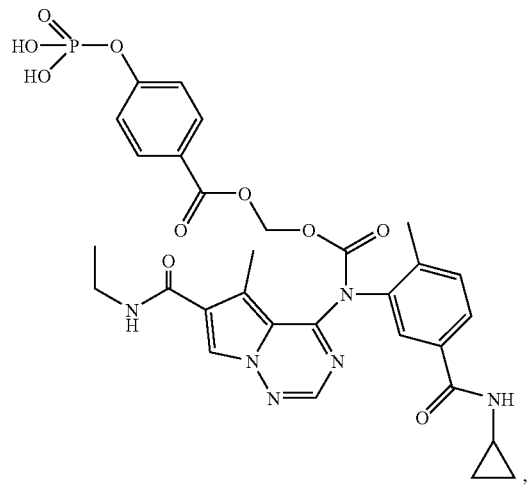
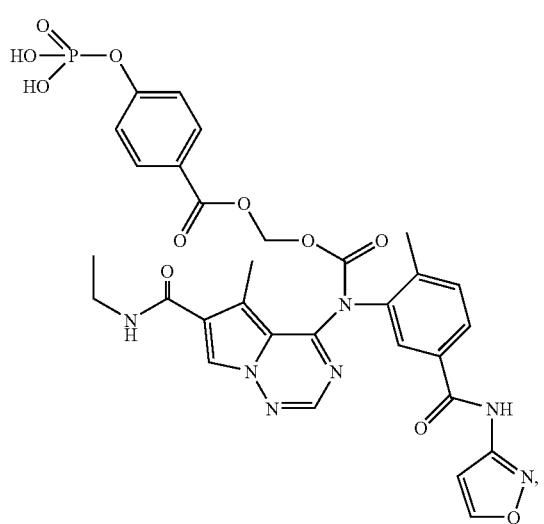
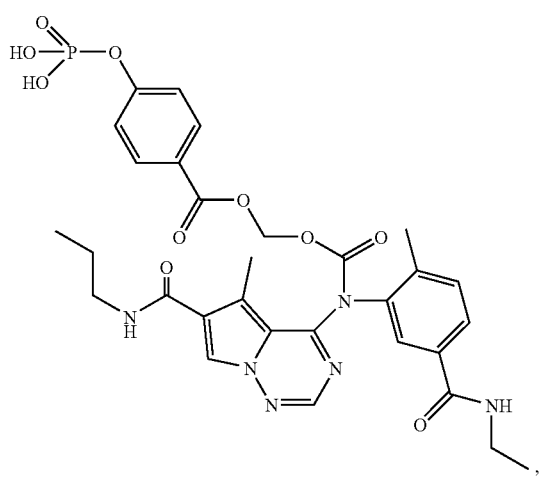
354
-continued
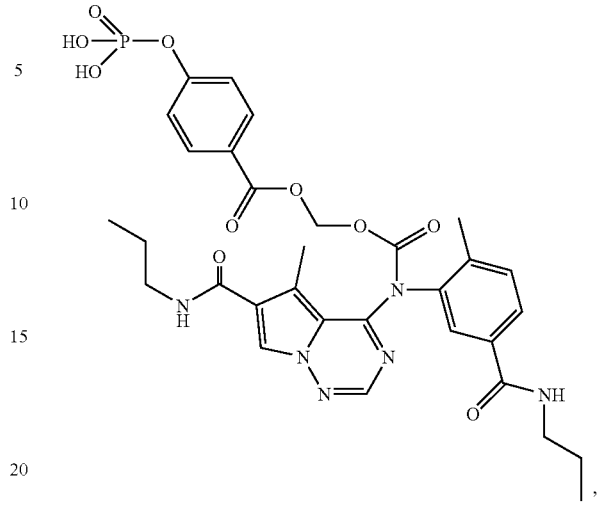
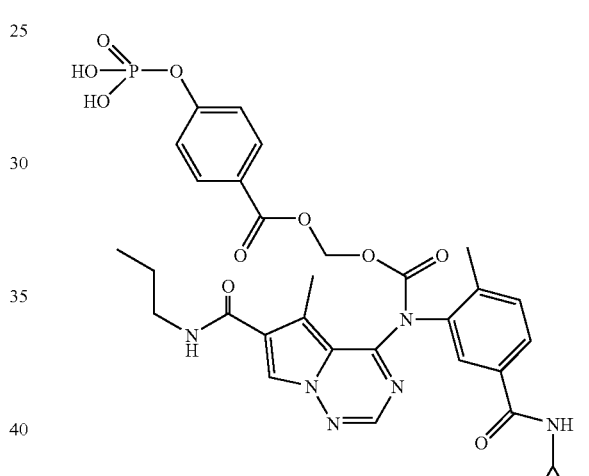
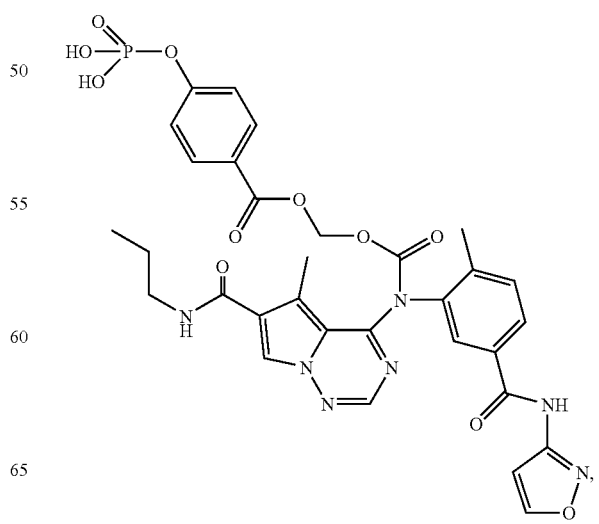

355
-continued
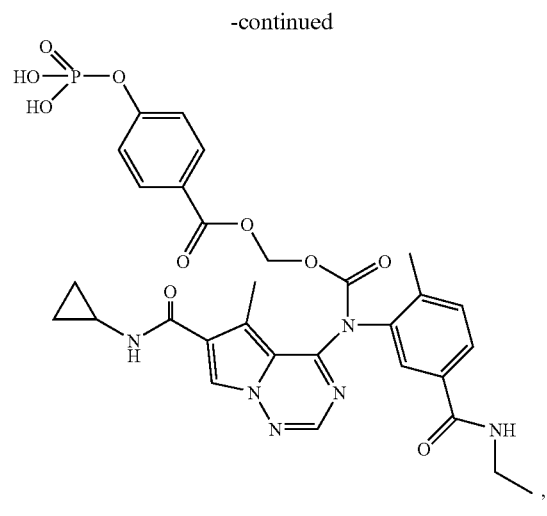
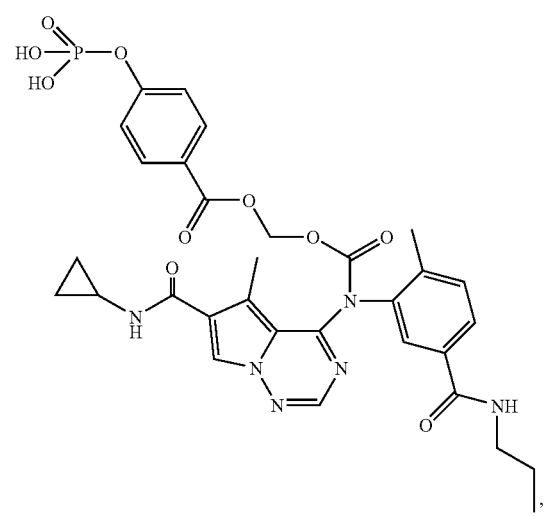
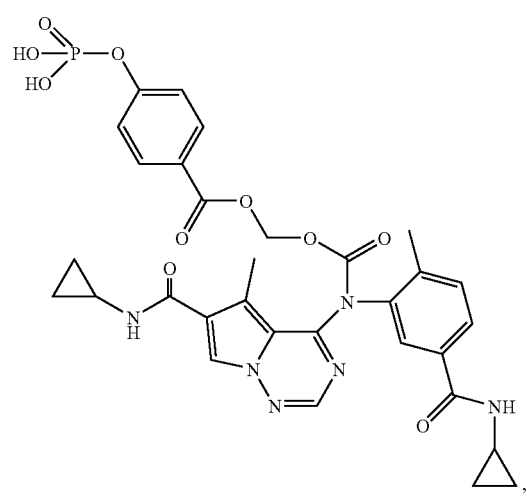
356
-continued
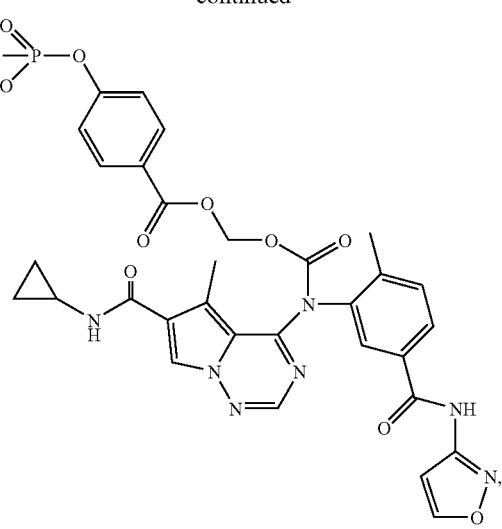
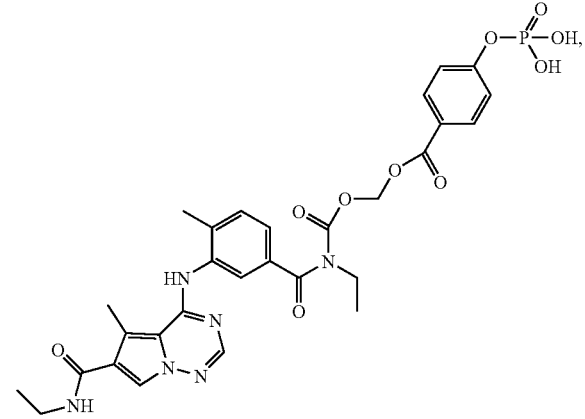

357                                358
-continued                         -continued
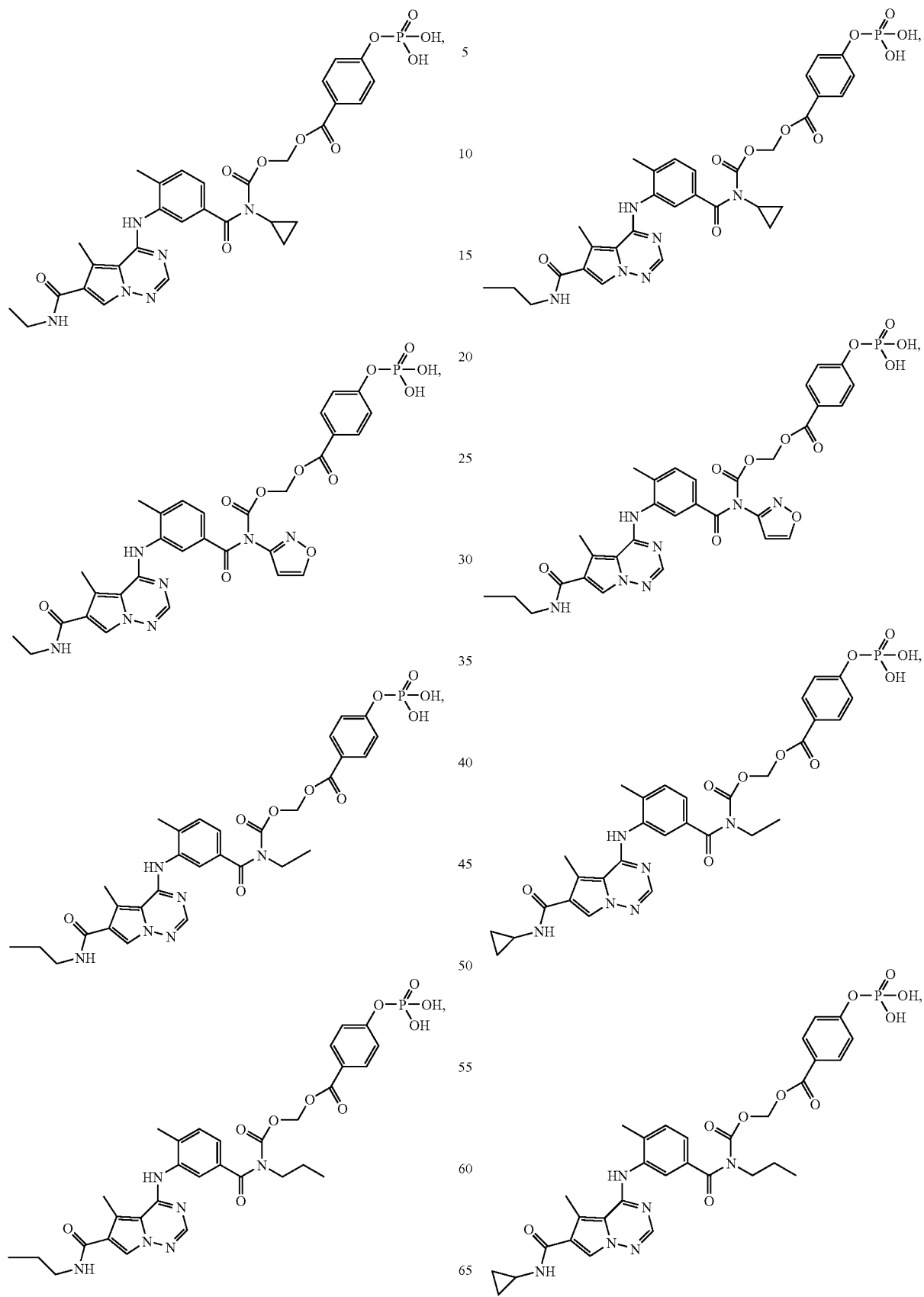

359
-continued
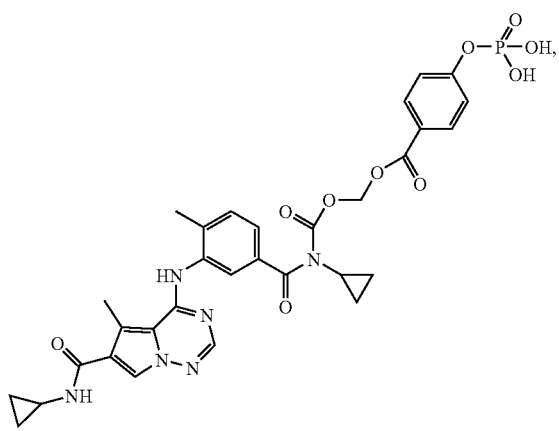
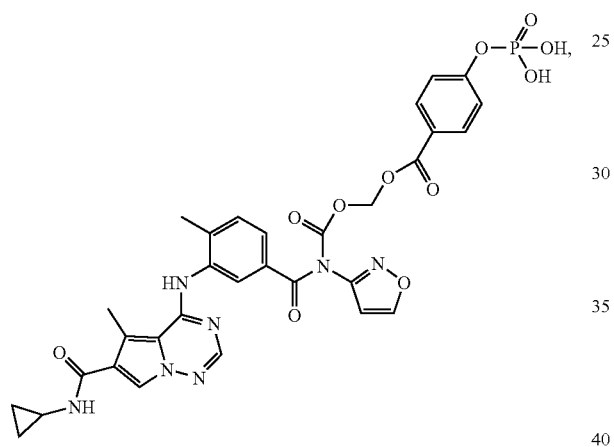
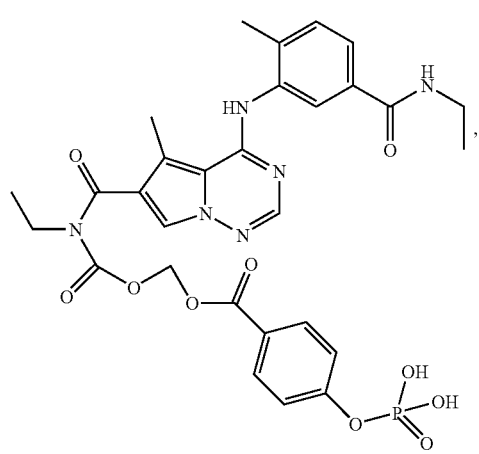
360
-continued
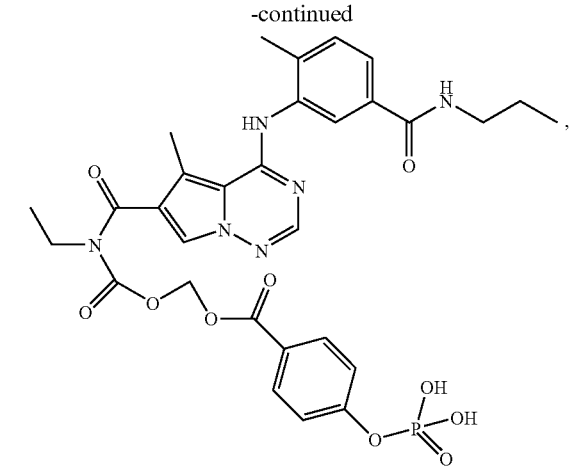
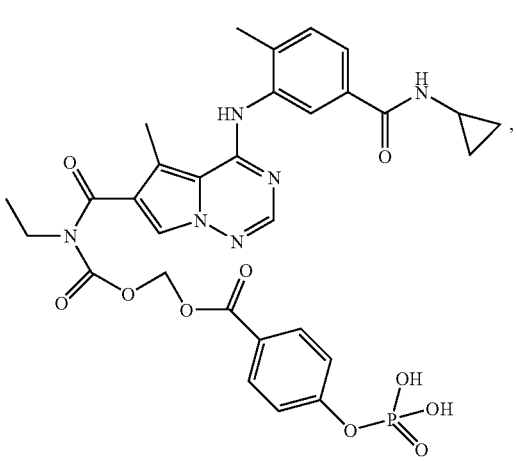
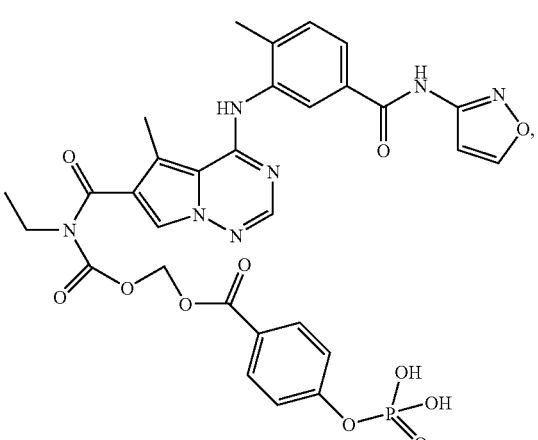

361
-continued
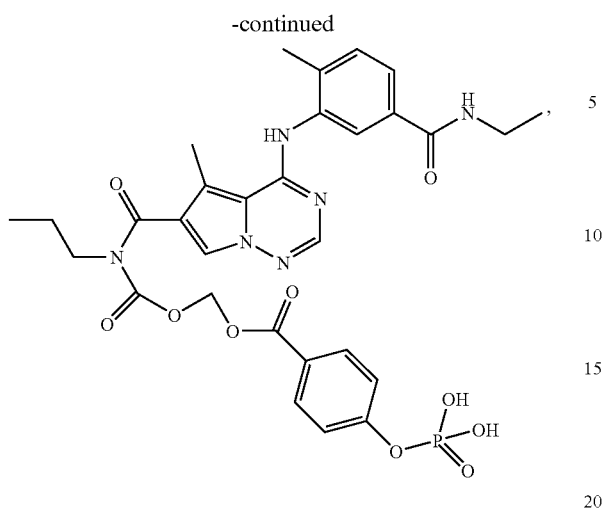
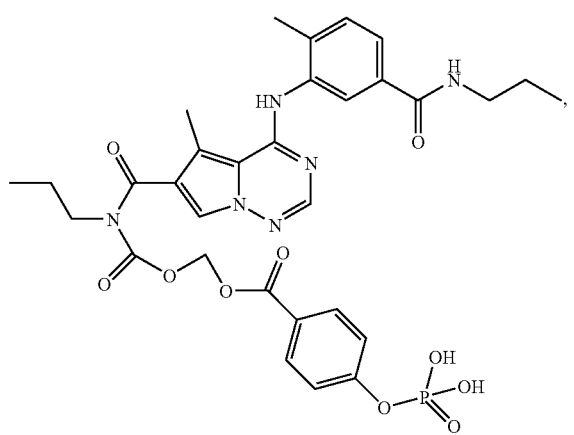
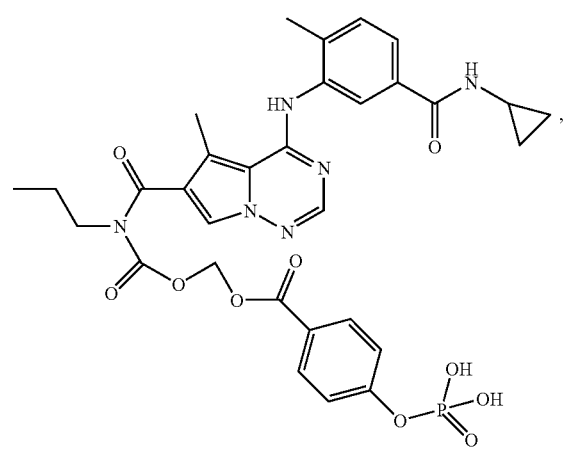
362
-continued
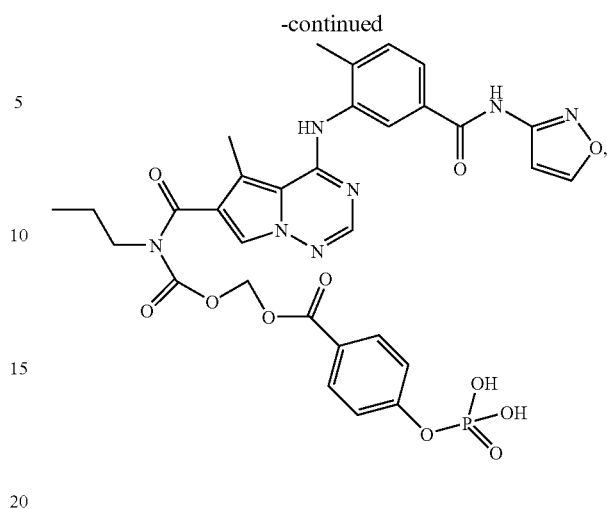
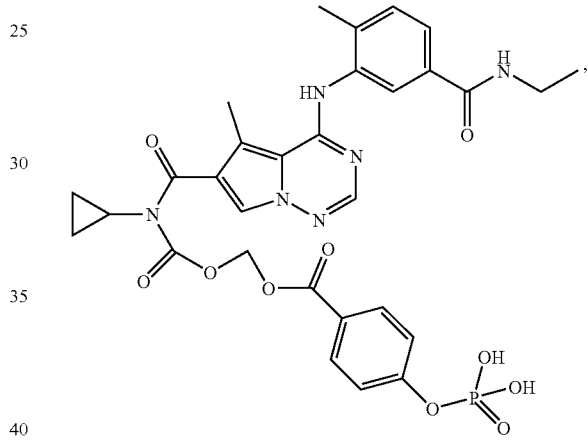
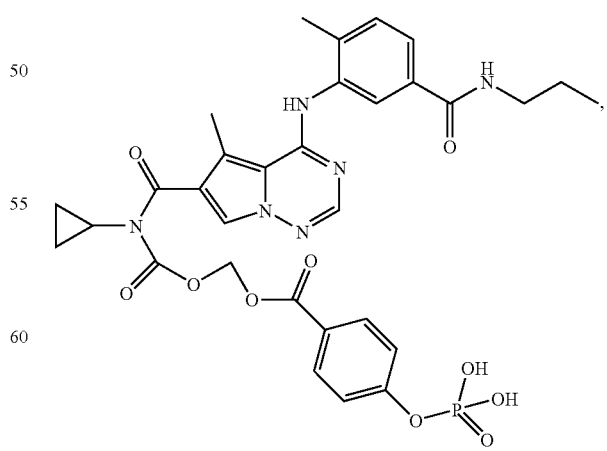

-continued

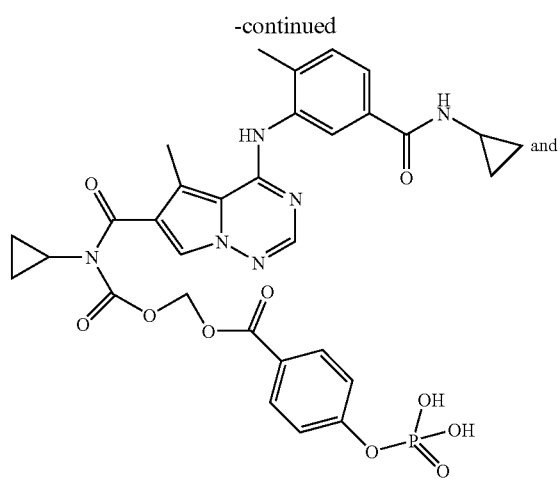

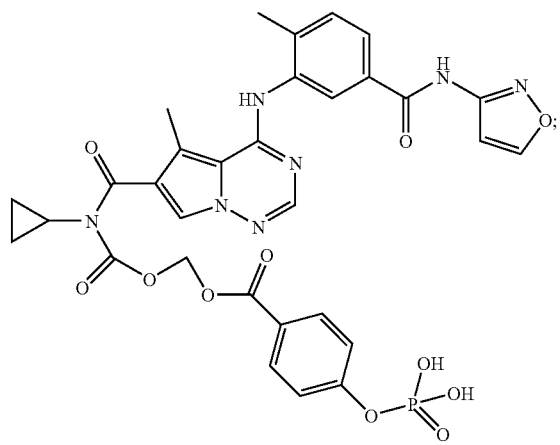

or a pharmaceutically-acceptable salt of any of the foregoing.

21. A compound according to claim 18 having the formula:

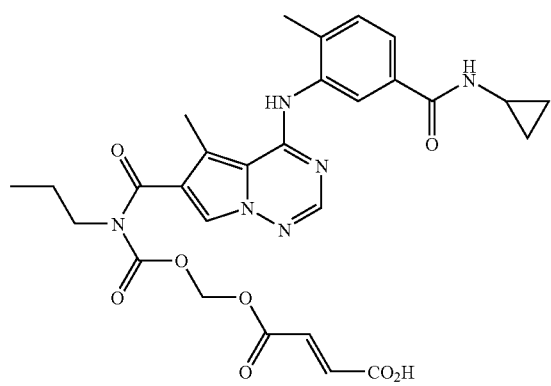

or a pharmaceutically-acceptable salt thereof.

22. A compound according to claim 18 having the formula:

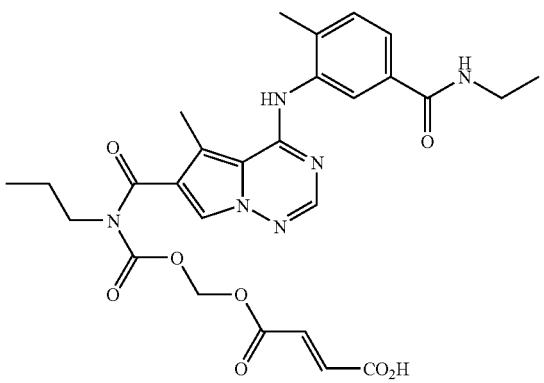

or a pharmaceutically-acceptable salt thereof.

23. A compound according to claim 20 having the formula:

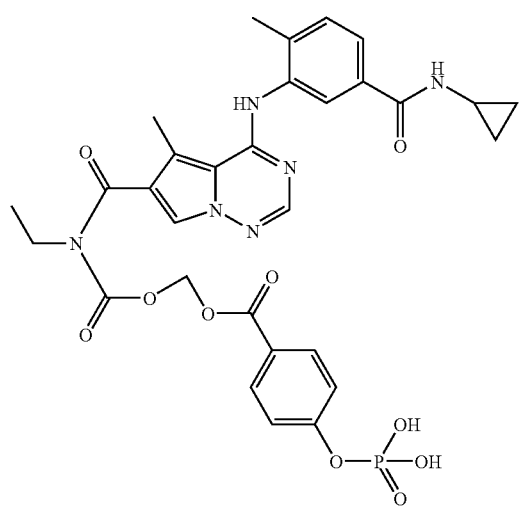

or a pharmaceutically-acceptable salt thereof.

24. A compound according to claim 18 having the formula:

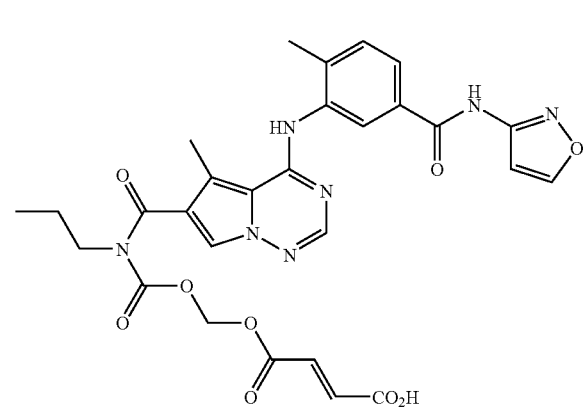

or a pharmaceutically-acceptable salt thereof.

25. A compound according to claim 18 having the formula:

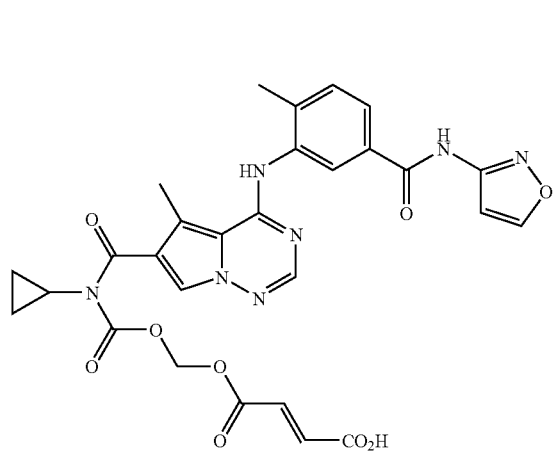

or a pharmaceutically-acceptable salt thereof.

26. A compound according to claim 19 having the formula:

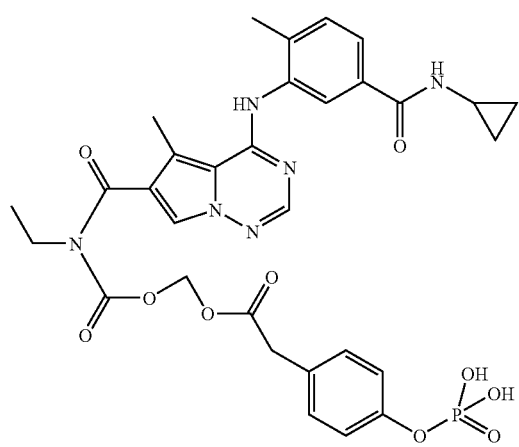

or a pharmaceutically-acceptable salt thereof.

27. A compound having the formula:

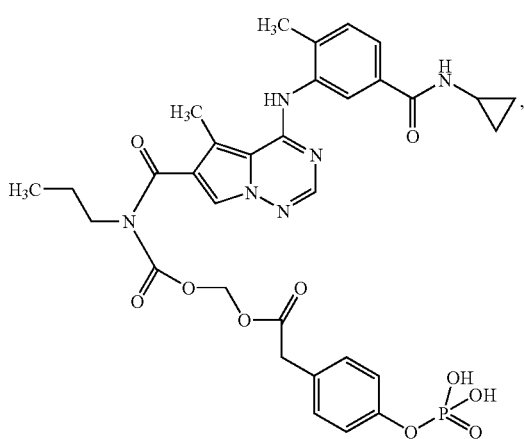

or a pharmaceutically-acceptable salt thereof.

28. A according to claim 19 having the formula:

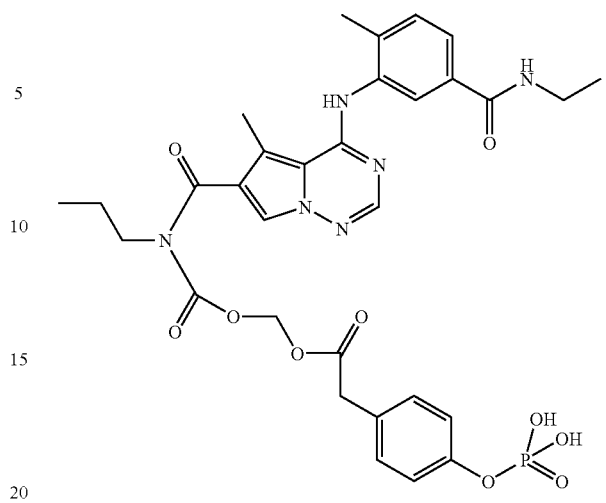

or a pharmaceutically-acceptable salt thereof.

29. A compound according to claim 19 which is

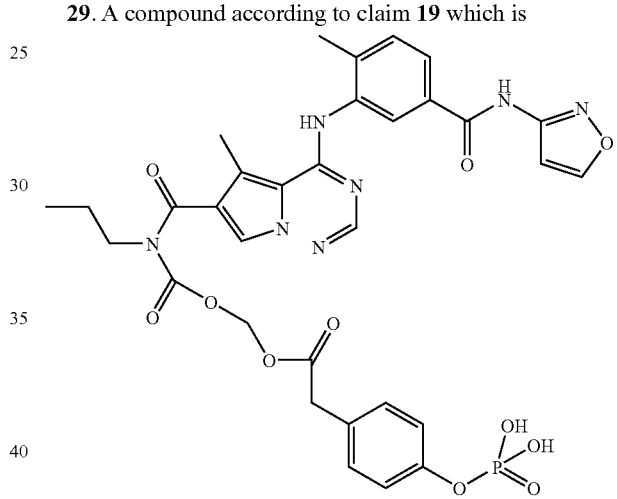

or a pharmaceutically-acceptable salt thereof.

30. A compound according to claim 20 having the formula:

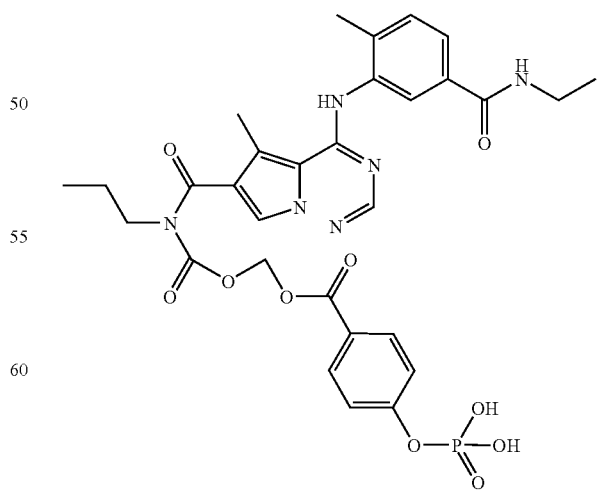

or a pharmaceutically-acceptable salt thereof.

31. A pharmaceutical composition, which comprises (a) a pharmaceutically effective amount of a compound of claim 27, and (b) one or more pharmaceutically-acceptable carriers, excipients or diluents.

32. A method of treating rheumatoid arthritis comprising administering to a patient in need of such treatment a pharmaceutical composition according to claim 31.

33. A method of treating psoriasis comprising administering to a patient in need of such treatment a pharmaceutical composition according to claim 31.

34. A method of treating atherosclerosis comprising administering to a patient in need of such treatment a pharmaceutical composition according to claim 31.

* * * * *

UNITED STATES PATENT AND TRADEMARK OFFICE
CERTIFICATE OF CORRECTION

PATENT NO.       : 7,572,795 B2
APPLICATION NO.  : 11/682331
DATED            : August 11, 2009
INVENTOR(S)      : Chunjian Liu et al.

It is certified that error appears in the above-identified patent and that said Letters Patent is hereby corrected as shown below:

In the Claims:

Claim 1:
   Column 214, line 67, change "pharmaceutically acceptable salt" to
-- pharmaceutically-acceptable salts --.
   Column 216, line 18, after "are", insert -- each --.

Claim 14:
   Column 216, line 55, change "R$_2$" to -- R$^2$ --.

Claim 15:
   Column 216, line 60, change "(b)one" to -- (b) one --.

Claim 16:
   Column 216, line 64, after "selected", insert -- from --.

Claim 17:
   Column 220, lines 19 to 35, change

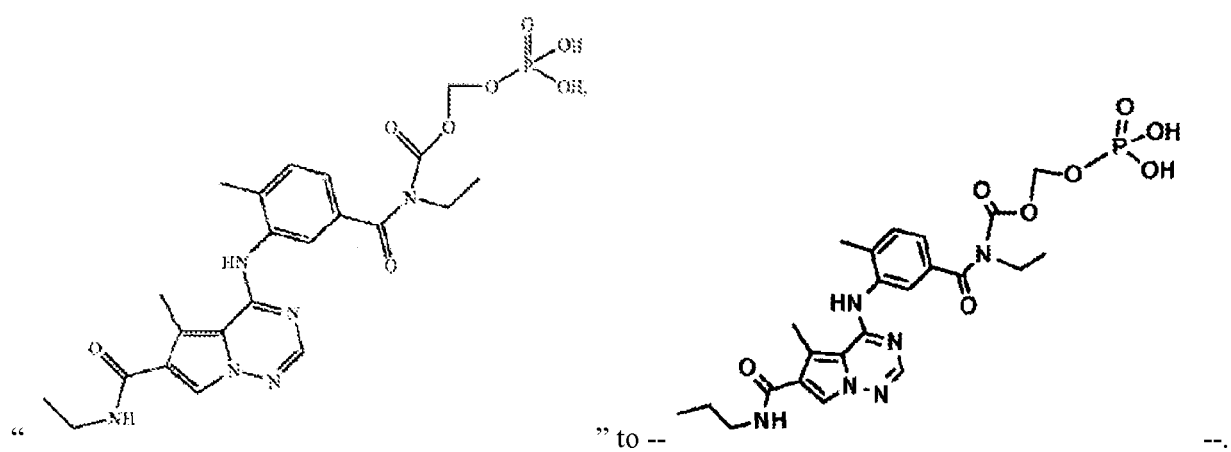

Signed and Sealed this
Thirteenth Day of March, 2012

David J. Kappos
*Director of the United States Patent and Trademark Office*

CERTIFICATE OF CORRECTION (continued)
U.S. Pat. No. 7,572,795 B2

In the Claims:

Claim 17 (continued):

Column 221, lines 3 to 15, change

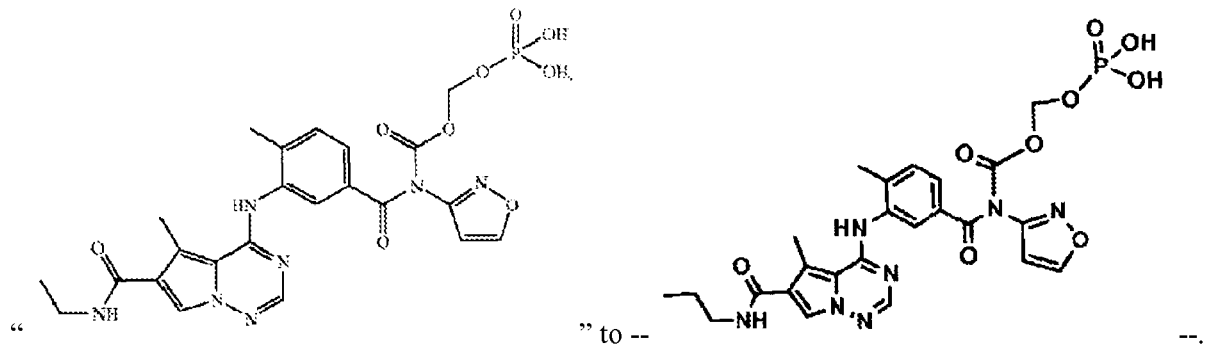

" to --   --.

Column 224, line 19, change "and" to -- , --.
Column 225, lines 23 to 32, change

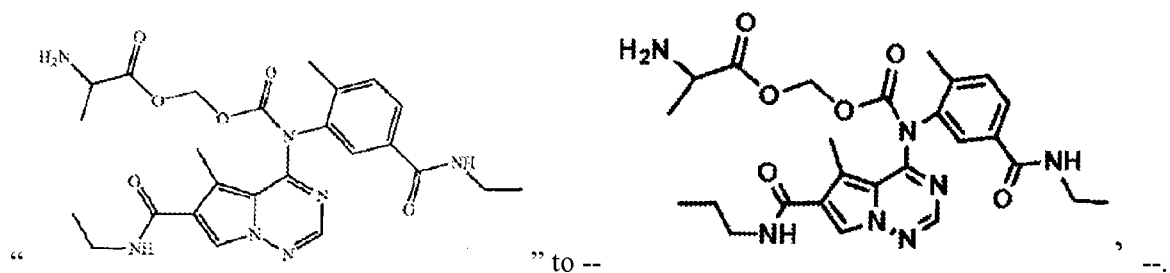

" to --   , --.

Column 226, lines 45 to 55, change

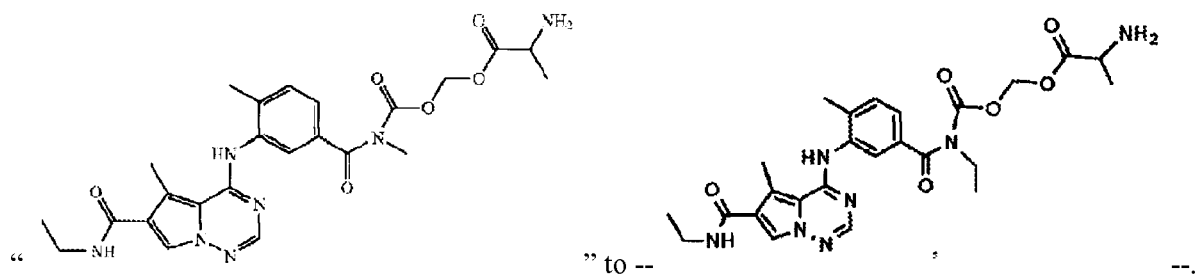

" to --   , --.

Column 231, line 22, change "and" to -- , --.
Column 241, line 6, change "and" to -- , --.
Column 248, line 6, change "and" to -- , --.

CERTIFICATE OF CORRECTION (continued)  Page 3 of 35
U.S. Pat. No. 7,572,795 B2

In the Claims:

Claim 17 (continued):

Column 250, lines 3 to 22, change

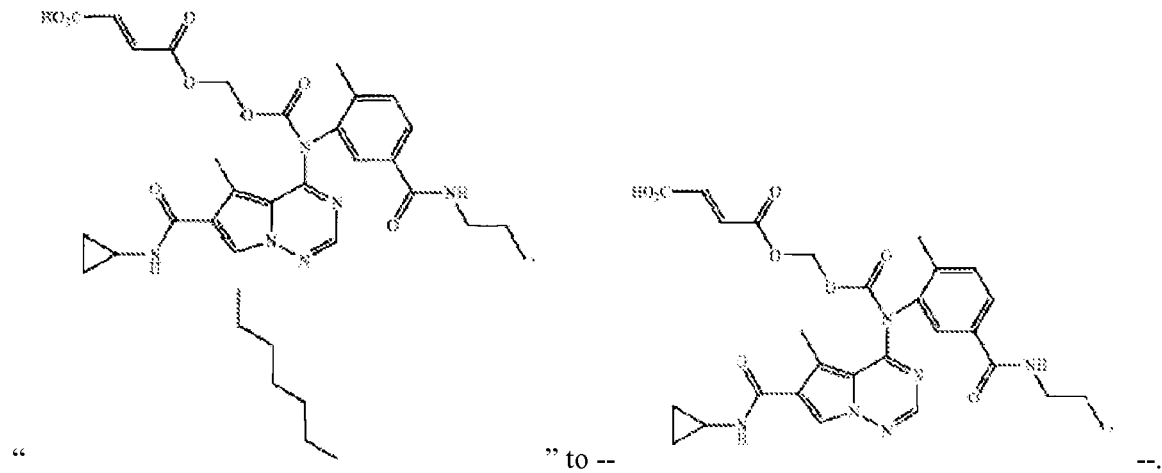

" to --    --.

Column 251, lines 28 to 38, change

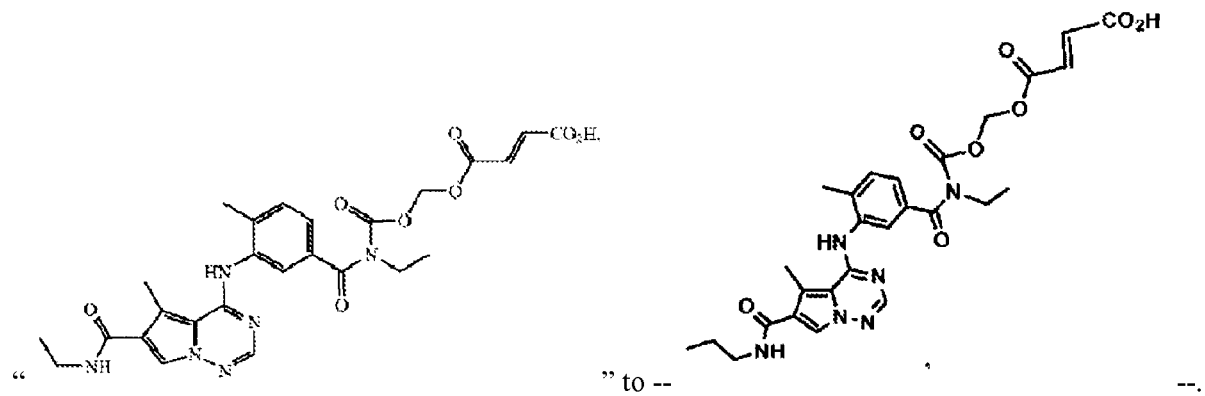

" to --    --.

CERTIFICATE OF CORRECTION (continued)
U.S. Pat. No. 7,572,795 B2

Column 252, lines 3 to 25, change

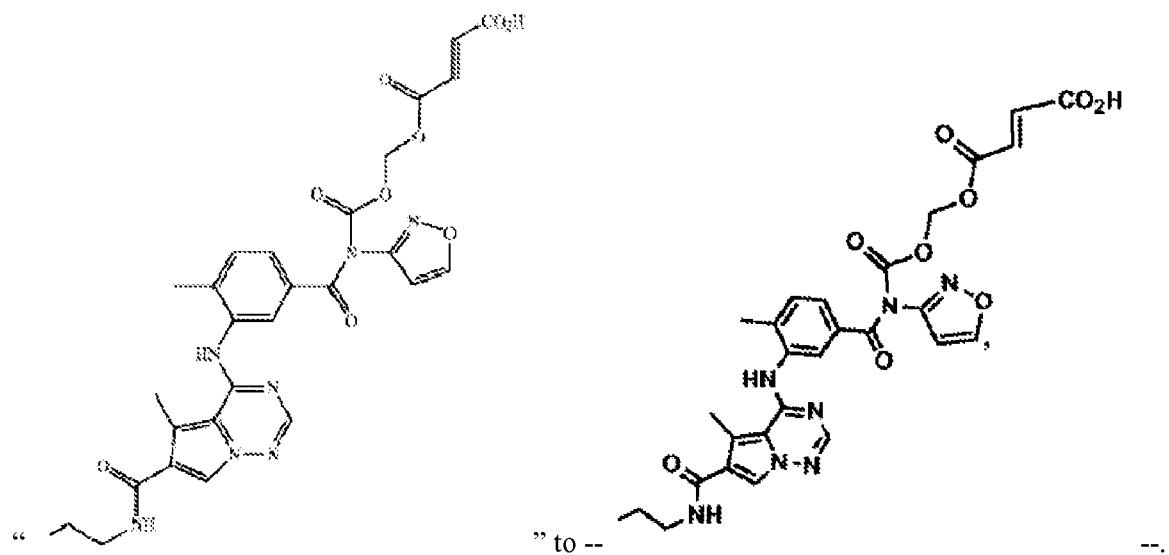

" to --        --.

Column 252, lines 42 to 65, change

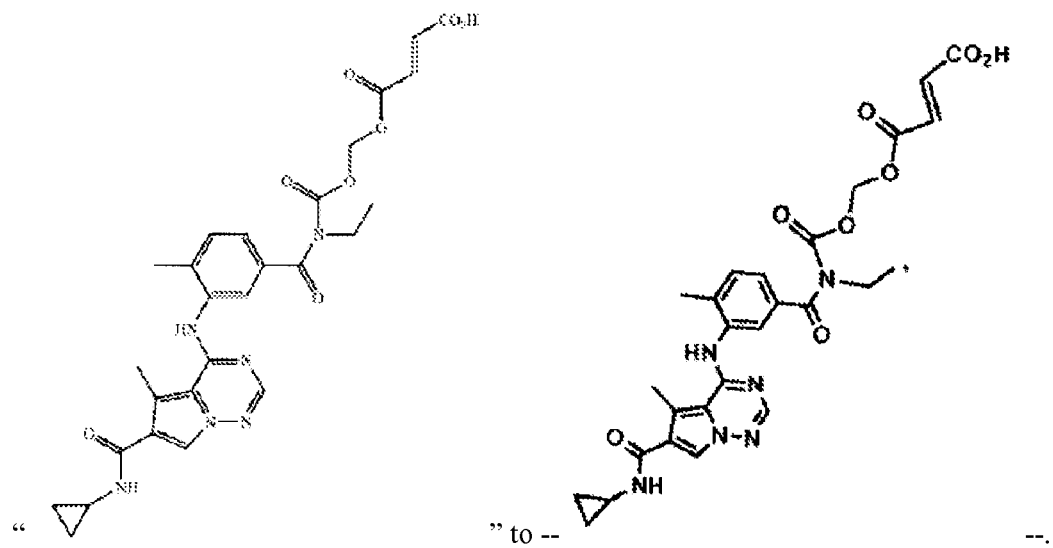

" to --        --.

CERTIFICATE OF CORRECTION (continued)
U.S. Pat. No. 7,572,795 B2

Page 5 of 35

In the Claims:

Claim 17 (continued):

Column 253, lines 3 to 26, change

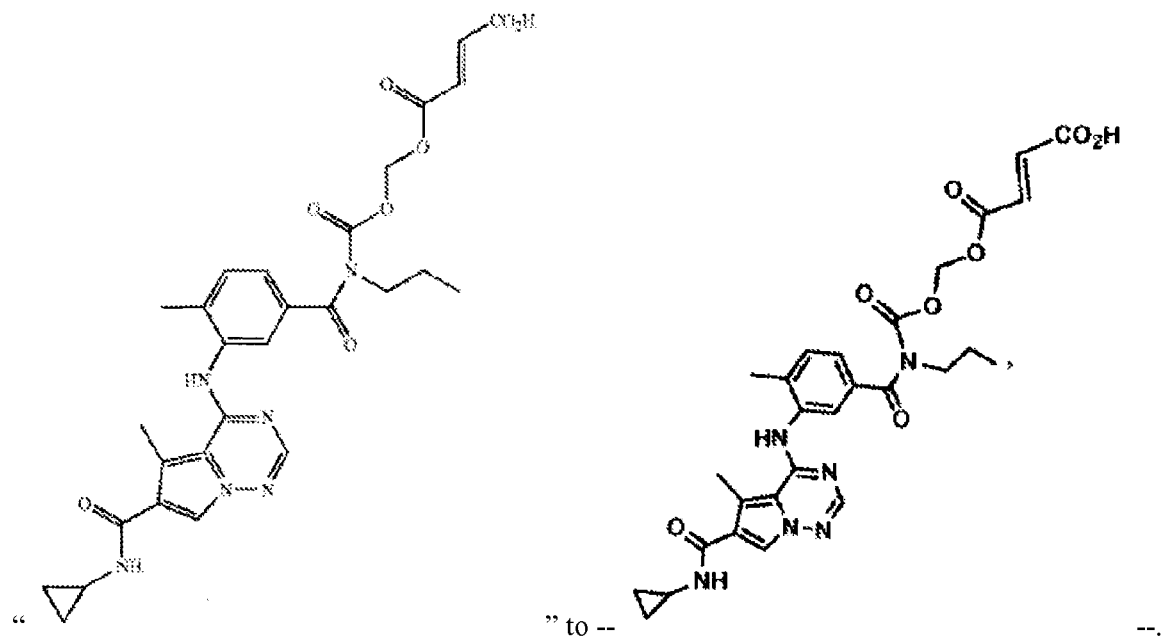

" to --            --.

Column 253, lines 42 to 65, change

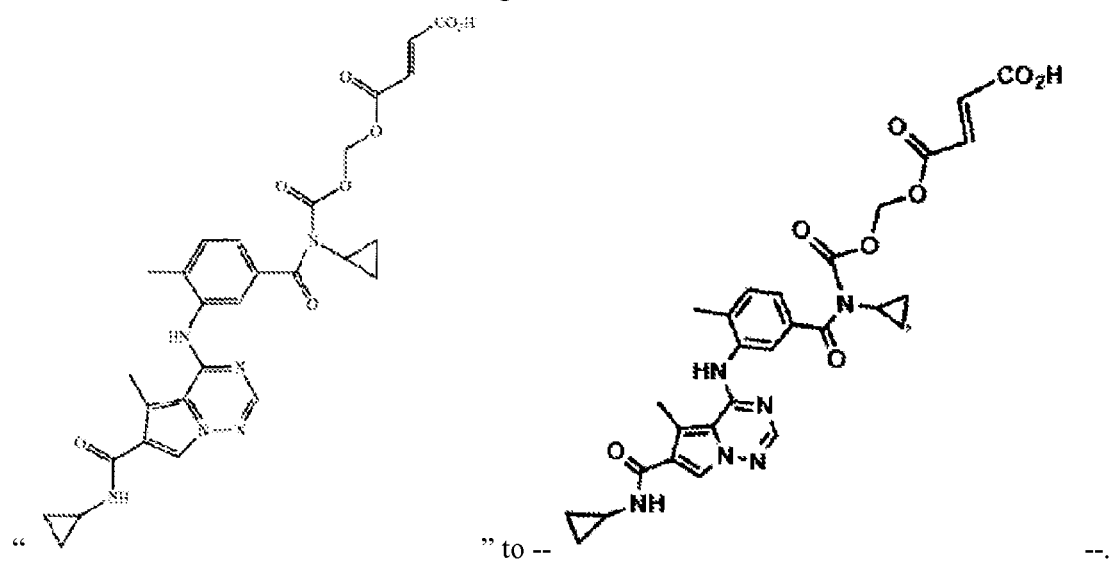

" to --            --.

CERTIFICATE OF CORRECTION (continued)
U.S. Pat. No. 7,572,795 B2

In the Claims:

Claim 17 (continued):

Column 254, lines 3 to 26, change

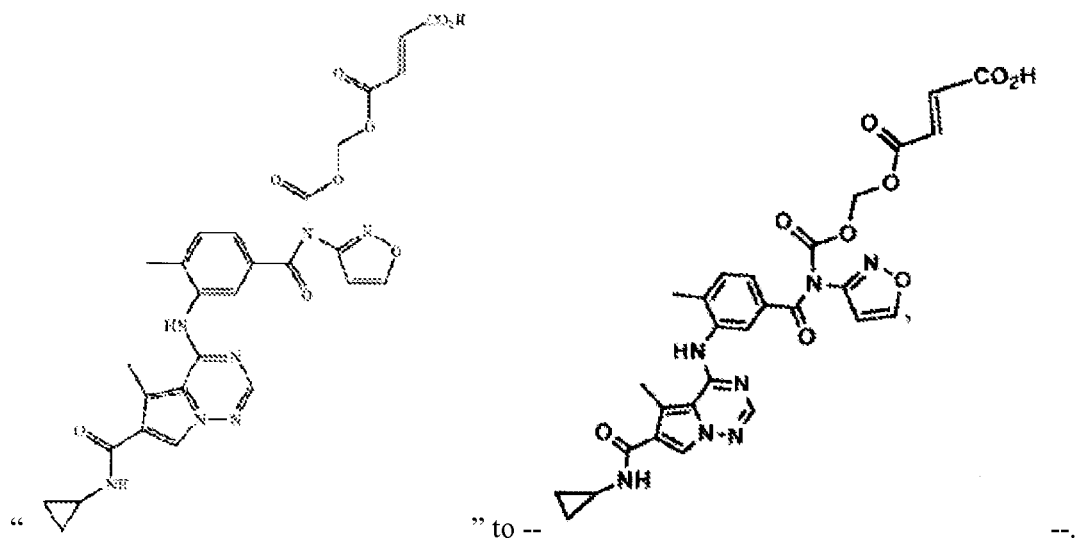

" to -- --.

Column 262, line 3, after "-continued", insert

-- , --.

Column 265, line 6, change "and" to -- , --.

ive
CERTIFICATE OF CORRECTION (continued)
U.S. Pat. No. 7,572,795 B2

Page 7 of 35

In the Claims:

Claim 17 (continued):

Column 266, lines 3 to 14, change

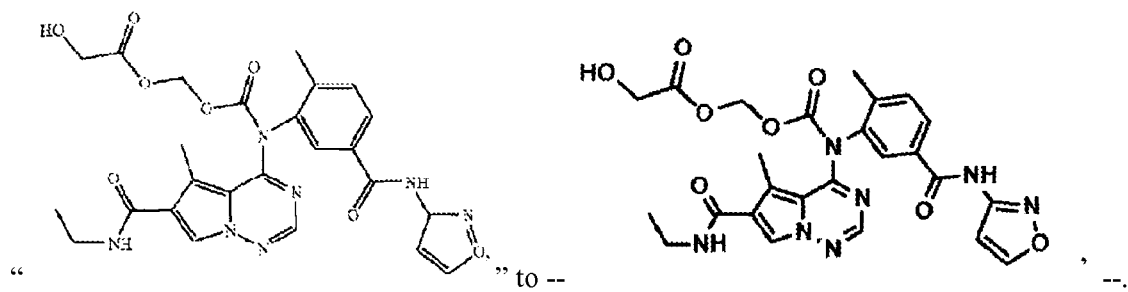

" to --                    --.

Column 272, line 38, change "and" to -- , --.
Column 279, line 56, change "and" to -- , --.
Column 280, lines 27 to 44, change

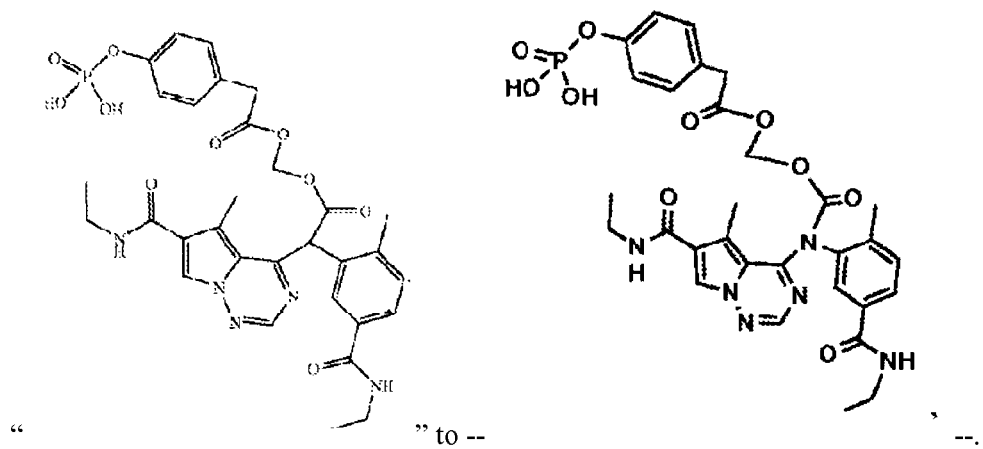

" to --                    --.

Column 284, lines 3 to 22, change

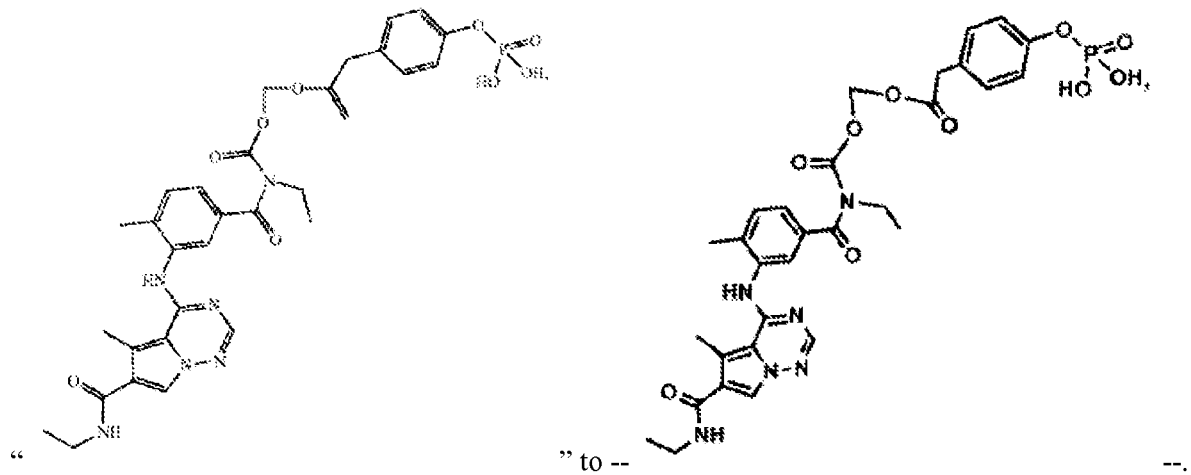

" to --                    --.

CERTIFICATE OF CORRECTION (continued)
U.S. Pat. No. 7,572,795 B2

In the Claims:

Claim 17 (continued):

Column 284, lines 25 to 44, change

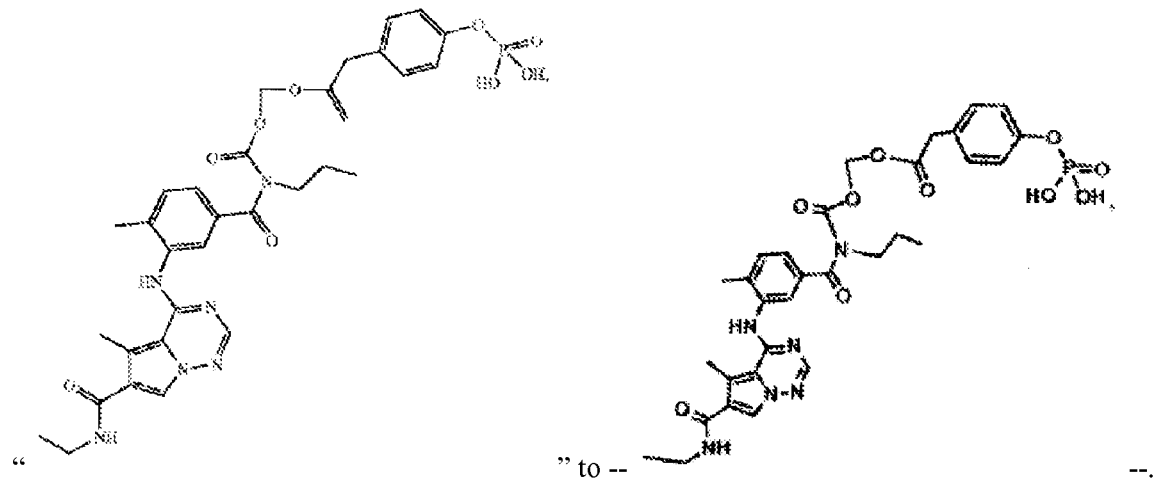

" to --    --.

Column 284, lines 47 to 65, change

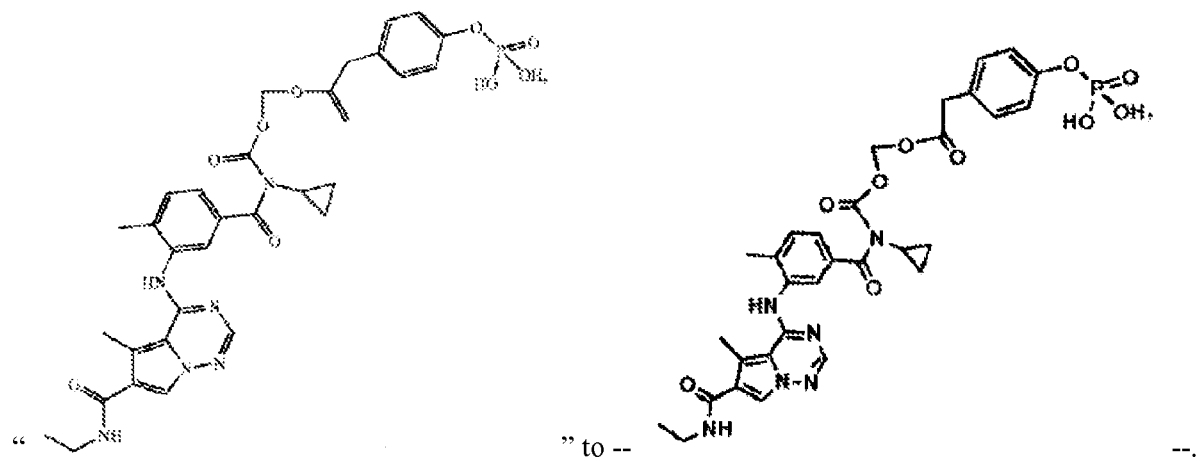

" to --    --.

CERTIFICATE OF CORRECTION (continued)
U.S. Pat. No. 7,572,795 B2

In the Claims:

Claim 17 (continued):

Column 285, lines 3 to 21, change

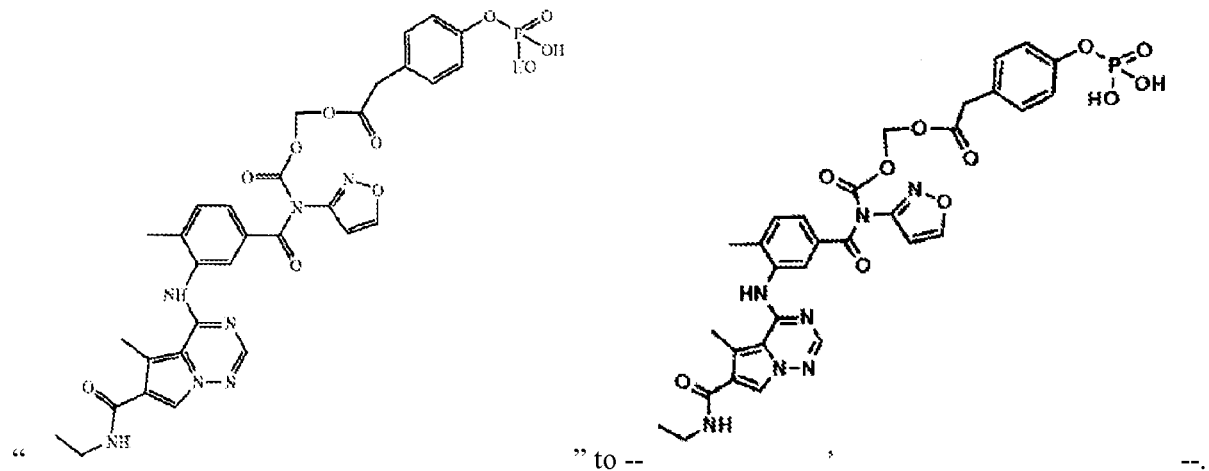

" to --                   --.

Column 285, lines 28 to 44, change

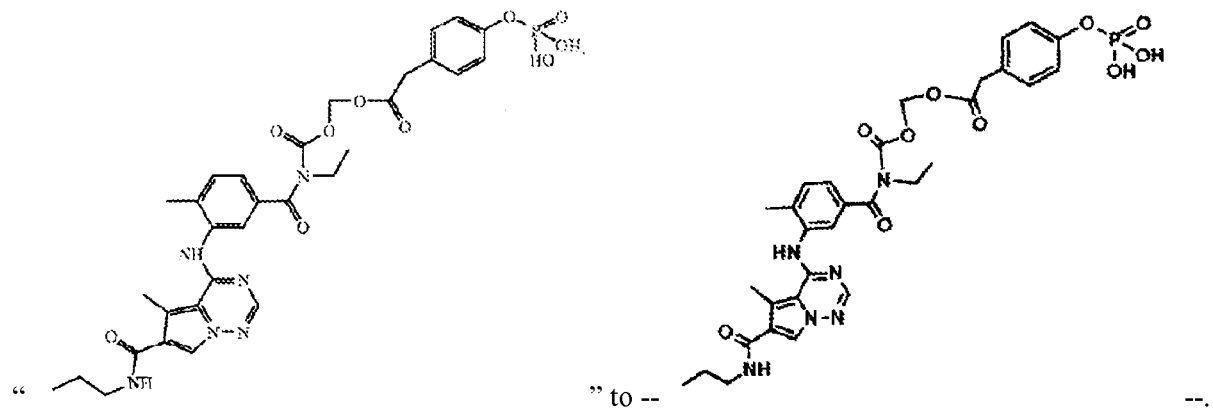

" to --                   --.

CERTIFICATE OF CORRECTION (continued)
U.S. Pat. No. 7,572,795 B2

In the Claims:

Claim 17 (continued):

Column 285, lines 50 to 66, change

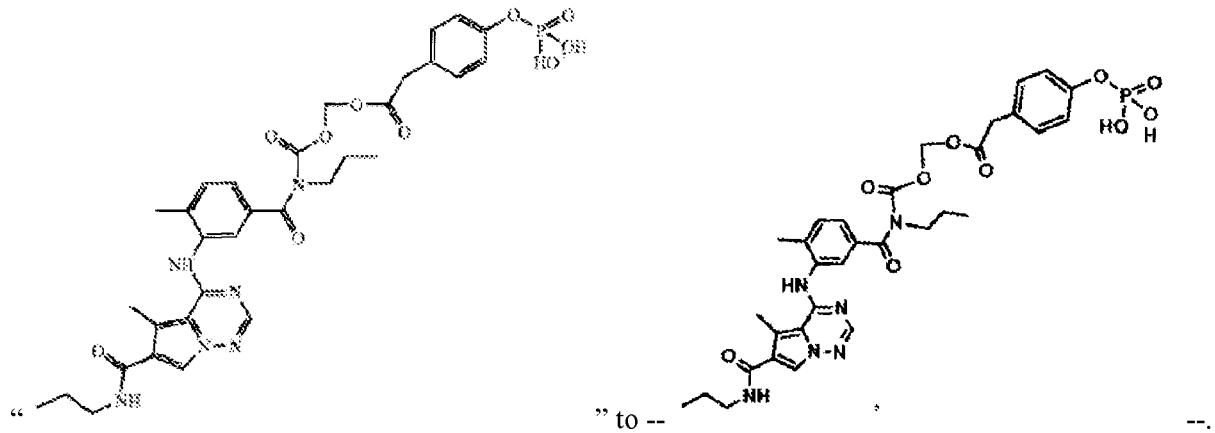

" to --                                          --.

Column 286, lines 3 to 18, change

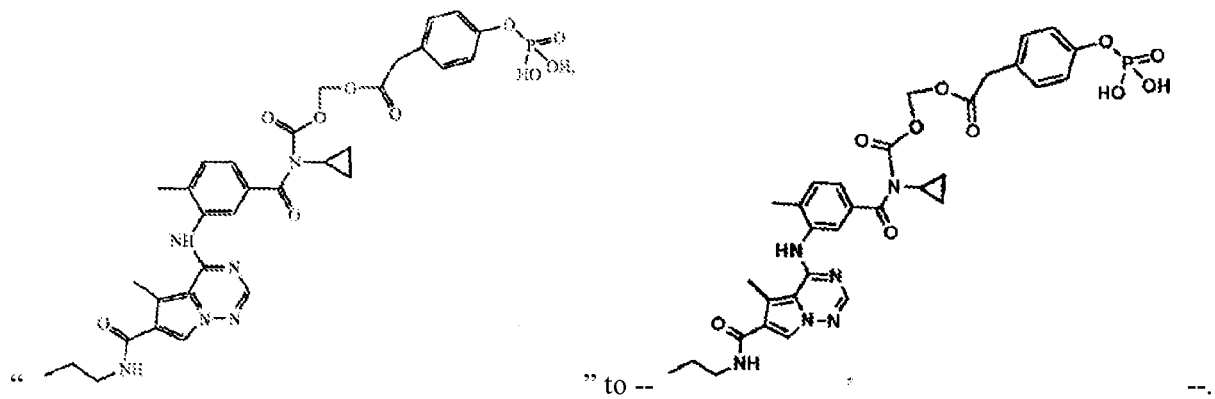

" to --                                          --.

Column 286, lines 25 to 40, change

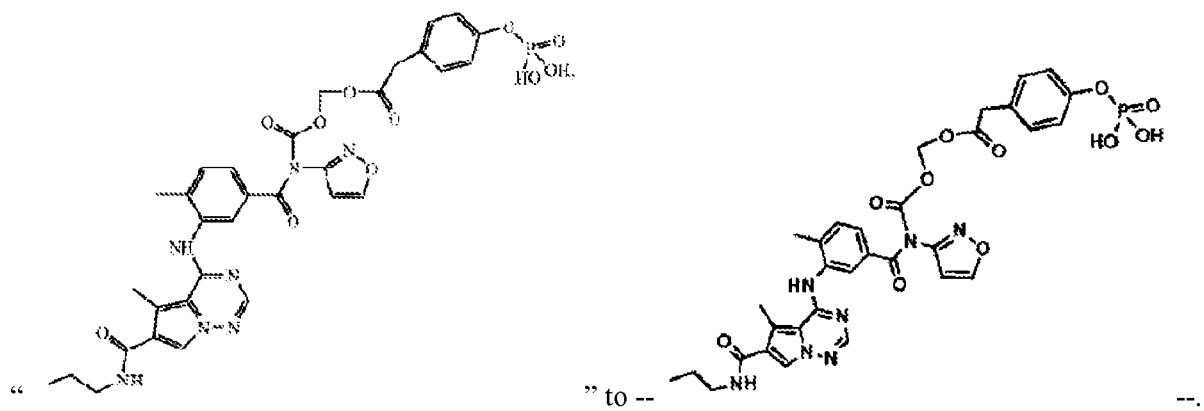

" to --                                          --.

CERTIFICATE OF CORRECTION (continued)
U.S. Pat. No. 7,572,795 B2

In the Claims:

Claim 17 (continued):

Column 286, lines 50 to 65, change

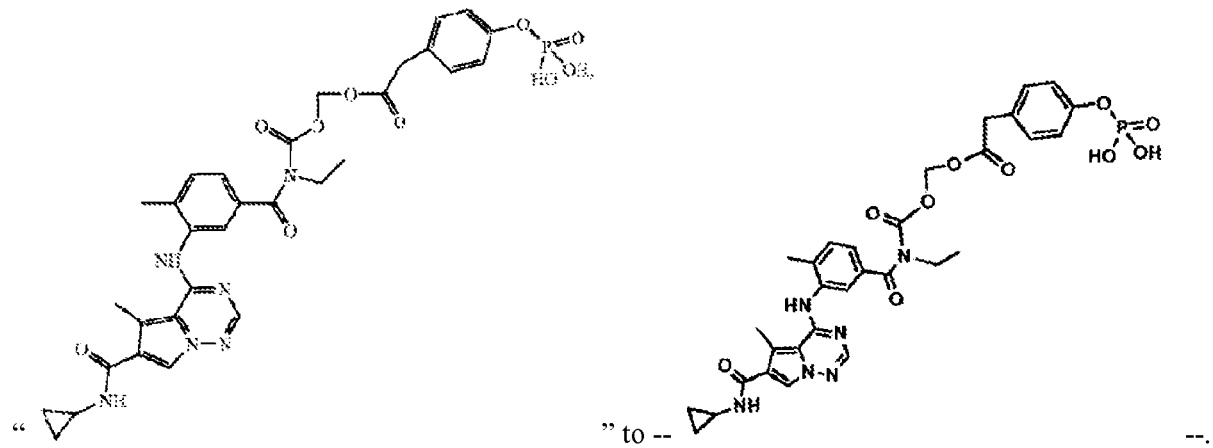

" to --                --.

Column 287, lines 3 to 19, change

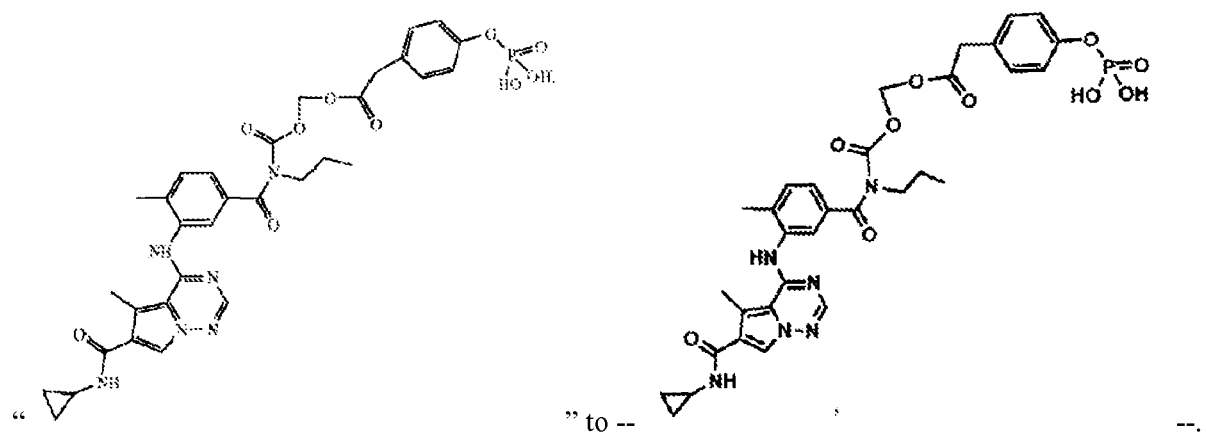

" to --                --.

Column 287, lines 26 to 42, change

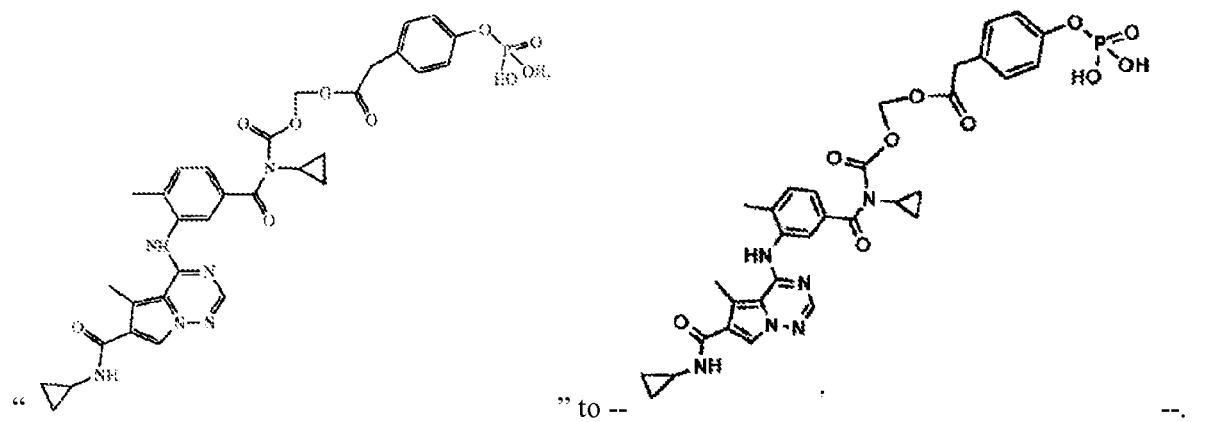

" to --                --.

CERTIFICATE OF CORRECTION (continued)
U.S. Pat. No. 7,572,795 B2

In the Claims:

Claim 17 (continued):

Column 287, lines 50 to 66, change

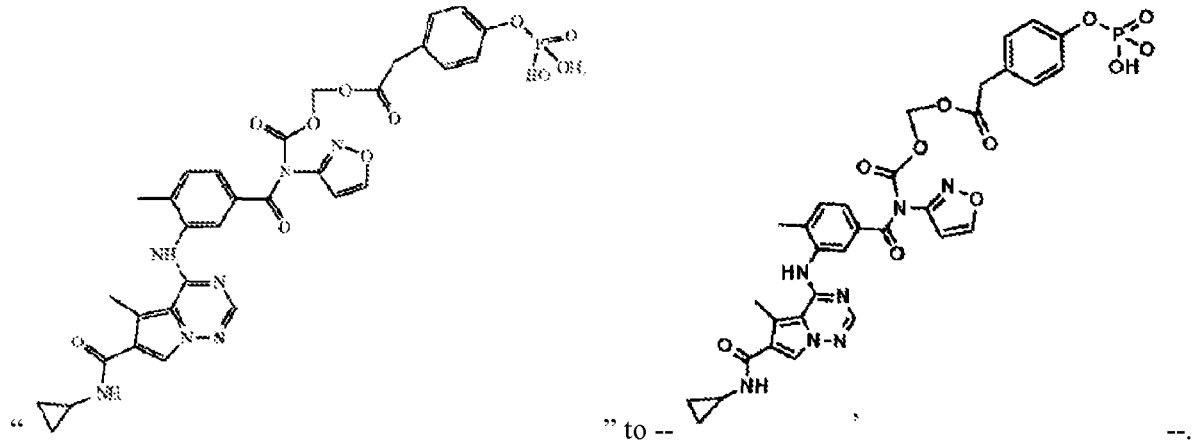

" to --          --.

Column 291, line 28, change "and" to -- , --.
Column 292, lines 3 to 20, change

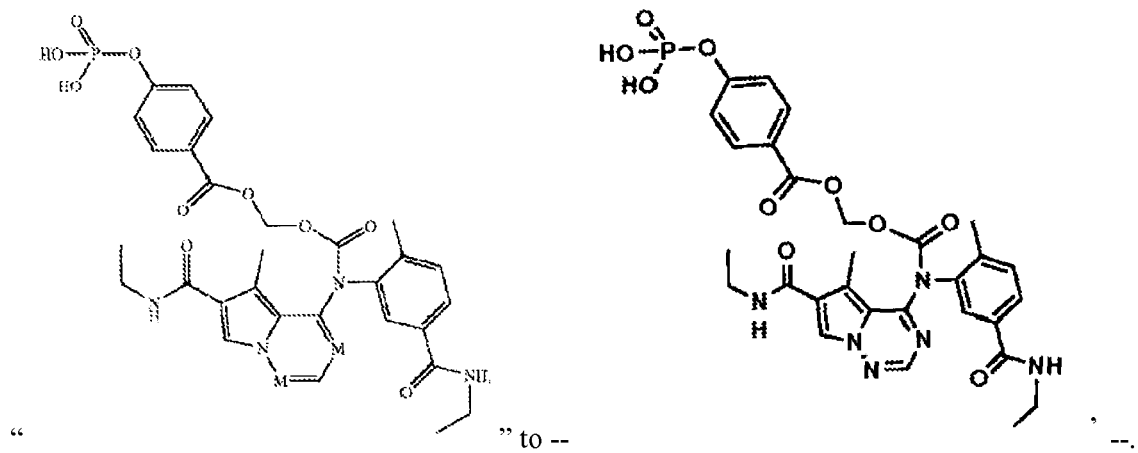

" to --          --.

CERTIFICATE OF CORRECTION (continued)
U.S. Pat. No. 7,572,795 B2

In the Claims:

Claim 17 (continued):

Column 292, lines 25 to 44, change

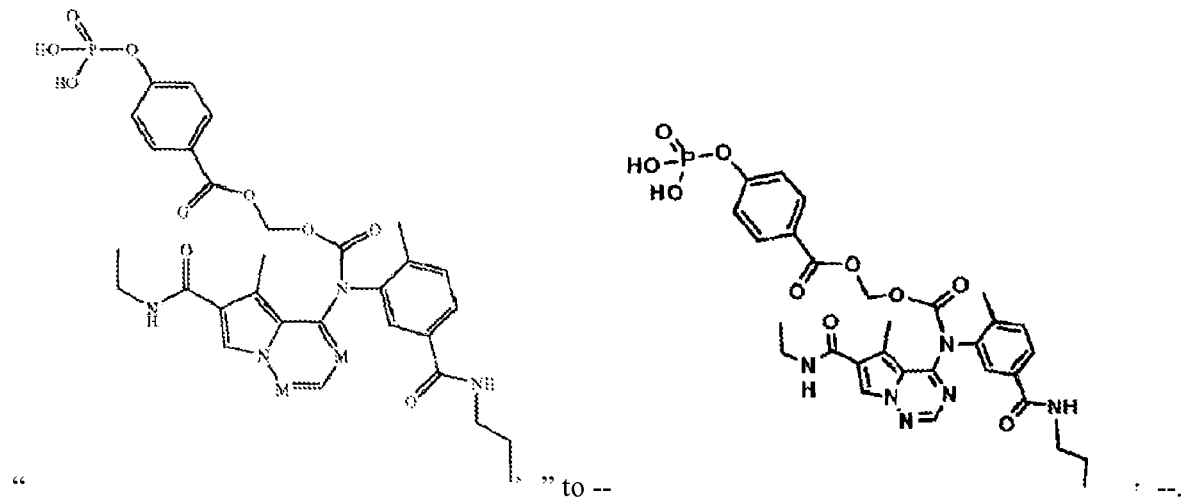

" to --                                         : --.

Column 292, lines 48 to 67, change

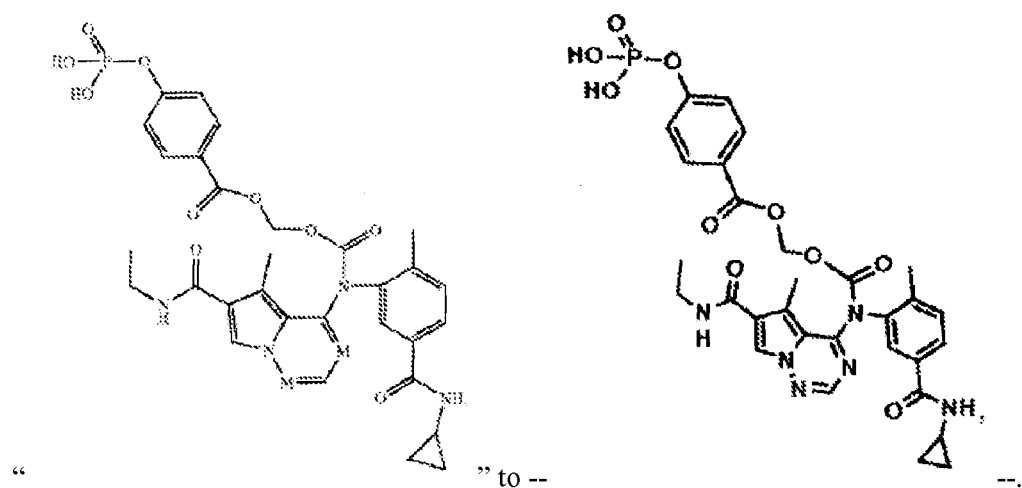

" to --                                         --.

CERTIFICATE OF CORRECTION (continued)
U.S. Pat. No. 7,572,795 B2

In the Claims:

Claim 17 (continued):

Column 293, lines 3 to 23, change

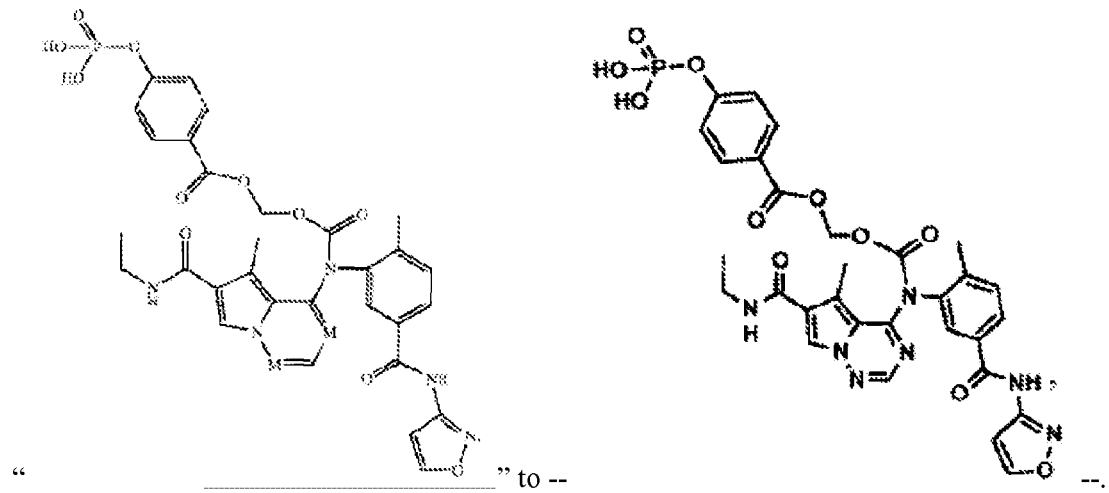

" _____ " to -- --.

Column 293, lines 24 to 43, change

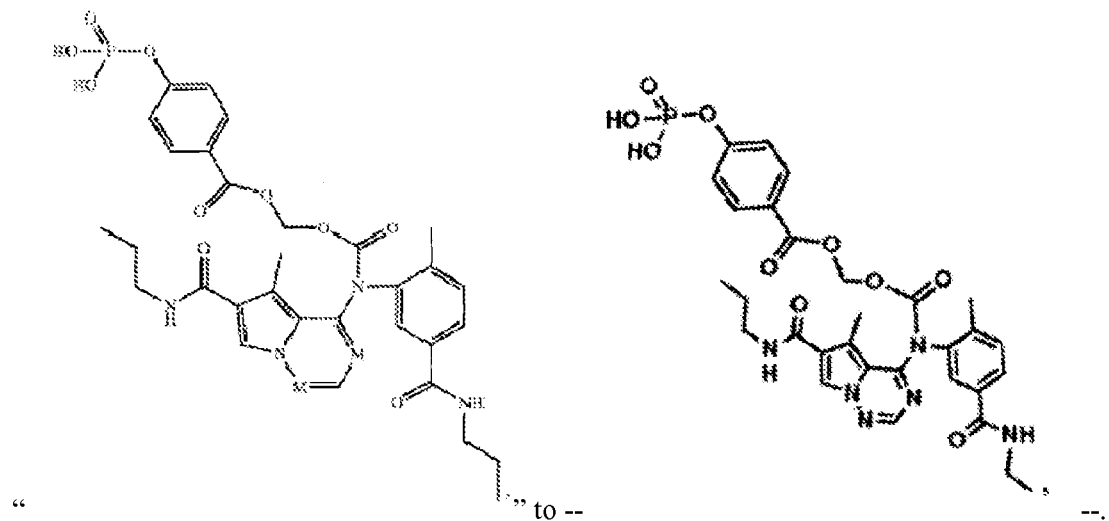

" _____ " to -- --.

CERTIFICATE OF CORRECTION (continued)
U.S. Pat. No. 7,572,795 B2

In the Claims:

Claim 17 (continued):

Column 293, lines 46 to 66, change

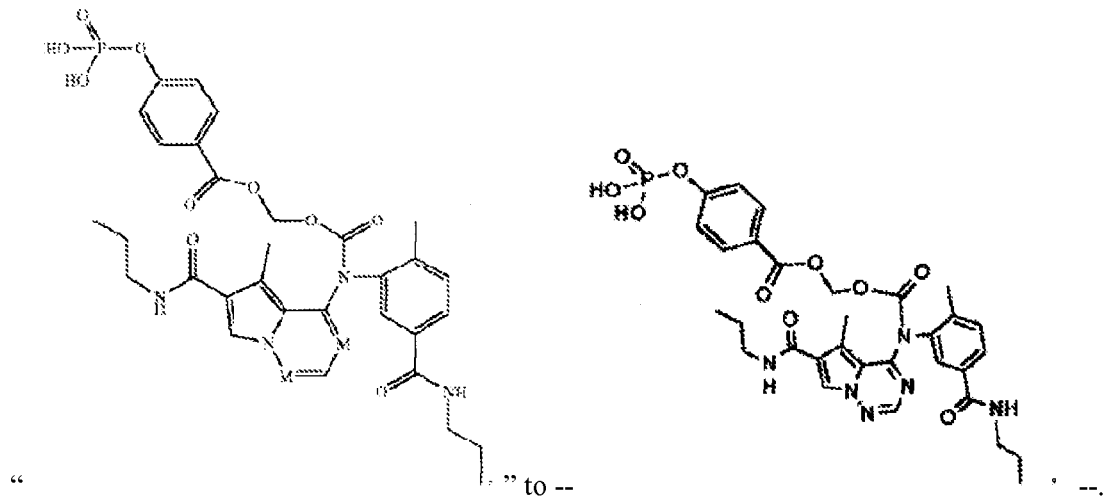

" " to -- --.

Column 294, lines 3 to 21, change

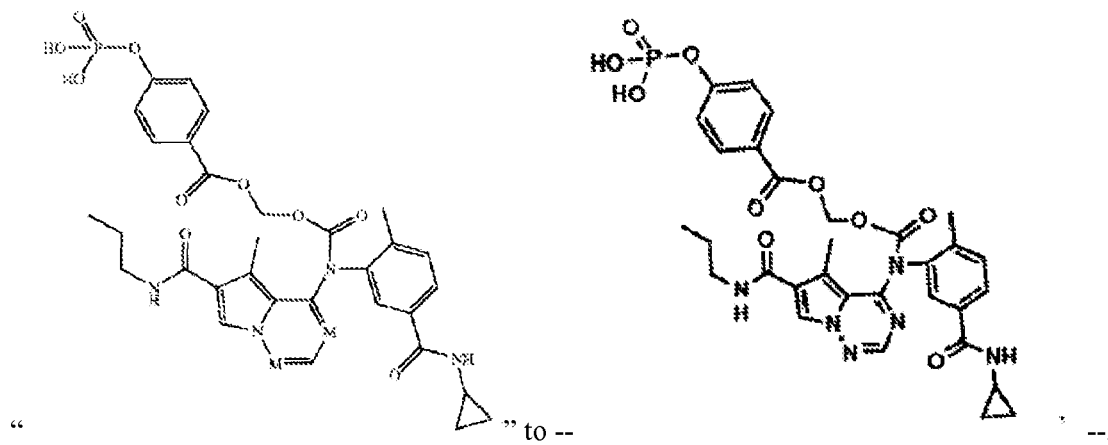

" " to -- --.

Column 294, lines 25 to 44, change

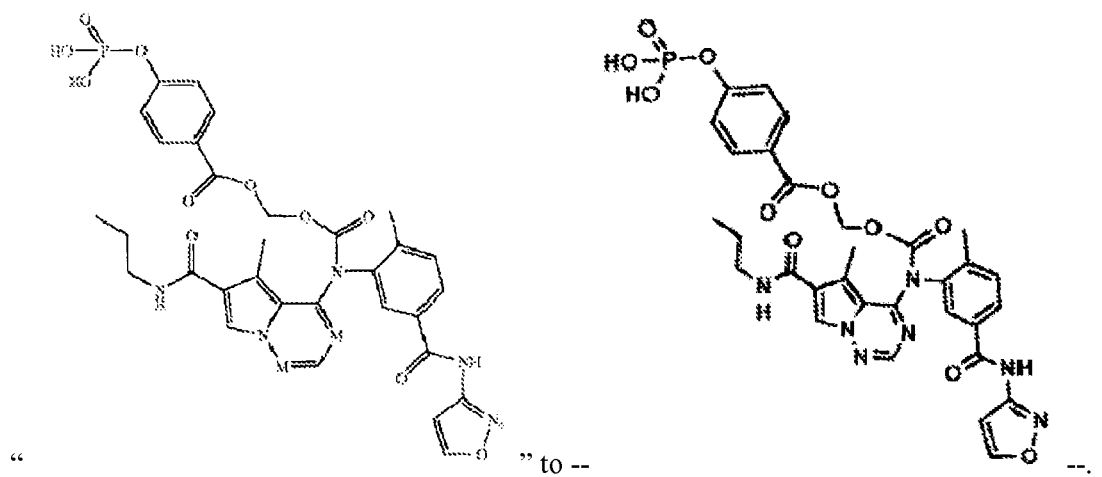

" " to -- --.

CERTIFICATE OF CORRECTION (continued)
U.S. Pat. No. 7,572,795 B2

In the Claims:

Claim 17 (continued):

Column 294, lines 49 to 66, change

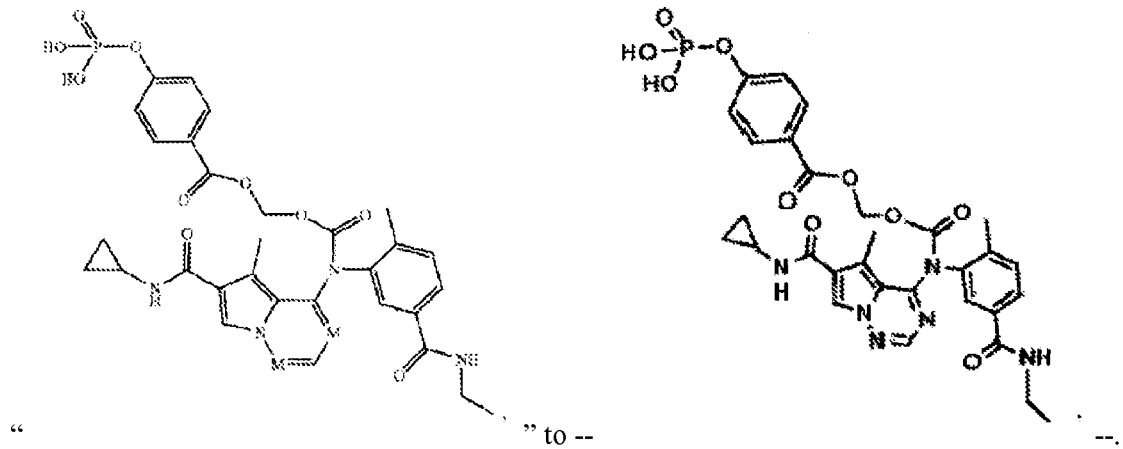

" " to -- --.

Column 295, lines 3 to 22, change

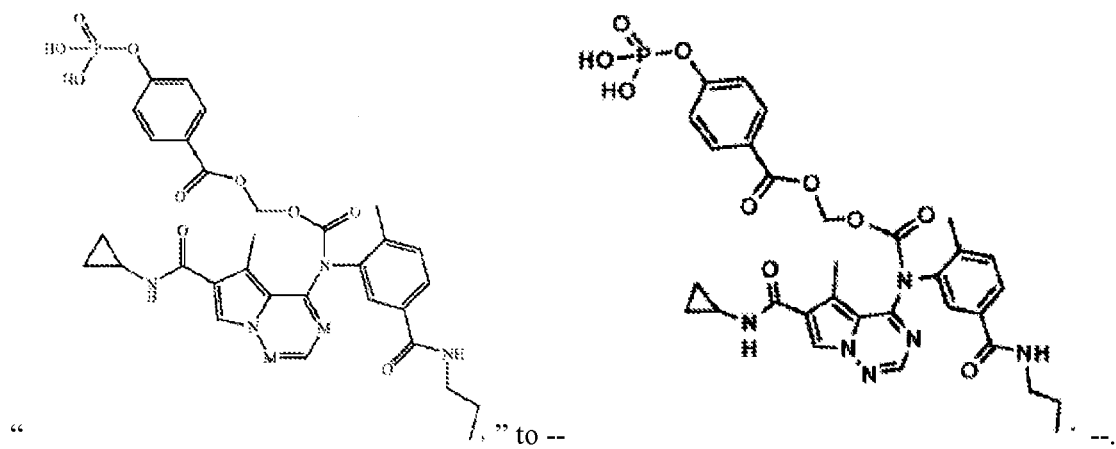

" " to -- --.

Column 295, lines 25 to 44, change

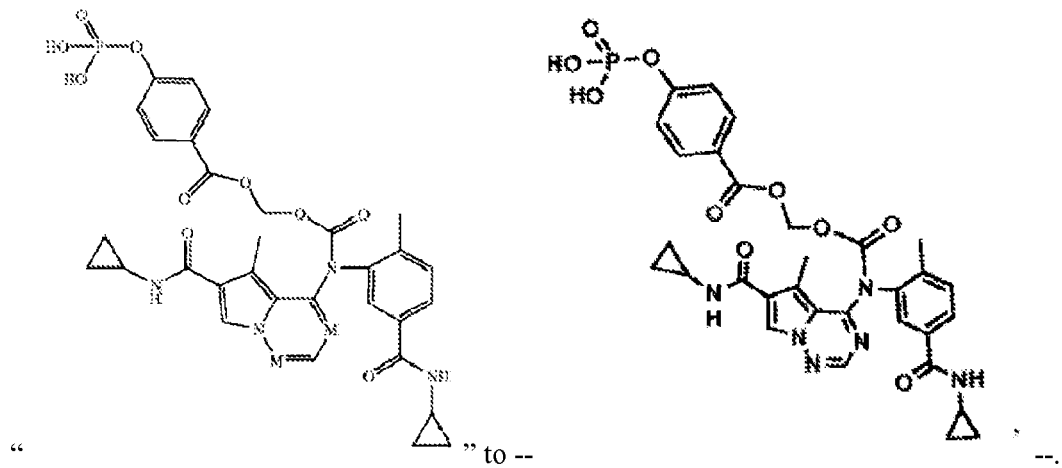

" " to -- --.

CERTIFICATE OF CORRECTION (continued)
U.S. Pat. No. 7,572,795 B2

In the Claims:

Claim 17 (continued):

Column 295, lines 46 to 66, change

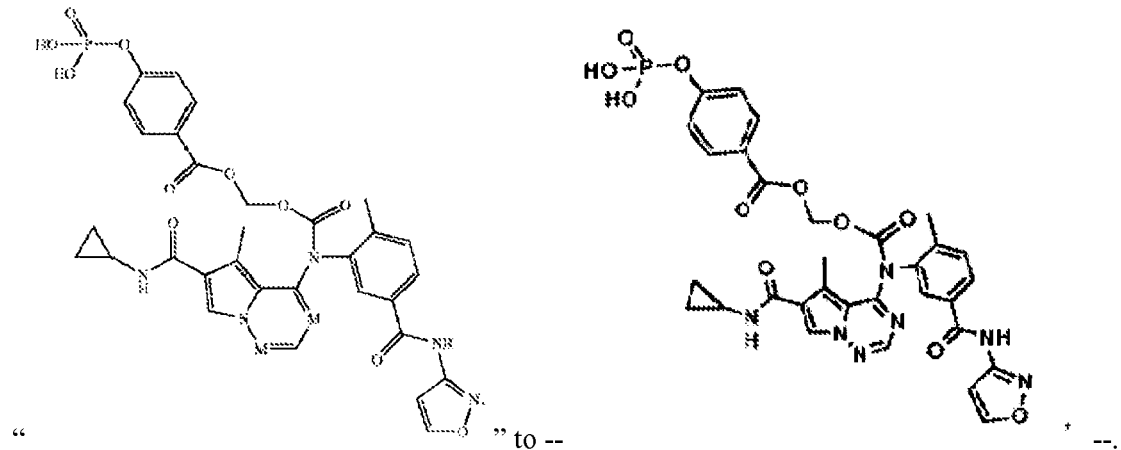

" to --    --.

Column 297, lines 3 to 17, change

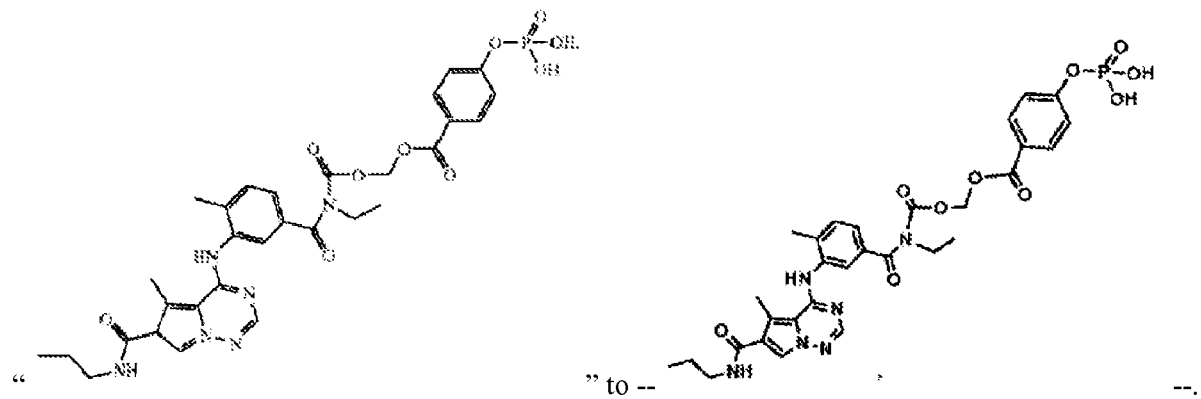

" to --    --.

Column 297, lines 19 to 32, change

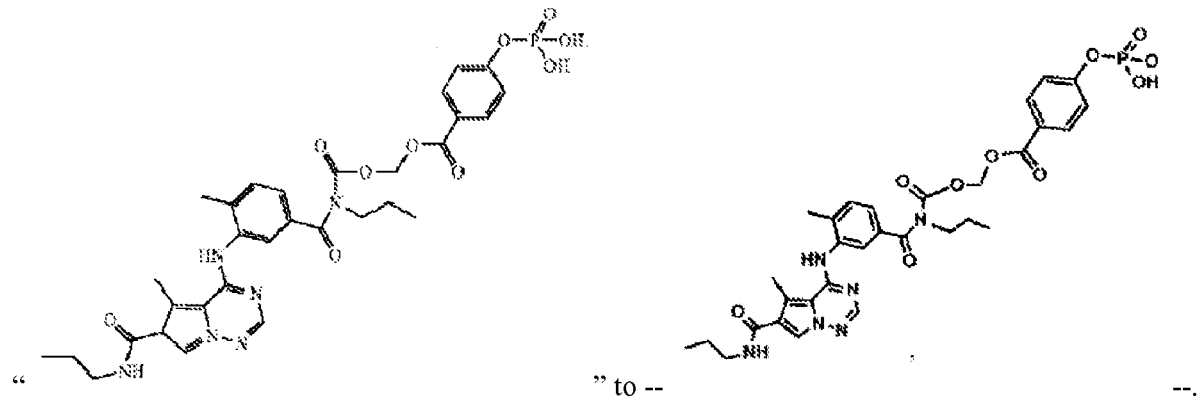

" to --    --.

CERTIFICATE OF CORRECTION (continued)
U.S. Pat. No. 7,572,795 B2

In the Claims:

Claim 17 (continued):

Column 297, lines 36 to 50, change

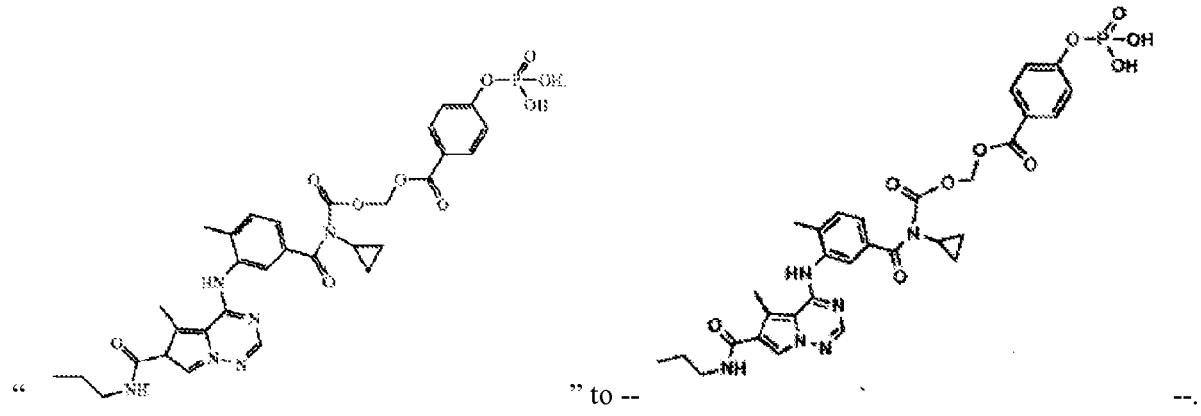

Column 297, lines 51 to 65, change

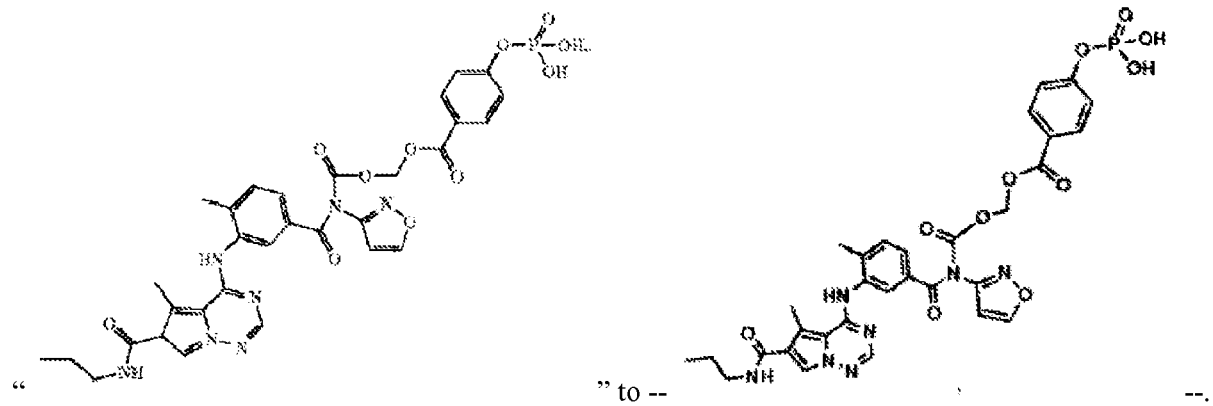

Column 298, lines 3 to 19, change

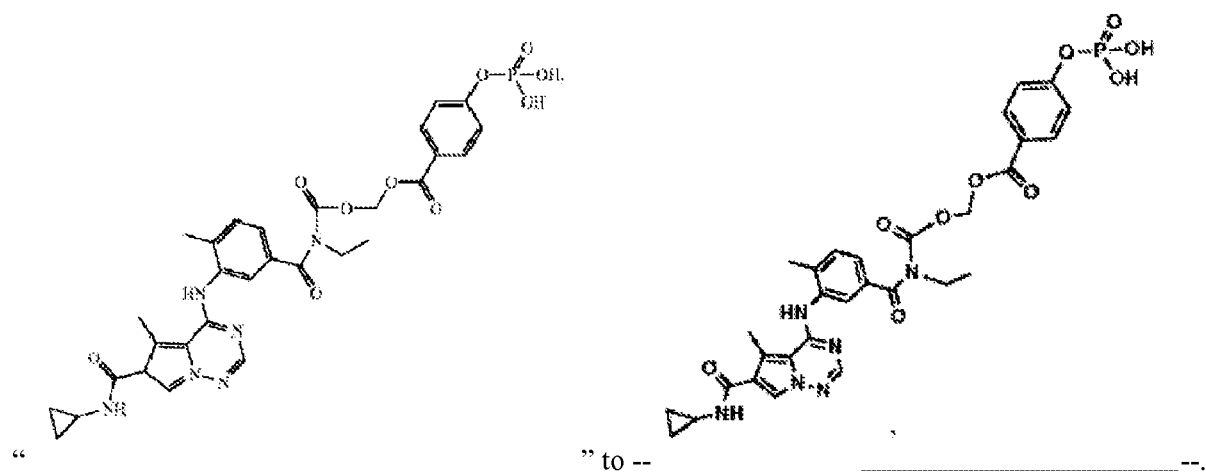

CERTIFICATE OF CORRECTION (continued)
U.S. Pat. No. 7,572,795 B2

In the Claims:

Claim 17 (continued):

Column 298, lines 26 to 41, change

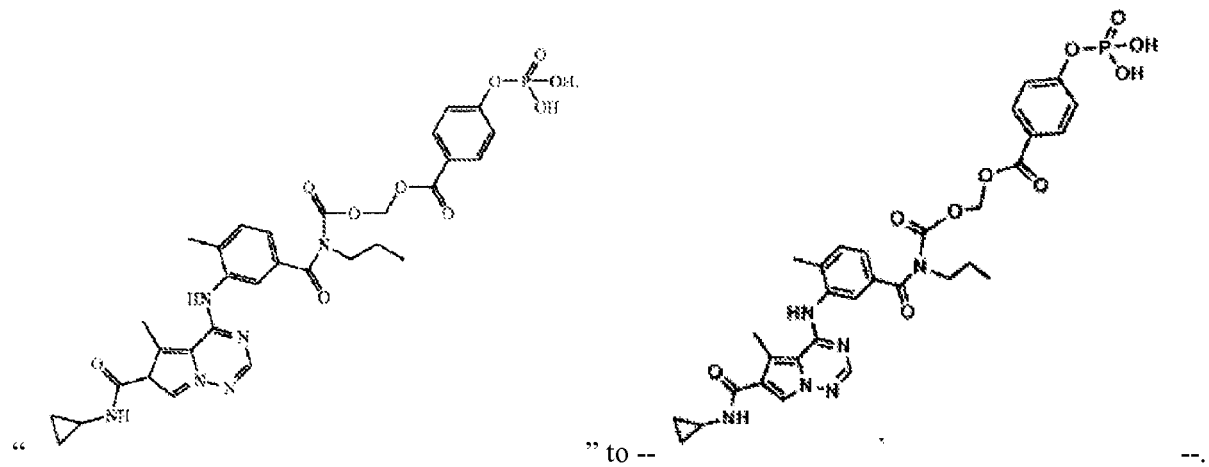

Column 298, lines 49 to 65, change

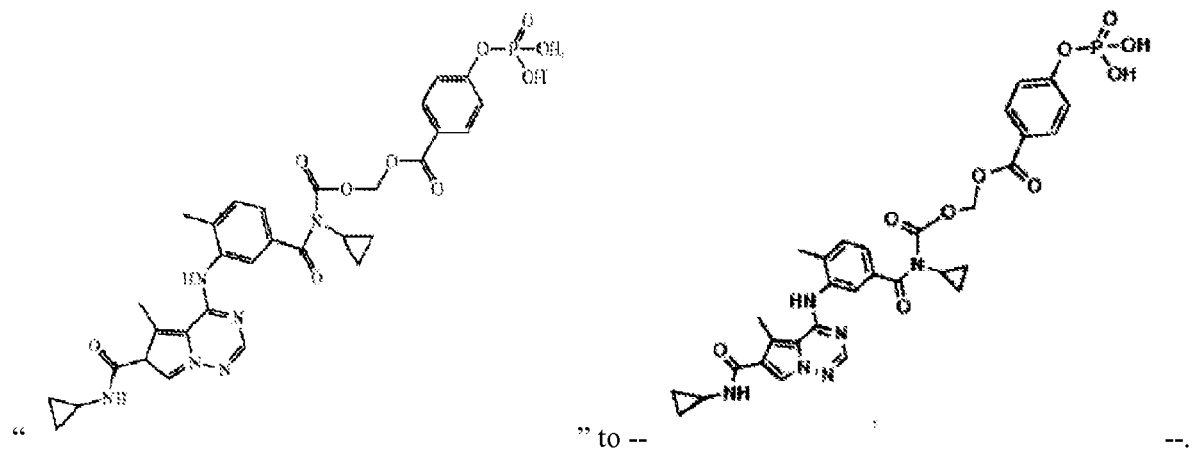

CERTIFICATE OF CORRECTION (continued)
U.S. Pat. No. 7,572,795 B2

In the Claims:

Claim 17 (continued):

Column 299, lines 3 to 19, change

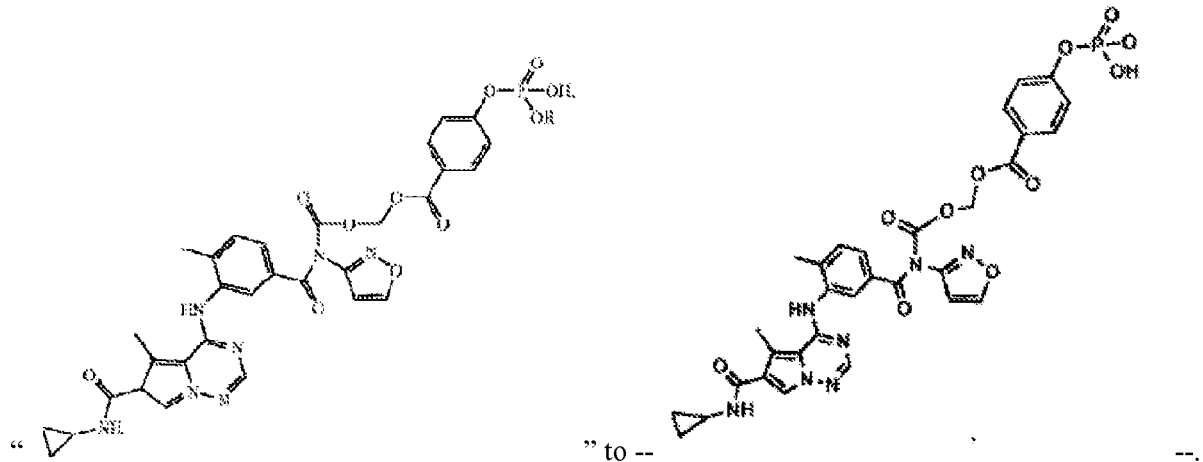

" to --                                               --.

Column 299, lines 26 to 42, change

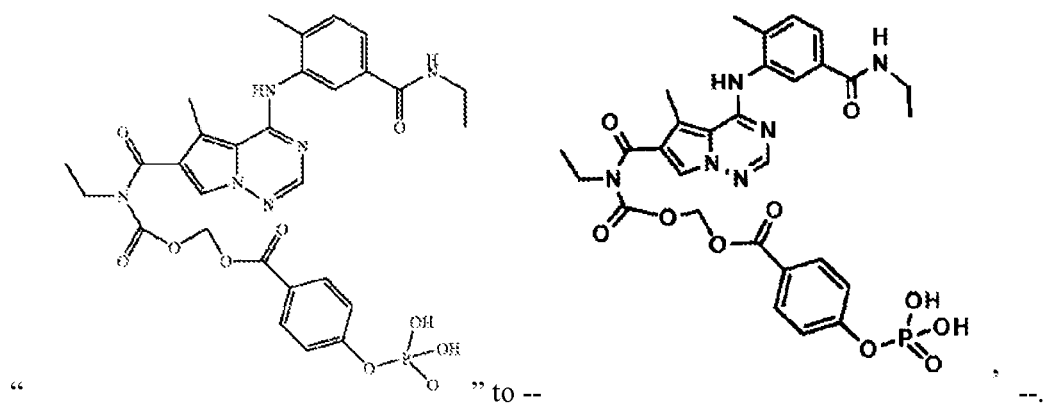

" to --                                               --.

Column 302, line 53, change "and" to -- , --.
Column 306, lines 26 to 44, change

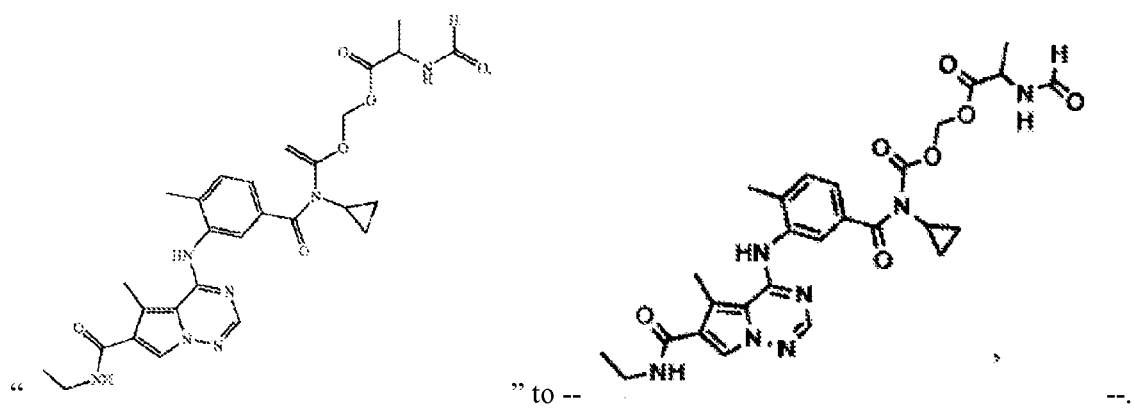

" to --                                               --.

CERTIFICATE OF CORRECTION (continued)
U.S. Pat. No. 7,572,795 B2

In the Claims:

Claim 17 (continued):

Column 309, lines 52 to 65, change

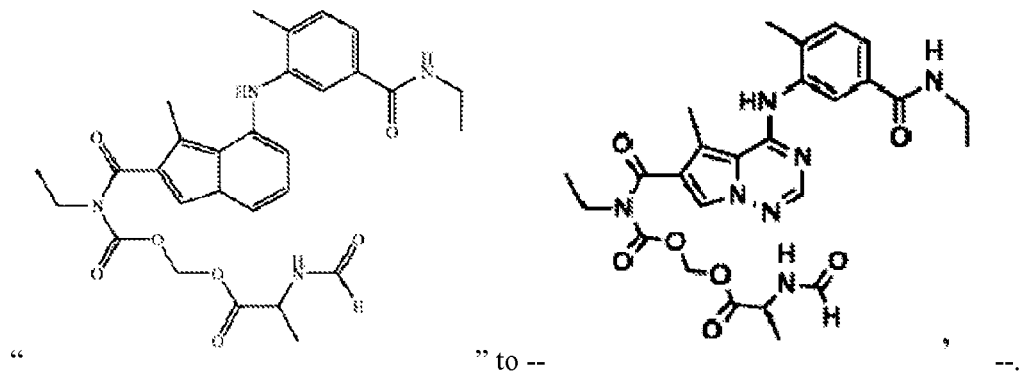

" to --         --.

Column 310, lines 3 to 16, change

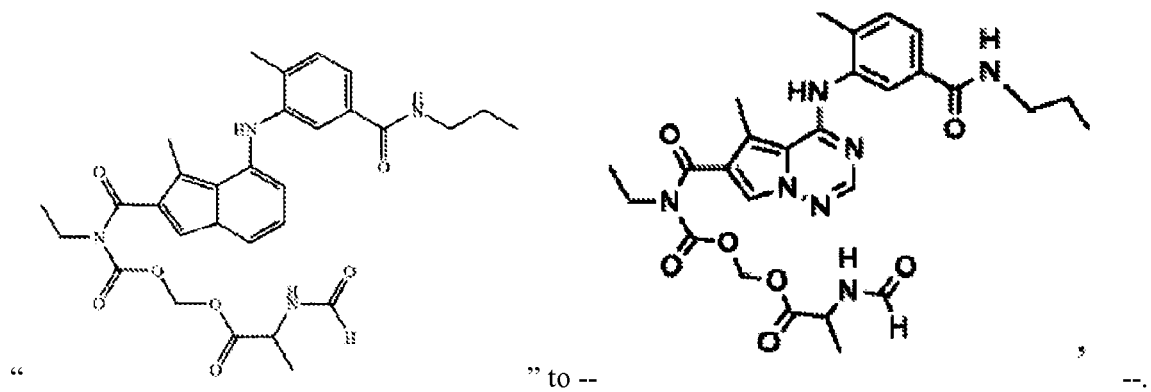

" to --         --.

Column 310, lines 20 to 33, change

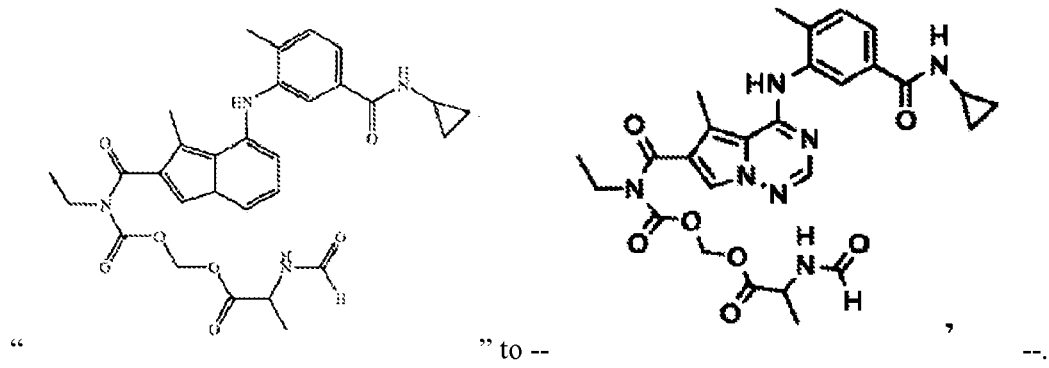

" to --         --.

CERTIFICATE OF CORRECTION (continued)
U.S. Pat. No. 7,572,795 B2

In the Claims:

Claim 17 (continued):

Column 310, lines 36 to 50, change

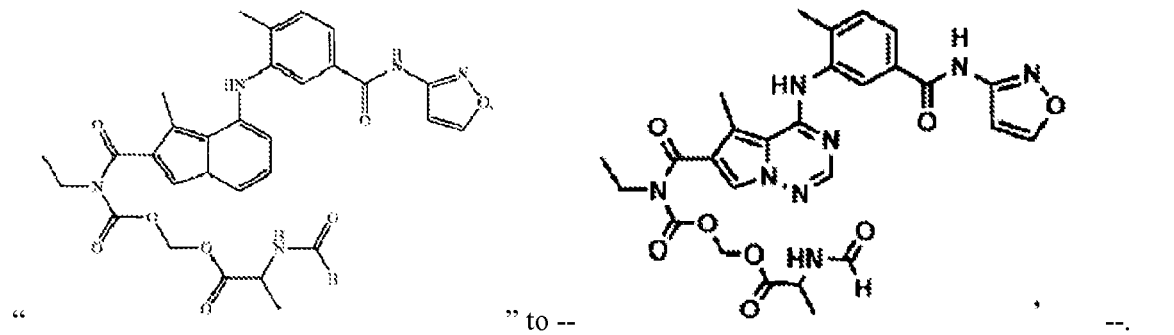 " to --  --.

Column 310, lines 53 to 66, change

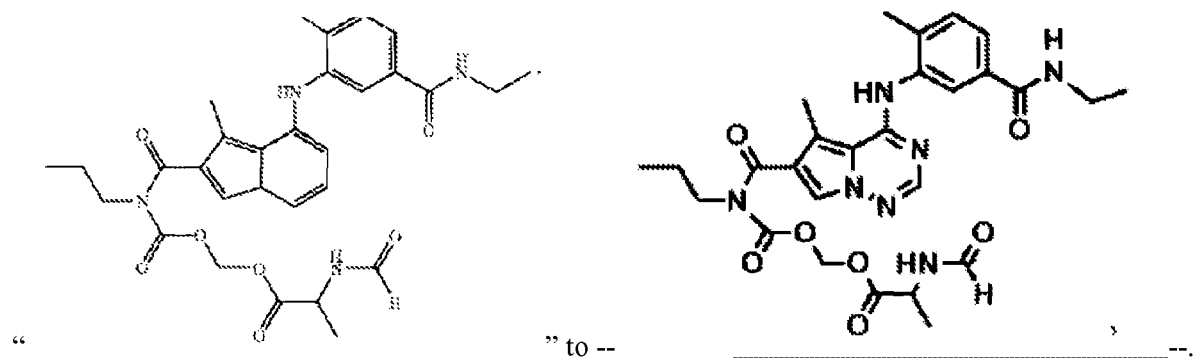 " to --  --.

Column 311, lines 3 to 16, change

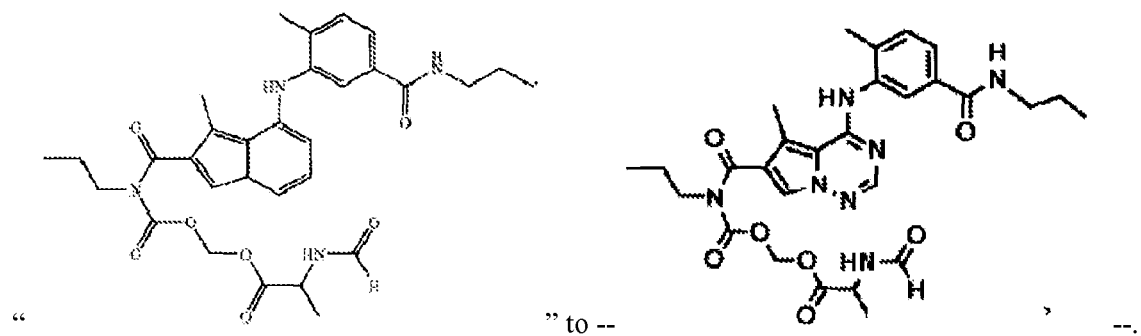 " to --  --.

CERTIFICATE OF CORRECTION (continued)
U.S. Pat. No. 7,572,795 B2

In the Claims:

Claim 17 (continued):

Column 311, lines 20 to 33, change

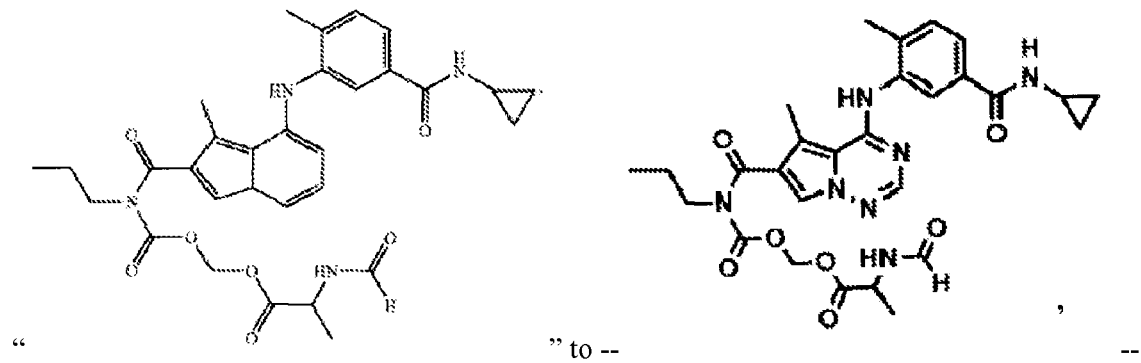

" to --    --.

Column 311, lines 36 to 49, change

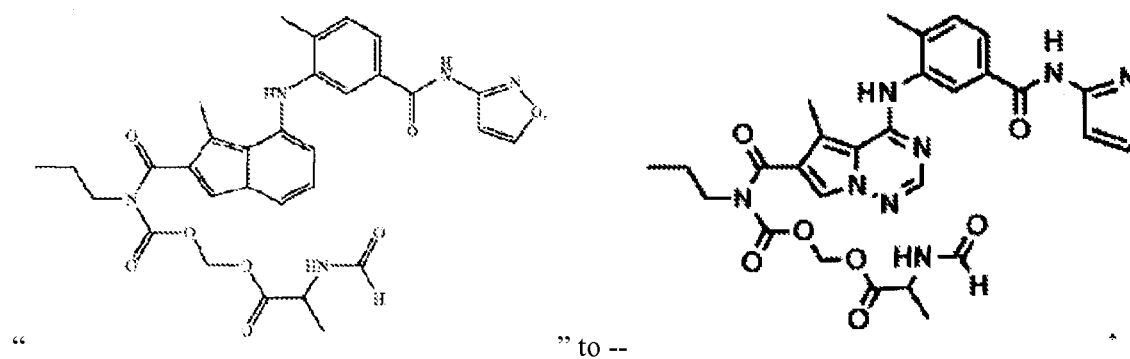

" to --    --.

Column 311, lines 52 to 66, change

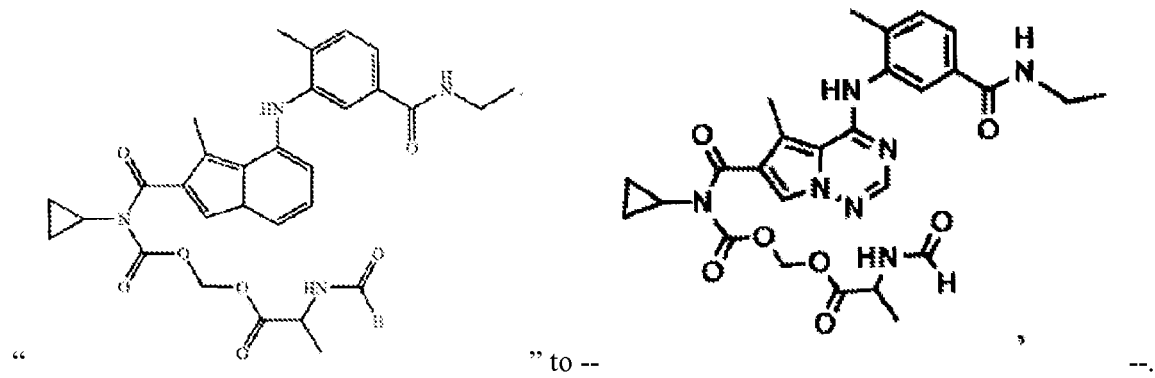

" to --    --.

CERTIFICATE OF CORRECTION (continued)

U.S. Pat. No. 7,572,795 B2

In the Claims:

Claim 17 (continued):

Column 312, lines 3 to 17, change

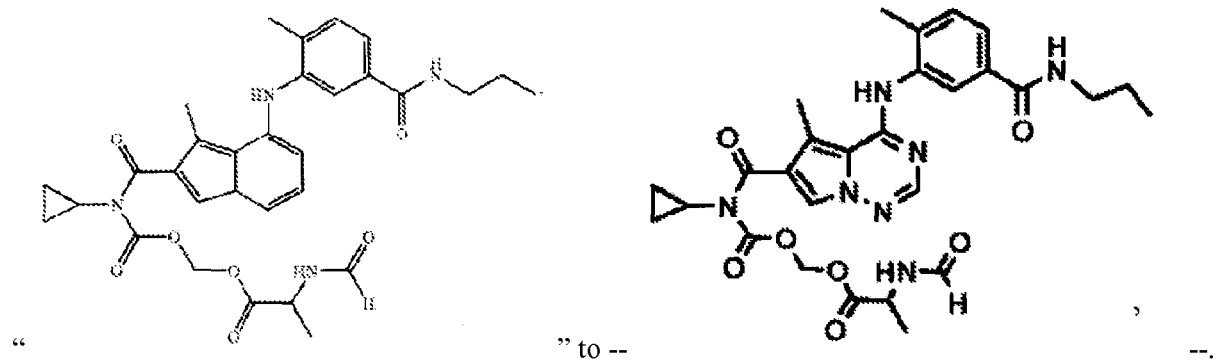

" to --                                       --.

Column 312, lines 20 to 33, change

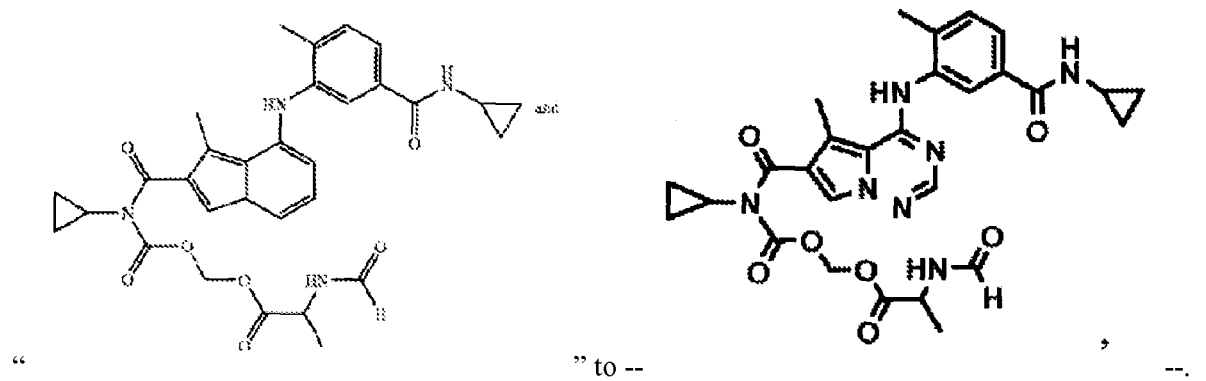

" to --                                       --.

Column 312, lines 36 to 50, change

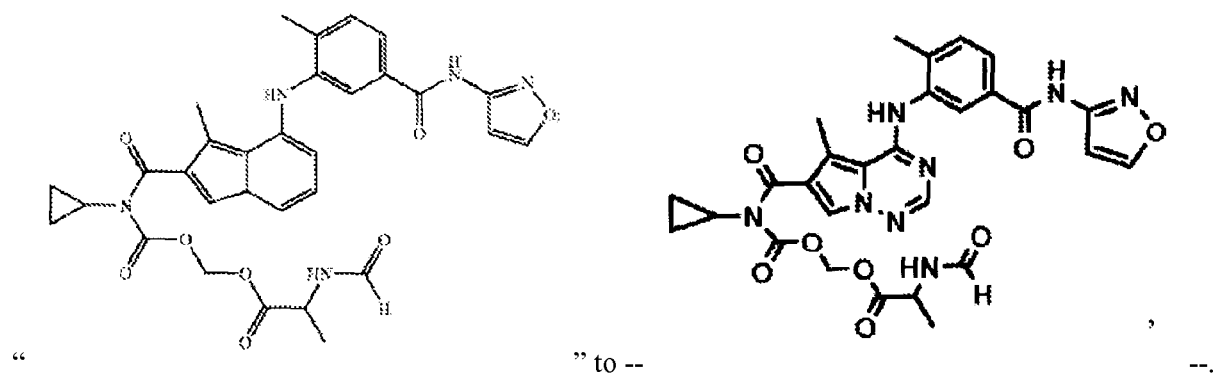

" to --                                       --.

In the Claims:
Claim 17 (continued):
Column 312, lines 53 to 66, change
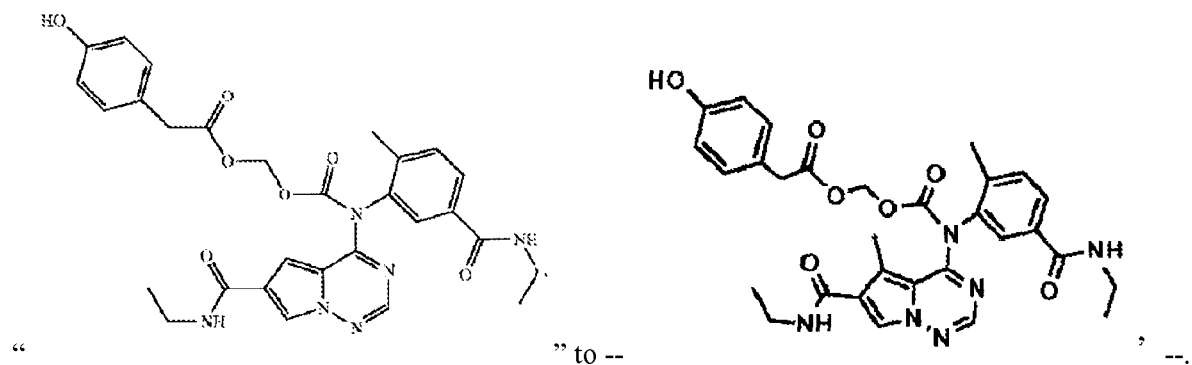
" to --
Column 313, lines 3 to 14, change
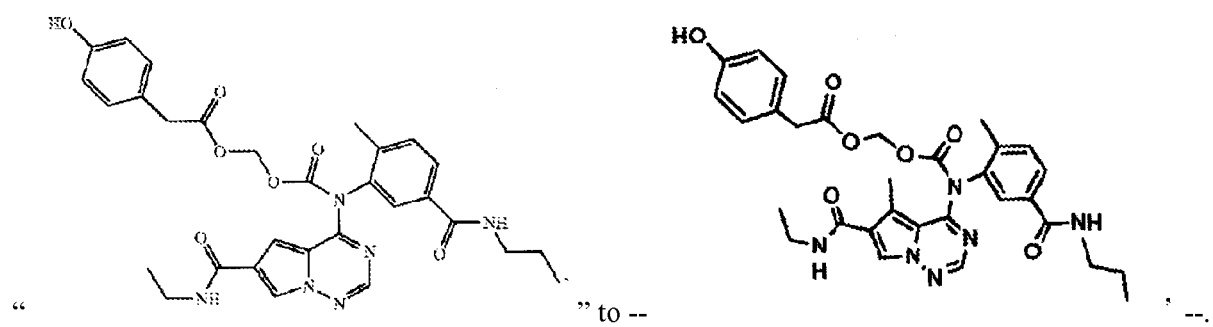
" to --
Column 313, lines 15 to 28, change
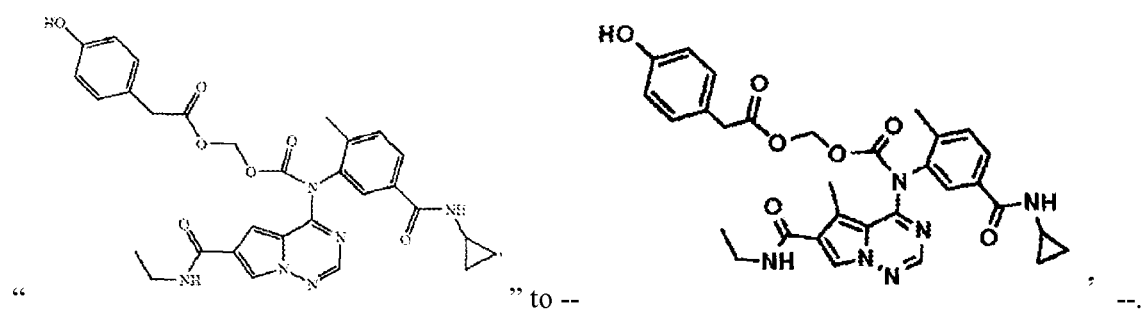
" to --

CERTIFICATE OF CORRECTION (continued)
U.S. Pat. No. 7,572,795 B2

In the Claims:

Claim 17 (continued):

Column 313, lines 29 to 40, change

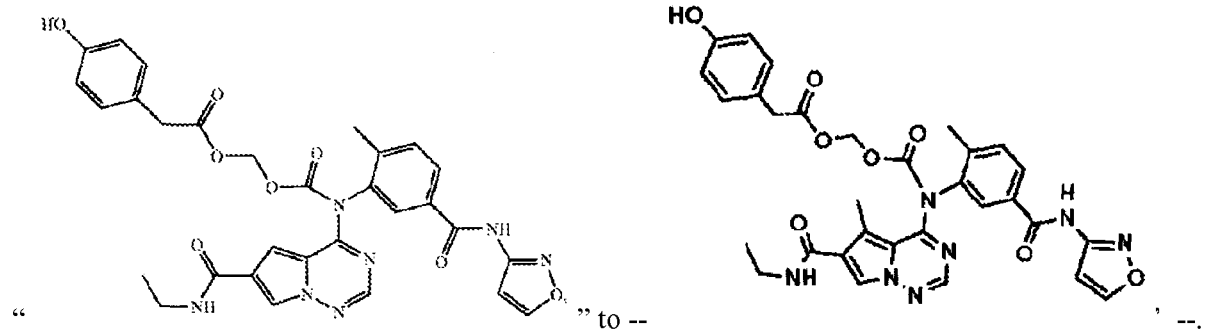

" to --

Column 313, lines 41 to 53, change

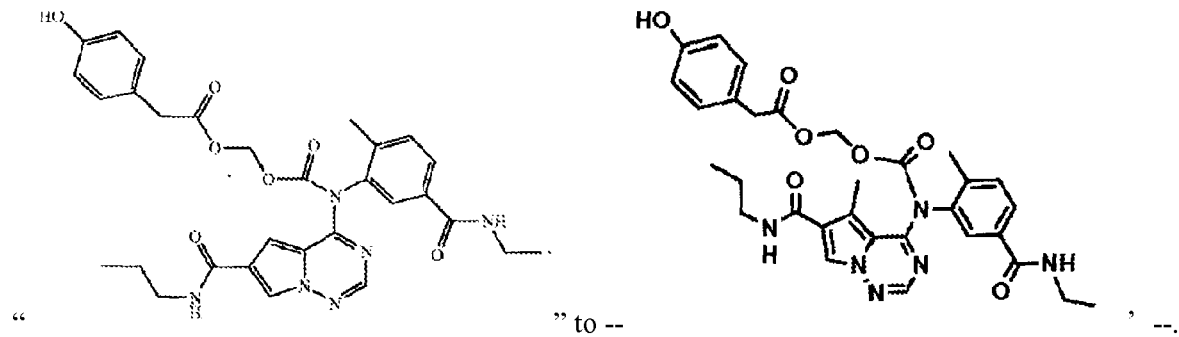

" to --

Column 313, lines 54 to 66, change

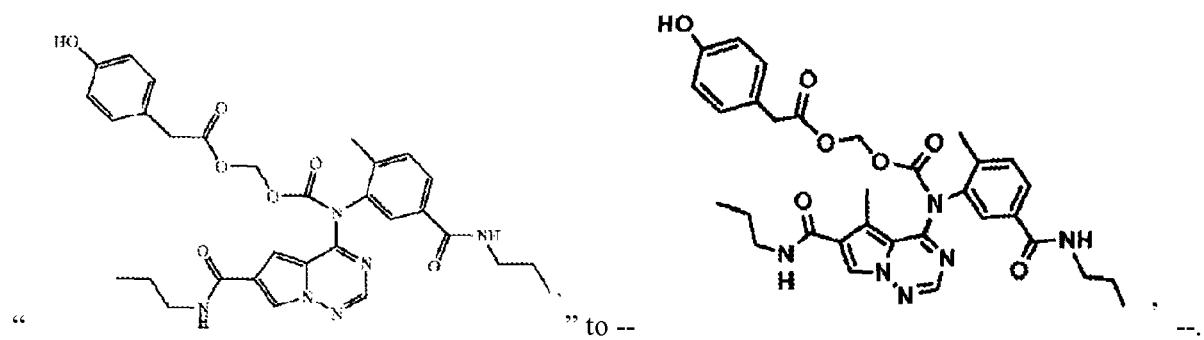

" to --

In the Claims:
Claim 17 (continued):
Column 314, lines 3 to 16, change
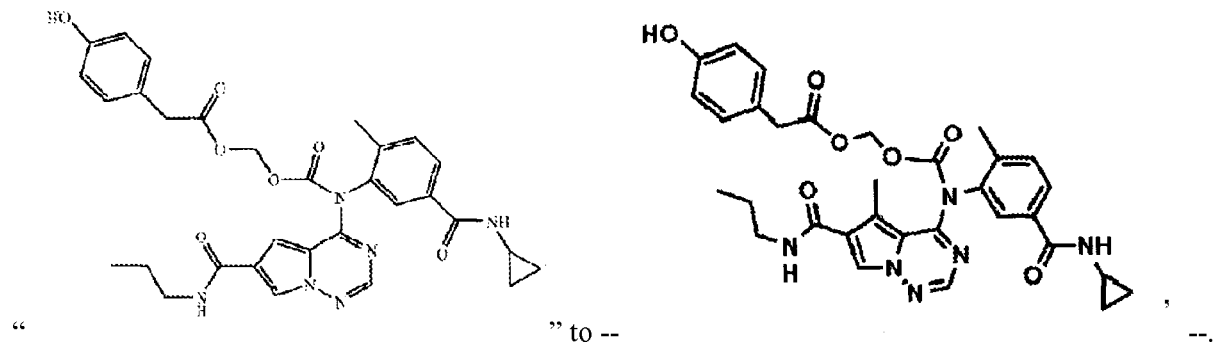
" to --  --.
Column 314, lines 19 to 32, change
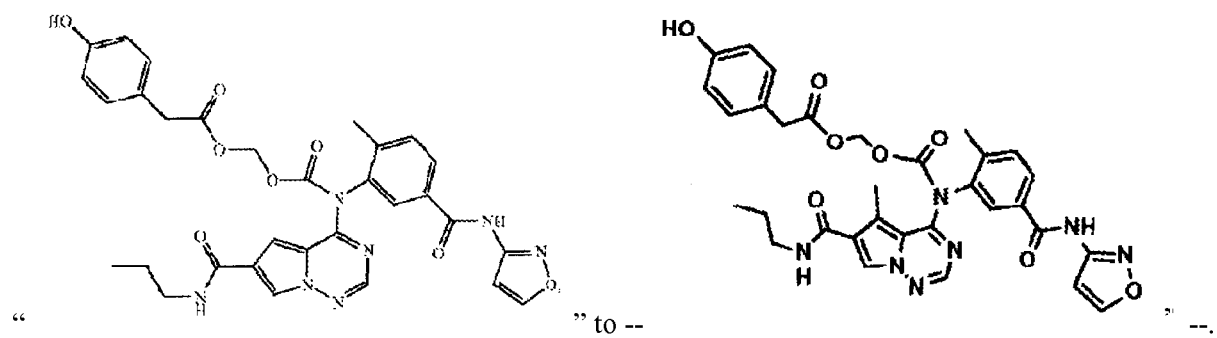
" to --  --.
Column 314, lines 35 to 48, change
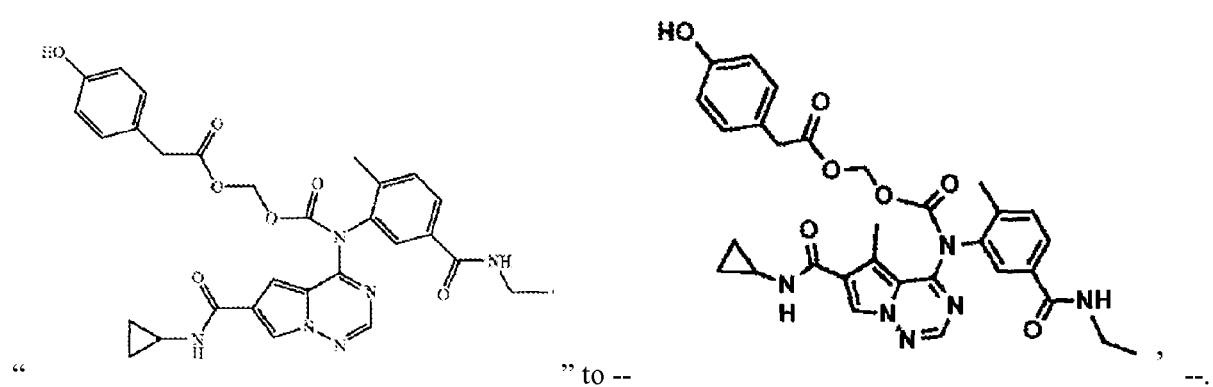
" to --  --.

CERTIFICATE OF CORRECTION (continued)
U.S. Pat. No. 7,572,795 B2

In the Claims:

Claim 17 (continued):

Column 314, lines 54 to 66, change

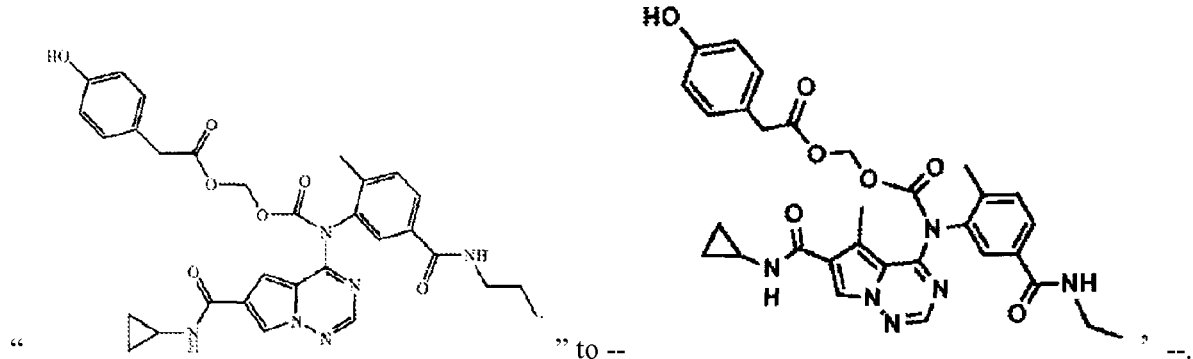

" to --         --.

Column 315, lines 3 to 16, change

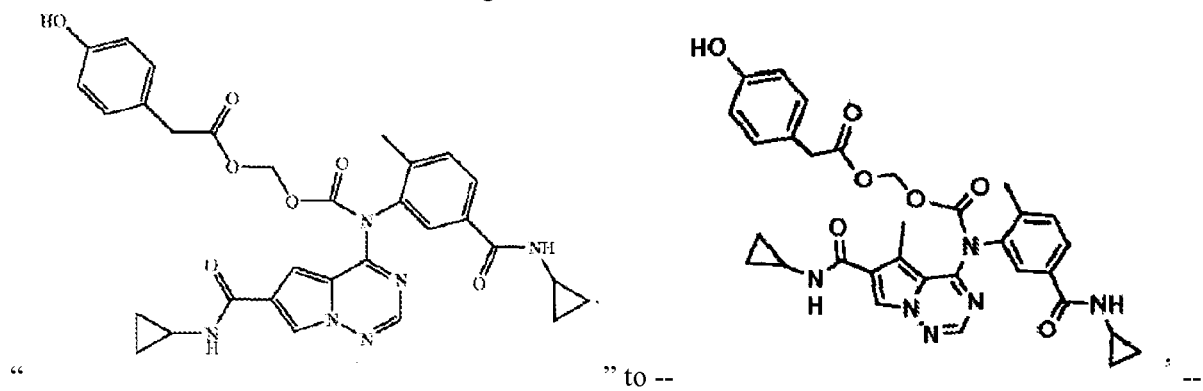

" to --         --.

Column 315, lines 17 to 29, change

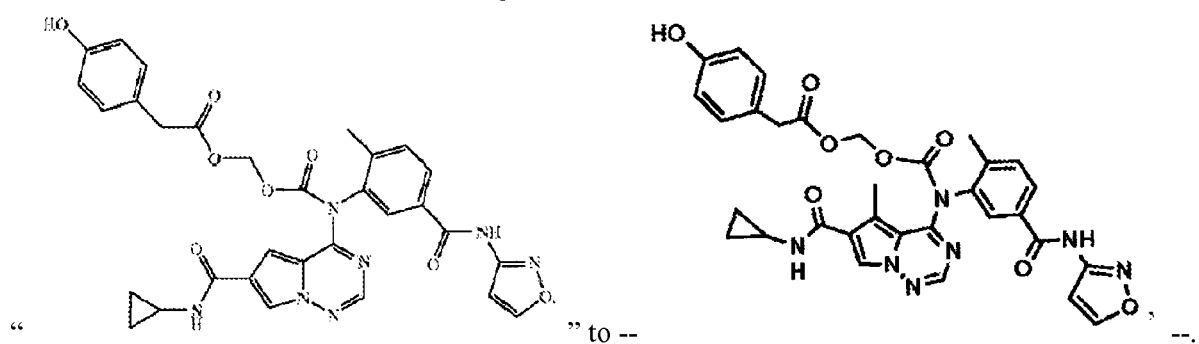

" to --         --.

In the Claims:
Claim 17 (continued):
Column 319, lines 25 to 37, change
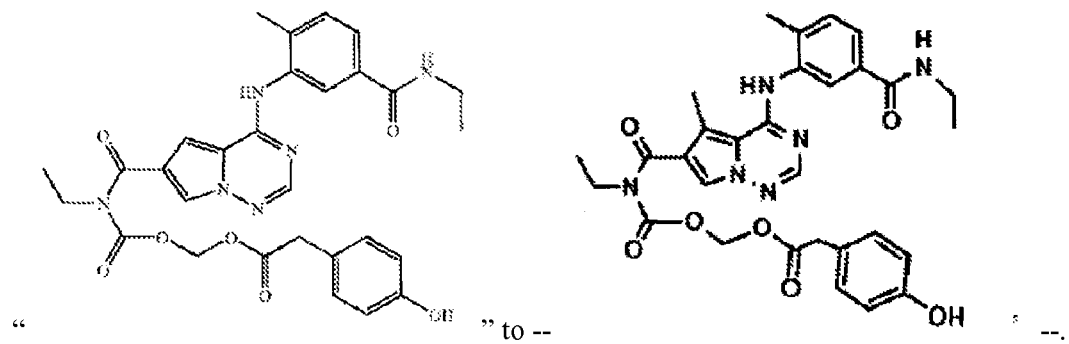 " to -- -- .
Column 319, lines 40 to 53, change
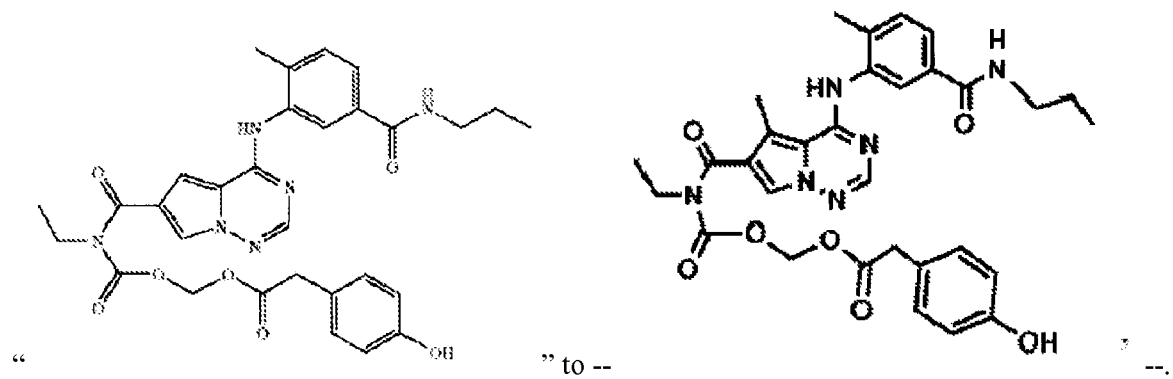 " to -- -- .
Column 319, lines 54 to 66, delete
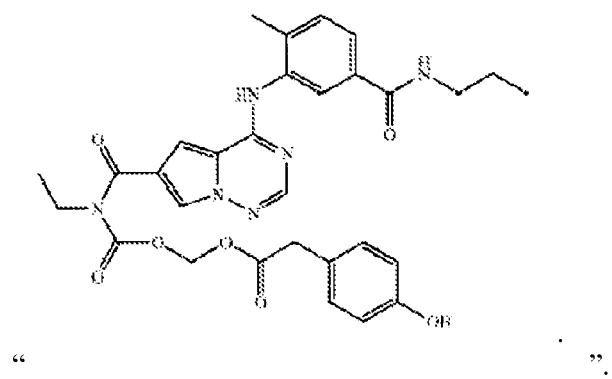 " ".
In the Claims:

CERTIFICATE OF CORRECTION (continued)
U.S. Pat. No. 7,572,795 B2

Claim 17 (continued):

Column 320, lines 3 to 15, change

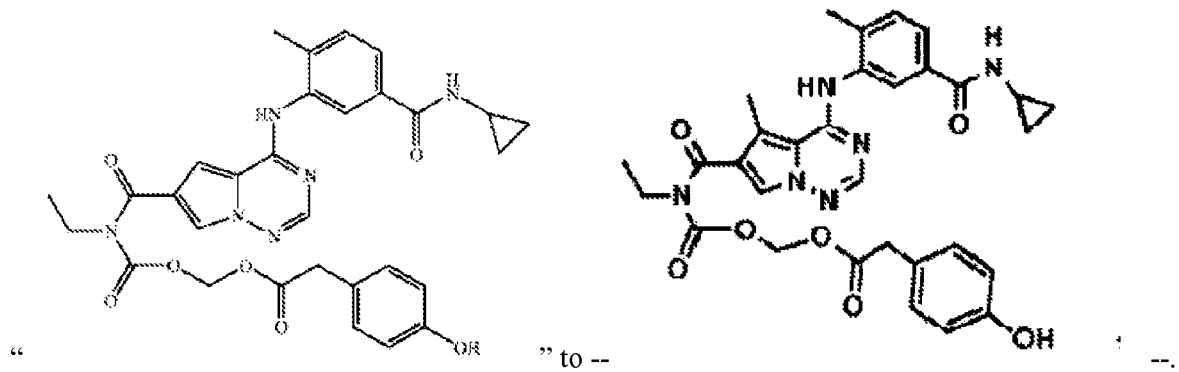

" to --       --.

Column 320, lines 21 to 33, change

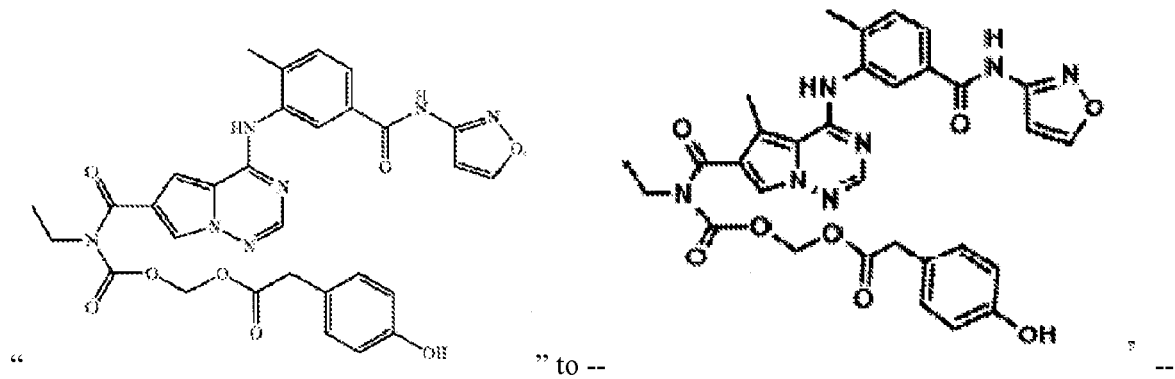

" to --       --.

Column 320, lines 36 to 48, change

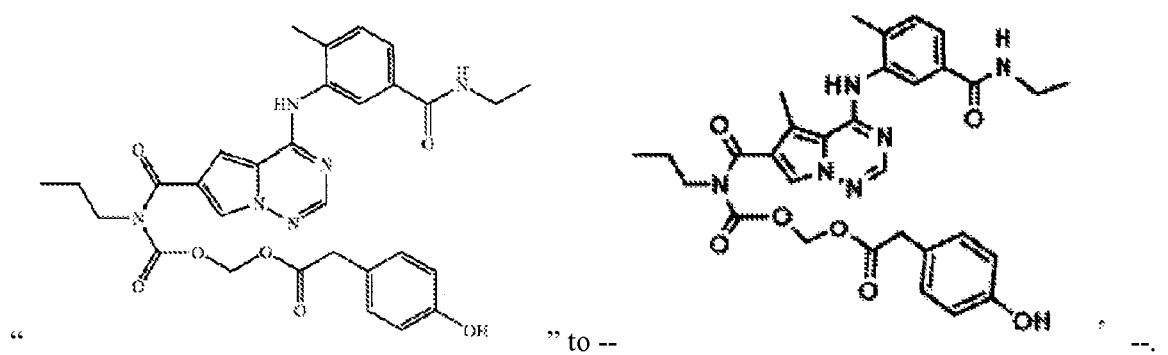

" to --       --.

In the Claims:

Claim 17 (continued):
Column 320, lines 54 to 66, change
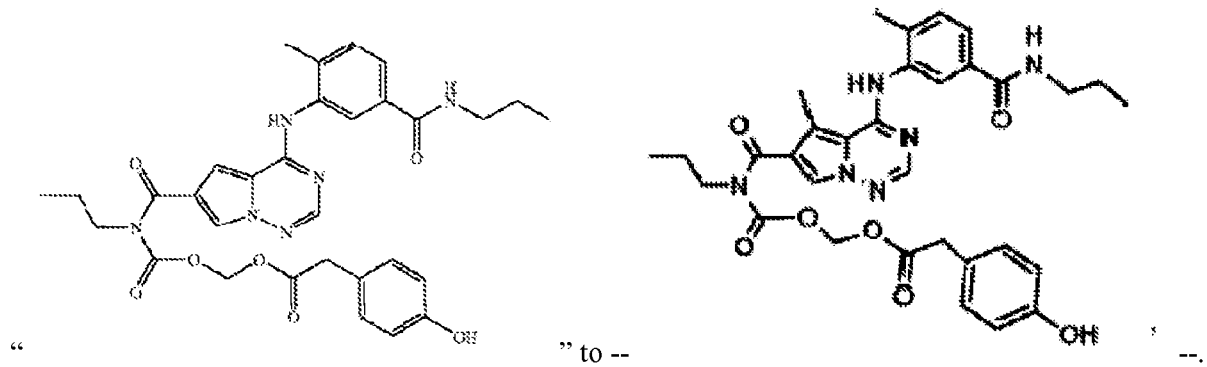
" to --  --.
Column 321, lines 3 to 15, change
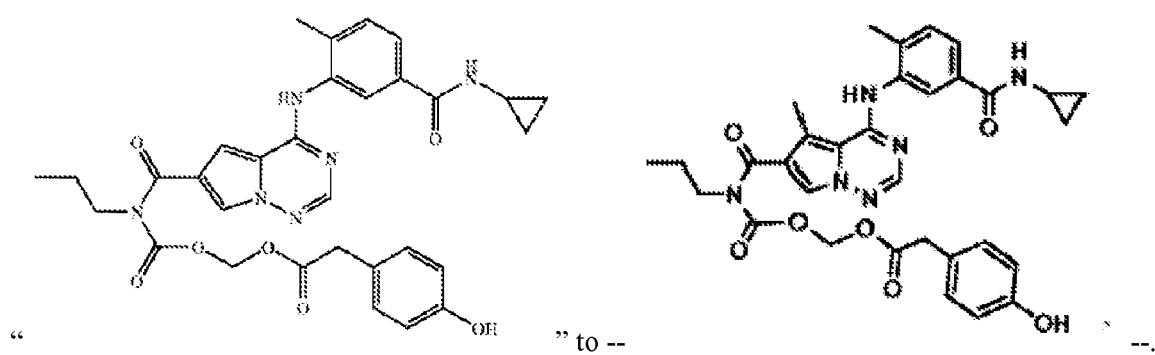
" to --  --.
Column 321, lines 20 to 33, change
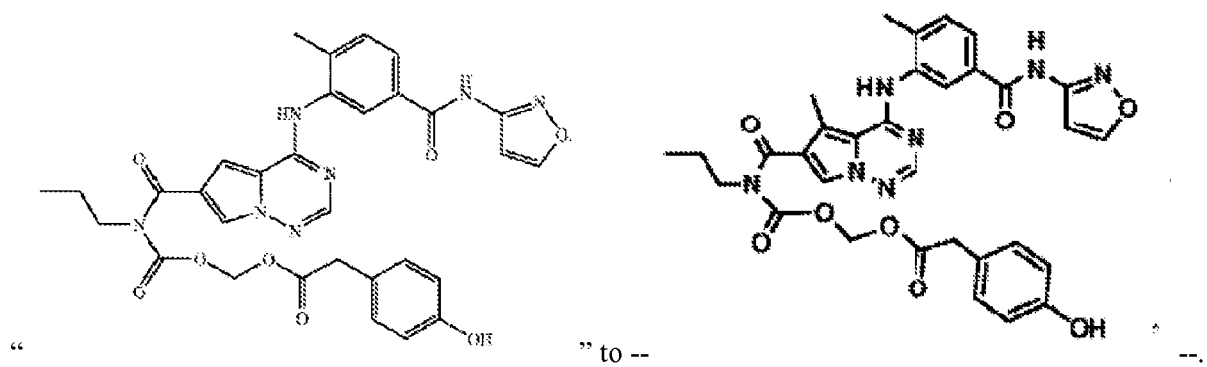
" to --  --.
In the Claims:

CERTIFICATE OF CORRECTION (continued)
U.S. Pat. No. 7,572,795 B2

Claim 17 (continued):

Column 321, lines 37 to 49, change

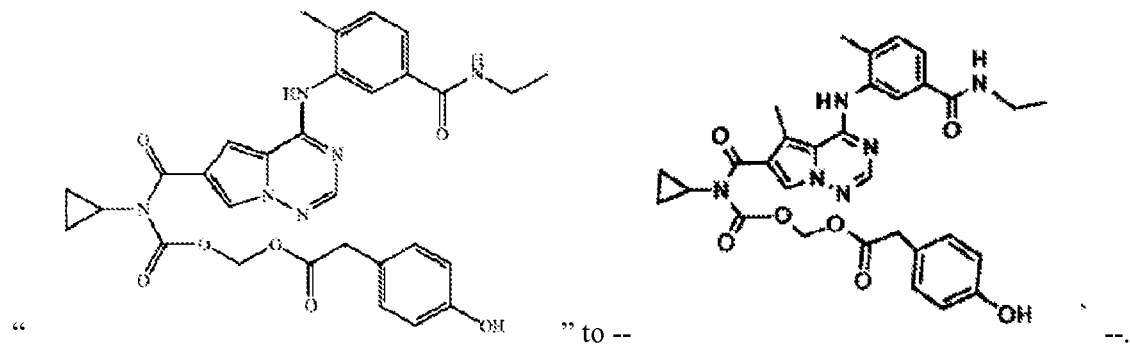

" to --                                                                            --.

Column 321, lines 54 to 66, change

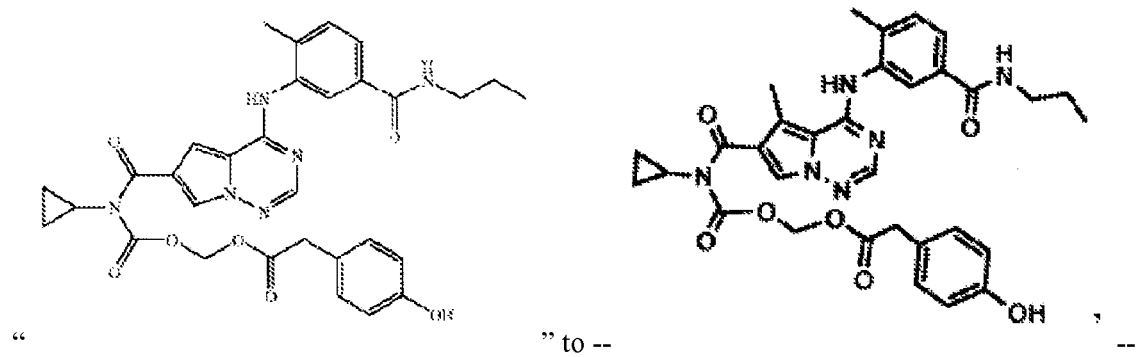

" to --                                                                            --.

Column 322, lines 3 to 15, change

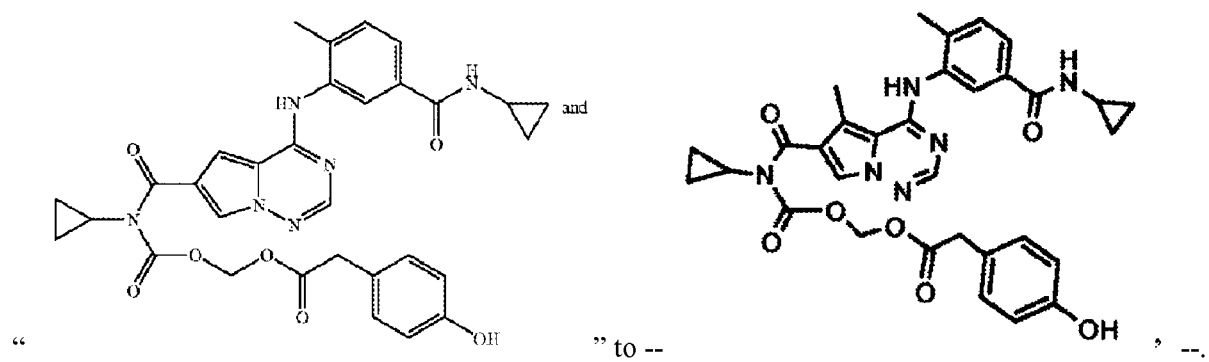

" to --                                                                            , --.

CERTIFICATE OF CORRECTION (continued)

In the Claims:

Claim 17 (continued):

Column 322, lines 16 to 29, change

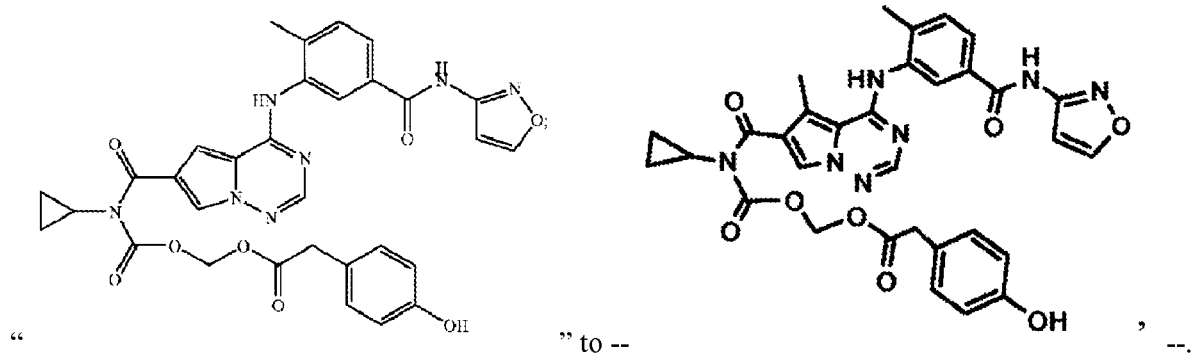

" " to -- --.

Column 327, lines 25 to 42, change

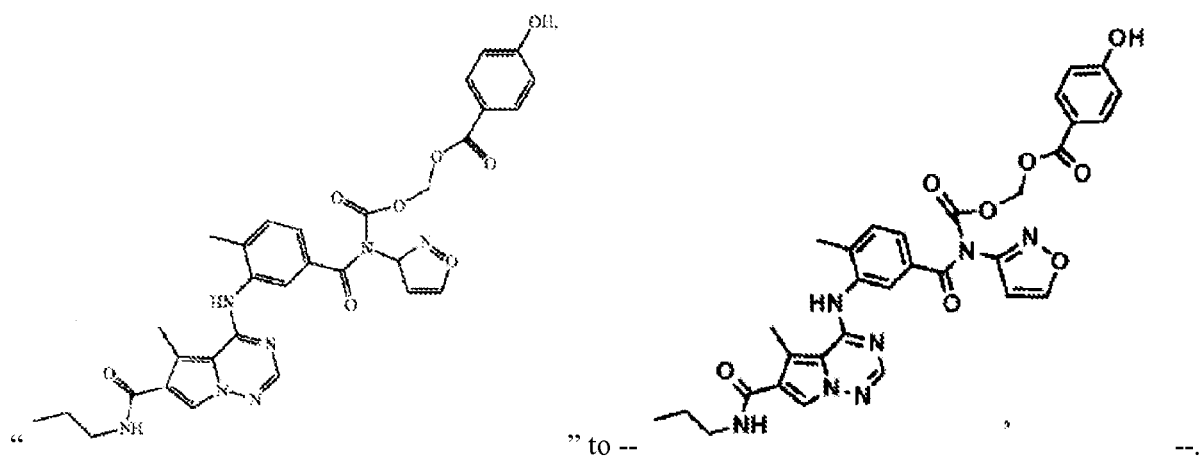

" " to -- --.

Claim 18:

Column 334, lines 3 to 13, change

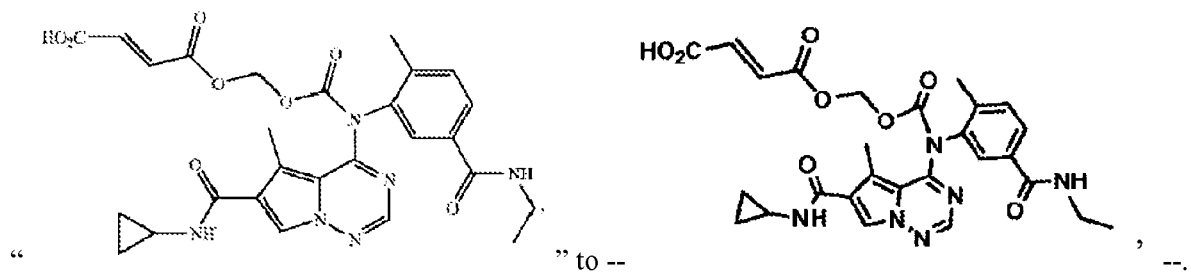

" " to -- --.

CERTIFICATE OF CORRECTION (continued)
U.S. Pat. No. 7,572,795 B2

In the Claims:

Claim 18 (continued):

Column 338, lines 36 to 50, change

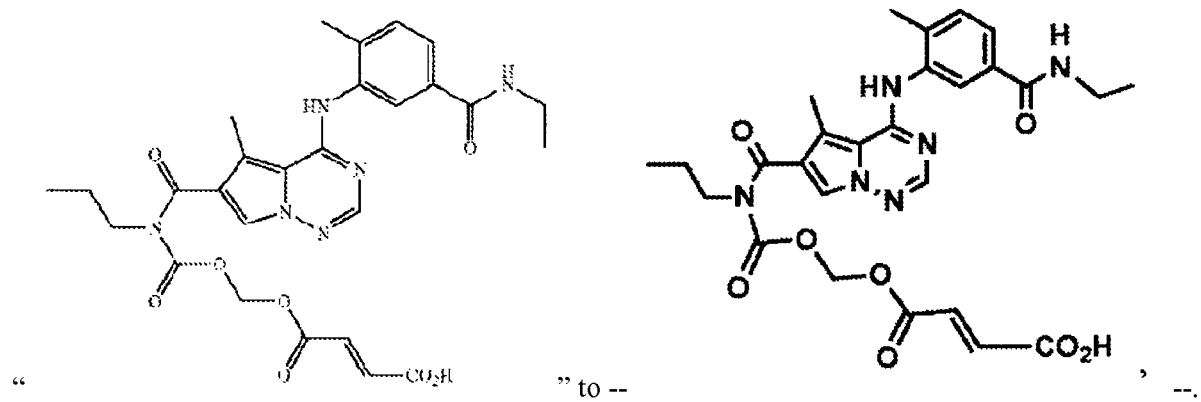

" to --            , --.

Column 339, lines 36 to 49, change

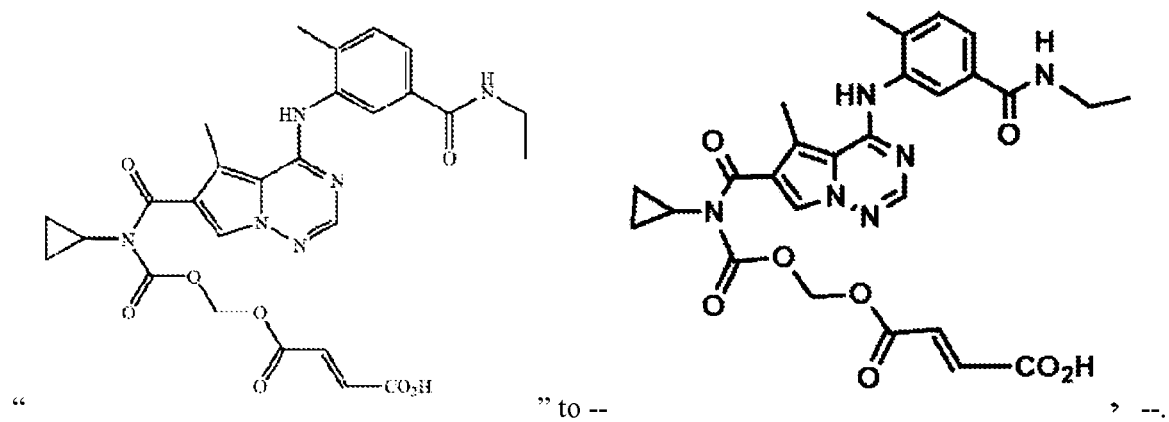

" to --            , --.

Claim 19:

Column 341, lines 51 to 66, change

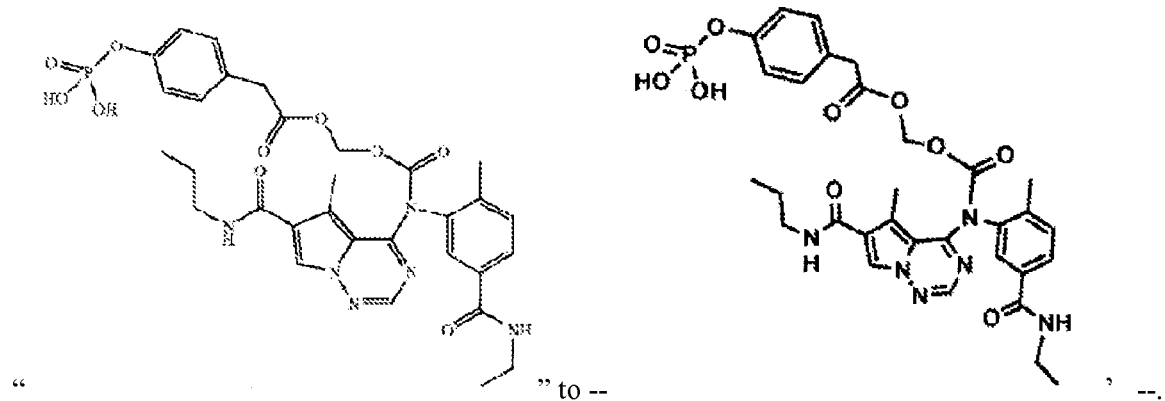

" to --            , --.

CERTIFICATE OF CORRECTION (continued)
U.S. Pat. No. 7,572,795 B2

In the Claims:

Claim 19 (continued):

Column 343, lines 3 to 18, change

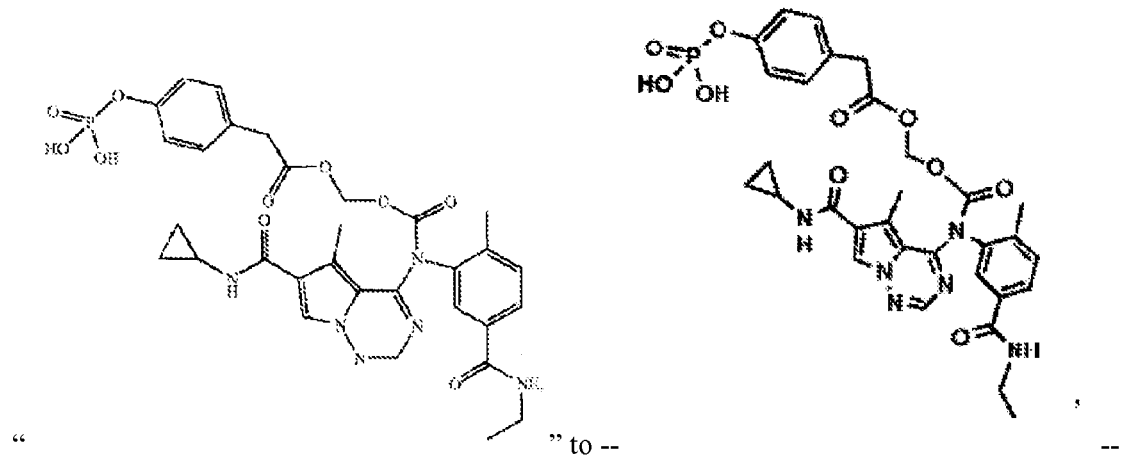

" " to -- --.

Column 345, lines 48 to 66, change

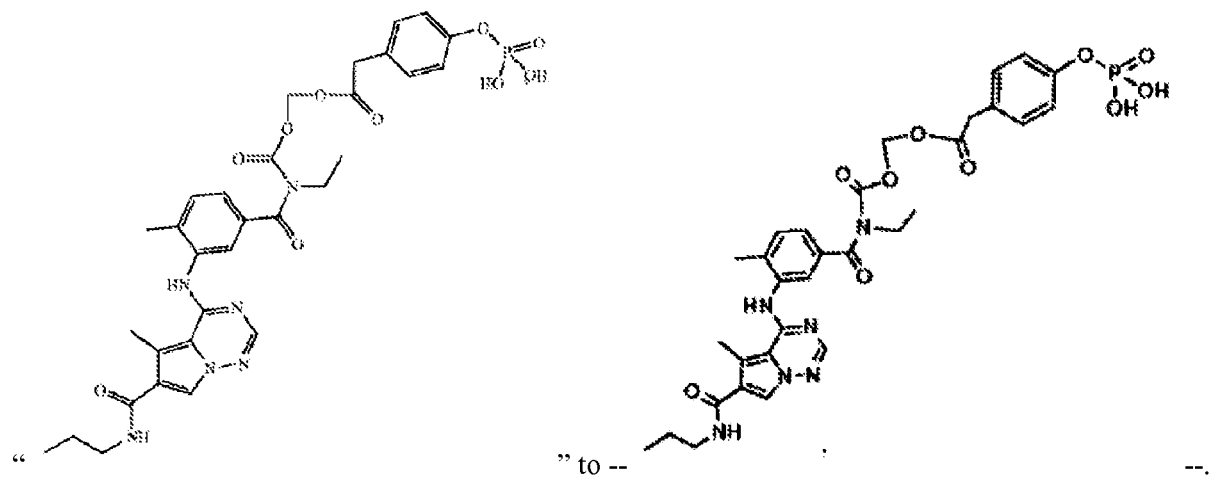

" " to -- --.

Claim 28:

Column 366, line 1, after "A", insert -- compound --.